United States Patent
Anderson et al.

(10) Patent No.: US 11,793,787 B2
(45) Date of Patent: Oct. 24, 2023

(54) METHODS AND COMPOSITIONS FOR ENHANCING ANTI-TUMOR IMMUNITY BY TARGETING STEROIDOGENESIS

(71) Applicants: The Broad Institute, Inc., Cambridge, MA (US); Massachusetts Institute of Technology, Cambridge, MA (US); The Brigham and Women's Hospital, Inc., Boston, MA (US)

(72) Inventors: Ana Carrizosa Anderson, Boston, MA (US); Asaf Madi, Boston, MA (US); Nandini Acharya, Boston, MA (US); Vijay K. Kuchroo, Boston, MA (US); Aviv Regev, Cambridge, MA (US)

(73) Assignees: The Broad Institute, Inc., Cambridge, MA (US); Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 272 days.

(21) Appl. No.: 17/065,328

(22) Filed: Oct. 7, 2020

(65) Prior Publication Data
US 2021/0100774 A1    Apr. 8, 2021

Related U.S. Application Data

(60) Provisional application No. 62/970,125, filed on Feb. 4, 2020, provisional application No. 62/911,957, filed on Oct. 7, 2019.

(51) Int. Cl.
*A61K 31/4015*    (2006.01)
*C12N 15/113*    (2010.01)
(Continued)

(52) U.S. Cl.
CPC ............ *A61K 31/4015* (2013.01); *C12N 9/10* (2013.01); *C12N 15/113* (2013.01);
(Continued)

(58) Field of Classification Search
CPC .............. A61K 31/4015; A61K 9/0019; C07K 16/2818; C07K 16/2827; C12N 15/113; C12N 2310/20; C12N 9/10
See application file for complete search history.

(56) References Cited

U.S. PATENT DOCUMENTS 4,737,323 A    4/1988 Martin et al.
4,837,028 A    6/1989 Allen
(Continued)

FOREIGN PATENT DOCUMENTS

EP    0 404 097 B1    9/1996
EP    0 785 280 B1    4/2003
(Continued)

OTHER PUBLICATIONS

Rettura et al. (Journal of the National Cancer Institute, vol. 51, No. 6, 1973). (Year: 1973).*
(Continued)

*Primary Examiner* — Savitha M Rao
(74) *Attorney, Agent, or Firm* — F. Brent Nix, Esq.; Johnson, Marcou, Isaacs & Nix, LLC; Michael B. Scher, Esq.

(57) ABSTRACT

The subject matter disclosed herein is generally directed to modulating anti-tumor T cell immunity by modulating steroidogenesis. Steroidogenesis may be modulated with inhibitors of enzymes that synthesize glucocorticoids in a tumor. The inhibitor may target Cyp11a1. The inhibitor may be metyrapone. The invention further relates to modulating immune states, such as CD8 T cell immune states, in vivo,
(Continued)

ex vivo and in vitro. The invention further relates to diagnostic and screening methods.

2 Claims, 77 Drawing Sheets

Specification includes a Sequence Listing.

(51) Int. Cl.
*C12N 9/10* (2006.01)
*C07K 16/28* (2006.01)
*A61K 9/00* (2006.01)

(52) U.S. Cl.
CPC ........ *A61K 9/0019* (2013.01); *C07K 16/2818* (2013.01); *C07K 16/2827* (2013.01); *C12N 2310/20* (2017.05)

(56) References Cited

U.S. PATENT DOCUMENTS

| | | |
|---|---|---|
| 5,143,854 A | 9/1992 | Fodor et al. |
| 5,288,644 A | 2/1994 | Beavis et al. |
| 5,324,633 A | 6/1994 | Fodor et al. |
| 5,432,049 A | 7/1995 | Fischer et al. |
| 5,470,710 A | 11/1995 | Weiss et al. |
| 5,492,806 A | 2/1996 | Drmanac et al. |
| 5,503,980 A | 4/1996 | Cantor |
| 5,510,270 A | 4/1996 | Fodor et al. |
| 5,525,464 A | 6/1996 | Drmanac et al. |
| 5,547,839 A | 8/1996 | Dower et al. |
| 5,580,732 A | 12/1996 | Grossman et al. |
| 5,580,737 A | 12/1996 | Polisky et al. |
| 5,641,870 A | 6/1997 | Rinderknecht et al. |
| 5,660,985 A | 8/1997 | Pieken et al. |
| 5,661,028 A | 8/1997 | Foote |
| 5,686,281 A | 11/1997 | Roberts |
| 5,800,992 A | 9/1998 | Fodor et al. |
| 5,811,097 A | 9/1998 | Allison et al. |
| 5,843,728 A | 12/1998 | Seed et al. |
| 5,851,828 A | 12/1998 | Seed et al. |
| 5,858,358 A | 1/1999 | June et al. |
| 5,883,223 A | 3/1999 | Gray |
| 5,906,936 A | 5/1999 | Eshhar et al. |
| 5,912,170 A | 6/1999 | Seed et al. |
| 5,912,172 A | 6/1999 | Eshhar et al. |
| 6,004,811 A | 12/1999 | Seed et al. |
| 6,040,177 A | 3/2000 | Riddell et al. |
| 6,284,240 B1 | 9/2001 | Seed et al. |
| 6,352,694 B1 | 3/2002 | June et al. |
| 6,392,013 B1 | 5/2002 | Seed et al. |
| 6,396,461 B1 | 5/2002 | Lewis et al. |
| 6,410,014 B1 | 6/2002 | Seed et al. |
| 6,479,626 B1 | 11/2002 | Kim et al. |
| 6,489,458 B2 | 12/2002 | Hackett et al. |
| 6,534,055 B1 | 3/2003 | June et al. |
| 6,534,261 B1 | 3/2003 | Cox et al. |
| 6,607,882 B1 | 8/2003 | Cox et al. |
| 6,746,838 B1 | 6/2004 | Choo et al. |
| 6,753,162 B1 | 6/2004 | Seed et al. |
| 6,794,136 B1 | 9/2004 | Eisenberg et al. |
| 6,797,514 B2 | 9/2004 | Berenson et al. |
| 6,824,978 B1 | 11/2004 | Cox et al. |
| 6,866,997 B1 | 3/2005 | Choo et al. |
| 6,867,041 B2 | 3/2005 | Berenson et al. |
| 6,887,466 B2 | 5/2005 | June et al. |
| 6,903,185 B2 | 6/2005 | Kim et al. |
| 6,905,680 B2 | 6/2005 | June et al. |
| 6,905,681 B1 | 6/2005 | June et al. |
| 6,905,874 B2 | 6/2005 | Berenson et al. |
| 6,933,113 B2 | 8/2005 | Case |
| 6,979,539 B2 | 12/2005 | Cox et al. |
| 7,013,219 B2 | 3/2006 | Case et al. |
| 7,030,215 B2 | 4/2006 | Liu et al. |
| 7,144,575 B2 | 12/2006 | June et al. |
| 7,148,203 B2 | 12/2006 | Hackett et al. |
| 7,160,682 B2 | 1/2007 | Hackett et al. |
| 7,175,843 B2 | 2/2007 | June et al. |
| 7,220,719 B2 | 5/2007 | Case et al. |
| 7,232,566 B2 | 6/2007 | June et al. |
| 7,241,573 B2 | 7/2007 | Choo et al. |
| 7,241,574 B2 | 7/2007 | Choo et al. |
| 7,446,190 B2 | 11/2008 | Sadelain et al. |
| 7,572,631 B2 | 8/2009 | Berenson et al. |
| 7,585,849 B2 | 9/2009 | Liu et al. |
| 7,595,376 B2 | 9/2009 | Kim et al. |
| 7,741,465 B1 | 6/2010 | Eshhar et al. |
| 7,985,739 B2 | 7/2011 | Kay et al. |
| 3,021,867 A1 | 9/2011 | Smith et al. |
| 8,034,334 B2 | 10/2011 | Dudley et al. |
| 8,088,379 B2 | 1/2012 | Robbins et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,211,422 B2 | 7/2012 | Eshhar et al. |
| 8,227,432 B2 | 7/2012 | Hackett et al. |
| 8,399,645 B2 | 3/2013 | Campana et al. |
| 8,697,854 B2 | 4/2014 | Schendel et al. |
| 8,735,553 B1 | 5/2014 | Li et al. |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,062,111 B2 | 6/2015 | Nichol et al. |
| 9,101,584 B2 | 8/2015 | June et al. |
| 9,102,760 B2 | 8/2015 | June et al. |
| 9,102,761 B2 | 8/2015 | June et al. |
| 9,132,281 B2 | 9/2015 | Zeng et al. |
| 9,181,527 B2 | 11/2015 | Sentman |
| 9,233,125 B2 | 1/2016 | Davila et al. |
| 9,320,811 B2 | 4/2016 | Jure-kunkel |
| 9,327,014 B2 | 5/2016 | Gurney et al. |
| 2004/0224402 A1 | 11/2004 | Bonyhadi et al. |
| 2010/0104509 A1 | 4/2010 | King et al. |
| 2012/0244133 A1 | 9/2012 | Rosenberg et al. |
| 2013/0071414 A1 | 3/2013 | Dotti et al. |
| 2015/0368342 A1 | 12/2015 | Wu et al. |
| 2015/0368360 A1 | 12/2015 | Liang et al. |
| 2016/0046724 A1 | 2/2016 | Brogdon et al. |
| 2016/0060691 A1 | 3/2016 | Giresi et al. |
| 2016/0129109 A1 | 5/2016 | Davila et al. |
| 2016/0166613 A1 | 6/2016 | Spencer et al. |
| 2016/0175359 A1 | 6/2016 | Spencer et al. |
| 2016/0208323 A1 | 7/2016 | Bernstein et al. |
| 2017/0283504 A1 | 10/2017 | Wiltzius et al. |
| 2018/0085444 A1 | 3/2018 | Morgan et al. |
| 2019/0365781 A1 | 12/2019 | Anderson et al. |

FOREIGN PATENT DOCUMENTS

| | | |
|---|---|---|
| EP | 0 373 203 B2 | 2/2007 |
| WO | 92/15322 A1 | 9/1992 |
| WO | 93/11161 A1 | 6/1993 |
| WO | 95/21265 A1 | 8/1995 |
| WO | 96/31622 A1 | 10/1996 |
| WO | 96/40281 A2 | 12/1996 |
| WO | 97/10365 A1 | 3/1997 |
| WO | 97/27317 A1 | 7/1997 |
| WO | 03/020763 A2 | 3/2003 |
| WO | 03/057171 A2 | 7/2003 |
| WO | 2004/005229 A1 | 1/2004 |
| WO | 2004/033685 A1 | 4/2004 |
| WO | 2004/044004 A2 | 5/2004 |
| WO | 2004/074322 A1 | 9/2004 |
| WO | 2005/113595 A2 | 12/2005 |
| WO | 2005/114215 A2 | 12/2005 |
| WO | 2006/000830 A2 | 1/2006 |
| WO | 2006/125962 A2 | 11/2006 |
| WO | 2008/038002 A2 | 4/2008 |
| WO | 2008/039818 A2 | 4/2008 |
| WO | 2009/012418 A2 | 1/2009 |

(56) References Cited

FOREIGN PATENT DOCUMENTS

| | | |
|---|---|---|
| WO | 2011/146862 A1 | 11/2011 |
| WO | 2012/058460 A2 | 5/2012 |
| WO | 2012/079000 A1 | 6/2012 |
| WO | 2013/039889 A1 | 3/2013 |
| WO | 2013/040371 A2 | 3/2013 |
| WO | 2013/044225 A1 | 3/2013 |
| WO | 2013/154760 A1 | 10/2013 |
| WO | 2013/166321 A1 | 11/2013 |
| WO | 2013/176915 A1 | 11/2013 |
| WO | 2014/011987 A1 | 1/2014 |
| WO | 2014/018863 A1 | 1/2014 |
| WO | 2014/059173 A2 | 4/2014 |
| WO | 2014/070874 A1 | 5/2014 |
| WO | 2014/083173 A1 | 6/2014 |
| WO | 2014/093622 A2 | 6/2014 |
| WO | 2014/133567 A1 | 9/2014 |
| WO | 2014/133568 A1 | 9/2014 |
| WO | 2014/134165 A1 | 9/2014 |
| WO | 2014/172606 A1 | 10/2014 |
| WO | 2014/184744 A1 | 11/2014 |
| WO | 2014/191128 A1 | 12/2014 |
| WO | 2014/210353 A2 | 12/2014 |
| WO | 2015/057834 A1 | 4/2015 |
| WO | 2015/057852 A1 | 4/2015 |
| WO | 2015/120096 A2 | 8/2015 |
| WO | 2015/142675 A2 | 9/2015 |
| WO | 2015/158671 A1 | 10/2015 |
| WO | 2015/187528 A1 | 12/2015 |
| WO | 2016/000304 A1 | 1/2016 |
| WO | 2016/011210 A2 | 1/2016 |
| WO | 2016/014789 A2 | 1/2016 |
| WO | 2016/040476 A1 | 3/2016 |
| WO | 2016/070061 A1 | 5/2016 |
| WO | 2016/089920 A1 | 6/2016 |
| WO | 2016/168584 A1 | 10/2016 |
| WO | 2016/196388 A1 | 12/2016 |
| WO | 2017/004916 A1 | 1/2017 |
| WO | 2017/011804 A1 | 1/2017 |
| WO | 2017/031370 A1 | 2/2017 |
| WO | 2017/069958 A2 | 4/2017 |
| WO | 2017/070395 A1 | 4/2017 |
| WO | 2017/075478 A2 | 5/2017 |
| WO | 2017/106290 A1 | 6/2017 |
| WO | 2017/156336 A1 | 9/2017 |
| WO | 2017/164936 A1 | 9/2017 |
| WO | 2017/211900 A1 | 12/2017 |
| WO | 2018/028647 A1 | 2/2018 |
| WO | 2018/049025 A2 | 3/2018 |
| WO | 2018/213708 A1 | 11/2018 |
| WO | 2018/213726 A1 | 11/2018 |
| WO | 2019/005884 A1 | 1/2019 |
| WO | 2019/005886 A1 | 1/2019 |
| WO | 2019/014581 A1 | 1/2019 |
| WO | 2019/018423 A1 | 1/2019 |
| WO | 2019/060746 A1 | 3/2019 |
| WO | 2019/068099 A1 | 4/2019 |
| WO | 2019/071048 A1 | 4/2019 |
| WO | 2019/094984 A1 | 5/2019 |
| WO | 2019/126709 A1 | 6/2019 |
| WO | 2019/126716 A1 | 6/2019 |
| WO | 2019/126762 A2 | 6/2019 |
| WO | 2020/033601 A1 | 2/2020 |
| WO | 2020/077236 A1 | 4/2020 |
| WO | 2020/131862 A1 | 6/2020 |

OTHER PUBLICATIONS

Seifter et al. (Journal of Surgical Oncology, 12:281-288, 1978). (Year: 1978).*

Asner et al.(Journal of Immunology, 2017, 198(i):31-39) (Year: 2017).*

Barrat, et al., "In Vitro Generation of Interleukin 10-producing Regulatory CD4(+) T Cells is Induced by Immunosuppressive drugs and Inhibited by T helper type 1 (Th1)- and Th2-inducing Cytokines", Journal of Experimental Medicine, vol. 195, No. 5, Mar. 4, 2002, 603-616.

Cain, et al., "Immune Regulation by Glucocorticoids", Nature Reviews Immunology, 2017, vol. 17, No. 4, Apr. 2017, 16 pages.

Karwacz, et al., "Critical Role of IRF1 and BATF in Forming Chromatin Landscape During Type 1 Regulatory Cell Differentiation", Nature Immunology, vol. 18, No. 4, Feb. 6, 2017, 12 pages.

Singer, et al., "A Distinct Gene Module for Dysfunction Uncoupled from Activation in Tumor-Infiltrating T Cells", Cell, vol. 166, No. 6, Sep. 8, 2016, 22 pages.

Weber, et al., "Phase I/II study of Ipilimumab for Patients with Metastatic Melanoma", Journal of Clinical Oncology, 2008, vol. 26, No. 36, Dec. 20, 2008, 5950-5956.

\* cited by examiner

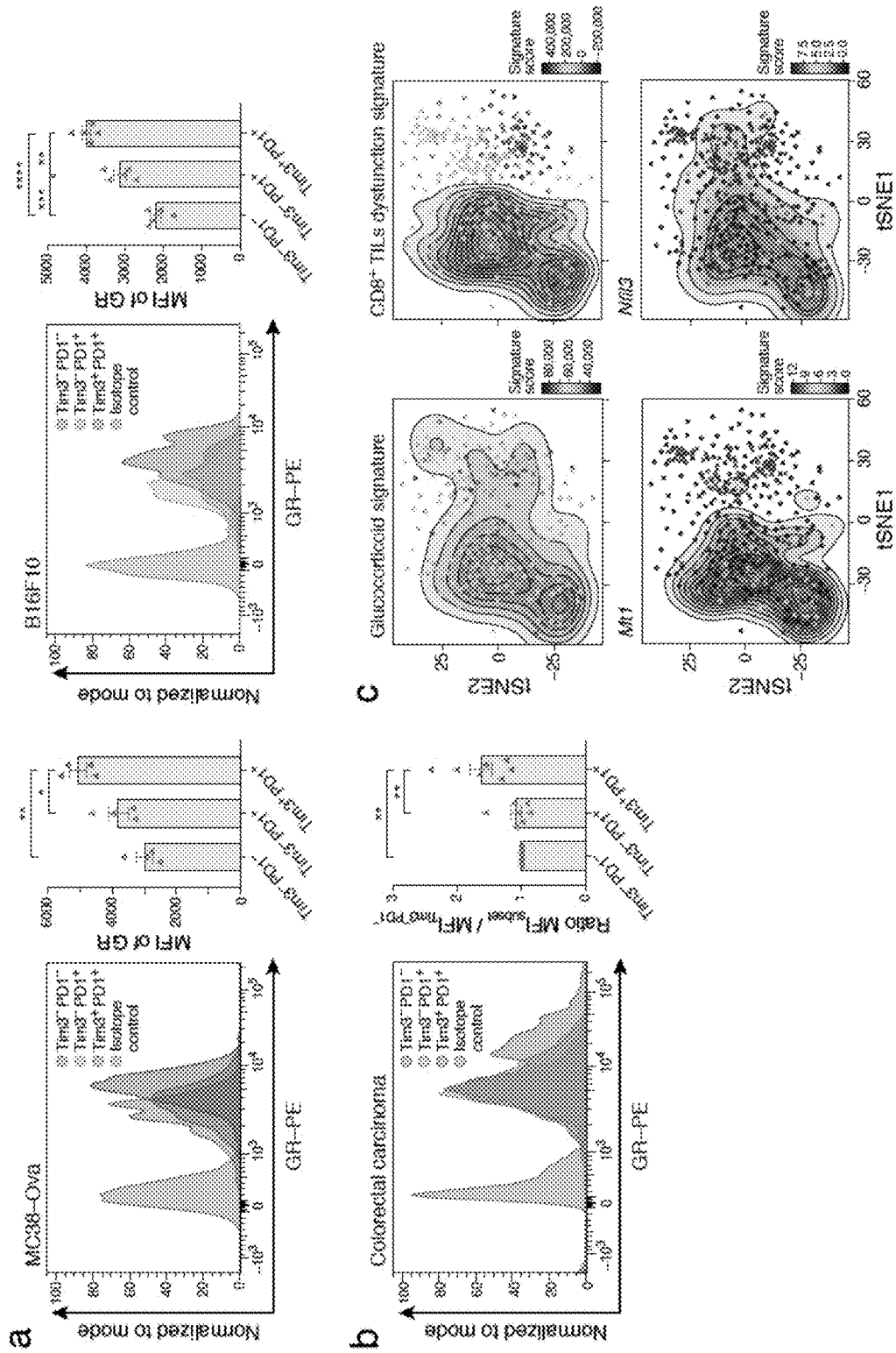
FIG. 1A-C

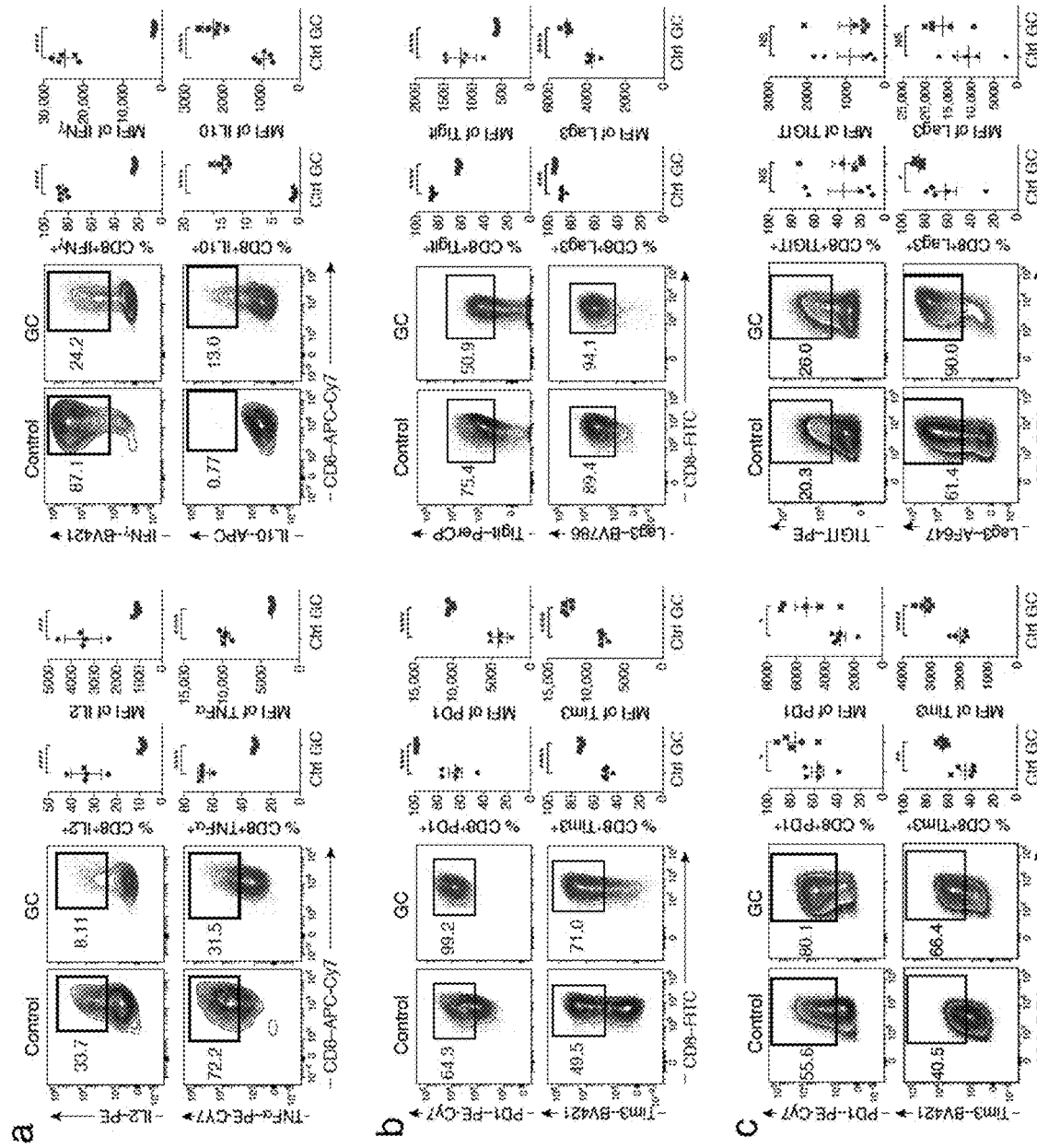
FIG. 2A-C

FIG. 3A-D

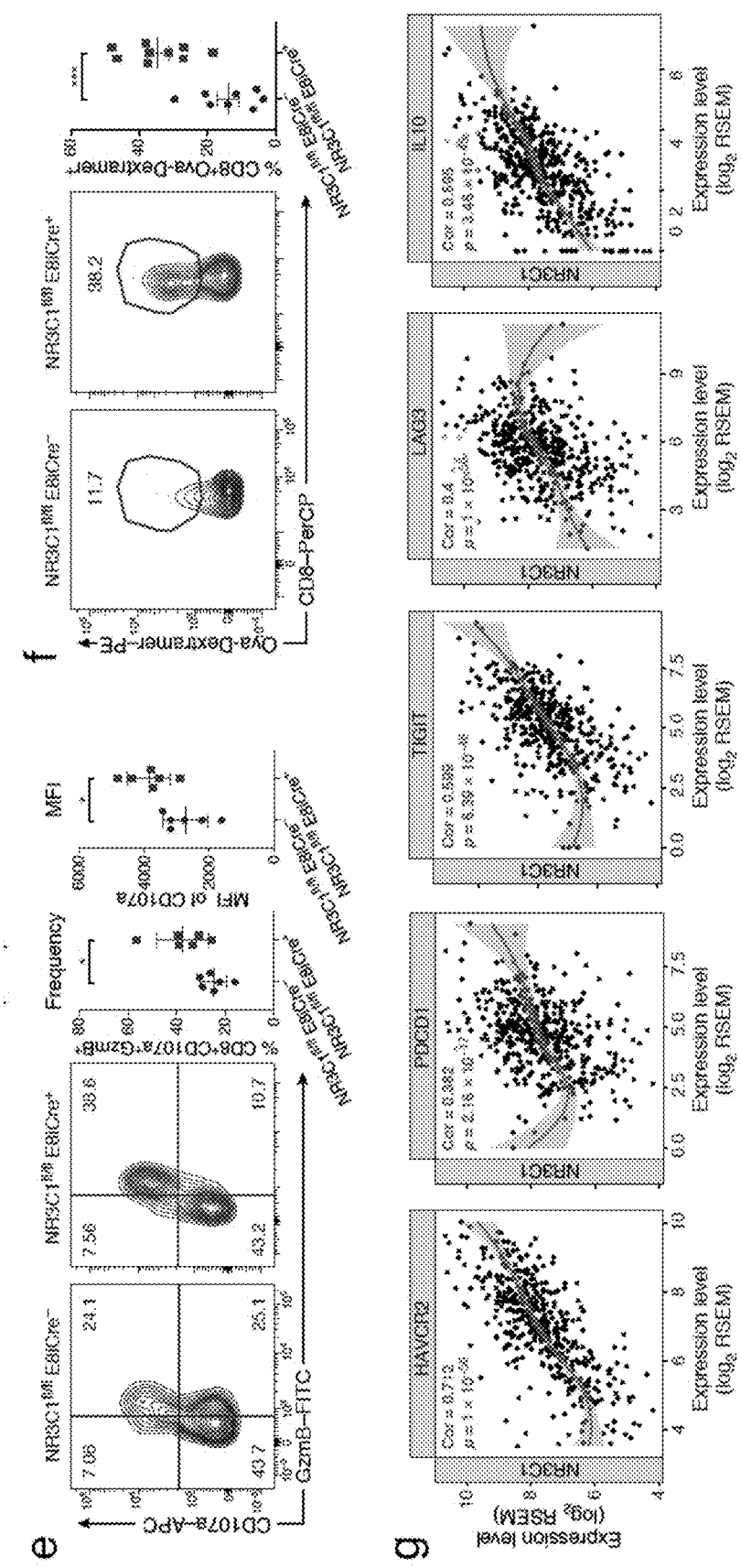
FIG. 3E-G

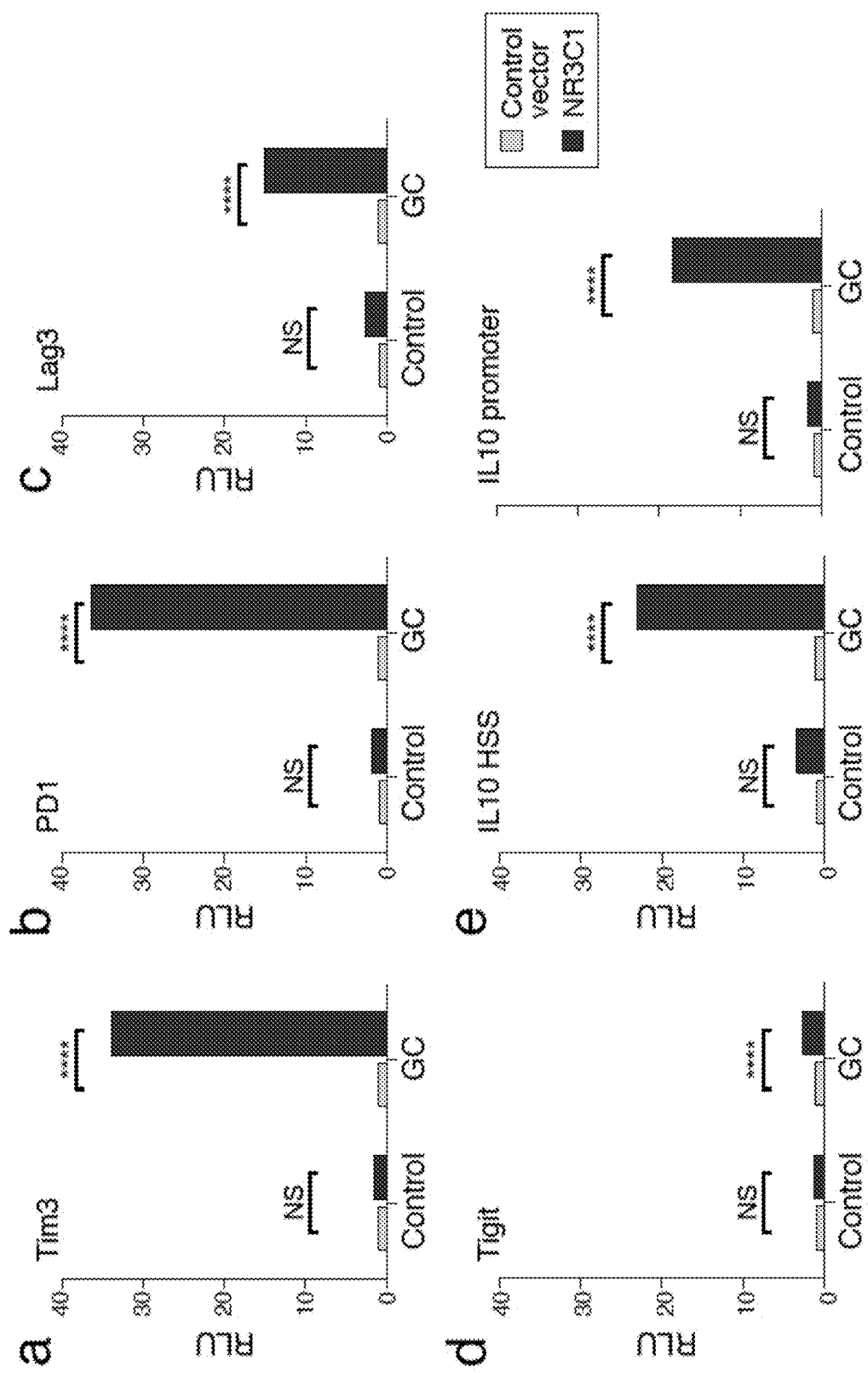
FIG. 4A-E

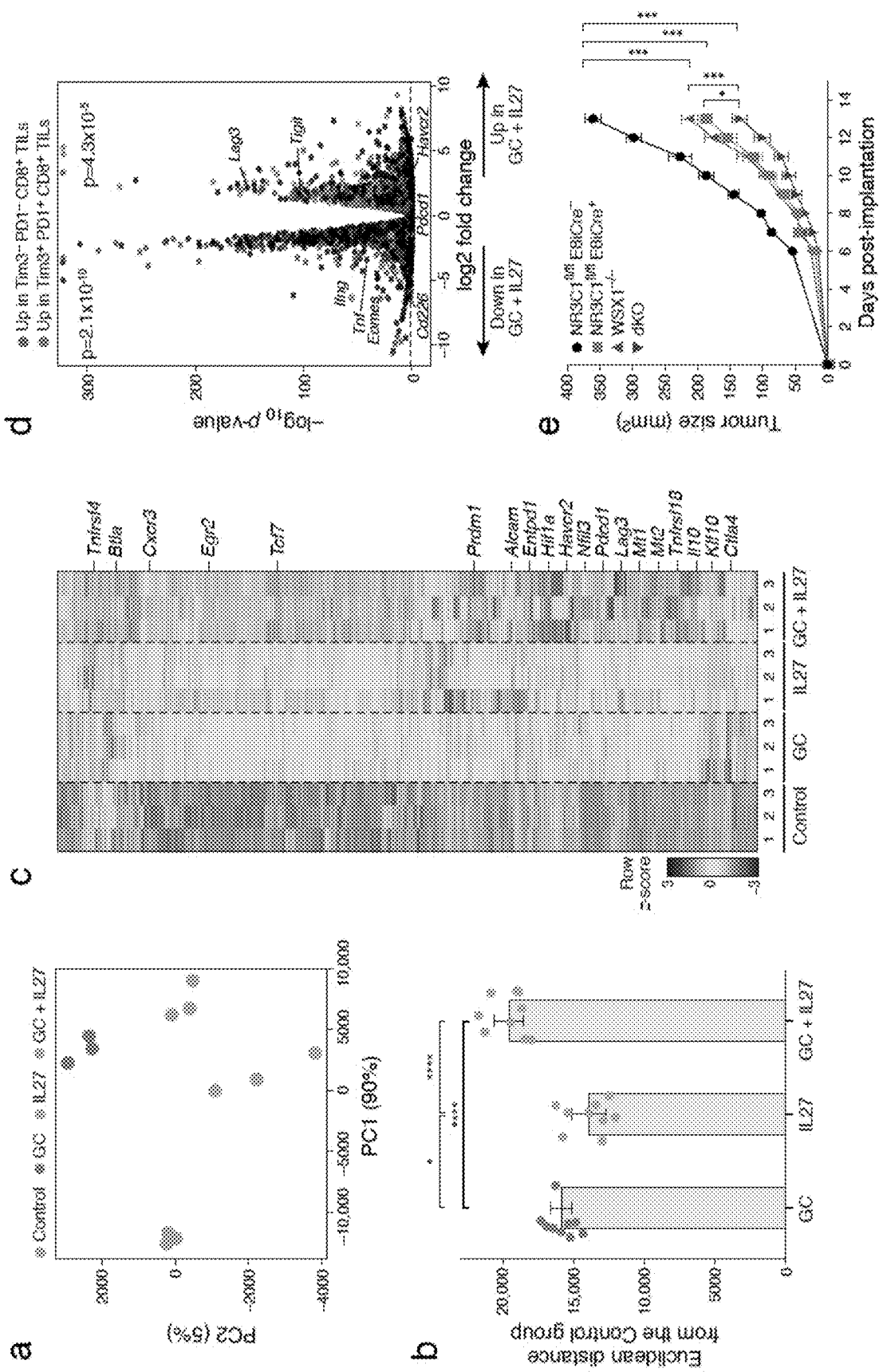
FIG. 5A-E

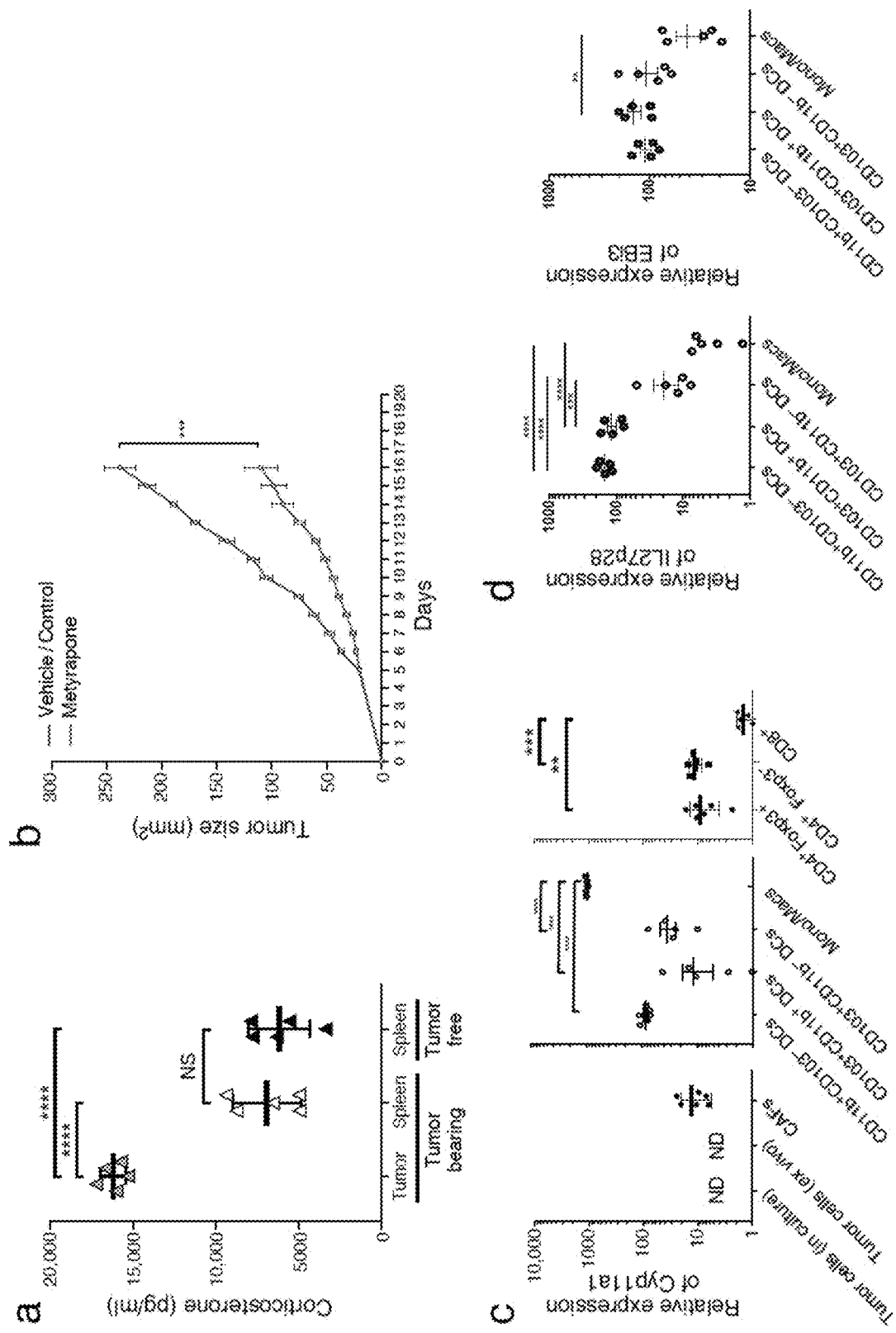
FIG. 6A-D

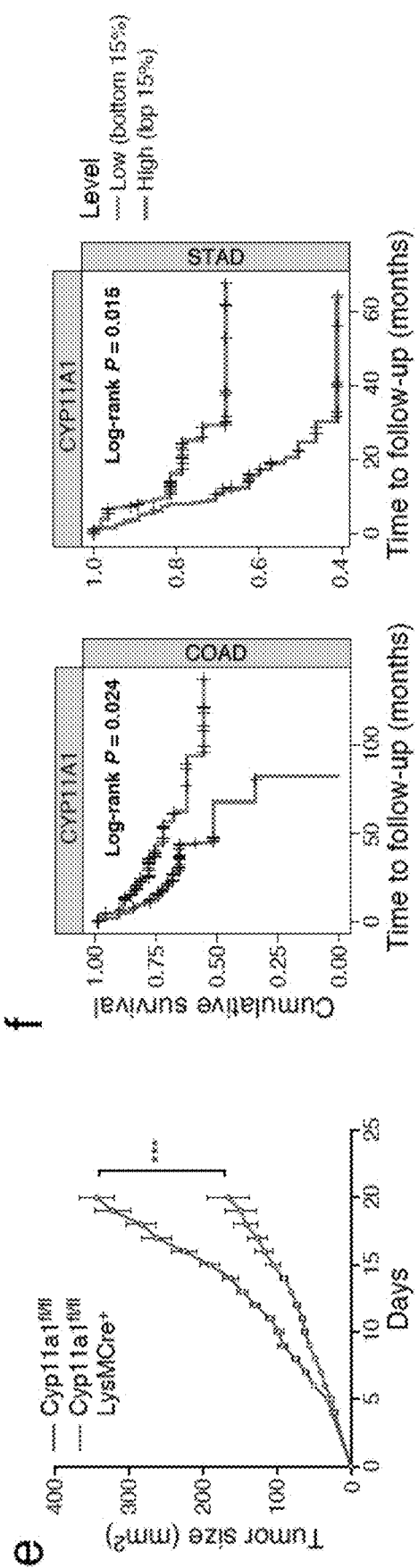
FIG. 6E-F

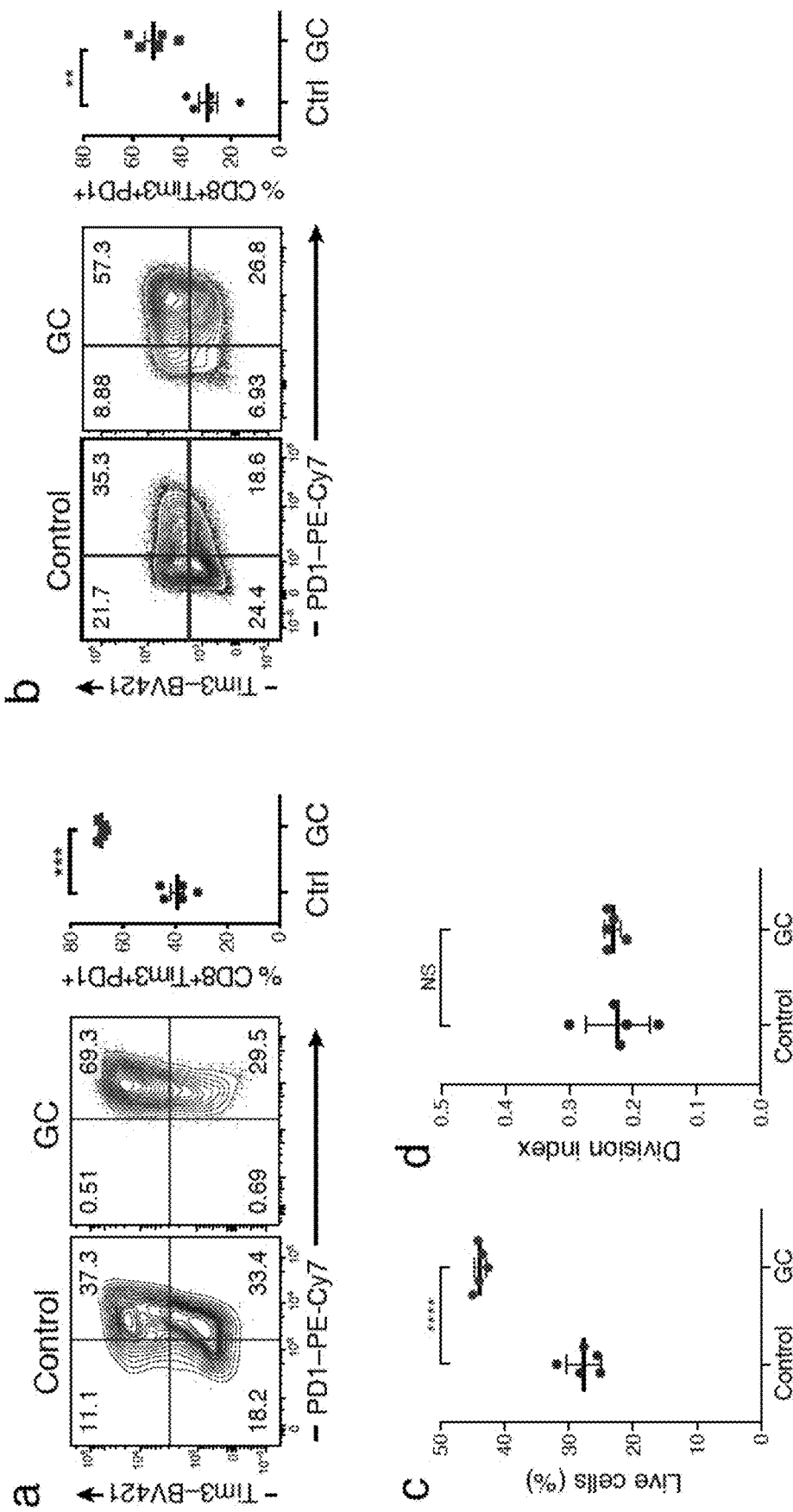
FIG. 8A-D

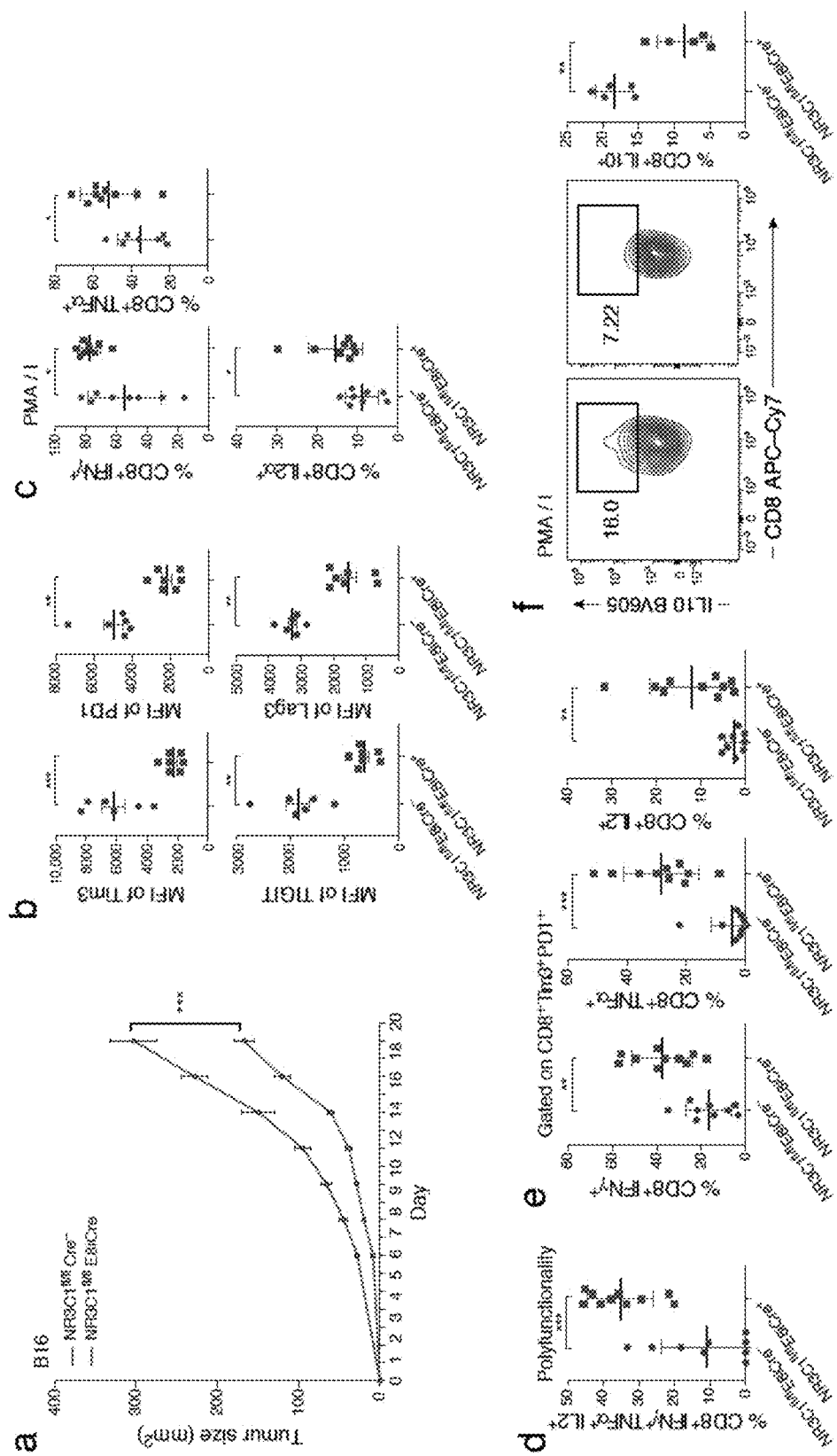
FIG. 11A-F

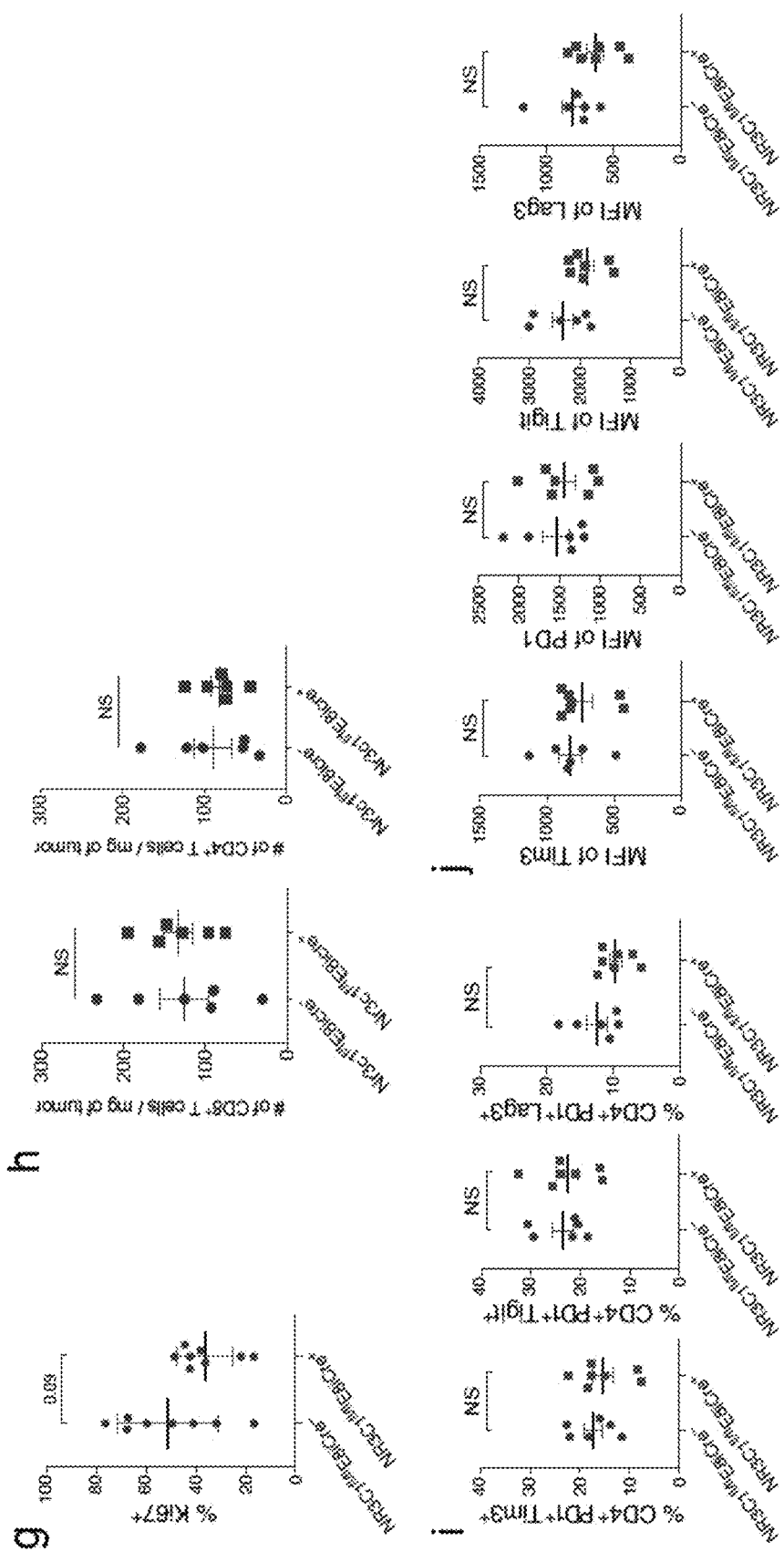
FIG. 11G-J

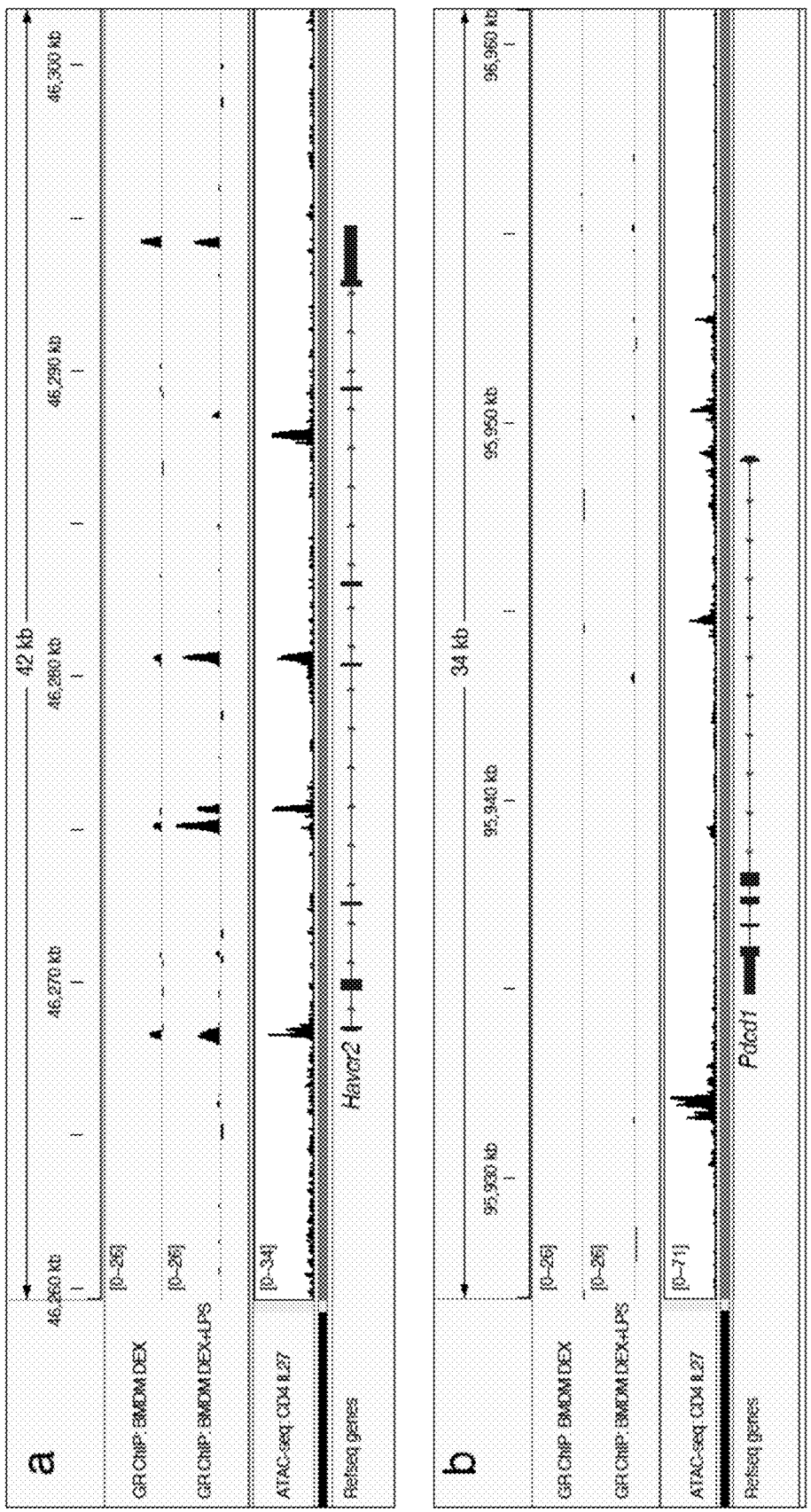
FIG. 12A-B

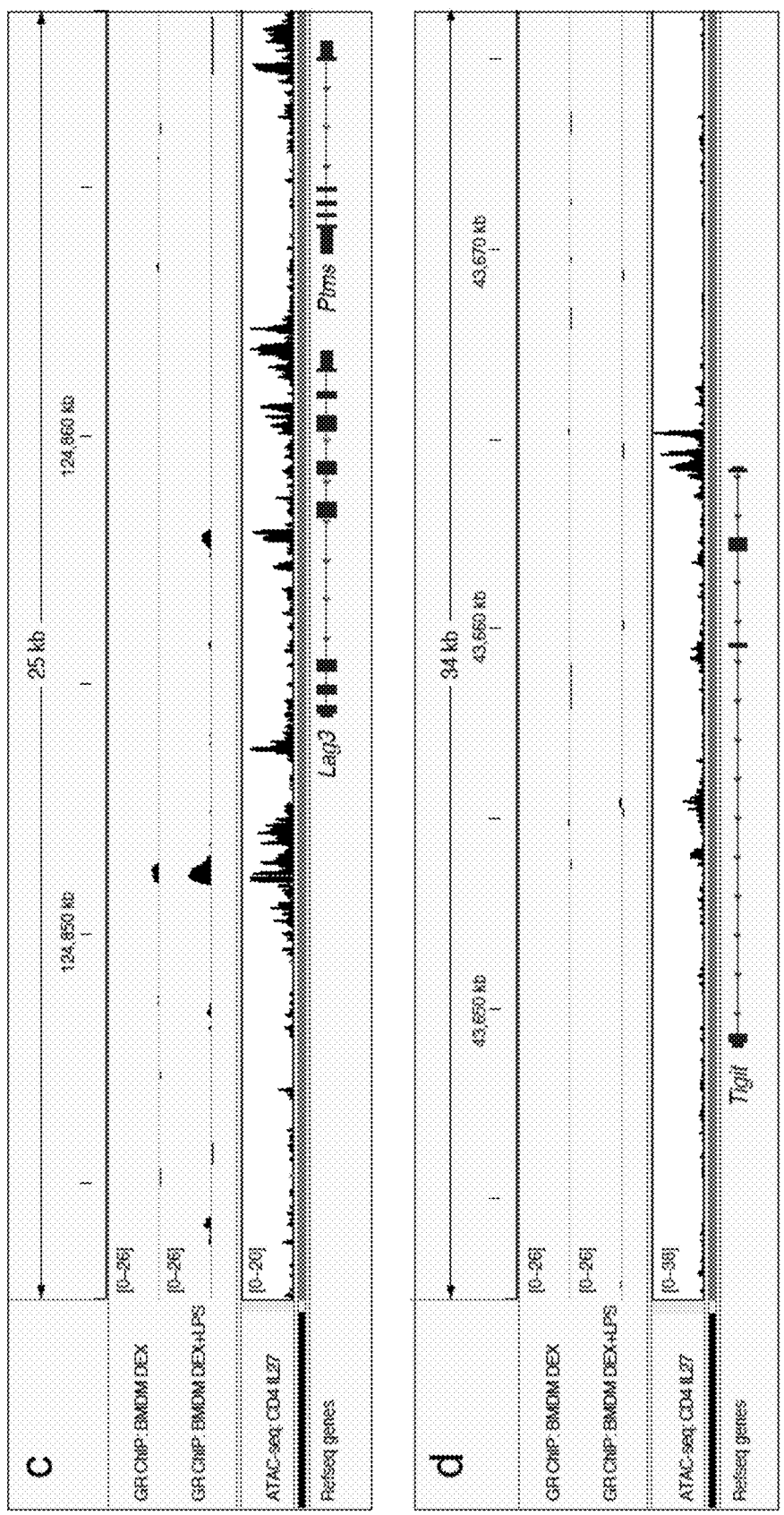
FIG. 12C-D

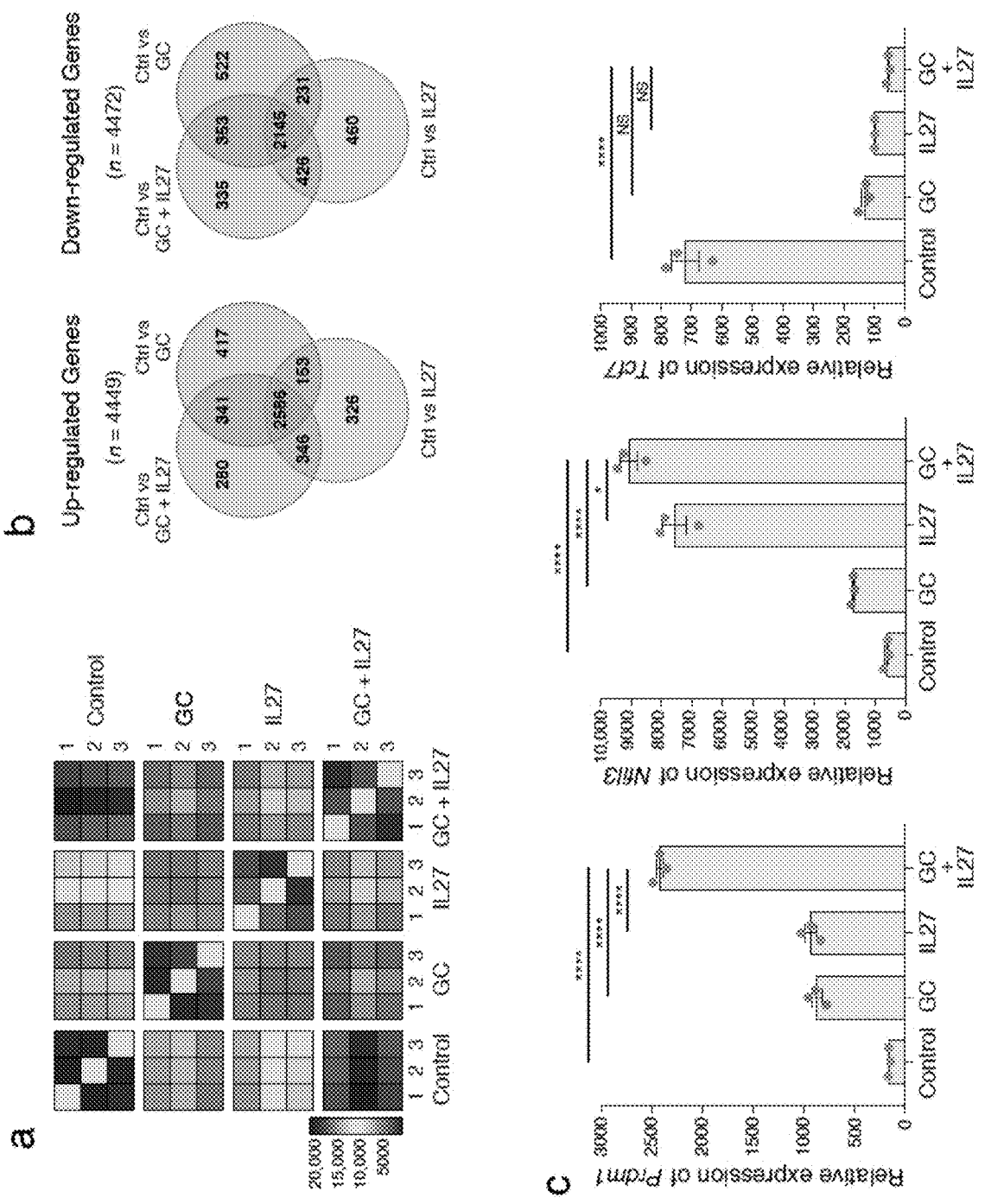
FIG. 13A-C

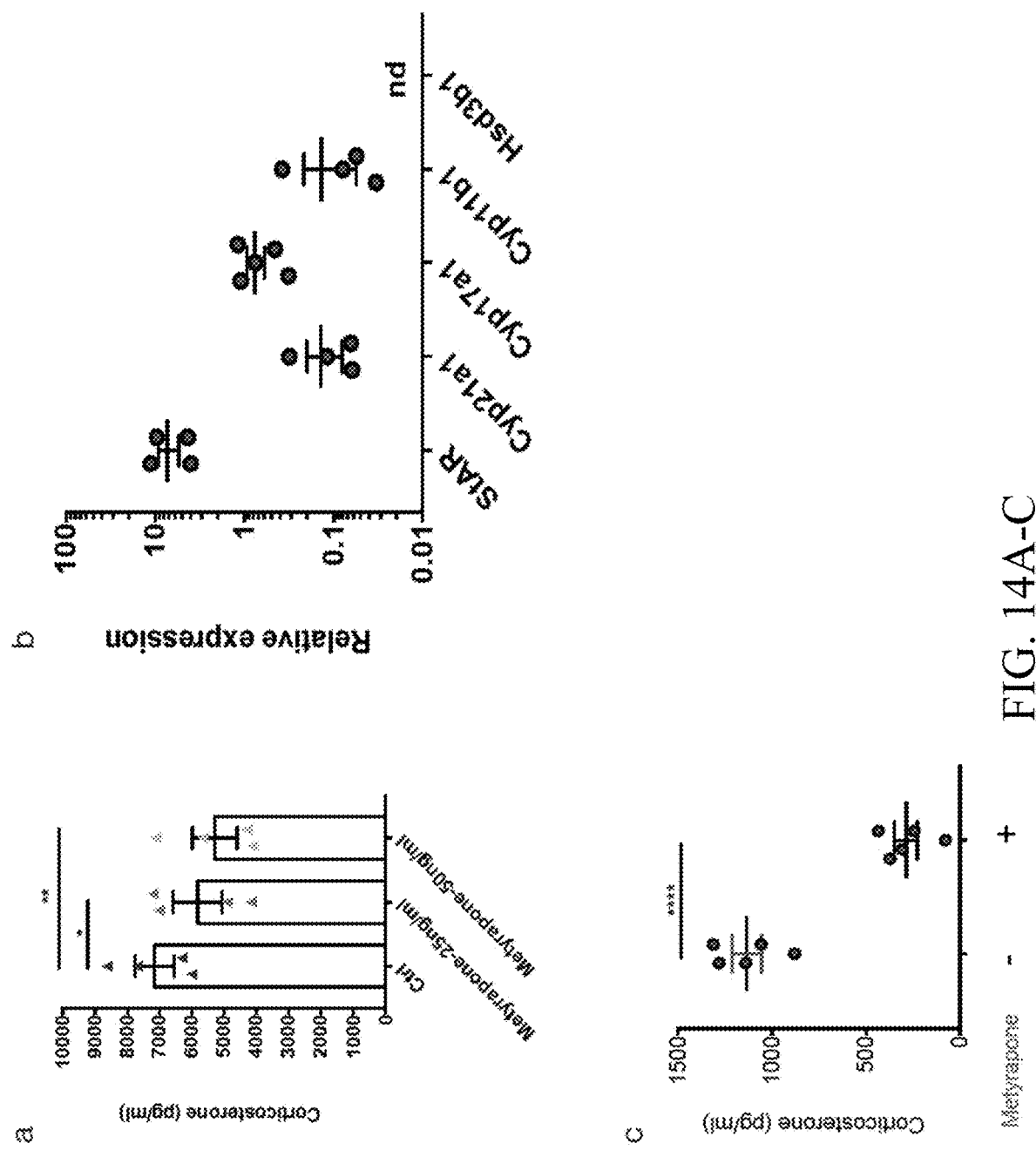
FIG. 14A-C

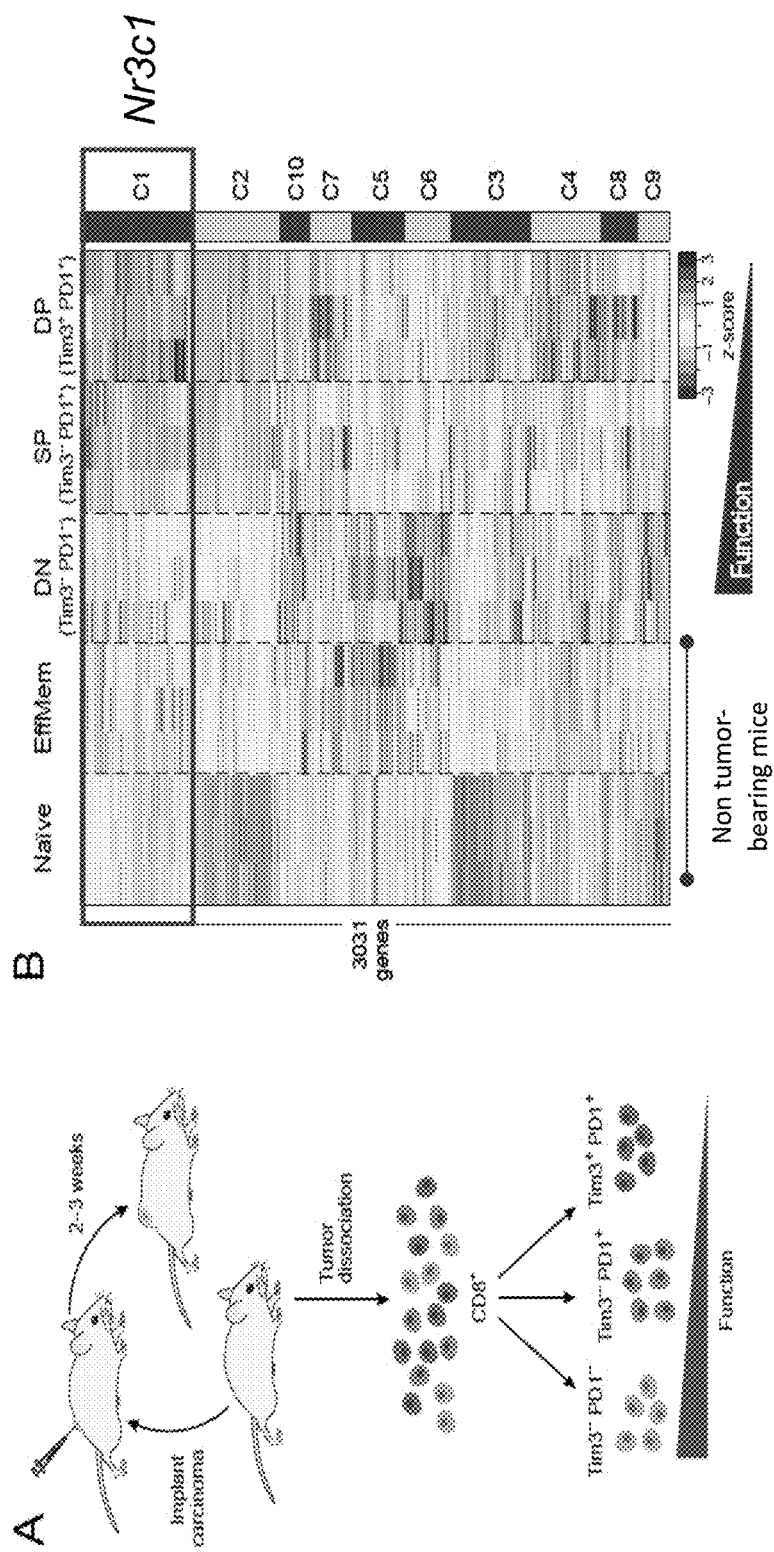
FIG. 15A-B

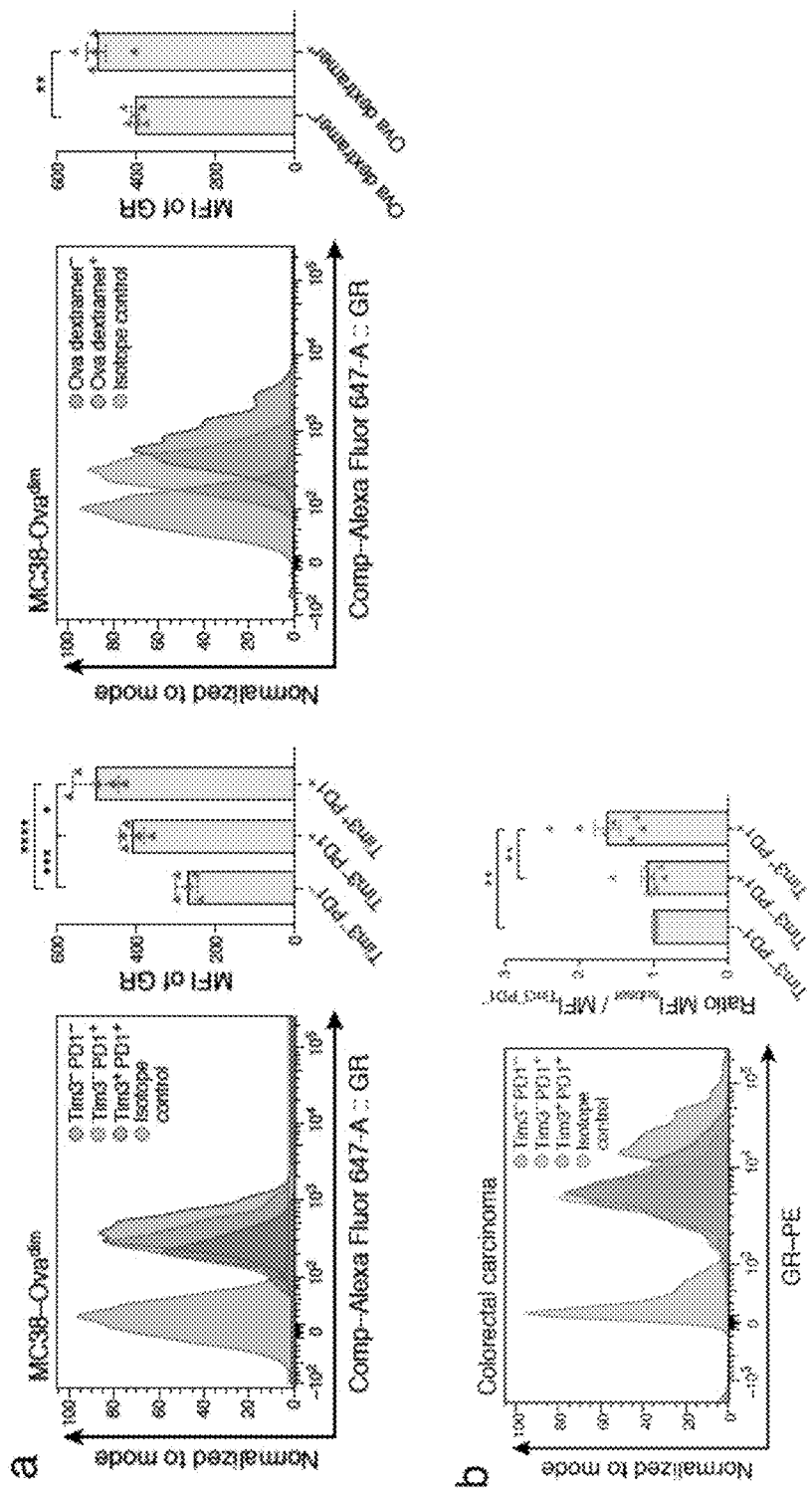
FIG. 16A-B

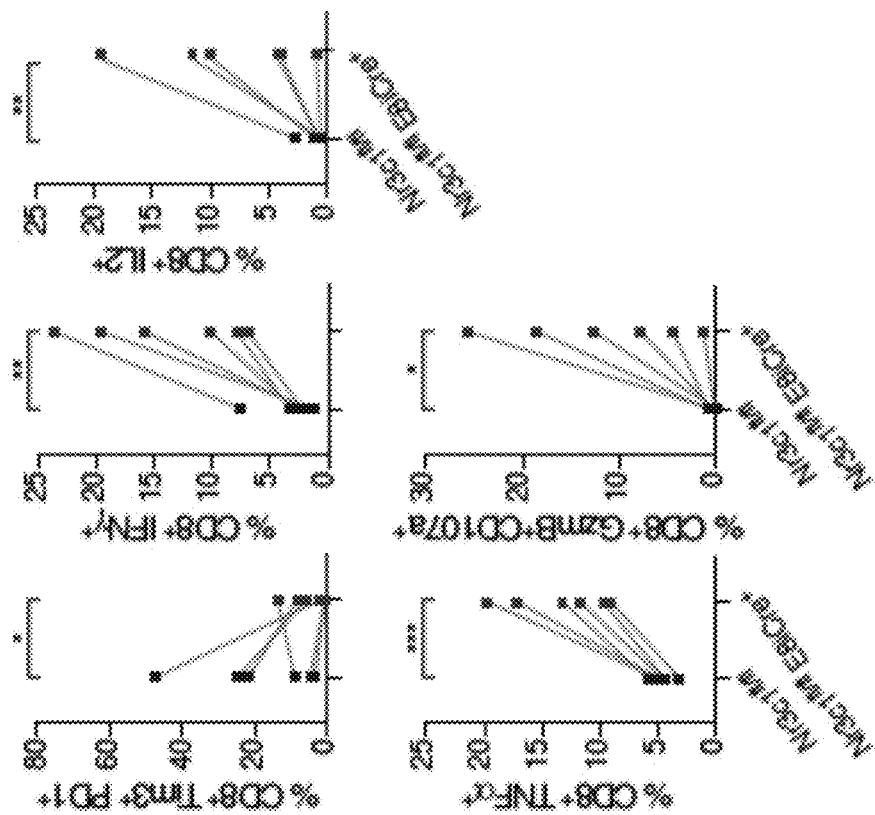
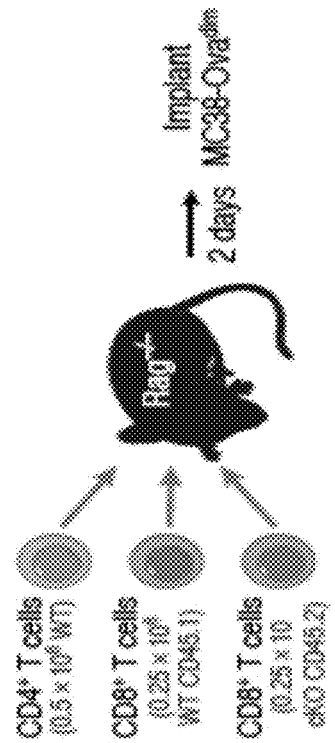
FIG. 24

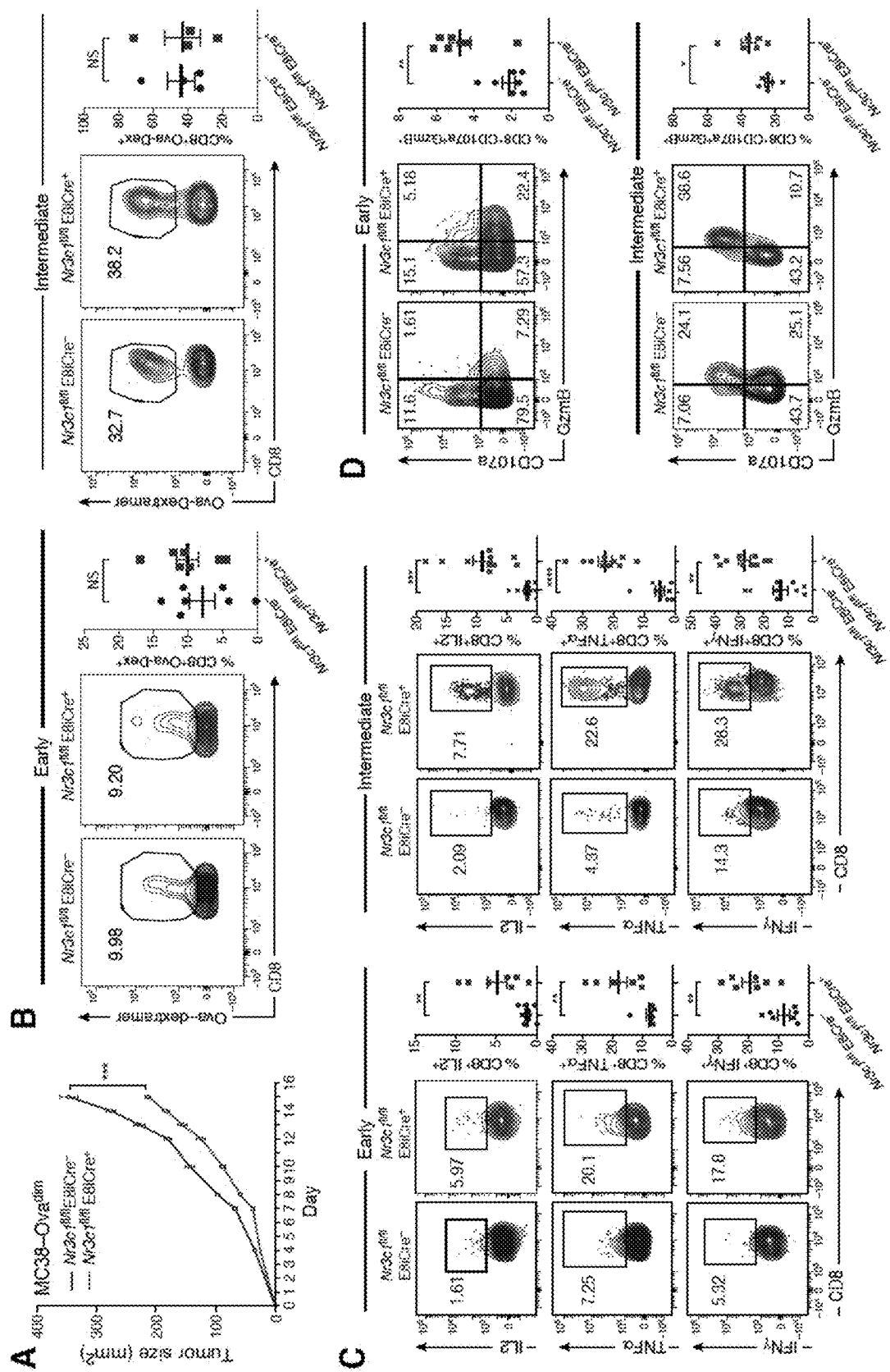
FIG. 35A-D

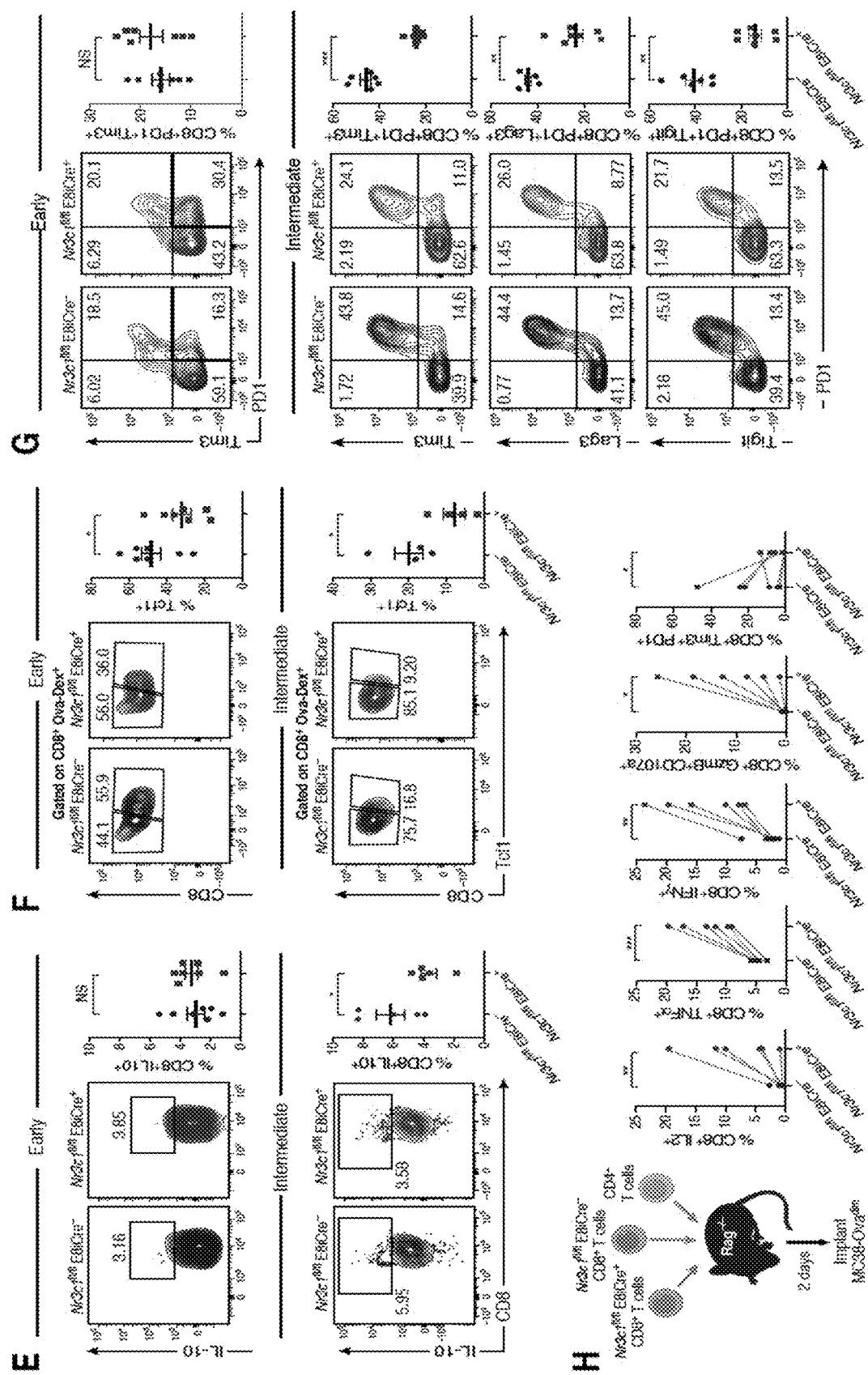
FIG. 35E-H

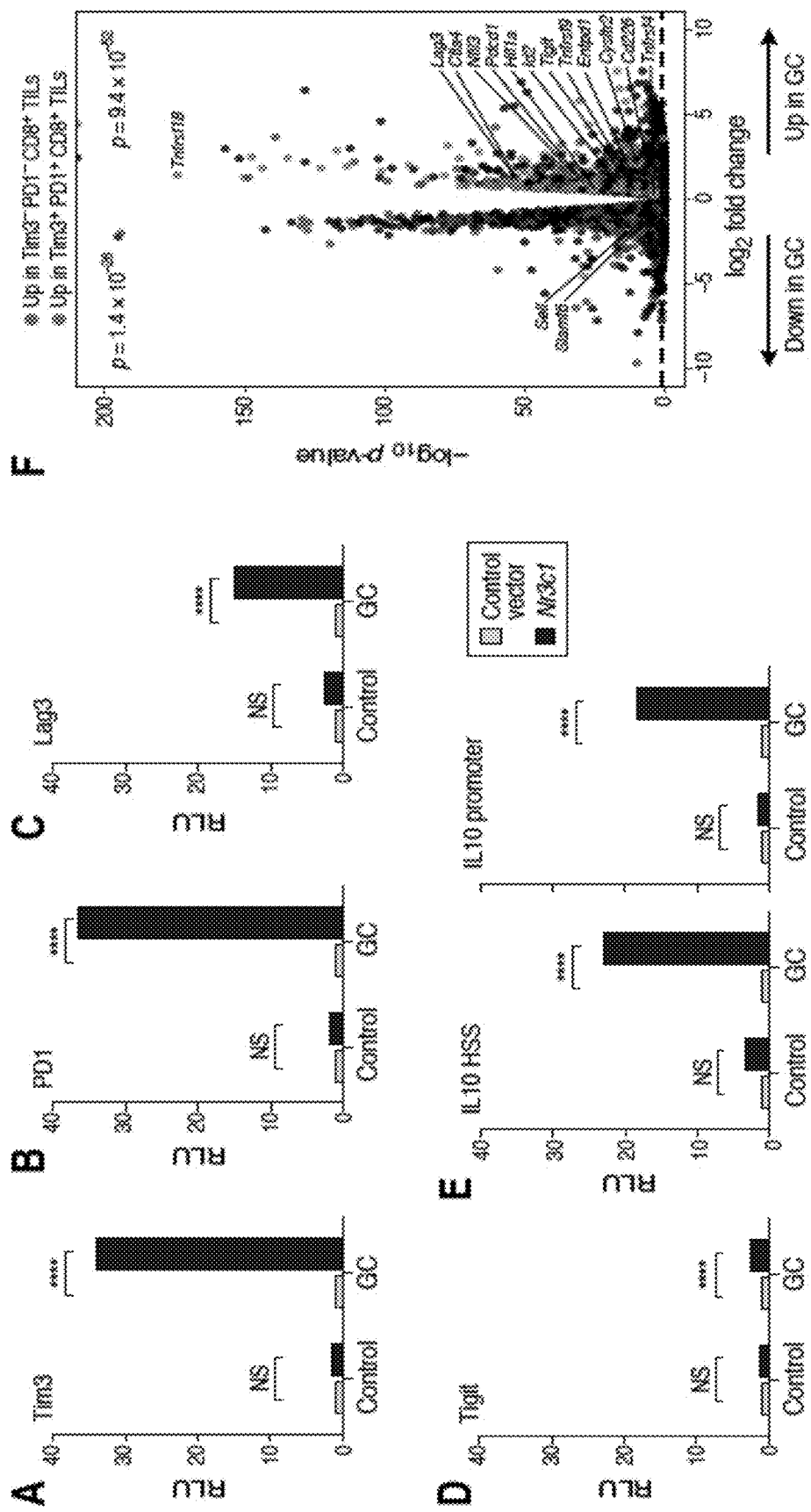
FIG. 36A-F

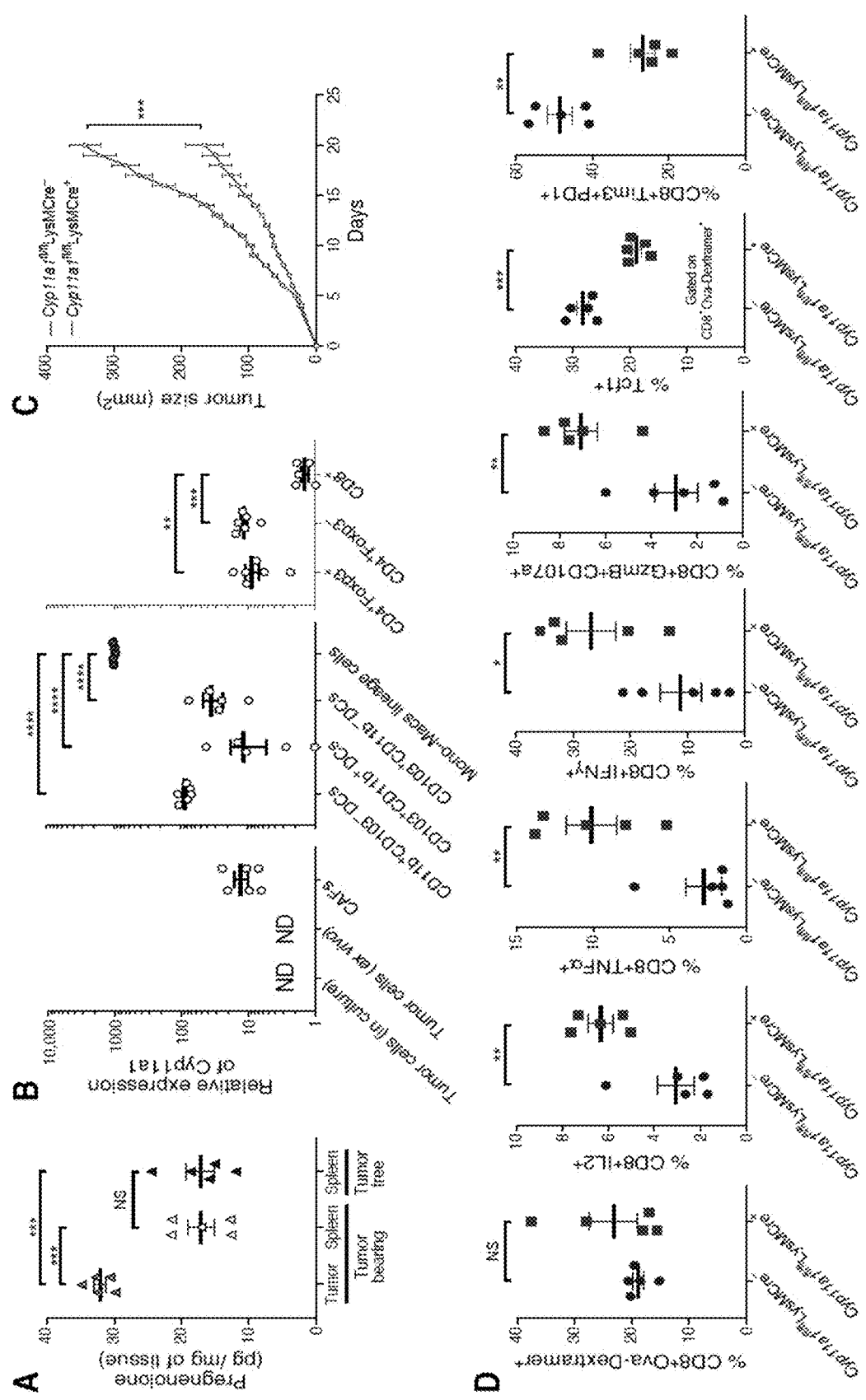
FIG. 37A-D

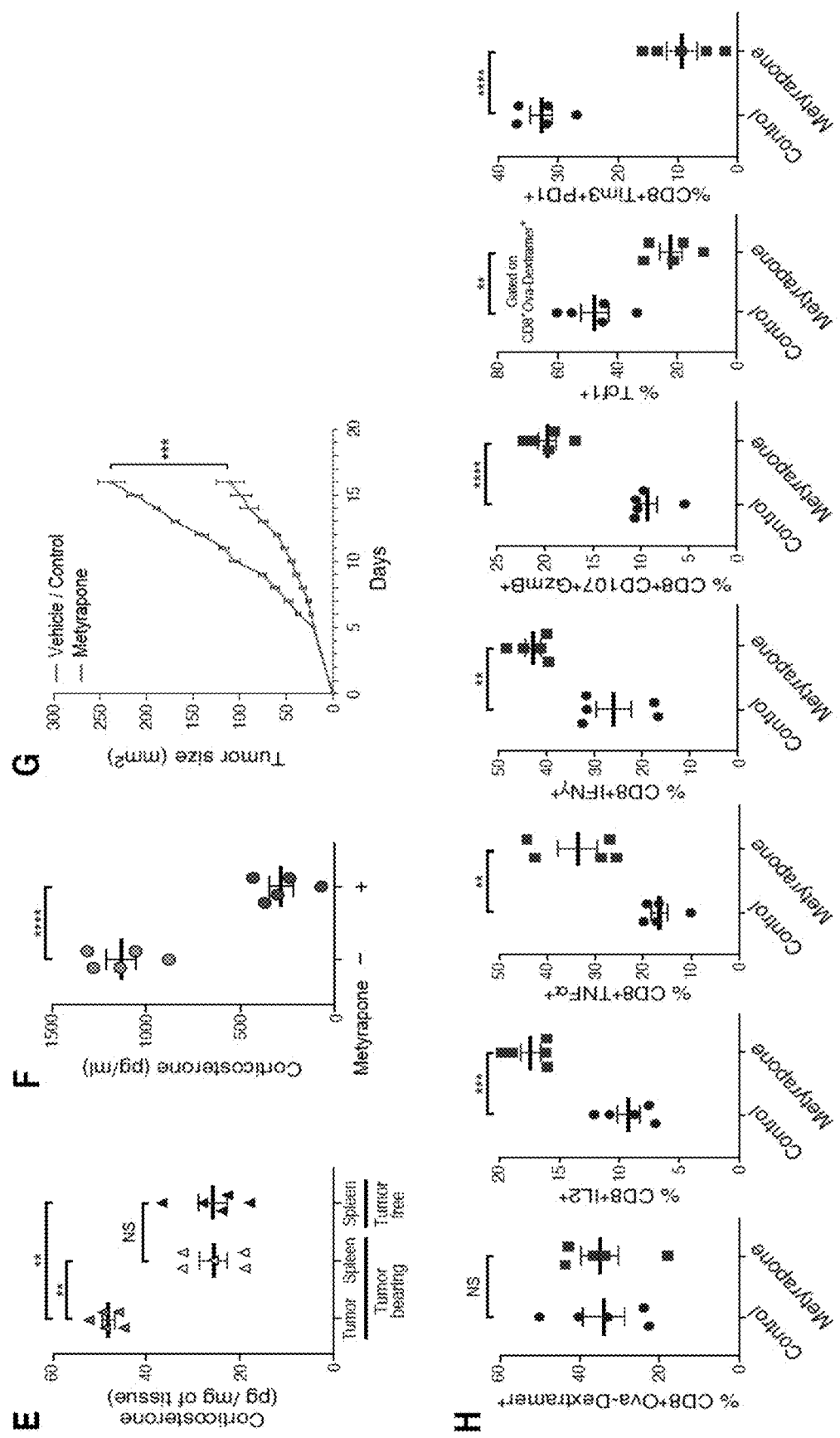
FIG. 37E-H

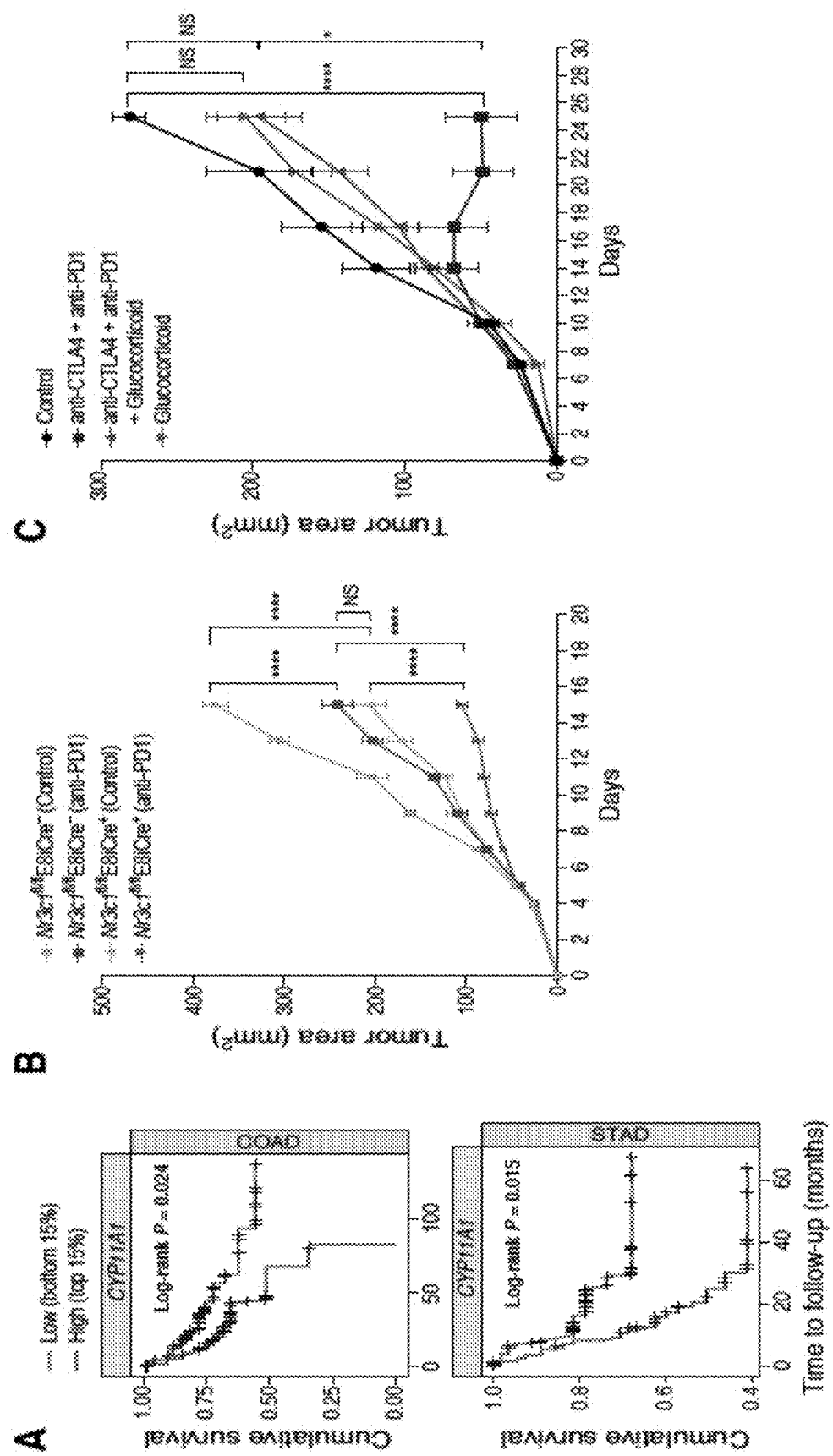
FIG. 38A-C

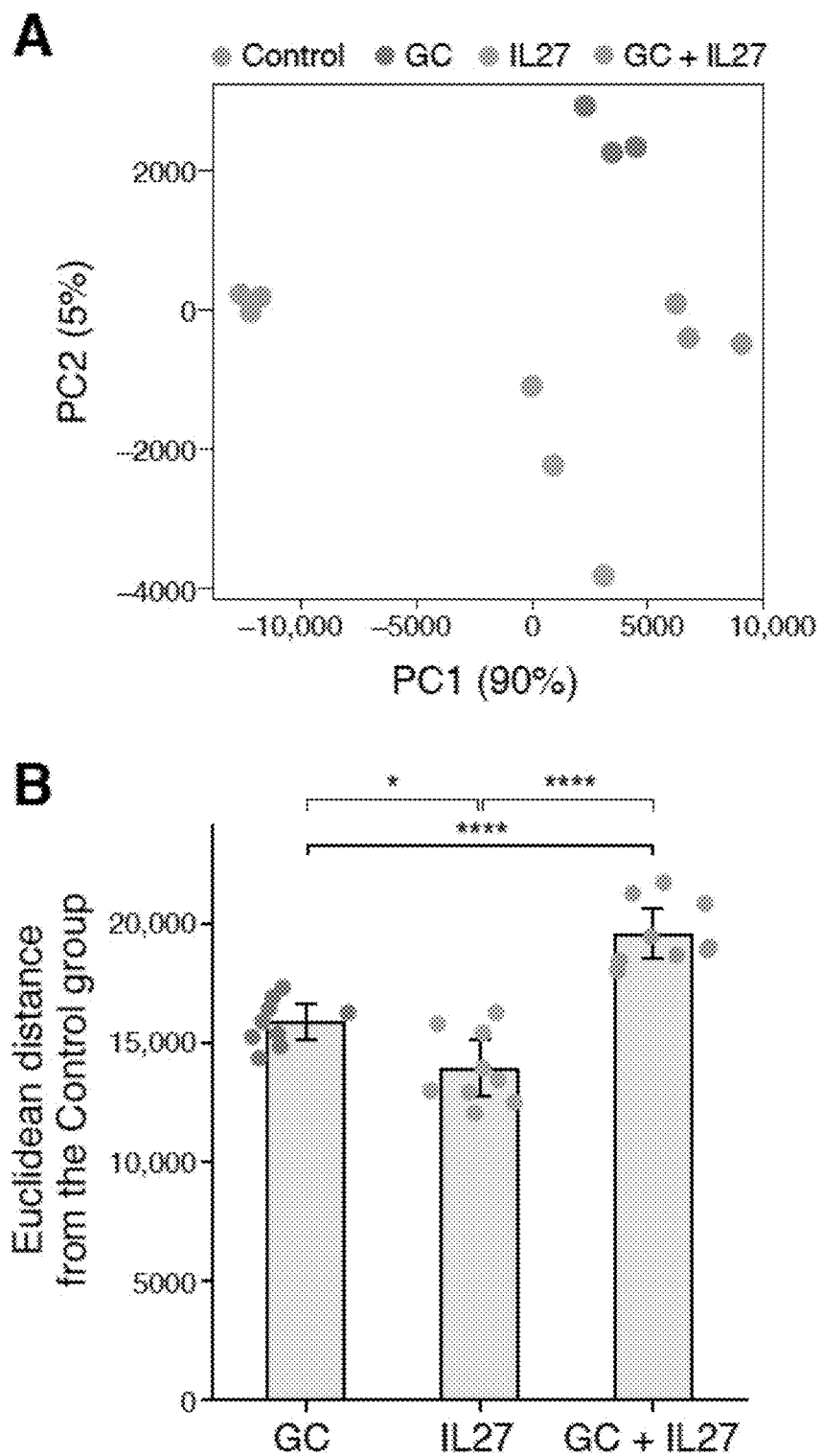
FIG. 39A-B

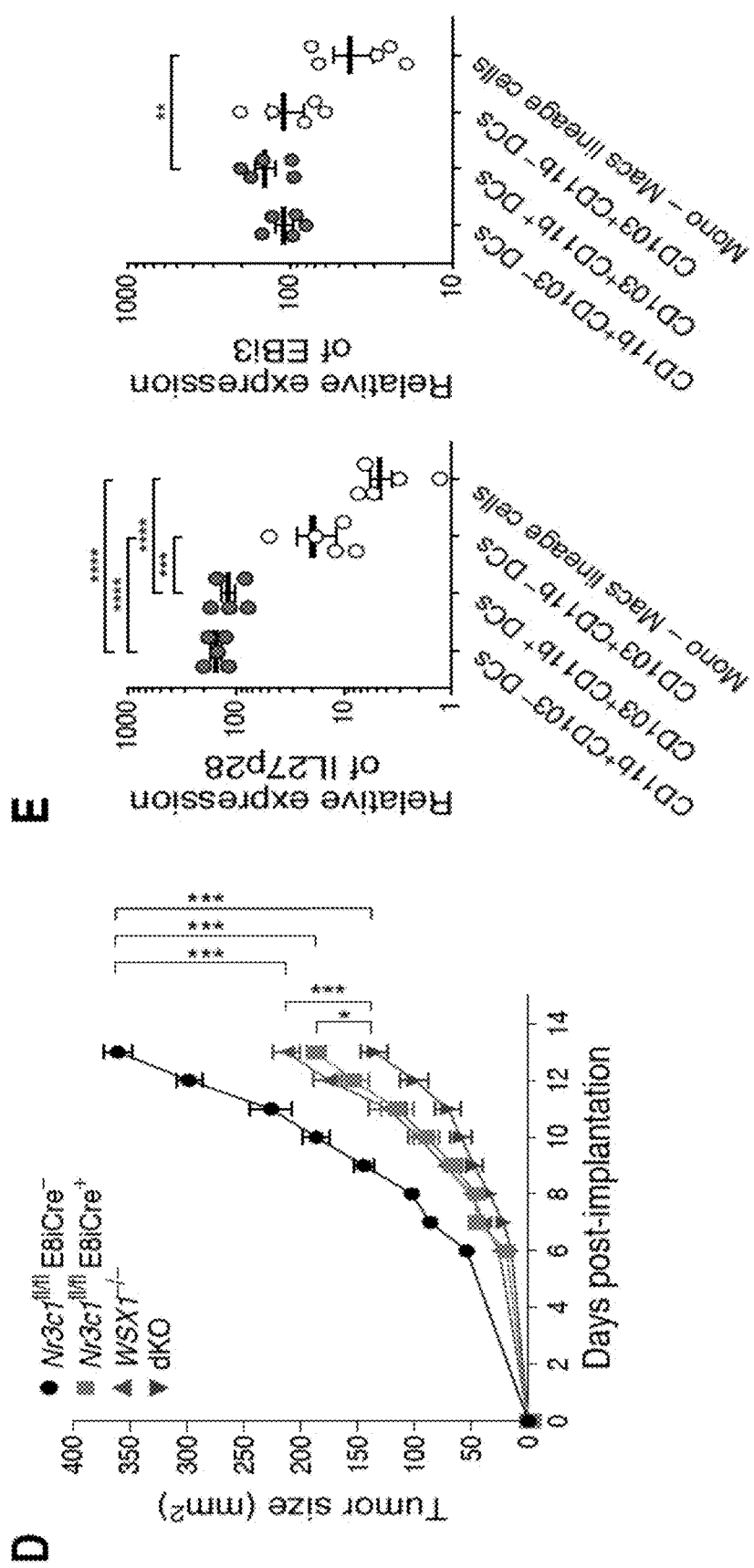
FIG. 39D-E

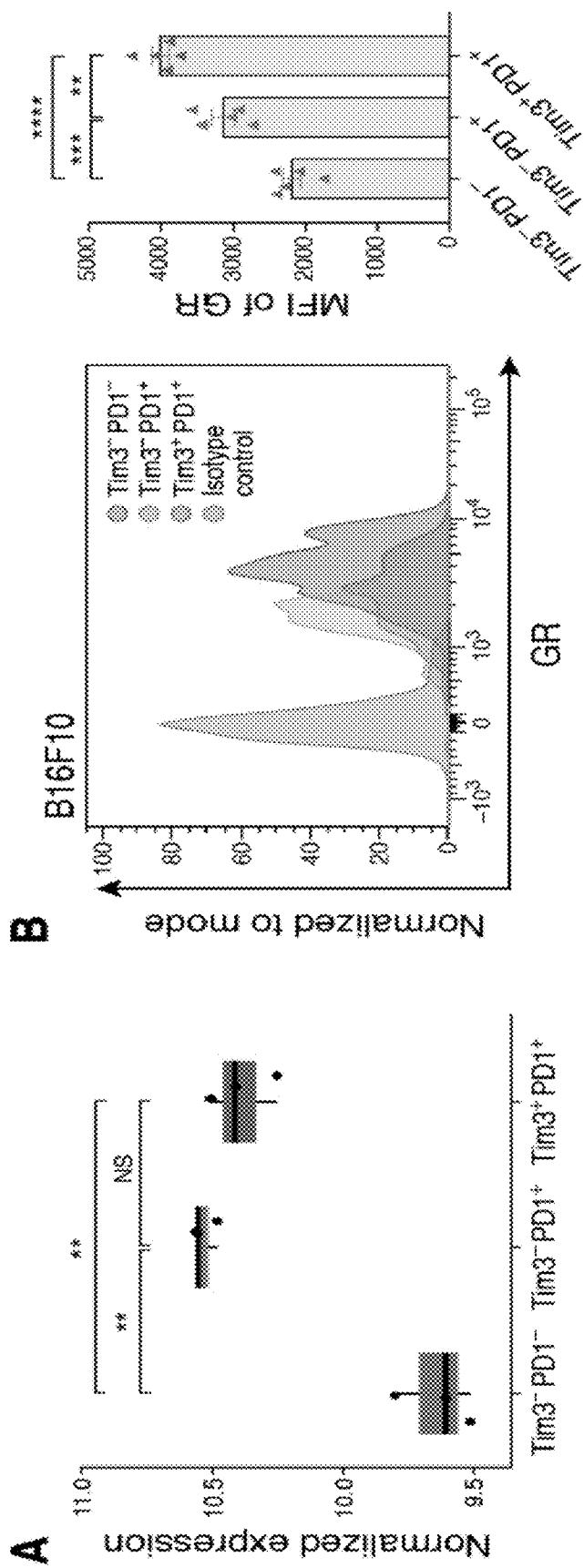
FIG. 40A-B

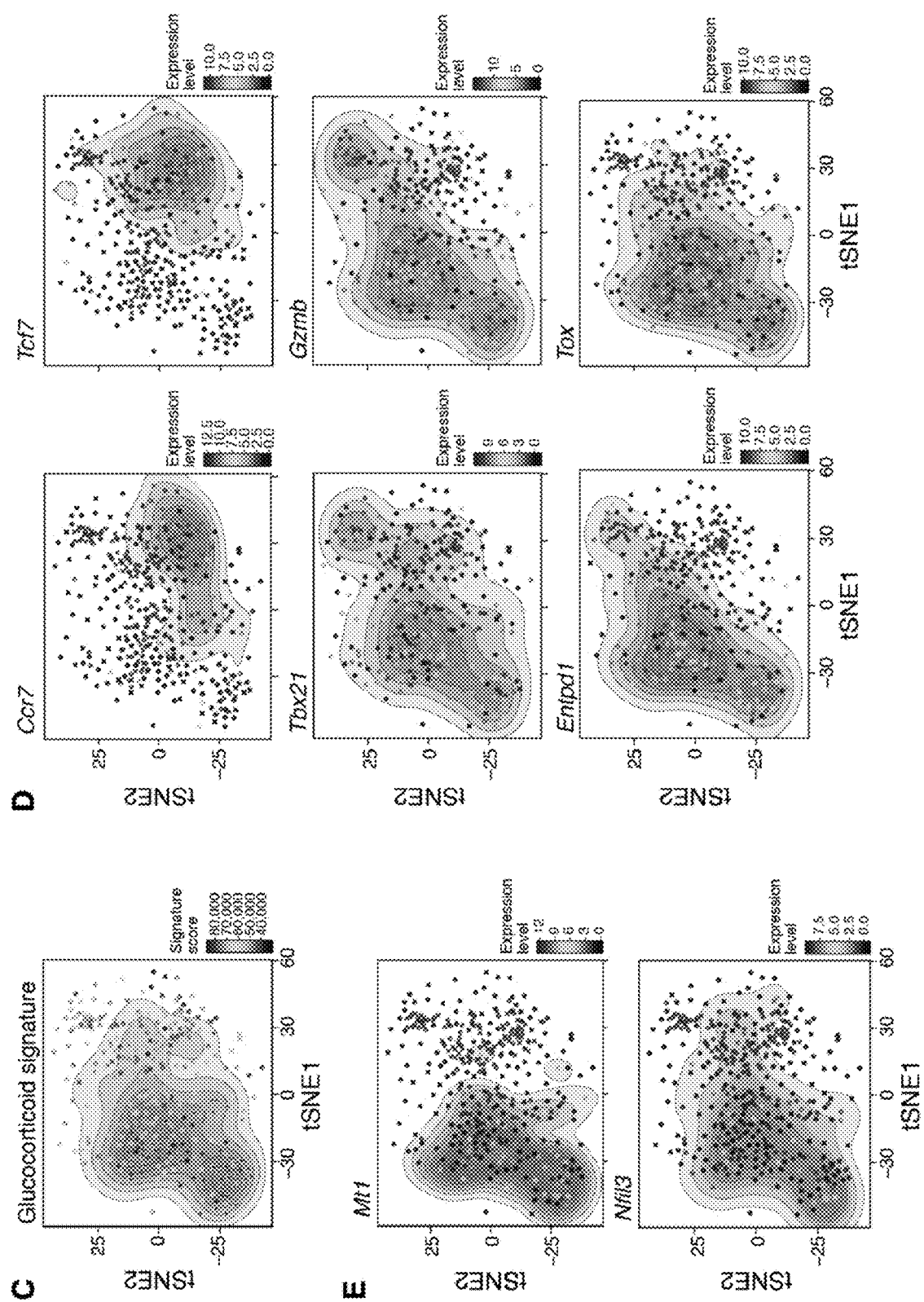
FIG. 40C-E

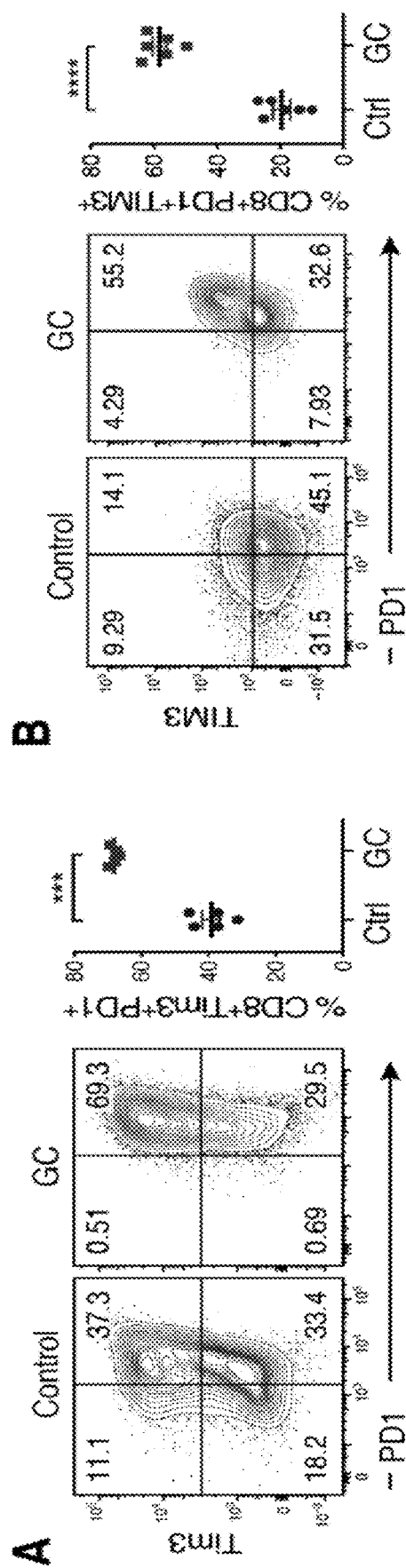
FIG. 41A-B

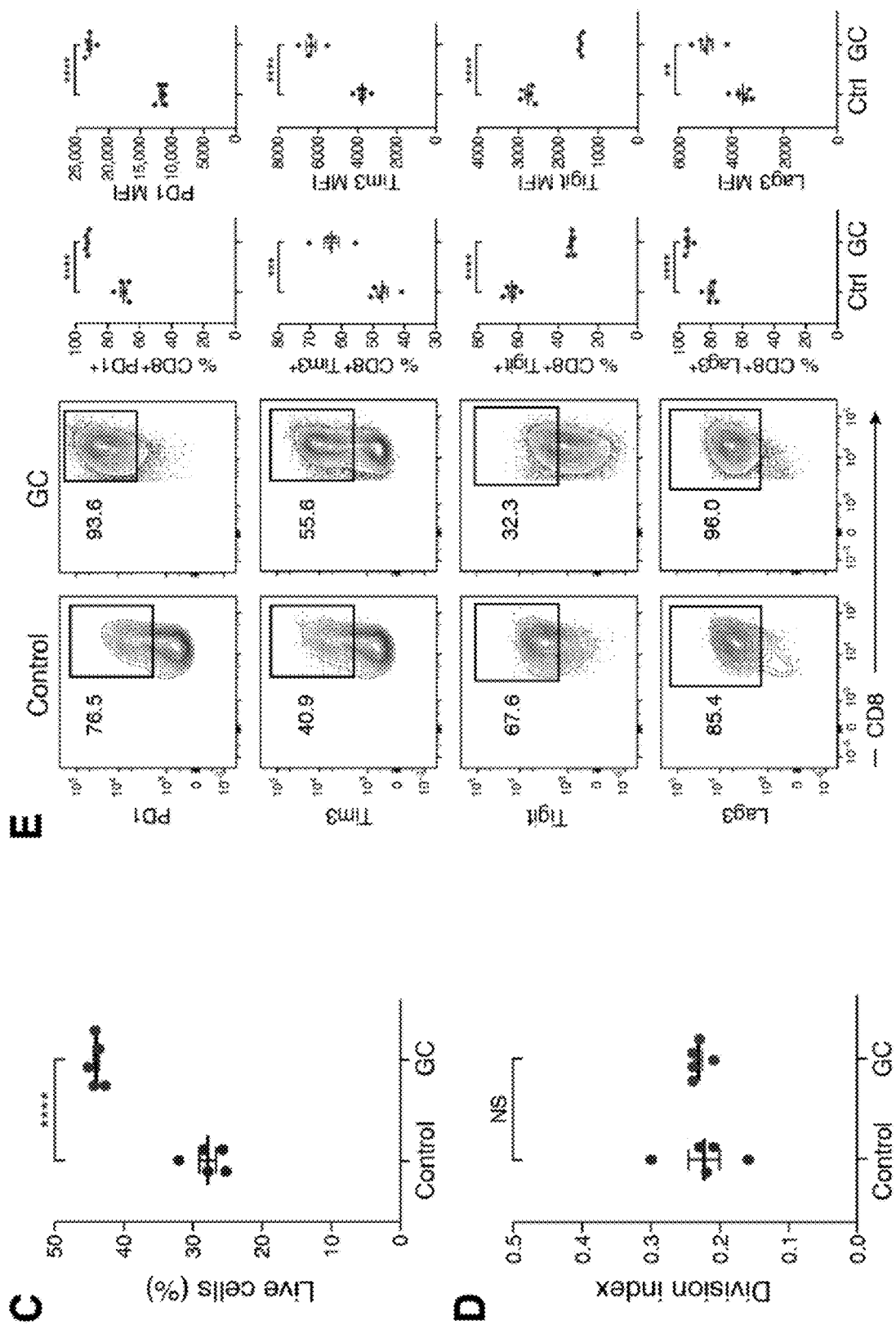
FIG. 41C-E

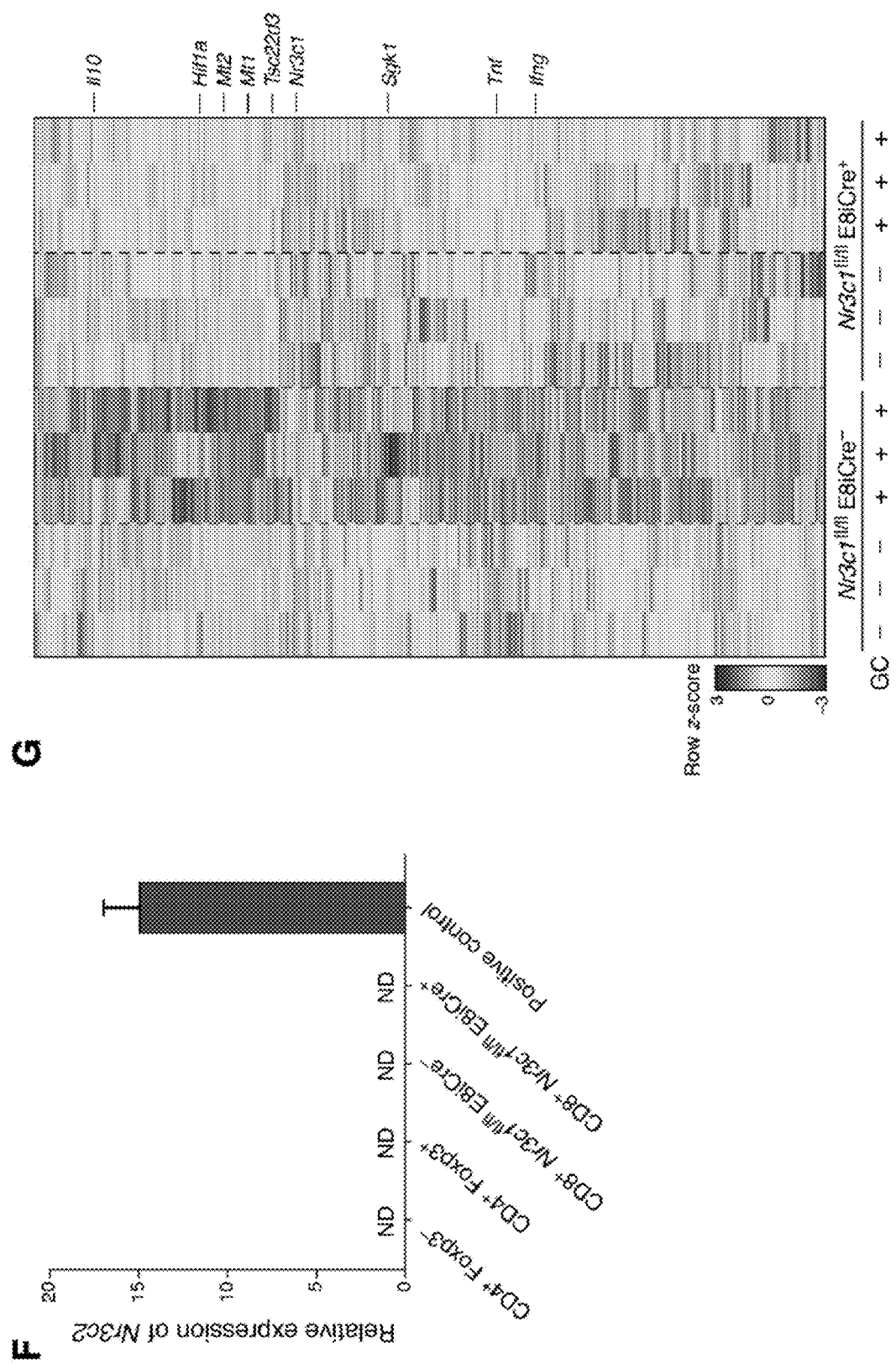
FIG. 41F-G

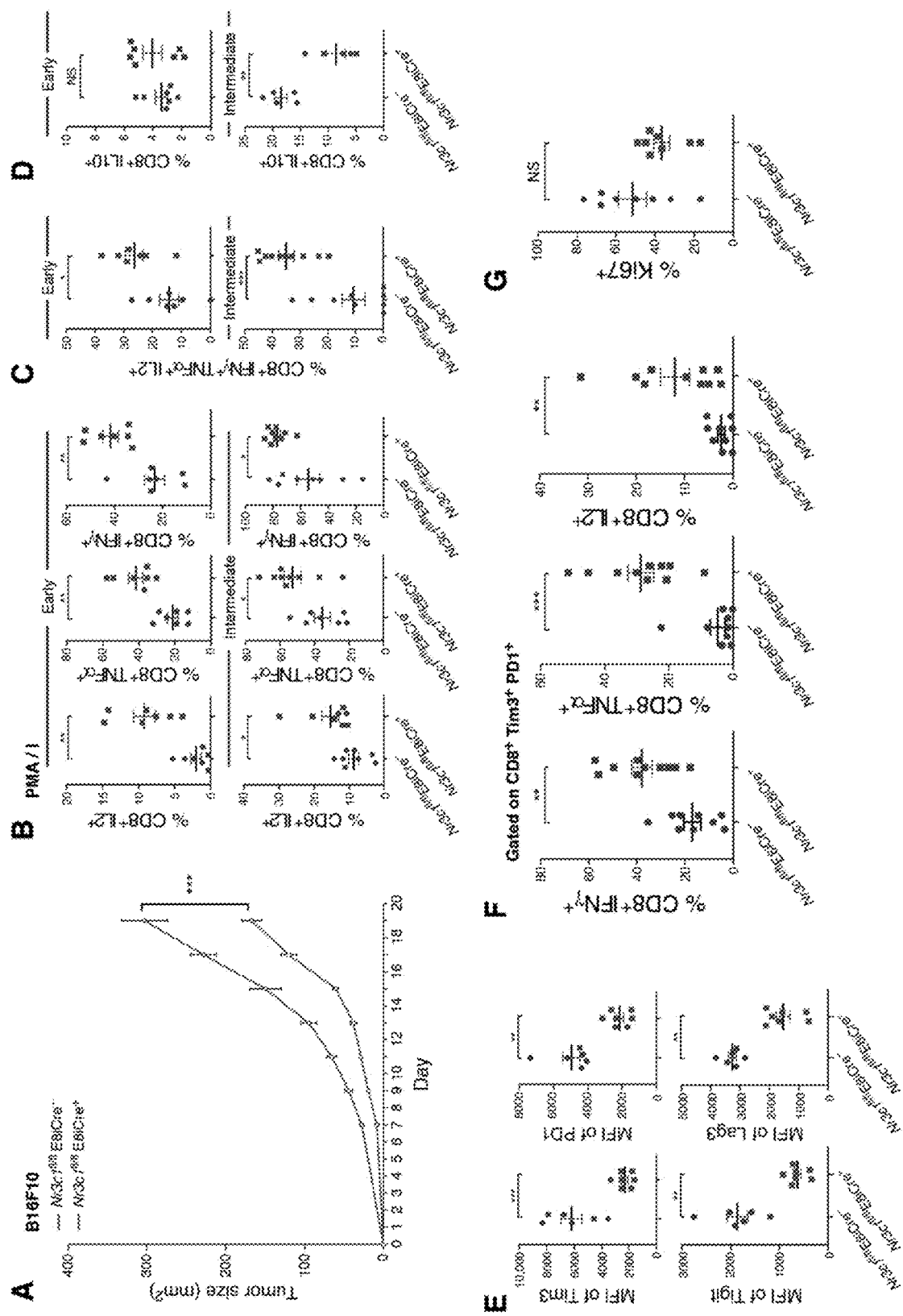
FIG. 43A-G

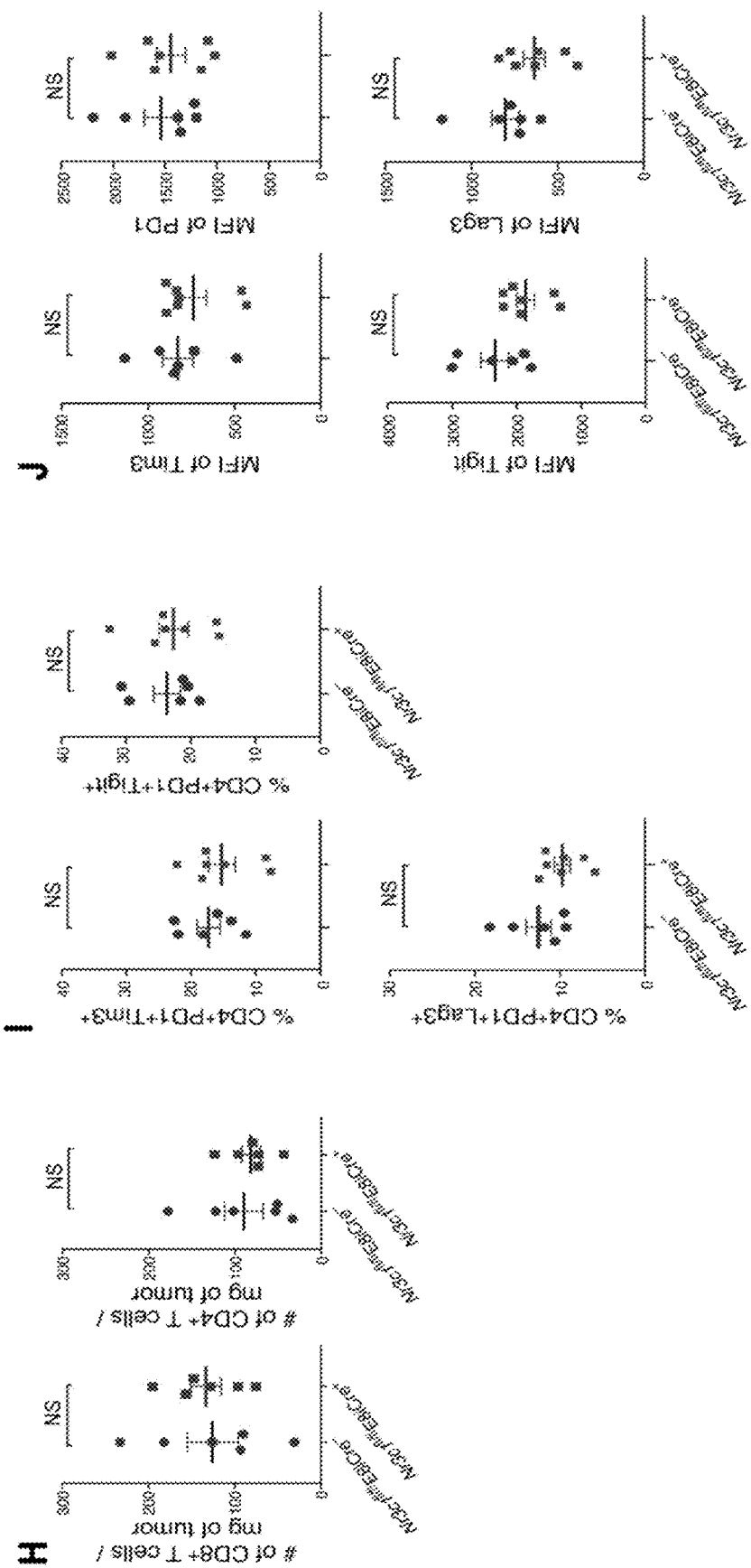
FIG. 43H-J

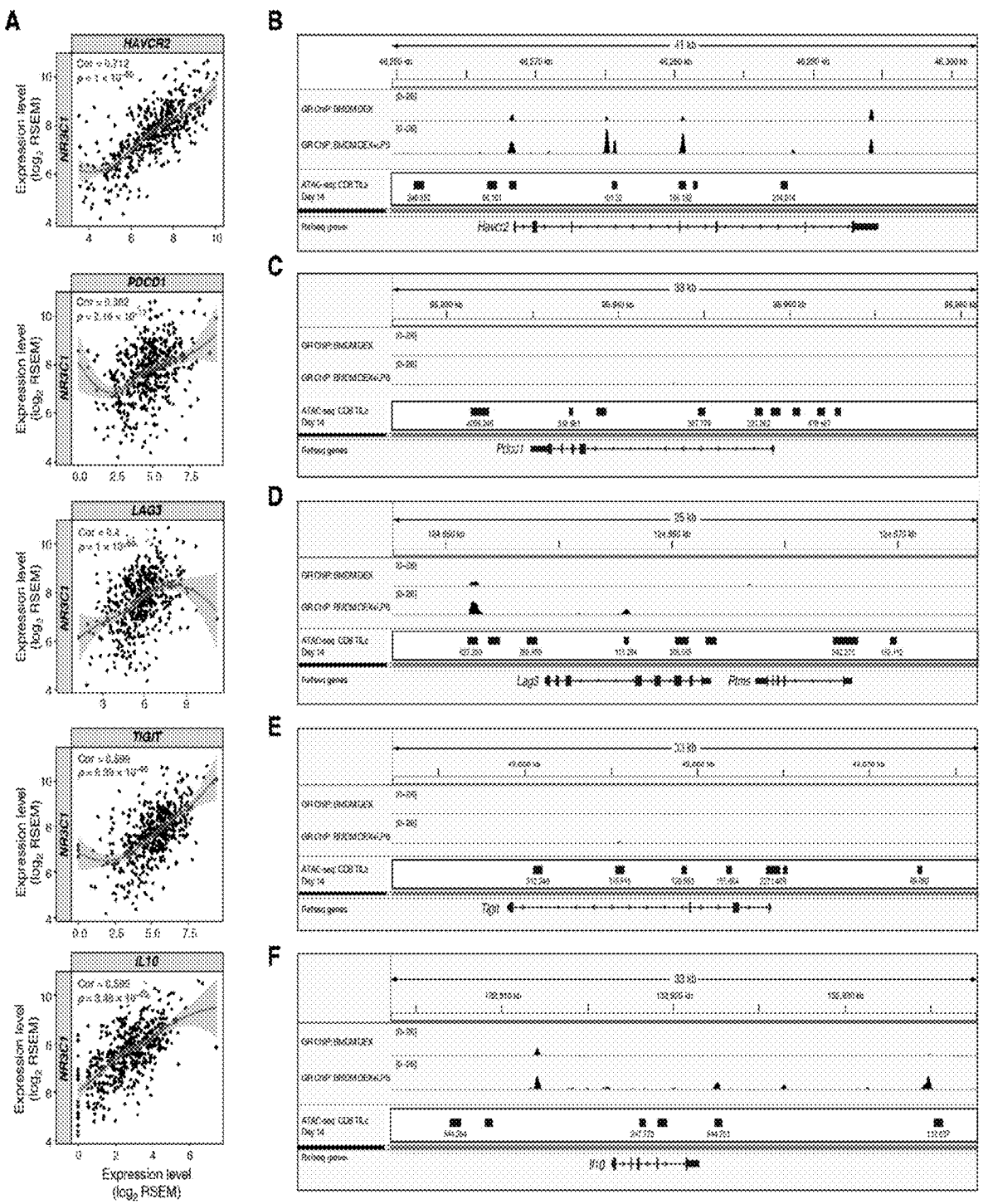
FIG. 44A-F

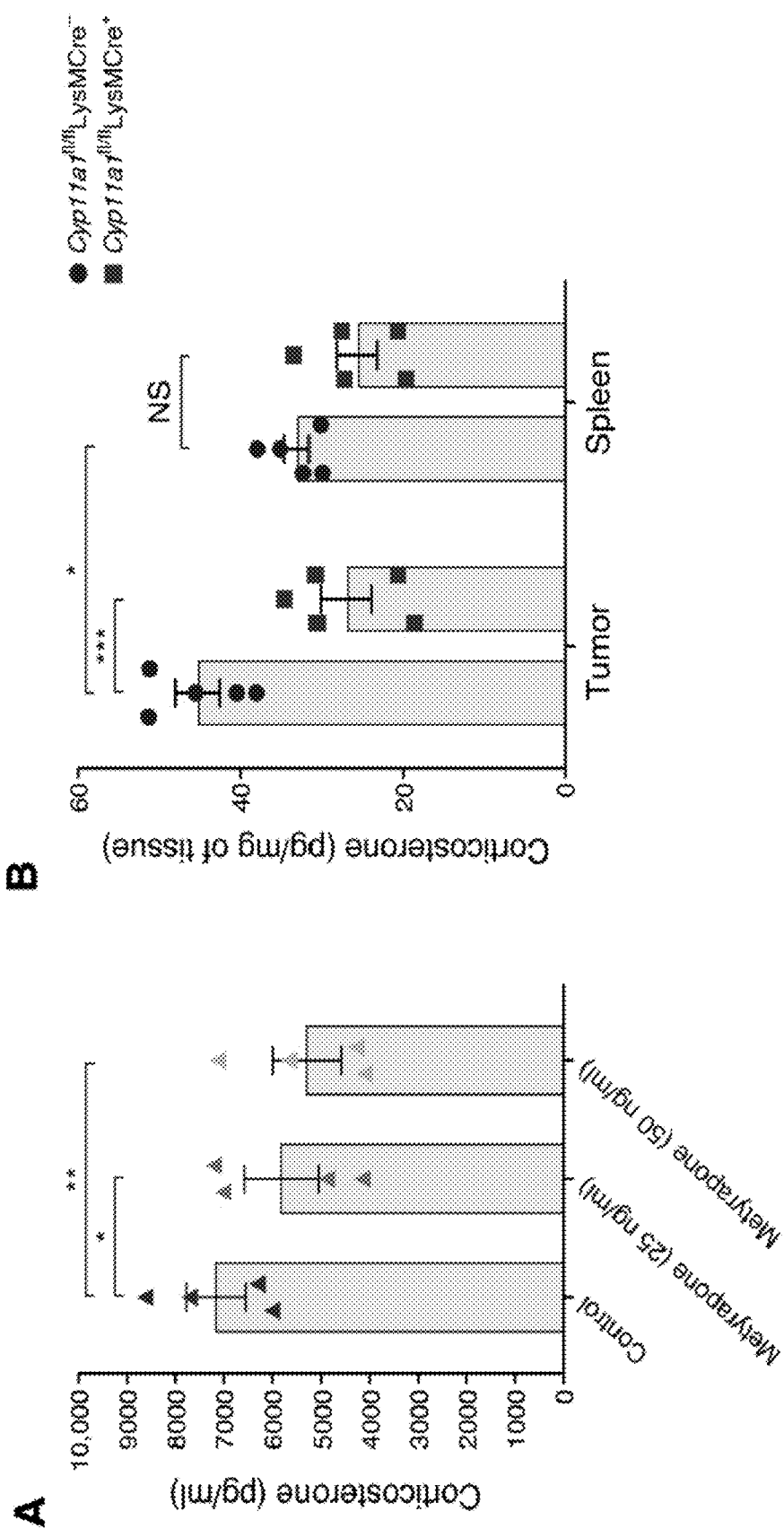
FIG. 45A-B

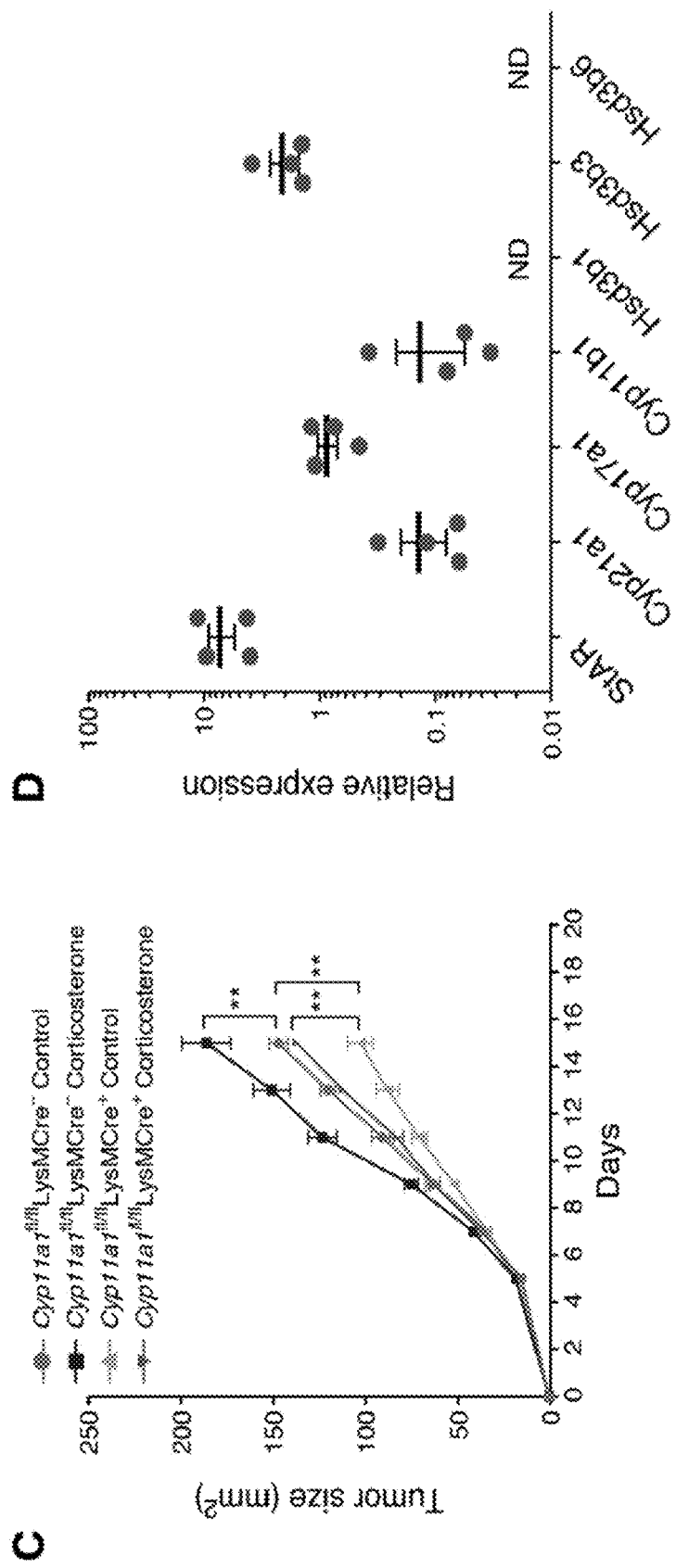
FIG. 45C-D

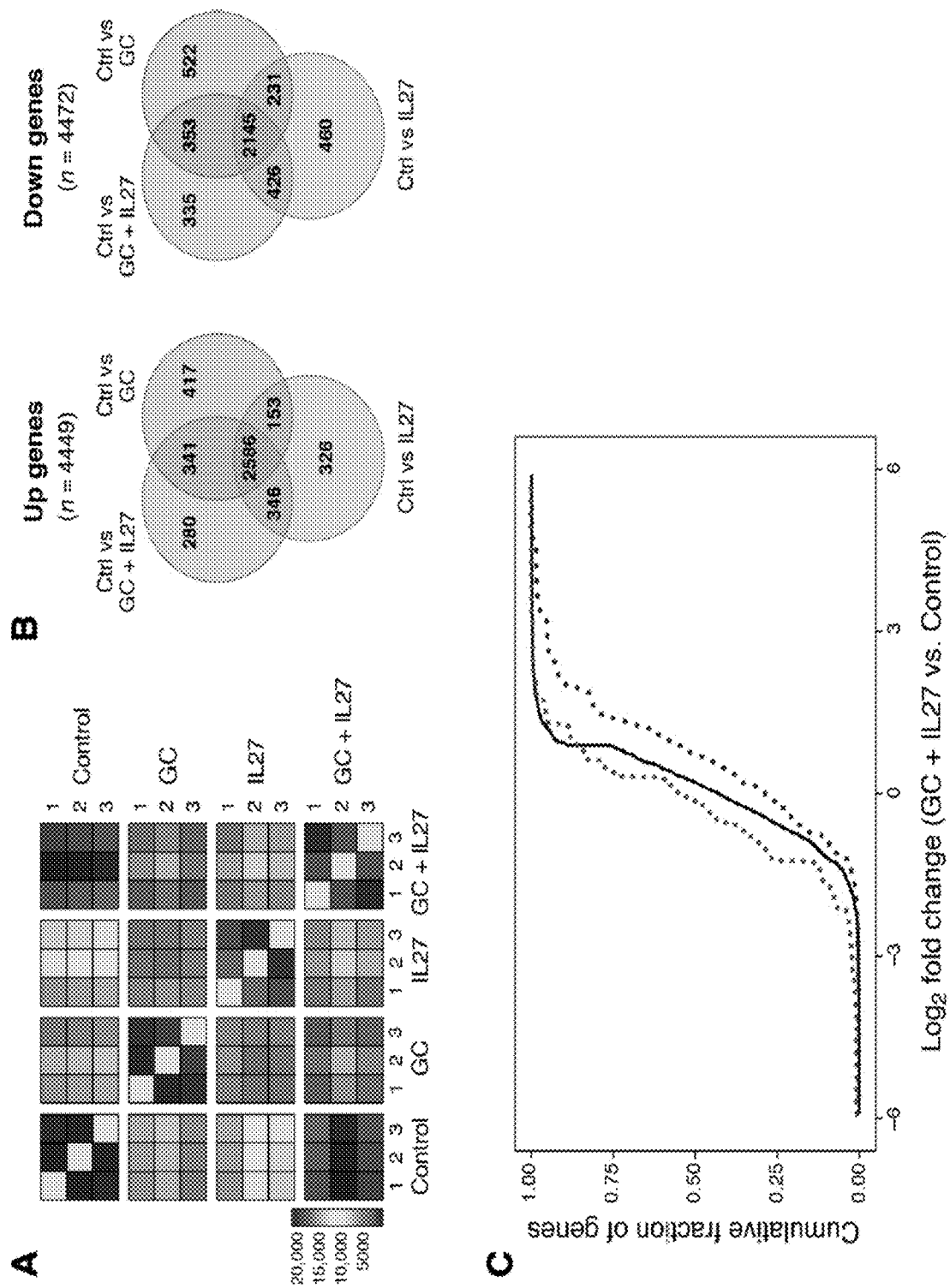
FIG. 46A-C

SEQUENCE LISTING

```
<160> NUMBER OF SEQ ID NOS: 21

<210> SEQ ID NO 1
<211> LENGTH: 288
<212> TYPE: PRT
<213> ORGANISM: Artificial
<220> FEATURE:
<223> OTHER INFORMATION: Synthetic

<400> SEQUENCE: 1

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Ala Pro Ser Pro Ala Phe
    50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Pro Thr Met Arg Val Ala Val Thr Ala Ala
        115                 120                 125

Arg Pro Pro Arg Ala Lys Pro Ala Pro Arg Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln Asp Met Ile Ala Ala Leu Pro Glu Ala Thr His Glu Ala
    210                 215                 220
```

-continued

```
Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
            260                 265                 270

Glu Ala Val His Ala Trp Arg Asn Ala Leu Thr Gly Ala Pro Leu Asn
        275                 280                 285
```

<210> SEQ ID NO 2
<211> LENGTH: 183
<212> TYPE: PRT
<213> ORGANISM: Artificial
<220> FEATURE:
<223> OTHER INFORMATION: Synthetic

<400> SEQUENCE: 2

```
Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
                20                  25                  30

Gly Gly Arg Pro Ala Leu Asp Ala Val Lys Lys Gly Leu Pro His Ala
            35                  40                  45

Pro Ala Leu Ile Lys Arg Thr Asn Arg Arg Ile Pro Glu Arg Thr Ser
50                  55                  60

His Arg Val Ala Asp His Ala Gln Val Arg Val Leu Gly Phe Phe
65                  70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
            100                 105                 110

Val Thr Glu Leu Glu Ala Arg Ser Gly Thr Leu Pro Pro Ala Ser Gln
        115                 120                 125

Arg Trp Asp Arg Ile Leu Gln Ala Ser Gly Met Lys Arg Ala Lys Pro
    130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
            180
```

<210> SEQ ID NO 3
<211> LENGTH: 7
<212> TYPE: PRT
<213> ORGANISM: Simian virus 40

<400> SEQUENCE: 3

```
Pro Lys Lys Lys Arg Lys Val
1               5
```

<210> SEQ ID NO 4
<211> LENGTH: 10
<212> TYPE: PRT
<213> ORGANISM: Simian virus 40

<400> SEQUENCE: 4

```
Pro Lys Lys Lys Arg Lys Val Glu Ala Ser
1               5                   10
```

```
<210> SEQ ID NO 5
<211> LENGTH: 16
<212> TYPE: PRT
<213> ORGANISM: Artificial
<220> FEATURE:
<223> OTHER INFORMATION: Nucleoplasmin bipartite NLS from Homo sapiens

<400> SEQUENCE: 5

Lys Arg Pro Ala Ala Thr Lys Lys Ala Gly Gln Ala Lys Lys Lys Lys
1               5                   10                  15

<210> SEQ ID NO 6
<211> LENGTH: 9
<212> TYPE: PRT
<213> ORGANISM: Artificial
<220> FEATURE:
<223> OTHER INFORMATION: c-myc NLS from Homo sapiens

<400> SEQUENCE: 6

Pro Ala Ala Lys Arg Val Lys Leu Asp
1               5

<210> SEQ ID NO 7
<211> LENGTH: 11
<212> TYPE: PRT
<213> ORGANISM: Artificial
<220> FEATURE:
<223> OTHER INFORMATION: c-myc NLS from Homo sapiens

<400> SEQUENCE: 7

Arg Gln Arg Arg Asn Glu Leu Lys Arg Ser Pro
1               5                   10

<210> SEQ ID NO 8
<211> LENGTH: 38
<212> TYPE: PRT
<213> ORGANISM: Artificial
<220> FEATURE:
<223> OTHER INFORMATION: hRNPA1 M9 NLS from Homo sapiens

<400> SEQUENCE: 8

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
                20                  25                  30

Arg Asn Gln Gly Gly Tyr
                35

<210> SEQ ID NO 9
<211> LENGTH: 42
<212> TYPE: PRT
<213> ORGANISM: Artificial
<220> FEATURE:
<223> OTHER INFORMATION: IBB domain from importin-alpha from Homo
      sapiens

<400> SEQUENCE: 9

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
                20                  25                  30

Asp Glu Gln Ile Leu Lys Arg Arg Asn Val
                35                  40
```

```
<210> SEQ ID NO 10
<211> LENGTH: 8
<212> TYPE: PRT
<213> ORGANISM: Artificial
<220> FEATURE:
<223> OTHER INFORMATION: Myoma T protein from Homo sapiens

<400> SEQUENCE: 10

Val Ser Arg Lys Arg Pro Arg Pro
1               5

<210> SEQ ID NO 11
<211> LENGTH: 8
<212> TYPE: PRT
<213> ORGANISM: Artificial
<220> FEATURE:
<223> OTHER INFORMATION: Myoma T protein from Homo sapiens

<400> SEQUENCE: 11

Pro Pro Lys Lys Ala Arg Glu Asp
1               5

<210> SEQ ID NO 12
<211> LENGTH: 8
<212> TYPE: PRT
<213> ORGANISM: Homo sapiens

<400> SEQUENCE: 12

Pro Gln Pro Lys Lys Lys Pro Leu
1               5

<210> SEQ ID NO 13
<211> LENGTH: 12
<212> TYPE: PRT
<213> ORGANISM: Mus sp.

<400> SEQUENCE: 13

Ser Ala Leu Ile Lys Lys Lys Lys Lys Met Ala Pro
1               5                   10

<210> SEQ ID NO 14
<211> LENGTH: 5
<212> TYPE: PRT
<213> ORGANISM: Influenza virus

<400> SEQUENCE: 14

Asp Arg Leu Arg Arg
1               5

<210> SEQ ID NO 15
<211> LENGTH: 7
<212> TYPE: PRT
<213> ORGANISM: Influenza virus

<400> SEQUENCE: 15

Pro Lys Gln Lys Lys Arg Lys
1               5

<210> SEQ ID NO 16
<211> LENGTH: 10
<212> TYPE: PRT
<213> ORGANISM: Hepatitis D virus

<400> SEQUENCE: 16

Arg Lys Leu Lys Lys Lys Ile Lys Lys Leu
```

-continued

```
1               5                  10

<210> SEQ ID NO 17
<211> LENGTH: 10
<212> TYPE: PRT
<213> ORGANISM: Mus sp.

<400> SEQUENCE: 17

Arg Glu Lys Lys Lys Phe Leu Lys Arg Arg
1               5                  10

<210> SEQ ID NO 18
<211> LENGTH: 20
<212> TYPE: PRT
<213> ORGANISM: Homo sapiens

<400> SEQUENCE: 18

Lys Arg Lys Gly Asp Glu Val Asp Gly Val Asp Glu Val Ala Lys Lys
1               5                  10                  15

Lys Ser Lys Lys
            20

<210> SEQ ID NO 19
<211> LENGTH: 17
<212> TYPE: PRT
<213> ORGANISM: Homo sapiens

<400> SEQUENCE: 19

Arg Lys Cys Leu Gln Ala Gly Met Asn Leu Glu Ala Arg Lys Thr Lys
1               5                  10                  15

Lys

<210> SEQ ID NO 20
<211> LENGTH: 107
<212> TYPE: PRT
<213> ORGANISM: Homo sapiens

<400> SEQUENCE: 20

Ile Glu Val Met Tyr Pro Pro Pro Tyr Leu Asp Asn Glu Lys Ser Asn
1               5                  10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
            100                 105

<210> SEQ ID NO 21
<211> LENGTH: 9
<212> TYPE: PRT
<213> ORGANISM: Homo sapiens
```

```
<400> SEQUENCE: 21

Ile Glu Val Met Tyr Pro Pro Pro Tyr
1               5
```

METHODS AND COMPOSITIONS FOR ENHANCING ANTI-TUMOR IMMUNITY BY TARGETING STEROIDOGENESIS

This application claims the benefit of U.S. Provisional Application Nos. 62/911,957, filed Oct. 7, 2019 and 62/970,125, filed Feb. 4, 2020. The entire contents of the above-identified applications are hereby fully incorporated herein by reference.

STATEMENT REGARDING FEDERALLY SPONSORED RESEARCH

This invention was made with government support under Grant No.(s) AI073748, NS045937 and CA229400 awarded by the National Institutes of Health. The government has certain rights in the invention.

REFERENCE TO AN ELECTRONIC SEQUENCE LISTING

The contents of the electronic sequence listing ("BROD_4980US_ST25.txt"; Size is 12.0 Kilobytes and it was created on Sep. 29, 2020) is herein incorporated by reference in its entirety.

REFERENCE TO AN ELECTRONIC TABLE

The instant application contains a "lengthy" Table which has been submitted electronically in ASCII format and is hereby incorporated by reference in its entirety. Said ASCII format, created on Apr. 22, 2019, is named Table_1.txt and is 1,900,000 bytes in size.

LENGTHY TABLES

The patent contains a lengthy table section. A copy of the table is available in electronic form from the USPTO web site (https://seqdata.uspto.gov/?pageRequest=docDetail&DocID=US11793787B2). An electronic copy of the table will also be available from the USPTO upon request and payment of the fee set forth in 37 CFR 1.19(b)(3).

TECHNICAL FIELD

The subject matter disclosed herein is generally directed to modulating anti-tumor T cell immunity by modulating synthesis of glucocorticoids.

BACKGROUND

Although the immune system has the capacity to fight cancer, signals present within the tumor microenvironment (TME) actively suppress anti-tumor immune responses. In particular, CD8+ T cells, key mediators of anti-tumor immunity, undergo altered effector differentiation that culminates in the development of a dysfunctional or "exhausted" state (Danilo et al., 2018; Wherry and Kurachi, 2015). Dysfunctional CD8+ T cells exhibit defective cytotoxicity, pro-inflammatory cytokine production, and induction of the immunosuppressive cytokine interleukin (IL)-10 (Jin et al., 2010). Thus, dysfunctional CD8+ T cells are not only poor mediators of tumor clearance but can also contribute to immunosuppression in the TME. Therefore, understanding the T cell intrinsic and extrinsic signals that contribute to the development of dysfunction is of key importance in devising effective therapies to improve anti-tumor CD8+ T cell responses.

Consequently, there exists a continuous need to provide additional and preferably improved markers, products and methods allowing to determine and modulate the functional state of immune cells. Likewise, there exists a continuous need to provide additional and preferably improved molecular targets involved in immune responses, as well as therapeutically useful substances and compositions impinging on such molecular targets to modulate immune responses.

SUMMARY

In certain example embodiments, the present invention provides for modulating T cell dysfunctional and effector immune states by modulating glucocorticoid and/or IL-27 signaling in T cells. The present invention may be advantageous for use in generating in vitro models, cells for adoptive transfer and for treatment of diseases requiring modulation of an immune response.

In one aspect, the present invention provides for a method of altering T cell dysfunction in a subject suffering from cancer comprising administering to the subject metyrapone, wherein anti-tumor immunity is enhanced in the subject. In certain embodiments, the metyrapone is administered directly to the tumor microenvironment of the cancer. In certain embodiments, the metyrapone is administered by intra-tumoral injection. In certain embodiments, the metyrapone is targeted to monocytes and/or macrophages. In certain embodiments, the metyrapone is targeted by conjugation to a bispecific antibody or antibody drug conjugate. In certain embodiments, metyrapone is administered before, after or concurrently with checkpoint blockade (CPB) therapy. In certain embodiments, the CPB therapy comprises anti-PD-1, anti-CTLA4, anti-PD-L1, anti-TIM3, anti-TIGIT, anti-LAG3, or combinations thereof. In certain embodiments, metyrapone is administered before, after or concurrently with adoptive cell transfer (ACT). In certain embodiments, the method further comprises administering to the subject an IL-27 antagonist in an amount sufficient to decrease dysfunction. In certain embodiments, the IL-27 antagonist binds IL-27 and reduces its binding to IL-27R. In certain embodiments, the IL-27 antagonist decreases expression of IL-27Ra. In certain embodiments, the IL-27 antagonist decreases expression of IL-27 or an IL-27 subunit in dendritic cells. In certain embodiments, the method further comprises administering to the subject one or more agents capable of modulating the expression, activity or function of one or more glucocorticoid+IL-27 signature genes or gene products, wherein the one or more genes are selected from the group consisting of: Lilrb4, Bcl2, Nupr1, Tgfb3, Tnfrsf4, Il24, Ramp1, Klf10, Cd27, Cd28, Tle2, Btla, Xcl1, Egr2, Entpd1, Tcf7, Nfil3, Prdm1, Mt1, Mt2, Stat3, Tigit, Havcr2, Lag3, Itga7, Acvrl1, Gprl25, Aqpl1, Kit, Trip6, Il10, Enpp2, Asb2, Jag2, Tnfrsf18, Smyd3, Dbp, Ddit3, Tnfrsf14, Zfp467, Crebl2, Hif1a, Irf6, Alcam, Bach1, Pdcd1, Ctla4, Epcam, Gpld1, Cd68, Prnp, Gab2, Vldlr, Il10, Il1r2, Nt5e, Itgae, Clqtnf4, Ccr7, Cd226, Ifng, Ccl4, Spp1, Ccl3, Cd48, Cxcr3, Nanog, Tfrc, Hmgn2, Ptrf, Icam2, Cd40lg and Il1a; or Table 7A and Table 7B; or Table 5A and Table 5B; or Table 6A and Table 6B; or Table 3; or Table 2A and Table 2B; or Table 1. In certain embodiments, the antagonist of IL-27 or the one or more agents capable of modulating the expression, activity or function of one or more glucocorticoid+IL-27 signature genes or gene products comprises an antibody, antibody fragment, intrabody, antibody-like protein scaffold, aptamer, polypeptide, small molecule, small molecule degrader, genetic modifying agent, or any combination thereof. In certain embodiments, the genetic modifying agent comprises a CRISPR system, RNAi system, a zinc finger nuclease system, a TALE, or a meganuclease. In certain embodiments, the CRISPR system comprises a CRISPR-Cas base editing system, a prime editor system, or a CAST system.

In another aspect, the present invention provides for a method of altering the differentiation trajectory of CD8+T cells comprising contacting a population of T cells with one or more agents capable of modulating glucocorticoid signaling. In certain embodiments, the one or more agents modulate TCF-1 expression. In certain embodiments, the one or more agents modulate the expression of one or more genes selected from the group consisting of: Lilrb4, Bcl2, Nupr1, Tgfb3, Tnfrsf4, Il24, Ramp1, Klf10, Cd27, Cd28, Tle2, Btla, Xcl1, Egr2, Entpd1, Tcf7, Nfil3, Prdm1, Mt1, Mt2, Stat3, Tigit, Havcr2, Lag3, Itga7, Acvrl1, Gprl25, Aqpl1, Kit, Trip6, Il10, Enpp2, Asb2, Jag2, Tnfrsf18, Smyd3, Dbp, Ddit3, Tnfrsf14, Zfp467, Crebl2, Hif1a, Irf6, Alcam, Bach1, Pdcd1, Ctla4, Epcam, Gpld1, Cd68, Prnp, Gab2, Vldlr, Il10, Il1r2, Nt5e, Itgae, Clqtnf4, Ccr7, Cd226, Ifng, Ccl4, Spp1, Ccl3, Cd48, Cxcr3, Nanog, Tfrc, Hmgn2, Ptrf, Icam2, Cd40lg and Il1a; or Table 7A and Table 7B; or Table 5A and Table 5B; or Table 6A and Table 6B; or Table 3; or Table 2A and Table 2B; or Table 1. In certain embodiments, the antagonist of IL-27 comprises an antibody, antibody fragment, intrabody, antibody-like protein scaffold, aptamer, polypeptide, small molecule, small molecule degrader, genetic modifying agent, or any combination thereof. In certain embodiments, the genetic modifying agent comprises a CRISPR system, RNAi system, a zinc finger nuclease system, a TALE, or a meganuclease. In certain embodiments, the CRISPR system comprises a CRISPR-Cas base editing system, a prime editor system, or a CAST system.

In another aspect, the present invention provides for an isolated T cell modified to comprise reduced glucocorticoid signaling. In certain embodiments, the glucocorticoid receptor is reduced or abolished. In another aspect, the present invention provides for an isolated T cell modified to comprise reduced TCF-1 expression.

In another aspect, the present invention provides for a method of altering T cell dysfunction in a subject suffering from cancer comprising administering to the subject metyrapone, wherein anti-tumor immunity is enhanced in the subject. In certain embodiments, the metyrapone is targeted to monocytes and/or macrophages. In certain embodiments, the metyrapone is administered before, after or concurrently with adoptive cell transfer (ACT).

In certain embodiments, the method further comprises administering to the subject an IL-27 antagonist in an amount sufficient to decrease dysfunction. In certain embodiments, the IL-27 antagonist binds IL-27 and reduces its binding to IL-27R. In certain embodiments, the IL-27 antagonist decreases expression of IL-27Ra. In certain embodiments, the IL-27 antagonist decreases expression of IL-27 or an IL-27 subunit in dendritic cells. In certain embodiments, the antagonist of IL-27 comprises an antibody, antibody fragment, intrabody, antibody-like protein scaffold, aptamer, polypeptide, small molecule, small molecule degrader, genetic modifying agent, or any combination thereof.

In certain embodiments, the genetic modifying agent comprises a CRISPR system, RNAi system, a zinc finger nuclease system, a TALE, or a meganuclease. In certain embodiments, the CRISPR system comprises Cas9, Cas12, or Cas14. In certain embodiments, the CRISPR system comprises a dCas fused or otherwise linked to a nucleotide deaminase. In certain embodiments, the nucleotide deaminase is a cytidine deaminase or an adenosine deaminase. In certain embodiments, the dCas is a dCas9, dCas12, dCas13, or dCas14. In certain embodiments, the CRISPR system is administered as a ribonucleoprotein (RNP) complex.

In certain embodiments, the method further comprises administering checkpoint blockade (CPB) therapy. In certain embodiments, the CPB therapy comprises anti-PD-1, anti-CTLA4+PD-1, or anti-CTLA4.

In certain embodiments, the metyrapone is administered by intra-tumoral injection.

In one aspect, the present invention provides for a method of altering T cell dysfunction in a subject in need thereof comprising administering to the subject one or more agents capable of modulating glucocorticoid signaling, wherein a dysfunctional immune state in the subject is increased when glucocorticoid signaling is enhanced, or wherein a dysfunctional immune state in the subject is decreased when glucocorticoid signaling is reduced. In certain embodiments, the method further comprises administering to the subject one or more agents capable of modulating IL-27 signaling, wherein a dysfunctional immune state in the subject is increased when both glucocorticoid signaling and IL-27 signaling are enhanced, or wherein a dysfunctional immune state in the subject is decreased when both glucocorticoid signaling and IL-27 signaling are reduced.

In certain embodiments, the one or more agents capable of modulating glucocorticoid signaling comprise a glucocorticoid or a glucocorticoid agonist in an amount sufficient to increase dysfunction. In certain embodiments, the glucocorticoid agonist binds glucocorticoid and enhances its binding to glucocorticoid receptor. In certain embodiments, the glucocorticoid agonist increases expression of glucocorticoid receptor. In certain embodiments, the glucocorticoid agonist increases expression or activity of an enzyme of steroid biogenesis in macrophages. In certain embodiments, the enzyme is Cyp11a1.

In certain embodiments, the one or more agents capable of modulating glucocorticoid signaling comprise a glucocorticoid antagonist in an amount sufficient to decrease dysfunction. In certain embodiments, the glucocorticoid antagonist binds glucocorticoid and decreases its binding to glucocorticoid receptor. In certain embodiments, the glucocorticoid antagonist decreases expression of glucocorticoid receptor. In certain embodiments, the glucocorticoid antagonist decreases expression or activity of an enzyme of steroid biogenesis in macrophages. In certain embodiments, the enzyme is Cyp11a1.

In certain embodiments, the one or more agents capable of modulating IL-27 signaling comprise IL-27 or an IL-27 agonist in an amount sufficient to increase dysfunction. In certain embodiments, the IL-27 agonist binds IL-27 and enhances its binding to IL-27R. In certain embodiments, the IL-27 agonist increases expression of IL-27Ra. In certain embodiments, the IL-27 agonist increases expression of IL-27 or an IL-27 subunit in dendritic cells.

In certain embodiments, the one or more agents capable of modulating IL-27 signaling comprise an IL-27 antagonist in an amount sufficient to decrease dysfunction. In certain embodiments, the IL-27 antagonist binds IL-27 and reduces its binding to IL-27R. In certain embodiments, the IL-27 antagonist decreases expression of IL-27Ra. In certain embodiments, the IL-27 antagonist decreases expression of IL-27 or an IL-27 subunit in dendritic cells.

In another aspect, the present invention provides for a method of altering T cell dysfunction in a subject in need thereof comprising administering to the subject one or more T cells contacted with one or more agents capable of modulating glucocorticoid signaling, wherein the dysfunctional state of the one or more T cells is increased when glucocorticoid signaling is enhanced, or wherein the dysfunctional state of the one or more T cells is decreased when glucocorticoid signaling is reduced. In certain embodiments, the one or more T cells are further contacted with one or more agents capable of modulating IL-27 signaling, wherein the dysfunctional state of the one or more T cells is increased when both glucocorticoid signaling and IL-27 signaling are enhanced, or wherein the dysfunctional state of the one or more T cells is decreased when both glucocorticoid signaling and IL-27 signaling are reduced.

In certain embodiments, the one or more T cells administered to the subject are in vitro differentiated in a culture media comprising IL-27 and a glucocorticoid. In certain embodiments, the T cells are CD8+ T cells or naïve T cells.

In certain embodiments, the one or more agents capable of modulating glucocorticoid signaling comprise a glucocorticoid or a glucocorticoid agonist in an amount sufficient to increase dysfunction. In certain embodiments, the glucocorticoid agonist binds glucocorticoid and enhances its binding to glucocorticoid receptor. In certain embodiments, the glucocorticoid agonist increases expression of glucocorticoid receptor.

In certain embodiments, the one or more agents capable of modulating glucocorticoid signaling comprise a glucocorticoid antagonist in an amount sufficient to decrease dysfunction. In certain embodiments, the glucocorticoid antagonist binds glucocorticoid and decreases its binding to glucocorticoid receptor. In certain embodiments, the glucocorticoid antagonist decreases expression of glucocorticoid receptor.

In certain embodiments, the one or more agents capable of modulating IL-27 signaling comprise IL-27 or an IL-27 agonist in an amount sufficient to increase dysfunction. In certain embodiments, the IL-27 agonist binds IL-27 and enhances its binding to IL-27R. In certain embodiments, the IL-27 agonist increases expression of IL-27Ra.

In certain embodiments, the one or more agents capable of modulating IL-27 signaling comprise an IL-27 antagonist in an amount sufficient to decrease dysfunction. In certain embodiments, the IL-27 antagonist binds IL-27 and reduces its binding to IL-27R. In certain embodiments, the IL-27 antagonist decreases expression of IL-27Ra.

In another aspect, the present invention provides for a method of altering T cell dysfunction in a subject in need thereof comprising administering to the subject one or more agents capable of modulating the expression, activity or function of one or more glucocorticoid+IL-27 signature genes or gene products; or administering one or more T cells contacted with the one or more agents, wherein the one or more genes are selected from the group consisting of: Lilrb4, Bcl2, Nupr1, Tgfb3, Tnfrsf4, Il24, Ramp1, Klf10, Cd27, Cd28, Tle2, Btla, Xcl1, Egr2, Entpd1, Tcf7, Nfil3, Prdm1, Mt1, Mt2, Stat3, Tigit, Havcr2, Lag3, Itga7, Acvrl1, Gpr125, Aqp11, Kit, Trip6, Il10, Enpp2, Asb2, Jag2, Tnfrsf18, Smyd3, Dbp, Ddit3, Tnfrsf14, Zfp467, Crebl2, Hif1a, Irf6, Alcam, Bach1, Pdcd1, Ctla4, Epcam, Gpld1, Cd68, Prnp, Gab2, Vldlr, Il10, Il1r2, Nt5e, Itgae, C1qtnf4, Ccr7, Cd226, Ifng, Ccl4, Spp1, Ccl3, Cd48, Cxcr3, Nanog, Tfrc, Hmgn2, Ptrf, Icam2, Cd40lg and Il1a; or Table 7A and Table 7B; or Table 5A and Table 5B; or Table 6A and Table 6B; or Table 3; or Table 2A and Table 2B; or Table 1, wherein modulating the expression, activity or function comprises increasing the expression, activity or function of glucocorticoid+IL-27 signature genes that are downregulated as compared to the control according to Table 1 and decreasing the expression, activity or function of glucocorticoid+IL-27 signature genes that are upregulated as compared to the control according to Table 1, whereby dysfunction is decreased, or wherein modulating the expression, activity or function comprises decreasing the expression, activity or function for glucocorticoid+IL-27 signature genes that are downregulated as compared to the control according to Table 1 and increasing the expression, activity or function for glucocorticoid+IL-27 signature genes that are upregulated as compared to the control according to Table 1, whereby dysfunction is increased. In certain embodiments, Epcam, Gpld1, Cd68, Prnp, Gab2, Vldlr, Il10, Il1r2, Nt5e, Itgae, C1qtnf4, Tgfb3, Itga7, Acvrl1, Gprl25, Aqp11, Ramp1, Kit, Trip6, Il10, Enpp2, Asb2, Jag2, Tnfrsf18, Prdm1, Smyd3, Tigit, Dbp, Tle2, Ddit3, Klf10, Tnfrsf14, Zfp467, Entpd1, Nfil3, Crebl2, Hif1a, Irf6, Lag3, Alcam, Mt2, Stat3, Mt1, Bach1, Cd28, Havcr2, Pdcd1, Ctla4 and Cd27 are upregulated in glucocorticoid+IL-27 as compared to the control. In certain embodiments, Ifng, Ccl4, Bcl2, Spp1, Btla, Ccl3, Cd48, Cxcr3, Nanog, Tfrc, Xcl1, Lilrb4, Nupr1, Hmgn2, Il24, Ptrf, Icam2, Cd40lg, Il1a, Tcf7, Tnfrsf4, Egr2, Ccr7 and Cd226 are downregulated in glucocorticoid+IL-27 as compared to the control.

In certain embodiments, the T cells are in vitro differentiated in a culture media comprising the one or more agents. In certain embodiments, the T cells are CD8+ T cells or naïve T cells.

In certain embodiments, the agent is capable of targeting or binding to one or more cell surface exposed gene products; or capable of targeting or binding to one or more receptors or ligands specific for a cell surface exposed gene product; or capable of targeting or binding to one or more secreted gene products; or capable of targeting or binding to one or more receptors specific for a secreted gene product. In certain embodiments, the one or more agents comprise an antibody, antibody fragment, intrabody, antibody-like protein scaffold, aptamer, polypeptide, small molecule, small molecule degrader, genetic modifying agent, or any combination thereof.

In certain embodiments, the genetic modifying agent comprises a CRISPR system, RNAi system, a zinc finger nuclease system, a TALE, or a meganuclease. In certain embodiments, the CRISPR system comprises Cas9, Cas12, or Cas14. In certain embodiments, the CRISPR system comprises a dCas fused or otherwise linked to a nucleotide deaminase. In certain embodiments, the nucleotide deaminase is a cytidine deaminase or an adenosine deaminase. In certain embodiments, the dCas is a dCas9, dCas12, dCas13, or dCas14. In certain embodiments, the CRISPR system is administered as a ribonucleoprotein (RNP) complex.

In certain embodiments, the method is for treating an autoimmune disease in a subject in need thereof. In certain embodiments, the autoimmune disease is selected from Multiple Sclerosis (MS), Irritable Bowel Disease (IBD), Crohn's disease, spondyloarthritides, Systemic Lupus Erythematosus (SLE), Vitiligo, rheumatoid arthritis, psoriasis, Sjögren's syndrome, and diabetes. In certain embodiments, the method is for treating an inflammatory disorder in a subject in need thereof. In certain embodiments, the inflammatory disorder is selected from psoriasis, inflammatory bowel diseases (IBD), allergic asthma, food allergies and rheumatoid arthritis. In certain embodiments, the method is for inducing immune tolerance or preventing graft versus host disease in a subject having received an organ transplant.

In certain embodiments, the method is for treating cancer in a subject in need thereof, whereby a tumor specific immune response is enhanced. In certain embodiments, the treatment is a cancer adjuvant therapy comprising administering glucocorticoid therapy and one or more agents capable of modulating one or more genes or gene products according to claim 37, whereby the subject maintains T cell immunity against tumor cells. In certain embodiments, the adjuvant therapy is administered to a subject having received chemotherapy. In certain embodiments, the one or more genes or gene products are selected from the group consisting of PD-1, TIM3, TIGIT, LAG3, MT1, MT2, and IL-10. In certain embodiments, the agent is an antibody or fragment thereof selected from the group consisting of anti-PD1, anti-TIM3, anti-TIGIT, anti-LAG3 and anti-IL-10. In certain embodiments, the agent is an MT1/2 antagonist. In certain embodiments, the glucocorticoid is dexamethasone (Dex).

In another aspect, the present invention provides for an isolated T cell modified to comprise altered IL-27 and glucocorticoid signaling. In certain embodiments, the T cell is in vitro differentiated in a culture media comprising IL-27 and a glucocorticoid, whereby dysfunction is increased. In certain embodiments, the T cell is modified to comprise decreased IL-27 signaling and glucocorticoid signaling, whereby dysfunction is decreased. In certain embodiments, the T cell comprises decreased or abolished expression or activity of the IL-27 receptor and the glucocorticoid receptor. In certain embodiments, the isolated T cell is modified to comprise modulated expression or activity of one or more genes or gene products according to claim 37. In certain embodiments, the T cell comprises a genetic modifying agent. In certain embodiments, the genetic modifying agent comprises a CRISPR system, RNAi system, a zinc finger nuclease system, a TALE, or a meganuclease. In certain embodiments, the CRISPR system comprises Cas9, Cas12, or Cas14. In certain embodiments, the CRISPR system comprises a dCas fused or otherwise linked to a nucleotide deaminase. In certain embodiments, the nucleotide deaminase is a cytidine deaminase or an adenosine deaminase. In certain embodiments, the dCas is a dCas9, dCas12, dCas13, or dCas14.

In certain embodiments, the T cell is obtained from PBMCs. In certain embodiments, the T cell is a tumor infiltrating lymphocyte (TIL). In certain embodiments, the T cell expresses an endogenous T cell receptor (TCR) or chimeric antigen receptor (CAR) specific for a tumor antigen. In certain embodiments, the T cell is expanded. In certain embodiments, the T cell is modified to express a suicide gene, wherein the T cell can be eliminated upon administration of a drug. In certain embodiments, the glucocorticoid is dexamethasone (Dex).

In another aspect, the present invention provides for a pharmaceutical composition comprising one or more isolated T cells according to any embodiment herein. In another aspect, the present invention provides for a method of treating cancer in a subject in need thereof comprising administering a pharmaceutical composition comprising one or more isolated T cells according to any embodiment herein where dysfunction is decreased. In another aspect, the present invention provides for a method of treating an autoimmune disease or inflammatory disorder, or for inducing immune tolerance in a subject in need thereof comprising administering a pharmaceutical composition comprising one or more isolated T cells according to any embodiment herein where dysfunction is increased.

In another aspect, the present invention provides for a method of generating an in vitro T cell that faithfully recapitulates an in vivo dysfunctional T cell comprising culturing a T cell in a culture media comprising IL-27 and a glucocorticoid.

In another aspect, the present invention provides for a method of detecting a checkpoint blockade (CPB) therapy non-responder gene signature in a subject in need thereof comprising detecting in T cells obtained from a pre-treatment biological sample from the subject the expression or activity of one or more glucocorticoid+IL-27 signature genes or gene products selected from the group consisting of. Table 2A and Table 2B; or Lilrb4, Bcl2, Nupr1, Tgfb3, Tnfrsf4, Il24, Ramp1, Klf10, Cd27, Cd28, Tle2, Btla, Xcl1, Egr2, Entpd1, Tcf7, Nfil3, Prdm1, Mt1, Mt2, Stat3, Tigit, Havcr2, Lag3, Itga7, Acvrl1, Gprl25, Aqp11, Kit, Trip6, Il10, Enpp2, Asb2, Jag2, Tnfrsf18, Smyd3, Dbp, Ddit3, Tnfrsf14, Zfp467, Crebl2, Hif1a, Irf6, Alcam, Bach1, Pdcd1, Ctla4, Epcam, Gpld1, Cd68, Prnp, Gab2, Vldlr, Il10, Il1r2, Nt5e, Itgae, Clqtnf4, Ccr7, Cd226, Ifng, Ccl4, Spp1, Ccl3, Cd48, Cxcr3, Nanog, Tfrc, Hmgn2, Ptrf, Icam2, Cd40lg and Il1a; or Table 7A and Table 7B; or Table 5A and Table 5B; or Table 6A and Table 6B; or Table 3; or Table 1, wherein Epcam, Gpld1, Cd68, Prnp, Gab2, Vldlr, Il10, Il1r2, Nt5e, Itgae, Clqtnf4, Tgfb3, Itga7, Acvrl1, Gprl25, Aqp11, Ramp1, Kit, Trip6, Il10, Enpp2, Asb2, Jag2, Tnfrsf18, Prdm1, Smyd3, Tigit, Dbp, Tle2, Ddit3, Klf10, Tnfrsf14, Zfp467, Entpd1, Nfil3, Crebl2, Hif1a, Irf6, Lag3, Alcam, Mt2, Stat3, Mt1, Bach1, Cd28, Havcr2, Pdcd1, Ctla4 and Cd27 are upregulated in glucocorticoid+IL-27 as compared to the control, and wherein Ifng, Ccl4, Bcl2, Spp1, Btla, Ccl3, Cd48, Cxcr3, Nanog, Tfrc, Xcl1, Lilrb4, Nupr1, Hmgn2, Il24, Ptrf, Icam2, Cd40lg, Il1a, Tcf7, Tnfrsf4, Egr2, Ccr7 and Cd226 are downregulated in glucocorticoid+IL-27 as compared to the control. In certain embodiments, the method further comprises treating the subject wherein if a non-responder signature is detected treating the subject according to any embodiment herein where dysfunction is decreased. In certain embodiments, the method further comprises administering checkpoint blockade (CPB) therapy. In certain embodiments, the CPB therapy comprises anti-PD-1, anti-CTLA4+PD-1, or anti-CTLA4.

In another aspect, the present invention provides for a method of determining a prognosis for cancer survival in a subject in need thereof comprising detecting the expression of Cyp11a1 in CD45+ cells obtained from a tumor sample of the subject, wherein low Cyp11a1 levels compared to a reference level indicates increased survival. In certain embodiments, expression is detected in CD11b+F4/80+ macrophages. In certain embodiments, the method further comprises treating the subject wherein if high Cyp11a1 levels are detected treating the subject according to any embodiment herein where dysfunction is decreased.

In another aspect, the present invention provides for a method of screening for one or more agents capable of modulating a glucocorticoid+IL-27 gene signature according to claim 83 comprising administering to a population of T cells one or more agents; and detecting expression, activity or function of one or more genes or gene products in the signature. In certain embodiments, the one or more genes detected are selected from the group consisting of PD-1, TIM3, LAG3, MT1, MT2, and IL-10. In certain embodiments, the population of cells express one or more reporter genes. In certain embodiments, the one or more agents bind to glucocorticoid receptor and/or IL-27 receptor. In certain embodiments, the one or more agents modify chromatin structure at one or more of the signature genes.

In another aspect, the present invention provides for a method of decreasing inflammation in a subject in need thereof comprising administering to the subject IL-27 and a glucocorticoid.

In another aspect, the present invention provides for a method of decreasing inflammation in a subject in need thereof comprising administering to the subject immune cells in vitro differentiated in a culture media comprising IL-27 and a glucocorticoid.

In another aspect, the present invention provides for a method of inducing immune tolerance in a subject having received an organ transplant comprising administering to the subject IL-27 and a glucocorticoid.

In another aspect, the present invention provides for a method of inducing immune tolerance in a subject having received an organ transplant comprising administering to the subject immune cells in vitro differentiated in a culture media comprising IL-27 and a glucocorticoid.

In another aspect, the present invention provides for a method of treating cancer in a subject in need thereof comprising administering one or more agents capable of inhibiting IL-27 signaling and glucocorticoid signaling.

In another aspect, the present invention provides for a method of administering cancer adjuvant glucocorticoid therapy to a subject in need thereof comprising measuring a T cell receptor (TCR) activation and/or T cell resting state in the subject and administering adjuvant glucocorticoid therapy to the subject when the subject has a TCR activation state and/or stopping adjuvant glucocorticoid therapy when the subject has a T cell resting state.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIGS. 1A-1C—Glucocorticoid signaling is active in dysfunctional CD8$^+$ TILs. TILs were harvested from (FIG. 1A) mice bearing MC38-Ova colon carcinoma (n=4) or B16F10 melanoma (n=5) or (FIG. 1B) from human colorectal carcinomas (n=7) for the examination of glucocorticoid receptor (GR) expression by intracellular staining. Representative histograms show GR expression in the indicated CD8$^+$ TILs populations. Summary plots show the mean fluorescence intensity (MFI) of GR expression in the indicated populations. For human colorectal carcinoma TILs, data are normalized to the expression level in Tim-3$^-$PD-1$^-$CD8$^+$ TILs. $*p<0.05$, $p<0.01$, $*p<0.001$, $****p<0.0001$. Ordinary one-way ANOVA (Tukey's multiple comparisons test). Mean±SEM is shown. FIG. 1C) tSNE plot showing projection of a glucocorticoid signature (top left), a CD8$^+$ T cell dysfunction signature (top right), and Mt1 (bottom left) and Nfil3 (bottom right) gene expression onto the single-cell RNA profiles of CD8$^+$ TILs (Singer et al., 2016). The contour marks cells showing highest expression and the color scale indicates low (dark blue) to high (red) expressing cells.

FIGS. 2A-2C—Glucocorticoid signaling promotes checkpoint receptor expression and dampens CD8$^+$ T cell effector functions. Naïve CD8$^+$ T cells from wild type mice (n=5) were activated in the presence or absence of Dex (GC) and harvested on Day 9. FIG. 2A) Cells were stimulated with PMA/ionomycin for 4 hrs followed by intracellular staining for IL-2, TNF-α, IFN-γ and IL10. FIG. 2B) Expression of Tim-3, PD-1, Lag3, and Tigit was examined by flow cytometry. Data shown are representative of 3 independent experiments. FIG. 2C) Human CD8$^+$ T cells were activated in the presence or absence of Dex (GC) and expression of Tim-3, PD-1, Lag-3, and TIGIT was examined by flow cytometry on Day 9. Data shown are representative of 2 independent experiments. $*p<0.05$, $p<0.01$, $*p<0.001$, $****p<0.0001$, two-tailed Student's t test. Mean±SEM is shown.

FIGS. 3A-3G—Glucocorticoid signaling dampens CD8$^+$ TILs effector functions. FIG. 3A) MC38-Ova was implanted into wild type (E8i-Cre$^-$Nr3c1$^{fl/fl}$) and E8i-Cre$^+$Nr3c1$^{fl/fl}$ mice (n=8-9). Mean tumor growth is shown, $***p<0.001$, linear mixed model. Data are representative of 3 independent experiments. FIG. 3B) TILs were harvested on Day 13 post tumor implantation and the expression of checkpoint receptors was analyzed by flow cytometry. Representative flow cytometry data are shown. Scatter plots show summary data (n=6-7). Data are representative of 3 independent experiments. FIG. 3C, FIG. 3D, FIG. 3E) TILs were harvested and activated with 5 g/ml OVA$_{257-264}$ (SIINFEKL). FIG. 3C) Representative flow cytometry data and summary scatter plots showing the frequency of IL-2, TNF-α, and IFN-γ-producing CD8$^+$ T cells (n=9-10). Data are pooled from 2 independent experiments. FIG. 3D) Representative flow cytometry data and summary scatter plots showing the frequency of IL10 producing CD8$^+$ T cells (n=5). FIG. 3E) Representative flow and summary scatter plots show the frequency of CD107a and Granzyme B expression (n=6). Data are representative of 2 independent experiments. FIG. 3F) TILs were stained with H-2 Kb/OVA257-264 dextramer, scatter plot shows the frequency of tumor antigen-specific CD8$^+$ T cells (n=8-9). Data are representative of 2 independent experiments. $*p<0.05$, $P<0.01$, $*p<0.001$, $****p<0.0001$, two-tailed Student's t-test. Mean±SEM are shown.

FIG. 3G) Correlation of NR3C1 mRNA with checkpoint receptor and IL10 mRNA in colon adenocarcinoma patients using TIMER.

FIGS. 4A-4E—Transactivation of checkpoint receptors and IL-10 by GR. Luciferase activity in 293T cells transfected with pGL4.23 or pGL4.10 luciferase reporters for the loci of FIG. 4A) Havcr2 (Tim3), FIG. 4B) Pdcd1 (PD1), FIG. 4C) Lag3 FIG. 4D) Tigit, and FIG. 4E) IL10 together with either empty vector (control) or constructs encoding Nr3c1. Cells were treated with GC after 24 h. Firefly luciferase activity was measured 48 h after transfection and is presented relative to constitutive Renilla luciferase activity. NS is not significant, $****p<0.0001$, two-way ANOVA (Tukey's multiple comparisons test). Data are mean S.E.M. The data are representative of 2 independent experiments.

FIGS. 5A-5F—The glucocorticoid and IL-27 pathways co-operate to promote dysfunction in CD8$^+$ T cells. FIG. 5A-5C) Naïve CD8$^+$ T cells were cultured in vitro with anti CD3/28 in the presence of Dex (GC), IL-27, or GC+IL-27. Cells were harvested on Day 9 and gene expression analyzed by RNA sequencing. FIG. 5A) Principle component analysis (PCA) of Ctrl, GC, IL-27, and GC+IL-27 treated CD8$^+$ T, the percentage of explained variance for each principal component is indicated. FIG. 5B) Bar graph shows the mean delta Euclidean distance between the GC, IL-27, or GC+IL-27 treated groups to the control group, adjusted p-values were calculated using one-way ANOVA (p-value=9.89e-09), followed by Tukey HSD, *p<0.05, ****p <0.001. FIG. 5C) Heatmap of DE genes between Ctrl and GC+IL-27 treatment. Tick marks indicate selected genes associated with T cell dysfunction. FIG. 5D) Volcano plot showing overlap of genes down-regulated by IL-27+GC with genes expressed in Tim-3$^-$PD-1$^-$ CD8$^+$ TILs (p=2.1×10$^{-10}$, Mean-rank Gene Set Test), and genes up-regulated by IL-27+GC with Tim-3$^+$PD-1$^+$ CD8$^+$ TILs (p=4.3×10$^{-5}$, Mean-rank Gene Set Test). FIG. 5E) CD8 T cells from either WT (E8i-Cre$^-$Nr3c1$^{fl/fl}$), E8i-Cre$^+$Nr3c$^{fl/fl}$, WSX1$^{-/-}$ and/or E8i-Cre$^+$Nr3c1$^{fl/fl}$ WSX1$^{-/-}$ (DKO) mice and CD4$^+$ T cells from WT mice were transferred to Rag$^{-/-}$ mice (n=5-6/group) that were implanted with MC38-Ova cells two days later. Mean tumor growth is shown. *p<0.05, ***p<0.001, linear mixed model. Data are representative of 2 independent experiments. FIG. 5F) tSNE plot of single-cell RNA profiles of TILs from melanoma patients. I) CD8 expression, II) CD4 expression, III) pre- (orange) versus post- (purple) treatment samples, IV) Responder (red) versus non-responder (blue), V) Projection of CD8$^+$ TILs dysfunction signature, VI) Projection of the GC+IL-27 signature. Box plots show the GC+IL-27 signature score in responder versus non-responders in pre- and post-treatment samples, p=4.048×10$^{-9}$ and p=5.028×10$^{-5}$, respectively (Welch Two Sample t-test). The lower and upper hinges correspond to the first and third quartiles. The upper and lower whiskers extend from the hinge to the largest and smallest value no further than 1.5 times the distance between the first and third quartiles, respectively. Data beyond the end of the whiskers are outlying points and are not plotted individually.

FIGS. 6A-6F—Glucocorticoid and IL-27 are synthesized by different cells in the TME. FIG. 6A) Corticosterone levels in the indicated tissues were quantified by ELISA. (n=5). FIG. 6B) MC38-Ova was implanted in wild-type mice. Metyrapone or vehicle control was administered intra-tumorally on Days 5, 6, 7 and 9 post tumor implantation (n=5/group). Mean tumor growth is shown *p<0.001, linear mixed model. Data are representative of 2 independent experiments. Quantitative RT-PCR analysis of (FIG. 6C) Cyp11a1 and (FIG. 6D) IL-27 (p28 and Ebi3) mRNA expression in the indicated cells. Data are pooled from 2 independent experiments. p<0.01, *p<0.001, p<0.0001. Ordinary-one way ANOVA (Tukey's multiple comparisons test). Data are mean S.E.M. FIG. 6E) MC38-Ova was implanted in Cyp11a1$^{fl/fl}$ and Cyp11a1$^{fl/fl}$ LysMCre$^+$ mice and tumor progression was studied (n=5). Mean tumor growth is shown, *p<0.001, linear mixed model. Data are representative of 2 independent experiments. FIG. 6F) Correlation of Cyp11a1 mRNA expression level with survival in patients with colon adenocarcinoma (COAD) and stomach adenocarcinoma (STAD) using TIMER.

FIGS. 8A-8E—Effect of synthetic and natural Glucocorticoids on CD8$^+$ T cells. Naïve CD8$^+$ T cells from wild type mice (n=5) (FIG. 8A, FIG. 8C, FIG. 8D) or from human samples (n=5) (FIG. 8B) were activated in the presence or absence of Dex (GC) as in FIG. 2a and harvested on Day 9. Representative flow cytometry data show Tim-3 and PD-1 expression. FIG. 8C) Frequency of viable CD8$^+$ T cells. FIG. 8D) Division index of CD8$^+$ T cells. FIG. 8E) Naïve CD8$^+$ T cells from wild type mice (n=5) were activated in the presence or absence of Corticosterone (GC) as in FIG. 2a and harvested on Day 9. Representative flow cytometry data shows the frequency of Tim-3$^+$, PD-1$^+$, Tigit$^+$ and Lag3$^+$ cells (n=5). NS is Not Significant p<0.01, *p<0.001, ****p<0.0001 two-tailed Student's t-test. Mean±SEM are shown.

FIG. 9A) Expression of Nr3c2 on T cells was quantified by qPCR. MC38-Ova cell-line was used as the positive control. Data are representative of 2 independent experiments. ND is Not Detected. FIG. 9B) Heatmap of differentially expressed genes in wild type (E8i-Cre$^-$Nr3c1$^{fl/fl}$) or E8i-Cre$^+$Nr3c1$^{fl/fl}$ CD8$^+$ T cells activated in the presence or absence of Dex (GC) for 72 hrs. Tick marks indicate selected known GC target genes.

FIG. 10C) Frequency of naïve and activated CD8$^+$ T cells in steady state. FIG. 10D) Frequency of naïve and activated CD4$^+$ T cells in steady state. FIG. 10E) Expression of Nr3c1 on T cells from Nr3c1$^{fl/fl}$ and Nr3c1$^{fl/fl}$E8iCre$^+$ mice was quantified by qPCR. **P<0.01, Ordinary one-way ANOVA (Tukey's multiple comparisons test). Mean±SEM are shown.

FIGS. 11A-11J—Glucocorticoid signaling dampens effector function of CD8$^+$ T cells. FIG. 11A) B16F10 was implanted into wild type (E8i-Cre$^-$Nr3c1$^{fl/fl}$) and E8i-Cre$^+$Nr3c1$^{fl/fl}$ mice (n=5). Mean tumor growth is shown. ***p<0.001, linear mixed model. Data are representative of 2 independent experiments. FIGS. 11B-11F) MC38-Ova was implanted into wild type (E8i-Cre$^-$Nr3c1$^{fl/fl}$) and E8i-Cre$^+$Nr3c1$^{fl/fl}$ mice. FIG. 11B) Expression level of Tim-3, PD-1, Lag-3 and Tigit as indicated by mean fluorescence intensity (MFI) in CD8$^+$ T cells from wild type (E8i-Cre$^-$Nr3c1$^{fl/fl}$) and E8i-Cre$^+$Nr3c1$^{fl/fl}$ mice (n=6-7). Data are representative of 3 independent experiments. TILs were isolated and activated with PMA/ionomycin (FIG. 11C, FIG. 11F) and with OVA$_{257-264}$ (SIINFEKL) (FIG. 11D, FIG. 11E) in the presence of Golgi Plug and Golgi Stop for 4 hr prior to extracellular and intracellular staining and analysis by flow cytometry. FIG. 11C) Summary plot showing cytokine production in CD8$^+$ TILs from wild type (E8i-Cre$^-$Nr3c1$^{fl/fl}$) and E8i-Cre$^+$Nr3c1$^{fl/fl}$ mice (n=9-10) following polyclonal activation. Data are pooled from 2 independent experiments. FIG. 11D) Summary plot showing poly-functionality of CD8$^+$ TILs from wild type (E8i-Cre$^-$Nr3c1$^{fl/fl}$) and E8i-Cre$^+$Nr3c1$^{fl/fl}$ mice (n=9-10). Data are pooled from 2 independent experiments. FIG. 11E) Summary plots representing cytokine production in Tim3$^+$PD1$^+$ CD8$^+$ TILs from wild type (E8i-Cre$^-$Nr3c1$^{fl/fl}$) and E8i-Cre$^+$Nr3c1$^{fl/fl}$ mice. Data are pooled from 2 independent experiments (n=9-10). FIG. 11F) Summary plots representing IL10 production in CD8+ TILs from wild type (E8i-Cre−Nr3c1$^{fl/fl}$) and E8i-Cre+Nr3c1$^{fl/fl}$ mice (n=5). FIG. 11G) Summary plots representing Ki67+ CD8+ TILs from wild type (E8i-Cre−Nr3c1$^{fl/fl}$) and E8i-Cre+Nr3c1$^{fl/fl}$ mice (n=8). FIG. 11H) Summary plots representing absolute number of CD8+ TILs from wild type (E8i-Cre−Nr3c1$^{fl/fl}$) and E8i-Cre+Nr3c1$^{fl/fl}$ mice (n=6). FIG. 11I) Summary plots representing the frequency of CD4+ T cells expressing checkpoint receptors in wild type (E8i-Cre−Nr3c1$^{fl/fl}$) and E8i-Cre+Nr3c1$^{fl/fl}$ mice (n=6-7). FIG. 11J) Summary plots of the MFI of checkpoint receptors on CD4+ T cells in WT and E8i-Cre+Nr3c1$^{fl/fl}$ mice (n=6-7). NS is not significant, *p<0.05, p<0.01, *p<0.001, two-tailed Student's t-test. Mean±SEM are shown.

FIGS. 12A-12E—GR binding sites and open chromatin in the loci of checkpoint receptors and IL10. Overlay of ChTP-seq data of GR (Jubb et al., 2017) and ATAC-seq data of naive CD4+ cells induced with IL-27 (Karwacz et al., 2017) in the loci of (FIG. 12A) Havcr2 (Tim3) (FIG. 12B) Pdcd1 (PD1) (FIG. 12C) Lag3 (FIG. 12D) Tigit and (FIG. 12E) Il10.

FIGS. 13A-13D—Effects of glucocorticoid and IL-27 in CD8+ T cells. Naïve CD8+ T cells were cultured in vitro with anti CD3/CD28 in the presence of Dex (GC), IL-27, or GC+IL-27. Cells were harvested on Day 9 for analysis. FIG. 13A) Heatmap display of the pairwise Euclidean distance between samples calculated for all genes. FIG. 13B) Venn plots showing the differentially expressed upregulated (left panel) and downregulated (right panel) genes between GC (Dex), IL-27, or GC+IL-27 treated cells relative to the control. FIG. 13C) Quantitative RT-PCR analysis of Prdm1, Nfil3, and Tcf7 mRNA expression in the Ctrl, GC, IL-27, or GC+IL-27 treated cells. NS is not significant, *p<0.05, ****p<0.0001. Ordinary one-way ANOVA (Tukey's multiple comparisons test). Mean±SEM are shown. FIG. 13D) Kolmogorov Smirnov one-sample curve (Tingey, 1951) showing overlap of genes down-regulated by GC+IL-27 with genes expressed in Tim-3−PD-1− CD8+TILs (p=5.5× $10^{-16}$), and genes up-regulated by GC+IL-27 with Tim-3+ PD-1+CD8+ TILs (p=7.7×$10^{-16}$).

FIGS. 14A-14C—Monocyte/macrophage are the chief source of glucocorticoid in the TME. FIG. 14A) MC38-Ova tumor explants were cultured in 48 well plates in the presence or absence of metyrapone. Supernatants were harvested after 24 hrs and the level of corticosterone was evaluated by ELISA. *p<0.05, P<0.01, Ordinary one-way ANOVA (Tukey's multiple comparisons test). Mean±SEM are shown. b and c) Lin-CD45+CD24− monocyte/macrophages were isolated from MC38-Ova tumors and FIG. 14B) RNA extracted for examination of the expression of the enzymes involved in steroid biogenesis by quantitative RT-PCR (FIG. 14C) cultured in the presence or absence of metyrapone. Supernatants were harvested after 24 hrs and the level of corticosterone was evaluated by ELISA. **p<0.0001, two-tailed Student's t-test. Mean±SEM are shown.

FIGS. 15 A-15B—FIG. 15A) schematic showing isolation and sorting of CD8+ T cells from a mouse tumor model (see, e.g., Singer et al., 2016). FIG. 15B) Heatmap showing differential gene expression between CD8+ TILs (tumor infiltrating lymphocytes). Dysfunction increases from DN to DP T cells.

FIGS. 16A-16B—Gradient of glucocorticoid receptor (nr3c1; GR) expression in CD8+ TILs. FIG. 16A-16B) TILs were harvested from mice bearing MC38-Ova colon carcinoma (FIG. 16A) or from human colorectal carcinomas (B FIG. 16) for the examination of glucocorticoid receptor (GR) expression by intracellular staining. Representative histograms show GR expression in the indicated CD8+ TILs populations. Summary plots show the mean fluorescence intensity (MFI) of GR expression in the indicated populations.

FIG. 24—Graphs showing that the effects of loss of GR are CD8+ T cell intrinsic shown by transfer of T cells to the tumor mouse.

FIG. 33A) Representative histograms of GR expression and summary data of mean fluorescence intensity (MFI) in the indicated CD8+ TILs populations. (n=5) FIG. 33B) Representative histograms of GR expression and summary data of MFI in OVA-specific CD8+ TILs. (n=5) FIG. 33C) Representative histograms of GR expression and summary data of MFI in CD8+ TILs. Data are normalized to the expression level in Tim-3−PD-1− CD8+ TILs. (n=7) FIG. 33D) tSNE plot showing projection of a (I) GC signature, (II) naïve CD8+T cell signature, (III) CD8+ T cell dysfunction signature onto the single-cell RNA profiles of CD8+ TILs (Singer et al., 2016). The contour marks cells showing highest expression and the color scale indicates low (blue) to high (red) expressing cells. (IV) Each cell in the dataset was scored for the three normalized signatures: GC, Naïve, and Dysfunction. Cells were then sorted based on their expression of the glucocorticoid signature from low (blue) to high (red) (x-Axis). The y-axis indicates the naive (blue) and dysfunction (red) signature score for each of the sorted cells. Moving average (shaded area) and smoothing conditional means (solid line) was used to aid visualization. *p<0.05, p<0.01, *p<0.001, ****p<0.0001. One-way ANOVA (Tukey's multiple comparisons test) or unpaired Student's t test. Mean±SEM is shown.

FIG. 34A) Representative flow cytometry data and summary plots of the frequency and MFI of the indicated cytokines following polyclonal activation (n=5), FIG. 34B and FIG. 34C) Representative flow cytometry data and summary plots of the frequency and MFI of the indicated checkpoint receptors (n=5 for B), (n=6 for C), *p<0.05, p<0.01, *p<0.001, ****p<0.0001, unpaired Student's t test. Mean SEM is shown.

FIGS. 35A-35H—Glucocorticoid signaling regulates effector differentiation in CD8+ TILs. FIG. 35A) MC38-Ova$^{dim}$ was implanted into WT (E8i-Cre$^-$Nr3c1$^{fl/fl}$) and E8i-Cre$^+$Nr3c1$^{fl/fl}$ mice (n=8-9). Mean tumor growth is shown, *p<0.001, linear mixed model. Data are representative of 3 independent experiments. FIGS. 35B-35G) TILs were harvested from mice bearing MC38-Ova$^{dim}$ at early (size 40-60 mm$^2$) and intermediate (size 120-150 mm$^2$) stages of tumor progression as determined by the growth observed in WT controls. FIG. 35B) Representative flow cytometry data and summary plots of the frequency of OVA-specific CD8+ TILs at early (n=7) and intermediate (n=4) stages. (FIGS. 35C-35E) TILs were activated with OVA$_{257-264}$ followed by intracellular staining. FIG. 35C) Representative flow cytometry data and summary plots of the frequency of the indicated cytokines in CD8+ TILs at early (n=7) and intermediate (n=9-10) stages. Data are pooled from 2 independent experiments for the intermediate stage. FIG. 35D) Representative flow cytometry data and summary plot of frequency of CD107a+ GzmB+ CD8+ TILs at early (n=7) and intermediate (n=6) stages. FIG. 35E) Representative flow cytometry data and summary plot of frequency of IL10-producing CD8+ TILs at early (n=7) and intermediate (n=5) stages. FIG. 35F) Representative flow cytometry data and summary plot of frequency of TCF-1+ cells within Ova-specific CD8+ TILs at early (n=7) and intermediate (n=4) stages. FIG. 35G) Representative flow cytometry data and summary plot of frequency of checkpoint receptor expressing CD8+ TILs at early (n=7) and intermediate (n=6-7) stages. NS, not significant, p<0.01, ***p<0.001, unpaired Student's t-test. Mean±SEM are shown. FIG. 35H) Experimental design: congenically marked WT (blue) and E8i-Cre$^+$Nr3c1$^{fl/fl}$ (red) CD8+ T cells were transferred to Rag$^{-/-}$ recipients along with WT CD4+ T cells (green). MC38-Ova$^{dim}$ was implanted 2 days post T cell transfer. TILs were harvested at the intermediate stage of tumor growth and analyzed (n=6). NS, not significant, *p<0.05, p<0.01, *p<0.001, ****p<0.0001, unpaired Student's t-test or paired Student's t-test (H). Mean±SEM are shown.

FIGS. 36A-36F—Glucocorticoid signaling transactivates checkpoint receptor and IL-10 expression and induces T cell dysfunction genes. (FIGS. 36A-36E) Luciferase activity in 293T cells transfected with pGL4.23 or pGL4.10 luciferase reporters for the loci of the indicated checkpoint receptors or IL10 together with either empty vector (control) or vector encoding Nr3c1. Cells were treated with GC (Dex) after 24 h. Firefly luciferase activity was measured 48 h after transfection and is presented relative to constitutive Renilla luciferase activity. NS, not significant, ****p<0.0001, two-way ANOVA (Tukey's multiple comparisons test). Data are mean±SEM and are representative of 2 independent experiments. FIG. 36F) Volcano plot showing the overlap of genes suppressed by GC (Dex) with genes expressed in Tim-3$^-$ PD-1$^-$ CD8+ TILs (p=1.4.0×10$^{-26}$) and genes induced by GC (Dex) with Tim-3$^+$PD-1$^+$ CD8+ TILs (p=9.4×10$^{-52}$) (Mean-rank Gene Set Test).

FIGS. 37A-37H—Intra-tumoral production of glucocorticoid affects tumor progression. FIG. 37A) Pregnenolone levels in the indicated tissues were quantified by ELISA (n=5). FIG. 37B) qPCR analysis of Cyp11a1 mRNA expression in the indicated cells. Data are pooled from 2 independent experiments (n=5-6). FIG. 37C) MC38-Ova$^{dim}$ was implanted in LysMCre$^-$ Cyp11a1$^{fl/fl}$ and LysMCre$^+$ Cyp11a1$^{fl/fl}$ mice (n=5). Mean tumor growth is shown, *p<0.001, linear mixed model. Data are representative of 2 independent experiments. FIG. 37D) Analysis of CD8+ TILs at early stage of tumor development (tumor size 40-60 mm$^2$) (n=5), FIG. 37E) Corticosterone levels were quantified by ELISA (n=5). FIG. 37F) Lin-CD45+CD24$^-$ monocyte-macrophage lineage cells were isolated from MC38-Ova$^{dim}$ tumors and cultured in the presence or absence of Metyrapone. At 24 hrs corticosterone levels were quantified by ELISA (n=5). FIG. 37G) MC38-Ova$^{dim}$ was implanted in WT mice (n=5). Metyrapone or vehicle control was administered intra-tumorally on Days 5, 6, 7 and 9 post-tumor implantation. Mean tumor growth is shown *p<0.001, linear mixed model. Data are representative of 2 independent experiments. FIG. 37H) MC38-Ova$^{dim}$ was implanted in WT mice (n=5). Metyrapone or vehicle control was administered intra-tumorally on Days 5 and 6 post-tumor implantation. 24 hrs later, TILs were harvested (tumor size 55-65 mm$^2$ in both groups) and analyzed by flow cytometry. Summary plots show the frequency of the indicated populations. ND, not detected, NS, not significant *p<0.05 p<0.01, *p<0.001, ****p<0.0001, unpaired Student's t-test or One-way ANOVA (Tukey's multiple comparisons test). Data are mean±SEM.

FIGS. 38A-38D—Glucocorticoid signaling in CD8+ T cells affects responses to immunotherapy. FIG. 38A) Correlation of Cyp11a1 mRNA expression with survival in patients with colon adenocarcinoma (COAD) and stomach adenocarcinoma (STAD) using TIMER. FIG. 38B) MC38-Ova$^{dim}$ was implanted into WT (E8i-Cre$^-$Nr3c1$^{fl/fl}$) and E8i-Cre$^+$Nr3c1$^{fl/fl}$ mice (n=7-8). Anti-PD1 was administered i.p on Days 5, 8 and 11. Mean tumor growth is shown. NS, not significant, ****p<0.0001, linear mixed model. FIG. 38C) MC38 was implanted into WT mice. On Day 7 post-tumor implantation, mice were treated with GC (Dex) or anti-PD1+anti-CTLA-4 or both. Antibody was administered bi-weekly for a total of 5 treatments (n=6-10). GC was administered for 10 consecutive days. NS, not significant, *p<0.05, ***p<0.001, linear mixed model. FIG. 38D) tSNE plot of single-cell TILs data from melanoma patients treated with anti-PD-1, anti-CTLA-4, or anti-CTLA-4+anti-PD-1 (Sade-Feldman et al., 2018). I) CD8 expression, II) CD4 expression, III) pre- (orange) versus post- (purple) treatment samples, IV) Responder (red) versus non-responder (blue), V) Projection of CD8+ TILs dysfunction signature, VI) Projection of the GC signature. VII) Box plots show the GC signature score in responder versus non-responders in pre- ($p=3.246 \times 10^{-13}$) and post- ($p<2.2 \times 10^{-16}$) treatment samples (Welch Two Sample t-test). The lower and upper hinges correspond to the first and third quartiles. The upper and lower whiskers extend from the hinge to the largest and smallest value no further than 1.5 times the distance between the first and third quartiles, respectively. Data beyond the end of the whiskers are outlying points and are not plotted individually.

FIGS. 39A-39E—Glucocorticoid and IL-27 signaling co-operate to regulate CD8+ T cell phenotype in the TME. FIGS. 39A-39C) Naïve CD8+ T cells were cultured in vitro with anti CD3/28 and GC (dexamethasone), IL-27, or GC+IL-27. Cells were harvested on Day 9 and gene expression analyzed by RNA sequencing. FIG. 39A) Principle component analysis (PCA) of Ctrl, GC, IL-27, and GC+IL-27 treated CD8+ T cells. The percentage of explained variance for each principal component is indicated. FIG. 39B) Mean delta Euclidean distance between the GC, IL-27, or GC+IL-27-treated groups to the control group, adjusted p-values were calculated using one-way ANOVA ($p=9.89 \times 10^{-09}$), followed by Tukey's multiple comparisons test, *p<0.05, ****p<0.001. FIG. 39C) Heatmap of DE genes between Ctrl and GC+IL-27 treatment. Tick marks indicate selected genes associated with CD8+ T cell dysfunction. FIG. 39D) CD8+ T cells from either WT (E8i-Cre$^-$Nr3c1$^{fl/fl}$), E8i-Cre$^+$Nr3c1$^{fl/fl}$, WSX1$^{-/-}$ and/or E8i-Cre$^+$Nr3c$^{fl/fl}$ WSX1$^{-/-}$ (DKO) mice and CD4+ T cells from WT mice were transferred to Rag$^{-/-}$ mice (n=5-6/group), MC38-Ova$^{dim}$ cells were implanted two days post T cell transfer. Mean tumor growth is shown. *p<0.05, *p<0.001, linear mixed model. Data are representative of 2 independent experiments. FIG. 39E) qRT-PCR analysis of IL-27 (p28 and Ebi3) mRNA expression in the indicated cells. Data are pooled from 2 independent experiments. p<0.01, *p<0.001, **p<0.0001. One-way ANOVA (Tukey's multiple comparisons test). Data are mean±SEM.

FIGS. 40A-40F—(related to FIG. 33). Expression of glucocorticoid receptor (GR) and signaling in CD8+ T cells in cancer and chronic viral infection. FIG. 40A) Gene expression value of Nr3c1 in CD8+ TILs from CT26 colon carcinoma (Singer et al., 2016). NS, not significant, p<0.01. One-way ANOVA. FIG. 40B) GR expression in CD8+ TILs harvested from mice bearing B16F10 melanoma (tumor size 100-120 mm$^2$) (n=5). Representative histograms show GR expression and summary plots show the MFI of GR expression in the indicated populations. p<0.01, *p<0.001, **p<0.0001. One-way ANOVA (Tukey's multiple comparisons test). Mean±SEM is shown. FIG. 40C) tSNE plot showing expression of the GC signature onto the single-cell RNA profiles of CD8+ TILs (Singer et al., 2016) as in FIG. 1D. As background to assess significance, Applicants used a scheme that controls for expression of the signature using expression-level matched subsets of genes. The p-value for each cell is calculated by generating random sets of signatures that are composed of genes with a similar average and variance expression levels as the original signature. This was followed by comparing the generated scores to the score obtained from the original signature. Cells that had a statistically significant score (FDR-adjusted p<0.05) were marked by '+'. FIG. 40D) tSNE plot showing the expression of indicated genes in single-cell CD8+ TILs data (Singer et al., 2016). FIG. 40E) tSNE plot showing the expression of Mt1 and Nfil3 in single-cell CD8+ TILs data (Singer et al., 2016). FIG. 40F) tSNE plot showing projection of the GC signature and CD8+ T cell dysfunction signature in single-cell CD8+ T cell data from chronic LCMV infection (Chen et al., 2019).

FIGS. 41A-41G—(related to FIG. 34). Effect of synthetic and natural glucocorticoids on CD8+ T cells. Murine (FIG. 41A, FIG. 41C, FIG. 41D) (n=5) or human naïve CD8+ T cells (FIG. 41B) (n=6) were repeatedly activated in the presence or absence of GC (Dex). FIG. 41A, FIG. 41B) Representative flow cytometry data showing Tim-3 and PD-1 expression. FIG. 41C) Summary plots showing the frequency of viable CD8+ T cells post-treatment with GC. FIG. 41D) Summary plots showing the division index of CD8+ T cells. FIG. 41E) Naïve CD8+ T cells from WT mice were activated in the presence or absence of natural GC (corticosterone) as in A. Representative flow cytometry data show the frequency of checkpoint receptor expressing cells (n=5). FIG. 41F) Expression of Nr3c2 in T cells was quantified by qPCR. MC38-Ova$^{dim}$ cell-line was used as the positive control. FIG. 41G) Heatmap of differentially expressed genes in WT (Nr3c1$^{fl/fl}$E8iCre) or Nr3c1$^{fl/fl}$ E8iCre$^+$ CD8+ T cells activated in the presence or absence of GC (Dex) for 72 hr. Tick marks indicate selected known GC target genes. ND, not detected, NS, not significant. *p<0.001, **p<0.0001, Student's t-test. Mean±SEM are shown.

FIG. 42A) Frequency of T cells in the thymus of Nr3c1$^{fl/fl}$ E8iCre (WT) and Nr3c1$^{fl/fl}$ E8iCre$^+$ mice. FIG. 42B) Frequency of T cells in the spleen of Nr3c1$^{fl/fl}$E8iCre-(WT) and Nr3c11$^{fl/fl}$ E8iCre$^+$ mice. FIG. 42C) Frequency of naïve and activated CD8$^+$ and CD4$^+$ T cells.

FIG. 42D) in the spleen of Nr3c11$^{fl/fl}$ E8iCre (WT) and Nr3c1$^{fl/fl}$ E8iCre$^+$ mice. E) MFI of GR expression on T cells from Nr3c1$^{fl/fl}$ E8iCre and Nr3c1$^{fl/fl}$ E8iCre$^+$ mice. NS, not significant. **p<0.01, One-way ANOVA (Tukey's multiple comparisons test). Mean±SEM are shown.

FIGS. 43A-43J—(related to FIG. 35). Glucocorticoid signaling regulates effector differentiation in CD8+ TILs. FIG. 43A) B16F10 was implanted into WT (Nr3c1'E8iCre) and Nr3c1$^{fl/fl}$ E8iCre$^+$ mice (n=5). Mean tumor growth is shown. *p<0.001, linear mixed model. Data are representative of two independent experiments. FIGS. 43B-43J) TILs were isolated from WT (Nr3c1$^{fl/fl}$E8iCre) and Nr3c1$^{fl/fl}$ E8iCre$^+$ mice bearing MC38—Ova$^{dim}$ tumors at early (size 40-60 mm$^2$) and intermediate (size 120-150 mm$^2$) stages of tumor progression as determined by growth in WT controls. FIG. 43B) Summary plot showing cytokine production in CD8+ TILs at early (n=7) and intermediate (n=9-10) stages of tumor progression (polyclonal activation). Data are pooled from two independent experiments for the intermediate stage analysis. FIG. 43C) Summary plot showing poly-functionality of CD8+ TILs following activation with OVA$_{257-264}$ at early (n=7) and intermediate (n=9-10) stages of tumor progression. Data are pooled from two independent experiments for the intermediate stage analysis. FIG. 43D) Summary plot showing IL-10 production in CD8+ TILs following polyclonal activation at early (n=7) and intermediate (n=5) stages of tumor progression. FIG. 43E) Summary plot of the MFI of checkpoint receptors at the intermediate stage of tumor progression, (n=6-7). FIG. 43F) Summary plots of cytokine production in Tim3$^+$PD1$^+$ CD8$^+$ TILs following activation with OVA$_{257-264}$ at the intermediate stage of tumor progression (n=9-10). Data are pooled from two independent experiments. FIG. 43**G) Summary plots of Ki67$^+$ CD8$^+$ TILs at the intermediate stage of tumor progression (n=8).

FIG. 43H) Summary plots showing the absolute number of CD8$^+$ TILs at the intermediate stage of tumor progression (n=6). FIG. 43I) Summary plots representing the frequency of CD4$^+$ T cells expressing checkpoint receptors at the intermediate stage of tumor progression (n=6-7). FIG. 43J) Summary plots of the MFI of checkpoint receptors on CD4$^+$ T cells at the intermediate stage of tumor progression, (n=6-7). NS, not significant, *p<0.05, p<0.01, *p<0.001, unpaired Student's t-test. Data are mean±SEM.

FIGS. 44A-44G—(related to FIG. 36). Relationship of the GR with checkpoint receptor and IL10 expression. FIG. 44A) Correlation of NR3C1 mRNA with checkpoint receptor and IL10 mRNA in colon adenocarcinoma patients using TIMER. FIGS. 44B-44F) Overlay of GR ChIP-seq data (Oh et al., 2017) and ATAC-seq data of dysfunctional CD8$^+$ T cells (Philip et al., 2017) in the loci of FIG. 44B) Havcr2 (Tim3), FIG. 44C) Pdcd1 (PD1), FIG. 44D) Lag3, FIG. 44E) Tigit, and FIG. 44F) Il10. FIG. 44G) Kolmogorov Smirnov one-sample curve showing overlap of the genes suppressed by GC (dexamethasone) with genes expressed in Tim-3$^-$ PD-1$^-$ CD8$^+$ TILs (red) (p=1.4×10$^{-26}$) and the genes induced by GC with Tim-3$^+$PD-1$^+$ CD8$^+$ TILs (blue) (p=9.4×10$^{-52}$).

FIGS. 45A-45D—(related to FIG. 37). Steroid biosynthesis in the TME. FIG. 45A) MC38-Ova$^{dim}$ tumor explants were cultured in the presence or absence of Metyrapone. Supernatants were harvested after 24 hr and the level of corticosterone was evaluated by ELISA (n=4). FIG. 45B) Corticosterone levels were measured in the tumor tissue and spleen of Cyp11a1$^{fl/fl}$LysMCreor Cyp11a1$^{fl/fl}$LysMCre$^+$ mice. *p<0.05, *p<0.001, NS, not significant. Two-way ANOVA (Tukey's multiple comparisons test). Mean i SEM are shown. FIG. 45C) MC38-Ova$^{dim}$ was implanted in Cyp11a1$^{fl/fl}$LysMCre and Cyp11a1$^{fl/fl}$LysMCre$^+$ mice. Corticosterone (2.5 mg/kg) was administered intra-tumorally on Days 5, 6, 7 and 9 and tumor progression studied (n=5). Mean tumor growth is shown, p<0.01, linear mixed model. FIG. 45D) Lin-CD45$^+$CD24$^-$ monocyte-macrophage lineage cells were isolated from MC38-Ova$^{dim}$ tumors (tumor size 70-100 mm$^2$). Expression of the enzymes involved in GC biogenesis in the isolated cells was determined by qPCR. ND is not detected.

FIGS. 46A-46C—(related to FIG. 39). Glucocorticoid and IL-27-induced gene programs in CD8$^+$ T cells. (FIGS. 46A-46C) Naïve CD8$^+$ T cells were cultured in vitro with anti CD3/CD28 in the presence of Dex (GC), IL-27, or GC+IL-27. Cells were harvested on Day 9 for analysis. FIG. 46A) Heatmap display of the pairwise Euclidean distance between samples calculated for all genes. FIG. 46B) Venn plots showing the differentially expressed up (left panel) and down (right panel) genes between GC (Dex), IL-27, or GC+IL-27-treated cells relative to the control. FIG. 46C) Kolmogorov-Smirnov one-sample curve showing overlap of genes suppressed by GC+IL-27 with genes expressed in Tim-3$^-$PD-1$^-$ CD8$^+$ TILs (red) (p=5.5×10$^{-16}$), and genes induced by GC+IL-27 with Tim-3$^+$PD-1$^+$ CD8$^+$ TILs (blue) (p=7.7×10$^{-16}$).

Figure 5F:
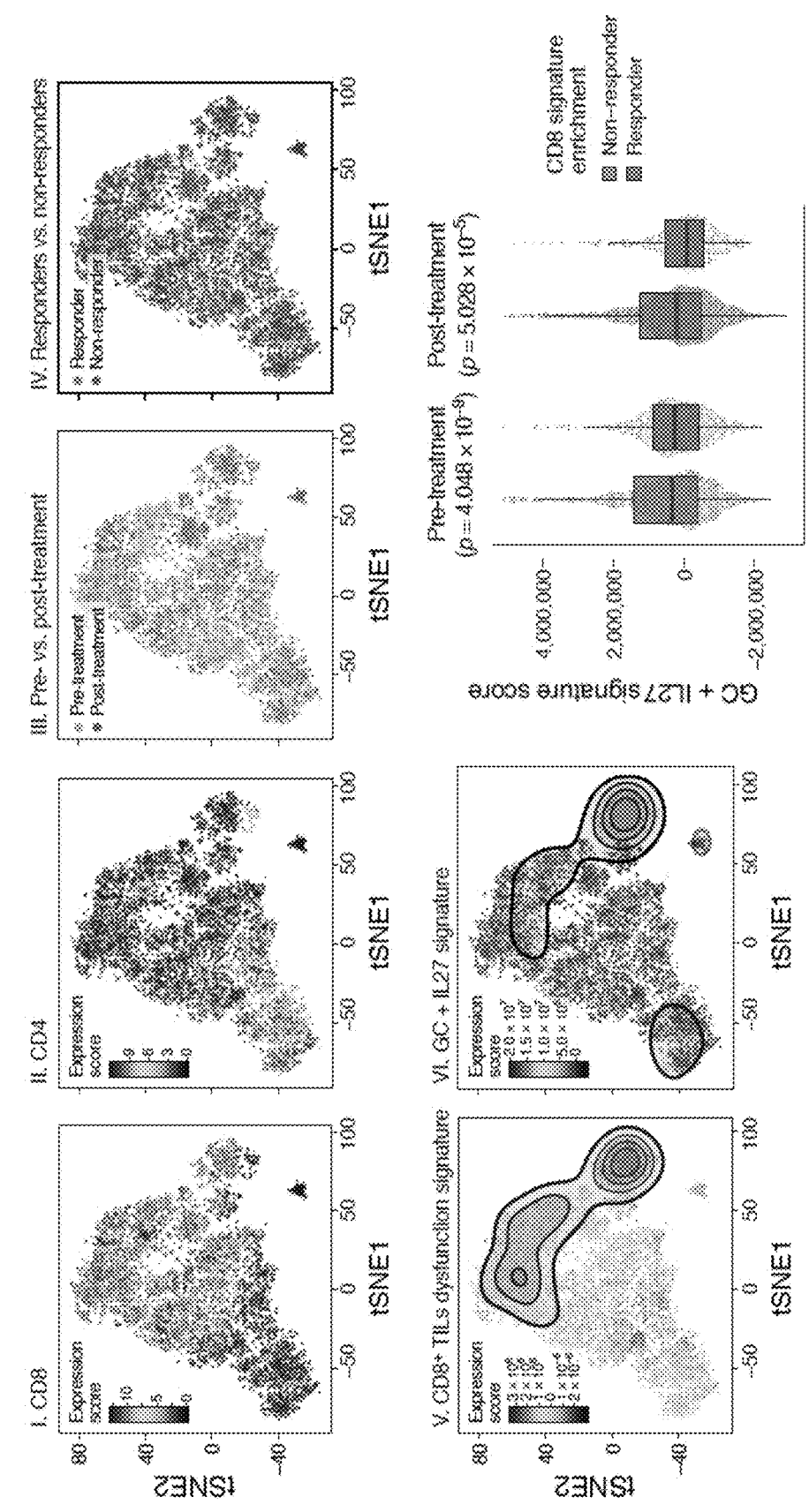

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2nd edition (1989) (Sambrook, Fritsch, and Maniatis); Molecular Cloning: A Laboratory Manual, 4th edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R.I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a" "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

Reference is made to PCT/US2013/067481, filed Oct. 30, 2013 and published as WO2014070874A1; PCT/US2016/056177, filed Oct. 7, 2016 and published as WO2017069958A2; PCT/US2016/059507, filed Oct. 28, 2016 and published as WO2017075478A2; PCT/US2017/050469, filed Sep. 7, 2017 and published as WO2018049025A2; PCT/US2018/042069, filed Jul. 13, 2018 and published as WO2019/014581; and PCT/US2018/053791, filed Oct. 1, 2018 and published as WO2019068099A1; and U76/396,461, filed Apr. 26, 2019, claiming priority to U.S. Provisional Application Nos. 62/663,251, filed Apr. 26, 2018 and 62/663,520, filed Apr. 27, 2018. Reference is also made to Acharya, et al., 2019, An endogenous glucocorticoid-cytokine signaling circuit promotes CD8+ T cell dysfunction in the tumor microenvironment, bioRxiv 799759; doi: doi.org/10.1101/799759.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide methods and compositions for modulating immune responses and immune states. Applicants have identified glucocorticoid signaling pathways for modulating T cell balance between dysfunctional and/or exhaustive T cell states and activated T cell states. As used herein the terms "dysfunctional" and "exhausted" are used interchangeably. Specifically, Applicants identified that glucocorticoid synthesis in the tumor microenvironment can be targeted to enhance immunity and/or decrease T cell dysfunction (e.g., to enhance anti-tumor immunity). In certain embodiments, metyrapone is administered to a subject in need of enhanced immunity (e.g., cancer). In certain embodiments, metyrapone is co-administered with checkpoint blockade therapy (CPB). In certain embodiments, in addition to targeting glucocorticoid synthesis, IL-27 or downstream targets of glucocorticoid and IL-27 signaling as further described herein can be modulated. Metyrapone can modulate glucocorticoid signaling in the tumor microenvironment, but may not modulate all pathways resulting in T cell dysfunction. In certain embodiments, metyrapone is co-administered with one or more agents targeting IL-27 signaling or downstream targets of glucocorticoid and IL-27 signaling. In certain embodiments, modulating glucocorticoid signaling encompasses modulating glucocorticoid binding to and activating glucocorticoid receptor, as well as, modulating any downstream targets activated or repressed as a result of activated GR. In certain embodiments, modulating IL-27 signaling encompasses modulating IL-27 binding to IL-27 receptor, as well as, modulating any downstream targets activated or repressed as a result. As used herein "modulating glucocorticoid and IL-27 signaling" may refer to modulation of either pathway individually, but also modulating the targets specific to the combination.

Embodiments disclosed herein also provide for methods of detecting gene signatures and biomarkers for use in diagnostic assays or for screening of therapeutic agents (e.g., signatures of the most dysfunctional T cells and agents capable of inhibiting glucocorticoid synthesis). Embodiments disclosed herein also provide for cell compositions for use in screening of therapeutic agents and identifying therapeutic targets for modulating T cell dysfunction.

Identifying signals in the tumor microenvironment (TME) that shape $CD8^+$ T cell phenotype can inform novel therapeutic approaches for cancer. Here, Applicants identified a gradient of increasing glucocorticoid receptor (GR) (also known as Nr3C1) expression and signaling from naive to dysfunctional $CD8^+$ tumor-infiltrating lymphocytes (TILs). As used herein "glucocorticoid signaling" refers to glucocorticoid binding to and activating glucocorticoid receptor (GR), as well as, all downstream targets activated or repressed as a result of the binding. Conditional deletion of the GR in $CD8^+$ TILs improved effector differentiation, reduced expression of the transcription factor TCF-1, and inhibited the dysfunctional phenotype, culminating in tumor growth inhibition. GR signaling transactivated the expression of multiple checkpoint receptors and promoted the induction of dysfunction-associated genes upon T cell activation. In the TME, monocyte-macrophage lineage cells produced glucocorticoids and genetic ablation of steroidogenesis in these cells as well as localized pharmacologic inhibition of glucocorticoid biosynthesis improved tumor growth control. Active glucocorticoid signaling associated with failure to respond to checkpoint blockade in both pre-clinical models and melanoma patients. Thus, endogenous steroid hormone signaling in $CD8^+$ TILs promotes dysfunction, with important implications for cancer immunotherapy.

Applicants previously defined a gene signature for dysfunctional $CD8^+$ tumor-infiltrating lymphocytes (TILs) based on the differential gene expression of $CD8^+$ TIL populations that exhibit distinct effector capacities (Sakuishi et al., 2010; Singer et al., 2016). Specifically, the expression of the checkpoint receptors Tim-3 and PD-1 distinguishes $CD8^+$ TILs subsets with different degrees of function: $Tim-3^+PD-1^+$ $CD8^+$ TILs are severely dysfunctional, $Tim-3^-PD-1^+$ $CD8^+$ TILs are partially dysfunctional with intermediate effector function, and $Tim-3^-PD-1^-$ $CD8^+$ TILs exhibit strong effector function (Fourcade et al., 2010; Sakuishi et al., 2010), with each of these populations exhibiting distinct transcriptional profiles (Singer et al., 2016). From the transcriptome data of these subsets of CD8$^+$ TILs, Applicants identified Nr3c1, the gene encoding the glucocorticoid receptor (GR), as being most highly expressed in severely dysfunctional Tim-3$^+$PD-1$^+$ CD8$^+$ TILs. Glucocorticoids (GC), steroid hormones derived from the metabolic breakdown of cholesterol, bind to the GR, which resides in the cytosol in its inactive state and translocates to the nucleus upon ligand binding. In the nucleus, the GR can regulate gene expression either directly by binding to the promoter of a given target gene or indirectly by affecting the binding of other transcription factors (TFs) to the promoter regions of their respective targets (Oakley and Cidlowski, 2013). Both natural and synthetic glucocorticoids suppress a number of inflammatory indices and have been used clinically since the 1950s for treating excessive inflammation in patients with asthma and autoimmune diseases. Currently, glucocorticoids are routinely used to manage excessive inflammation in cancer patients treated with checkpoint blockade (Kumar et al., 2017).

Despite their widespread use, surprisingly little is known regarding the molecular circuitry by which glucocorticoids suppress immune responses (Cain and Cidlowski, 2017; Munck et al., 1984). The prevailing dogma attributes the anti-inflammatory effects of glucocorticoids to transrepression, whereby the GR inhibits the function of TFs that have key roles in driving pro-inflammatory responses. The GR binds to and directly interferes with AP-1 (Jonat et al., 1990; Yang-Yen et al., 1990). The GR can also interfere with NF-κB either directly or indirectly by modulating IκBα (Auphan et al., 1995; Rhen and Cidlowski, 2005; Scheinman et al., 1995; Smoak and Cidlowski, 2004). However, glucocorticoids have also been associated with enhanced expression of anti-inflammatory cytokines, such as IL10 (Barrat et al., 2002), raising the possibility that in addition to actively repressing pro-inflammatory gene expression, they may also promote suppression via transactivation of immune-suppressive genes.

Applicants show that activation of GR signaling in CD8$^+$ T cells promotes T cell dysfunction in the TME and that the GR transactivates the expression of the checkpoint receptors Tim-3, PD-1, and Lag-3, and of the anti-inflammatory cytokine IL-10. Accordingly, loss of GR in CD8$^+$ T cells results in tumor growth inhibition. Applicants further demonstrate that monocyte/macrophage lineage cells are a chief source of glucocorticoid in the TME, that reduced steroidogenesis is correlated with better survival in cancer patients, and that glucocorticoid signaling co-operates with IL-27 signaling to form an immunoregulatory circuit that promotes T cell dysfunction in the TME. As used herein "IL-27 signaling" refers to IL-27 binding to IL-27 receptor and the activation of all signaling pathways as a result of the binding. Activation of both glucocorticoid and IL-27 pathways results in T cells having a dysfunctional phenotype that recapitulates the most dysfunctional cells in vivo. Applicants have also discovered downstream targets of glucocorticoid and IL-27 activation that are transcriptionally distinct to the combination. High expression of the glucocorticoid+IL-27 signature correlates with failure to respond to checkpoint blockade in melanoma patients, highlighting the relevance of this immunoregulatory circuit in human disease.

In certain embodiments, modulating glucocorticoid signaling, IL-27 signaling and/or the expression or activity of downstream targets can be used to modulate an immune state. In certain embodiments, modulation of T cell dysfunction as described herein can promote tolerance or dampen an inappropriate, unwanted, or undesirable immune response, thereby permitting treatment of autoimmune disease and/or conditions associated with transplants (e.g., graft vs. host disease). In certain embodiments, modulation of T cell dysfunction as described herein can promote an enhanced immune response, thereby permitting treatment of chronic disease and/or conditions (e.g., cancer, infection). In certain embodiments, modulation of glucocorticoid and IL-27 signaling and/or downstream targets are used to treat diseases requiring a shift in T cell balance. In certain embodiments, modulation of glucocorticoid and IL-27 signaling and/or downstream targets are used to generate cells for adoptive cell transfer. In certain embodiments, immune cells are modulated, such that upon transfer an immune response is dampened (e.g., treating autoimmune diseases). In certain embodiments, immune cells are modulated, such that upon transfer an immune response is enhanced.

In certain embodiments, modulation of glucocorticoid and IL-27 signaling and/or downstream targets are used to generate dysfunctional cells that recapitulate in vivo dysfunctional cells. Embodiments disclosed herein provide for in vitro cell-based systems that faithfully recapitulate an in vivo dysfunctional phenotype and methods of generating and using the cell-based systems. In certain embodiments, dysfunctional cells are characterized by assaying dysfunctional markers as described herein. In certain embodiments, the cells can be used to screen for immunomodulators as described further herein.

Applicants have further discovered that the glucocorticoid receptor, Nr3C1, is dynamically regulated with TCR activation, i.e. downregulated with TCR activation and re-expressed when T cells return to resting state. In certain embodiments, glucocorticoid administration can be adjusted based on the T cell state. In certain embodiments, glucocorticoid administration is coordinated in cancer patients to ameliorate the effects of a cancer treatment and to avoid dampening an anti-tumor adaptive immune response. In certain embodiments, glucocorticoids can be administered when the glucocorticoid receptor is downregulated on T cells. In certain embodiments, metyrapone is administered when glucocorticoid is not administered.

Functional T Cell Immune States

In certain embodiments, the present invention provides for modulating immune states. In certain embodiments, T cell dysfunction is modulated. In particular embodiments, T cell dysfunction is modulated by targeting glucocorticoid synthesis. In certain embodiments, T cells can affect the overall immune state, such as other immune cells in proximity (e.g., by secreting IL-10). The term "immune cell" as used throughout this specification generally encompasses any cell derived from a hematopoietic stem cell that plays a role in the immune response. The term is intended to encompass immune cells both of the innate or adaptive immune system. The immune cell as referred to herein may be a leukocyte, at any stage of differentiation (e.g., a stem cell, a progenitor cell, a mature cell) or any activation stage. Immune cells include lymphocytes (such as natural killer cells, T-cells (including, e.g., thymocytes, Th or Tc; Th1, Th2, Th17, Thαβ, CD4$^+$, CD8$^+$, effector Th, memory Th, regulatory Th, CD4$^+$/CD8$^+$ thymocytes, CD4−/CD8− thymocytes, γδ T cells, etc.) or B-cells (including, e.g., pro-B cells, early pro-B cells, late pro-B cells, pre-B cells, large pre-B cells, small pre-B cells, immature or mature B-cells, producing antibodies of any isotype, T1 B-cells, T2, B-cells, naïve B-cells, GC B-cells, plasmablasts, memory B-cells, plasma cells, follicular B-cells, marginal zone B-cells, B-1 cells, B-2 cells, regulatory B cells, etc.), such as for instance, monocytes (including, e.g., classical, non-classical, or intermediate monocytes), (segmented or banded) neutrophils, eosinophils, basophils, mast cells, histiocytes, microglia, including various subtypes, maturation, differentiation, or activation stages, such as for instance hematopoietic stem cells, myeloid progenitors, lymphoid progenitors, myeloblasts, promyelocytes, myelocytes, metamyelocytes, monoblasts, promonocytes, lymphoblasts, prolymphocytes, small lymphocytes, macrophages (including, e.g., Kupffer cells, stellate macrophages, M1 or M2 macrophages), (myeloid or lymphoid) dendritic cells (including, e.g., Langerhans cells, conventional or myeloid dendritic cells, plasmacytoid dendritic cells, mDC-1, mDC-2, Mo-DC, HP-DC, veiled cells), granulocytes, polymorphonuclear cells, antigen-presenting cells (APC), etc.

As used throughout this specification, "immune response" refers to a response by a cell of the immune system, such as a B cell, T cell (CD4+ or CD8+), regulatory T cell, antigen-presenting cell, dendritic cell, monocyte, macrophage, NKT cell, NK cell, basophil, eosinophil, or neutrophil, to a stimulus. In some embodiments, the response is specific for a particular antigen (an "antigen-specific response"), and refers to a response by a CD4 T cell, CD8 T cell, or B cell via their antigen-specific receptor. In some embodiments, an immune response is a T cell response, such as a CD4+ response or a CD8+ response. Such responses by these cells can include, for example, cytotoxicity, proliferation, cytokine or chemokine production, trafficking, or phagocytosis, and can be dependent on the nature of the immune cell undergoing the response.

T cell response refers more specifically to an immune response in which T cells directly or indirectly mediate or otherwise contribute to an immune response in a subject. T cell-mediated response may be associated with cell mediated effects, cytokine mediated effects, and even effects associated with B cells if the B cells are stimulated, for example, by cytokines secreted by T cells. By means of an example but without limitation, effector functions of MHC class I restricted Cytotoxic T lymphocytes (CTLs), may include cytokine and/or cytolytic capabilities, such as lysis of target cells presenting an antigen peptide recognized by the T cell receptor (naturally-occurring TCR or genetically engineered TCR, e.g., chimeric antigen receptor, CAR), secretion of cytokines, preferably IFN gamma, TNF alpha and/or or more immunostimulatory cytokines, such as IL-2, and/or antigen peptide-induced secretion of cytotoxic effector molecules, such as granzymes, perforins or granulysin. By means of example but without limitation, for NMC class II restricted T helper (Th) cells, effector functions may be antigen peptide-induced secretion of cytokines, preferably, IFN gamma, TNF alpha, IL-4, IL5, IL-10, and/or IL-2. By means of example but without limitation, for T regulatory (Treg) cells, effector functions may be antigen peptide-induced secretion of cytokines, preferably, IL-10, IL-35, and/or TGF-beta. B cell response refers more specifically to an immune response in which B cells directly or indirectly mediate or otherwise contribute to an immune response in a subject. Effector functions of B cells may include in particular production and secretion of antigen-specific antibodies by B cells (e.g., polyclonal B cell response to a plurality of the epitopes of an antigen (antigen-specific antibody response)), antigen presentation, and/or cytokine secretion.

During persistent immune activation, such as during uncontrolled tumor growth or chronic infections, subpopulations of immune cells, particularly of CD8+ or CD4+ T cells, become compromised to different extents with respect to their cytokine and/or cytolytic capabilities. Such immune cells, particularly CD8+ or CD4+ T cells, are commonly referred to as "dysfunctional" or as "functionally exhausted" or "exhausted". As used herein, the term "dysfunctional" or "functional exhaustion" refer to a state of a cell where the cell does not perform its usual function or activity in response to normal input signals, and includes refractivity of immune cells to stimulation, such as stimulation via an activating receptor or a cytokine. Such a function or activity includes, but is not limited to, proliferation (e.g., in response to a cytokine, such as IFN-gamma) or cell division, entrance into the cell cycle, cytokine production, cytotoxicity, migration and trafficking, phagocytotic activity, or any combination thereof. Normal input signals can include, but are not limited to, stimulation via a receptor (e.g., T cell receptor, B cell receptor, co-stimulatory receptor). Unresponsive immune cells can have a reduction of at least 10%, 20%, 30%, 40%, 50%, 60%, 70%, 80%, 90%, 95%, or even 100% in cytotoxic activity, cytokine production, proliferation, trafficking, phagocytotic activity, or any combination thereof, relative to a corresponding control immune cell of the same type. In some particular embodiments of the aspects described herein, a cell that is dysfunctional is a CD8+ T cell that expresses the CD8+ cell surface marker. Such CD8+ cells normally proliferate and produce cell killing enzymes, e.g., they can release the cytotoxins perforin, granzymes, and granulysin. However, exhausted/dysfunctional T cells do not respond adequately to TCR stimulation, and display poor effector function, sustained expression of inhibitory receptors and a transcriptional state distinct from that of functional effector or memory T cells. Dysfunction/exhaustion of T cells thus prevents optimal control of infection and tumors. Exhausted/dysfunctional immune cells, such as T cells, such as CD8+ T cells, may produce reduced amounts of IFN-gamma, TNF-alpha and/or one or more immunostimulatory cytokines, such as IL-2, compared to functional immune cells. Exhausted/dysfunctional immune cells, such as T cells, such as CD8+ T cells, may further produce (increased amounts of) one or more immunosuppressive transcription factors or cytokines, such as IL-10 and/or Foxp3, compared to functional immune cells, thereby contributing to local immunosuppression. Dysfunctional CD8+ T cells can be both protective and detrimental against disease control. As used herein, a "dysfunctional immune state" refers to an overall suppressive immune state in a subject or microenvironment of the subject (e.g., tumor microenvironment). For example, increased IL-10 production leads to suppression of other immune cells in a population of immune cells.

CD8+ T cell function is associated with their cytokine profiles. It has been reported that effector CD8+ T cells with the ability to simultaneously produce multiple cytokines (polyfunctional CD8+ T cells) are associated with protective immunity in patients with controlled chronic viral infections as well as cancer patients responsive to immune therapy (Spranger et al., 2014, J. Immunother. Cancer, vol. 2, 3). In the presence of persistent antigen CD8+ T cells were found to have lost cytolytic activity completely over time (Moskophidis et al., 1993, Nature, vol. 362, 758-761). It was subsequently found that dysfunctional T cells can differentially produce IL-2, TNFa and IFNg in a hierarchical order (Wherry et al., 2003, J. Virol., vol. 77, 4911-4927). Decoupled dysfunctional and activated CD8+ cell states have also been described (see, e.g., Singer, et al. (2016). A Distinct Gene Module for Dysfunction Uncoupled from Activation in Tumor-Infiltrating T Cells. Cell 166, 1500-1511 e1509; WO/2017/075478; and WO/2018/049025).

Genes and Polypeptides

In certain embodiments, genes are modulated. Reference to a gene is intended to include both the gene and gene product (e.g., protein). All gene name symbols refer to the gene as commonly known in the art. The examples described herein that refer to the mouse gene names are to be understood to also encompasses human genes, as well as genes in any other organism (e.g., homologous, orthologous genes). Mouse gene symbols are generally italicized, with only the first letter in upper-case (e.g., 1127). Mouse protein symbols are generally not italicized, and all letters are in upper-case (e.g., IL-27). As used herein mouse gene symbols may be shown with only the first letter in upper-case and not italicized (e.g., 1127). Any reference to the gene symbol is a reference made to the entire gene or variants of the gene. Any reference to the gene symbol is also a reference made to the gene product (e.g., protein, non-coding RNA). The term, homolog, may apply to the relationship between genes separated by the event of speciation (e.g., ortholog). Orthologs are genes in different species that evolved from a common ancestral gene by speciation. Normally, orthologs retain the same function in the course of evolution. Gene symbols may be those referred to by the HUGO Gene Nomenclature Committee (HGNC) or National Center for Biotechnology Information (NCBI). The signature as described herein may encompass any of the genes described herein.

The gene name NR33C1, Nr3c1 or Nr3C1 may refer to the glucocorticoid receptor gene or polypeptide according to NCBI Reference Sequence accession numbers NM_001204264.1, NM_001204263.1, NM 001204262.1, NM_001204261.1, NM 001204260.1, NM_001204259.1, NM 001204258.1, NM 001024094.1, NM 001018077.1, NM 001018076.1, NM_001018075.1, NM_001018074.1, NM_000176.2, NM_001204265.1, NM_001020825.1 and NM_008173.3.

Interleukin 27 (IL-27) is a member of the IL-12 cytokine family. It is a heterodimeric cytokine that is composed of two distinct genes, Epstein-Barr virus-induced gene 3 (EBI3) and IL-27p28. The IL-27 receptor (IL-27R) consists of two proteins, IL-27α and gp130.

The gene name EBI3 may refer to the Epstein-Barr virus-induced gene 3 gene or polypeptide according to NCBI Reference Sequence accession numbers NM_005755.2 and NM_015766.2.

The gene name IL27, IL-27, p28, IL-27A, IL27A, IL27p28 and IL30 may refer to the interleukin 27 gene or polypeptide according to NCBI Reference Sequence accession numbers NM_145659.3 and NM_145636.1. The gene name IL27RA, CRL1, IL-27RA, IL27R, TCCR, WSX1, and zcytor1 may refer to the interleukin 27 receptor subunit alpha gene or polypeptide according to NCBI Reference Sequence accession numbers NM_004843.3 and NM_016671.3.

In certain example embodiments, the therapeutic, diagnostic, and screening methods disclosed herein target, detect, or otherwise make use of one or more biomarkers of an expression signature. As used herein, the term "biomarker" can refer to a gene, an mRNA, cDNA, an antisense transcript, a miRNA, a polypeptide, a protein, a protein fragment, or any other nucleic acid sequence or polypeptide sequence that indicates either gene expression levels or protein production levels. Accordingly, it should be understood that reference to a "signature" in the context of those embodiments may encompass any biomarker or biomarkers whose expression profile or whose occurrence is associated with a specific cell type, subtype, or cell state of a specific cell type or subtype within a population of cells (e.g., dysfunctional T cells) or a specific biological program. As used herein the term "module" or "biological program" can be used interchangeably with "expression program" and refers to a set of biomarkers that share a role in a biological function (e.g., a dysfunction program, activation program, cell differentiation program, proliferation program). Biological programs can include a pattern of biomarker expression that result in a corresponding physiological event or phenotypic trait. Biological programs can include up to several hundred biomarkers that are expressed in a spatially and temporally controlled fashion. Expression of individual biomarkers can be shared between biological programs. Expression of individual biomarkers can be shared among different single cell types; however, expression of a biological program may be cell type specific or temporally specific (e.g., the biological program is expressed in a cell type at a specific time). Expression of a biological program may be regulated by a master switch, such as a nuclear receptor (e.g., (GR) or transcription factor).

The invention further relates to various biomarkers for detecting CD8+ and/or CD4+ T cell subpopulations. In certain example embodiments, these CD8+ and/or CD4+ T cell populations are tumor infiltrating lymphocytes (TIL). The methods may comprise detecting a first population of CD8+ and/or CD4+ T cell population as described further below, a second population of CD8+ and/or CD4+ T cell population as described further below, a third population of CD8+ and/or CD4+ T cell population as described further below or any combination of two subtypes or all three subtypes. The first, second and third CD8+ and/or CD4+ T cell populations may be detected by detecting one or more biomarkers in a sample.

The term "biomarker" is widespread in the art and commonly broadly denotes a biological molecule, more particularly an endogenous biological molecule, and/or a detectable portion thereof, whose qualitative and/or quantitative evaluation in a tested object (e.g., in or on a cell, cell population, tissue, organ, or organism, e.g., in a biological sample of a subject) is predictive or informative with respect to one or more aspects of the tested object's phenotype and/or genotype. The terms "marker" and "biomarker" may be used interchangeably throughout this specification. Biomarkers as intended herein may be nucleic acid-based or peptide-, polypeptide- and/or protein-based. For example, a marker may be comprised of peptide(s), polypeptide(s) and/or protein(s) encoded by a given gene, or of detectable portions thereof. Further, whereas the term "nucleic acid" generally encompasses DNA, RNA and DNA/RNA hybrid molecules, in the context of markers the term may typically refer to heterogeneous nuclear RNA (hnRNA), pre-mRNA, messenger RNA (mRNA), or complementary DNA (cDNA), or detectable portions thereof. Such nucleic acid species are particularly useful as markers, since they contain qualitative and/or quantitative information about the expression of the gene. Particularly preferably, a nucleic acid-based marker may encompass mRNA of a given gene, or cDNA made of the mRNA, or detectable portions thereof. Any such nucleic acid(s), peptide(s), polypeptide(s) and/or protein(s) encoded by or produced from a given gene are encompassed by the term "gene product(s)".

Preferably, markers as intended herein may be extracellular or cell surface markers, as methods to measure extracellular or cell surface marker(s) need not disturb the integrity of the cell membrane and may not require fixation/permeabilization of the cells.

Unless otherwise apparent from the context, reference herein to any marker, such as a peptide, polypeptide, protein, or nucleic acid, may generally also encompass modified forms of said marker, such as bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

The term "peptide" as used throughout this specification preferably refers to a polypeptide as used herein consisting essentially of 50 amino acids or less, e.g., 45 amino acids or less, preferably 40 amino acids or less, e.g., 35 amino acids or less, more preferably 30 amino acids or less, e.g., 25 or less, 20 or less, 15 or less, 10 or less or 5 or less amino acids.

The term "polypeptide" as used throughout this specification generally encompasses polymeric chains of amino acid residues linked by peptide bonds. Hence, insofar a protein is only composed of a single polypeptide chain, the terms "protein" and "polypeptide" may be used interchangeably herein to denote such a protein. The term is not limited to any minimum length of the polypeptide chain. The term may encompass naturally, recombinantly, semi-synthetically or synthetically produced polypeptides. The term also encompasses polypeptides that carry one or more co- or post-expression-type modifications of the polypeptide chain, such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes polypeptide variants or mutants which carry amino acid sequence variations vis-à-vis a corresponding native polypeptide, such as, e.g., amino acid deletions, additions and/or substitutions. The term contemplates both full-length polypeptides and polypeptide parts or fragments, e.g., naturally-occurring polypeptide parts that ensue from processing of such full-length polypeptides.

The term "protein" as used throughout this specification generally encompasses macromolecules comprising one or more polypeptide chains, i.e., polymeric chains of amino acid residues linked by peptide bonds. The term may encompass naturally, recombinantly, semi-synthetically or synthetically produced proteins. The term also encompasses proteins that carry one or more co- or post-expression-type modifications of the polypeptide chain(s), such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes protein variants or mutants which carry amino acid sequence variations vis-à-vis a corresponding native protein, such as, e.g., amino acid deletions, additions and/or substitutions. The term contemplates both full-length proteins and protein parts or fragments, e.g., naturally-occurring protein parts that ensue from processing of such full-length proteins.

The reference to any marker, including any peptide, polypeptide, protein, or nucleic acid, corresponds to the marker commonly known under the respective designations in the art. The terms encompass such markers of any organism where found, and particularly of animals, preferably warm-blooded animals, more preferably vertebrates, yet more preferably mammals, including humans and non-human mammals, still more preferably of humans.

The terms particularly encompass such markers, including any peptides, polypeptides, proteins, or nucleic acids, with a native sequence, i.e., ones of which the primary sequence is the same as that of the markers found in or derived from nature. A skilled person understands that native sequences may differ between different species due to genetic divergence between such species. Moreover, native sequences may differ between or within different individuals of the same species due to normal genetic diversity (variation) within a given species. Also, native sequences may differ between or even within different individuals of the same species due to somatic mutations, or post-transcriptional or post-translational modifications. Any such variants or isoforms of markers are intended herein. Accordingly, all sequences of markers found in or derived from nature are considered "native". The terms encompass the markers when forming a part of a living organism, organ, tissue or cell, when forming a part of a biological sample, as well as when at least partly isolated from such sources. The terms also encompass markers when produced by recombinant or synthetic means.

In certain embodiments, markers, including any peptides, polypeptides, proteins, or nucleic acids, may be human, i.e., their primary sequence may be the same as a corresponding primary sequence of or present in a naturally occurring human markers. Hence, the qualifier "human" in this connection relates to the primary sequence of the respective markers, rather than to their origin or source. For example, such markers may be present in or isolated from samples of human subjects or may be obtained by other means (e.g., by recombinant expression, cell-free transcription or translation, or non-biological nucleic acid or peptide synthesis).

The reference herein to any marker, including any peptide, polypeptide, protein, or nucleic acid, also encompasses fragments thereof. Hence, the reference herein to measuring (or measuring the quantity of) any one marker may encompass measuring the marker and/or measuring one or more fragments thereof.

For example, any marker and/or one or more fragments thereof may be measured collectively, such that the measured quantity corresponds to the sum amounts of the collectively measured species. In another example, any marker and/or one or more fragments thereof may be measured each individually. The terms encompass fragments arising by any mechanism, in vivo and/or in vitro, such as, without limitation, by alternative transcription or translation, exo- and/or endo-proteolysis, exo- and/or endo-nucleolysis, or degradation of the peptide, polypeptide, protein, or nucleic acid, such as, for example, by physical, chemical and/or enzymatic proteolysis or nucleolysis.

The term "fragment" as used throughout this specification with reference to a peptide, polypeptide, or protein generally denotes a portion of the peptide, polypeptide, or protein, such as typically an N- and/or C-terminally truncated form of the peptide, polypeptide, or protein. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the amino acid sequence length of said peptide, polypeptide, or protein. For example, insofar not exceeding the length of the full-length peptide, polypeptide, or protein, a fragment may include a sequence of $\geq 5$ consecutive amino acids, or $\geq 10$ consecutive amino acids, or $\geq 20$ consecutive amino acids, or $\geq 30$ consecutive amino acids, e.g., $\geq 40$ consecutive amino acids, such as for example $\geq 50$ consecutive amino acids, e.g., $\geq 60$, $\geq 70$, $\geq 80$, $\geq 90$, $\geq 100$, $\geq 200$, $\geq 300$, $\geq 400$, $\geq 500$ or $\geq 600$ consecutive amino acids of the corresponding full-length peptide, polypeptide, or protein.

The term "fragment" as used throughout this specification with reference to a nucleic acid (polynucleotide) generally denotes a 5'- and/or 3'-truncated form of a nucleic acid. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the nucleic acid sequence length of said nucleic acid. For example, insofar not exceeding the length of the full-length nucleic acid, a fragment may include a sequence of ≥5 consecutive nucleotides, or ≥10 consecutive nucleotides, or ≥20 consecutive nucleotides, or ≥30 consecutive nucleotides, e.g., ≥40 consecutive nucleotides, such as for example ≥50 consecutive nucleotides, e.g., ≥60, ≥70, ≥80, ≥90, ≥100, ≥200, ≥300, ≥400, ≥500 or ≥600 consecutive nucleotides of the corresponding full-length nucleic acid.

Cells such as immune cells as disclosed herein may in the context of the present specification be said to "comprise the expression" or conversely to "not express" one or more markers, such as one or more genes or gene products; or be described as "positive" or conversely as "negative" for one or more markers, such as one or more genes or gene products; or be said to "comprise" a defined "gene or gene product signature".

Such terms are commonplace and well-understood by the skilled person when characterizing cell phenotypes. By means of additional guidance, when a cell is said to be positive for or to express or comprise expression of a given marker, such as a given gene or gene product, a skilled person would conclude the presence or evidence of a distinct signal for the marker when carrying out a measurement capable of detecting or quantifying the marker in or on the cell. Suitably, the presence or evidence of the distinct signal for the marker would be concluded based on a comparison of the measurement result obtained for the cell to a result of the same measurement carried out for a negative control (for example, a cell known to not express the marker) and/or a positive control (for example, a cell known to express the marker). Where the measurement method allows for a quantitative assessment of the marker, a positive cell may generate a signal for the marker that is at least 1.5-fold higher than a signal generated for the marker by a negative control cell or than an average signal generated for the marker by a population of negative control cells, e.g., at least 2-fold, at least 4-fold, at least 10-fold, at least 20-fold, at least 30-fold, at least 40-fold, at least 50-fold higher or even higher. Further, a positive cell may generate a signal for the marker that is 3.0 or more standard deviations, e.g., 3.5 or more, 4.0 or more, 4.5 or more, or 5.0 or more standard deviations, higher than an average signal generated for the marker by a population of negative control cells.

Gene Signatures

The present invention is also directed to signatures and uses thereof (e.g., glucocorticoid, dysfunction, exhaustion, IL-27, and glucocorticoid+IL-27 signatures). As used herein a "signature" may encompass any gene or genes, protein or proteins, or epigenetic element(s) whose expression profile or whose occurrence is associated with a specific cell type, subtype, or cell state of a specific cell type or subtype within a population of cells (e.g., tumor infiltrating lymphocytes). In certain embodiments, the expression of the CD8+ and/or CD4+ TIL signatures are dependent on epigenetic modification of the genes or regulatory elements associated with the genes. Thus, in certain embodiments, use of signature genes includes epigenetic modifications that may be detected or modulated. For ease of discussion, when discussing gene expression, any gene or genes, protein or proteins, or epigenetic element(s) may be substituted. Reference to a gene name throughout the specification encompasses the human gene, mouse gene and all other orthologues as known in the art in other organisms. As used herein, the terms "signature", "expression profile", or "expression program" may be used interchangeably. It is to be understood that also when referring to proteins (e.g. differentially expressed proteins), such may fall within the definition of "gene" signature. Levels of expression or activity or prevalence may be compared between different cells in order to characterize or identify for instance signatures specific for cell (sub)populations. Increased or decreased expression or activity of signature genes may be compared between different cells in order to characterize or identify for instance specific cell (sub)populations. The detection of a signature in single cells may be used to identify and quantitate for instance specific cell (sub)populations. A signature may include a gene or genes, protein or proteins, or epigenetic element(s) whose expression or occurrence is specific to a cell (sub)population, such that expression or occurrence is exclusive to the cell (sub) population. A gene signature as used herein, may thus refer to any set of up- and down-regulated genes that are representative of a cell type or subtype. A gene signature as used herein, may also refer to any set of up- and down-regulated genes between different cells or cell (sub)populations derived from a gene-expression profile. For example, a gene signature may comprise a list of genes differentially expressed in a distinction of interest.

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. tumor samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. Not being bound by a theory the signatures of the present invention may be microenvironment specific, such as their expression in a particular spatio-temporal context. Not being bound by a theory, signatures as discussed herein are specific to a particular pathological context. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type.

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In certain embodiments, a signature is characterized as being specific for a particular immune cell or immune cell (sub)population if it is upregulated or only present, detected or detectable in that particular immune cell or immune cell (sub)population, or alternatively is downregulated or only absent, or undetectable in that particular immune cell or immune cell (sub)population. In this context, a signature consists of one or more differentially expressed genes/proteins or differential epigenetic elements when comparing different cells or cell (sub)populations, including comparing different immune cell or immune cell (sub)populations, as well as comparing immune cell or immune cell (sub)populations with non-immune cell or non-immune cell (sub)populations. It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population or subpopulation level, refer to genes that are differentially expressed in all or substantially all cells of the population or subpopulation (such as at least 80%, preferably at least 90%, such as at least 95% of the individual cells). This allows one to define a particular subpopulation of immune cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

When referring to induction, or alternatively suppression of a particular signature, preferable is meant induction or alternatively suppression (or upregulation or downregulation) of at least one gene/protein and/or epigenetic element of the signature, such as for instance at least two, at least three, at least four, at least five, at least six, or all genes/proteins and/or epigenetic elements of the signature.

Various aspects and embodiments of the invention may involve analyzing gene signatures, protein signature, and/or other genetic or epigenetic signature based on single cell analyses (e.g. single cell RNA sequencing) or alternatively based on cell population analyses, as is defined herein elsewhere.

In certain example embodiments, the signature genes may be used to deconvolute the network of cells present in a tumor based on comparing them to data from bulk analysis of a tumor sample. In certain example embodiments, the presence of specific immune cells and immune cell subtypes may be indicative of tumor growth, invasiveness and/or resistance to treatment. In one example embodiment, detection of one or more signature genes may indicate the presence of a particular cell type or cell types. In certain example embodiments, the presence of immune cell types within a tumor may indicate that the tumor will be sensitive to a treatment (e.g., checkpoint blockade therapy). In one embodiment, the signature genes of the present invention are applied to bulk sequencing data from a tumor sample obtained from a subject, such that information relating to disease outcome and personalized treatments is determined.

Glucocorticoid and Glucocorticoid+IL-27 Signature

In certain embodiments, a glucocorticoid+IL-27 (GC+IL-27) signature comprises one or more genes that are differentially expressed in T cells in response to combined glucocorticoid signaling and IL-27 signaling activation as compared to a control not activated. In certain embodiments, the glucocorticoid+IL-27 signature comprises one or more genes selected from Table 1. In certain embodiments, the glucocorticoid signature includes genes differentially expressed in response to glucocorticoid treatment (Dex) (Table 1).

Table 1 is divided into genes that are non-additive (first 3416 genes) and genes that are additive (last 3396 genes) pertaining to differential expression of the genes after the combination GC+IL-27 treatment. Non-additive means that GC+IL-27 does not equal GC+IL-27, meaning that the effect of the combination cannot be predicted by the sum of each individual condition. The non-additive effect can be either positive or negative. It is important to note that non-additive does not mean synergy (e.g., it does not mean that GC+IL-27 combination>GC+IL-27). Additive means that GC+IL-27 combination equals GC+IL-27, meaning that the effect of the combination is the sum of the effect of each individual condition.

In certain embodiments, the signature comprises the non-additive genes (Table 1). In certain embodiments, the signature comprises the additive genes. In preferred embodiments, non-additive genes are used as biomarkers and therapeutic targets.

In one example embodiment, the glucocorticoid+IL-27 signature comprises any gene in Table 1 and at least N additional biomarkers selected in Table 1, wherein N equals 1, 2, 3, 4, . . . , or up to 6811. In certain embodiments, the genes are non-additive.

In preferred embodiments, the GC+IL-27 signature comprises a subset of genes in Table 1, wherein the genes are filtered based on a threshold of adjusted p-value <0.01 and the additional threshold of fold change >2 resulting in a subset of 1558 genes downregulated (e.g., Tcf7) (Table 2A) and 1592 genes upregulated (e.g., Prdm1, Nfil3, and Entpd1) (Table 2B) in response to glucocorticoid and IL-27 treatment. Table 2A and B genes are ranked based on their adjusted p-value (from low to high). Therefore, the signature may include one or more of the ranked genes starting from the first ranked genes for the upregulated and/or downregulated genes. In certain embodiments, the signature includes the top 5, 10, 20, 30, 40, 50, 60, 70, 80, 90, 100 or up to 3150 top ranking genes. Note, Table 2 shows the glucocorticoid+IL-27 signature used for FIGS. 1C and 5F.

In certain embodiments, the glucocorticoid+IL-27 signature comprises one or more genes overlapping with a dysfunction signature (Table 3). In certain embodiments, the dysfunction signature comprises one or more genes in Table 4. The dysfunction signature in Table 4 is a $CD8^+$ T cell dysfunction signature that includes genes differentially expressed in $Tim-3^+PD-1^+$ $CD8^+$ TILs (tumor infiltrating lymphocytes) as compared to $Tim-3^-PD-1^-$ $CD8^+$ TILs isolated from MC38-OVA tumor-bearing C57BL/6 mice (see, e.g., Kurtulus, S. et al. Checkpoint Blockade Immunotherapy Induces Dynamic Changes in PD-1(−)CD8(+) Tumor-Infiltrating T Cells. *Immunity* 50, 181-194 e186 (2019); and WO2019/014581).

In certain embodiments, the glucocorticoid+IL-27 signature comprises one or more genes differentially expressed after GC+IL27 treatment and overlapping with the MC38 dysfunction signature (Table 4) and a CT26 dysfunction signature previously obtained by a similar method as for MC38 (see, e.g., Singer, M. et al. A Distinct Gene Module for Dysfunction Uncoupled from Activation in Tumor-Infiltrating T Cells. *Cell* 171, 1221-1223 (2017); and WO2017075478A2).

In certain embodiments, the glucocorticoid+IL-27 signature comprises one or more non-additive genes differentially expressed after GC+IL27 treatment and overlapping with the MC38 dysfunction signature and the CT26 dysfunction signature (Table 5 and 6). The gene signatures are induced by GC+IL27 treatment, indicating the most dysfunctional cells, as discovered in the present invention. The gene signatures also include the genes that are non-additive when induced by GC+IL27 treatment indicating that the response is not predictable. In certain embodiments, the genes in Tables 5 and 6 indicate the genes in the dysfunction signatures most strongly associated with dysfunction. In certain embodiments, these genes are used as biomarkers and therapeutic targets.

TABLE 5A

Non-additive genes downregulated following DEX + IL27 treatment and downregulated in both exhaustion models.

| Tcf7 | Cmah | Rras2 | Icam2 | Abcc4 |
| St6gal1 | Rbm38 | Ptcra | Pim2 | Adk |
| Iigp1 | Slfn5 | Ifngr2 | Fgr | Pepd |
| Fads2 | Slco3a1 | Stk38 | Top1mt | Pde7a |
| Btla | Hs3st3b1 | Zdhhc13 | Ehd3 | Lrrc33 |
| Dnajc7 | Soc7 | Gpx1 | Tnfsf8 | Nxf1 |
| Gpd1l | Tlr1 | | | |

TABLE 5B

Non-additive genes upregulated following DEX + IL27 treatment and upregulated in both exhaustion models.

| Entpd1 | 5330426P16Rik | Filip1 | Syngr3 | Oit3 |
| Prdm1 | Arsb | Pmaip1 | Uhrf2 | Tmem159 |
| Cysltr2 | Il1r2 | Lgals3 | Dapk2 | Aldoc |
| Aplp1 | Ppp1r3b | Gdpd5 | Hip1r | Ephb6 |
| Gpr160 | Samsn1 | BC068157 | Amigo1 | Dkkl1 |
| Tmem171 | Tmbim4 | Arhgef9 | Acadl | Abhd4 |
| Plekhb2 | Casp4 | Nrn1 | Scyl2 | Impa2 |
| Sdf4 | Tnfrsf18 | AA467197 | 1110007C09Rik | Farp1 |
| Ndrg1 | Ndfip2 | Polk | Icos | Hif1a |
| Chst12 | Gm11110 | Zfp52 | Itgav | Stab1 |
| Ccdc109b | Arhgap18 | Dynlt3 | Apbb1 | |

TABLE 6A

Non-additive genes downregulated following DEX + IL27 treatment and downregulated in both exhaustion models (different threshold used).

| | | | | |
|---|---|---|---|---|
| Dnajc7 | Slco3a1 | Sema4f | Ptcra | Traf4 |
| Fas | Ddr1 | Pde4b | Ifngr2 | Lpin1 |
| Samhd1 | Ctsl | Aldh6a1 | Stk38 | Ipcef1 |
| Lrp12 | Btla | Soc7 | Zdhhc13 | Top1mt |
| Rftn1 | Epcam | Tlr1 | Arid5a | Chst15 |
| Il4ra | Gramd4 | Camkk1 | Phc1 | Ehd3 |
| Idua | Atp10d | Tspan13 | Gtf2i | Rcn3 |
| Psap | Rere | Vmac | Gpx1 | Tnfsf8 |
| Bcl3 | Hs3st3b1 | Fads2 | Icam2 | Abcc4 |
| Zscan12 | St6gal1 | Kbtbd11 | Irf7 | Ephx1 |
| Gpd1l | Mbp | AB124611 | Utrn | P2rx4 |
| Tmem50b | Arhgef3 | Sesn3 | Zfp260 | Socs3 |
| Tcp11l2 | Satb1 | Serinc5 | Trib2 | Zeb1 |
| Atp2a1 | Acss2 | Fosl2 | Klhdc1 | Tcf7 |
| Vdr | Iigp1 | Map4k4 | Pim2 | Adk |
| Cmah | 2610035D17Rik | Rras2 | Osbpl9 | Cyp27 |
| Npc1 | Als2cl | Rgs10 | Cdc14b | Pepd |
| Gpr18 | Jhdm1d | Ifnar2 | Tom1 | Pde7a |
| Rbm38 | Tpd52 | Ccpg1 | Fgr | St8sia1 |
| Gimap6 | Ralgps2 | Dzip1 | Slamf6 | Pik3ip1 |
| Cd24a | Itgae | Prcp | Sgip1 | Lrrc33 |
| Slfn5 | Atp1b3 | Zcchc11 | Uvrag | Nxf1 |

TABLE 6B

Non-additive genes upregulated following DEX + IL27 treatment and upregulated in both exhaustion models (different threshold used).

| | | | | |
|---|---|---|---|---|
| Chst12 | Tmem171 | Lgals3 | Cenpp | Ccdc14 |
| Cysltr2 | Casp4 | Gdpd5 | Degs1 | Apbb1 |
| Alg8 | Tnfrsf18 | Ccdc50 | Cdca5 | Oit3 |
| Aplp1 | Ube2i | Zbtb32 | Dapk2 | Hmmr |
| Kif22 | Plekhb2 | BC068157 | Hip1r | Tmem159 |
| Ccdc109b | Sdf4 | Arhgef9 | Amigo1 | Cenph |
| Nup107 | Ccl3 | Nrn1 | Ctsc | Kdm2b |
| Ifng | Anapc4 | Tacc3 | Mrps36 | Ptplad1 |
| Rabgef1 | Ndfip2 | Spry2 | Acadl | Aldoc |
| 5330426P16Rik | Stard4 | Nr4a2 | Nqo2 | Mmd |
| Ccl4 | Fasl | Trappc4 | Scyl2 | Ephb6 |
| Gpr160 | Tmem48 | AA467197 | Myo1e | Nedd9 |
| Serpine2 | Cenpt | Polk | Tmem39a | Dkkl1 |
| Rpa2 | Gm11110 | Ndrg1 | Nuf2 | Abhd4 |
| Arsb | Ttk | Sh2d2a | Rnaseh2c | Exo1 |
| Cdca3 | Arhgap18 | Cox17 | Atad5 | Slc37a2 |
| Il1r2 | Mlf1 | Zfp52 | Ncaph | Impa2 |
| Shcbp1 | Cenpa | Dynlt3 | 2610318N02Rik | Farp1 |
| Dclk1 | Nrp1 | Syngr3 | Traip | Tmem126a |
| Esco2 | Sephs1 | Uhrf2 | Gem | Fam188a |
| Ppp1r3b | Prdm1 | Ino80c | Elk3 | Hif1a |
| Eno3 | Sh3bgrl | Ttc39c | Egr1 | Mtmr7 |
| Abcb1b | Filip1 | Usp46 | 1110007C09Rik | Casp3 |
| Birc5 | Plek | B4galt5 | Icos | Dut |
| Magohb | Kif20a | Gzmc | Tbc1d7 | Stab1 |
| Samsn1 | Idh3a | Tk1 | Itgav | 2810417H13Rik |
| Zwilch | Pmaip1 | Osbpl3 | C330027C09Rik | Pilra |
| Tmbim4 | Prf1 | Smc2 | Entpd1 | Tnfrsf4 |

In certain embodiments, the glucocorticoid+IL-27 signature comprises one or more genes in Table 7. The genes in Table 7 are highlighted in FIGS. 13, 14 and 22C. In certain embodiments, the genes in Table 7 are used as biomarkers and therapeutic targets.

TABLE 7A

Genes upregulated following DEX + IL27 treatment. Upregulated after combo

| | | | | |
|---|---|---|---|---|
| Epcam | C1qtnf4 | Asb2 | Tnfrsf14 | Stat3 |
| Gpld1 | Tgfb3 | Jag2 | Zfp467 | Mt1 |
| Cd68 | Itga7 | Tnfrsf18 | Entpd1 | Bach1 |
| Prnp | Acvrl1 | Prdm1 | Nfil3 | Cd28 |
| Gab2 | Gpr125 | Smyd3 | Crebl2 | Havcr2 |
| Vldlr | Aqp11 | Tigit | Hif1a | Pdcd1 |
| Il10 | Ramp1 | Dbp | Irf6 | Ctla4 |
| Il1r2 | Kit | Tle2 | Lag3 | Cd27 |
| Nt5e | Trip6 | Ddit3 | Alcam | |
| Itgae | Enpp2 | Klf10 | Mt2 | |

TABLE 7B

Genes downregulated following DEX + IL27 treatment.
Downregulated after combo

| Ifng | Ccl3 | Xcl1 | Ptrf | Tnfrsf4 |
|---|---|---|---|---|
| Ccl4 | Cd48 | Lilrb4 | Icam2 | Egr2 |
| Bcl2 | Cxcr3 | Nupr1 | Cd40lg | Ccr7 |
| Spp1 | Nanog | Hmgn2 | Il1a | Cd226 |
| Btla | Tfrc | Il24 | Tcf7 | |

In certain embodiments, the one or more glucocorticoid+ IL-27 signature genes are upregulated or downregulated in response to activation of glucocorticoid signaling or IL-27 signaling separately or only one of glucocorticoid signaling and IL-27 signaling, however, the differential expression is enhanced when both glucocorticoid and IL-27 signaling is activated, such that a downregulated gene is further downregulated and an upregulated gene is further upregulated (see, Table 1).

In certain embodiments, the signature includes genes whose expression is further enhanced by the combination. For example, Tgfb3 expression is further enhanced, where the control cells show expression levels of 0.1, 0.12, 0.03, the Dex only cells show expression levels of 8.53, 5.51, 5.9, the IL-27 only cells show expression levels of 3.6, 1.14, 2.06, and the combo cells show expression levels of 12.08, 11.67, 16.33. Also, CD28 expression is further enhanced, where the control cells show expression levels of 19.54, 18.14, 18.29, the Dex only cells show expression levels of 31.98, 33.89, 35.83, the IL-27 only cells show expression levels of 48.93, 37.2, 39.84, and the combo cells show expression levels of 61.19, 60.85, 56.07. In certain embodiments, genes in Table 1 having enhanced expression in response to both glucocorticoid signaling and IL-27 signaling activation are used as biomarkers and therapeutic targets.

In certain embodiments, the signature includes genes whose expression is further reduced by the combination. For example, Il24 expression is further reduced, where the control cells show expression levels of 280.07, 260.93, 314.42, the Dex only cells show expression levels of 156.6, 224.35, 191, the IL-27 only cells show expression levels of 86.97, 190.89, 192.77, and the combo cells show expression levels of 12.82, 44.26, 14.08. Also, Tcf7 expression is further reduced, where the control cells show expression levels of 9.93, 8.28, 11.45 the Dex only cells show expression levels of 9.54, 8.42, 8.72, the IL-27 only cells show expression levels of 5.37, 7.39, 5.57, and the combo cells show expression levels of 1.62, 1.39, 3.32. In certain embodiments, genes in Table 1 having reduced expression in response to both glucocorticoid signaling and IL-27 signaling activation are used as biomarkers and therapeutic targets.

In certain embodiments, the gene signature includes genes that are upregulated or downregulated in response to activation of only one of glucocorticoid signaling and IL-27 signaling, but are downregulated or upregulated when the combination is activated (e.g., the response is reversed from either single treatment). For example, Lilrb4 expression is reversed, where the control cells show expression levels of 87.12, 92.82, 96.51, the Dex only cells show expression levels of 179.28, 174.41, 160.09 (increased as compared to control), the IL-27 only cells show expression levels of 73.62, 94.25, 105.87 (increased as compared to control), and the combo cells show expression levels of 31.55, 29.82, 27.03 (decreased as compared to control). Also, Nupr1 expression is reversed, where the control cells show expression levels of 12.77, 13.57, 13.47, the Dex only cells show expression levels of 11.81, 14.26, 21.7, the IL-27 only cells show expression levels of 11.93, 21.86, 19.79, and the combo cells show expression levels of 3.56, 7.19, 3.68. Differential expression of the genes in this group as compared to the control after the combination treatment indicates genes that have differential expression in the most dysfunctional cells. Based on the change in direction of expression as compared to either Dex or IL-27 alone, these genes are unexpected targets for modulation of T cell dysfunction (e.g., the direction of modulation is unexpected). In certain embodiments, based on the differential expression as compared to control, these genes are used as biomarkers and therapeutic targets.

In certain embodiments, the glucocorticoid+IL-27 signature is referred to as a checkpoint blockade (CPB) therapy non-responder signature. In certain embodiments, the presence of dysfunctional T cells having the signature correlate with non-response to CPB therapy.

Methods of Modulating T Cell Dysfunction

The following section provides multiple example embodiments for inducing, increasing or enhancing T cell dysfunction or for suppressing, decreasing or reducing T cell dysfunction. The compositions of the methods may be administered to subjects having aberrant activation and/or expansion of T cells or subjects requiring an enhanced immune response. Thus, the embodiments may be used to prevent and/or treat diseases and disorders characterized by aberrant activation, expansion or suppression of immune cells.

In certain embodiments, an agent capable of inhibiting synthesis of endogenous glucocorticoids is administered to a subject to decrease dysfunction. In certain embodiments, the agent is targeted to monocytes and/or macrophages. In certain embodiments, the agent is a steroidogenesis inhibitor. In certain embodiments, the agent is metyrapone. In certain embodiments, the invention additionally comprises co-administering one or more agents capable of modulating expression, activity, or function of glucocorticoid receptor, IL-27, IL-27 receptor or one or more biomarkers of the glucocorticoid+IL-27 gene signature as defined herein.

As used herein, "modulating" or "to modulate" generally means either reducing or inhibiting the expression or activity of, or alternatively increasing the expression or activity of a target (e.g., Nr3C1, IL-27 receptor, downstream target of glucocorticoid and IL-27 signaling described herein). In particular, "modulating" or "to modulate" can mean either reducing or inhibiting the activity of, or alternatively increasing a (relevant or intended) biological activity of, a target or antigen as measured using a suitable in vitro, cellular or in vivo assay (which will usually depend on the target involved), by at least 5%, at least 10%, at least 25%, at least 50%, at least 60%, at least 70%, at least 80%, at least 90%, or more, compared to activity of the target in the same assay under the same conditions but without the presence of an agent. An "increase" or "decrease" refers to a statistically significant increase or decrease respectively. For the avoidance of doubt, an increase or decrease will be at least 10% relative to a reference, such as at least 10%, at least 20%, at least 30%, at least 40%, at least 50%, at least 60%, at least 70%, at least 80%, at least 90%, at least 95%, at least 97%, at least 98%, or more, up to and including at least 100% or more, in the case of an increase, for example, at least 2-fold, at least 3-fold, at least 4-fold, at least 5-fold, at least 6-fold, at least 7-fold, at least 8-fold, at least 9-fold, at least 10-fold, at least 50-fold, at least 100-fold, or more. "Modulating" can also involve effecting a change (which can either be an increase or a decrease) in affinity, avidity, specificity and/or selectivity of a target or antigen, such as glucocorticoid or IL-27. "Modulating" can also mean effecting a change with respect to one or more biological or physiological mechanisms, effects, responses, functions, pathways or activities in which the target or antigen (or in which its substrate(s), ligand(s) or pathway(s) are involved, such as its signaling pathway or metabolic pathway and their associated biological or physiological effects) is involved. Again, as will be clear to the skilled person, such an action as an agonist or an antagonist can be determined in any suitable manner and/or using any suitable assay known or described herein (e.g., in vitro or cellular assay), depending on the target or antigen involved.

Modulating can, for example, also involve allosteric modulation of the target and/or reducing or inhibiting the binding of the target to one of its substrates or ligands and/or competing with a natural ligand, substrate for binding to the target. Modulating can also involve activating the target or the mechanism or pathway in which it is involved. Modulating can, for example, also involve effecting a change in respect of the folding or confirmation of the target, or in respect of the ability of the target to fold, to change its conformation (for example, upon binding of a ligand), to associate with other (sub)units, or to disassociate. Modulating can, for example, also involve effecting a change in the ability of the target to signal, phosphorylate, dephosphorylate, and the like.

T Cell Modulating Agents

In certain embodiments T cell dysfunction is modulated in a population of cells or in a subject in need thereof by contacting with one or more agents. As used herein, an "agent" can refer to a protein-binding agent that permits modulation of activity of proteins or disrupts interactions of proteins and other biomolecules, such as but not limited to disrupting protein-protein interaction, ligand-receptor interaction, or protein-nucleic acid interaction. Agents can also refer to DNA targeting or RNA targeting agents. In certain embodiments, the one or more agents comprise an antibody, antibody fragment, intrabody, antibody-like protein scaffold, aptamer, polypeptide, small molecule, small molecule degrader (e.g., PROTAC), genetic modifying agent, or any combination thereof.

In certain embodiments, the agent is a therapeutic agent used for treating a subject in need thereof. The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. As used herein "treating" includes ameliorating, curing, preventing it from becoming worse, slowing the rate of progression, or preventing the disorder from re-occurring (i.e., to prevent a relapse). In certain embodiments, the present invention provides for one or more therapeutic agents against combinations of targets identified. Targeting the identified combinations may provide for enhanced or otherwise previously unknown activity in the treatment of disease.

Steroidogenesis Inhibitors

In certain embodiments, methods of decreasing T cell dysfunction and increasing anti-tumor immunity comprises administering an agent that inhibits glucocorticoid signaling. In certain embodiments, glucocorticoid synthesis is inhibited. In certain embodiments, the agent is a steroidogenesis inhibitor that prevents production of glucocorticoids. A steroidogenesis inhibitor, also known as a steroid biosynthesis inhibitor, is a type of drug which inhibits one or more of the enzymes that are involved in the process of steroidogenesis, the biosynthesis of endogenous steroids and steroid hormones. They may inhibit the production of cholesterol and other sterols, sex steroids such as androgens, estrogens, and progestogens, corticosteroids such as glucocorticoids and mineralocorticoids, and neurosteroids. They are currently used in the treatment of a variety of medical conditions that depend on endogenous steroids. In preferred embodiments, the agent is metyrapone. Non-limiting examples of inhibitors useful in the present invention are provided herein.

Cholesterol side-chain cleavage enzyme (P450scc, CYP11A1) inhibitors such as aminoglutethimide, ketoconazole, and mitotane inhibit the production of pregnenolone from cholesterol and thereby prevent the synthesis of all steroid hormones. They have been used to inhibit corticosteroid synthesis in the treatment of Cushing's syndrome and adrenocortical carcinoma. Ketoconazole has also been used to inhibit androgen production in the treatment of prostate cancer. Other inhibitors of Cyp11a1 applicable to the present invention include, but are not limited to 22-ABC, 3,3'-Dimethoxybenzidine, 3-Methoxybenzidine, Aminoglutethimide, Amphenone B, Canrenone, Cyanoketone, Danazol, Etomidate, Ketoconazole, Levoketoconazole, Mitotane, Spironolactone and Trilostane.

3β-Hydroxysteroid dehydrogenase (3β-HSD) inhibitors such as amphenone B, azastene, cyanoketone, epostane, mitotane, and trilostane inhibit the conversion of $\Delta^5$-3β-hydroxysteroids into $\Delta^4$-3-ketosteroids and thereby inhibit the production of most of the steroid hormones. Trilostane was formerly used to inhibit corticosteroid synthesis in the treatment of Cushing's syndrome.

17α-Hydroxylase/17,20-lyase (CYP17A1) inhibitors such as abiraterone acetate, etomidate, galeterone, ketoconazole, and orteronel inhibit the production of androgens and glucocorticoids and are used to reduce androgen levels in the treatment of prostate cancer.

21-Hydroxylase (CYP21A2) inhibitors prevent the production of corticosteroids from progesterone and 17α-hydroxyprogesterone. Non-limiting examples include Aminoglutethimide, Amphenone B, Bifonazole, Canrenone, Clotrimazole, Diazepam, Econazole, Genistein, Isoconazole, Ketoconazole, Levoketoconazole, Metyrapone, Miconazole, Midazolam, Spironolactone, Abiraterone, Abiraterone acetate, and Tioconazole.

11β-Hydroxylase (CYP11B1) inhibitors such as amphenone B, etomidate, ketoconazole, metyrapone, mitotane, and osilodrostat inhibit the production of the potent corticosteroids cortisol, corticosterone, and aldosterone from the less potent corticosteroids 11-deoxycorticosterone and 11-deoxycortisol and are used in the diagnosis and treatment of Cushing's syndrome.

Checkpoint Blockade Therapy

In certain embodiments, an immunotherapy is administered in combination with one or more agents capable of inhibiting glucocorticoid signaling. In certain embodiments, immunotherapy, including immune checkpoint blockade therapy (CPB or ICB), is administered to a subject in need thereof. Immunotherapy can include checkpoint blockers (CPB), chimeric antigen receptors (CARs), and adoptive T-cell therapy. In certain embodiments, one or more agents capable of inhibiting glucocorticoid synthesis is administered to make a subject more responsive to checkpoint blockade therapy (e.g., metyrapone). Applicants show that active glucocorticoid signaling is associated with a failure to respond to checkpoint blockade in both pre-clinical models and melanoma patients. In certain embodiments, high glucocorticoid levels correlate with failure to respond to checkpoint blockade. Antibodies that block the activity of checkpoint receptors, including CTLA-4, PD-1, Tim-3, Lag-3, and TIGIT, either alone or in combination, have been associated with improved effector $CD8^+$ T cell responses in multiple pre-clinical cancer models (Johnston et al., 2014. The immunoreceptor TIGIT regulates antitumor and antiviral CD8(+) T cell effector function. Cancer cell 26, 923-937; Ngiow et al., 2011. Anti-TIM3 antibody promotes T cell IFN-gamma-mediated antitumor immunity and suppresses established tumors. Cancer research 71, 3540-3551; Sakuishi et al., 2010. Targeting Tim-3 and PD-1 pathways to reverse T cell exhaustion and restore anti-tumor immunity. The Journal of experimental medicine 207, 2187-2194; and Woo et al., 2012. Immune inhibitory molecules LAG-3 and PD-1 synergistically regulate T-cell function to promote tumoral immune escape. Cancer research 72, 917-927). Similarly, blockade of CTLA-4 and PD-1 in patients (Brahmer et al., 2012. Safety and activity of anti-PD-L1 antibody in patients with advanced cancer. The New England journal of medicine 366, 2455-2465; Hodi et al., 2010. Improved survival with ipilimumab in patients with metastatic melanoma. The New England journal of medicine 363, 711-723; Schadendorf et al., 2015. Pooled Analysis of Long-Term Survival Data From Phase II and Phase III Trials of Ipilimumab in Unresectable or Metastatic Melanoma. Journal of clinical oncology: official journal of the American Society of Clinical Oncology 33, 1889-1894; Topalian et al., 2012. Safety, activity, and immune correlates of anti-PD-1 antibody in cancer. The New England journal of medicine 366, 2443-2454; and Wolchok et al., 2017. Overall Survival with Combined Nivolumab and Ipilimumab in Advanced Melanoma. The New England journal of medicine 377, 1345-1356) has shown increased frequencies of proliferating T cells, often with specificity for tumor antigens, as well as increased $CD8^+$ T cell effector function (Ayers et al., 2017. IFN-gamma-related mRNA profile predicts clinical response to PD-1 blockade. The Journal of clinical investigation 127, 2930-2940; Das et al., 2015. Combination therapy with anti-CTLA-4 and anti-PD-1 leads to distinct immunologic changes in vivo. Journal of immunology 194, 950-959; Gubin et al., 2014. Checkpoint blockade cancer immunotherapy targets tumour-specific mutant antigens. Nature 515, 577-581; Huang et al., 2017. T-cell invigoration to tumour burden ratio associated with anti-PD-1 response. Nature 545, 60-65; Kamphorst et al., 2017. Proliferation of PD-1+ CD8 T cells in peripheral blood after PD-1-targeted therapy in lung cancer patients. Proceedings of the National Academy of Sciences of the United States of America 114, 4993-4998; Kvistborg et al., 2014. Anti-CTLA-4 therapy broadens the melanoma-reactive CD8+ T cell response. Science translational medicine 6, 254rai28; van Rooij et al., 2013. Tumor exome analysis reveals neoantigen-specific T-cell reactivity in an ipilimumab-responsive melanoma. Journal of clinical oncology: official journal of the American Society of Clinical Oncology 31, e439-442; and Yuan et al., 2008. CTLA-4 blockade enhances polyfunctional NY-ESO-1 specific T cell responses in metastatic melanoma patients with clinical benefit. Proceedings of the National Academy of Sciences of the United States of America 105, 20410-20415). Accordingly, the success of checkpoint receptor blockade has been attributed to the binding of blocking antibodies to checkpoint receptors expressed on dysfunctional CD8+ T cells and restoring effector function in these cells. The checkpoint blockade therapy may be an inhibitor of any check point protein described herein. The checkpoint blockade therapy may comprise anti-TIM3, anti-CTLA4, anti-PD-L1, anti-PD1, anti-TIGIT, anti-LAG3, or combinations thereof. Anti-PD1 antibodies are disclosed in U.S. Pat. No. 8,735,553. Antibodies to LAG-3 are disclosed in U.S. Pat. No. 9,132,281. Anti-CTLA4 antibodies are disclosed in U.S. Pat. Nos. 9,327,014; 9,320,811; and 9,062,111. Specific check point inhibitors include, but are not limited to anti-CTLA4 antibodies (e.g., Ipilimumab and tremelimumab), anti-PD-1 antibodies (e.g., Nivolumab, Pembrolizumab), and anti-PD-L1 antibodies (e.g., Atezolizumab).

In certain embodiments, immunotherapy leads to immune-related adverse events (irAEs) (see, e.g., Kumar, V. et al. Current Diagnosis and Management of Immune Related Adverse Events (irAEs) Induced by Immune Checkpoint Inhibitor Therapy. Front Pharmacol 8, 49 (2017); Byun et al., (2017) Cancer immunotherapy-immune checkpoint blockade and associated endocrinopathies. Nat Rev Endocrinol. 2017 April; 13(4): 195-207; Abdel-Wahab et al., (2016) Adverse Events Associated with Immune Checkpoint Blockade in Patients with Cancer: A Systematic Review of Case Reports. PLoS ONE 11 (7): e0160221. doi:10.1371/journal.pone.0160221; and Gelao et al., Immune Checkpoint Blockade in Cancer Treatment: A Double-Edged Sword Cross-Targeting the Host as an "Innocent Bystander", Toxins 2014, 6, 914-933; doi:10.3390/toxins6030914). Thus, patients receiving immunotherapy are at risk for adverse autoimmune responses. Glucocorticoids (GC) are used to treat IRAEs in ICB-treated patients. Initial studies have indicated that GCs can be used without negative impact on ICB response (Weber, et al., Phase I/II Study of Ipilimumab for Patients With Metastatic Melanoma. Journal of Clinical Oncology 2008 26:36, 5950-5956). However, more recent studies show that patients on CTLA-4 therapy that receive low-dose glucocorticoids do better than the patients who receive high-dose glucocorticoid (Faje et al., High-dose glucocorticoids for the treatment of ipilimumab-induced hypophysitis is associated with reduced survival in patients with melanoma. Cancer. 2018 Sep. 15; 124(18):3706-3714). Moreover, baseline steroids associated with poor response to PD-1/L1 blockade (Arbour et al., Impact of Baseline Steroids on Efficacy of Programmed Cell Death-1 and Programmed Death-Ligand 1 Blockade in Patients With Non-Small-Cell Lung Cancer. Journal of Clinical Oncology 36, no. 28 (Oct. 1, 2018) 2872-2878).

In certain embodiments, glucocorticoid treatment is administered to prevent immune-related adverse events (irAEs). In certain embodiments, the glucocorticoid treatment is a low dose treatment. In certain embodiments, the glucocorticoid treatment is administered in combination with one or more agents capable of inhibiting or blocking one or more genes activated in CD8 T cells by glucocorticoids and/or IL-27 (e.g., GC+IL-27 signature genes). In certain embodiments, CD8 T cell anti-tumor immunity is maintained due to blockade of the downstream signaling in CD8 T cells, however irAEs are inhibited.

IL-27

In certain embodiments, agents can refer to proteins, such as IL-27. IL-27 is a heterodimeric cytokine and a member of the IL-12 family of cytokines that is produced by antigen presenting cells. Although IL-27 was initially shown to promote pro-inflammatory Type 1 immune responses, emerging evidence suggests that this cytokine plays an important role in the resolution of tissue inflammation (Yoshida and Hunter, (2015) Annual review of immunology 33, 417-443). IL-27 administration in vivo suppresses the pathogenicity of primed effector T cells and inhibits the development of autoimmunity (Fitzgerald et al., (2007a) Journal of immunology 179, 3268-3275). Consistent with a suppressive function for IL-27, IL-27ra (WSX-1) deficient mice exhibit increased inflammation during *Toxoplasma gondii* infection and exacerbated disease in a model of central nervous system autoimmunity (Awasthi et al., (2007) Nature immunology 8, 1380-1389; Hirahara et al., (2012) Immunity 36, 1017-1030; Villarino et al., (2003) Immunity 19, 645-655). Indeed, Applicants (Awasthi et al., 2007) and others (Fitzgerald et al., 2007a; Stumhofer et al., (2007) Nature immunology 8, 1363-1371) have shown that exposure of naïve T cells to IL-27 induces IL-10-secreting Type 1 regulatory (Tr1) cells that are immune suppressive. Moreover, Applicants have recently shown that IL-27 induces Tim-3 (Zhu et al., (2015) Nature communications 6, 6072), which has been shown to cooperate with PD-1 in promoting a dysfunctional phenotype in T cells (Sakuishi et al., 2010, The Journal of experimental medicine 207, 2187-2194). Applicants, previously used a systems biology approach to find that IL-27 signaling drives the expression of a gene module that includes not only Tim-3, but also Lag-3, TIGIT, and IL-10, all molecules that are associated with T cell dysfunction (see, e.g., WO/2017/069958).

The present invention provides methods of using agonists and antagonists of IL-27. An agonist of IL-27 encompasses, e.g., IL-27, an IL-27 variant, hyperkine, or peptide mimetic thereto, agonistic antibodies to WSX-1/TCCR or gp130, and nucleic acids encoding these agonists. Antagonists of IL-27 include, e.g., antibodies to IL-27, antibodies to p28 or EBI3, blocking antibodies to WSX-1/TCCR or gp130, a soluble receptor based on the extracellular region of a subunit of WSX-1/TCCR or gp130, peptide mimetics thereto, and nucleic acids encoding these antagonists. Anti-idiotypic antibodies may also be used.

The present invention provides methods of using agonists and antagonists of p28, agonists and antagonists of the complex of p28 and EBI3, agonists and antagonists of WSX-1/TCCR, agonists and antagonists of gp130, and agonists and antagonists of the complex of WSX-1/TCCR and gp130.

An IL-27 hyperkine encompasses, e.g., a fusion protein comprising the polypeptide sequence of p28 and EBI3, where p28 and EBI3 occur in one continuous polypeptide chain. The sequences of p28 and EBI3 may be in either order in the continuous polypeptide chain. The fusion protein may contain a linker sequence, residing in between the sequences of p28 and EBI3, in one continuous polypeptide chain.

Antibodies to p28, EBI3, WSX-1/TCCR, and gp130 are available (see, e.g., Pflanz, et al. (2004) J. Immunol. 172: 2225-2231; Larousserie, et al. (2004) J. Pathol. 202:164-171; Devergne, et al. (2001) Am. J. Pathol. 159:1763-1776; Autissier, et al. (1998) Int. Immunol. 10:1881-1889). Also contemplated are antibodies that specifically bind the complex of p28 and EBI3, and antibodies that specifically bind to the complex of WSX-1/TCCR and gp130.

Also provided are soluble receptors corresponding to an extracellular domain of WSX-1/TCCR and gp130. The extracellular domain of mature human WSX-1/TCCR comprises amino acids 33 to 514 of the amino acid sequence of GenBank BC028003 or NM 004843. This extracellular domain includes a classical cytokine binding domain, and also three fibronectin (FN) domains. The invention contemplates a soluble receptor comprising the cytokine binding domain and none, one, or, or three of the FN domains. Soluble gp130 is available (see, e.g., Hui, et al. (2000) Cytokine 12:151-155).

Glucocorticoids

In certain embodiments, methods of increasing T cell dysfunction may comprise contacting a population of cells with a glucocorticoid or administering a glucocorticoid to a subject in need thereof. In certain embodiments, a glucocorticoid and IL-27 is contacted or administered. Glucocorticoids (GCs) are a class of corticosteroids, which are a class of steroid hormones. Glucocorticoids are corticosteroids that bind to the glucocorticoid receptor (GR) that is present in almost every vertebrate animal cell. The name glucocorticoid (glucose+cortex+steroid) is composed from its role in regulation of glucose metabolism, synthesis in the adrenal cortex, and its steroidal structure. The glucocorticoid receptor (GR, or GCR) also known as NR3C1 (nuclear receptor subfamily 3, group C, member 1) is the receptor to which cortisol and other glucocorticoids bind. Glucocorticoids (GCs) are derived from the metabolic breakdown of cholesterol. The GR resides in the cytosol in its inactive state and translocates to the nucleus upon binding to GC. In the nucleus, the GR can regulate gene expression either directly (trans-activation) or indirectly (trans-repression) by affecting the binding of other transcription factors (TFs) to the promoter regions of their respective targets (Oakley and Cidlowski, 2013). GCs suppress a number of inflammatory indices and have been used since the 1950s for treating excessive inflammation in patients with asthma and autoimmune diseases. Currently, GCs are routinely used to manage excessive inflammation in cancer patients treated with immune checkpoint blockade (ICB) (Kumar et al., 2017).

Despite their widespread use, surprisingly little is known regarding the molecular circuitry by which GCs suppress immune responses (Cain and Cidlowski, 2017; Munck et al., 1984). The prevailing dogma attributes the anti-inflammatory effects of GCs to transrepression, whereby the GR interferes with the function of TFs that have key roles in driving pro-inflammatory responses, such as AP-1 (Jonat et al., 1990; Yang-Yen et al., 1990) and NF-κB (Auphan et al., 1995; Rhen and Cidlowski, 2005; Scheinman et al., 1995; Smoak and Cidlowski, 2004). However, GCs have also been associated with enhanced expression of IL-10 (Barrat et al., 2002), raising the possibility that in addition to actively repressing pro-inflammatory gene expression, they may also promote suppression via transactivation of immune-suppressive genes. Example glucocorticoids applicable to the present invention include, but are not limited to:

| Name | Glucocorticoid potency | Mineralocorticoid potency | Terminal half-life (hours) |
| --- | --- | --- | --- |
| Cortisol (hydrocortisone) | 1 | 1 | 8 |
| Cortisone | 0.8 | 0.8 | 8 |
| Prednisone | 3.5-5 | 0.8 | 16-36 |
| Prednisolone | 4 | 0.8 | 16-36 |

| Name | Glucocorticoid potency | Mineralocorticoid potency | Terminal half-life (hours) |
|---|---|---|---|
| Methylprednisolone | 5-7.5 | 0.5 | 18-40 |
| Dexamethasone | 25-80 | 0 | 36-54 |
| Betamethasone | 25-30 | 0 | 36-54 |
| Triamcinolone | 5 | 0 | 12-36 |
| Fludrocortisone acetate | 15 | 200 | 24 |
| Deoxycorticosterone acetate | 0 | 20 | — |

In certain embodiments, the agent modulates glucocorticoid signaling. In certain embodiments, the agent is an agonist or antagonist of glucocorticoid receptor activity. Agonists and antagonists of the glucocorticoid receptor have been described and are applicable to the present invention (see, e.g., WO2004005229A1).

Adoptive Cell Transfer

In certain embodiments, T cells or populations of cells comprising T cells modified according to the present invention (e.g., altered glucocorticoid signaling or altered glucocorticoid and IL-27 signaling or altered TCF-1) are used in adoptive cell transfer. In certain embodiments, T cells are modified to have decreased glucocorticoid receptor. In certain embodiments, a steroidogenesis inhibitor is administered in an adoptive cell transfer treatment regimen to prevent the transferred cells from being suppressed or to obtain a less immune suppressive environment for the cells to be transferred into. The transferred cells may be used to treat a subject in need thereof (e.g., cancer or autoimmune diseases). Specific diseases are described further herein. As used herein, "ACT", "adoptive cell therapy" and "adoptive cell transfer" may be used interchangeably. In certain embodiments, Adoptive cell therapy (ACT) can refer to the transfer of cells to a patient with the goal of transferring the functionality and characteristics into the new host by engraftment of the cells (see, e.g., Mettananda et al., Editing an α-globin enhancer in primary human hematopoietic stem cells as a treatment for β-thalassemia, Nat Commun. 2017 Sep. 4; 8(1):424). As used herein, the term "engraft" or "engraftment" refers to the process of cell incorporation into a tissue of interest in vivo through contact with existing cells of the tissue. Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Zacharakis et al., (2018) Nat Med. 2018 June; 24(6):724-730; Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57.) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma, metastatic breast cancer and colorectal carcinoma, as well as patients with CD19-expressing hematologic malignancies (Kalos et al., (2011) Science Translational Medicine 3 (95): 95ra73). In certain embodiments, allogenic cells immune cells are transferred (see, e.g., Ren et al., (2017) Clin Cancer Res 23 (9) 2255-2266). As described further herein, allogenic cells can be edited to reduce alloreactivity and prevent graft-versus-host disease. Thus, use of allogenic cells allows for cells to be obtained from healthy donors and prepared for use in patients as opposed to preparing autologous cells from a patient after diagnosis.

Aspects of the invention involve the adoptive transfer of immune system cells, such as T cells, specific for selected antigens, such as tumor associated antigens or tumor specific neoantigens (see, e.g., Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144; and Rajasagi et al., 2014, Systematic identification of personal tumor-specific neoantigens in chronic lymphocytic leukemia. Blood. 2014 Jul. 17; 124(3):453-62).

In certain embodiments, immune cells to be transferred are differentiated in culture conditions to modify the immune cell state. In certain embodiments, immune cells are differentiated to have an enhanced (e.g., activated immune response). In certain embodiments, immune cells are differentiated to have a suppressive immune state (e.g., dysfunctional). Previous studies showed that bone marrow cells differentiated with dexamethasone (Dex) combined with granulocyte macrophage colony stimulating factor (GM-CSF) generated Myeloid derived suppressor cells (MDSCs) in vitro and adoptive transfer of these MDSCs significantly prolonged heart allograft survival and also favored the expansion of regulatory T cells in vivo (Zhao et al., Dexamethasone-Induced Myeloid-Derived Suppressor Cells Prolong Allo Cardiac Graft Survival through iNOS- and Glucocorticoid Receptor-Dependent Mechanism, Front. Immunol., 15 Feb. 2018). In certain embodiments, suppressive immune cells are obtained by differentiating the immune cells according to the present invention with combined glucocorticoid and IL-27 treatment.

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: B cell maturation antigen (BCMA) (see, e.g., Friedman et al., Effective Targeting of Multiple BCMA-Expressing Hematological Malignancies by Anti-BCMA CAR T Cells, Hum Gene Ther. 2018 Mar. 8; Berdeja J G, et al. Durable clinical responses in heavily pretreated patients with relapsed/refractory multiple myeloma: updated results from a multicenter study of bb2121 anti-Bcma CAR T cell therapy. Blood. 2017; 130:740; and Mouhieddine and Ghobrial, Immunotherapy in Multiple Myeloma: The Era of CAR T Cell Therapy, Hematologist, May-June 2018, Volume 15, issue 3); PSA (prostate-specific antigen); prostate-specific membrane antigen (PSMA); PSCA (Prostate stem cell antigen); Tyrosine-protein kinase transmembrane receptor ROR1; fibroblast activation protein (FAP); Tumor-associated glycoprotein 72 (TAG72); Carcinoembryonic antigen (CEA); Epithelial cell adhesion molecule (EPCAM); Mesothelin; Human Epidermal growth factor Receptor 2 (ERBB2 (Her2/neu)); Prostase; Prostatic acid phosphatase (PAP); elongation factor 2 mutant (ELF2M); Insulin-like growth factor 1 receptor (IGF-1R); gplOO; BCR-ABL (breakpoint cluster region-Abelson); tyrosinase; New York esophageal squamous cell carcinoma 1 (NY-ESO-1); K-light chain, LAGE (L antigen); MAGE (melanoma antigen); Melanoma-associated antigen 1 (MAGE-A1); MAGE A3; MAGE A6; legumain; Human papillomavirus (HPV) E6; HPV E7; prostein; survivin; PCTA1 (Galectin 8); Melan-A/MART-1; Ras mutant; TRP-1 (tyrosinase related protein 1, or gp75); Tyrosinase-related Protein 2 (TRP2); TRP-2/INT2 (TRP-2/intron 2); RAGE (renal antigen); receptor for advanced glycation end products 1 (RAGE1); Renal ubiquitous 1, 2 (RU1, RU2); intestinal carboxyl esterase (iCE); Heat shock protein 70-2 (HSP70-2) mutant; thyroid stimulating hormone receptor (TSHR); CD123; CD171; CD19; CD20; CD22; CD26; CD30; CD33; CD44v7/8 (cluster of differentiation 44, exons 7/8); CD53; CD92; CD100; CD148; CD150; CD200; CD261; CD262; CD362; CS-1 (CD2 subset 1, CRACC, SLAMF7, CD319, and 19A24); C-type lectin-like molecule-1 (CLL-1); ganglioside GD3 (aNeu5Ac (2-8)aNeu5Ac(2-3)bDGalp(1-4)bDGlcp(1-1)Cer); Tn antigen (Tn Ag); Fms-Like Tyrosine Kinase 3 (FLT3); CD38; CD138; CD44v6; B7H3 (CD276); KIT (CD117); Interleukin-13 receptor subunit alpha-2 (IL-13Ra2); Interleukin 11 receptor alpha (IL-11Ra); prostate stem cell antigen (PSCA); Protease Serine 21 (PRSS21); vascular endothelial growth factor receptor 2 (VEGFR2); Lewis(Y) antigen; CD24; Platelet-derived growth factor receptor beta (PDGFR-beta); stage-specific embryonic antigen-4 (SSEA-4); Mucin 1, cell surface associated (MUC1); mucin 16 (MUC16); epidermal growth factor receptor (EGFR); epidermal growth factor receptor variant III (EGFRvIII); neural cell adhesion molecule (NCAM); carbonic anhydrase IX (CAIX); Proteasome (Prosome, Macropain) Subunit, Beta Type, 9 (LMP2); ephrin type-A receptor 2 (EphA2); Ephrin B2; Fucosyl GM1; sialyl Lewis adhesion molecule (sLe); ganglioside GM3 (aNeu5Ac(2-3)bDGalp(1-4)bDGlcp(1-1) Cer); TGS5; high molecular weight-melanoma-associated antigen (HMWMAA); o-acetyl-GD2 ganglioside (OAcGD2); Folate receptor alpha; Folate receptor beta; tumor endothelial marker 1 (TEM1/CD248); tumor endothelial marker 7-related (TEM7R); claudin 6 (CLDN6); G protein-coupled receptor class C group 5, member D (GPRC5D); chromosome X open reading frame 61 (CX-ORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); CT (cancer/testis (antigen)); melanoma cancer testis antigen-1 (MAD-CT-1); melanoma cancer testis antigen-2 (MAD-CT-2); Fos-related antigen 1; p53; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; Cyclin D1; v-myc avian myelocytomatosis viral oncogene neuroblastoma derived homolog (MYCN); Ras Homolog Family Member C (RhoC); Cytochrome P450 1B1 (CYP1B1); CCCTC-Binding Factor (Zinc Finger Protein)-Like (BORIS); Squamous Cell Carcinoma Antigen Recognized By T Cells-1 or 3 (SART1, SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint-1, -2, -3 or -4 (SSX1, SSX2, SSX3, SSX4); CD79a; CD79b; CD72; Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); C-type lectin domain family 12 member A (CLECl2A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); mouse double minute 2 homolog (MDM2); livin; alphafetoprotein (AFP); transmembrane activator and CAML Interactor (TACI); B-cell activating factor receptor (BAFF-R); V-Ki-ras2 Kirsten rat sarcoma viral oncogene homolog (KRAS); immunoglobulin lambda-like polypeptide 1 (IGLL1); 707-AP (707 alanine proline); ART-4 (adenocarcinoma antigen recognized by T4 cells); BAGE (B antigen; b-catenin/m, b-catenin/mutated); CAMEL (CTL-recognized antigen on melanoma); CAPl (carcinoembryonic antigen peptide 1); CASP-8 (caspase-8); CDC27m (cell-division cycle 27 mutated); CDK4/m (cyclin-dependent kinase 4 mutated); Cyp-B (cyclophilin B); DAM (differentiation antigen melanoma); EGP-2 (epithelial glycoprotein 2); EGP-40 (epithelial glycoprotein 40); Erbb2, 3, 4 (erythroblastic leukemia viral oncogene homolog-2, -3, 4); FBP (folate binding protein); fAchR (Fetal acetylcholine receptor); G250 (glycoprotein 250); GAGE (G antigen); GnT-V (N-acetylglucosaminyltransferase V); HAGE (helicase antigen); ULA-A (human leukocyte antigen-A); HST2 (human signet ring tumor 2); KIAA0205; KDR (kinase insert domain receptor); LDLR/FUT (low density lipid receptor/GDP L-fucose: b-D-galactosidase 2-a-L fucosyl-transferase); L1CAM (L1 cell adhesion molecule); MC1R (melanocortin 1 receptor); Myosin/m (myosin mutated); MUM-1, -2, -3 (melanoma ubiquitous mutated 1, 2, 3); NA88-A (NA cDNA clone of patient M88); KG2D (Natural killer group 2, member D) ligands; oncofetal antigen (h5T4); p190 minor bcr-abl (protein of 190 KD bcr-abl); Pml/RARa (promyelocytic leukemia/retinoic acid receptor a); PRAME (preferentially expressed antigen of melanoma); SAGE (sarcoma antigen); TEL/AML1 (translocation Ets-family leukemia/acute myeloid leukemia 1); TPI/m (triose-phosphate isomerase mutated); CD70; and any combination thereof.

In certain embodiments, an antigen to be targeted in adoptive cell therapy (such as particularly CAR or TCR T-cell therapy) of a disease (such as particularly of tumor or cancer) is a tumor-specific antigen (TSA).

In certain embodiments, an antigen to be targeted in adoptive cell therapy (such as particularly CAR or TCR T-cell therapy) of a disease (such as particularly of tumor or cancer) is a neoantigen.

In certain embodiments, an antigen to be targeted in adoptive cell therapy (such as particularly CAR or TCR T-cell therapy) of a disease (such as particularly of tumor or cancer) is a tumor-associated antigen (TAA).

In certain embodiments, an antigen to be targeted in adoptive cell therapy (such as particularly CAR or TCR T-cell therapy) of a disease (such as particularly of tumor or cancer) is a universal tumor antigen. In certain preferred embodiments, the universal tumor antigen is selected from the group consisting of: a human telomerase reverse transcriptase (hTERT), survivin, mouse double minute 2 homolog (MDM2), cytochrome P450 1B 1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (Dl), and any combinations thereof.

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: CD19, BCMA, CD70, CLL-1, MAGE A3, MAGE A6, HPV E6, HPV E7, WT1, CD22, CD171, ROR1, MUC16, and SSX2. In certain preferred embodiments, the antigen may be CD19. For example, CD19 may be targeted in hematologic malignancies, such as in lymphomas, more particularly in B-cell lymphomas, such as without limitation in diffuse large B-cell lymphoma, primary mediastinal b-cell lymphoma, transformed follicular lymphoma, marginal zone lymphoma, mantle cell lymphoma, acute lymphoblastic leukemia including adult and pediatric ALL, non-Hodgkin lymphoma, indolent non-Hodgkin lymphoma, or chronic lymphocytic leukemia. For example, BCMA may be targeted in multiple myeloma or plasma cell leukemia (see, e.g., 2018 American Association for Cancer Research (AACR) Annual meeting Poster: Allogeneic Chimeric Antigen Receptor T Cells Targeting B Cell Maturation Antigen). For example, CLL1 may be targeted in acute myeloid leukemia. For example, MAGE A3, MAGE A6, SSX2, and/or KRAS may be targeted in solid tumors. For example, HPV E6 and/or HPV E7 may be targeted in cervical cancer or head and neck cancer. For example, WT1 may be targeted in acute myeloid leukemia (AML), myelodysplastic syndromes (MDS), chronic myeloid leukemia (CML), non-small cell lung cancer, breast, pancreatic, ovarian or colorectal cancers, or mesothelioma. For example, CD22 may be targeted in B cell malignancies, including non-Hodgkin lymphoma, diffuse large B-cell lymphoma, or acute lymphoblastic leukemia. For example, CD171 may be targeted in neuroblastoma, glioblastoma, or lung, pancreatic, or ovarian cancers. For example, ROR1 may be targeted in ROR1+ malignancies, including non-small cell lung cancer, triple negative breast cancer, pancreatic cancer, prostate cancer, ALL, chronic lymphocytic leukemia, or mantle cell lymphoma. For example, MUC16 may be targeted in MUC16ecto+ epithelial ovarian, fallopian tube or primary peritoneal cancer. For example, CD70 may be targeted in both hematologic malignancies as well as in solid cancers such as renal cell carcinoma (RCC), gliomas (e.g., GBM), and head and neck cancers (HNSCC). CD70 is expressed in both hematologic malignancies as well as in solid cancers, while its expression in normal tissues is restricted to a subset of lymphoid cell types (see, e.g., 2018 American Association for Cancer Research (AACR) Annual meeting Poster: Allogeneic CRISPR Engineered Anti-CD70 CAR-T Cells Demonstrate Potent Preclinical Activity Against Both Solid and Hematological Cancer Cells).

Various strategies may for example be employed to genetically modify T cells by altering the specificity of the T cell receptor (TCR) for example by introducing new TCR α and β chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and, PCT Publication WO9215322).

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand.

The antigen-binding domain of a CAR is generally separated from the transmembrane domain by a hinge or spacer. The spacer is also not particularly limited, and it is designed to provide the CAR with flexibility. For example, a spacer domain may comprise a portion of a human Fc domain, including a portion of the CH3 domain, or the hinge region of any immunoglobulin, such as IgA, IgD, IgE, IgG, or IgM, or variants thereof. Furthermore, the hinge region may be modified so as to prevent off-target binding by FcRs or other potential interfering objects. For example, the hinge may comprise an IgG4 Fc domain with or without a S228P, L235E, and/or N297Q mutation (according to Kabat numbering) in order to decrease binding to FcRs. Additional spacers/hinges include, but are not limited to, CD4, CD8, and CD28 hinge regions.

The transmembrane domain of a CAR may be derived either from a natural or from a synthetic source. Where the source is natural, the domain may be derived from any membrane bound or transmembrane protein. Transmembrane regions of particular use in this disclosure may be derived from CD8, CD28, CD3, CD45, CD4, CD5, CDS, CD9, CD 16, CD22, CD33, CD37, CD64, CD80, CD86, CD 134, CD137, CD 154, TCR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Alternative CAR constructs may be characterized as belonging to successive generations. First-generation CARs typically consist of a single-chain variable fragment of an antibody specific for an antigen, for example comprising a VL linked to a VH of a specific antibody, linked by a flexible linker, for example by a CD8a hinge domain and a CD8α transmembrane domain, to the transmembrane and intracellular signaling domains of either CD3ζ or FcRγ (scFv-CD3ζ or scFv-FcRγ; see U.S. Pat. Nos. 7,741,465; 5,912,172; U.S. Pat. No. 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761). Third-generation CARs include a combination of costimulatory endodomains, such a CD3ζ-chain, CD97, GDI 1a-CD18, CD2, ICOS, CD27, CD154, CDS, OX40, 4-1BB, CD2, CD7, LIGHT, LFA-1, NKG2C, B7-H3, CD30, CD40, PD-1, or CD28 signaling domains (for example scFv-CD28-4-1BB-CD3ζ or scFv-CD28-OX40-CD3ζ; see U.S. Pat. Nos. 8,906,682; 8,399,645; 5,686,281; PCT Publication No. WO2014134165; PCT Publication No. WO2012079000). In certain embodiments, the primary signaling domain comprises a functional signaling domain of a protein selected from the group consisting of CD3 zeta, CD3 gamma, CD3 delta, CD3 epsilon, common FcR gamma (FCERIG), FcR beta (Fc Epsilon Rib), CD79a, CD79b, Fc gamma RIIa, DAP10, and DAP12. In certain preferred embodiments, the primary signaling domain comprises a functional signaling domain of CD3ζ or FcRγ. In certain embodiments, the one or more costimulatory signaling domains comprise a functional signaling domain of a protein selected, each independently, from the group consisting of: CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D. In certain embodiments, the one or more costimulatory signaling domains comprise a functional signaling domain of a protein selected, each independently, from the group consisting of: 4-1BB, CD27, and CD28. In certain embodiments, a chimeric antigen receptor may have the design as described in U.S. Pat. No. 7,446,190, comprising an intracellular domain of CD3ζ chain (such as amino acid residues 52-163 of the human CD3 zeta chain, as shown in SEQ ID NO: 14 of U.S. Pat. No. 7,446,190), a signaling region from CD28 and an antigen-binding element (or portion or domain; such as scFv). The CD28 portion, when between the zeta chain portion and the antigen-binding element, may suitably include the transmembrane and signaling domains of CD28 (such as amino acid residues 114-220 of SEQ ID NO: 10, full sequence shown in SEQ ID NO: 6 of U.S. Pat. No. 7,446,190; these can include the following portion of CD28 as set forth in Genbank identifier NM_006139 (sequence version 1, 2 or 3):

```
                                      (SEQ ID NO: 20)
IEVMYPPPYLDNEKSNGTIIHVKGKHLCPSPLFPGPSKPFWVLVVVG

GVLACYSLLVTVAFIIFWVRSKRSRLLHSDYMNMTPRRPGPTRKHYQ

PYAPPRDFAAYRS.
```

Alternatively, when the zeta sequence lies between the CD28 sequence and the antigen-binding element, intracellular domain of CD28 can be used alone (such as amino acid sequence set forth in SEQ ID NO: 9 of U.S. Pat. No. 7,446,190). Hence, certain embodiments employ a CAR comprising (a) a zeta chain portion comprising the intracellular domain of human CD3ζ chain, (b) a costimulatory signaling region, and (c) an antigen-binding element (or portion or domain), wherein the costimulatory signaling region comprises the amino acid sequence encoded by SEQ ID NO: 6 of U.S. Pat. No. 7,446,190.

Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects.

By means of an example and without limitation, Kochenderfer et al., (2009) J Immunother. 32 (7): 689-702 described anti-CD19 chimeric antigen receptors (CAR). FMC63-28Z CAR contained a single chain variable region moiety (scFv) recognizing CD19 derived from the FMC63 mouse hybridoma (described in Nicholson et al., (1997) Molecular Immunology 34: 1157-1165), a portion of the human CD28 molecule, and the intracellular component of the human TCR-ζ molecule. FMC63-CD828BBZ CAR contained the FMC63 scFv, the hinge and transmembrane regions of the CD8 molecule, the cytoplasmic portions of CD28 and 4-1BB, and the cytoplasmic component of the TCR-ζ molecule. The exact sequence of the CD28 molecule included in the FMC63-28Z CAR corresponded to Genbank identifier NM_006139; the sequence included all amino acids starting with the amino acid sequence IEVMYPPPY (SEQ ID NO: 21) and continuing all the way to the carboxy-terminus of the protein. To encode the anti-CD19 scFv component of the vector, the authors designed a DNA sequence which was based on a portion of a previously published CAR (Cooper et al., (2003) Blood 101: 1637-1644). This sequence encoded the following components in frame from the 5' end to the 3' end: an XhoI site, the human granulocyte-macrophage colony-stimulating factor (GM-CSF) receptor α-chain signal sequence, the FMC63 light chain variable region (as in Nicholson et al., supra), a linker peptide (as in Cooper et al., supra), the FMC63 heavy chain variable region (as in Nicholson et al., supra), and a NotI site. A plasmid encoding this sequence was digested with XhoI and NotI. To form the MSGV-FMC63-28Z retroviral vector, the XhoI and NotI-digested fragment encoding the FMC63 scFv was ligated into a second XhoI and NotI-digested fragment that encoded the MSGV retroviral backbone (as in Hughes et al., (2005) Human Gene Therapy 16: 457-472) as well as part of the extracellular portion of human CD28, the entire transmembrane and cytoplasmic portion of human CD28, and the cytoplasmic portion of the human TCR-ζ molecule (as in Maher et al., 2002) Nature Biotechnology 20: 70-75. The FMC63-28Z CAR is included in the KTE-C19 (axicabtagene ciloleucel) anti-CD19 CAR-T therapy product in development by Kite Pharma, Inc. for the treatment of inter alia patients with relapsed/refractory aggressive B-cell non-Hodgkin lymphoma (NHL). Accordingly, in certain embodiments, cells intended for adoptive cell therapies, more particularly immunoresponsive cells such as T cells, may express the FMC63-28Z CAR as described by Kochenderfer et al. (supra). Hence, in certain embodiments, cells intended for adoptive cell therapies, more particularly immunoresponsive cells such as T cells, may comprise a CAR comprising an extracellular antigen-binding element (or portion or domain; such as scFv) that specifically binds to an antigen, an intracellular signaling domain comprising an intracellular domain of a CD3ζ chain, and a costimulatory signaling region comprising a signaling domain of CD28. Preferably, the CD28 amino acid sequence is as set forth in Genbank identifier NM_006139 (sequence version 1, 2 or 3) starting with the amino acid sequence IEVMYPPPY (SEQ ID NO: 21) and continuing all the way to the carboxy-terminus of the protein. The sequence is reproduced herein:

(SEQ ID NO: 20)
IEVMYPPPYLDNEKSNGTIIHVKGKHLCPSPLFPGPSKPFWVLVVVG

GVLACYSLLVTVAFIIFWVRSKRSRLLHSDYMNMTPRRPGPTRKHYQ

PYAPPRDFAAYRS.

Preferably, the antigen is CD19, more preferably the antigen-binding element is an anti-CD19 scFv, even more preferably the anti-CD19 scFv as described by Kochenderfer et al. (supra).

Additional anti-CD19 CARs are further described in WO2015187528. More particularly Example 1 and Table 1 of WO2015187528, incorporated by reference herein, demonstrate the generation of anti-CD19 CARs based on a fully human anti-CD19 monoclonal antibody (47G4, as described in US20100104509) and murine anti-CD19 monoclonal antibody (as described in Nicholson et al. and explained above). Various combinations of a signal sequence (human CD8-alpha or GM-CSF receptor), extracellular and transmembrane regions (human CD8-alpha) and intracellular T-cell signaling domains (CD28-CD3ζ; 4-1BB-CD3ζ; CD27-CD3ζ; CD28-CD27-CD3ζ, 4-1BB-CD27-CD3ζ; CD27-4-1BB-CD3ζ; CD28-CD27-FcεRI gamma chain; or CD28-FcεRI gamma chain) were disclosed. Hence, in certain embodiments, cells intended for adoptive cell therapies, more particularly immunoresponsive cells such as T cells, may comprise a CAR comprising an extracellular antigen-binding element that specifically binds to an antigen, an extracellular and transmembrane region as set forth in Table 1 of WO2015187528 and an intracellular T-cell signaling domain as set forth in Table 1 of WO2015187528. Preferably, the antigen is CD19, more preferably the antigen-binding element is an anti-CD19 scFv, even more preferably the mouse or human anti-CD19 scFv as described in Example 1 of WO2015187528. In certain embodiments, the CAR comprises, consists essentially of or consists of an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13 as set forth in Table 1 of WO2015187528.

By means of an example and without limitation, chimeric antigen receptor that recognizes the CD70 antigen is described in WO2012058460A2 (see also, Park et al., CD70 as a target for chimeric antigen receptor T cells in head and neck squamous cell carcinoma, Oral Oncol. 2018 March; 78:145-150; and Jin et al., CD70, a novel target of CAR T-cell therapy for gliomas, Neuro Oncol. 2018 Jan. 10; 20(1):55-65). CD70 is expressed by diffuse large B-cell and follicular lymphoma and also by the malignant cells of Hodgkins lymphoma, Waldenstrom's macroglobulinemia and multiple myeloma, and by HTLV-1- and EBV-associated malignancies. (Agathanggelou et al. Am. J. Pathol. 1995; 147: 1152-1160; Hunter et al., Blood 2004; 104:4881. 26; Lens et al., J Immunol. 2005; 174:6212-6219; Baba et al., J Virol. 2008; 82:3843-3852.) In addition, CD70 is expressed by non-hematological malignancies such as renal cell carcinoma and glioblastoma. (Junker et al., J Urol. 2005; 173:2150-2153; Chahlavi et al., Cancer Res 2005; 65:5428-5438) Physiologically, CD70 expression is transient and restricted to a subset of highly activated T, B, and dendritic cells.

By means of an example and without limitation, chimeric antigen receptor that recognizes BCMA has been described (see, e.g., US20160046724A1; WO2016014789A2; WO2017211900A1; WO2015158671A1; US20180085444A1; WO2018028647A1; US20170283504A1; and WO2013154760A1).

In certain embodiments, the immune cell may, in addition to a CAR or exogenous TCR as described herein, further comprise a chimeric inhibitory receptor (inhibitory CAR) that specifically binds to a second target antigen and is capable of inducing an inhibitory or immunosuppressive or repressive signal to the cell upon recognition of the second target antigen. In certain embodiments, the chimeric inhibitory receptor comprises an extracellular antigen-binding element (or portion or domain) configured to specifically bind to a target antigen, a transmembrane domain, and an intracellular immunosuppressive or repressive signaling domain. In certain embodiments, the second target antigen is an antigen that is not expressed on the surface of a cancer cell or infected cell or the expression of which is downregulated on a cancer cell or an infected cell. In certain embodiments, the second target antigen is an MHC-class I molecule. In certain embodiments, the intracellular signaling domain comprises a functional signaling portion of an immune checkpoint molecule, such as for example PD-1 or CTLA4. Advantageously, the inclusion of such inhibitory CAR reduces the chance of the engineered immune cells attacking non-target (e.g., non-cancer) tissues.

Alternatively, T-cells expressing CARs may be further modified to reduce or eliminate expression of endogenous TCRs in order to reduce off-target effects. Reduction or elimination of endogenous TCRs can reduce off-target effects and increase the effectiveness of the T cells (U.S. Pat. No. 9,181,527). T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

In some instances, CAR may also comprise a switch mechanism for controlling expression and/or activation of the CAR. For example, a CAR may comprise an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises a target antigen binding domain (e.g., an scFv or a bispecific antibody that is specific for both the target antigen and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T-cell that expresses the CAR can be administered to a subject, but the CAR cannot bind its target antigen until the second composition comprising an antigen-specific binding domain is administered.

Alternative switch mechanisms include CARs that require multimerization in order to activate their signaling function (see, e.g., US 2015/0368342, US 2016/0175359, US 2015/0368360) and/or an exogenous signal, such as a small molecule drug (US 2016/0166613, Yung et al., Science, 2015), in order to elicit a T-cell response. Some CARs may also comprise a "suicide switch" to induce cell death of the CAR T-cells following treatment (Buddee et al., PLoS One, 2013) or to downregulate expression of the CAR following binding to the target antigen (WO 2016/011210).

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3ζ and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to treat tumor xenografts.

In certain embodiments, ACT includes co-transferring $CD4^+$ Th1 cells and CD8+ CTLs to induce a synergistic antitumour response (see, e.g., Li et al., Adoptive cell therapy with CD4+ T helper 1 cells and CD8+ cytotoxic T cells enhances complete rejection of an established tumour, leading to generation of endogenous memory responses to non-targeted tumour epitopes. Clin Transl Immunology. 2017 October; 6(10): e160).

In certain embodiments, Th17 cells are transferred to a subject in need thereof. Th17 cells have been reported to directly eradicate melanoma tumors in mice to a greater extent than Th1 cells (Muranski P, et al., Tumor-specific Th17-polarized cells eradicate large established melanoma. Blood. 2008 Jul. 15; 112(2):362-73; and Martin-Orozco N, et al., T helper 17 cells promote cytotoxic T cell activation in tumor immunity. Immunity. 2009 Nov. 20; 31(5):787-98). Those studies involved an adoptive T cell transfer (ACT) therapy approach, which takes advantage of $CD4^+$ T cells that express a TCR recognizing tyrosinase tumor antigen. Exploitation of the TCR leads to rapid expansion of Th17 populations to large numbers ex vivo for reinfusion into the autologous tumor-bearing hosts.

In certain embodiments, ACT may include autologous iPSC-based vaccines, such as irradiated iPSCs in autologous anti-tumor vaccines (see e.g., Kooreman, Nigel G. et al., Autologous iPSC-Based Vaccines Elicit Anti-tumor Responses In Vivo, Cell Stem Cell 22, 1-13, 2018, doi.org/10.1016/j.stem.2018.01.016).

Unlike T-cell receptors (TCRs) that are MHC restricted, CARs can potentially bind any cell surface-expressed antigen and can thus be more universally used to treat patients (see Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267). In certain embodiments, in the absence of endogenous T-cell infiltrate (e.g., due to aberrant antigen processing and presentation), which precludes the use of TIL therapy and immune checkpoint blockade, the transfer of CAR T-cells may be used to treat patients (see, e.g., Hinrichs C S, Rosenberg S A. Exploiting the curative potential of adoptive T-cell therapy for cancer. Immunol Rev (2014) 257(1):56-71. doi:10.1111/imr.12132).

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction).

In certain embodiments, the treatment can be administered after lymphodepleting pretreatment in the form of chemotherapy (typically a combination of cyclophosphamide and fludarabine) or radiation therapy. Initial studies in ACT had short lived responses and the transferred cells did not persist in vivo for very long (Houot et al., T-cell-based immunotherapy: adoptive cell transfer and checkpoint inhibition. Cancer Immunol Res (2015) 3(10):1115-22; and Kamta et al., Advancing Cancer Therapy with Present and Emerging Immuno-Oncology Approaches. Front. Oncol. (2017) 7:64). Immune suppressor cells like Tregs and MDSCs may attenuate the activity of transferred cells by outcompeting them for the necessary cytokines. Not being bound by a theory lymphodepleting pretreatment may eliminate the suppressor cells allowing the TILs to persist.

In one embodiment, the treatment can be administrated into patients undergoing an immunosuppressive treatment (e.g., glucocorticoid treatment). The cells or population of cells, may be made resistant to at least one immunosuppressive agent due to the inactivation of a gene encoding a receptor for such immunosuppressive agent (e.g., Nr3C1, IL-27 receptor). In certain embodiments, the immunosuppressive treatment provides for the selection and expansion of the immunoresponsive T cells within the patient.

In certain embodiments, the treatment can be administered before primary treatment (e.g., surgery or radiation therapy) to shrink a tumor before the primary treatment. In another embodiment, the treatment can be administered after primary treatment to remove any remaining cancer cells.

In certain embodiments, immunometabolic barriers can be targeted therapeutically prior to and/or during ACT to enhance responses to ACT or CAR T-cell therapy and to support endogenous immunity (see, e.g., Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267).

The administration of cells or population of cells, such as immune system cells or cell populations, such as more particularly immunoresponsive cells or cell populations, as disclosed herein may be carried out in any convenient manner, including by aerosol inhalation, injection, ingestion, transfusion, implantation or transplantation. The cells or population of cells may be administered to a patient subcutaneously, intradermally, intra-tumorally, intranodally, intramedullary, intramuscularly, intrathecally, by intravenous or intralymphatic injection, or intraperitoneally. In some embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of $10^4$-$10^9$ cells per kg body weight, preferably $10^1$ to $10^6$ cells/kg body weight including all integer values of cell numbers within those ranges. Dosing in CAR T cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administered as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853; Ren et al., 2017, Multiplex genome editing to generate universal CAR T cells resistant to PD1 inhibition, Clin Cancer Res. 2017 May 1; 23(9):2255-2266. doi: 10.1158/1078-0432.CCR-16-1300. Epub 2016 November 4; Qasim et al., 2017, Molecular remission of infant B-ALL after infusion of universal TALEN gene-edited CAR T cells, Sci Transl Med. 2017 Jan. 25; 9(374); Legut, et al., 2018, CRISPR-mediated TCR replacement generates superior anticancer transgenic T cells. Blood, 131(3), 311-322; and Georgiadis et al., Long Terminal Repeat CRISPR-CAR-Coupled "Universal" T Cells Mediate Potent Anti-leukemic Effects, Molecular Therapy, In Press, Corrected Proof, Available online 6 Mar. 2018). Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed for example to insert or knock-in an exogenous gene, such as an exogenous gene encoding a CAR or a TCR, at a preselected locus in a cell (e.g. TRAC locus); to eliminate potential alloreactive T-cell receptors (TCR) or to prevent inappropriate pairing between endogenous and exogenous TCR chains, such as to knock-out or knock-down expression of an endogenous TCR in a cell; to disrupt the target of a chemotherapeutic agent in a cell; to block an immune checkpoint, such as to knock-out or knock-down expression of an immune checkpoint protein or receptor in a cell; to knock-out or knock-down expression of other gene or genes in a cell, the reduced expression or lack of expression of which can enhance the efficacy of adoptive therapies using the cell; to knock-out or knock-down expression of an endogenous gene in a cell, said endogenous gene encoding an antigen targeted by an exogenous CAR or TCR; to knock-out or knock-down expression of one or more MHC constituent proteins in a cell; to activate a T cell; to modulate cells such that the cells are resistant to exhaustion or dysfunction; and/or increase the differentiation and/or proliferation of functionally exhausted or dysfunctional CD8+ T-cells (see PCT Patent Publications: WO2013176915, WO2014059173, WO2014172606, WO2014184744, and WO2014191128).

In certain embodiments, editing may result in inactivation of a gene. By inactivating a gene, it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art. In certain embodiments, homology directed repair (HDR) is used to concurrently inactivate a gene (e.g., TRAC) and insert an endogenous TCR or CAR into the inactivated locus.

Hence, in certain embodiments, editing of cells (such as by CRISPR/Cas), particularly cells intended for adoptive cell therapies, more particularly immunoresponsive cells such as T cells, may be performed to insert or knock-in an exogenous gene, such as an exogenous gene encoding a CAR or a TCR, at a preselected locus in a cell. Conventionally, nucleic acid molecules encoding CARs or TCRs are transfected or transduced to cells using randomly integrating vectors, which, depending on the site of integration, may lead to clonal expansion, oncogenic transformation, variegated transgene expression and/or transcriptional silencing of the transgene. Directing of transgene(s) to a specific locus in a cell can minimize or avoid such risks and advantageously provide for uniform expression of the transgene(s) by the cells. Without limitation, suitable 'safe harbor' loci for directed transgene integration include CCR5 or AAVS1. Homology-directed repair (HDR) strategies are known and described elsewhere in this specification allowing to insert transgenes into desired loci (e.g., TRAC locus).

Further suitable loci for insertion of transgenes, in particular CAR or exogenous TCR transgenes, include without limitation loci comprising genes coding for constituents of endogenous T-cell receptor, such as T-cell receptor alpha locus (TRA) or T-cell receptor beta locus (TRB), for example T-cell receptor alpha constant (TRAC) locus, T-cell receptor beta constant 1 (TRBC1) locus or T-cell receptor beta constant 2 (TRBC1) locus. Advantageously, insertion of a transgene into such locus can simultaneously achieve expression of the transgene, potentially controlled by the endogenous promoter, and knock-out expression of the endogenous TCR. This approach has been exemplified in Eyquem et al., (2017) Nature 543: 113-117, wherein the authors used CRISPR/Cas9 gene editing to knock-in a DNA molecule encoding a CD19-specific CAR into the TRAC locus downstream of the endogenous promoter; the CAR-T cells obtained by CRISPR were significantly superior in terms of reduced tonic CAR signaling and exhaustion.

T cell receptors (TCR) are cell surface receptors that participate in the activation of T cells in response to the presentation of antigen. The TCR is generally made from two chains, α and β, which assemble to form a heterodimer and associates with the CD3-transducing subunits to form the T cell receptor complex present on the cell surface. Each α and β chain of the TCR consists of an immunoglobulin-like N-terminal variable (V) and constant (C) region, a hydrophobic transmembrane domain, and a short cytoplasmic region. As for immunoglobulin molecules, the variable region of the α and β chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCRα or TCRβ can result in the elimination of the TCR from the surface of T cells preventing recognition of alloantigen and thus GVHD. However, TCR disruption generally results in the elimination of the CD3 signaling component and alters the means of further T cell expansion.

Hence, in certain embodiments, editing of cells (such as by CRISPR/Cas), particularly cells intended for adoptive cell therapies, more particularly immunoresponsive cells such as T cells, may be performed to knock-out or knock-down expression of an endogenous TCR in a cell. For example, NHEJ-based or HDR-based gene editing approaches can be employed to disrupt the endogenous TCR alpha and/or beta chain genes. For example, gene editing system or systems, such as CRISPR/Cas system or systems, can be designed to target a sequence found within the TCR beta chain conserved between the beta 1 and beta 2 constant region genes (TRBC1 and TRBC2) and/or to target the constant region of the TCR alpha chain (TRAC) gene.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

In certain embodiments, editing of cells (such as by CRISPR/Cas), particularly cells intended for adoptive cell therapies, more particularly immunoresponsive cells such as T cells, may be performed to block an immune checkpoint, such as to knock-out or knock-down expression of an immune checkpoint protein or receptor in a cell. Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT2 inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1, TIM-3, CEACAM-1, CEACAM-3, or CEACAM-5. In preferred embodiments, the gene locus involved in the expression of PD-1 or CTLA-4 genes is targeted. In other preferred embodiments, combinations of genes are targeted, such as but not limited to PD-1 and TIGIT.

By means of an example and without limitation, WO2016196388 concerns an engineered T cell comprising (a) a genetically engineered antigen receptor that specifically binds to an antigen, which receptor may be a CAR; and (b) a disrupted gene encoding a PD-L1, an agent for disruption of a gene encoding a PD-L1, and/or disruption of a gene encoding PD-LI, wherein the disruption of the gene may be mediated by a gene editing nuclease, a zinc finger nuclease (ZFN), CRISPR/Cas9 and/or TALEN. WO2015142675 relates to immune effector cells comprising a CAR in combination with an agent (such as CRISPR, TALEN or ZFN) that increases the efficacy of the immune effector cells in the treatment of cancer, wherein the agent may inhibit an immune inhibitory molecule, such as PD1, PD-L1, CTLA-4, TIM-3, LAG-3, VISTA, BTLA, TIGIT, LAIR1, CD160, 2B4, TGFR beta, CEACAM-1, CEACAM-3, or CEACAM-5. Ren et al., (2017) Clin Cancer Res 23 (9) 2255-2266 performed lentiviral delivery of CAR and electro-transfer of Cas9 mRNA and gRNAs targeting endogenous TCR, β-2 microglobulin (B2M) and PD1 simultaneously, to generate gene-disrupted allogeneic CAR T cells deficient of TCR, HLA class I molecule and PD1.

In certain embodiments, cells may be engineered to express a CAR, wherein expression and/or function of methylcytosine dioxygenase genes (TET1, TET2 and/or TET3) in the cells has been reduced or eliminated, such as by CRISPR, ZNF or TALEN (for example, as described in WO201704916).

In certain embodiments, editing of cells (such as by CRISPR/Cas), particularly cells intended for adoptive cell therapies, more particularly immunoresponsive cells such as T cells, may be performed to knock-out or knock-down expression of an endogenous gene in a cell, said endogenous gene encoding an antigen targeted by an exogenous CAR or TCR, thereby reducing the likelihood of targeting of the engineered cells. In certain embodiments, the targeted antigen may be one or more antigen selected from the group consisting of CD38, CD138, CS-1, CD33, CD26, CD30, CD53, CD92, CD100, CD148, CD150, CD200, CD261, CD262, CD362, human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (D1), B cell maturation antigen (BCMA), transmembrane activator and CAML Interactor (TACI), and B-cell activating factor receptor (BAFF-R) (for example, as described in WO2016011210 and WO2017011804).

In certain embodiments, editing of cells (such as by CRISPR/Cas), particularly cells intended for adoptive cell therapies, more particularly immunoresponsive cells such as T cells, may be performed to knock-out or knock-down expression of one or more MHC constituent proteins, such as one or more HLA proteins and/or beta-2 microglobulin (B2M), in a cell, whereby rejection of non-autologous (e.g., allogeneic) cells by the recipient's immune system can be reduced or avoided. In preferred embodiments, one or more HLA class I proteins, such as HLA-A, B and/or C, and/or B2M may be knocked-out or knocked-down. Preferably, B2M may be knocked-out or knocked-down. By means of an example, Ren et al., (2017) Clin Cancer Res 23 (9) 2255-2266 performed lentiviral delivery of CAR and electro-transfer of Cas9 mRNA and gRNAs targeting endogenous TCR, J-2 microglobulin (B2M) and PD1 simultaneously, to generate gene-disrupted allogeneic CAR T cells deficient of TCR, HLA class I molecule and PD1.

In other embodiments, at least two genes are edited. Pairs of genes may include, but are not limited to PD1 and TCRα, PD1 and TCRθ, CTLA-4 and TCRα, CTLA-4 and TCRθ, LAG3 and TCRα, LAG3 and TCRθ, Tim3 and TCRα, Tim3 and TCRθ, BTLA and TCRα, BTLA and TCRθ, BY55 and TCRα, BY55 and TCRθ, TIGIT and TCRα, TIGIT and TCRθ, B7H5 and TCRα, B7H5 and TCRθ, LAIR1 and TCRα, LAIR1 and TCRθ, SIGLEC10 and TCRα, SIGLEC10 and TCRθ, 2B4 and TCRα, 2B4 and TCRθ, B2M and TCRα, B2M and TCRθ.

In certain embodiments, editing of cells may include editing T cells for modulating expression, preferably decrease or knockout expression, of the glucocorticoid receptor and IL-27 receptor. In certain embodiments, editing of cells may include editing T cells for modulating expression, preferably decrease or knockout expression, of downstream targets of glucocorticoid and IL-27 combined signaling as described herein. In certain embodiments, editing these targets can generate T cells resistant to immunosuppressive treatments, such as glucocorticoid treatment. In certain embodiments, the T cells can provide enhanced immune responses.

In certain embodiments, a cell may be multiply edited (multiplex genome editing) as taught herein to (1) knock-out or knock-down expression of an endogenous TCR (for example, TRBC1, TRBC2 and/or TRAC), (2) knock-out or knock-down expression of an immune checkpoint protein or receptor (for example PD1, PD-L1 and/or CTLA4); and (3) knock-out or knock-down expression of one or more MHC constituent proteins (for example, HLA-A, B and/or C, and/or B2M, preferably B2M).

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

Immune cells may be obtained using any method known in the art. In one embodiment, allogenic T cells may be obtained from healthy subjects. In one embodiment T cells that have infiltrated a tumor are isolated. T cells may be removed during surgery. T cells may be isolated after removal of tumor tissue by biopsy. T cells may be isolated by any means known in the art. In one embodiment, T cells are obtained by apheresis. In one embodiment, the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal" refers to any mammal including, but not limited to, mammals of the order Lagomorpha, such as rabbits; the order Carnivora, including Felines (cats) and Canines (dogs); the order Artiodactyla, including Bovines (cows) and Swines (pigs); or of the order Perissodactyla, including Equines (horses). The mammals may be non-human primates, e.g., of the order Primates, Ceboids, or Simoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells (PBMC), bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one preferred embodiment, T cells are isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (i.e., CD14+ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments, the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may also be antigen-specific T cells. For example, tumor-specific T cells can be used. In certain embodiments, antigen-specific T cells can be isolated from a patient of interest, such as a patient afflicted with a cancer or an infectious disease. In one embodiment, neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation and Isolation of Antigen-Specific T Cells, or in U.S. Pat. Nos. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-MHC tetramers (Altman, et al., Science. 1996 Oct. 4; 274(5284):94-6). In another embodiment, the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MHC molecule of interest and any antigen of interest as described herein. Specific epitopes to be used in this context can be identified using numerous assays known in the art. For example, the ability of a polypeptide to bind to MHC class I may be evaluated indirectly by monitoring the ability to promote incorporation of $^{125}$I labeled β2-microglobulin (β2m) into MHC class I/β2m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one embodiment, T cells are isolated by contacting with T cell specific antibodies. Sorting of antigen-specific T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™, BD™ LSR II, and FACSCalibur™ (BD Biosciences, San Jose, Calif.).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

In certain embodiments, T cells comprising a CAR or an exogenous TCR, may be manufactured as described in WO2015120096, by a method comprising: enriching a population of lymphocytes obtained from a donor subject; stimulating the population of lymphocytes with one or more T-cell stimulating agents to produce a population of activated T cells, wherein the stimulation is performed in a closed system using serum-free culture medium; transducing the population of activated T cells with a viral vector comprising a nucleic acid molecule which encodes the CAR or TCR, using a single cycle transduction to produce a population of transduced T cells, wherein the transduction is performed in a closed system using serum-free culture medium; and expanding the population of transduced T cells for a predetermined time to produce a population of engineered T cells, wherein the expansion is performed in a closed system using serum-free culture medium. In certain embodiments, T cells comprising a CAR or an exogenous TCR, may be manufactured as described in WO2015120096, by a method comprising: obtaining a population of lymphocytes; stimulating the population of lymphocytes with one or more stimulating agents to produce a population of activated T cells, wherein the stimulation is performed in a closed system using serum-free culture medium; transducing the population of activated T cells with a viral vector comprising a nucleic acid molecule which encodes the CAR or TCR, using at least one cycle transduction to produce a population of transduced T cells, wherein the transduction is performed in a closed system using serum-free culture medium; and expanding the population of transduced T cells to produce a population of engineered T cells, wherein the expansion is performed in a closed system using serum-free culture medium. The predetermined time for expanding the population of transduced T cells may be 3 days. The time from enriching the population of lymphocytes to producing the engineered T cells may be 6 days. The closed system may be a closed bag system. Further provided is population of T cells comprising a CAR or an exogenous TCR obtainable or obtained by said method, and a pharmaceutical composition comprising such cells.

In certain embodiments, T cell maturation or differentiation in vitro may be delayed or inhibited by the method as described in WO2017070395, comprising contacting one or more T cells from a subject in need of a T cell therapy with an AKT inhibitor (such as, e.g., one or a combination of two or more AKT inhibitors disclosed in claim 8 of WO2017070395) and at least one of exogenous Interleukin-7 (IL-7) and exogenous Interleukin-15 (IL-15), wherein the resulting T cells exhibit delayed maturation or differentiation, and/or wherein the resulting T cells exhibit improved T cell function (such as, e.g., increased T cell proliferation; increased cytokine production; and/or increased cytolytic activity) relative to a T cell function of a T cell cultured in the absence of an AKT inhibitor.

In certain embodiments, a patient in need of a T cell therapy may be conditioned by a method as described in WO2016191756 comprising administering to the patient a dose of cyclophosphamide between 200 mg/m2/day and 2000 mg/m2/day and a dose of fludarabine between 20 mg/m2/day and 900 mg/m$^2$/day.

In certain embodiments, a patient in need of adoptive cell transfer may be administered a TLR agonist to enhance anti-tumor immunity (see, e.g., Urban-Wojciuk, et al., The Role of TLRs in Anti-cancer Immunity and Tumor Rejection, Front Immunol. 2019; 10: 2388; and Kaczanowska et al., TLR agonists: our best frenemy in cancer immunotherapy, J Leukoc Biol. 2013 June; 93(6): 847-863). In certain embodiments, TLR agonists are delivered in a nanoparticle system (see, e.g., Buss and Bhatia, Nanoparticle delivery of immunostimulatory oligonucleotides enhances response to checkpoint inhibitor therapeutics, Proc Natl Acad Sci USA. 2020 Jun. 3; 202001569). In certain embodiments, the agonist is a TLR9 agonist. Id.

Standard of Care

Aspects of the invention involve modifying therapeutic methods within a standard of care. In one embodiment, therapy comprising an agent is administered within a standard of care where addition of the agent is synergistic within the steps of the standard of care. In certain embodiments, a steroidogenesis inhibitor is administered within a standard of care. In one embodiment, the agent targets glucocorticoid and IL27 signaling. In one embodiment, the agent inhibits expression or activity of a gene or polypeptide selected from the downstream targets of glucocorticoid and IL-27 described herein. The term "standard of care" as used herein refers to the current treatment that is accepted by medical experts as a proper treatment for a certain type of disease and that is widely used by healthcare professionals. Standard of care is also called best practice, standard medical care, and standard therapy. Standards of care for cancer generally include surgery, lymph node removal, radiation, chemotherapy, targeted therapies, antibodies targeting the tumor, and immunotherapy. Immunotherapy can include checkpoint blockers (CBP), chimeric antigen receptors (CARs), and adoptive T-cell therapy. In certain embodiments, immunotherapy leads to immune-related adverse events (irAEs) and the standard of care includes treatment with glucocorticoids (see, e.g., Kumar, V. et al. Current Diagnosis and Management of Immune Related Adverse Events (irAEs) Induced by Immune Checkpoint Inhibitor Therapy. Front Pharmacol 2017, 8, 49; and Gelao et al., Immune Checkpoint Blockade in Cancer Treatment: A Double-Edged Sword Cross-Targeting the Host as an "Innocent Bystander", Toxins 2014, 6, 914-933; doi:10.3390/toxins6030914). In certain embodiments, glucocorticoids may inhibit adaptive immunity when administered as part of a therapeutic regimen (e.g., in cancer).

Glucocorticoids are often administered to help patients tolerate treatment, rather than as a chemotherapeutic that targets the cancer itself (see, e.g., Pufall, Glucocorticoids and Cancer, Adv Exp Med Biol. 2015; 872: 315-333. doi: 10.1007/978-1-4939-2895-8_14). In some chemotherapeutic regimens, for example those that include cisplatin, glucocorticoids are first-line antiemetics. For others, such as folate inhibitors, they are used to blunt hypersensitivity, which can result in severe skin rashes. Glucocorticoids are used for their anti-inflammatory properties to relieve bone pain other discomfort that may arise from metastatic disease and CNS compression due to metastatic disease. Though effective for these purposes, the use of glucocorticoids in patients with cancer caries some risk of protecting the tumor against chemotherapeutic or immunotherapy agents, or even increasing proliferation rates.

In certain embodiments, downstream targets of glucocorticoid and IL-27 signaling are targeted to make T cells resistant to or blocked from becoming exhausted or dysfunctional while maintaining the anti-inflammatory activity required for patients to tolerate treatment. In certain embodiments, glucocorticoid and/or IL-27 signaling is blocked.

The standards of care for the most common cancers can be found on the website of National Cancer Institute (www.cancer.gov/cancertopics). A treatment clinical trial is a research study meant to help improve current treatments or obtain information on new treatments for patients with cancer. When clinical trials show that a new treatment is better than the standard treatment, the new treatment may be considered the new standard treatment.

The term "Adjuvant therapy" as used herein refers to any treatment given after primary therapy to increase the chance of long-term disease-free survival. The term "Neoadjuvant therapy" as used herein refers to any treatment given before primary therapy. The term "Primary therapy" as used herein refers to the main treatment used to reduce or eliminate the cancer.

In certain embodiments, glucocorticoid treatment does not provide a desired anti-inflammatory response. As described further herein, treatment targeting glucocorticoid signaling and IL-27 signaling or downstream targets of the combination treatment may be used to elicit an improved anti-inflammatory response.
Additional Classes of Agents In certain embodiments, an agent capable of modulating a target described herein is administered. Agents may include a fragment, derivative and analog of an active agent. The terms "fragment," "derivative" and "analog" when referring to polypeptides as used herein refers to polypeptides which either retain substantially the same biological function or activity as such polypeptides. An analog includes a proprotein which can be activated by cleavage of the proprotein portion to produce an active mature polypeptide. Such agents include, but are not limited to, antibodies ("antibodies" includes antigen-binding portions of antibodies such as epitope- or antigen-binding peptides, paratopes, functional CDRs; recombinant antibodies; chimeric antibodies; humanized antibodies; nanobodies; tribodies; midibodies; or antigen-binding derivatives, analogs, variants, portions, or fragments thereof), protein-binding agents, nucleic acid molecules, small molecules, recombinant protein, peptides, aptamers, avimers and protein-binding derivatives, portions or fragments thereof. An "agent" as used herein, may also refer to an agent that inhibits expression of a gene, such as but not limited to a DNA targeting agent (e.g., CRISPR system, TALE, Zinc finger protein) or RNA targeting agent (e.g., inhibitory nucleic acid molecules such as RNAi, miRNA, ribozyme).

The composition of the invention can also advantageously be formulated in order to release an agent in the subject in a timely controlled fashion. In certain embodiments, the agent is a time released agent. The active agent may be released upon contact with a certain pH. The agent may be administered in a time release device.

The agents of the present invention may be modified, such that they acquire advantageous properties for therapeutic use (e.g., stability and specificity), but maintain their biological activity.

It is well known that the properties of certain proteins can be modulated by attachment of polyethylene glycol (PEG) polymers, which increases the hydrodynamic volume of the protein and thereby slows its clearance by kidney filtration. (See, e.g., Clark et al., J. Biol. Chem. 271: 21969-21977 (1996)). Therefore, it is envisioned that certain agents can be PEGylated (e.g., on peptide residues) to provide enhanced therapeutic benefits such as, for example, increased efficacy by extending half-life in vivo. In certain embodiments, PEGylation of the agents may be used to extend the serum half-life of the agents and allow for particular agents to be capable of crossing the blood-brain barrier. Thus, in one embodiment, PEGylating the agonists or antagonists improve their pharmacokinetics and pharmacodynamics.

In regards to peptide PEGylation methods, reference is made to Lu et al., Int. J. Pept. Protein Res. 43: 127-38 (1994); Lu et al., Pept. Res. 6: 140-6 (1993); Felix et al., Int. J. Pept. Protein Res. 46: 253-64 (1995); Gaertner et al., Bioconjug. Chem. 7: 38-44 (1996); Tsutsumi et al., Thromb. Haemost. 77: 168-73 (1997); Francis et al., hit. J. Hematol. 68: 1-18 (1998); Roberts et al., J. Pharm. Sci. 87: 1440-45 (1998); and Tan et al., Protein Expr. Purif. 12: 45-52 (1998). Polyethylene glycol or PEG is meant to encompass any of the forms of PEG that have been used to derivatize other proteins, including, but not limited to, mono-(C1-10) alkoxy or aryloxy-polyethylene glycol. Suitable PEG moieties include, for example, 40 kDa methoxy poly(ethylene glycol) propionaldehyde (Dow, Midland, Mich.); 60 kDa methoxy poly(ethylene glycol) propionaldehyde (Dow, Midland, Mich.); 40 kDa methoxy poly(ethylene glycol) maleimidopropionamide (Dow, Midland, Mich.); 31 kDa alpha-methyl-w-(3-oxopropoxy), polyoxyethylene (NOF Corporation, Tokyo); mPEG2-NHS-40k (Nektar); mPEG2-MAL-40k (Nektar), SUNBRIGHT GL2-400MA ((PEG)240 kDa) (NOF Corporation, Tokyo), SUNBRIGHT ME-200MA (PEG20 kDa) (NOF Corporation, Tokyo). The PEG groups are generally attached to the peptide via acylation or alkylation through a reactive group on the PEG moiety (for example, a maleimide, an aldehyde, amino, thiol, or ester group) to a reactive group on the peptide (for example, an aldehyde, amino, thiol, a maleimide, or ester group).

The PEG molecule(s) may be covalently attached to any Lys, Cys, or K(CO(CH2)2SH) residues at any position in a peptide. In certain embodiments, the agents described herein can be PEGylated directly to any amino acid at the N-terminus by way of the N-terminal amino group. A "linker arm" may be added to a peptide to facilitate PEGylation. PEGylation at the thiol side-chain of cysteine has been widely reported (see, e.g., Caliceti & Veronese, Adv. Drug Deliv. Rev. 55: 1261-77 (2003)). If there is no cysteine residue in the peptide, a cysteine residue can be introduced through substitution or by adding a cysteine to the N-terminal amino acid. In certain embodiments, protein agents are PEGylated through the side chains of a cysteine residue added to the N-terminal amino acid.

In exemplary embodiments, the PEG molecule(s) may be covalently attached to an amide group in the C-terminus of a peptide. In preferred embodiments, there is at least one PEG molecule covalently attached to the agent. In certain embodiments, the PEG molecule used in modifying an agent of the present invention is branched while in other embodiments, the PEG molecule may be linear. In particular aspects, the PEG molecule is between 1 kDa and 100 kDa in molecular weight. In further aspects, the PEG molecule is selected from 10, 20, 30, 40, 50, 60, and 80 kDa. In further still aspects, it is selected from 20, 40, or 60 kDa. Where there are two PEG molecules covalently attached to the agent of the present invention, each is 1 to 40 kDa and in particular aspects, they have molecular weights of 20 and 20 kDa, 10 and 30 kDa, 30 and 30 kDa, 20 and 40 kDa, or 40 and 40 kDa. In particular aspects, the agent (e.g., neuromedin U receptor agonists or antagonists) contain mPEG-cysteine. The mPEG in mPEG-cysteine can have various molecular weights. The range of the molecular weight is preferably 5 kDa to 200 kDa, more preferably 5 kDa to 100 kDa, and further preferably 20 kDa to 60 kDA. The mPEG can be linear or branched.

In particular embodiments, the agents (e.g., agonist or antagonists) include a protecting group covalently joined to the N-terminal amino group. In exemplary embodiments, a protecting group covalently joined to the N-terminal amino group of the agent reduces the reactivity of the amino terminus under in vivo conditions. Amino protecting groups include C1-10 alkyl, C1-10 substituted alkyl, C2-10 alkenyl, C2-10 substituted alkenyl, aryl, C1-6 alkyl aryl, C(O)—(CH2)1-6-COOH, C(O)—C1-6 alkyl, C(O)-aryl, C(O)—O—C1-6 alkyl, or C(O)—O-aryl. In particular embodiments, the amino terminus protecting group is selected from the group consisting of acetyl, propyl, succinyl, benzyl, benzyloxycarbonyl, and t-butyloxycarbonyl. In other embodiments, deamination of the N-terminal amino acid is another modification that may be used for reducing the reactivity of the amino terminus under in vivo conditions.

Chemically modified compositions of the agents wherein the agent is linked to a polymer are also included within the scope of the present invention. The polymer selected is usually modified to have a single reactive group, such as an active ester for acylation or an aldehyde for alkylation, so that the degree of polymerization may be controlled. Included within the scope of polymers is a mixture of polymers. Preferably, for therapeutic use of the end-product preparation, the polymer will be pharmaceutically acceptable. The polymer or mixture thereof may include but is not limited to polyethylene glycol (PEG), monomethoxy-polyethylene glycol, dextran, cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (for example, glycerol), and polyvinyl alcohol.

In other embodiments, the agents are modified by PEGylation, cholesterylation, or palmitoylation. The modification can be to any amino acid residue. In preferred embodiments, the modification is to the N-terminal amino acid of the agent (e.g., agonist or antagonists), either directly to the N-terminal amino acid or by way coupling to the thiol group of a cysteine residue added to the N-terminus or a linker added to the N-terminus such as trimesoyl tris(3,5-dibromosalicylate) (Ttds). In certain embodiments, the N-terminus of the agent comprises a cysteine residue to which a protecting group is coupled to the N-terminal amino group of the cysteine residue and the cysteine thiolate group is derivatized with N-ethylmaleimide, PEG group, cholesterol group, or palmitoyl group. In other embodiments, an acetylated cysteine residue is added to the N-terminus of the agents, and the thiol group of the cysteine is derivatized with N-ethylmaleimide, PEG group, cholesterol group, or palmitoyl group. In certain embodiments, the agent of the present invention is a conjugate. In certain embodiments, the agent of the present invention (e.g., agonists or antagonists) is a polypeptide consisting of an amino acid sequence which is bound with a methoxypolyethylene glycol(s) via a linker.

Substitutions of amino acids may be used to modify an agent of the present invention. The phrase "substitution of amino acids" as used herein encompasses substitution of amino acids that are the result of both conservative and non-conservative substitutions. Conservative substitutions are the replacement of an amino acid residue by another similar residue in a polypeptide. Typical but not limiting conservative substitutions are the replacements, for one another, among the aliphatic amino acids Ala, Val, Leu and Ile; interchange of Ser and Thr containing hydroxy residues, interchange of the acidic residues Asp and Glu, interchange between the amide-containing residues Asn and Gln, interchange of the basic residues Lys and Arg, interchange of the aromatic residues Phe and Tyr, and interchange of the small-sized amino acids Ala, Ser, Thr, Met, and Gly. Non-conservative substitutions are the replacement, in a polypeptide, of an amino acid residue by another residue which is not biologically similar. For example, the replacement of an amino acid residue with another residue that has a substantially different charge, a substantially different hydrophobicity, or a substantially different spatial configuration.

Small Molecule

In certain embodiments, the one or more agents is a small molecule. The term "small molecule" refers to compounds, preferably organic compounds, with a size comparable to those organic molecules generally used in pharmaceuticals. The term excludes biological macromolecules (e.g., proteins, peptides, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da. In certain embodiments, the small molecule may act as an antagonist or agonist (e.g., blocking a binding site or activating a receptor by binding to a ligand binding site).

One type of small molecule applicable to the present invention is a degrader molecule (see, e.g., Ding, et al., Emerging New Concepts of Degrader Technologies, Trends Pharmacol Sci. 2020 July; 41(7):464-474). The terms "degrader" and "degrader molecule" refer to all compounds capable of specifically targeting a protein for degradation (e.g., ATTEC, AUTAC, LYTAC, or PROTAC, reviewed in Ding, et al. 2020). Proteolysis Targeting Chimera (PROTAC) technology is a rapidly emerging alternative therapeutic strategy with the potential to address many of the challenges currently faced in modern drug development programs. PROTAC technology employs small molecules that recruit target proteins for ubiquitination and removal by the proteasome (see, e.g., Zhou et al., Discovery of a Small-Molecule Degrader of Bromodomain and Extra-Terminal (BET) Proteins with Picomolar Cellular Potencies and Capable of Achieving Tumor Regression. J. Med. Chem. 2018, 61, 462-481; Bondeson and Crews, Targeted Protein Degradation by Small Molecules, Annu Rev Pharmacol Toxicol. 2017 Jan. 6; 57: 107-123; and Lai et al., Modular PROTAC Design for the Degradation of Oncogenic BCR-ABL Angew Chem Int Ed Engl. 2016 Jan. 11; 55(2): 807-810). In certain embodiments, LYTACs are particularly advantageous for cell surface proteins as described herein.

In certain embodiments, combinations of targets are modulated (e.g., one or more targets in a gene signature). In certain embodiments, an agent against one of the targets in a combination may already be known or used clinically. In certain embodiments, targeting the combination may require less of the agent as compared to the current standard of care and provide for less toxicity and improved treatment.

Antibodies

In certain embodiments, the agent is an antibody. The term "antibody" is used interchangeably with the term "immunoglobulin" herein, and includes intact antibodies, fragments of antibodies, e.g., Fab, F(ab')2 fragments, and intact antibodies and fragments that have been mutated either in their constant and/or variable region (e.g., mutations to produce chimeric, partially humanized, or fully humanized antibodies, as well as to produce antibodies with a desired trait, e.g., enhanced binding and/or reduced FcR binding). The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc, Fd, dAb, VHH and scFv and/or Fv fragments.

As used herein, a preparation of antibody protein having less than about 50% of non-antibody protein (also referred to herein as a "contaminating protein"), or of chemical precursors, is considered to be "substantially free." 40%, 30%, 20%, 10% and more preferably 5% (by dry weight), of non-antibody protein, or of chemical precursors is considered to be substantially free. When the antibody protein or biologically active portion thereof is recombinantly produced, it is also preferably substantially free of culture medium, i.e., culture medium represents less than about 30%, preferably less than about 20%, more preferably less than about 10%, and most preferably less than about 5% of the volume or mass of the protein preparation.

The term "antigen-binding fragment" refers to a polypeptide fragment of an immunoglobulin or antibody that binds antigen or competes with intact antibody (i.e., with the intact antibody from which they were derived) for antigen binding (i.e., specific binding). As such these antibodies or fragments thereof are included in the scope of the invention, provided that the antibody or fragment binds specifically to a target molecule.

It is intended that the term "antibody" encompass any Ig class or any Ig subclass (e.g. the IgG1, IgG2, IgG3, and IgG4 subclasses of IgG) obtained from any source (e.g., humans and non-human primates, and in rodents, lagomorphs, caprines, bovines, equines, ovines, etc.).

The term "Ig class" or "immunoglobulin class", as used herein, refers to the five classes of immunoglobulin that have been identified in humans and higher mammals, IgG, IgM, IgA, IgD, and IgE. The term "Ig subclass" refers to the two subclasses of IgM (H and L), three subclasses of IgA (IgA1, IgA2, and secretory IgA), and four subclasses of IgG (IgG1, IgG2, IgG3, and IgG4) that have been identified in humans and higher mammals. The antibodies can exist in monomeric or polymeric form; for example, lgM antibodies exist in pentameric form, and IgA antibodies exist in monomeric, dimeric or multimeric form.

The term "IgG subclass" refers to the four subclasses of immunoglobulin class IgG—IgG1, IgG2, IgG3, and IgG4 that have been identified in humans and higher mammals by the heavy chains of the immunoglobulins, V1-γ4, respectively. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by p pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of an antibody light chain are referred to interchangeably as "light chain constant regions", "light chain constant domains", "CL" regions or "CL" domains. The "constant" domains of an antibody heavy chain are referred to interchangeably as "heavy chain constant regions", "heavy chain constant domains", "CH" regions or "CH" domains. The "variable" domains of an antibody light chain are referred to interchangeably as "light chain variable regions", "light chain variable domains", "VL" regions or "VL" domains. The "variable" domains of an antibody heavy chain are referred to interchangeably as "heavy chain constant regions", "heavy chain constant domains", "VH" regions or "VH" domains.

The term "region" can also refer to a part or portion of an antibody chain or antibody chain domain (e.g., a part or portion of a heavy or light chain or a part or portion of a constant or variable domain, as defined herein), as well as more discrete parts or portions of said chains or domains. For example, light and heavy chains or light and heavy chain variable domains include "complementarity determining regions" or "CDRs" interspersed among "framework regions" or "FRs", as defined herein.

The term "conformation" refers to the tertiary structure of a protein or polypeptide (e.g., an antibody, antibody chain, domain or region thereof). For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof.

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from nonimmunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alternative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alpha-helices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (10Fn3), which adopts an Ig-like beta-sandwich fold (94 residues) with 2-3 exposed loops, but lacks the central disulphide bridge (Koide and Koide, Monobodies: antibody mimics based on the scaffold of the fibronectin type III domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins—harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

"Specific binding" of an antibody means that the antibody exhibits appreciable affinity for a particular antigen or epitope and, generally, does not exhibit significant cross reactivity. "Appreciable" binding includes binding with an affinity of at least 25 µM. Antibodies with affinities greater than $1\times10^7$ M-1 (or a dissociation coefficient of 1 µM or less or a dissociation coefficient of 1 nm or less) typically bind with correspondingly greater specificity. Values intermediate of those set forth herein are also intended to be within the scope of the present invention and antibodies of the invention bind with a range of affinities, for example, 100 nM or less, 75 nM or less, 50 nM or less, 25 nM or less, for example 10 nM or less, 5 nM or less, 1 nM or less, or in embodiments 500 pM or less, 100 pM or less, 50 pM or less or 25 pM or less. An antibody that "does not exhibit significant crossreactivity" is one that will not appreciably bind to an entity other than its target (e.g., a different epitope or a different molecule). For example, an antibody that specifically binds to a target molecule will appreciably bind the target molecule but will not significantly react with non-target molecules or peptides. An antibody specific for a particular epitope will, for example, not significantly cross-react with remote epitopes on the same protein or peptide. Specific binding can be determined according to any art-recognized means for determining such binding. Preferably, specific binding is determined according to Scatchard analysis and/or competitive binding assays.

As used herein, the term "affinity" refers to the strength of the binding of a single antigen-combining site with an antigenic determinant. Affinity depends on the closeness of stereochemical fit between antibody combining sites and antigen determinants, on the size of the area of contact between them, on the distribution of charged and hydrophobic groups, etc. Antibody affinity can be measured by equilibrium dialysis or by the kinetic BIACORE™ method. The dissociation constant, Kd, and the association constant, Ka, are quantitative measures of affinity.

As used herein, the term "monoclonal antibody" refers to an antibody derived from a clonal population of antibody-producing cells (e.g., B lymphocytes or B cells) which is homogeneous in structure and antigen specificity. The term "polyclonal antibody" refers to a plurality of antibodies originating from different clonal populations of antibody-producing cells which are heterogeneous in their structure and epitope specificity but which recognize a common antigen. Monoclonal and polyclonal antibodies may exist within bodily fluids, as crude preparations, or may be purified, as described herein.

The term "binding portion" of an antibody (or "antibody portion") includes one or more complete domains, e.g., a pair of complete domains, as well as fragments of an antibody that retain the ability to specifically bind to a target molecule. It has been shown that the binding function of an antibody can be performed by fragments of a full-length antibody. Binding fragments are produced by recombinant DNA techniques, or by enzymatic or chemical cleavage of intact immunoglobulins. Binding fragments include Fab, Fab', F(ab')2, Fabc, Fd, dAb, Fv, single chains, single-chain antibodies, e.g., scFv, and single domain antibodies.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, FR residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

Examples of portions of antibodies or epitope-binding proteins encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., 341 Nature 544 (1989)) which consists of a VH domain or a VL domain that binds antigen; (vii) isolated CDR regions or isolated CDR regions presented in a functional framework; (viii) F(ab')2 fragments which are bivalent fragments including two Fab' fragments linked by a disulphide bridge at the hinge region; (ix) single chain antibody molecules (e.g., single chain Fv; scFv) (Bird et al., 242 Science 423 (1988); and Huston et al., 85 PNAS 5879 (1988)); (x) "diabodies" with two antigen binding sites, comprising a heavy chain variable domain (VH) connected to a light chain variable domain (VL) in the same polypeptide chain (see, e.g., EP 404,097; WO 93/11161; Hollinger et al., 90 PNAS 6444 (1993)); (xi) "linear antibodies" comprising a pair of tandem Fd segments (VH-Ch1-VH-Ch1) which, together with complementary light chain polypeptides, form a pair of antigen binding regions (Zapata et al., Protein Eng. 8(10):1057-62 (1995); and U.S. Pat. No. 5,641, 870).

As used herein, a "blocking" antibody or an antibody "antagonist" is one which inhibits or reduces biological activity of the antigen(s) it binds. For example, an antagonist antibody may bind glucocorticoid receptor, glucocorticoid, IL-27 receptor, or IL-27 and inhibit the ability to suppress an immune response. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex. Likewise, encompassed by the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides disclosed herein. The antibody agonists and antagonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16): 3668-3678 (1998); Harrop et al., J. Immunol. 161(4):1786-1794 (1998); Zhu et al., Cancer Res. 58(15):3209-3214 (1998); Yoon et al., J. Immunol. 160(7):3170-3179 (1998); Prat et al., J. Cell. Sci. III (Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996).

The antibodies as defined for the present invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Simple binding assays can be used to screen for or detect agents that bind to a target protein, or disrupt the interaction between proteins (e.g., a receptor and a ligand). Because certain targets of the present invention are transmembrane proteins, assays that use the soluble forms of these proteins rather than full-length protein can be used, in some embodiments. Soluble forms include, for example, those lacking the transmembrane domain and/or those comprising the IgV domain or fragments thereof which retain their ability to bind their cognate binding partners. Further, agents that inhibit or enhance protein interactions for use in the compositions and methods described herein, can include recombinant peptido-mimetics.

Detection methods useful in screening assays include antibody-based methods, detection of a reporter moiety, detection of cytokines as described herein, and detection of a gene signature as described herein.

Another variation of assays to determine binding of a receptor protein to a ligand protein is through the use of affinity biosensor methods. Such methods may be based on the piezoelectric effect, electrochemistry, or optical methods, such as ellipsometry, optical wave guidance, and surface plasmon resonance (SPR).

Bi-Specific Antibodies

In certain embodiments, the one or more therapeutic agents can be bi-specific antigen-binding constructs, e.g., bi-specific antibodies (bsAb) or BiTEs, that bind two antigens (see, e.g., Suurs et al., A review of bispecific antibodies and antibody constructs in oncology and clinical challenges. Pharmacol Ther. 2019 September; 201:103-119; and Huehls, et al., Bispecific T cell engagers for cancer immunotherapy. Immunol Cell Biol. 2015 March; 93(3): 290-296). The bi-specific antigen-binding construct includes two antigen-binding polypeptide constructs, e.g., antigen binding domains, wherein at least one polypeptide construct specifically binds to a cell surface protein (e.g., monocytes and/or macrophages). Non-limiting examples of monocyte markers include CD2, CD11b, CD14, CD16, CD31, CD56, CD62L, CD115, CD192, CX3CR1, CXCR3, CXCR4; and non-limiting examples of macrophage markers include CD14, CD16, CD64, CD68, CD71 and CCR5 (see, e.g., Chavez-Galan L. et al. (2015). Much more than M1 and M2 macrophages, there are also CD169+ and TCR+ macrophages. Front Immunol. 6:263; Duluc D. et al. (2007). Tumor-associated leukemia inhibitory factor and IL-6 skew monocyte differentiation into tumor-associated macrophage-like cells. Blood 110, 4319-4330; Geissmann F et al. (2010). Development of monocytes, macrophages and dendritic cells. Science. 327(5966):656-661; Heusinkveld M and van der Burg H (2011). Identification and manipulation of tumor associated macrophages in human cancers. J Transl Med 9, 216-229; Murray P J. & Wynn T A. (2011). Protective and pathogenic functions of macrophage subsets. Nat Rev Immunol. 11:723-737; Roszer T. (2015). Understanding the Mysterious M2 Macrophage through Activation Markers and Effector Mechanism. Mediators of Inflammation. 2015: 816460; and Geissmann F. et al. (2003). Blood Monocytes Consist of Two Principal Subsets with Distinct Migratory Properties. Immunity. 19:71-82). In some embodiments, the antigen-binding construct is derived from known antibodies or antigen-binding constructs. In some embodiments, the antigen-binding polypeptide constructs comprise two antigen binding domains that comprise antibody fragments. In some embodiments, the first antigen binding domain and second antigen binding domain each independently comprises an antibody fragment selected from the group of: an scFv, a Fab, and an Fc domain. The antibody fragments may be the same format or different formats from each other. For example, in some embodiments, the antigen-binding polypeptide constructs comprise a first antigen binding domain comprising an scFv and a second antigen binding domain comprising a Fab. In some embodiments, the antigen-binding polypeptide constructs comprise a first antigen binding domain and a second antigen binding domain, wherein both antigen binding domains comprise an scFv. In some embodiments, the first and second antigen binding domains each comprise a Fab. In some embodiments, the first and second antigen binding domains each comprise an Fc domain. Any combination of antibody formats is suitable for the bi-specific antibody constructs disclosed herein.

In certain embodiments, cells are targeted with a bsAb having affinity for both the immune cell and a payload (e.g., metyrapone). By means of an example, an agent, such as a bi-specific antibody, capable of specifically binding to a gene product expressed on the cell surface of the immune cells and a payload (e.g., metyrapone) may be used for decreasing glucocorticoid synthesis in the immune cells. A bsAb with affinity for the immune cells and the payload can be incubated with the payload before injection. Pre-targeted delivery could also be achieved by first injecting the bsAb with affinity for an immune cell marker and for a payload, and then injecting the payload.

Antibody Drug Conjugates

In certain embodiments, the one or more therapeutic agents can be and antibody-drug-conjugate. The term "antibody-drug-conjugate" or "ADC" refers to a binding protein, such as an antibody or antigen binding fragment thereof, chemically linked to one or more chemical drug(s) (also referred to herein as agent(s)) that may optionally be therapeutic or cytotoxic agents. In a preferred embodiment, an ADC includes an agent capable of inhibiting glucocorticoid synthesis (e.g., metyrapone) and a linker that enables attachment or conjugation of the drug to the antibody. An ADC typically has anywhere from 1 to 8 drugs conjugated to the antibody, including drug loaded species of 2, 4, 6, or 8.

In certain embodiments, the ADC specifically binds to a marker expressed on the cell surface of a monocyte and/or macrophage. By means of an example, an agent, such as an antibody, capable of specifically binding to a marker expressed on the cell surface of a monocyte and/or macrophage may be conjugated with an agent capable of inhibiting glucocorticoid synthesis (e.g., metyrapone) for targeted delivery of the agent to the immune cells.

Aptamers

In certain embodiments, the one or more agents is an aptamer. Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, cells, tissues and organisms. Nucleic acid aptamers have specific binding affinity to molecules through interactions other than classic Watson-Crick base pairing. Aptamers are useful in biotechnological and therapeutic applications as they offer molecular recognition properties similar to antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. In certain embodiments, RNA aptamers may be expressed from a DNA construct. In other embodiments, a nucleic acid aptamer may be linked to another polynucleotide sequence. The polynucleotide sequence may be a double stranded DNA polynucleotide sequence. The aptamer may be covalently linked to one strand of the polynucleotide sequence. The aptamer may be ligated to the polynucleotide sequence. The polynucleotide sequence may be configured, such that the polynucleotide sequence may be linked to a solid support or ligated to another polynucleotide sequence.

Aptamers, like peptides generated by phage display or monoclonal antibodies ("mAbs"), are capable of specifically binding to selected targets and modulating the target's activity, e.g., through binding, aptamers may block their target's ability to function. A typical aptamer is 10-15 kDa in size (30-45 nucleotides), binds its target with sub-nanomolar affinity, and discriminates against closely related targets (e.g., aptamers will typically not bind other proteins from the same gene family). Structural studies have shown that aptamers are capable of using the same types of binding interactions (e.g., hydrogen bonding, electrostatic complementarity, hydrophobic contacts, steric exclusion) that drives affinity and specificity in antibody-antigen complexes.

Aptamers have a number of desirable characteristics for use in research and as therapeutics and diagnostics including high specificity and affinity, biological efficacy, and excellent pharmacokinetic properties. In addition, they offer specific competitive advantages over antibodies and other protein biologics. Aptamers are chemically synthesized and are readily scaled as needed to meet production demand for research, diagnostic or therapeutic applications. Aptamers are chemically robust. They are intrinsically adapted to regain activity following exposure to factors such as heat and denaturants and can be stored for extended periods (>1 yr) at room temperature as lyophilized powders. Not being bound by a theory, aptamers bound to a solid support or beads may be stored for extended periods.

Oligonucleotides in their phosphodiester form may be quickly degraded by intracellular and extracellular enzymes such as endonucleases and exonucleases. Aptamers can include modified nucleotides conferring improved characteristics on the ligand, such as improved in vivo stability or improved delivery characteristics. Examples of such modifications include chemical substitutions at the ribose and/or phosphate and/or base positions. SELEX identified nucleic acid ligands containing modified nucleotides are described, e.g., in U.S. Pat. No. 5,660,985, which describes oligonucleotides containing nucleotide derivatives chemically modified at the 2' position of ribose, 5 position of pyrimidines, and 8 position of purines, U.S. Pat. No. 5,756,703 which describes oligonucleotides containing various 2'-modified pyrimidines, and U.S. Pat. No. 5,580,737 which describes highly specific nucleic acid ligands containing one or more nucleotides modified with 2'-amino (2'-$NH_2$), 2'-fluoro (2'-F), and/or 2'-O-methyl (2'-OMe) substituents. Modifications of aptamers may also include, modifications at exocyclic amines, substitution of 4-thiouridine, substitution of 5-bromo or 5-iodo-uracil; backbone modifications, phosphorothioate or allyl phosphate modifications, methylations, and unusual base-pairing combinations such as the isobases isocytidine and isoguanosine. Modifications can also include 3' and 5' modifications such as capping. As used herein, the term phosphorothioate encompasses one or more non-bridging oxygen atoms in a phosphodiester bond replaced by one or more sulfur atoms. In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, O-allyl, S-alkyl, S-allyl, or halo group. Methods of synthesis of 2'-modified sugars are described, e.g., in Sproat, et al., Nucl. Acid Res. 19:733-738 (1991); Cotten, et al, Nucl. Acid Res. 19:2629-2635 (1991); and Hobbs, et al, Biochemistry 12:5138-5145 (1973). Other modifications are known to one of ordinary skill in the art. In certain embodiments, aptamers include aptamers with improved off-rates as described in International Patent Publication No. WO 2009012418, "Method for generating aptamers with improved off-rates," incorporated herein by reference in its entirety. In certain embodiments aptamers are chosen from a library of aptamers. Such libraries include, but are not limited to those described in Rohloff et al., "Nucleic Acid Ligands With Protein-like Side Chains: Modified Aptamers and Their Use as Diagnostic and Therapeutic Agents," Molecular Therapy Nucleic Acids (2014) 3, e201. Aptamers are also commercially available (see, e.g., SomaLogic, Inc., Boulder, Colo.). In certain embodiments, the present invention may utilize any aptamer containing any modification as described herein.

The disclosure also encompasses nucleic acid molecules. Exemplary nucleic acid molecules include aptamers, siRNA, artificial microRNA, interfering RNA or RNAi, dsRNA, ribozymes, antisense oligonucleotides, and DNA expression cassettes encoding said nucleic acid molecules. Preferably, the nucleic acid molecule is an antisense oligonucleotide. Antisense oligonucleotides (ASO) generally inhibit their target by binding target mRNA and sterically blocking expression by obstructing the ribosome. ASOs can also inhibit their target by binding target mRNA thus forming a DNA-RNA hybrid that can be a substance for RNase H. Preferred ASOs include Locked Nucleic Acid (LNA), Peptide Nucleic Acid (PNA), and morpholinos Preferably, the nucleic acid molecule is an RNAi molecule, i.e., RNA interference molecule. Preferred RNAi molecules include siRNA, shRNA, and artificial miRNA. The design and production of siRNA molecules is well known to one of skill in the art (e.g., Hajeri P B, Singh S K. Drug Discov Today. 2009 14(17-18):851-8). The nucleic acid molecule inhibitors may be chemically synthesized and provided directly to cells of interest. The nucleic acid compound may be provided to a cell as part of a gene delivery vehicle. Such a vehicle is preferably a liposome or a viral gene delivery vehicle.

Genetic Modifying Agents

In certain embodiments, the one or more modulating agents may be a genetic modifying agent. The genetic modifying agents may manipulate nucleic acids (e.g., genomic DNA or mRNA). The genetic modulating agent can be used to up- or downregulate expression of a gene either by targeting a nuclease or functional domain to a DNA or RNA sequence. The genetic modifying agent may comprise a CRISPR system, a zinc finger nuclease system, a TALEN, a meganuclease or RNAi system.

CRISPR-Cas Modification

In some embodiments, a polynucleotide of the present invention described elsewhere herein can be modified using a CRISPR-Cas and/or Cas-based system (e.g., genomic DNA or mRNA, preferably, for a disease gene). The nucleotide sequence may be or encode one or more components of a CRISPR-Cas system. For example, the nucleotide sequences may be or encode guide RNAs. The nucleotide sequences may also encode CRISPR proteins, variants thereof, or fragments thereof.

In general, a CRISPR-Cas or CRISPR system as used herein and in other documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g., CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g., Shmakov et al. (2015) "Discovery and Functional Characterization of Diverse Class 2 CRISPR-Cas Systems", Molecular Cell, DOI: dx.doi.org/10.1016/j.molcel.2015.10.008.

CRISPR-Cas systems can generally fall into two classes based on their architectures of their effector molecules, which are each further subdivided by type and subtype. The two class are Class 1 and Class 2. Class 1 CRISPR-Cas systems have effector modules composed of multiple Cas proteins, some of which form crRNA-binding complexes, while Class 2 CRISPR-Cas systems include a single, multi-domain crRNA-binding protein.

In some embodiments, the CRISPR-Cas system that can be used to modify a polynucleotide of the present invention described herein can be a Class 1 CRISPR-Cas system. In some embodiments, the CRISPR-Cas system that can be used to modify a polynucleotide of the present invention described herein can be a Class 2 CRISPR-Cas system.

Class 1 CRISPR-Cas Systems

In some embodiments, the CRISPR-Cas system that can be used to modify a polynucleotide of the present invention described herein can be a Class 1 CRISPR-Cas system. Class 1 CRISPR-Cas systems are divided into types I, II, and IV. Makarova et al. 2020. Nat. Rev. 18: 67-83., particularly as described in FIG. 1. Type I CRISPR-Cas systems are divided into 9 subtypes (I-A, I-B, I-C, I-D, I-E, I-F1, I-F2, I-F3, and IG). Makarova et al., 2020. Class 1, Type I CRISPR-Cas systems can contain a Cas3 protein that can have helicase activity. Type III CRISPR-Cas systems are divided into 6 subtypes (III-A, III-B, III-C, III-D, III-E, and III-F). Type III CRISPR-Cas systems can contain a Cas10 that can include an RNA recognition motif called Palm and a cyclase domain that can cleave polynucleotides. Makarova et al., 2020. Type IV CRISPR-Cas systems are divided into 3 subtypes. (IV-A, IV-B, and IV-C). Makarova et al., 2020. Class 1 systems also include CRISPR-Cas variants, including Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems. Peters et al., PNAS 114 (35) (2017); DOI: 10.1073/pnas.1709035114; see also, Makarova et al. 2018. The CRISPR Journal, v. 1, n5, FIG. 5.

The Class 1 systems typically use a multi-protein effector complex, which can, in some embodiments, include ancillary proteins, such as one or more proteins in a complex referred to as a CRISPR-associated complex for antiviral defense (Cascade), one or more adaptation proteins (e.g., Cas1, Cas2, RNA nuclease), and/or one or more accessory proteins (e.g., Cas 4, DNA nuclease), CRISPR associated Rossman fold (CARF) domain containing proteins, and/or RNA transcriptase.

The backbone of the Class 1 CRISPR-Cas system effector complexes can be formed by RNA recognition motif domain-containing protein(s) of the repeat-associated mysterious proteins (RAMPs) family subunits (e.g., Cas 5, Cas6, and/or Cas7). RAMP proteins are characterized by having one or more RNA recognition motif domains. In some embodiments, multiple copies of RAMPs can be present. In some embodiments, the Class I CRISPR-Cas system can include 1, 2, 3, 4, 5, 6, 7, 8, 9, 10, 11, 12 or more Cas5, Cas6, and/or Cas 7 proteins. In some embodiments, the Cas6 protein is an RNAse, which can be responsible for pre-crRNA processing. When present in a Class 1 CRISPR-Cas system, Cas6 can be optionally physically associated with the effector complex.

Class 1 CRISPR-Cas system effector complexes can, in some embodiments, also include a large subunit. The large subunit can be composed of or include a Cas8 and/or Cas10 protein. See, e.g., FIGS. 1 and 2. Koonin E V, Makarova K S. 2019. Phil. Trans. R. Soc. B 374: 20180087, DOI: 10.1098/rstb.2018.0087 and Makarova et al. 2020.

Class 1 CRISPR-Cas system effector complexes can, in some embodiments, include a small subunit (for example, Cas11). See, e.g., FIGS. 1 and 2. Koonin E V, Makarova K S. 2019 Origins and Evolution of CRISPR-Cas systems. Phil. Trans. R. Soc. B 374: 20180087, DOI: 10.1098/rstb.2018.0087.

In some embodiments, the Class 1 CRISPR-Cas system can be a Type I CRISPR-Cas system. In some embodiments, the Type I CRISPR-Cas system can be a subtype I-A CRISPR-Cas system. In some embodiments, the Type I CRISPR-Cas system can be a subtype I-B CRISPR-Cas system. In some embodiments, the Type I CRISPR-Cas system can be a subtype I-C CRISPR-Cas system. In some embodiments, the Type I CRISPR-Cas system can be a subtype I-D CRISPR-Cas system. In some embodiments, the Type I CRISPR-Cas system can be a subtype I-E CRISPR-Cas system. In some embodiments, the Type I CRISPR-Cas system can be a subtype I-F1 CRISPR-Cas system. In some embodiments, the Type I CRISPR-Cas system can be a subtype I-F2 CRISPR-Cas system. In some embodiments, the Type I CRISPR-Cas system can be a subtype I-F3 CRISPR-Cas system. In some embodiments, the Type I CRISPR-Cas system can be a subtype I-G CRISPR-Cas system. In some embodiments, the Type I CRISPR-Cas system can be a CRISPR Cas variant, such as a Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems as previously described.

In some embodiments, the Class 1 CRISPR-Cas system can be a Type III CRISPR-Cas system. In some embodiments, the Type III CRISPR-Cas system can be a subtype III-A CRISPR-Cas system. In some embodiments, the Type III CRISPR-Cas system can be a subtype III-B CRISPR-Cas system. In some embodiments, the Type III CRISPR-Cas system can be a subtype III-C CRISPR-Cas system. In some embodiments, the Type III CRISPR-Cas system can be a subtype III-D CRISPR-Cas system. In some embodiments, the Type III CRISPR-Cas system can be a subtype III-E CRISPR-Cas system. In some embodiments, the Type III CRISPR-Cas system can be a subtype III-F CRISPR-Cas system.

In some embodiments, the Class 1 CRISPR-Cas system can be a Type IV CRISPR-Cas-system. In some embodiments, the Type IV CRISPR-Cas system can be a subtype IV-A CRISPR-Cas system. In some embodiments, the Type IV CRISPR-Cas system can be a subtype IV-B CRISPR-Cas system. In some embodiments, the Type IV CRISPR-Cas system can be a subtype IV-C CRISPR-Cas system.

The effector complex of a Class 1 CRISPR-Cas system can, in some embodiments, include a Cas3 protein that is optionally fused to a Cas2 protein, a Cas4, a Cas5, a Cas6, a Cas7, a Cas8, a Cas10, a Cas11, or a combination thereof. In some embodiments, the effector complex of a Class 1 CRISPR-Cas system can have multiple copies, such as 1, 2, 3, 4, 5, 6, 7, 8, 9, 10, 11, 12, 13, or 14, of any one or more Cas proteins.

Class 2 CRISPR-Cas Systems

The compositions, systems, and methods described in greater detail elsewhere herein can be designed and adapted for use with Class 2 CRISPR-Cas systems. Thus, in some embodiments, the CRISPR-Cas system is a Class 2 CRISPR-Cas system. Class 2 systems are distinguished from Class 1 systems in that they have a single, large, multi-domain effector protein. In certain example embodiments, the Class 2 system can be a Type II, Type V, or Type VI system, which are described in Makarova et al. "Evolutionary classification of CRISPR-Cas systems: a burst of class 2 and derived variants" Nature Reviews Microbiology, 18:67-81 (February 2020), incorporated herein by reference. Each type of Class 2 system is further divided into subtypes.

See Markova et al. 2020, particularly at Figure. 2. Class 2, Type II systems can be divided into 4 subtypes: II-A, II-B, II-C1, and II-C2. Class 2, Type V systems can be divided into 17 subtypes: V-A, V-B1, V-B2, V-C, V-D, V-E, V-F1, V-F1(V-U3), V-F2, V-F3, V-G, V-H, V-I, V-K (V-U5), V-U1, V-U2, and V-U4. Class 2, Type IV systems can be divided into 5 subtypes: VI-A, VI-B1, VI-B2, VI-C, and VI-D.

The distinguishing feature of these types is that their effector complexes consist of a single, large, multi-domain protein. Type V systems differ from Type II effectors (e.g., Cas9), which contain two nuclear domains that are each responsible for the cleavage of one strand of the target DNA, with the HNH nuclease inserted inside the Ruv-C like nuclease domain sequence. The Type V systems (e.g., Cas12) only contain a RuvC-like nuclease domain that cleaves both strands. Type VI (Cas13) are unrelated to the effectors of Type II and V systems and contain two HEPN domains and target RNA. Cas13 proteins also display collateral activity that is triggered by target recognition. Some Type V systems have also been found to possess this collateral activity with two single-stranded DNA in in vitro contexts.

In some embodiments, the Class 2 system is a Type II system. In some embodiments, the Type II CRISPR-Cas system is a II-A CRISPR-Cas system. In some embodiments, the Type II CRISPR-Cas system is a II-B CRISPR-Cas system. In some embodiments, the Type II CRISPR-Cas system is a II-C1 CRISPR-Cas system. In some embodiments, the Type II CRISPR-Cas system is a II-C2 CRISPR-Cas system. In some embodiments, the Type II system is a Cas9 system. In some embodiments, the Type II system includes a Cas9.

In some embodiments, the Class 2 system is a Type V system. In some embodiments, the Type V CRISPR-Cas system is a V-A CRISPR-Cas system. In some embodiments, the Type V CRISPR-Cas system is a V-B1 CRISPR-Cas system. In some embodiments, the Type V CRISPR-Cas system is a V-B2 CRISPR-Cas system. In some embodiments, the Type V CRISPR-Cas system is a V-C CRISPR-Cas system. In some embodiments, the Type V CRISPR-Cas system is a V-D CRISPR-Cas system. In some embodiments, the Type V CRISPR-Cas system is a V-E CRISPR-Cas system. In some embodiments, the Type V CRISPR-Cas system is a V-F1 CRISPR-Cas system. In some embodiments, the Type V CRISPR-Cas system is a V-F1 (V-U3) CRISPR-Cas system. In some embodiments, the Type V CRISPR-Cas system is a V-F2 CRISPR-Cas system. In some embodiments, the Type V CRISPR-Cas system is a V-F3 CRISPR-Cas system. In some embodiments, the Type V CRISPR-Cas system is a V-G CRISPR-Cas system. In some embodiments, the Type V CRISPR-Cas system is a V-H CRISPR-Cas system. In some embodiments, the Type V CRISPR-Cas system is a V-I CRISPR-Cas system. In some embodiments, the Type V CRISPR-Cas system is a V-K (V-U5) CRISPR-Cas system. In some embodiments, the Type V CRISPR-Cas system is a V-U1 CRISPR-Cas system. In some embodiments, the Type V CRISPR-Cas system is a V-U2 CRISPR-Cas system. In some embodiments, the Type V CRISPR-Cas system is a V-U4 CRISPR-Cas system. In some embodiments, the Type V CRISPR-Cas system includes a Cas12a (Cpf1), Cas12b (C2c1), Cas12c (C2c3), CasX, and/or Cas14.

In some embodiments the Class 2 system is a Type VI system. In some embodiments, the Type VI CRISPR-Cas system is a VI-A CRISPR-Cas system. In some embodiments, the Type VI CRISPR-Cas system is a VI-B1 CRISPR-Cas system. In some embodiments, the Type VI CRISPR-Cas system is a VI-B2 CRISPR-Cas system. In some embodiments, the Type VI CRISPR-Cas system is a VI-C CRISPR-Cas system. In some embodiments, the Type VI CRISPR-Cas system is a VI-D CRISPR-Cas system. In some embodiments, the Type VI CRISPR-Cas system includes a Cas13a (C2c2), Cas13b (Group 29/30), Cas13c, and/or Cas13d.

Specialized Cas-Based Systems

In some embodiments, the system is a Cas-based system that is capable of performing a specialized function or activity. For example, the Cas protein may be fused, operably coupled to, or otherwise associated with one or more functionals domains. In certain example embodiments, the Cas protein may be a catalytically dead Cas protein ("dCas") and/or have nickase activity. A nickase is a Cas protein that cuts only one strand of a double stranded target. In such embodiments, the dCas or nickase provide a sequence specific targeting functionality that delivers the functional domain to or proximate a target sequence. Example functional domains that may be fused to, operably coupled to, or otherwise associated with a Cas protein can be or include, but are not limited to a nuclear localization signal (NLS) domain, a nuclear export signal (NES) domain, a translational activation domain, a transcriptional activation domain (e.g. VP64, p65, MyoD1, HSF1, RTA, and SET7/9), a translation initiation domain, a transcriptional repression domain (e.g., a KRAB domain, NuE domain, NcoR domain, and a SID domain such as a SID4X domain), a nuclease domain (e.g., FokI), a histone modification domain (e.g., a histone acetyltransferase), a light inducible/controllable domain, a chemically inducible/controllable domain, a transposase domain, a homologous recombination machinery domain, a recombinase domain, an integrase domain, and combinations thereof. Methods for generating catalytically dead Cas9 or a nickase Cas9 (WO 2014/204725, Ran et al. Cell. 2013 September 12; 154(6):1380-1389), Cas12 (Liu et al. Nature Communications, 8, 2095 (2017)), and Cas13 (WO 2019/005884, WO2019/060746) are known in the art and incorporated herein by reference.

In some embodiments, the functional domains can have one or more of the following activities: methylase activity, demethylase activity, translation activation activity, translation initiation activity, translation repression activity, transcription activation activity, transcription repression activity, transcription release factor activity, histone modification activity, nuclease activity, single-strand RNA cleavage activity, double-strand RNA cleavage activity, single-strand DNA cleavage activity, double-strand DNA cleavage activity, molecular switch activity, chemical inducibility, light inducibility, and nucleic acid binding activity. In some embodiments, the one or more functional domains may comprise epitope tags or reporters. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporters include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and auto-fluorescent proteins including blue fluorescent protein (BFP).

The one or more functional domain(s) may be positioned at, near, and/or in proximity to a terminus of the effector protein (e.g., a Cas protein). In embodiments having two or more functional domains, each of the two can be positioned at or near or in proximity to a terminus of the effector protein (e.g., a Cas protein). In some embodiments, such as those where the functional domain is operably coupled to the effector protein, the one or more functional domains can be tethered or linked via a suitable linker (including, but not limited to, GlySer linkers) to the effector protein (e.g., a Cas protein). When there is more than one functional domain, the functional domains can be same or different. In some embodiments, all the functional domains are the same. In some embodiments, all of the functional domains are different from each other. In some embodiments, at least two of the functional domains are different from each other. In some embodiments, at least two of the functional domains are the same as each other.

Other suitable functional domains can be found, for example, in International Application Publication No. WO 2019/018423.

Split CRISPR-Cas Systems

In some embodiments, the CRISPR-Cas system is a split CRISPR-Cas system. See e.g., Zetche et al., 2015. Nat. Biotechnol. 33(2): 139-142 and WO 2019/018423, the compositions and techniques of which can be used in and/or adapted for use with the present invention. Split CRISPR-Cas proteins are set forth herein and in documents incorporated herein by reference in further detail herein. In certain embodiments, each part of a split CRISPR protein are attached to a member of a specific binding pair, and when bound with each other, the members of the specific binding pair maintain the parts of the CRISPR protein in proximity. In certain embodiments, each part of a split CRISPR protein is associated with an inducible binding pair. An inducible binding pair is one which is capable of being switched "on" or "off" by a protein or small molecule that binds to both members of the inducible binding pair. In some embodiments, CRISPR proteins may preferably split between domains, leaving domains intact. In particular embodiments, said Cas split domains (e.g., RuvC and HNH domains in the case of Cas9) can be simultaneously or sequentially introduced into the cell such that said split Cas domain(s) process the target nucleic acid sequence in the algae cell. The reduced size of the split Cas compared to the wild type Cas allows other methods of delivery of the systems to the cells, such as the use of cell penetrating peptides as described herein.

DNA and RNA Base Editing

In some embodiments, a polynucleotide of the present invention described elsewhere herein can be modified using a base editing system. In some embodiments, a Cas protein is connected or fused to a nucleotide deaminase. Thus, in some embodiments the Cas-based system can be a base editing system. As used herein "base editing" refers generally to the process of polynucleotide modification via a CRISPR-Cas-based or Cas-based system that does not include excising nucleotides to make the modification. Base editing can convert base pairs at precise locations without generating excess undesired editing byproducts that can be made using traditional CRISPR-Cas systems.

In certain example embodiments, the nucleotide deaminase may be a DNA base editor used in combination with a DNA binding Cas protein such as, but not limited to, Class 2 Type II and Type V systems. Two classes of DNA base editors are generally known: cytosine base editors (CBEs) and adenine base editors (ABEs). CBEs convert a C·G base pair into a T·A base pair (Komor et al. 2016. Nature. 533:420-424; Nishida et al. 2016. Science. 353; and Li et al. Nat. Biotech. 36:324-327) and ABEs convert an A·T base pair to a G·C base pair. Collectively, CBEs and ABEs can mediate all four possible transition mutations (C to T, A to G, T to C, and G to A). Rees and Liu. 2018. Nat. Rev. Genet. 19(12): 770-788, particularly at FIGS. 1*b*, 2*a*-2*c*, 3*a*-3*f*, and Table 1. In some embodiments, the base editing system includes a CBE and/or an ABE. In some embodiments, a polynucleotide of the present invention described elsewhere herein can be modified using a base editing system. Rees and Liu. 2018. Nat. Rev. Gent. 19(12):770-788. Base editors also generally do not need a DNA donor template and/or rely on homology-directed repair. Komor et al. 2016. Nature. 533: 420-424; Nishida et al. 2016. Science. 353; and Gaudeli et al. 2017. Nature. 551:464-471. Upon binding to a target locus in the DNA, base pairing between the guide RNA of the system and the target DNA strand leads to displacement of a small segment of ssDNA in an "R-loop". Nishimasu et al. Cell. 156:935-949. DNA bases within the ssDNA bubble are modified by the enzyme component, such as a deaminase. In some systems, the catalytically disabled Cas protein can be a variant or modified Cas can have nickase functionality and can generate a nick in the non-edited DNA strand to induce cells to repair the non-edited strand using the edited strand as a template. Komor et al. 2016. Nature. 533:420-424; Nishida et al. 2016. Science. 353; and Gaudeli et al. 2017. Nature. 551:464-471. Base editors may be further engineered to optimize conversion of nucleotides (e.g. A:T to G:C). Richter et al. 2020. Nature Biotechnology.doi.org/10.1038/s41587-020-0453-z.

Other Example Type V base editing systems are described in WO 2018/213708, WO 2018/213726, PCT/US2018/067207, PCT/US2018/067225, and PCT/US2018/067307 which are incorporated by referenced herein.

In certain example embodiments, the base editing system may be a RNA base editing system. As with DNA base editors, a nucleotide deaminase capable of converting nucleotide bases may be fused to a Cas protein. However, in these embodiments, the Cas protein will need to be capable of binding RNA. Example RNA binding Cas proteins include, but are not limited to, RNA-binding Cas9s such as *Francisella novicida* Cas9 ("FnCas9"), and Class 2 Type VI Cas systems. The nucleotide deaminase may be a cytidine deaminase or an adenosine deaminase, or an adenosine deaminase engineered to have cytidine deaminase activity. In certain example embodiments, the RNA based editor may be used to delete or introduce a post-translation modification site in the expressed mRNA. In contrast to DNA base editors, whose edits are permanent in the modified cell, RNA base editors can provide edits where finer temporal control may be needed, for example in modulating a particular immune response. Example Type VI RNA-base editing systems are described in Cox et al. 2017. Science 358: 1019-1027, WO 2019/005884, WO 2019/005886, WO 2019/071048, PCT/US20018/05179, PCT/US2018/067207, which are incorporated herein by reference. An example FnCas9 system that may be adapted for RNA base editing purposes is described in WO 2016/106236, which is incorporated herein by reference.

An example method for delivery of base-editing systems, including use of a split-intein approach to divide CBE and ABE into reconstitutable halves, is described in Levy et al. Nature Biomedical Engineering doi.org/10.1038/s41441-019-0505-5 (2019), which is incorporated herein by reference.

Prime Editors

In some embodiments, a polynucleotide of the present invention described elsewhere herein can be modified using a prime editing system (See e.g. Anzalone et al. 2019. Nature. 576: 149-157). Like base editing systems, prime editing systems can be capable of targeted modification of a polynucleotide without generating double stranded breaks and does not require donor templates. Further prime editing systems can be capable of all 12 possible combination swaps. Prime editing can operate via a "search-and-replace" methodology and can mediate targeted insertions, deletions, all 12 possible base-to-base conversion, and combinations thereof. Generally, a prime editing system, as exemplified by PE1, PE2, and PE3 (Id.), can include a reverse transcriptase fused or otherwise coupled or associated with an RNA-programmable nickase, and a prime-editing extended guide RNA (pegRNA) to facility direct copying of genetic information from the extension on the pegRNA into the target polynucleotide. Embodiments that can be used with the present invention include these and variants thereof. Prime editing can have the advantage of lower off-target activity than traditional CRIPSR-Cas systems along with few byproducts and greater or similar efficiency as compared to traditional CRISPR-Cas systems.

In some embodiments, the prime editing guide molecule can specify both the target polynucleotide information (e.g. sequence) and contain a new polynucleotide cargo that replaces target polynucleotides. To initiate transfer from the guide molecule to the target polynucleotide, the PE system can nick the target polynucleotide at a target side to expose a 3'hydroxyl group, which can prime reverse transcription of an edit-encoding extension region of the guide molecule (e.g. a prime editing guide molecule or peg guide molecule) directly into the target site in the target polynucleotide. See e.g. Anzalone et al. 2019. Nature. 576: 149-157, particularly at FIGS. 1b, 1c, related discussion, and Supplementary discussion.

In some embodiments, a prime editing system can be composed of a Cas polypeptide having nickase activity, a reverse transcriptase, and a guide molecule. The Cas polypeptide can lack nuclease activity. The guide molecule can include a target binding sequence as well as a primer binding sequence and a template containing the edited polynucleotide sequence. The guide molecule, Cas polypeptide, and/ or reverse transcriptase can be coupled together or otherwise associate with each other to form an effector complex and edit a target sequence. In some embodiments, the Cas polypeptide is a Class 2, Type V Cas polypeptide. In some embodiments, the Cas polypeptide is a Cas9 polypeptide (e.g. is a Cas9 nickase). In some embodiments, the Cas polypeptide is fused to the reverse transcriptase. In some embodiments, the Cas polypeptide is linked to the reverse transcriptase.

In some embodiments, the prime editing system can be a PE1 system or variant thereof, a PE2 system or variant thereof, or a PE3 (e.g. PE3, PE3b) system. See e.g., Anzalone et al. 2019. Nature. 576: 149-157, particularly at pgs. 2-3, FIGS. 2a, 3a-3f, 4a-4b, Extended data FIGS. 3a-3b, 4.

The peg guide molecule can be about 10 to about 200 or more nucleotides in length, such as 10 to/or 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 or more nucleotides in length. Optimization of the peg guide molecule can be accomplished as described in Anzalone et al. 2019. Nature. 576: 149-157, particularly at pg. 3, FIG. 2a-2b, and Extended Data FIGS. 5a-c.

CRISPR Associated Transposase (CAST) Systems

In some embodiments, a polynucleotide of the present invention described elsewhere herein can be modified using a CRISPR Associated Transposase ("CAST") system. CAST system can include a Cas protein that is catalytically inactive, or engineered to be catalytically active, and further comprises a transposase (or subunits thereof) that catalyze RNA-guided DNA transposition. Such systems are able to insert DNA sequences at a target site in a DNA molecule without relying on host cell repair machinery. CAST systems can be Class1 or Class 2 CAST systems. An example Class 1 system is described in Klompe et al. Nature, doi: 10.1038/s41586-019-1323, which is in incorporated herein by reference. An example Class 2 system is described in Strecker et al. Science. 10/1126/science. aax9181 (2019), and PCT/US2019/066835 which are incorporated herein by reference.

Guide Molecules

The CRISPR-Cas or Cas-Based system described herein can, in some embodiments, include one or more guide molecules. The terms guide molecule, guide sequence and guide polynucleotide, refer to polynucleotides capable of guiding Cas to a target genomic locus and are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. The guide molecule can be a polynucleotide.

The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay (Qui et al. 2004. BioTechniques. 36(4)702-707). Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible and will occur to those skilled in the art.

In some embodiments, the guide molecule is an RNA. The guide molecule(s) (also referred to interchangeably herein as guide polynucleotide and guide sequence) that are included in the CRISPR-Cas or Cas based system can be any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, can be about or more than about 50%, 60%, 75%, 80%, 85%, 90%, 95%, 97.5%, 99%, or more. Optimal alignment may be determined with the use of any suitable algorithm for aligning sequences, non-limiting examples of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net).

A guide sequence, and hence a nucleic acid-targeting guide may be selected to target any target nucleic acid sequence. The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and P A Carr and G M Church, 2009, Nature Biotechnology 27(12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27 to 30 nt, e.g., 27, 28, 29, or 30 nt, from 30 to 35 nt, e.g., 30, 31, 32, 33, 34, or 35 nt, or 35 nt or longer.

The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and crRNA sequence are contained within a single transcript, such that hybridization between the two produces a transcript having a secondary structure, such as a hairpin.

In general, degree of complementarity is with reference to the optimal alignment of the sca sequence and tracr sequence, along the length of the shorter of the two sequences. Optimal alignment may be determined by any suitable alignment algorithm, and may further account for secondary structures, such as self-complementarity within either the sca sequence or tracr sequence. In some embodiments, the degree of complementarity between the tracr sequence and sca sequence along the length of the shorter of the two when optimally aligned is about or more than about 25%, 30%, 40%, 50%, 60%, 70%, 80%, 90%, 95%, 97.5%, 99%, or higher.

In some embodiments, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and tracr RNA can be 30 or 50 nucleotides in length. In some embodiments, the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In some embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e., an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence. Where the tracr RNA is on a different RNA than the RNA containing the guide and tracr sequence, the length of each RNA may be optimized to be shortened from their respective native lengths, and each may be independently chemically modified to protect from degradation by cellular RNase or otherwise increase stability.

Many modifications to guide sequences are known in the art and are further contemplated within the context of this invention. Various modifications may be used to increase the specificity of binding to the target sequence and/or increase the activity of the Cas protein and/or reduce off-target effects. Example guide sequence modifications are described in PCT US2019/045582, specifically paragraphs [0178]-[0333]. which is incorporated herein by reference.

Target Sequences, PAMs, and PFSs

Target Sequences

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to an RNA polynucleotide being or comprising the target sequence. In other words, the target polynucleotide can be a polynucleotide or a part of a polynucleotide to which a part of the guide sequence is designed to have complementarity with and to which the effector function mediated by the complex comprising the CRISPR effector protein and a guide molecule is to be directed. In some embodiments, a target sequence is located in the nucleus or cytoplasm of a cell.

The guide sequence can specifically bind a target sequence in a target polynucleotide. The target polynucleotide may be DNA. The target polynucleotide may be RNA. The target polynucleotide can have one or more (e.g., 1, 2, 3, 4, 5, 6, 7, 8, 9, 10, etc. or more) target sequences. The target polynucleotide can be on a vector. The target polynucleotide can be genomic DNA. The target polynucleotide can be episomal. Other forms of the target polynucleotide are described elsewhere herein.

The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence (also referred to herein as a target polynucleotide) may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

PAM and PFS Elements

PAM elements are sequences that can be recognized and bound by Cas proteins. Cas proteins/effector complexes can then unwind the dsDNA at a position adjacent to the PAM element. It will be appreciated that Cas proteins and systems that include them that target RNA do not require PAM sequences (Marraffini et al. 2010. Nature. 463:568-571). Instead, many rely on PFSs, which are discussed elsewhere herein. In certain embodiments, the target sequence should be associated with a PAM (protospacer adjacent motif) or PFS (protospacer flanking sequence or site), that is, a short sequence recognized by the CRISPR complex. Depending on the nature of the CRISPR-Cas protein, the target sequence should be selected, such that its complementary sequence in the DNA duplex (also referred to herein as the non-target sequence) is upstream or downstream of the PAM. In the embodiments, the complementary sequence of the target sequence is downstream or 3' of the PAM or upstream or 5' of the PAM. The precise sequence and length requirements for the PAM differ depending on the Cas protein used, but PAMs are typically 2-5 base pair sequences adjacent the protospacer (that is, the target sequence). Examples of the natural PAM sequences for different Cas proteins are provided herein below and the skilled person will be able to identify further PAM sequences for use with a given Cas protein.

The ability to recognize different PAM sequences depends on the Cas polypeptide(s) included in the system. See e.g., Gleditzsch et al. 2019. RNA Biology. 16(4):504-517. Table A below shows several Cas polypeptides and the PAM sequence they recognize.

TABLE A

Example PAM Sequences

| Cas Protein | PAM Sequence |
| --- | --- |
| SpCas9 | NGG/NRG |
| SaCas9 | NGRRT or NGRRN |
| NmeCas9 | NNNNGATT |
| CjCas9 | NNNNRYAC |
| StCas9 | NNAGAAW |
| Cas12a (Cpf1) (including LbCpf1 and AsCpf1) | TTTV |
| Cas12b (C2c1) | TTT, TTA, and TTC |
| Cas12c (C2c3) | TA |
| Cas12d (CasY) | TA |
| Cas12e (CasX) | 5'-TTCN-3' |

In a preferred embodiment, the CRISPR effector protein may recognize a 3' PAM. In certain embodiments, the CRISPR effector protein may recognize a 3' PAM which is 5'H, wherein H is A, C or U.

Further, engineering of the PAM Interacting (PI) domain on the Cas protein may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523(7561):481-5. doi: 10.1038/nature14592. As further detailed herein, the skilled person will understand that Cas13 proteins may be modified analogously. Gao et al, "Engineered Cpf1 Enzymes with Altered PAM Specificities," bioRxiv 091611; doi: dx.doi.org/10.1101/091611 (Dec. 4, 2016). Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

PAM sequences can be identified in a polynucleotide using an appropriate design tool, which are commercially available as well as online. Such freely available tools include, but are not limited to, CRISPRFinder and CRISPRTarget. Mojica et al. 2009. Microbiol. 155(Pt. 3):733-740;

Atschul et al. 1990. J. Mol. Biol. 215:403-410; Biswass et al. 2013 RNA Biol. 10:817-827; and Grissa et al. 2007. Nucleic Acid Res. 35:W52-57. Experimental approaches to PAM identification can include, but are not limited to, plasmid depletion assays (Jiang et al. 2013. Nat. Biotechnol. 31:233-239; Esvelt et al. 2013. Nat. Methods. 10:1116-1121; Kleinstiver et al. 2015. Nature. 523:481-485), screened by a high-throughput in vivo model called PAM-SCNAR (Pattanayak et al. 2013. Nat. Biotechnol. 31:839-843 and Leenay et al. 2016. Mol. Cell. 16:253), and negative screening (Zetsche et al. 2015. Cell. 163:759-771).

As previously mentioned, CRISPR-Cas systems that target RNA do not typically rely on PAM sequences. Instead such systems typically recognize protospacer flanking sites (PFSs) instead of PAMs Thus, Type VI CRISPR-Cas systems typically recognize protospacer flanking sites (PFSs) instead of PAMs. PFSs represents an analogue to PAMs for RNA targets. Type VI CRISPR-Cas systems employ a Cas13. Some Cas13 proteins analyzed to date, such as Cas13a (C2c2) identified from Leptotrichia shahii (LShCAs13a) have a specific discrimination against G at the 3'end of the target RNA. The presence of a C at the corresponding crRNA repeat site can indicate that nucleotide pairing at this position is rejected. However, some Cas13 proteins (e.g., LwaCAs13a and PspCas13b) do not seem to have a PFS preference. See e.g., Gleditzsch et al. 2019. RNA Biology. 16(4):504-517.

Some Type VI proteins, such as subtype B, have 5'-recognition of D (G, T, A) and a 3'-motif requirement of NAN or NNA. One example is the Cas13b protein identified in *Bergeyella zoohelcum* (BzCas13b). See e.g., Gleditzsch et al. 2019. RNA Biology. 16(4):504-517.

Overall Type VI CRISPR-Cas systems appear to have less restrictive rules for substrate (e.g., target sequence) recognition than those that target DNA (e.g., Type V and type II).

Zinc Finger Nucleases

In some embodiments, the polynucleotide is modified using a Zinc Finger nuclease or system thereof. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

TALE Nucleases

In some embodiments, a TALE nuclease or TALE nuclease system can be used to modify a polynucleotide. In some embodiments, the methods provided herein use isolated, non-naturally occurring, recombinant or engineered DNA binding proteins that comprise TALE monomers or TALE monomers or half monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", "TALE monomers" or "monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X_{1-11}$—$(X_{12}X_{13})$—$X_{14-33}$ or 34 or 35, where the subscript indicates the amino acid position and X represents any amino acid. $X_{12}X_{13}$ indicate the RVDs. In some polypeptide monomers, the variable amino acid at position 13 is missing or absent and in such monomers, the RVD consists of a single amino acid. In such cases the RVD may be alternatively represented as X*, where X represents $X_{12}$ and (*) indicates that $X_{13}$ is absent. The DNA binding domain comprises several repeats of TALE monomers and this may be represented as $(X_{11}$—$(X_{12}X_{13})$—$X_{14}$ 33 or 34 or 35$)_z$, where in an advantageous embodiment, z is at least 5 to 40. In a further advantageous embodiment, z is at least 10 to 26.

The TALE monomers can have a nucleotide binding affinity that is determined by the identity of the amino acids in its RVD. For example, polypeptide monomers with an RVD of NI can preferentially bind to adenine (A), monomers with an RVD of NG can preferentially bind to thymine (T), monomers with an RVD of HD can preferentially bind to cytosine (C) and monomers with an RVD of NN can preferentially bind to both adenine (A) and guanine (G). In some embodiments, monomers with an RVD of IG can preferentially bind to T. Thus, the number and order of the polypeptide monomer repeats in the nucleic acid binding domain of a TALE determines its nucleic acid target specificity. In some embodiments, monomers with an RVD of NS can recognize all four base pairs and can bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011).

The polypeptides used in methods of the invention can be isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In some embodiments, polypeptide monomers having RVDs RN, NN, NK, SN, NH, KN, HN, NQ, HH, RG, KH, RH and SS can preferentially bind to guanine. In some embodiments, polypeptide monomers having RVDs RN, NK, NQ, HH, KH, RH, SS and SN can preferentially bind to guanine and can thus allow the generation of TALE polypeptides with high binding specificity for guanine containing target nucleic acid sequences. In some embodiments, polypeptide monomers having RVDs HH, KH, NH, NK, NQ, RH, RN and SS can preferentially bind to guanine and thereby allow the generation of TALE polypeptides with high binding specificity for guanine containing target nucleic acid sequences. In some embodiments, the RVDs that have high binding specificity for guanine are RN, NH RH and KH. Furthermore, polypeptide monomers having an RVD of NV can preferentially bind to adenine and guanine. In some embodiments, monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the polypeptides of the invention will bind. As used herein the monomers and at least one or more half monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases, this region may be referred to as repeat 0. In animal genomes, TALE binding sites do not necessarily have to begin with a thymine (T) and polypeptides of the invention may target DNA sequences that begin with T, A, G or C. The tandem repeat of TALE monomers always ends with a half-length repeat or a stretch of sequence that may share identity with only the first 20 amino acids of a repetitive full-length TALE monomer and this half repeat may be referred to as a half-monomer. Therefore, it follows that the length of the nucleic acid or DNA being targeted is equal to the number of full monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

```
                                          (SEQ ID NO: 1)
M D P I R S R T P S P A R E L L S G P Q P D G V

Q P T A D R G V S P P A G G P L D G L P A R R T

M S R T R L P S P P A P S P A F S A D S F S D L

L R Q F D P S L F N T S L F D S L P P F G A H H

T E A A T G E W D E V Q S G L R A A D A P P P T

M R V A V T A A R P P R A K P A P R R R A A Q P

S D A S P A A Q V D L R T L G Y S Q Q Q Q E K I

K P K V R S T V A Q H H E A L V G H G F T H A H

I V A L S Q H P A A L G T V A V K Y Q D M I A A

L P E A T H E A I V G V G K Q W S G A R A L E A

L L T V A G E L R G P P L Q L D T G Q L L K I A

K R G G V T A V E A V H A W R N A L T G A P L N
```

An exemplary amino acid sequence of a C-terminal capping region is:

```
                                          (SEQ ID NO: 2)
R P A L E S I V A Q L S R P D P A L A A L T N D

H L V A L A C L G G R P A L D A V K K G L P H A

P A L I K R T N R R I P E R T S H R V A D H A Q

V V R V L G F F Q C H S H P A Q A F D D A M T Q

F G M S R H G L L Q L F R R V G V T E L E A R S

G T L P P A S Q R W D R I L Q A S G M K R A K P

S P T S T Q T P D Q A S L H A F A D S L E R D L

D A P S P M H E G D Q T R A S
```

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full-length capping region, while fragments that include the C-terminal 20 amino acids retain greater than 50% of the efficacy of the full-length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies can be generated by any of a number of computer programs known in the art, which include but are not limited to BLAST or FASTA. Suitable computer programs for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In some embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Kruppel-associated box (KRAB) or fragments of the KRAB domain. In some embodiments the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination of the activities described herein.

Meganucleases

In some embodiments, a meganuclease or system thereof can be used to modify a polynucleotide. Meganucleases, which are endodeoxyribonucleases characterized by a large recognition site (double-stranded DNA sequences of 12 to 40 base pairs). Exemplary methods for using meganucleases can be found in U.S. Pat. Nos. 8,163,514, 8,133,697, 8,021,867, 8,119,361, 8,119,381, 8,124,369, and 8,129,134, which are specifically incorporated by reference.

Sequences Related to Nucleus Targeting and Transportation

In some embodiments, one or more components (e.g., the Cas protein and/or deaminase, Zn Finger protein, TALE, or meganuclease) in the composition for engineering cells may comprise one or more sequences related to nucleus targeting and transportation. Such sequence may facilitate the one or more components in the composition for targeting a sequence within a cell. In order to improve targeting of the CRISPR-Cas protein and/or the nucleotide deaminase protein or catalytic domain thereof used in the methods of the present disclosure to the nucleus, it may be advantageous to provide one or both of these components with one or more nuclear localization sequences (NLSs).

In some embodiments, the NLSs used in the context of the present disclosure are heterologous to the proteins. Non-limiting examples of NLSs include an NLS sequence derived from: the NLS of the SV40 virus large T-antigen, having the amino acid sequence PKKKRKV (SEQ ID NO: 3) or PKKKRKVEAS (SEQ ID NO: 4); the NLS from nucleoplasmin (e.g., the nucleoplasmin bipartite NLS with the sequence KRPAATKKAGQAKKKK (SEQ ID NO: 5)); the c-myc NLS having the amino acid sequence PAAKRVKLD (SEQ ID NO: 6) or RQRRNELKRSP (SEQ ID NO: 7); the hRNPA1 M9 NLS having the sequence NQSSNFGPMKGGNFGGRSSGPYGGGGQYFAK-PRNQGGY (SEQ ID NO: 8); the sequence RMRIZFKNKGKDTAELRRRRVEVSVELRKAKKD-EQILKRRNV (SEQ ID NO: 9) of the IBB domain from importin-alpha; the sequences VSRKRPRP (SEQ ID NO: 10) and PPKKARED (SEQ ID NO: 11) of the myoma T protein; the sequence PQPKKKPL (SEQ ID NO: 12) of human p53; the sequence SALIKKKKKMAP (SEQ ID NO: 13) of mouse c-abl IV; the sequences DRLRR (SEQ ID NO: 14) and PKQKKRK (SEQ ID NO: 15) of the influenza virus NS1; the sequence RKLKKKIKKL (SEQ ID NO: 16) of the Hepatitis virus delta antigen; the sequence REKKKFLKRR (SEQ ID NO: 17) of the mouse Mx1 protein; the sequence KRKGDEVDGVDEVAKKKSKK (SEQ ID NO: 18) of the human poly(ADP-ribose) polymerase; and the sequence RKCLQAGMNLEARKTKK (SEQ ID NO: 19) of the steroid hormone receptors (human) glucocorticoid. In general, the one or more NLSs are of sufficient strength to drive accumulation of the DNA-targeting Cas protein in a detectable amount in the nucleus of a eukaryotic cell. In general, strength of nuclear localization activity may derive from the number of NLSs in the CRISPR-Cas protein, the particular NLS(s) used, or a combination of these factors. Detection of accumulation in the nucleus may be performed by any suitable technique. For example, a detectable marker may be fused to the nucleic acid-targeting protein, such that location within a cell may be visualized, such as in combination with a means for detecting the location of the nucleus (e.g., a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of nucleic acid-targeting complex formation (e.g., assay for deaminase activity) at the target sequence, or assay for altered gene expression activity affected by DNA-targeting complex formation and/or DNA-targeting, as compared to a control not exposed to the CRISPR-Cas protein and deaminase protein, or exposed to a CRISPR-Cas and/or deaminase protein lacking the one or more NLSs.

The CRISPR-Cas and/or nucleotide deaminase proteins may be provided with 1 or more, such as with, 2, 3, 4, 5, 6, 7, 8, 9, 10, or more heterologous NLSs. In some embodiments, the proteins comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g., zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. In preferred embodiments of the CRISPR-Cas proteins, an NLS attached to the C-terminal of the protein.

In certain embodiments, the CRISPR-Cas protein and the deaminase protein are delivered to the cell or expressed within the cell as separate proteins. In these embodiments, each of the CRISPR-Cas and deaminase protein can be provided with one or more NLSs as described herein. In certain embodiments, the CRISPR-Cas and deaminase proteins are delivered to the cell or expressed with the cell as a fusion protein. In these embodiments one or both of the CRISPR-Cas and deaminase protein is provided with one or more NLSs. Where the nucleotide deaminase is fused to an adaptor protein (such as MS2) as described above, the one or more NLS can be provided on the adaptor protein, provided that this does not interfere with aptamer binding. In particular embodiments, the one or more NLS sequences may also function as linker sequences between the nucleotide deaminase and the CRISPR-Cas protein.

In certain embodiments, guides of the disclosure comprise specific binding sites (e.g. aptamers) for adapter proteins, which may be linked to or fused to an nucleotide deaminase or catalytic domain thereof. When such a guide forms a CRISPR complex (e.g., CRISPR-Cas protein binding to guide and target) the adapter proteins bind and, the nucleotide deaminase or catalytic domain thereof associated with the adapter protein is positioned in a spatial orientation which is advantageous for the attributed function to be effective.

The skilled person will understand that modifications to the guide which allow for binding of the adapter+nucleotide deaminase, but not proper positioning of the adapter+nucleotide deaminase (e.g. due to steric hindrance within the three dimensional structure of the CRISPR complex) are modifications which are not intended. The one or more modified guide may be modified at the tetra loop, the stem loop 1, stem loop 2, or stem loop 3, as described herein, preferably at either the tetra loop or stem loop 2, and in some cases at both the tetra loop and stem loop 2.

In some embodiments, a component (e.g., the dead Cas protein, the nucleotide deaminase protein or catalytic domain thereof, or a combination thereof) in the systems may comprise one or more nuclear export signals (NES), one or more nuclear localization signals (NLS), or any combinations thereof. In some cases, the NES may be an HIV Rev NES. In certain cases, the NES may be MAPK NES. When the component is a protein, the NES or NLS may be at the C terminus of component. Alternatively or additionally, the NES or NLS may be at the N terminus of component. In some examples, the Cas protein and optionally said nucleotide deaminase protein or catalytic domain thereof comprise one or more heterologous nuclear export signal(s) (NES(s)) or nuclear localization signal(s) (NLS(s)), preferably an HIV Rev NES or MAPK NES, preferably C-terminal.

Templates

In some embodiments, the composition for engineering cells comprise a template, e.g., a recombination template. A template may be a component of another vector as described herein, contained in a separate vector, or provided as a separate polynucleotide. In some embodiments, a recombination template is designed to serve as a template in homologous recombination, such as within or near a target sequence nicked or cleaved by a nucleic acid-targeting effector protein as a part of a nucleic acid-targeting complex.

In an embodiment, the template nucleic acid alters the sequence of the target position. In an embodiment, the template nucleic acid results in the incorporation of a modified, or non-naturally occurring base into the target nucleic acid.

The template sequence may undergo a breakage mediated or catalyzed recombination with the target sequence. In an embodiment, the template nucleic acid may include sequence that corresponds to a site on the target sequence that is cleaved by a Cas protein mediated cleavage event. In an embodiment, the template nucleic acid may include sequence that corresponds to both, a first site on the target sequence that is cleaved in a first Cas protein mediated event, and a second site on the target sequence that is cleaved in a second Cas protein mediated event.

In certain embodiments, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation. In certain embodiments, the template nucleic acid can include sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position in a target gene may be used to alter the structure of a target sequence. The template sequence may be used to alter an unwanted structure, e.g., an unwanted or mutant nucleotide. The template nucleic acid may include sequence which, when integrated, results in: decreasing the activity of a positive control element; increasing the activity of a positive control element; decreasing the activity of a negative control element; increasing the activity of a negative control element; decreasing the expression of a gene; increasing the expression of a gene; increasing resistance to a disorder or disease; increasing resistance to viral entry; correcting a mutation or altering an unwanted amino acid residue conferring, increasing, abolishing or decreasing a biological property of a gene product, e.g., increasing the enzymatic activity of an enzyme, or increasing the ability of a gene product to interact with another molecule.

The template nucleic acid may include sequence which results in: a change in sequence of 1, 2, 3, 4, 5, 6, 7, 8, 9, 10, 11, 12 or more nucleotides of the target sequence.

A template polynucleotide may be of any suitable length, such as about or more than about 10, 15, 20, 25, 50, 75, 100, 150, 200, 500, 1000, or more nucleotides in length. In an embodiment, the template nucleic acid may be 20+/−10, 30+/−10, 40+/−10, 50+/−10, 60+/−10, 70+/−10, 80+/−10, 90+/−10, 100+/−10, 110+/−10, 120+/−10, 130+/−10, 140+/−10, 150+/−10, 160+/−10, 170+/−10, 180+/−10, 190+/−10, 200+/−10, 210+/−10, of 220+/−10 nucleotides in length. In an embodiment, the template nucleic acid may be 30+/−20, 40+/−20, 50+/−20, 60+/−20, 70+/−20, 80+/−20, 90+/−20, 100+/−20, 110+/−20, 120+/−20, 130+/−20, 140+/−20, 150+/−20, 160+/−20, 170+/−20, 180+/−20, 190+/−20, 200+/−20, 210+/−20, of 220+/−20 nucleotides in length. In an embodiment, the template nucleic acid is 10 to 1,000, 20 to 900, 30 to 800, 40 to 700, 50 to 600, 50 to 500, 50 to 400, 50 to 300, 50 to 200, or 50 to 100 nucleotides in length.

In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

In certain embodiments, one or both homology arms may be shortened to avoid including certain sequence repeat elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the disclosure can be constructed using recombinant techniques (see, for example, Sambrook et al., 2001 and Ausubel et al., 1996).

In certain embodiments, a template nucleic acid for correcting a mutation may be designed for use as a single-stranded oligonucleotide. When using a single-stranded oligonucleotide, 5' and 3' homology arms may range up to about 200 base pairs (bp) in length, e.g., at least 25, 50, 75, 100, 125, 150, 175, or 200 bp in length.

In certain embodiments, a template nucleic acid for correcting a mutation may be designed for use with a homology-independent targeted integration system. Suzuki et al. describe in vivo genome editing via CRISPR/Cas9 mediated homology-independent targeted integration (2016, Nature 540:144-149). Schmid-Burgk, et al. describe use of the CRISPR-Cas9 system to introduce a double-strand break (DSB) at a user-defined genomic location and insertion of a universal donor DNA (Nat Commun. 2016 Jul. 28; 7:12338). Gao, et al. describe "Plug-and-Play Protein Modification Using Homology-Independent Universal Genome Engineering" (Neuron. 2019 Aug. 21; 103(4):583-597).

RNAi

In some embodiments, the genetic modulating agents may be interfering RNAs. In certain embodiments, diseases caused by a dominant mutation in a gene is targeted by silencing the mutated gene using RNAi. In some cases, the nucleotide sequence may comprise coding sequence for one or more interfering RNAs. In certain examples, the nucleotide sequence may be interfering RNA (RNAi). As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene.

In certain embodiments, a modulating agent may comprise silencing one or more endogenous genes. As used herein, "gene silencing" or "gene silenced" in reference to an activity of an RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and/or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 1 16:281-297), comprises a dsRNA molecule.

Chromatin Modifying Agents

In certain embodiments, agents capable of modifying the chromatin structure of one or more genes described herein are used. Chromatin modifying agents, such as histone modifying enzymes, may be targeted to specific genomic loci using a genetic modifying agent described herein. Chromatin modifying agents may modulate contact domains or chromatin looping (see e.g., WO2016/089920; WO 2017/031370; and WO2017106290A1).

Administration

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

The medicaments of the invention are prepared in a manner known to those skilled in the art, for example, by means of conventional dissolving, lyophilizing, mixing, granulating or confectioning processes. Methods well known in the art for making formulations are found, for example, in Remington: The Science and Practice of Pharmacy, 20th ed., ed. A. R. Gennaro, 2000, Lippincott Williams & Wilkins, Philadelphia, and Encyclopedia of Pharmaceutical Technology, eds. J. Swarbrick and J. C. Boylan, 1988-1999, Marcel Dekker, New York.

Administration of medicaments of the invention may be by any suitable means that results in a compound concentration that is effective for treating or inhibiting (e.g., by delaying) the development of a disease. The compound is admixed with a suitable carrier substance, e.g., a pharmaceutically acceptable excipient that preserves the therapeutic properties of the compound with which it is administered. One exemplary pharmaceutically acceptable excipient is physiological saline. The suitable carrier substance is generally present in an amount of 1-95% by weight of the total weight of the medicament. The medicament may be provided in a dosage form that is suitable for administration. Thus, the medicament may be in form of, e.g., tablets, capsules, pills, powders, granulates, suspensions, emulsions, solutions, gels including hydrogels, pastes, ointments, creams, plasters, drenches, delivery devices, injectables, implants, sprays, or aerosols.

The agents disclosed herein may be used in a pharmaceutical composition when combined with a pharmaceutically acceptable carrier. Such compositions comprise a therapeutically-effective amount of the agent and a pharmaceutically acceptable carrier. Such a composition may also further comprise (in addition to an agent and a carrier) diluents, fillers, salts, buffers, stabilizers, solubilizers, and other materials well known in the art. Compositions comprising the agent can be administered in the form of salts provided the salts are pharmaceutically acceptable. Salts may be prepared using standard procedures known to those skilled in the art of synthetic organic chemistry.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/ diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, pamoate, valerate, and the like which can be used as a dosage form for modifying the solubility or hydrolysis characteristics or can be used in sustained release or prodrug formulations. It will be understood that, as used herein, references to specific agents (e.g., neuromedin U receptor agonists or antagonists), also include the pharmaceutically acceptable salts thereof.

Methods of administrating the pharmacological compositions, including agonists, antagonists, antibodies or fragments thereof, to an individual include, but are not limited to, intradermal, intrathecal, intramuscular, intraperitoneal, intravenous, subcutaneous, intranasal, epidural, by inhalation, and oral routes. The compositions can be administered by any convenient route, for example by infusion or bolus injection, by absorption through epithelial or mucocutaneous linings (for example, oral mucosa, rectal and intestinal mucosa, and the like), ocular, and the like and can be administered together with other biologically-active agents. Administration can be systemic or local. In addition, it may be advantageous to administer the composition into the central nervous system by any suitable route, including intraventricular and intrathecal injection. Pulmonary administration may also be employed by use of an inhaler or nebulizer, and formulation with an aerosolizing agent. It may also be desirable to administer the agent locally to the area in need of treatment; this may be achieved by, for example, and not by way of limitation, local infusion during surgery, topical application, by injection, by means of a catheter, by means of a suppository, or by means of an implant.

Various delivery systems are known and can be used to administer the pharmacological compositions including, but not limited to, encapsulation in liposomes, microparticles, microcapsules; minicells; polymers; capsules; tablets; and the like. In one embodiment, the agent may be delivered in a vesicle, in particular a liposome. In a liposome, the agent is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,837,028 and 4,737,323. In yet another embodiment, the pharmacological compositions can be delivered in a controlled release system including, but not limited to: a delivery pump (See, for example, Saudek, et al., New Engl. J. Med. 321: 574 (1989) and a semi-permeable polymeric material (See, for example, Howard, et al., J. Neurosurg. 71: 105 (1989)). Additionally, the controlled release system can be placed in proximity of the therapeutic target (e.g., a tumor), thus requiring only a fraction of the systemic dose. See, for example, Goodson, In: Medical Applications of Controlled Release, 1984. (CRC Press, Boca Raton, Fla.).

The amount of the agents (e.g., metyrapone, glucocorticoid antagonists, IL-27 antagonists) which will be effective in the treatment of a particular disorder or condition will depend on the nature of the disorder or condition, and may be determined by standard clinical techniques by those of skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of the agent with which to treat each individual patient. In certain embodiments, the attending physician will administer low doses of the agent and observe the patient's response. Larger doses of the agent may be administered until the optimal therapeutic effect is obtained for the patient, and at that point the dosage is not increased further. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases. In certain embodiments, suitable dosage ranges for intravenous administration of the agent are generally about 5-500 micrograms (g) of active compound per kilogram (Kg) body weight. Suitable dosage ranges for intranasal administration are generally about 0.01 pg/kg body weight to 1 mg/kg body weight. In certain embodiments, a composition containing an agent of the present invention is subcutaneously injected in adult patients with dose ranges of approximately 5 to 5000 μg/human and preferably approximately 5 to 500 μg/human as a single dose. It is desirable to administer this dosage 1 to 3 times daily. Effective doses may be extrapolated from dose-response curves derived from in vitro or animal model test systems. Suppositories generally contain active ingredient in the range of 0.5% to 10% by weight; oral formulations preferably contain 10% to 95% active ingredient. Ultimately the attending physician will decide on the appropriate duration of therapy using compositions of the present invention.

Dosage will also vary according to the age, weight and response of the individual patient.

Suitable doses of IL-27 are generally in the range of between about 1 and about 250 g/kg body weight, and may be administered from once a week up to about six times daily. Treatment may continue for a period of between one day and six months, or for as long as is deemed necessary and safe in the treatment of the aforementioned disorders, as is readily ascertained by standard tests by the attending physician, depending upon the nature of the disorder being treated.

Suitable dosages for administering glucocorticoids is known in the art. Exemplary dosages are described below. In certain embodiments, based on the discovery of synergism between IL-27 and glucocorticoids, a lower dose is administered in a combination therapy.

betamethasone: For oral dosage forms (syrup, tablets, effervescent tablets): Adults and teenagers—Dose may range from 0.25 to 7.2 milligrams (mg) a day, as a single dose or divided into several doses. For long-acting oral dosage form (extended-release tablets): Adults and teenagers—Dose may range from 1.2 to 12 mg injected into a joint, lesion, muscle, or vein as often as necessary, as determined by your doctor. For injection dosage form: Adults and teenagers-2 to 6 mg a day.

budesonide: For long-acting oral dosage form (extended-release capsules): Adults At first, the dose is 9 milligrams (mg) a day for up to eight weeks. Then your doctor may decrease the dose to 6 mg a day. Each dose should be taken in the morning before breakfast. Children-Use and dose must be determined by your doctor.

cortisone: For oral dosage form (tablets): Adults and teenagers—25 to 300 milligrams (mg) a day, as a single dose or divided into several doses. For injection dosage form: Adults and teenagers-20 to 300 mg a day, injected into a muscle.

dexamethasone: For oral dosage forms (elixir, oral solution, tablets): Adults and teenagers—0.5 to 10 milligrams (mg) taken as often as necessary, as determined by your doctor. For injection dosage form: Adults and teenagers-20.2 to 40 mg injected into a joint, lesion, muscle, or vein as often as necessary, as determined by your doctor.

hydrocortisone: For oral dosage forms (oral suspension, tablets): Adults and teenagers-20 to 800 milligrams (mg) every one or two days, as a single dose or divided into several doses. For injection dosage form: Adults and teenagers-5 to 500 mg injected into a joint, lesion, muscle, or vein, or under the skin as often as necessary, as determined by your doctor.

methylprednisolone: For oral dosage form (tablets): Adults and teenagers-4 to 160 milligrams (mg) every one or two days, as a single dose or divided into several doses. For injection dosage form: Adults and teenagers-4 to 160 mg injected into a joint, lesion, muscle, or vein as often as necessary, as determined by your doctor.

prednisolone: For oral dosage forms (oral solution, syrup, tablets): Adults and teenagers-5 to 200 milligrams (mg) taken as often as necessary, as determined by your doctor. For injection dosage form: Adults and teenagers-2 to 100 mg injected into a joint, lesion, muscle, or vein as often as necessary, as determined by your doctor.

prednisone: For oral dosage forms (oral solution, syrup, tablets): Adults and teenagers-5 to 200 milligrams (mg) every one or two days, as a single dose or divided into several doses.

triamcinolone: For oral dosage forms (syrup, tablets): Adults and teenagers-2 to 60 milligrams (mg) a day, as a single dose or divided into several doses. For injection dosage form: Adults and teenagers-0.5 to 100 mg injected into a joint, lesion, or muscle, or under the skin as often as necessary, as determined by your doctor.

In certain embodiments, dosages of IL-27 and glucocorticoid can be decreased because of the synergistic effect of the combination treatment. In certain embodiments, a combination treatment can be tolerated by a subject for a longer period of time and have less side effects. In certain embodiments, dosages are decreased 2-fold, 10-fold, or more than 100-fold.

Methods for administering antibodies for therapeutic use is well known to one skilled in the art. In certain embodiments, small particle aerosols of antibodies or fragments thereof may be administered (see e.g., Piazza et al., J. Infect. Dis., Vol. 166, pp. 1422-1424, 1992; and Brown, Aerosol Science and Technology, Vol. 24, pp. 45-56, 1996). In certain embodiments, antibodies are administered in metered-dose propellant driven aerosols. In preferred embodiments, antibodies are used as agonists to depress inflammatory diseases or allergen-induced asthmatic responses. In certain embodiments, antibodies may be administered in liposomes, i.e., immunoliposomes (see, e.g., Maruyama et al., Biochim. Biophys. Acta, Vol. 1234, pp. 74-80, 1995). In certain embodiments, immunoconjugates, immunoliposomes or immunomicrospheres containing an agent of the present invention is administered by inhalation.

In certain embodiments, antibodies may be topically administered to mucosa, such as the oropharynx, nasal cavity, respiratory tract, gastrointestinal tract, eye such as the conjunctival mucosa, vagina, urogenital mucosa, or for dermal application. In certain embodiments, antibodies are administered to the nasal, bronchial or pulmonary mucosa. In order to obtain optimal delivery of the antibodies to the pulmonary cavity in particular, it may be advantageous to add a surfactant such as a phosphoglyceride, e.g. phosphatidylcholine, and/or a hydrophilic or hydrophobic complex of a positively or negatively charged excipient and a charged antibody of the opposite charge.

Other excipients suitable for pharmaceutical compositions intended for delivery of antibodies to the respiratory tract mucosa may be a) carbohydrates, e.g., monosaccharides such as fructose, galactose, glucose. D-mannose, sorbose, and the like; disaccharides, such as lactose, trehalose, cellobiose, and the like; cyclodextrins, such as 2-hydroxypropyl-p-cyclodextrin; and polysaccharides, such as raffinose, maltodextrins, dextrans, and the like; b) amino acids, such as glycine, arginine, aspartic acid, glutamic acid, cysteine, lysine and the like; c) organic salts prepared from organic acids and bases, such as sodium citrate, sodium ascorbate, magnesium gluconate, sodium gluconate, tromethamine hydrochloride, and the like: d) peptides and proteins, such as aspartame, human serum albumin, gelatin, and the like; e) alditols, such mannitol, xylitol, and the like, and f) polycationic polymers, such as chitosan or a chitosan salt or derivative.

For dermal application, the antibodies of the present invention may suitably be formulated with one or more of the following excipients: solvents, buffering agents, preservatives, humectants, chelating agents, antioxidants, stabilizers, emulsifying agents, suspending agents, gel-forming agents, ointment bases, penetration enhancers, and skin protective agents.

Examples of solvents are e.g. water, alcohols, vegetable or marine oils (e.g. edible oils like almond oil, castor oil, cacao butter, coconut oil, corn oil, cottonseed oil, linseed oil, olive oil, palm oil, peanut oil, poppy seed oil, rapeseed oil, sesame oil, soybean oil, sunflower oil, and tea seed oil), mineral oils, fatty oils, liquid paraffin, polyethylene glycols, propylene glycols, glycerol, liquid polyalkylsiloxanes, and mixtures thereof.

Examples of buffering agents are e.g. citric acid, acetic acid, tartaric acid, lactic acid, hydrogenphosphoric acid, diethyl amine etc. Suitable examples of preservatives for use in compositions are parabens, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalkonium chloride, and benzylalcohol, or mixtures of preservatives.

Examples of humectants are glycerin, propylene glycol, sorbitol, lactic acid, urea, and mixtures thereof.

Examples of antioxidants are butylated hydroxy anisole (BHA), ascorbic acid and derivatives thereof, tocopherol and derivatives thereof, cysteine, and mixtures thereof.

Examples of emulsifying agents are naturally occurring gums, e.g. gum acacia or gum tragacanth; naturally occurring phosphatides, e.g. soybean lecithin, sorbitan monooleate derivatives: wool fats; wool alcohols; sorbitan esters; monoglycerides; fatty alcohols; fatty acid esters (e.g. triglycerides of fatty acids); and mixtures thereof.

Examples of suspending agents are e.g. celluloses and cellulose derivatives such as, e.g., carboxymethyl cellulose, hydroxyethylcellulose, hydroxypropylcellulose, hydroxypropylmethylcellulose, carrageenan, acacia gum, arabic gum, tragacanth, and mixtures thereof.

Examples of gel bases, viscosity-increasing agents or components which are able to take up exudate from a wound are: liquid paraffin, polyethylene, fatty oils, colloidal silica or aluminum, zinc soaps, glycerol, propylene glycol, tragacanth, carboxyvinyl polymers, magnesium-aluminum silicates, Carbopol®, hydrophilic polymers such as, e.g. starch or cellulose derivatives such as, e.g., carboxymethylcellulose, hydroxyethylcellulose and other cellulose derivatives, water-swellable hydrocolloids, carragenans, hyaluronates (e.g. hyaluronate gel optionally containing sodium chloride), and alginates including propylene glycol alginate.

Examples of ointment bases are e.g. beeswax, paraffin, cetanol, cetyl palmitate, vegetable oils, sorbitan esters of fatty acids (Span), polyethylene glycols, and condensation products between sorbitan esters of fatty acids and ethylene oxide, e.g. polyoxyethylene sorbitan monooleate (Tween).

Examples of hydrophobic or water-emulsifying ointment bases are paraffins, vegetable oils, animal fats, synthetic glycerides, waxes, lanolin, and liquid polyalkylsiloxanes. Examples of hydrophilic ointment bases are solid macrogols (polyethylene glycols). Other examples of ointment bases are triethanolamine soaps, sulphated fatty alcohol and polysorbates.

Examples of other excipients are polymers such as carmelose, sodium carmelose, hydroxypropylmethylcellulose, hydroxyethylcellulose, hydroxypropylcellulose, pectin, xanthan gum, locust bean gum, acacia gum, gelatin, carbomer, emulsifiers like vitamin E, glyceryl stearates, cetearyl glucoside, collagen, carrageenan, hyaluronates and alginates and chitosans.

The dose of antibody required in humans to be effective in the treatment or prevention of allergic inflammation differs with the type and severity of the allergic condition to be treated, the type of allergen, the age and condition of the patient, etc. Typical doses of antibody to be administered are in the range of 1 µg to 1 g, preferably 1-1000 µg, more preferably 2-500, even more preferably 5-50, most preferably 10-20 µg per unit dosage form. In certain embodiments, infusion of antibodies of the present invention may range from 10-500 mg/m$^2$.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection.

In another aspect, provided is a pharmaceutical pack or kit, comprising one or more containers filled with one or more of the ingredients of the pharmaceutical compositions described herein.

Detection and Isolation Using Biomarkers

In certain embodiments, dysfunctional cells are detected, isolated or quantified. A marker, for example a gene or gene product, for example a peptide, polypeptide, protein, or nucleic acid, or a group of two or more markers, is "detected" or "measured" in a tested object (e.g., in or on a cell, cell population, tissue, organ, or organism, e.g., in a biological sample of a subject) when the presence or absence and/or quantity of said marker or said group of markers is detected or determined in the tested object, preferably substantially to the exclusion of other molecules and analytes, e.g., other genes or gene products.

The terms "increased" or "increase" or "upregulated" or "upregulate" as used herein generally mean an increase by a statically significant amount. For avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, as that term is defined herein.

The term "reduced" or "reduce" or "decrease" or "decreased" or "downregulate" or "downregulated" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least 50%, or at least 60%, or at least 70%, or at least 80%, at least 90% or more, up to and including a 100% decrease (i.e., absent level as compared to a reference sample), or any decrease between 10-100% as compared to a reference level, as that.

The terms "quantity", "amount" and "level" are synonymous and generally well-understood in the art. The terms as used throughout this specification may particularly refer to an absolute quantification of a marker in a tested object (e.g., in or on a cell, cell population, tissue, organ, or organism, e.g., in a biological sample of a subject), or to a relative quantification of a marker in a tested object, i.e., relative to another value such as relative to a reference value, or to a range of values indicating a base-line of the marker. Such values or ranges may be obtained as conventionally known.

An absolute quantity of a marker may be advantageously expressed as weight or as molar amount, or more commonly as a concentration, e.g., weight per volume or mol per volume. A relative quantity of a marker may be advantageously expressed as an increase or decrease or as a fold-increase or fold-decrease relative to said another value, such as relative to a reference value. Performing a relative comparison between first and second variables (e.g., first and second quantities) may but need not require determining first the absolute values of said first and second variables. For example, a measurement method may produce quantifiable readouts (such as, e.g., signal intensities) for said first and second variables, wherein said readouts are a function of the value of said variables, and wherein said readouts may be directly compared to produce a relative value for the first variable vs. the second variable, without the actual need to first convert the readouts to absolute values of the respective variables.

Reference values may be established according to known procedures previously employed for other cell populations, biomarkers and gene or gene product signatures. For example, a reference value may be established in an individual or a population of individuals characterized by a particular diagnosis, prediction and/or prognosis of said disease or condition (i.e., for whom said diagnosis, prediction and/or prognosis of the disease or condition holds true). Such population may comprise without limitation 2 or more, 10 or more, 100 or more, or even several hundred or more individuals.

A "deviation" of a first value from a second value may generally encompass any direction (e.g., increase: first value>second value; or decrease: first value <second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., $\pm 1 \times SD$ or $\pm 2 \times SD$ or $\pm 3 \times SD$, or $1 \times SE$ or $\pm 2 \times SE$ or $\pm 3 \times SE$). Deviation may also refer to a value falling outside of a reference range defined by values in a given population (for example, outside of a range which comprises ≥40%, ≥50%, ≥60%, ≥70%, ≥75% or ≥80% or ≥85% or ≥90% or ≥95% or even ≥100% of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

For example, receiver-operating characteristic (ROC) curve analysis can be used to select an optimal cut-off value of the quantity of a given immune cell population, biomarker or gene or gene product signatures, for clinical use of the present diagnostic tests, based on acceptable sensitivity and specificity, or related performance measures which are well-known per se, such as positive predictive value (PPV), negative predictive value (NPV), positive likelihood ratio (LR+), negative likelihood ratio (LR−), Youden index, or similar.

The method may allow to detect or conclude the presence or absence of the specified immune cells in a tested object (e.g., in a cell population, tissue, organ, organism, or in a biological sample of a subject). The method may also allow to quantify the specified immune cells in a tested object (e.g., in a cell population, tissue, organ, organism, or in a biological sample of a subject). The quantity of the specified immune cells in the tested object such as the biological sample may be suitably expressed for example as the number (count) of the specified immune cells per standard unit of volume (e.g., ml, µl or nl) or weight (e.g., g or mg or ng) of the tested object such as the biological sample. The quantity of the specified immune cells in the tested object such as the biological sample may also be suitably expressed as a percentage or fraction (by number) of all cells comprised in the tested object such as the biological sample, or as a percentage or fraction (by number) of a select subset of the cells comprised in the tested object such as the biological sample, e.g., as a percentage or fraction (by number) of white blood cells, peripheral blood mononuclear cells, immune cells, antigen presenting cells, or dendritic cells comprised in the tested object such as the biological sample. The quantity of the specified immune cells in the tested object such as the biological sample may also be suitably represented by an absolute or relative quantity of a suitable surrogate analyte, such as a peptide, polypeptide, protein, or nucleic acid expressed or comprised by the specified immune cells.

Where a marker is detected in or on a cell, the cell may be conventionally denoted as positive (+) or negative (−) for the marker. Semi-quantitative denotations of marker expression in cells are also commonplace in the art, such as particularly in flow cytometry quantifications, for example, "dim" vs. "bright", or "low" vs. "medium"/"intermediate" vs. "high", or "−" vs. "+" vs. "++", commonly controlled in flow cytometry quantifications by setting of the gates. Where a marker is quantified in or on a cell, absolute quantity of the marker may also be expressed for example as the number of molecules of the marker comprised by the cell.

Where a marker is detected and/or quantified on a single cell level in a cell population, the quantity of the marker may also be expressed as a percentage or fraction (by number) of cells comprised in said population that are positive for said marker, or as percentages or fractions (by number) of cells comprised in said population that are "dim" or "bright", or that are "low" or "medium"/"intermediate" or "high", or that are "−" or "+" or "++". By means of an example, a sizeable proportion of the tested cells of the cell population may be positive for the marker, e.g., at least about 20%, at least about 40%, at least about 50%, at least about 60%, at least about 70%, at least about 80%, at least about 90%, at least about 95%, or up to 100%.

In certain embodiments, the CD8+ and/or CD4$^+$ T cell subtypes may be detected, quantified or isolated using a technique selected from the group consisting of flow cytometry, mass cytometry, fluorescence activated cell sorting (FACS), fluorescence microscopy, affinity separation, magnetic cell separation, microfluidic separation, RNA-seq (e.g., bulk or single cell), quantitative PCR, MERFISH (multiplex (in situ) RNA FISH), Flow-FISH and combinations thereof. The technique may employ one or more agents capable of specifically binding to one or more gene products expressed or not expressed by the CD8$^+$ T cells, preferably on the cell surface of the CD8$^+$ T cells. The one or more agents may be one or more antibodies. Other methods including absorbance assays and colorimetric assays are known in the art and may be used herein.

Depending on factors that can be evaluated and decided on by a skilled person, such as, inter alia, the type of a marker (e.g., peptide, polypeptide, protein, or nucleic acid), the type of the tested object (e.g., a cell, cell population, tissue, organ, or organism, e.g., the type of biological sample of a subject, e.g., whole blood, plasma, serum, tissue biopsy), the expected abundance of the marker in the tested object, the type, robustness, sensitivity and/or specificity of the detection method used to detect the marker, etc., the marker may be measured directly in the tested object, or the tested object may be subjected to one or more processing steps aimed at achieving an adequate measurement of the marker.

Immunoassays

Immunoassay methods are based on the reaction of an antibody to its corresponding target or analyte and can detect the analyte in a sample depending on the specific assay format. To improve specificity and sensitivity of an assay method based on immunoreactivity, monoclonal antibodies are often used because of their specific epitope recognition. Polyclonal antibodies have also been successfully used in various immunoassays because of their increased affinity for the target as compared to monoclonal antibodies Immunoassays have been designed for use with a wide range of biological sample matrices Immunoassay formats have been designed to provide qualitative, semi-quantitative, and quantitative results.

Quantitative results may be generated through the use of a standard curve created with known concentrations of the specific analyte to be detected. The response or signal from an unknown sample is plotted onto the standard curve, and a quantity or value corresponding to the target in the unknown sample is established.

Numerous immunoassay formats have been designed. ELISA or EIA can be quantitative for the detection of an analyte/biomarker. This method relies on attachment of a label to either the analyte or the antibody and the label component includes, either directly or indirectly, an enzyme. ELISA tests may be formatted for direct, indirect, competitive, or sandwich detection of the analyte. Other methods rely on labels such as, for example, radioisotopes ($I^{125}$) or fluorescence. Additional techniques include, for example, agglutination, nephelometry, turbidimetry, Western blot, immunoprecipitation, immunocytochemistry, immunohistochemistry, flow cytometry, Luminex assay, and others (see ImmunoAssay: A Practical Guide, edited by Brian Law, published by Taylor & Francis, Ltd., 2005 edition).

Exemplary assay formats include enzyme-linked immunosorbent assay (ELISA), radioimmunoassay, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

Methods of detecting and/or quantifying a detectable label or signal generating material depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Any of the methods for detection can be performed in any format that allows for any suitable preparation, processing, and analysis of the reactions. This can be, for example, in multi-well assay plates (e.g., 96 wells or 384 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

In other example embodiments, detection of a marker may include immunological assay methods, wherein the ability of an assay to separate, detect and/or quantify a marker (such as, preferably, peptide, polypeptide, or protein) is conferred by specific binding between a separable, detectable and/or quantifiable immunological binding agent (antibody) and the marker. Immunological assay methods include without limitation immunohistochemistry, immunocytochemistry, flow cytometry, mass cytometry, fluorescence activated cell sorting (FACS), fluorescence microscopy, fluorescence based cell sorting using microfluidic systems, immunoaffinity adsorption based techniques such as affinity chromatography, magnetic particle separation, magnetic activated cell sorting or bead based cell sorting using microfluidic systems, enzyme-linked immunosorbent assay (ELISA) and ELISPOT based techniques, radioimmunoassay (RIA), Western blot, etc.

In certain example embodiments, detection of a marker or signature may include biochemical assay methods, including inter alia assays of enzymatic activity, membrane channel activity, substance-binding activity, gene regulatory activity, or cell signaling activity of a marker, e.g., peptide, polypeptide, protein, or nucleic acid.

MS Methods

Biomarker detection may also be evaluated using mass spectrometry methods. A variety of configurations of mass spectrometers can be used to detect biomarker values. Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption.

Common mass analyzers include a quadrupole mass filter, ion trap mass analyzer and time-of-flight mass analyzer. Additional mass spectrometry methods are well known in the art (see Burlingame et al., Anal. Chem. 70:647 R-716R (1998); Kinter and Sherman, New York (2000)).

Protein biomarkers and biomarker values can be detected and measured by any of the following: electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), tandem time-of-flight (TOF/TOF) technology, called ultraflex III TOF/TOF, atmospheric pressure chemical ionization mass spectrometry (APCI-MS), APCI-MS/MS, APCI-(MS).sup.N, atmospheric pressure photoionization mass spectrometry (APPI-MS), APPI-MS/MS, and APPI-(MS).sup.N, quadrupole mass spectrometry, Fourier transform mass spectrometry (FTMS), quantitative mass spectrometry, and ion trap mass spectrometry.

Sample preparation strategies are used to label and enrich samples before mass spectroscopic characterization of protein biomarkers and determination biomarker values. Labeling methods include but are not limited to isobaric tag for relative and absolute quantitation (iTRAQ) and stable isotope labeling with amino acids in cell culture (SILAC). Capture reagents used to selectively enrich samples for candidate biomarker proteins prior to mass spectroscopic analysis include but are not limited to aptamers, antibodies, nucleic acid probes, chimeras, small molecules, an F(ab')2 fragment, a single chain antibody fragment, an Fv fragment, a single chain Fv fragment, a nucleic acid, a lectin, a ligand-binding receptor, affibodies, nanobodies, ankyrins, domain antibodies, alternative antibody scaffolds (e.g. diabodies etc.) imprinted polymers, aimers, peptidomimetics, peptoids, peptide nucleic acids, threose nucleic acid, a hormone receptor, a cytokine receptor, and synthetic receptors, and modifications and fragments of these.

In other example embodiments, detection of a marker may include mass spectrometry analysis methods. Generally, any mass spectrometric (MS) techniques that are capable of obtaining precise information on the mass of peptides, and preferably also on fragmentation and/or (partial) amino acid sequence of selected peptides (e.g., in tandem mass spectrometry, MS/MS; or in post source decay, TOF MS), may be useful herein for separation, detection and/or quantification of markers (such as, preferably, peptides, polypeptides, or proteins). Suitable peptide MS and MS/MS techniques and systems are well-known per se (see, e.g., Methods in Molecular Biology, vol. 146: "Mass Spectrometry of Proteins and Peptides", by Chapman, ed., Humana Press 2000, ISBN 089603609x; Biemann 1990. Methods Enzymol 193: 455-79; or Methods in Enzymology, vol. 402: "Biological Mass Spectrometry", by Burlingame, ed., Academic Press 2005, ISBN 9780121828073) and may be used herein. MS arrangements, instruments and systems suitable for biomarker peptide analysis may include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)n (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-(MS)n; atmospheric pressure photoionization mass spectrometry (APPI-MS); APPI-MS/MS; and APPI-(MS)n. Peptide ion fragmentation in tandem MS (MS/MS) arrangements may be achieved using manners established in the art, such as, e.g., collision induced dissociation (CID). Detection and quantification of markers by mass spectrometry may involve multiple reaction monitoring (MRM), such as described among others by Kuhn et al. 2004 (Proteomics 4: 1175-86). MS peptide analysis methods may be advantageously combined with upstream peptide or protein separation or fractionation methods, such as for example with the chromatographic and other methods.

Separation

In other example embodiments, detection of a marker may include chromatography methods. In a one example embodiment, chromatography refers to a process in which a mixture of substances (analytes) carried by a moving stream of liquid or gas ("mobile phase") is separated into components as a result of differential distribution of the analytes, as they flow around or over a stationary liquid or solid phase ("stationary phase"), between said mobile phase and said stationary phase. The stationary phase may be usually a finely divided solid, a sheet of filter material, or a thin film of a liquid on the surface of a solid, or the like. Chromatography may be columnar. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993. Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immunoaffinity, immobilized metal affinity chromatography, and the like.

In certain embodiments, further techniques for separating, detecting and/or quantifying markers may be used in conjunction with any of the above described detection methods. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

In certain examples, such methods may include separating, detecting and/or quantifying markers at the nucleic acid level, more particularly RNA level, e.g., at the level of hnRNA, pre-mRNA, mRNA, or cDNA. Standard quantitative RNA or cDNA measurement tools known in the art may be used. Non-limiting examples include hybridization-based analysis, microarray expression analysis, digital gene expression profiling (DGE), RNA-in-situ hybridization (RISH), Northern-blot analysis and the like; PCR, RT-PCR, RT-qPCR, end-point PCR, digital PCR or the like; supported oligonucleotide detection, pyrosequencing, polony cyclic sequencing by synthesis, simultaneous bi-directional sequencing, single-molecule sequencing, single molecule real time sequencing, true single molecule sequencing, hybridization-assisted nanopore sequencing, sequencing by synthesis, single-cell RNA sequencing (sc-RNA seq), or the like. By means of an example, methods to profile the RNA content of large numbers of individual cells have been recently developed.

Hybridization Assays

Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of a signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively. Specific hybridization technology which may be practiced to generate the expression profiles employed in the subject methods includes the technology described in U.S. Pat. Nos. 5,143,854; 5,288,644; 5,324, 633; 5,432,049; 5,470,710; 5,492,806; 5,503,980; 5,510, 270; 5,525,464; 5,547,839; 5,580,732; 5,661,028; 5,800, 992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the biomarkers whose expression is being assayed is contacted with target nucleic acids as described above. Contact is carried out under hybridization conditions, e.g., stringent hybridization conditions as described above, and unbound nucleic acid is then removed. The resultant pattern of hybridized nucleic acids provides information regarding expression for each of the biomarkers that have been probed, where the expression information is in terms of whether or not the gene is expressed and, typically, at what level, where the expression data, i.e., expression profile, may be both qualitative and quantitative.

Optimal hybridization conditions will depend on the length (e.g., oligomer vs. polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., "Current Protocols in Molecular Biology", Greene Publishing and Wiley-interscience, NY (1987), which is incorporated in its entirety for all purposes. When the cDNA microarrays are used, typical hybridization conditions are hybridization in 5×SSC plus 0.2% SDS at 65 C for 4 hours followed by washes at 25° C. in low stringency wash buffer (1×SSC plus 0.2% SDS) followed by 10 minutes at 25° C. in high stringency wash buffer (0.1SSC plus 0.2% SDS) (see Shena et al., Proc. Natl. Acad. Sci. USA, Vol. 93, p. 10614 (1996)). Useful hybridization conditions are also provided in, e.g., Tijessen, Hybridization With Nucleic Acid Probes", Elsevier Science Publishers B.V. (1993) and Kricka, "Nonisotopic DNA Probe Techniques", Academic Press, San Diego, Calif. (1992).

Sequencing and Single Cell Sequencing

In certain embodiments, the invention involves targeted nucleic acid profiling (e.g., sequencing, quantitative reverse transcription polymerase chain reaction, and the like) (see e.g., Geiss G K, et al., Direct multiplexed measurement of gene expression with color-coded probe pairs. Nat Biotechnol. 2008 March; 26(3):317-25). In certain embodiments, a target nucleic acid molecule (e.g., RNA molecule), may be sequenced by any method known in the art, for example, methods of high-throughput sequencing, also known as next generation sequencing or deep sequencing. A nucleic acid target molecule labeled with a barcode (for example, an origin-specific barcode) can be sequenced with the barcode to produce a single read and/or contig containing the sequence, or portions thereof, of both the target molecule and the barcode. Exemplary next generation sequencing technologies include, for example, Illumina sequencing, Ion Torrent sequencing, 454 sequencing, SOLiD sequencing, and nanopore sequencing amongst others.

In certain embodiments, the invention involves single cell RNA sequencing (see, e.g., Kalisky, T., Blainey, P. & Quake, S. R. Genomic Analysis at the Single-Cell Level. Annual review of genetics 45, 431-445, (2011); Kalisky, T. & Quake, S. R. Single-cell genomics. Nature Methods 8, 311-314 (2011); Islam, S. et al. Characterization of the single-cell transcriptional landscape by highly multiplex RNA-seq. Genome Research, (2011); Tang, F. et al. RNA-Seq analysis to capture the transcriptome landscape of a single cell. Nature Protocols 5, 516-535, (2010); Tang, F. et al. mRNA-Seq whole-transcriptome analysis of a single cell. Nature Methods 6, 377-382, (2009); Ramskold, D. et al. Full-length mRNA-Seq from single-cell levels of RNA and individual circulating tumor cells. Nature Biotechnology 30, 777-782, (2012); and Hashimshony, T., Wagner, F., Sher, N. & Yanai, I. CEL-Seq: Single-Cell RNA-Seq by Multiplexed Linear Amplification. Cell Reports, Cell Reports, Volume 2, Issue 3, p666-673, 2012).

In certain embodiments, the invention involves plate based single cell RNA sequencing (see, e.g., Picelli, S. et al., 2014, "Full-length RNA-seq from single cells using Smart-seq2" Nature protocols 9, 171-181, doi:10.1038/nprot.2014.006).

In certain embodiments, the invention involves high-throughput single-cell RNA-seq. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Rosenberg et al., "Single-cell profiling of the developing mouse brain and spinal cord with split-pool barcoding" Science 15 Mar. 2018; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; Gierahn et al., "Seq-Well: portable, low-cost RNA sequencing of single cells at high throughput" Nature Methods 14, 395-398 (2017); and Hughes, et al., "Highly Efficient, Massively-Parallel Single-Cell RNA-Seq Reveals Cellular States and Molecular Features of Human Skin Pathology" bioRxiv 689273; doi: doi.org/10.1101/689273, all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; International Patent Application No. PCT/US2016/059239, published as WO2017164936 on Sep. 28, 2017; International Patent Application No. PCT/US2018/060860, published as WO/2019/094984 on May 16, 2019; International Patent Application No. PCT/US2019/055894, published as WO/2020/077236 on Apr. 16, 2020; and Drokhlyansky, et al., "The enteric nervous system of the human and mouse colon at a single-cell resolution," bioRxiv 746743; doi: doi.org/10.1101/746743, which are herein incorporated by reference in their entirety.

In certain embodiments, the invention involves the Assay for Transposase Accessible Chromatin using sequencing (ATAC-seq) as described. (see, e.g., Buenrostro, et al., Transposition of native chromatin for fast and sensitive epigenomic profiling of open chromatin, DNA-binding proteins and nucleosome position. Nature methods 2013; 10 (12): 1213-1218; Buenrostro et al., Single-cell chromatin accessibility reveals principles of regulatory variation. Nature 523, 486-490 (2015); Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. Science. 2015 May 22; 348(6237): 910-4. doi: 10.1126/science.aab1601. Epub 2015 May 7; US20160208323A1; US20160060691A1; and WO2017156336A1).

Diagnosis, Prognosis and Monitoring

In a further embodiment, the present invention provides for a method for determining the T cell status of a subject, or for diagnosing, prognosing or monitoring a disease comprising an immune component in a subject by detecting or quantifying CD8+ T cells as defined in any embodiment herein in a biological sample of the subject. In certain embodiments, T cells expressing a glucocorticoid+IL-27 signature are detected. In certain embodiments, enzymes of steroid biogenesis are detected in a population of immune cells obtained from a subject (e.g., Cyp11a1 in macrophages). In certain embodiments, expression of IL-27 is detected in a population of immune cells obtained from a subject (e.g., in dendritic cells). In certain embodiments, the frequency of cells expressing a gene signature, Cyp11a1 and/or IL-27 are determined. In certain embodiments, a subject having a high frequency of macrophages expressing Cyp11a1 and/or dendritic cells expressing IL-27 indicates a suppressed immune response (e.g., against a tumor). In certain embodiments, a treatment is monitored, such as a treatment as described herein, by monitoring a biomarker or signature gene as described herein. For example, treatment with an agonist of glucocorticoid signaling or agonists glucocorticoid and IL-27 signaling can decrease the expression of the glucocorticoid+IL-27 signature. Specific markers in the signature may be detected (e.g., checkpoint proteins).

The terms "diagnosis" and "monitoring" are commonplace and well-understood in medical practice. By means of further explanation and without limitation the term "diagnosis" generally refers to the process or act of recognizing, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

The term "monitoring" generally refers to the follow-up of a disease or a condition in a subject for any changes which may occur over time.

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

The terms also encompass prediction of a disease. The terms "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

Diseases

In certain example embodiments, the methods, pharmaceutical compositions and adoptive cell transfer strategies described herein may be used to treat various cancers. The cancer may include, without limitation, liquid tumors such as leukemia (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease, non-Hodgkin's disease), Waldenstrom's macroglobulinemia, heavy chain disease, or multiple myeloma.

The cancer may include, without limitation, solid tumors such as sarcomas and carcinomas. Examples of solid tumors include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, epithelial carcinoma, bronchogenic carcinoma, hepatoma, colorectal cancer (e.g., colon cancer, rectal cancer), anal cancer, pancreatic cancer (e.g., pancreatic adenocarcinoma, islet cell carcinoma, neuroendocrine tumors), breast cancer (e.g., ductal carcinoma, lobular carcinoma, inflammatory breast cancer, clear cell carcinoma, mucinous carcinoma), ovarian carcinoma (e.g., ovarian epithelial carcinoma or surface epithelial-stromal tumour including serous tumour, endometrioid tumor and mucinous cystadenocarcinoma, sex-cord-stromal tumor), prostate cancer, liver and bile duct carcinoma (e.g., hepatocellular carcinoma, cholangiocarcinoma, hemangioma), choriocarcinoma, seminoma, embryonal carcinoma, kidney cancer (e.g., renal cell carcinoma, clear cell carcinoma, Wilm's tumor, nephroblastoma), cervical cancer, uterine cancer (e.g., endometrial adenocarcinoma, uterine papillary serous carcinoma, uterine clear-cell carcinoma, uterine sarcomas and leiomyosarcomas, mixed mullerian tumors), testicular cancer, germ cell tumor, lung cancer (e.g., lung adenocarcinoma, squamous cell carcinoma, large cell carcinoma, bronchioloalveolar carcinoma, non-small-cell carcinoma, small cell carcinoma, mesothelioma), bladder carcinoma, signet ring cell carcinoma, cancer of the head and neck (e.g., squamous cell carcinomas), esophageal carcinoma (e.g., esophageal adenocarcinoma), tumors of the brain (e.g., glioma, glioblastoma, astrocytoma, medulloblastoma, craniopharyngioma, ependymoma, pinealoma, hemangioblastoma, acoustic neuroma, oligodendroglioma, schwannoma, meningioma), neuroblastoma, retinoblastoma, neuroendocrine tumor, melanoma, cancer of the stomach (e.g., stomach adenocarcinoma, gastrointestinal stromal tumor), or carcinoids. Lymphoproliferative disorders are also considered to be proliferative diseases.

In certain example embodiments, the methods, pharmaceutical compositions and adoptive cell transfer strategies may be used to treat various autoimmune diseases. As used throughout the present specification, the terms "autoimmune disease" or "autoimmune disorder" are used interchangeably refer to a diseases or disorders caused by an immune response against a self-tissue or tissue component (self-antigen) and include a self-antibody response and/or cell-mediated response. The terms encompass organ-specific autoimmune diseases, in which an autoimmune response is directed against a single tissue, as well as non-organ specific autoimmune diseases, in which an autoimmune response is directed against a component present in two or more, several or many organs throughout the body.

Examples of autoimmune diseases include but are not limited to acute disseminated encephalomyelitis (ADEM); Addison's disease; ankylosing spondylitis; antiphospholipid antibody syndrome (APS); aplastic anemia; autoimmune gastritis; autoimmune hepatitis; autoimmune thrombocytopenia; Behçet's disease; coeliac disease; dermatomyositis; diabetes mellitus type I; Goodpasture's syndrome; Graves' disease; Guillain-Barre syndrome (GBS); Hashimoto's disease; idiopathic thrombocytopenic purpura; inflammatory bowel disease (IBD) including Crohn's disease and ulcerative colitis; mixed connective tissue disease; multiple sclerosis (MS); myasthenia gravis; opsoclonus myoclonus syndrome (OMS); optic neuritis; Ord's thyroiditis; pemphigus; pernicious anaemia; polyarteritis nodosa; polymyositis; primary biliary cirrhosis; primary myxedema; psoriasis; rheumatic fever; rheumatoid arthritis; Reiter's syndrome; scleroderma; Sjögren's syndrome; systemic lupus erythematosus; Takayasu's arteritis; temporal arteritis; vitiligo; warm autoimmune hemolytic anemia; or Wegener's granulomatosis.

Examples of inflammatory diseases or disorders include, but are not limited to, asthma, allergy, allergic rhinitis, allergic airway inflammation, atopic dermatitis (AD), chronic obstructive pulmonary disease (COPD), inflammatory bowel disease (IBD), multiple sclerosis, arthritis, psoriasis, eosinophilic esophagitis, eosinophilic pneumonia, eosinophilic psoriasis, hypereosinophilic syndrome, graft-versus-host disease, uveitis, cardiovascular disease, pain, multiple sclerosis, lupus, vasculitis, chronic idiopathic urticaria and Eosinophilic Granulomatosis with Polyangiitis (Churg-Strauss Syndrome).

The asthma may be allergic asthma, non-allergic asthma, severe refractory asthma, asthma exacerbations, viral-induced asthma or viral-induced asthma exacerbations, steroid resistant asthma, steroid sensitive asthma, eosinophilic asthma or non-eosinophilic asthma and other related disorders characterized by airway inflammation or airway hyperresponsiveness (AHR).

The COPD may be a disease or disorder associated in part with, or caused by, cigarette smoke, air pollution, occupational chemicals, allergy or airway hyperresponsiveness.

The allergy may be associated with foods, pollen, mold, dust mites, animals, or animal dander.

The IBD may be ulcerative colitis (UC), Crohn's Disease, collagenous colitis, lymphocytic colitis, ischemic colitis, diversion colitis, Behcet's syndrome, infective colitis, indeterminate colitis, and other disorders characterized by inflammation of the mucosal layer of the large intestine or colon.

It will be understood by the skilled person that treating as referred to herein encompasses enhancing treatment, or improving treatment efficacy. Treatment may include inhibition of an inflammatory response, tumor regression as well as inhibition of tumor growth, metastasis or tumor cell proliferation, or inhibition or reduction of otherwise deleterious effects associated with the tumor.

Efficaciousness of treatment is determined in association with any known method for diagnosing or treating the particular disease. The invention comprehends a treatment method comprising any one of the methods or uses herein discussed.

The phrase "therapeutically effective amount" as used herein refers to a sufficient amount of a drug, agent, or compound to provide a desired therapeutic effect.

As used herein "patient" refers to any human being receiving or who may receive medical treatment and is used interchangeably herein with the term "subject".

Therapy or treatment according to the invention may be performed alone or in conjunction with another therapy, and may be provided at home, the doctor's office, a clinic, a hospital's outpatient department, or a hospital. Treatment generally begins at a hospital so that the doctor can observe the therapy's effects closely and make any adjustments that are needed. The duration of the therapy depends on the age and condition of the patient, the stage of the cancer, and how the patient responds to the treatment. Additionally, a person having a greater risk of developing an inflammatory response (e.g., a person who is genetically predisposed or predisposed to allergies or a person having a disease characterized by episodes of inflammation) may receive prophylactic treatment to inhibit or delay symptoms of the disease.

Methods of Screening

A further aspect of the invention relates to a method for identifying an agent capable of modulating one or more phenotypic aspects of a cell or cell population as disclosed herein, comprising: a) applying a candidate agent to the cell or cell population; b) detecting modulation of one or more phenotypic aspects of the cell or cell population by the candidate agent, thereby identifying the agent. The phenotypic aspects of the cell or cell population that is modulated may be a gene signature or biological program specific to a cell type or cell phenotype or phenotype specific to a population of cells (e.g., an inflammatory phenotype or suppressive immune phenotype). In certain embodiments, steps can include administering candidate modulating agents to cells, detecting identified cell (sub)populations for changes in signatures, or identifying relative changes in cell (sub) populations which may comprise detecting relative abundance of particular gene signatures.

The term "agent" broadly encompasses any condition, substance or agent capable of modulating one or more phenotypic aspects of a cell or cell population as disclosed herein. Such conditions, substances or agents may be of physical, chemical, biochemical and/or biological nature. The term "candidate agent" refers to any condition, substance or agent that is being examined for the ability to modulate one or more phenotypic aspects of a cell or cell population as disclosed herein in a method comprising applying the candidate agent to the cell or cell population (e.g., exposing the cell or cell population to the candidate agent or contacting the cell or cell population with the candidate agent) and observing whether the desired modulation takes place.

Agents may include any potential class of biologically active conditions, substances or agents, such as for instance antibodies, proteins, peptides, nucleic acids, oligonucleotides, small molecules, or combinations thereof, as described herein.

The methods of phenotypic analysis can be utilized for evaluating environmental stress and/or state, for screening of chemical libraries, and to screen or identify structural, syntenic, genomic, and/or organism and species variations. For example, a culture of cells, can be exposed to an environmental stress, such as but not limited to heat shock, osmolarity, hypoxia, cold, oxidative stress, radiation, starvation, a chemical (for example a therapeutic agent or potential therapeutic agent) and the like. After the stress is applied, a representative sample can be subjected to analysis, for example at various time points, and compared to a control, such as a sample from an organism or cell, for example a cell from an organism, or a standard value. By exposing cells, or fractions thereof, tissues, or even whole animals, to different members of the chemical libraries, and performing the methods described herein, different members of a chemical library can be screened for their effect on immune phenotypes thereof simultaneously in a relatively short amount of time, for example using a high throughput method.

Aspects of the present disclosure relate to the correlation of an agent with the spatial proximity and/or epigenetic profile of the nucleic acids in a sample of cells. In some embodiments, the disclosed methods can be used to screen chemical libraries for agents that modulate chromatin architecture, epigenetic profiles, and/or relationships thereof.

In some embodiments, screening of test agents involves testing a combinatorial library containing a large number of potential modulator compounds. A combinatorial chemical library may be a collection of diverse chemical compounds generated by either chemical synthesis or biological synthesis, by combining a number of chemical "building blocks" such as reagents. For example, a linear combinatorial chemical library, such as a polypeptide library, is formed by combining a set of chemical building blocks (amino acids) in every possible way for a given compound length (for example the number of amino acids in a polypeptide compound). Millions of chemical compounds can be synthesized through such combinatorial mixing of chemical building blocks.

In certain embodiments, the present invention provides for gene signature screening. The concept of signature screening was introduced by Stegmaier et al. (Gene expression-based high-throughput screening (GE-HTS) and application to leukemia differentiation. Nature Genet. 36, 257-263 (2004)), who realized that if a gene-expression signature was the proxy for a phenotype of interest, it could be used to find small molecules that effect that phenotype without knowledge of a validated drug target. The signatures or biological programs of the present invention may be used to screen for drugs that reduce the signature or biological program in cells as described herein. The signature or biological program may be used for GE-HTS. In certain embodiments, pharmacological screens may be used to identify drugs that are selectively toxic to cells having a signature.

The Connectivity Map (cmap) is a collection of genome-wide transcriptional expression data from cultured human cells treated with bioactive small molecules and simple pattern-matching algorithms that together enable the discovery of functional connections between drugs, genes and diseases through the transitory feature of common gene-expression changes (see, Lamb et al., The Connectivity Map: Using Gene-Expression Signatures to Connect Small Molecules, Genes, and Disease. Science 29 Sep. 2006: Vol. 313, Issue 5795, pp. 1929-1935, DOI: 10.1126/science.1132939; and Lamb, J., The Connectivity Map: a new tool for biomedical research. Nature Reviews Cancer January 2007: Vol. 7, pp. 54-60). In certain embodiments, Cmap can be used to screen for small molecules capable of modulating a signature or biological program of the present invention in silico.

Identifying Immunomodulators

A further aspect of the invention relates to a method for identifying an immunomodulant capable of modulating one or more phenotypic aspects of an immune cell or immune cell population as disclosed herein, comprising: a) applying a candidate immunomodulant to the immune cell or immune cell population; b) detecting modulation of one or more phenotypic aspects of the immune cell or immune cell population by the candidate immunomodulant, thereby identifying the immunomodulant.

The term "immunomodulant" broadly encompasses any condition, substance or agent capable of modulating one or more phenotypic aspects of an immune cell or immune cell population as disclosed herein. Such conditions, substances or agents may be of physical, chemical, biochemical and/or biological nature. The term "candidate immunomodulant" refers to any condition, substance or agent that is being examined for the ability to modulate one or more phenotypic aspects of an immune cell or immune cell population as disclosed herein in a method comprising applying the candidate immunomodulant to the immune cell or immune cell population (e.g., exposing the immune cell or immune cell population to the candidate immunomodulant or contacting the immune cell or immune cell population with the candidate immunomodulant) and observing whether the desired modulation takes place (e.g. using functional assays, detecting biomarkers and/or gene signatures).

Immunomodulants may include any potential class of biologically active conditions, substances or agents, such as for instance antibodies, proteins, peptides, nucleic acids, oligonucleotides, small molecules, or combinations thereof.

In Vitro Cell-Based Systems

In certain embodiments, modulation of glucocorticoid and IL-27 signaling and/or downstream targets are used to generate dysfunctional cells that recapitulate in vivo dysfunctional cells. Embodiments disclosed herein provide for in vitro cell-based systems that faithfully recapitulate an in vivo dysfunctional phenotype and methods of generating and using the cell-based systems. In certain embodiments, in vitro dysfunctional T cells can be used to screen for immunomodulators.

In certain embodiments, T cells are obtained from a biological sample subject (e.g., from a mouse or human subject). The terms "sample" or "biological sample" as used throughout this specification include any biological specimen obtained from a subject. Particularly useful samples are those known to comprise, or expected or predicted to comprise immune cells as taught herein. Preferably, a sample may be readily obtainable by minimally invasive methods, such as blood collection or tissue biopsy, allowing the removal/isolation/provision of the sample from the subject. Examples of particularly useful samples include without limitation whole blood or a cell-containing fraction of whole blood, such as serum, white blood cells, or peripheral blood mononuclear cells (PBMC), lymph, lymphatic tissue, inflammation fluid, tissue specimens, or tissue biopsies. The term "tissue" as used throughout this specification refers to any animal tissue types including, but not limited to, bone, bone marrow, neural tissue, fibrous connective tissue, cartilage, muscle, vasculature, skin, adipose tissue, blood and glandular tissue or other non-bone tissue. The tissue may be healthy or affected by pathological alterations, e.g., tumor tissue or tissue affected by a disease comprising an immune component. The tissue may be from a living subject or may be cadaveric tissue. The tissue may be autologous tissue or syngeneic tissue or may be allograft or xenograft tissue. A biological sample may also include cells grown in tissue culture, such as cells used for screening drugs or primary cells grown in culture for expansion.

In certain embodiments, T cells are obtained from peripheral blood mononuclear cells (PBMC) (e.g., using Dynabeads® described further herein). In certain embodiments, the T cells are treated with Glucocorticoid (dexamethasone) and IL-27 in combination. In certain embodiments, the T cells are treated with an agent that modulates a downstream target of combined glucocorticoid and TL-27 signaling. In certain embodiments, dysfunctional cells are characterized by assaying dysfunctional markers as described herein.

The invention is further described in the following examples, which do not limit the scope of the invention described in the claims.

EXAMPLES

Example 1—Glucocorticoid Signaling is Active in Dysfunctional CD8$^+$ TILs

Figure 7:
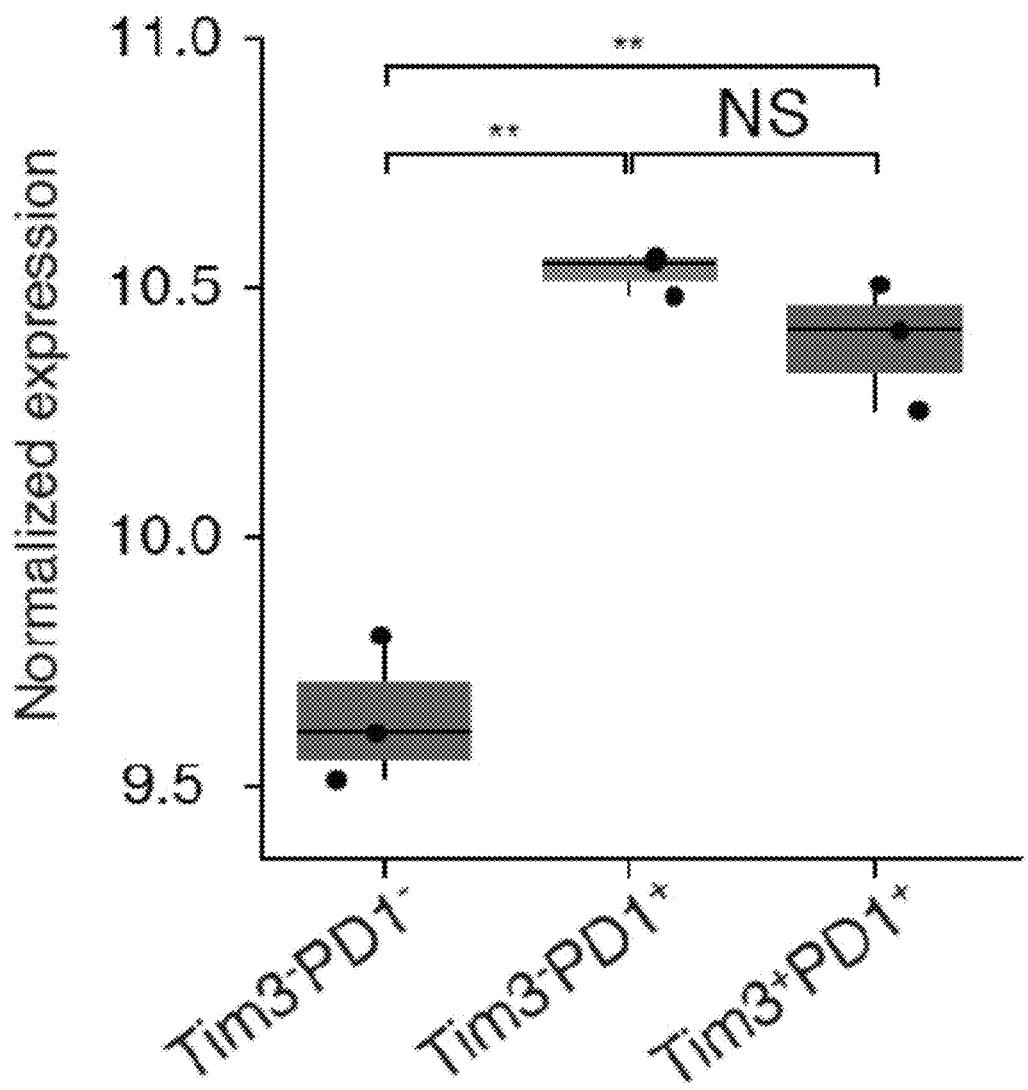
FIG. 7—Glucocorticoid receptor expression in CD8$^+$ TILs populations. Gene expression value of Nr3c1 on Tim3$^-$PD1$^-$, Tim3$^-$PD1$^+$, and Tim3$^+$PD1$^+$ CD8$^+$ TILs from CT26 colon carcinoma (Singer et al., 2016). NS is not significant, **p<0.01. One-way ANOVA.

Analysis of transcriptional profiles (Singer et al., 2016), showed that Nr3c1, the gene encoding the glucocorticoid receptor (GR) is highly expressed in the PD-1+ CD8+ and Tim-3+PD-1+ CD8+TIL subsets that exhibit intermediate and severe dysfunctional phenotype, respectively (FIG. 7). Examination of GR protein showed that it is most highly expressed in severely dysfunctional Tim3+PD1+ CD8+ TILs in two different tumor models, MC38-Ova colon carcinoma and B16F10 melanoma (FIG. 1a), indicating that dysfunctional CD8+ T cells may have increased sensitivity to glucocorticoid signaling. Consistent with the expression pattern on murine CD8+ TILs subsets, the GR was also most highly expressed in Tim-3+PD-1+ CD8+ TILs from human colon carcinoma tumors (FIG. 1b). Thus, Applicants hypothesized that glucocorticoid signaling may be associated with the development of CD8+ T cell dysfunction in both murine and human tumors.

To further test the possible association of glucocorticoid signaling with CD8+ T cell dysfunction, Applicants scored the expression of a previously established glucocorticoid signature (Phuc Le et al., 2005) (Methods) in the single-cell RNA-Seq (scRNA-Seq) profiles of CD8+ TILs (Singer et al., 2017) from B16F10 melanoma (FIG. 1c). Cells expressing the glucocorticoid signature and known GR target genes, such as Mt1 (Karin and Herschman, 1979) and Nfil3 (Carey et al., 2013), also scored highly for expression of the T cell dysfunction or "exhaustion" signature (Methods), indicating that glucocorticoid signaling was active in CD8+ TILs that exhibit dysfunctional phenotype.

Figure 8E:
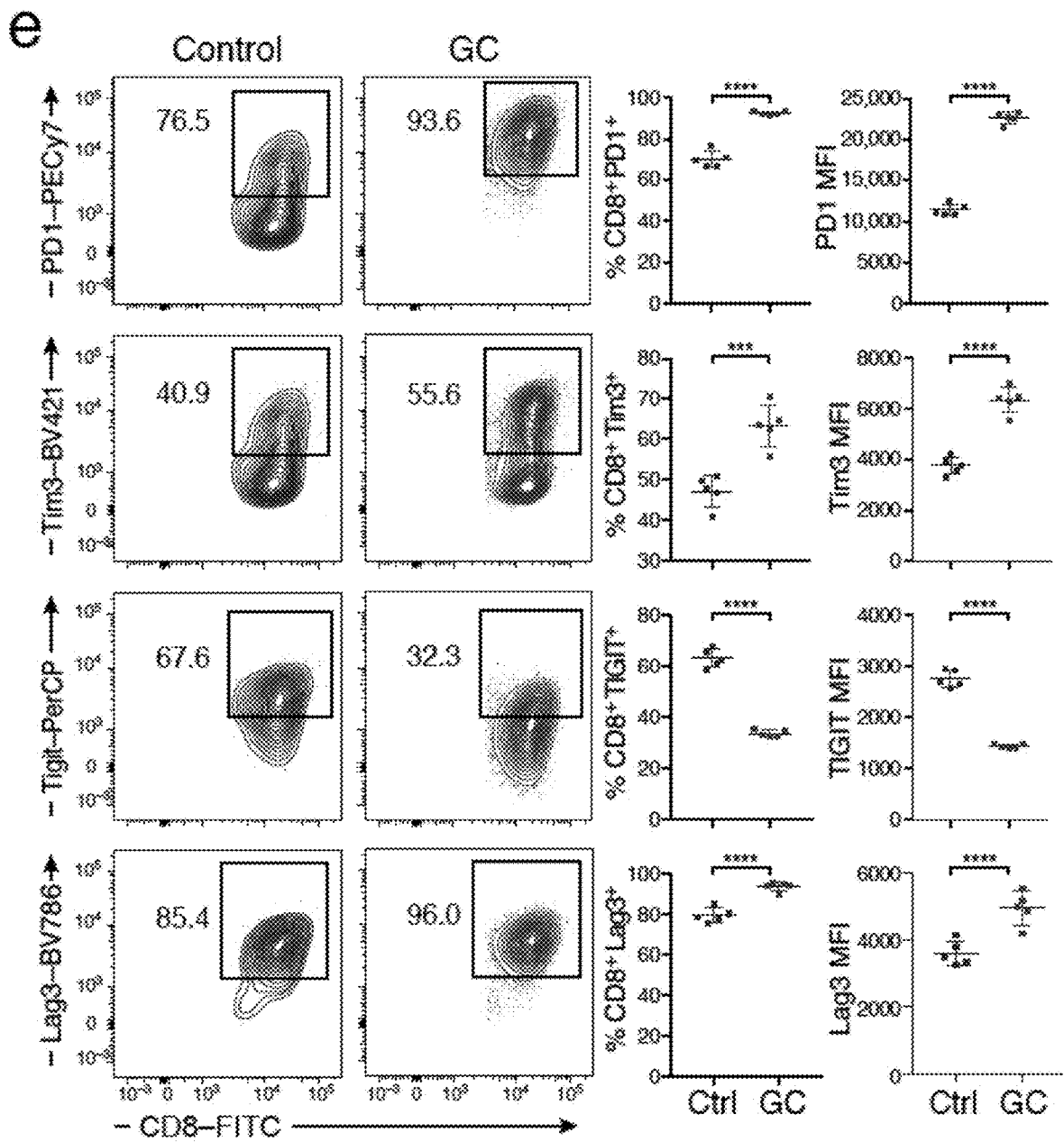

Example 2—Glucocorticoid Signaling Promotes Features of Dysfunctional Phenotype in CD8$^+$ T Cells Accordingly, Applicants hypothesized that glucocorticoid signaling might promote T cell dysfunction in murine and human cells. Applicants tested the effect of repeated activation of CD8$^+$ T cells in the presence of exogenous glucocorticoid (dexamethasone; Dex) in vitro. In line with observations in acutely activated cells (Barrat et al., 2002; Brattsand and Linden, 1996; Rhen and Cidlowski, 2005), Applicants found that repeated activation in the presence of glucocorticoid profoundly suppressed the production of the pro-inflammatory cytokines IFN-γ, IL-2, and TNF-α, and up-regulated the immune-suppressive cytokine IL-10 (FIG. 2a), a phenotype consistent with dysfunctional T cells. Indeed, Applicants found that glucocorticoid treatment dramatically upregulated checkpoint receptors associated with dysfunctional phenotype including PD-1, Tim-3, and Lag-3, but not Tigit (FIG. 2b). Notably, the glucocorticoid-mediated induction of checkpoint receptor expression was conserved in human CD8$^+$ T cells (FIG. 2c). Additionally, Applicants observed that glucocorticoid increased the frequency of Tim-3+PD-1+ CD8+ T cells in both murine and human samples (FIG. 8a,b). The observed effects of glucocorticoid were not due to reduced T cell survival or altered proliferation (FIG. 8c,d). Applicants further tested the effect of a natural glucocorticoid, corticosterone, on the expression of checkpoint receptors and found that it recapitulated the effects of Dex (FIG. 8e).

Figure 9A:
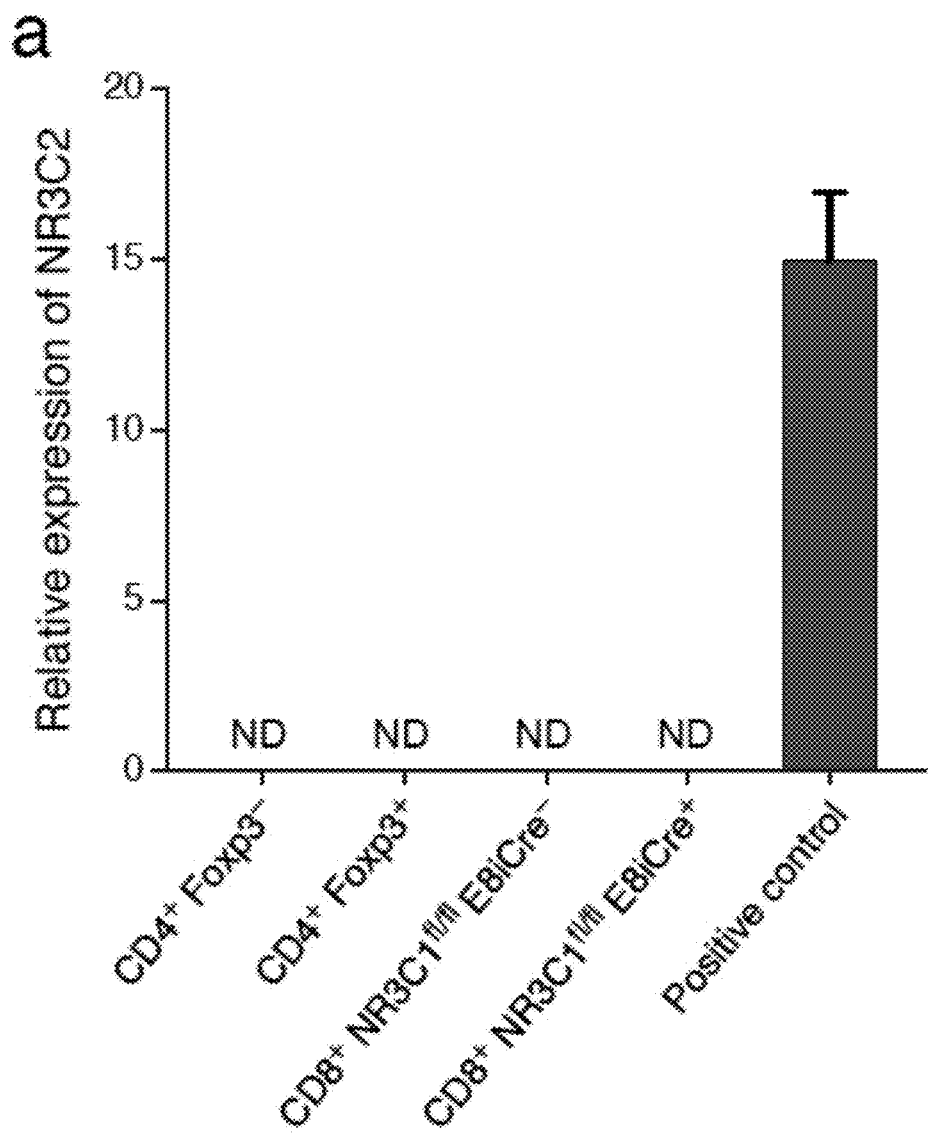
FIGS. 9A-9B—Glucocorticoid-mediated effects on CD8$^+$ T cells requires Nr3c1.
Figure 9B:
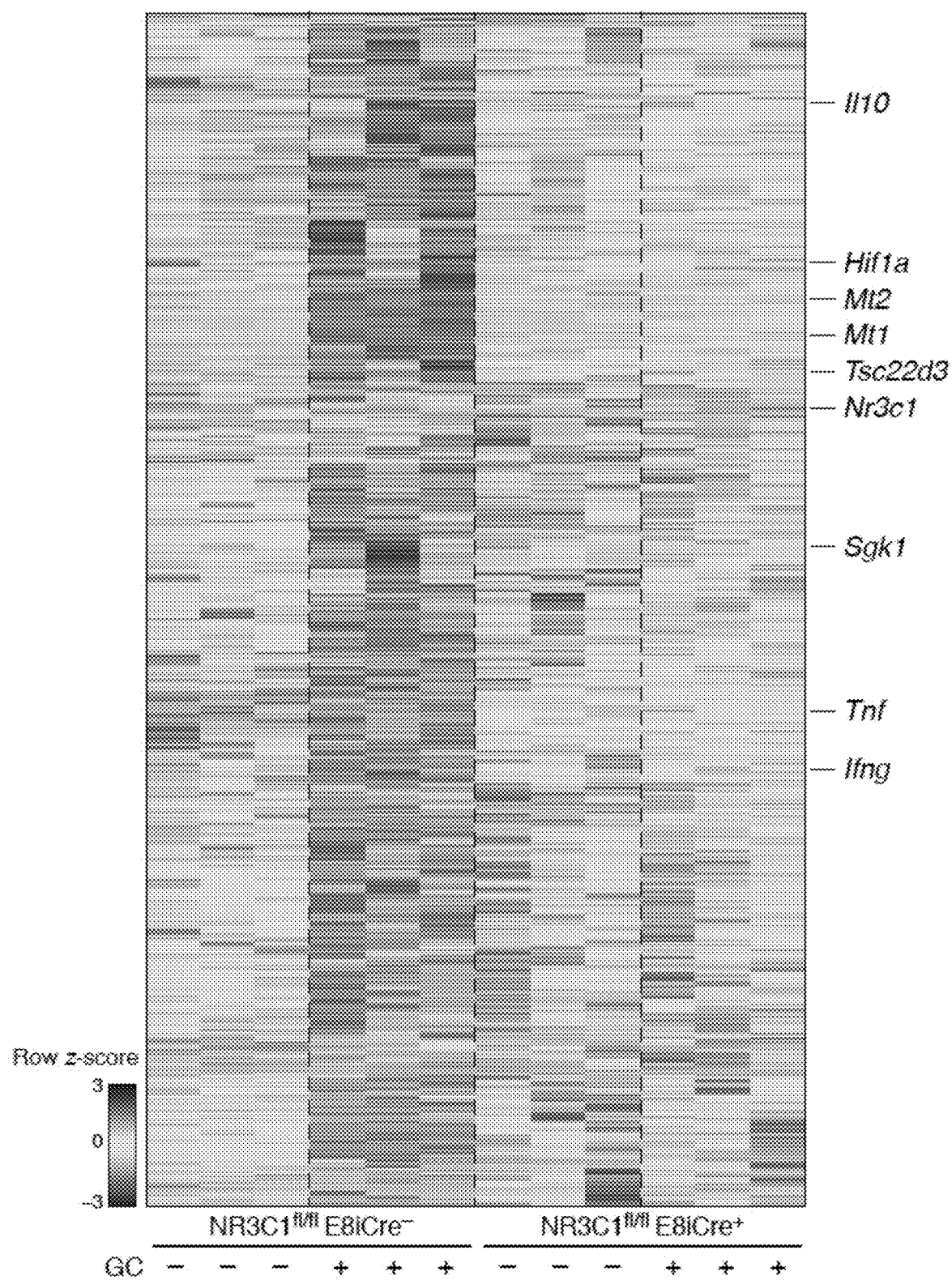

The observed effects of glucocorticoid on CD8+ T cells depended on Nr3c1. Applicants examined expression of Nr3c2, which encodes the mineralocorticoid receptor (MR) that shares high structural homology with GR and can bind glucocorticoids with high affinity (Arriza et al., 1987). Applicants found that Nr3c2 is not expressed by wild type CD4+ and CD8+ T cells or in CD8+ T cells from mice that lack Nr3c1 expression specifically in mature CD8+ T cells (E8i-Cre×Nr3c1fl/fl) (FIG. 9a). Further, comparison of the RNA profiles of wild type and E8i-Cre×Nr3c1fl/fl CD8+ T cells stimulated with or without glucocorticoid showed distinct glucocorticoid-induced changes in wild type but not E8i-Cre×Nr3c1fl/fl CD8+ T cells, indicating that glucocorticoid-induced transcription in CD8+ T cells was Nr3c1 dependent (FIG. 9b). Thus, repeated stimulation in the presence of active glucocorticoid signaling dramatically influenced the effector differentiation of CD8+ T cells, resulting in cells that exhibited features shared with dysfunctional T cells, including up-regulation of multiple checkpoint receptors, dampened pro-inflammatory cytokine production, and increased IL-10 production.

Example 3—Glucocorticoid Signaling in CD8+ TILs Promotes Tumor Progression

Figure 10A:
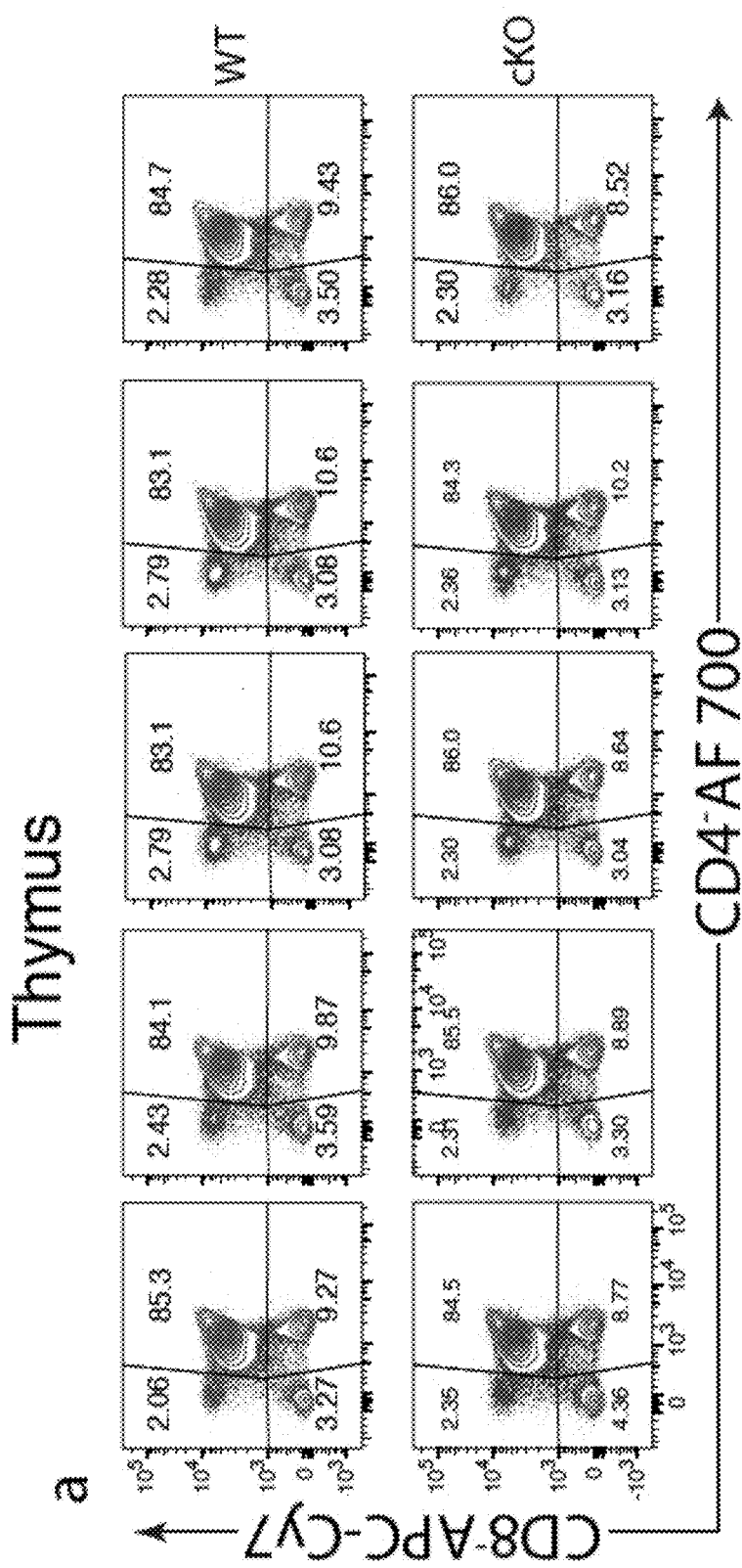
FIGS. 10A-10E—Deletion of Nr3c1 using E8iCre does not affect the development of T cells. Frequency of T cells in the thymus (FIG. 10A) and spleen (FIG. 10B) of Nr3c11$^{fl/fl}$ (WT) and Nr3c1$^{fl/fl}$E8iCre$^+$ (Dodd et al.) mice.
Figure 10B:
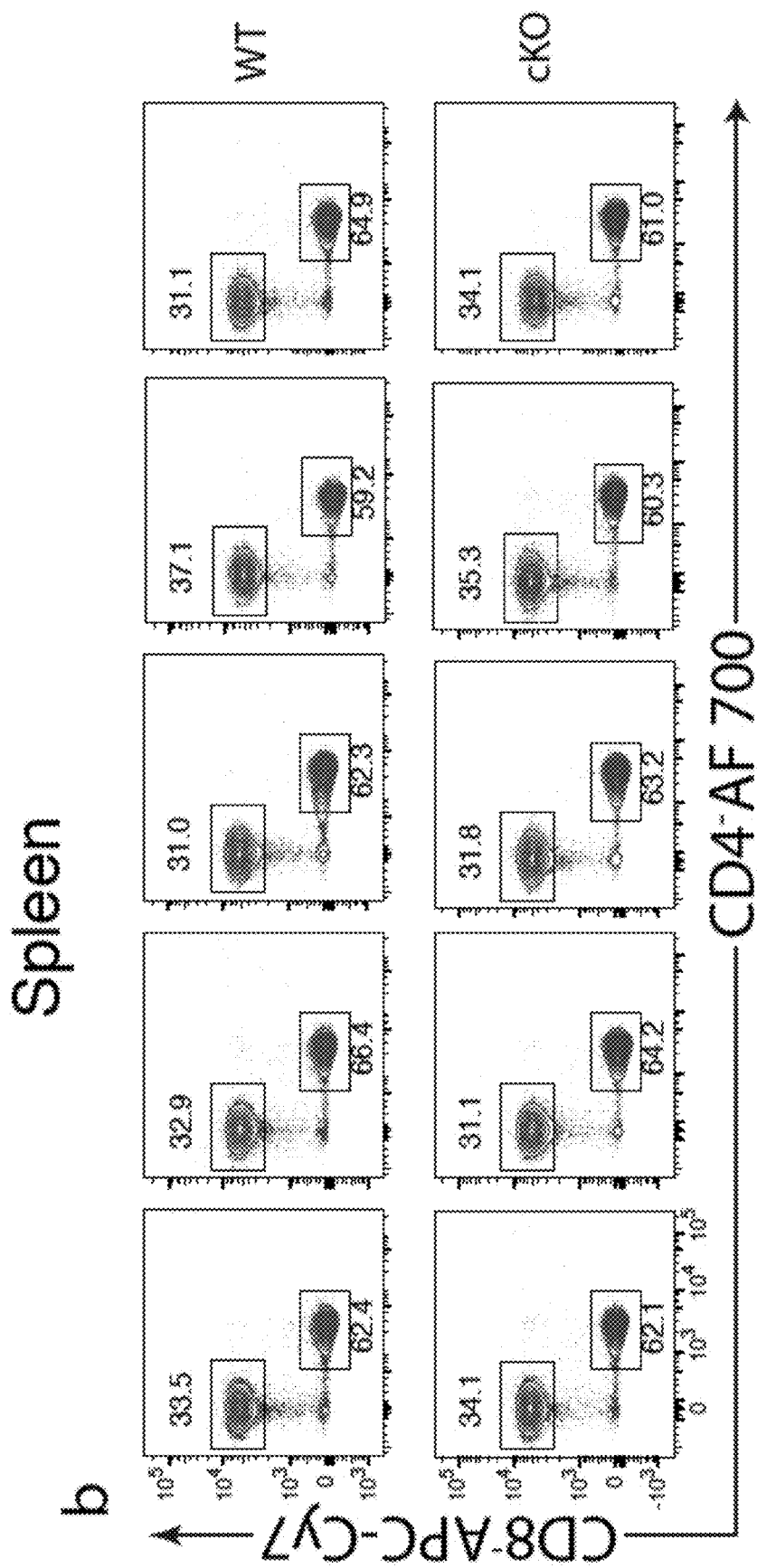
Figure 10C:
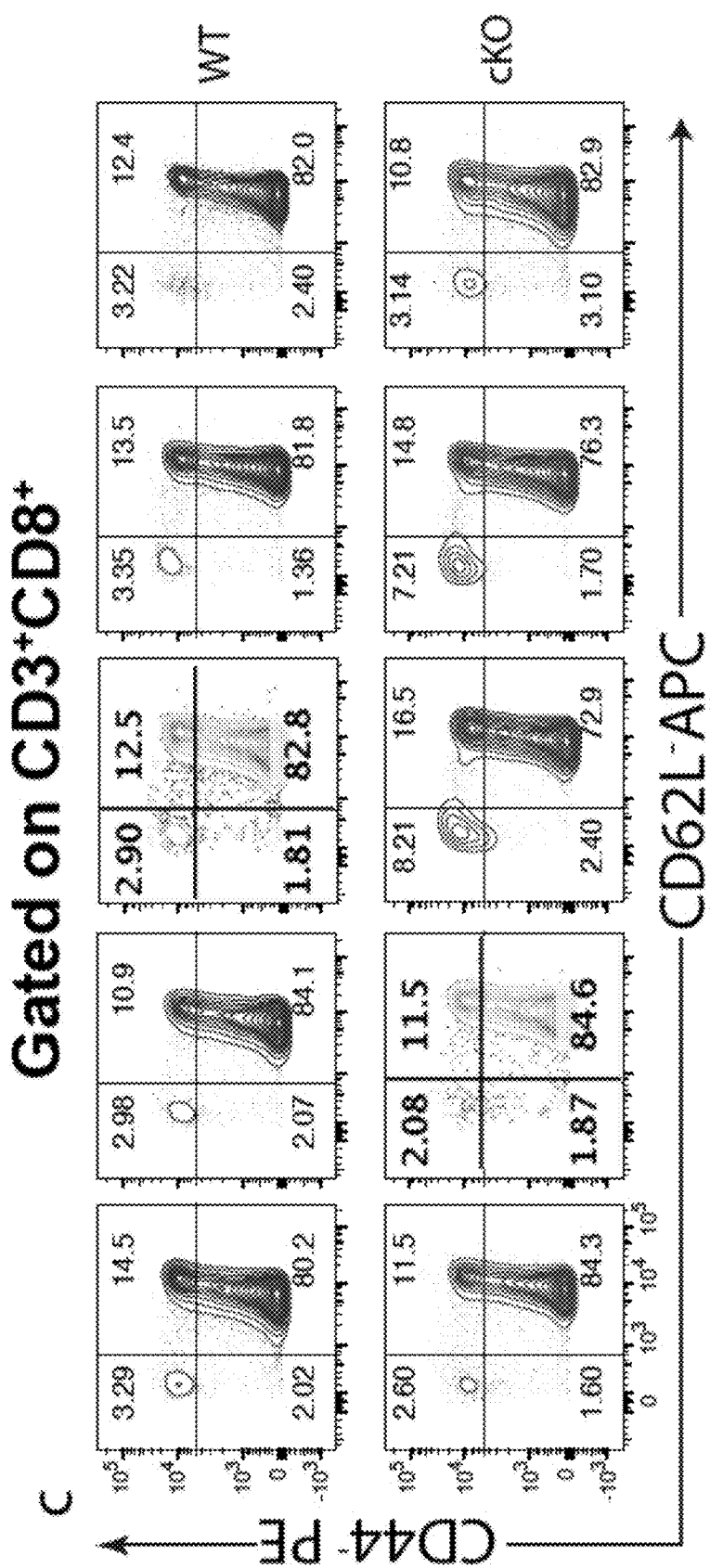
Figure 10D:
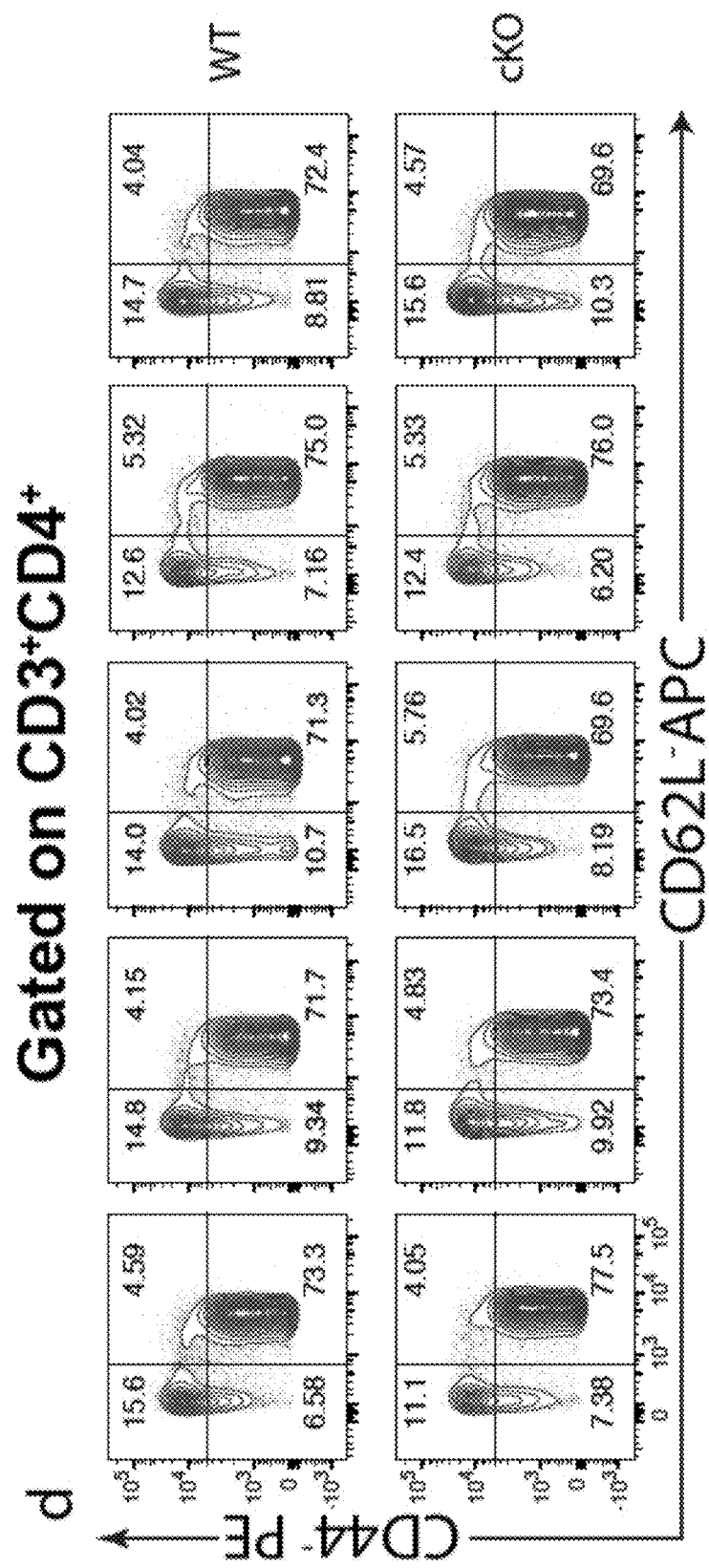
Figure 10E:
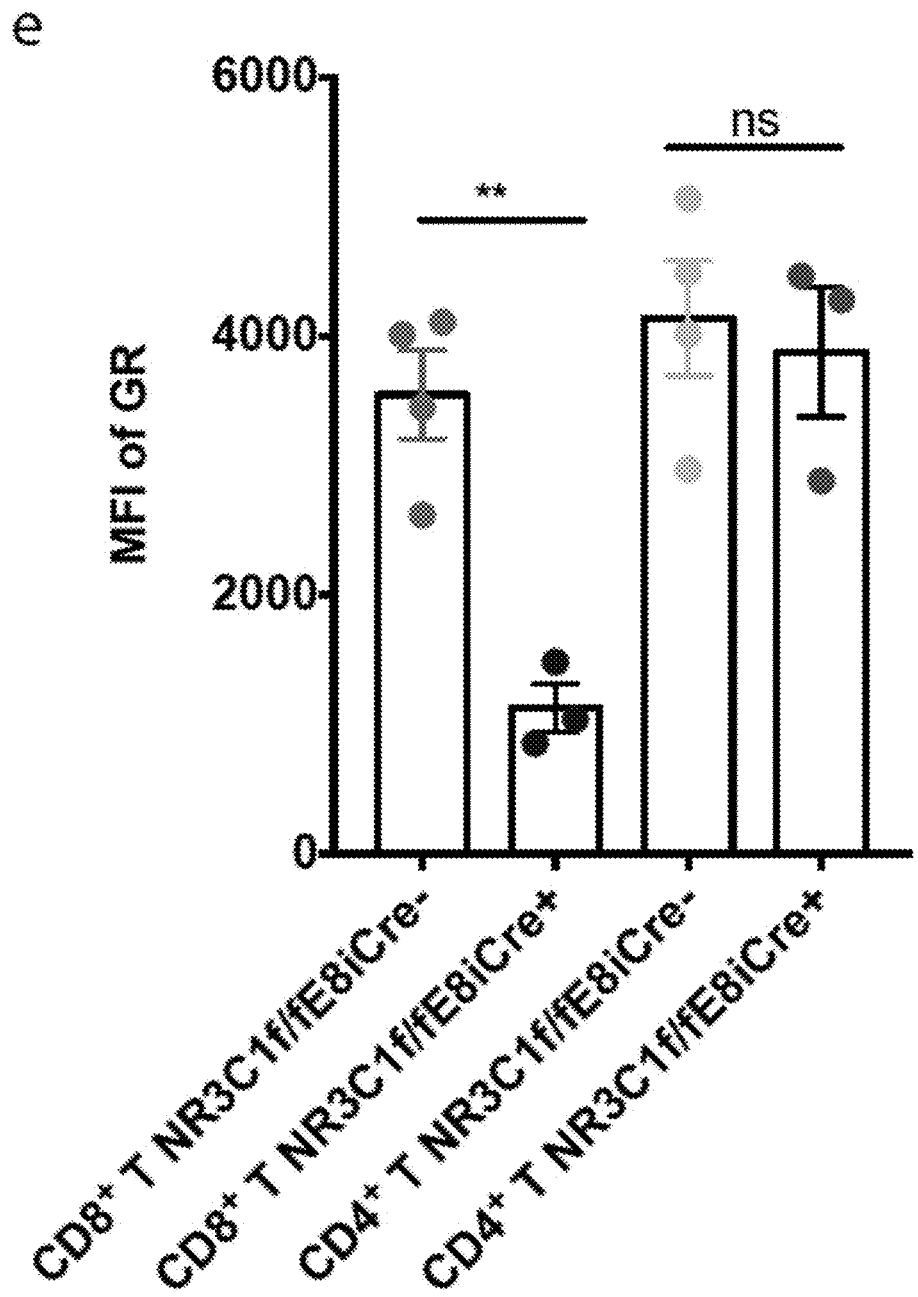

Applicants next tested whether glucocorticoid signaling impacts the functional state of CD8+ TILs in vivo. For this, Applicants employed E8i-Cre×Nr3c1$^{fl/fl}$ mice. Examination of T cell development and the steady state peripheral immune compartment of these mice showed no gross differences compared to wild type (Nr3c1$^{fl/fl}$) littermate controls (FIG. 10a-d). Further, Applicants confirmed that the deletion of N3rc1 was specific to CD8+ T cells (FIG. 10e). Applicants implanted either ovalbumin expressing MC38 colon carcinoma (MC38-Ova) or B16F10 melanoma cells into wild type and E8i-Cre×Nr3c1$^{fl/fl}$ mice and found that E8i-Cre×Nr3c1$^{fl/fl}$ mice exhibited improved tumor growth control in both models (FIG. 3a and FIG. 11a), indicating that the effect of glucocorticoid signaling in CD8+ T cells was conserved across tumor types.

Glucocorticoid signaling impacted the functional state of CD8+ TILs in vivo, based on the difference in several key parameters between E8i-Cre×Nr3c1$^{fl/fl}$ and wild type MC38-Ova-bearing mice. First, not only was there a dramatic reduction in the frequency of CD8+ TILs co-expressing PD-1, Tim-3, Lag-3, and Tigit in CD8+ TILs from E8i-Cre× Nr3 c1$^{fl/fl}$ mice (FIG. 3b), but also the expression level of each of these checkpoint receptors was significantly reduced (FIG. 11b). Of note, Tigit expression was down-regulated in CD8+ TILs from E8i-Cre×Nr3c11$^{fl/fl}$ mice (FIG. 3b and FIG. 11b), in contrast to the in vitro observations where Tigit expression was not induced by GR stimulation (FIG. 2b). Second, CD8+ TILs from E8i-Cre×Nr3c1$^{fl/fl}$ mice had enhanced responses to tumor-antigen (OVA$_{257-264}$) as well as polyclonal stimulation, producing more IL-2, TNF-α, and IFN-γ (FIG. 3c and FIG. 11c). Indeed, the CD8+ TILs from E8i-Cre×Nr3c1$^{fl/fl}$ mice were more polyfunctional in terms of pro-inflammatory cytokine production (FIG. 11d). Furthermore, the few Tim-3+PD-1+CD8+ TILs in E8i-Cre× Nr3c1$^{fl/fl}$ mice exhibited increased pro-inflammatory cytokine production in response to OVA$_{257-264}$ stimulation (FIG. 11e), in contrast to their typical severe dysfunctional phenotype observed in wild type mice. Third, the CD8+ TILs from E8i-Cre×Nr3c1$^{fl/fl}$ mice produced lower amounts of the immune-suppressive cytokine IL10 (FIG. 3d and FIG. 11f). Fourth, CD8+ TILs from E8i-Cre×Nr3c1$^{fl/fl}$ mice had higher cytotoxic capacity, as shown by the increased frequency of Granzyme B+CD107a+ cells upon OVA$_{257-264}$ stimulation (FIG. 3e). Finally, E8i-Cre×Nr3c1$^{fl/fl}$ mice harbored more H-2K$^b$/OVA$_{257-264}$ dextramer+ CD8+ TILs (FIG. 3f). Applicants analyzed the proliferation status and the absolute number of the CD8+ TILs in wild-type and E8i-Cre× Nr3c1$^{fl/fl}$ mice and observed no significant differences (FIG. 11g,h). Notably, checkpoint receptor expression on CD4+ TILs in E8i-Cre×Nr3c1$^{fl/fl}$ mice was not significantly different from that of wild type CD4+ TILs, indicating that the regulation of checkpoint receptors in CD8+ TILs was cell-intrinsic and not due to a secondary effect of loss of GR in CD8+ TILs (FIG. 11i,j). Finally, in human colon adenocarcinoma from TCGA (cancergenome.nih.gov/), Applicants found (using TIMER (Li et al., 2016)) that NR3C1 mRNA levels positively correlated with HAVCR2 (Tim-3), PDCD1 (PD-1), LAG3, TIGIT and IL10 mRNA levels (FIG. 3g). Collectively, these data supported that glucocorticoid signaling is active in the TME of both murine and human tumors and functions to promote checkpoint receptor expression and dampen the effector function of CD8+ TILs.

Example 4—the Glucocorticoid Receptor Transactivates the Expression of Checkpoint Receptors and IL-10

Figure 12E:
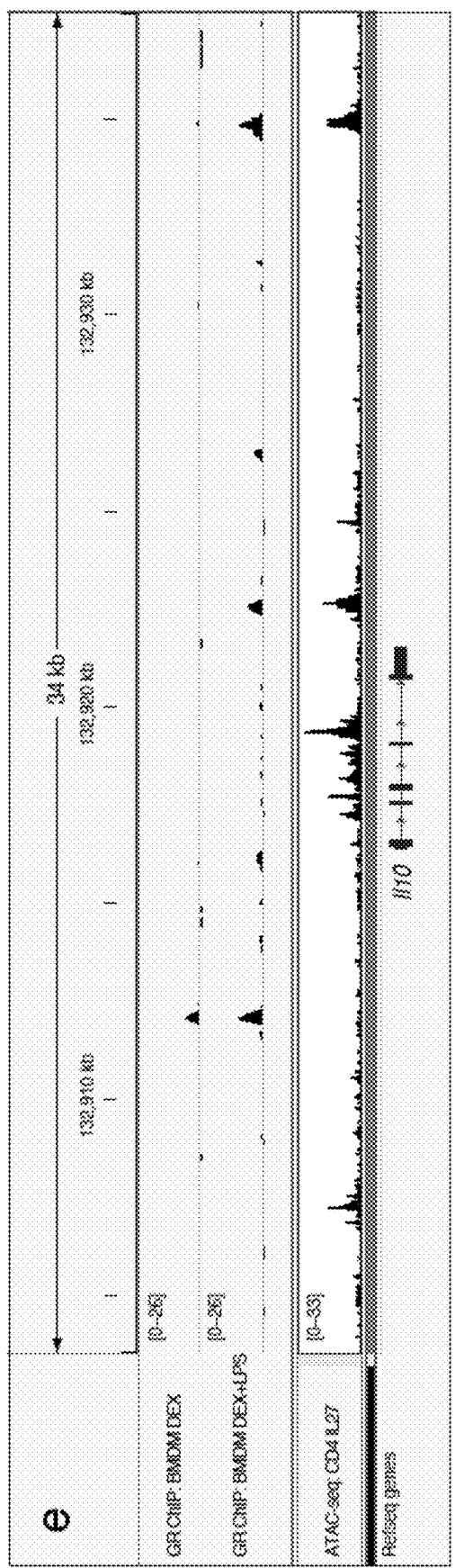

Applicants next tested if the GR directly regulates the expression of checkpoint receptor genes and IL-10. First, Applicants analyzed GR-binding peaks in the loci of Havcr2 (Tim-3), Pdcd1 (PD-1), Lag3, Tigit, and IL10 in publicly available ChIP-seq data (Oh et al., 2017) from bone marrow-derived macrophages (BMDMs) (FIG. 12). Applicants found GR-binding peaks in the loci of Havcr2, Lag3, and IL10 but not Pdcd1 or Tigit, reflecting the lack of PD-1 and Tigit expression in BMDMs. Applicants further found that some of the GR binding peaks in the Havcr2, Lag3, and IL10 loci overlapped regions of accessible chromatin (based on ATAC-seq) in IL-27-stimulated T cells (Karwacz et al., 2017), which are known to express high levels of these molecules (Chihara et al., 2018) (FIG. 12). Applicants therefore tested the effect of GR binding to the cis-regulatory elements in these peaks in the Havcr2, Pdcd1, Lag3, and Tigit loci using luciferase reporter assays. For IL10, Applicants utilized luciferase reporters of a previously established enhancer element of Il10—HSS+2.98 as well as the proximal promoter (−1.5 kb)(Karwacz et al., 2017). Applicants transfected the different luciferase reporter constructs along with a Nr3c1 expressing vector or empty vector into 293T cells and treated the cells with glucocorticoid to assay the transactivation capability of the GR. In line with the observations in glucocorticoid treated CD8+ T cells (FIG. 2), the GR potently transactivated Tim-3, PD-1, Lag-3, and IL-10 expression (FIG. 4). Tigit was also induced but to a much lower degree (FIG. 4d).

Figure 13D:
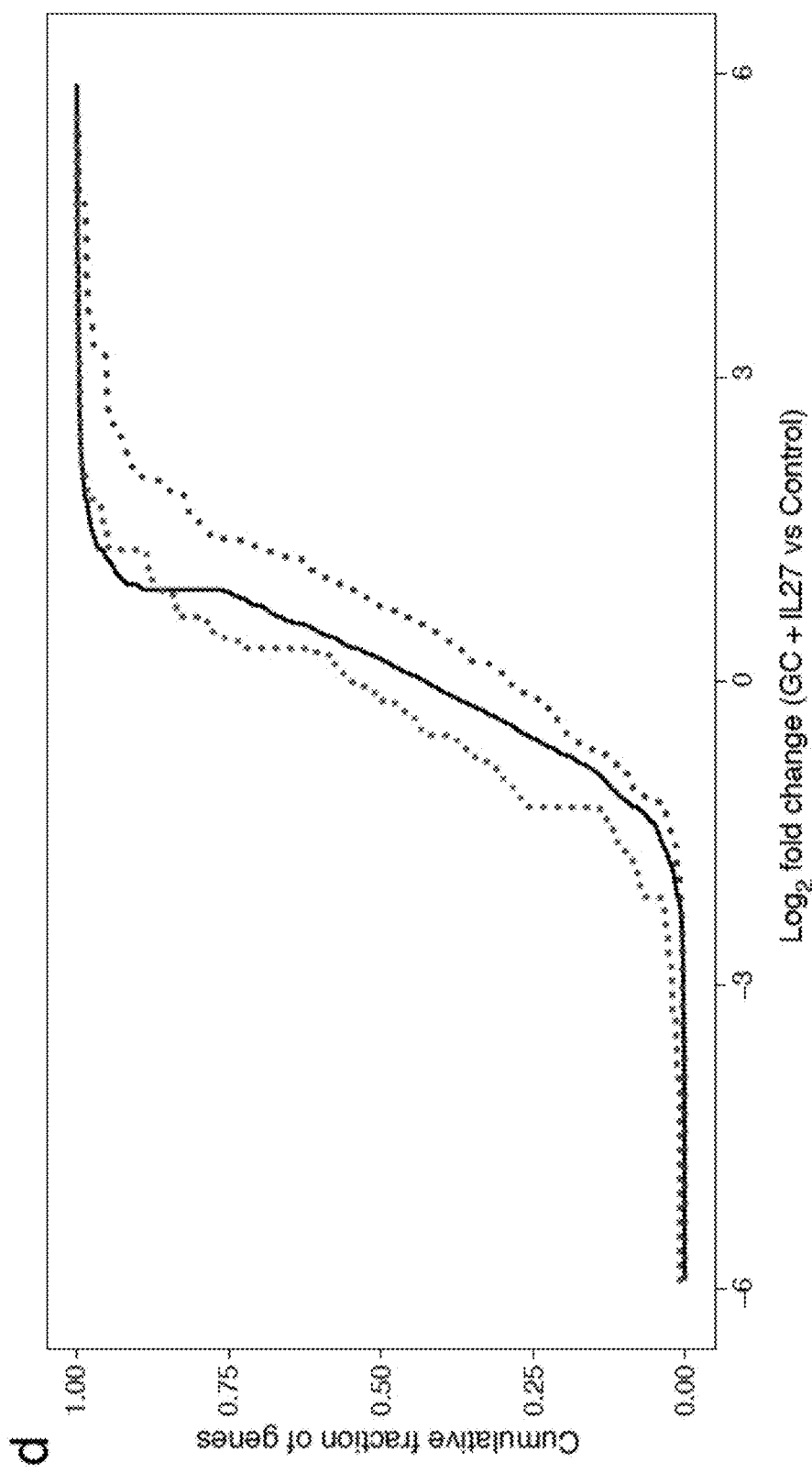

Example 5—Glucocorticoid and IL-27 Signaling Co-Operate to Promote CD8+ T Cell Dysfunction The transactivation of multiple checkpoint receptors and IL-10 by GR and the effect of glucocorticoid signaling on the effector responses of CD8+ TILs were reminiscent of the recent observation that IL-27 regulates a gene module that includes checkpoint receptors (Tim-3, Lag3, Tigit) and IL-10 and suppresses the responses of CD8+ TILs (Chihara et al., 2018; Zhu et al., 2015). Interestingly, glucocorticoids have been shown to work in concert with TFs such as the STAT family (Petta et al., 2016) and STAT1 and STAT3 are downstream of IL-27. These observations prompted Applicants to address the relationship of the glucocorticoid and IL-27 pathways. Applicants collected and analyzed the RNA-Seq profiles from cells treated with glucocorticoid, IL-27, or both. Unsupervised principle component analysis (PCA) showed that glucocorticoid and IL-27 each induced a distinct transcriptional profile with glucocorticoid+IL-27 treatment inducing the largest transcriptional change relative to control (FIGS. 5a and b and FIG. 13a). Examination of differentially expressed genes across all three conditions relative to control showed some common as well as some distinct genes (FIG. 13b). 6,812 genes were differentially expressed (DE) between glucocorticoid+IL-27 compared to control out of which 3,417 (50%) showed non-additive regulation (FIG. 5c and Table 1). Among the genes that were highly up-regulated by glucocorticoid+IL-27 compared to glucocorticoid or IL-27 alone were Prdm1 and Nfil3, which encode TFs with known roles in promoting or maintaining T cell dysfunction (Chihara et al., 2018; Rutishauser et al., 2009; Shin et al., 2009; Zhu et al., 2015). In contrast, Tcf7, which encodes TCF-1, a TF important for maintaining stem-like T cells critical for the response to checkpoint blockade and which shows antagonism with Tim-3 expression (Im et al., 2016; Kurtulus et al., 2019; Miller et al., 2019; Siddiqui et al., 2019), was down-regulated by glucocorticoid+IL-27. Using qPCR, Applicants confirmed that Prdm1 and Nfil3 expression was most highly up-regulated by treatment with glucocorticoid+IL-27 compared to glucocorticoid or IL-27 alone (FIG. 13c). Tcf7 was dramatically reduced by both glucocorticoid or IL27 alone and treatment with glucocorticoid+IL-27 showed a trend of further reduction (FIG. 13c). These observations indicated that glucocorticoid+IL-27 signaling may co-operate to promote gene programs associated with T cell dysfunction in CD8$^+$ T cells. Accordingly, Applicants tested all of the differentially expressed genes induced by glucocorticoid+IL-27 for overlap with the T cell dysfunction signature. 1,022 out of 6,812 DE genes overlapped with the dysfunction signature (Table 3). The genes down-regulated by glucocorticoid+IL-27 significantly overlapped with genes expressed in CD8$^+$ TIM-3$^-$PD-1$^-$ TILs (p=2.1×10$^{-10}$, Mean-rank Gene Set Test) and the genes up-regulated by glucocorticoid+IL-27 showed significant overlap with the genes expressed in severely dysfunctional CD8$^+$Tim-3$^+$PD-1$^+$ TILs (p=4.3×10$^{-5}$, Mean-rank Gene Set Test) (FIG. 5d and FIG. 13d).

To determine the functional consequences of the glucocorticoid+IL-27 signaling pathways on T cell dysfunction in vivo, Applicants crossed E8i-Cre$^+$Nr3c1$^{fl/fl}$ mice with WSX1$^{-/-}$ (IL27ra$^{-/-}$) mice to generate mice that can be used as a source of double knock-out (DKO) CD8$^+$ T cells, lacking both the glucocorticoid and IL-27 signaling pathways. Applicants isolated CD8$^+$ T cells from wild type, E8i-Cre$^+$Nr3c1$^{fl/fl}$, WSX-1$^{-/-}$, or DKO mice and transferred them along with wild type CD4$^+$ T cells into Rag-1$^{-/-}$ mice followed by implant of MC38-Ova colon carcinoma cells. In line with the previous findings (FIG. 3a and FIG. 11a) (Zhu et al., 2015), absence of either glucocorticoid or IL-27 signaling alone individually conferred tumor growth control; however, absence of both of pathways together led to significantly greater tumor growth inhibition (FIG. 5e).

To examine the relevance of glucocorticoid+IL-27 signaling in human disease, Applicants scored the glucocorticoid+IL-27 signature in the single-cell data of TILs from melanoma patients pre- and post-treatment with checkpoint blockade (Sade-Feldman et al., 2018). Applicants found that the glucocorticoid+IL-27 signature scored highly in CD8$^+$ TILs that also scored highly for the T cell dysfunction signature (FIG. 5f, panels V and VI). Most importantly, Applicants found that high expression of the glucocorticoid+ IL-27 signature correlated with non-responsiveness to checkpoint inhibitor in CD8$^+$ TILs in both pre- (p=4.048× 10$^{-9}$) and post-(p=5.028×10$^{-05}$) treatment samples (FIG. 5f). Altogether, the data indicated that glucocorticoid and IL-27 signaling combined in the TME to promote CD8$^+$T cell dysfunction and dampen anti-tumor immunity.

Example 6—Myeloid Cells are the Primary Sources of Glucocorticoid and IL-27 in the TME Applicants next asked whether local sources in the TME provided endogenous glucocorticoid and IL-27 signals. Although steroids are mainly synthesized in the adrenal cortex, it has been suggested that tumor cells are capable of extra-adrenal steroidogenesis (Sidler et al., 2011). To test whether glucocorticoid was indeed produced in tumor tissue, Applicants measured corticosterone production in the spleen and tumor tissue from MC38-Ova tumor-bearing mice. Applicants found that corticosterone was produced at high levels in the tumor relative to the spleen from tumor-bearing mice while the levels of corticosterone in the spleen of tumor-bearing and non-tumor bearing mice were similar (FIG. 6a). Further, Applicants cultured tumor explants in the presence or absence of Metyrapone, an inhibitor of glucocorticoid synthesis, and observed reduced levels of corticosterone in the presence of the inhibitor (FIG. 14a). Together these data indicated local glucocorticoid production in the TME. To test the impact of this on tumor growth, Applicants administered Metyrapone to MC38-Ova tumor-bearing mice by intra-tumoral injection and observed dramatic tumor growth inhibition in the treated mice (FIG. 6b).

Steroids are produced by the enzymatic breakdown of cholesterol, where cytochrome P450 cholesterol side-chain cleavage enzyme (Cyp11a1 or P450scc) catalyzes the first and the rate-limiting step that catalyzes the breakdown of cholesterol to pregnenolone, the precursor of all steroid hormones (Payne and Hales, 2004). Thus, to identify which cell types were responsible for steroid production in the TME, Applicants first examined the expression of Cyp11a1. Applicants examined the MC38-Ova tumor cell line and found that in vitro cultured MC38-Ova cells did not express Cyp11a1 (FIG. 6c). To test if factors present in the TME could induce expression of Cyp11a1 in MC38-Ova tumor cells, Applicants implanted MC38-Ova-GFP cells in mice and examined Cyp11a1 expression in tumor cells (CD45$^-$ GFP$^+$). Applicants did not detect Cyp11a1 expression in the isolated tumor cells (FIG. 6c). Examination of other cells in the TME showed that cancer-associated fibroblasts (CAFs) (CD45$^-$GFP$^-$PDGFRa$^+$), tumor-associated dendritic cells (TADCs), and T cells (mostly CD4$^+$ T cells) expressed Cyp11a1 but at much lower levels compared to tumor-associated monocyte/macrophages (FIG. 6c). Applicants further examined the expression of the other enzymes involved in glucocorticoid biosynthesis (StAR, Cyp21a1, Cyp17a1, Cyp11b1, Hsd3b1) in monocytes/macrophages from MC38-Ova tumors and found that they expressed all enzymes to varying degrees with the exception of Hsd3b1, which was difficult to detect (FIG. 14b). To confirm that tumor-associated monocyte/macrophages could indeed produce glucocorticoid, Applicants measured their corticosterone production after culture in the presence or absence of Metyrapone. Applicants found that the cells produced corticosterone and this was dramatically reduced by the addition of Metyrapone (FIG. 14c). Together these data indicated that monocyte/macrophages, which are present from early time points during tumor progression and comprise more than 50% of CD45$^+$ cells in MC38-Ova tumors, are a major source of glucocorticoid in the TME. Conversely, Applicants found that TADCs were the main source of IL-27, as they expressed high levels of both p28 and EBi3 (FIG. 6d). Therefore, different cell types within the TME produced glucocorticoid and IL-27.

To study the relevance of steroid production from monocyte/macrophages on tumor growth, Applicants implanted tumors in LysMCre$^+$ x Cyp11a1$^{fl/fl}$ mice and observed significant tumor growth control (FIG. 6e). Lastly, Applicants examined the relevance of steroid abundance in the TME in human cancers. Using TIMER, Applicants found that low Cyp11a1 mRNA levels were associated with a substantial survival benefit in patients with colon adenocarcinoma and stomach adenocarcinoma (FIG. 6f). Collectively, the data demonstrate that endogenous glucocorticoid signaling co-operates with IL-27 signaling to form an immunoregulatory circuit that dampens effective anti-tumor immunity by promoting T cell dysfunction in the TME.

Example 7—Discussion

Glucocorticoids, steroid hormones, have been shown to suppress immune responses by interfering with AP-1- and NF-κB-mediated induction of pro-inflammatory cytokines (Auphan et al., 1995; Jonat et al., 1990; Rhen and Cidlowski, 2005; Scheinman et al., 1995; Smoak and Cidlowski, 2004; Yang-Yen et al., 1990). Here, Applicants identify a novel molecular mechanism by which glucocorticoids suppress effector T cell responses through the transactivation of multiple checkpoint receptors (Tim-3, PD-1, and Lag3) together with IL-10. Glucocorticoids can be produced in the TME and combine with the immune suppressive cytokine IL-27 to form an immunoregulatory circuit that promotes gene programs associated with CD8$^+$ T cell dysfunction. The relevance of glucocorticoid signaling pathways to human cancer is supported by the observation that increased steroidogenic capacity in the TME correlated with decreased survival and that high expression of the glucocorticoid+IL-27 signature in the CD8$^+$ TILs of melanoma patients correlated with failure to respond to checkpoint blockade therapy (Sade-Feldman et al., 2018).

The observation that Prdm1 and Nfil3, TFs known to be involved in T cell dysfunction (Chihara et al., 2018; Rutishauser et al., 2009; Shin et al., 2009; Zhu et al., 2015), are most highly induced by the combination of glucocorticoid and IL-27 provides a potential mechanism for the co-operativity of these two pathways in the promotion of T cell dysfunction. Moreover, glucocorticoid+IL-27 strongly reduced the expression of Tcf7, which encodes TCF-1, a TF involved in maintenance of stem-like memory precursor CD8$^+$ TILs that are required for the success of checkpoint blockade therapy (Im et al., 2016; Kurtulus et al., 2019; Miller et al., 2019; Siddiqui et al., 2019). Thus, glucocorticoid+IL-27 signaling may subvert anti-tumor immunity by two mechanisms, promoting T cell dysfunction and decreasing stemness and memory potential in CD8$^+$ TILs.

The GR has also been shown to act via chromatin remodeling (Jubb et al., 2017). Therefore, it is possible that glucocorticoid signaling may drive epigenetic changes that together with IL-27 set the stage for CD8$^+$ T cell dysfunction. The contributions of glucocorticoid and IL-27 signaling to the distinct epigenetic changes that have been described in dysfunctional CD8$^+$ T cells (Pauken et al., 2016; Philip et al., 2017; Sen et al., 2016) remains to be determined.

The data demonstrate that activation of glucocorticoid and IL-27 signaling promotes the dysfunction gene program in CD8$^+$ TILs. However, a previous study implicated the GR in the maintenance of memory-precursor CD8$^+$ T cells in the context of bacterial infection (Yu et al., 2017). Thus, the effect of glucocorticoid signaling favoring differentiation into memory or dysfunctional CD8$^+$ T cells may be context dependent. It is also possible that the GR may partner with other signaling pathways and TFs depending on the tissue environment to achieve different effects. Further molecular investigation will help delineate the mechanisms operative in different contexts.

Using conditional knockout mice and in vitro studies Applicants provide insight into the CD8$^+$ T cell intrinsic effects of glucocorticoid signaling. However, glucocorticoid signaling may also act intrinsically in other immune and non-immune cell populations in the TME. Indeed, glucocorticoids have been implicated in increasing the frequency of T$_{reg}$ cells in both humans and mice (Chen et al., 2006; Hu et al., 2012; Ling et al., 2007; Suarez et al., 2006). In myeloid cells, glucocorticoids have been implicated in modulating both antigen presentation and inflammatory cytokine production by DCs (Piemonti et al., 1999) with consequences for the efficacy of anticancer therapies (Yang et al., 2019). Further, in line with the data, a recent study suggested that endogenous glucocorticoids regulate the expression of PD-1 on NK cells in the context of viral infection (Quatrini et al., 2018). Whether these effects of glucocorticoid are due to cell intrinsic or extrinsic effects will require detailed molecular dissection using cell type specific knockouts.

The observations that extra-adrenal glucocorticoid biogenesis can occur in tumor tissue and that its ablation has important consequences for tumor growth underscore the need to identify the signals that promote steroidogenesis in cells within the TME. This study highlights monocyte/macrophages lineage cells as one of the major sources of glucocorticoid in colon carcinomas. Whether other cell types are the predominant source of extra-adrenal steroid in other cancer types remains to be determined. Further, inhibitors of the enzymes of steroid biogenesis are used in the clinical management of cancers that are predominantly driven by steroid hormone signaling, such as breast and prostate cancer. The data indicate the potential of such drugs in a broader spectrum of cancer types.

This study focuses on the effects of endogenous glucocorticoid in the TME; however, exogenous glucocorticoid is often administered to cancer patients. In patients with glioblastoma, dexamethasone is given to prevent cerebral edema. Whether this negatively impacts on the ability of these patients to respond to checkpoint blockade immunotherapy is not known. Glucocorticoids are also used as first-line agents for managing immune-related adverse events (IRAEs) (Kumar et al., 2017) associated with checkpoint blockade immunotherapy. Although initial studies indicated that glucocorticoids can be used to treat IRAEs without negative impact on therapeutic outcome (Beck et al., 2006; Downey et al., 2007; Johnson et al., 2015; Weber et al., 2008), a recent study comparing patients who received checkpoint blockade and developed a severe IRAE followed by treatment with either low- or high-dose glucocorticoids showed that patients who received high-dose exogenous glucocorticoid had both reduced survival and time to treatment failure (Faje et al., 2018). Further, another recent study showed that low-affinity memory T cells are inhibited by corticosterone and that overall survival (OS) was reduced in melanoma patients who received corticosteroids along with ICB (Tokunaga et al., 2019). These observations highlight the need to understand the effects of low- versus high-dose administration of exogenous glucocorticoids and how these relate to the effects of endogenous glucocorticoid. Notwithstanding these considerations, Applicants have observed that patients who fail to respond to checkpoint blockade (Sade-Feldman et al., 2018) have higher expression of the glucocorticoid+IL-27 signature. Thus, having a better understanding of the mechanisms downstream of glucocorticoids and IL-27 could inform the clinical development of more precise therapies for modulating immune responses in the clinic, the relevance of which extends beyond cancer.

Figure 26:
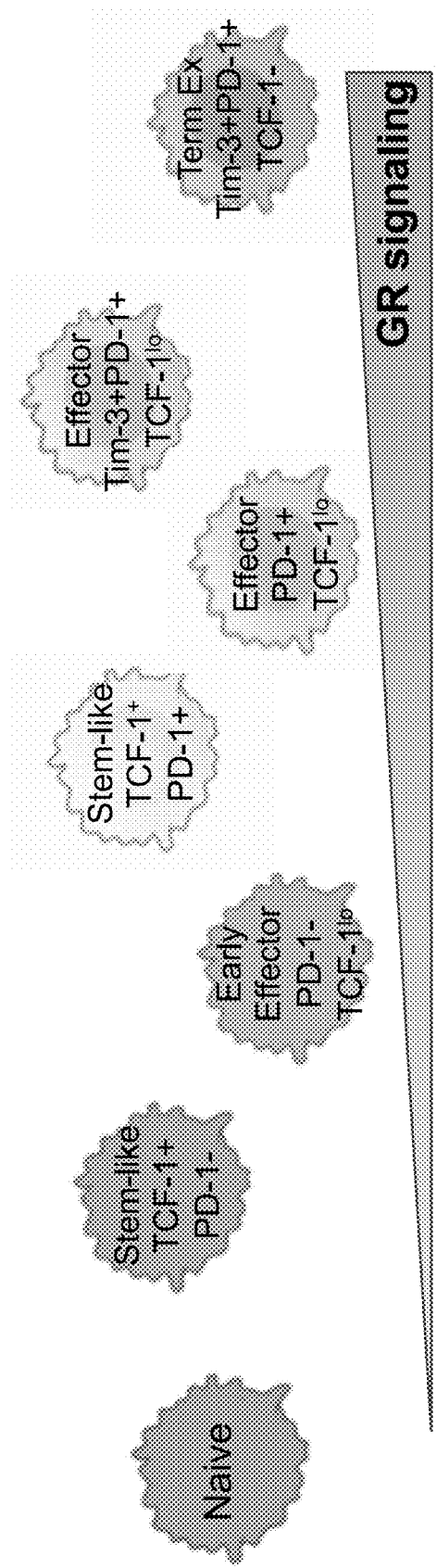
FIG. 26—Diagram showing a gradient of increasing GR expression across effector and terminally dysfunctional CD8+ TILs.
Figure 27:
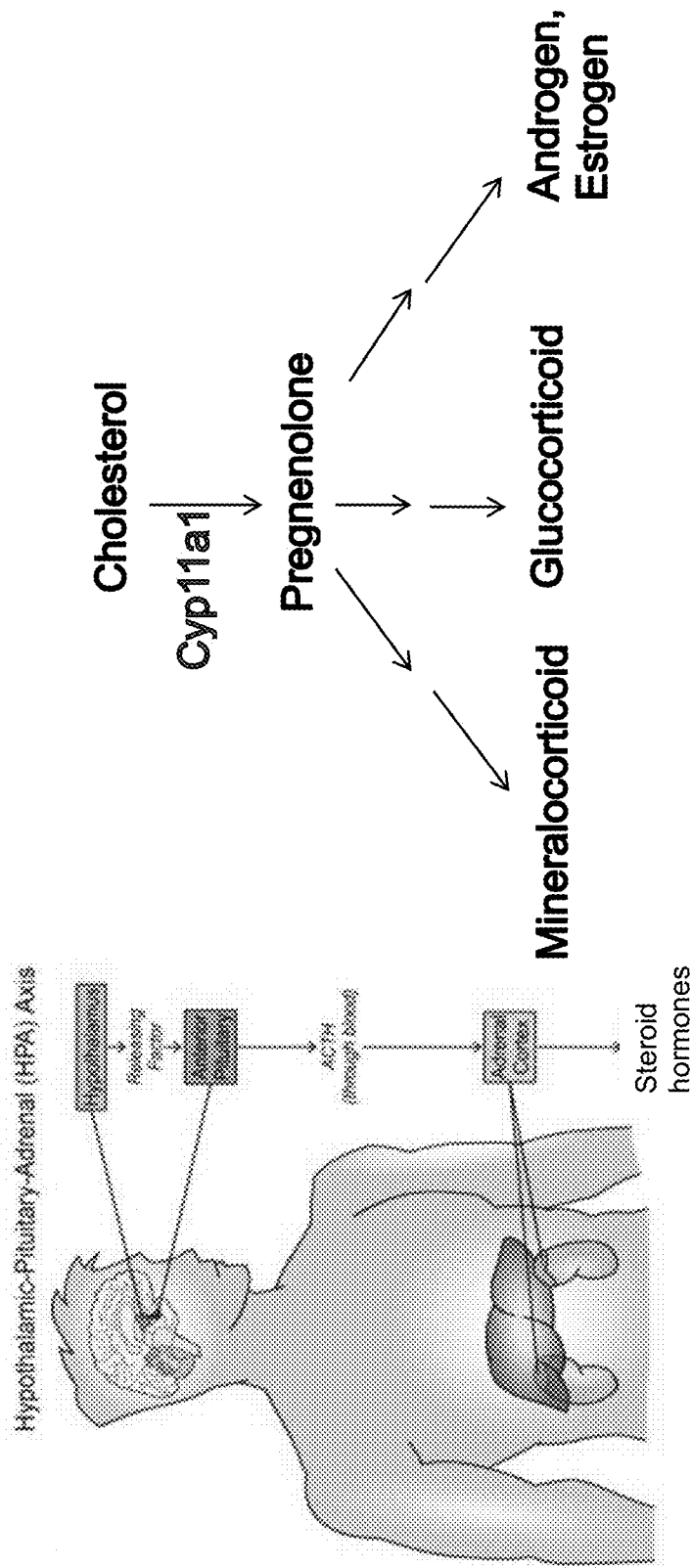
FIG. 27—Diagram showing steroid hormone biosynthesis and a key enzyme in the pathway (Cyp11a1).

Example 8—Steroid Hormone Signaling Alters $CD8^+$ T Cell Differentiation in the Tumor Microenvironment Applicants identified that the glucocorticoid receptor (GR) has increased expression as dysfunction of T cells increases (FIG. 15, 16). CD8 T cells that are specific for tumor antigens also have increased GR (FIG. 16). Applicants identified that there is a gradient of increasing GR expression across effector and terminally dysfunctional $CD8^+$ TILs (FIG. 26).

Figure 17:
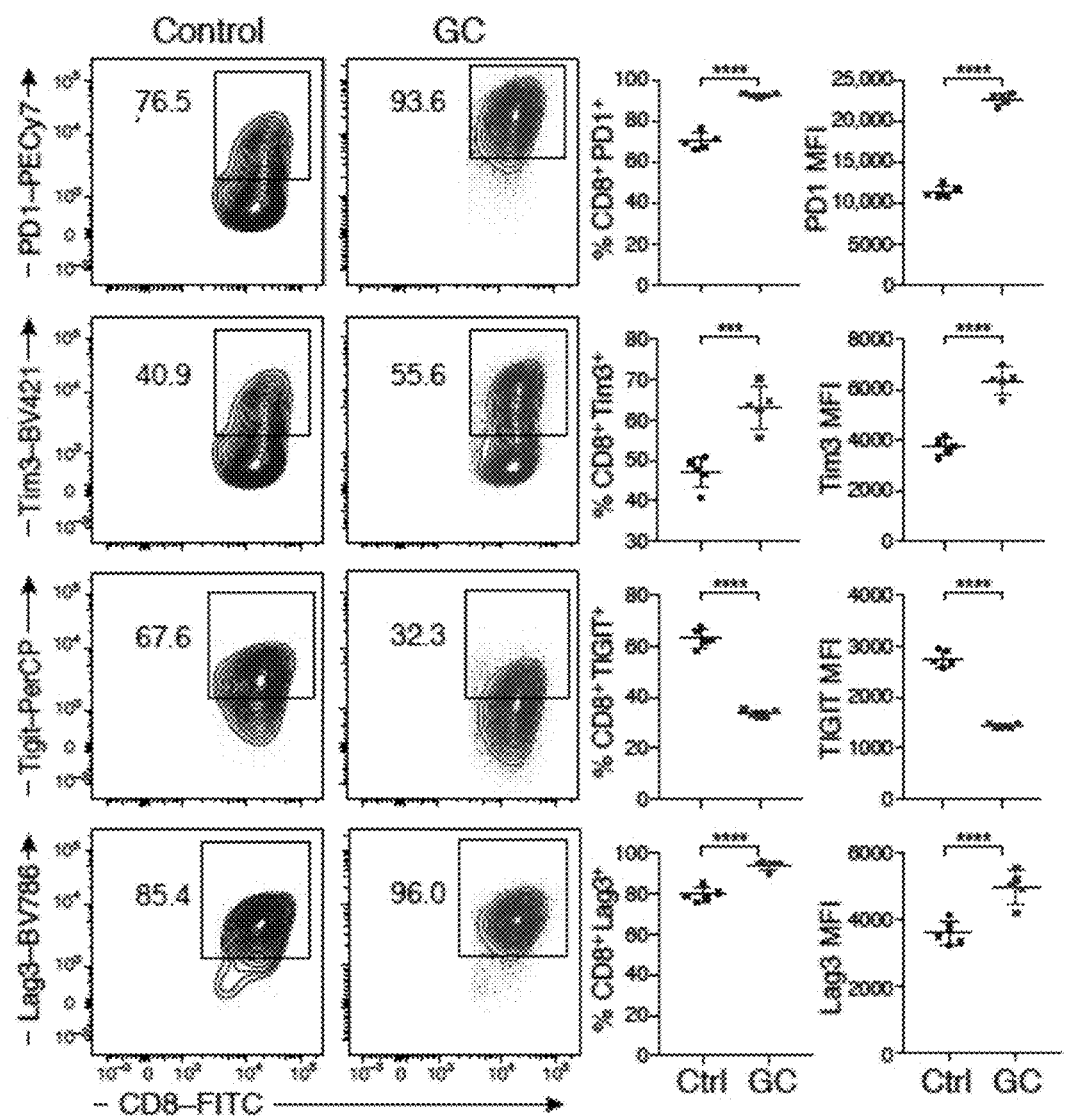
FIG. 17—Natural glucocorticoid (corticosterone) also induces checkpoint receptors. CD8+ T cells were activated in the presence or absence of GC and expression of Tim-3, PD-1, Lag-3, and TIGIT was examined by flow cytometry on Day 9.
Figure 18:
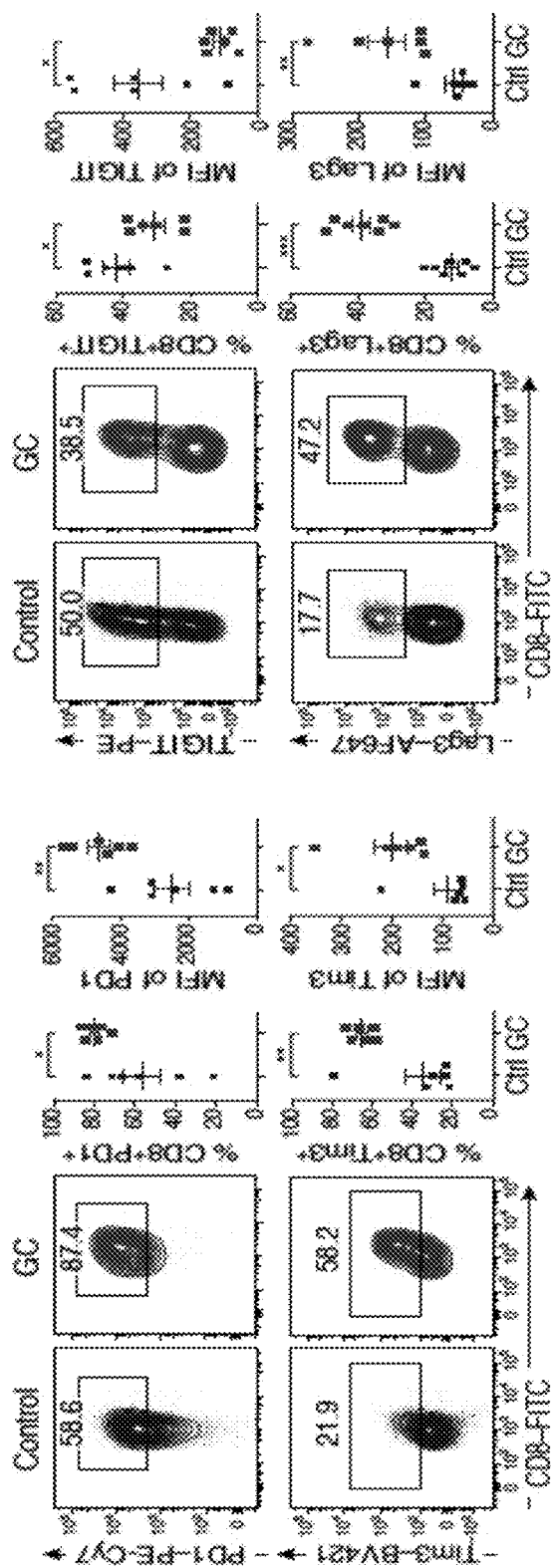
FIG. 18—Chronic activation with GC also induces checkpoint receptor expression in human CD8+ T cells. CD8+ T cells were activated in the presence or absence of Dex (GC) and expression of Tim-3, PD-1, Lag-3, and TIGIT was examined by flow cytometry on Day 9.
Figure 19:
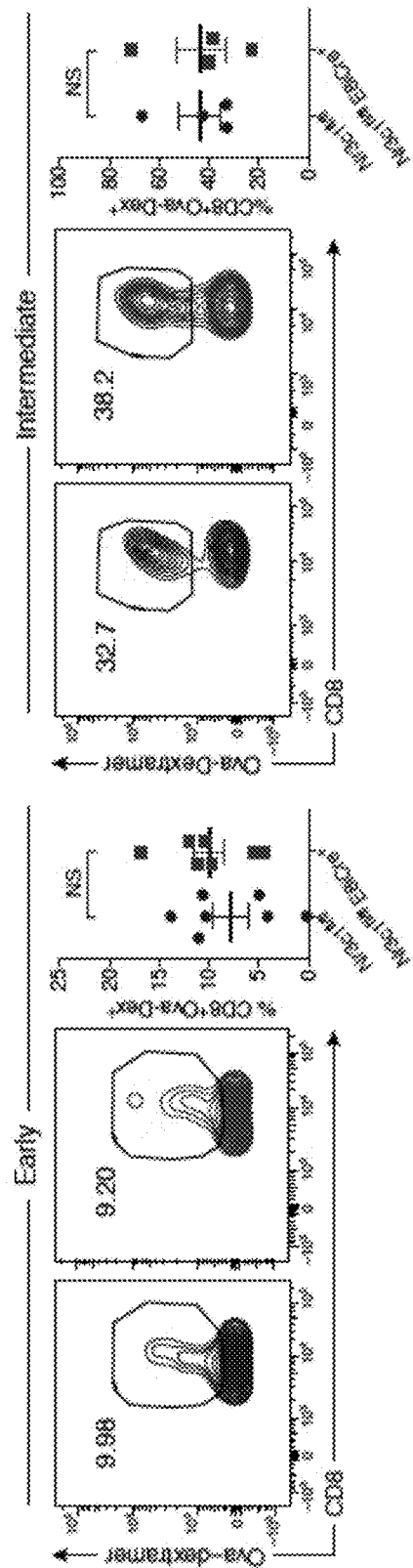
FIG. 19—Loss of glucocorticoid sensing does not change the frequency of tumor antigen-specific (Ova-dextramer) CD8+ TILs.
Figure 20:
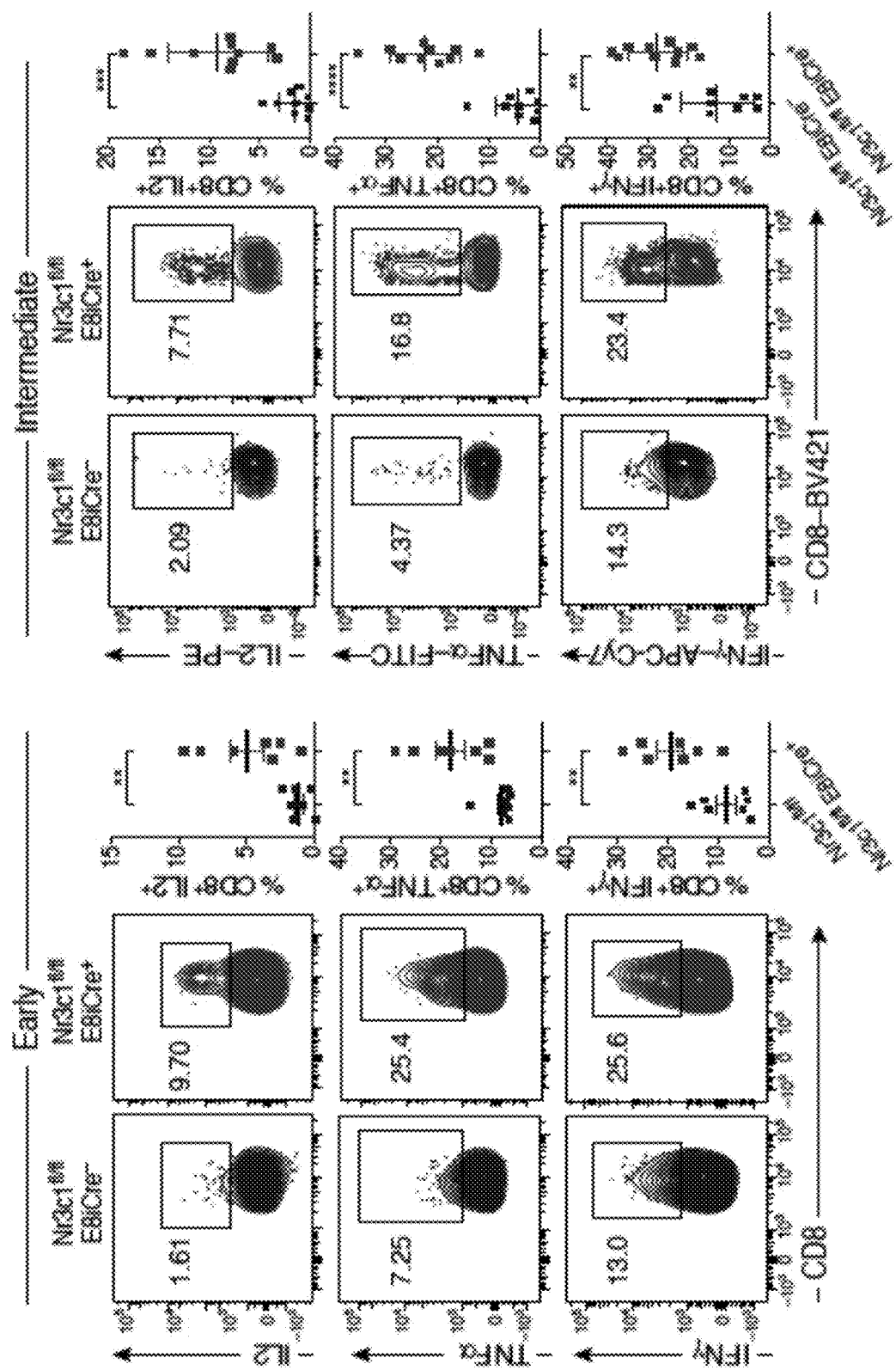
FIG. 20—FACS showing that loss of glucocorticoid sensing improves tumor antigen-specific pro-inflammatory cytokine production in CD8+ TILs.
Figure 21:
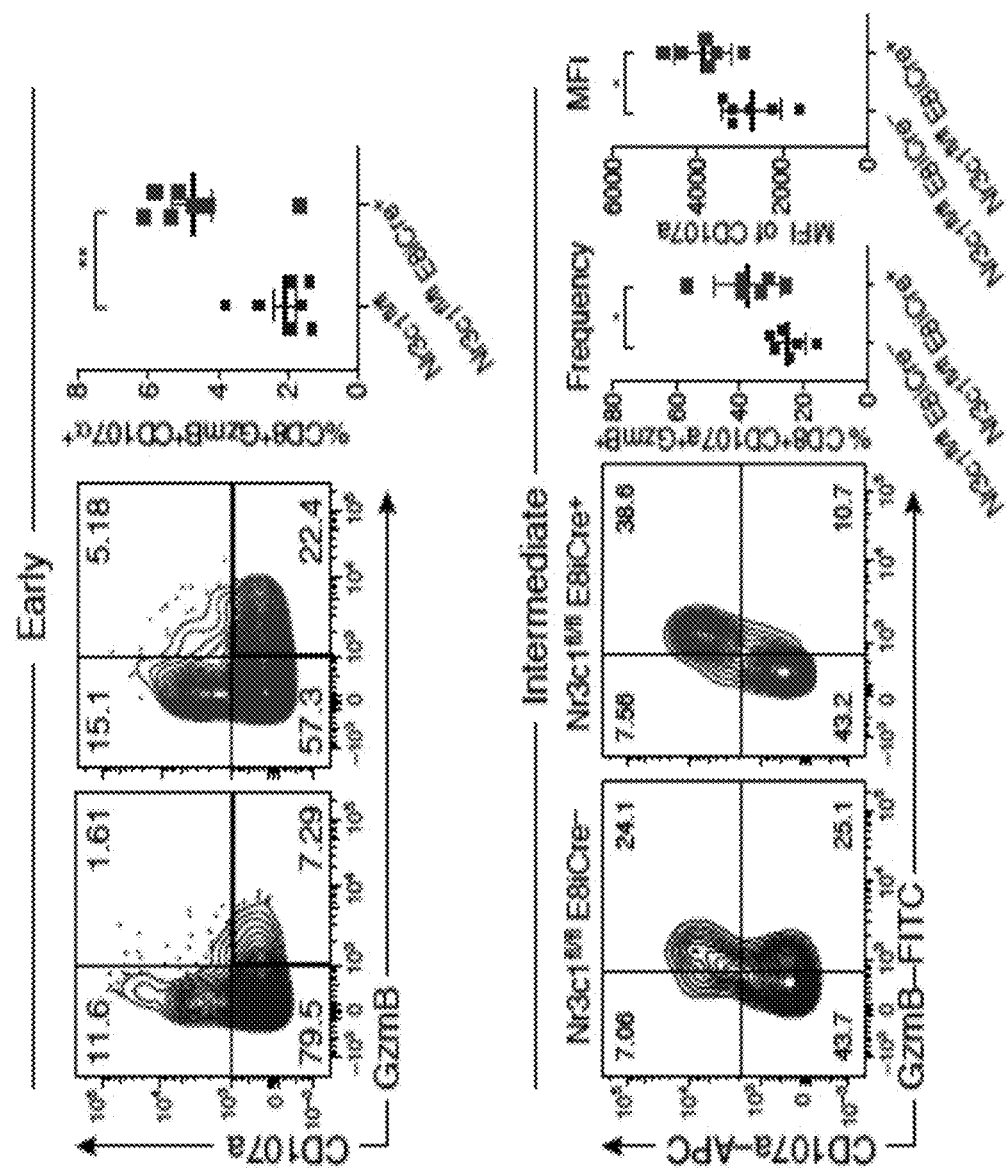
FIG. 21—FACS showing that loss of glucocorticoid sensing improves tumor antigen-specific cytotoxic capacity.
Figure 25:
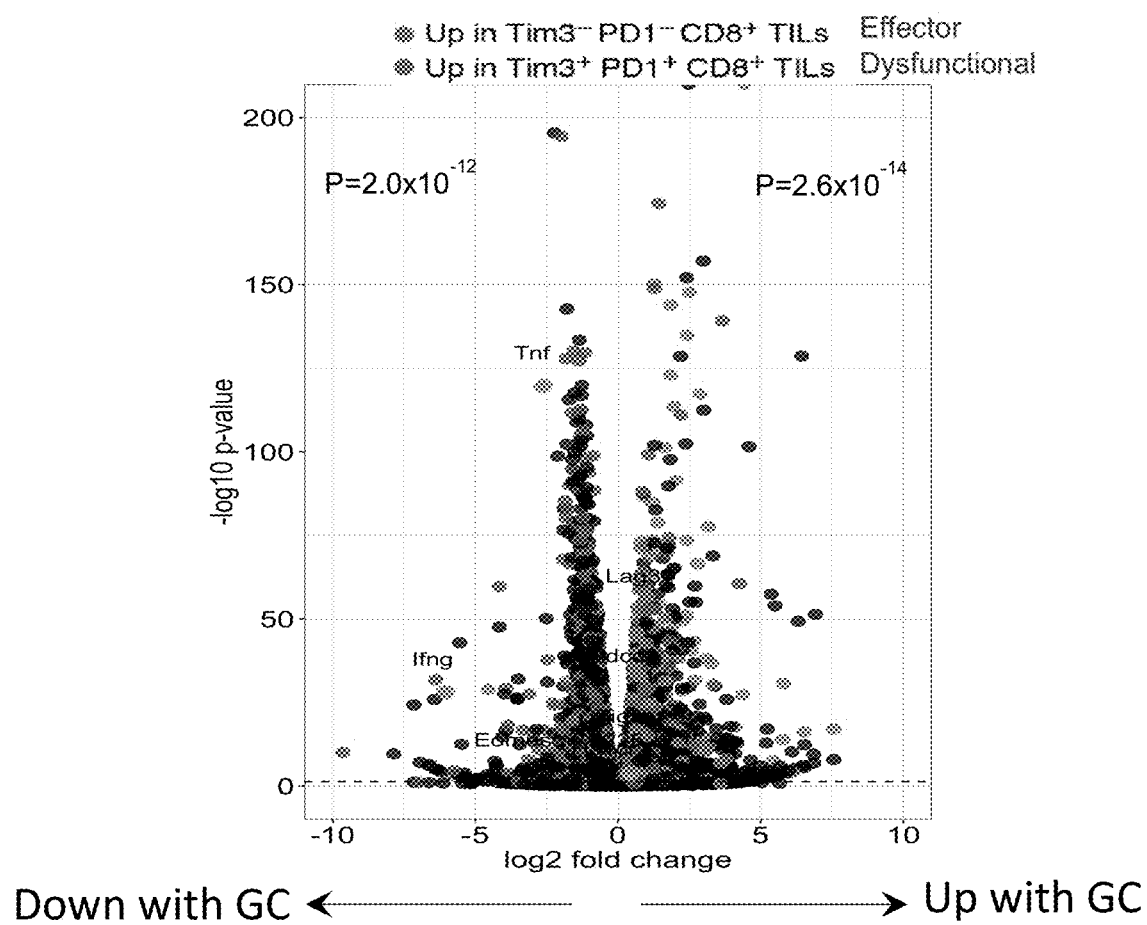
FIG. 25—Volcano plot showing overlap of the glucocorticoid-induced gene program with the T cell dysfunction gene program in CD8+ T cells.

Applicants identified that endogenous glucocorticoid signaling impacts on CD8+ T cell effector differentiation in the TME by restraining initial effector differentiation by maintaining TCF-1 (FIG. 22) and driving checkpoint receptor expression (FIG. 17, 18, 23) and expression of the dysfunction gene program (FIG. 25). Applicants also identified the effects of GC on the frequency of tumor antigen-specific CD8+ TILs (FIG. 19), tumor antigen-specific pro-inflammatory cytokine production in CD8+ TILs (FIG. 20), and tumor antigen-specific cytotoxic capacity (FIG. 21). The effects of loss of GR are CD8+ T cell intrinsic as the effects can be seen by transfer of CD8 T cells to a tumor bearing mouse (FIG. 24).

Figure 28:
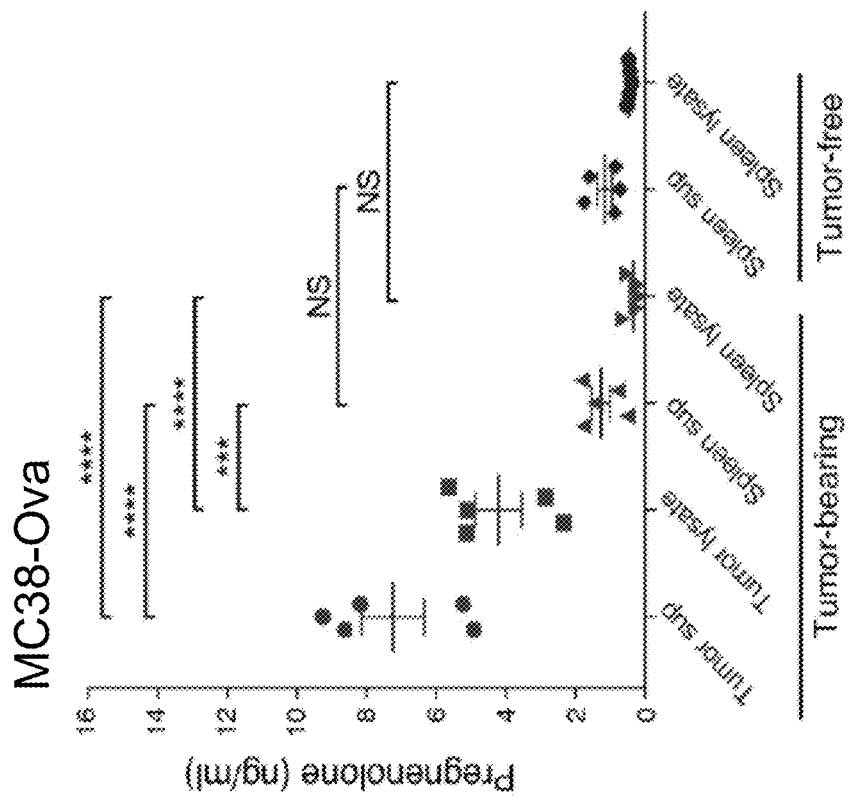
FIG. 28—Graph showing increased extra-adrenal steroid hormone production in tumor tissue.
Figure 29:
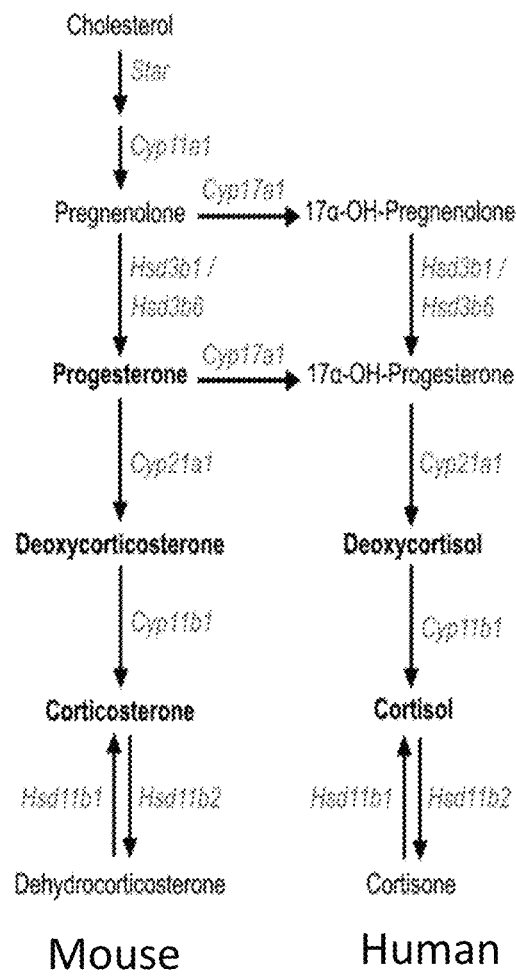
FIG. 29—Diagram showing the pathway and enzymes for production of glucocorticoids in mouse and human.

Applicants identified that steroid hormones are produced locally within the TME (FIG. 28) and that monocyte/macrophages are the major producers of glucocorticoid in the TME.

Figure 30:
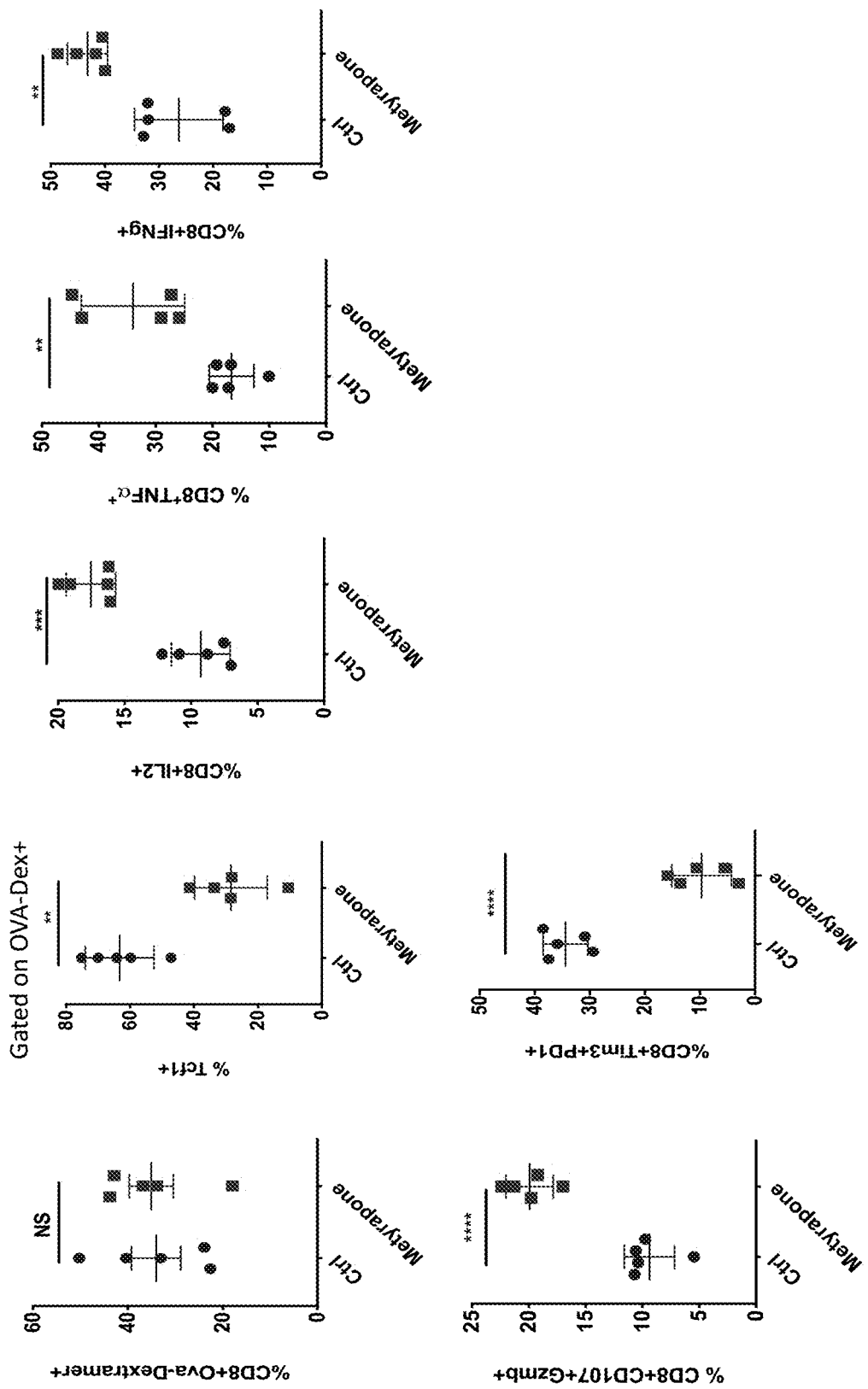
FIG. 30—Graphs showing glucocorticoid inhibition by metyrapone phenocopies CD8 GR cKO.

Applicants identified that inhibition of glucocorticoid biosynthesis in the TME phenocopies loss of glucocorticoid signaling in $CD8^+$ T cells (FIG. 30).

Figure 31:
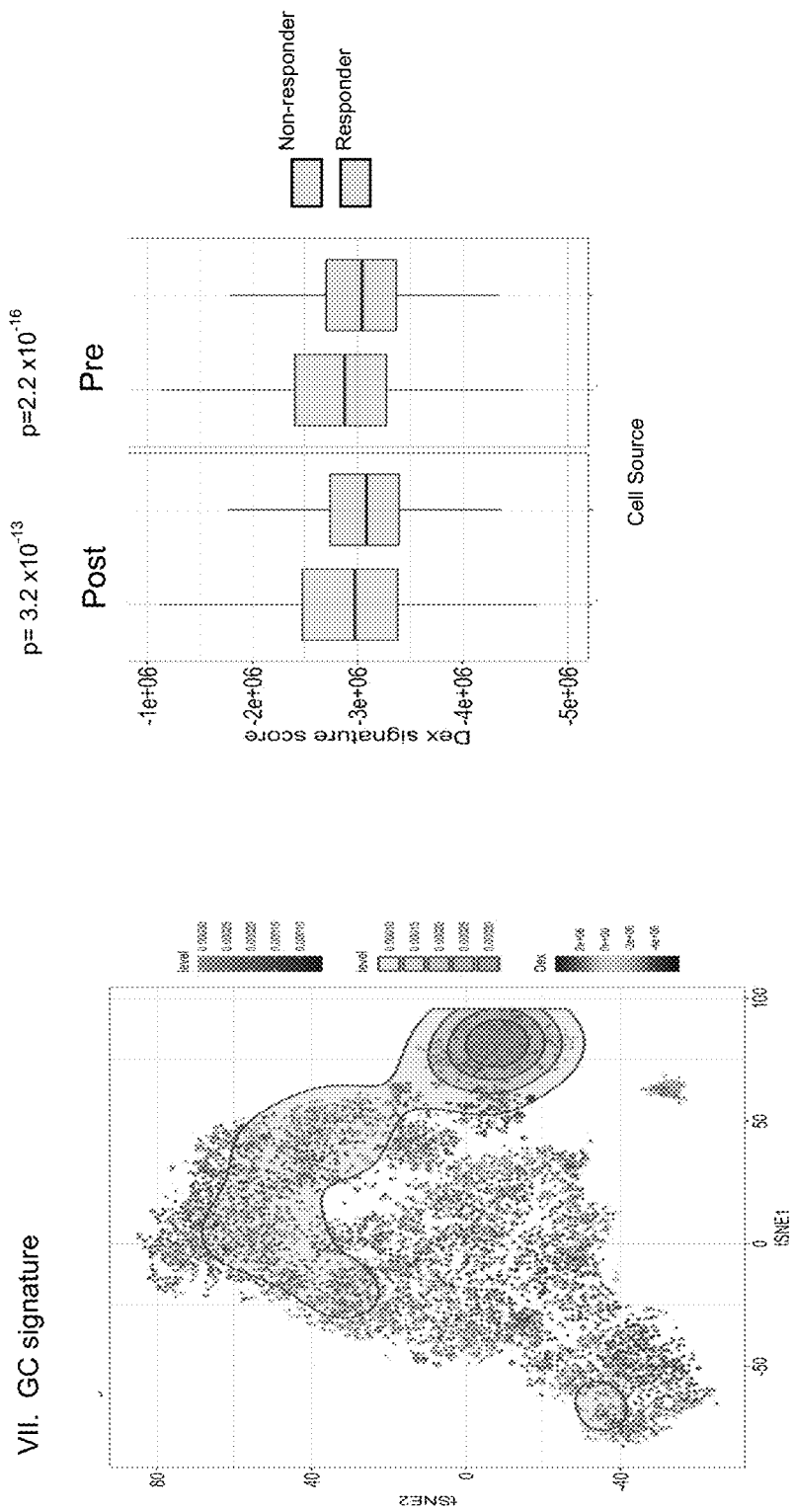
FIG. 31—tSNE plot of single-cell RNA profiles of TILs from melanoma patients (Moshe Sade-Feldman et al., Cell 2018). VII) Projection of the GC signature. Box plots show the GC (Dex) signature score in responder versus non-responders in pre- and post-treatment samples.

Applicants identified that steroid hormone production and GC-induced gene programs correlate with poor survival and response to immunotherapy (FIG. 31). The clinical implications relate to the current use of glucocorticoids to treat IRAEs in ICB-treated patients. Glucocorticoids are also used in glioma to prevent cerebral edema.

Figure 32:
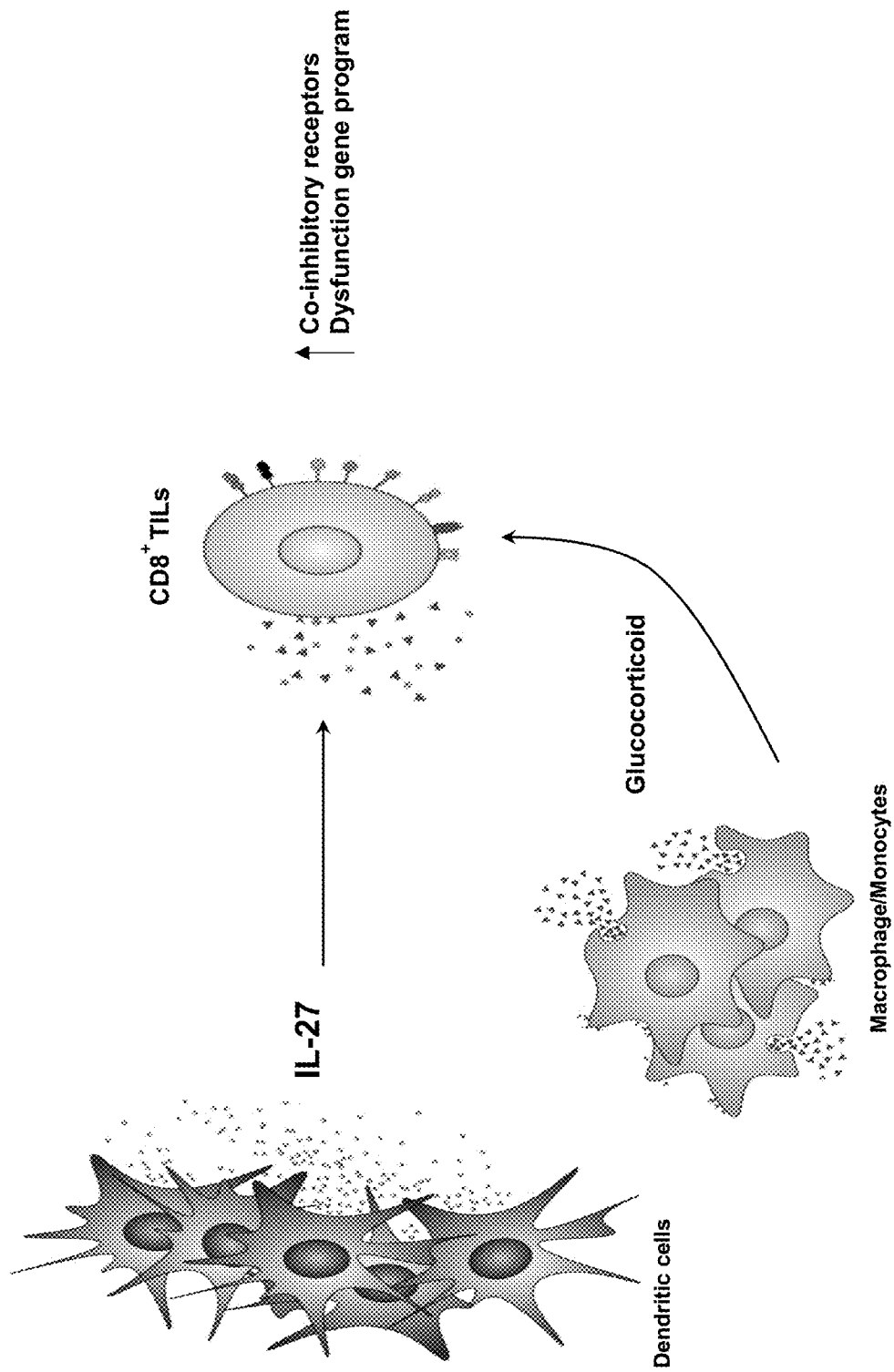
FIG. 32—Diagram showing that glucocorticoid and IL-27 signaling co-operate to promote T cell dysfunction in the TME.

Applicants have established that glucocorticoid and IL-27 signaling co-operate to promote T cell dysfunction in the TME (FIG. 32).

Figure 22:
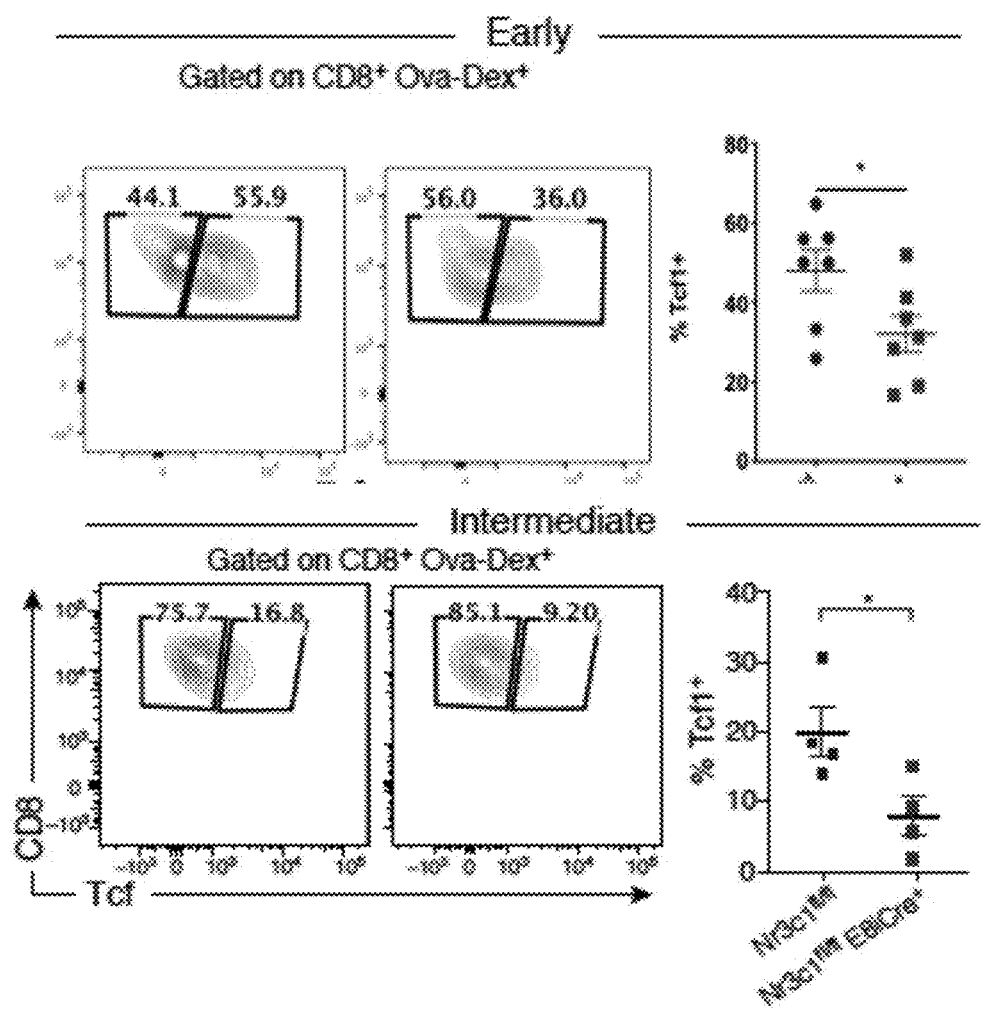
FIG. 22—FACS showing that loss of glucocorticoid sensing promotes differentiation of effector CD8+ TILs through reduction of TCF-1.
Figure 23:
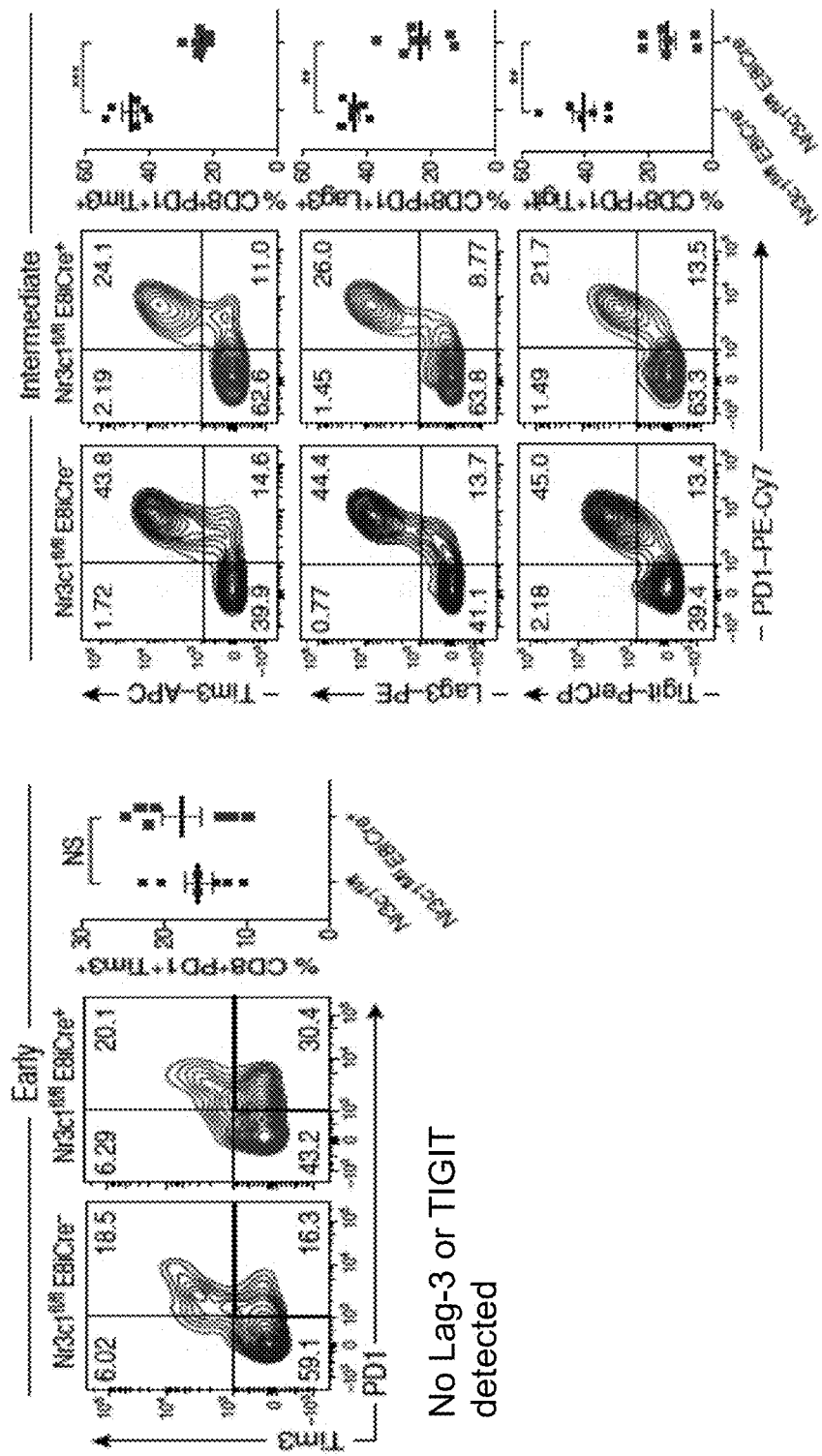
FIG. 23—FACS showing decreased acquisition of checkpoint receptor expression in GR KO CD8+ TILs.

In conclusion, Applicants have identified that Nr3C1 (glucocorticoid receptor) impacts on TCF-1 (Tcf7 gene) expression such that loss of Nr3C1 leads to reduced TCF-1 levels in tumor antigen specific cells (FIG. 22). Applicants have also identified that the glucocorticoid signature alone has significant overlap with the T cell exhaustion/dysfunction gene signature (FIG. 25) and the presence of this signature in melanoma $CD8^+$ TILs correlates with failure to respond to checkpoint blockade (FIG. 31). Applicants have also identified that local inhibition of glucocorticoid biosynthesis in tumor tissue phenocopies the loss of glucocorticoid signaling in $CD8^+$ TILs (FIG. 30). Applicants have further verified that glucocorticoid signaling drives T cell dysfunction/exhaustion. Glucocorticoid signaling also has effects early in Cd8+ T cell activation/differentiation in that it restrains effector differentiation by maintaining higher levels of TCF-1. Thus, loss of GR allows for cells to undergo better effector differentiation but then these cells cannot progress to develop dysfunction/exhaustion.

Example 9—Endogenous Glucocorticoid Signaling Regulates Effector Differentiation and Development of Dysfunction in $CD8^+$ T Cells in the Tumor Microenvironment Here, Applicants examined whether GC signaling had a role in shaping anti-tumor $CD8^+$ T cell responses. From the analyses of the RNA profiles of $CD8^+$ tumor-infiltrating (TIL) populations that exhibit distinct effector capacities and are identified by their pattern of Tim-3 and PD-1 checkpoint receptor expression (Sakuishi et al., 2010; Singer et al., 2016), Applicants identified Nr3c1, the gene encoding the glucocorticoid receptor (GR), as being most highly expressed in terminally dysfunctional Tim-3$^+$PD-1$^+$ $CD8^+$ TILs. Accordingly, Applicants identified a gradient of increasing GC signaling from naïve to dysfunctional $CD8^+$ TILs. GR-deficient $CD8^+$ TILs exhibited reduced expression of TCF-1, improved effector differentiation and function, but failed to develop dysfunctional phenotype, resulting in tumor growth inhibition. The GR promoted dysfunctional phenotype by transactivating the expression of multiple checkpoint receptors together with IL-10 and inducing multiple T cell dysfunction genes. Applicants further found that monocyte-macrophage lineage cells were a chief source of GC within the TME, and that the presence of active GC signaling correlated with failure to respond to checkpoint blockade in both pre-clinical tumor models and melanoma patients. The findings highlight a role for endogenous steroid hormone signaling in $CD8^+$ TILs in non-hormonally driven cancers with important implications for the application of ICB therapy.

Example 10—A Gradient of Glucocorticoid Signaling in $CD8^+$ TILs

Figure 33A:
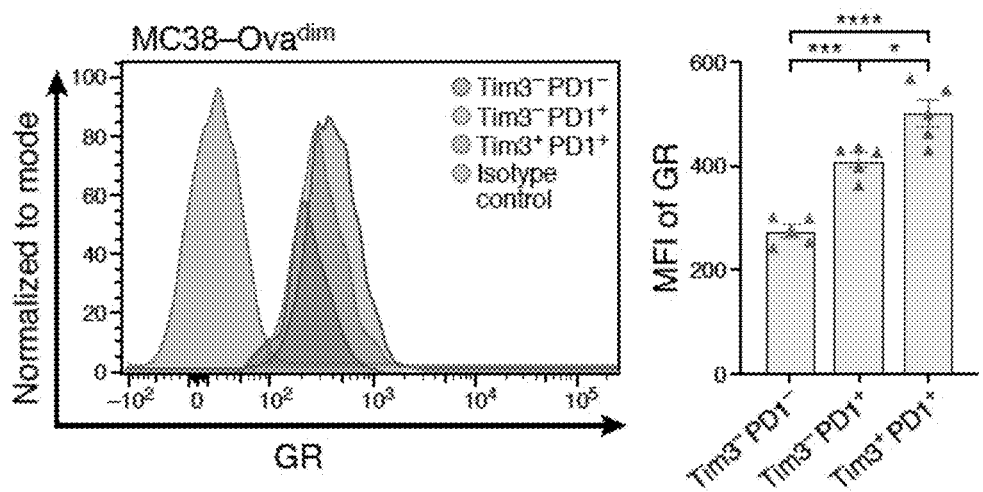
FIGS. 33A-33D—A gradient of glucocorticoid receptor expression and signaling in CD8+ TILs. GR expression in TILs harvested from mice bearing MC38-Ova$^{dim}$ colon carcinoma (tumor size 100-120 mm$^2$) (FIG. 33A, FIG. 33B) or from human colon carcinoma (FIG. 33C).
Figure 33B:
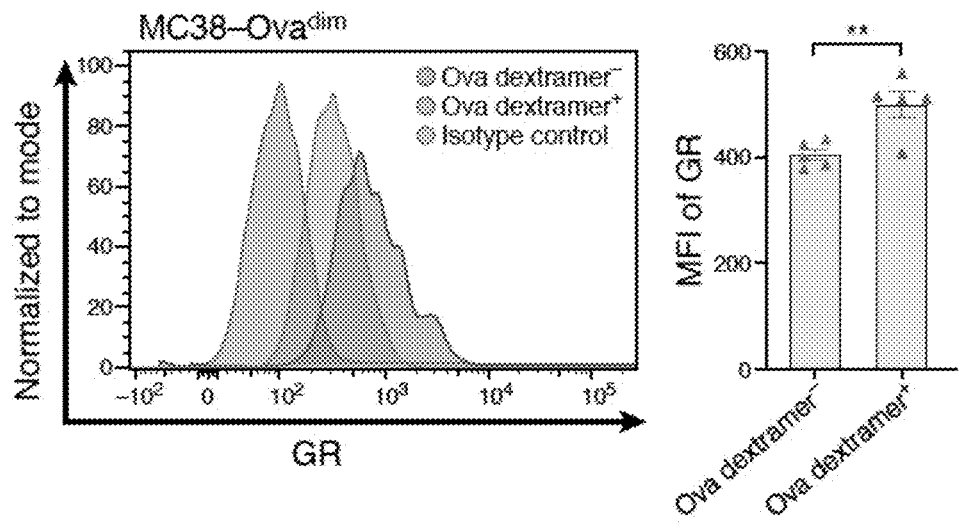
Figure 33C:
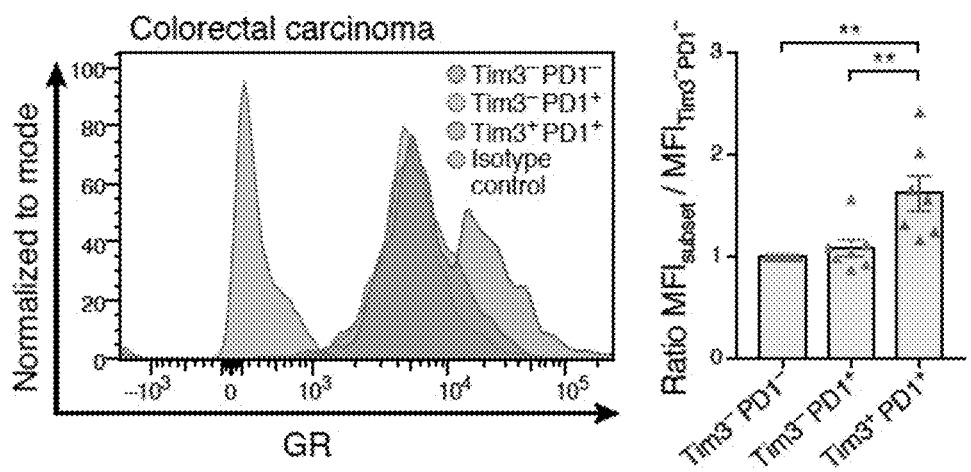

Analysis of RNA profiles (Singer et al., 2016), showed that Nr3c1, the gene encoding the glucocorticoid receptor (GR), is most highly expressed in the Tim-3$^-$PD-1$^+$ $CD8^+$ and Tim-3$^+$PD-1$^+$ $CD8^+$TIL subsets that contain effector and terminal dysfunctional $CD8^+$ TILs, respectively (FIG. 40A). Indeed, examination of GR protein showed a gradient of increasing expression across $CD8^+$ TILs with highest expression in Tim-3$^+$PD-1$^+$ $CD8^+$TILs in two different tumor models, MC38-Ova$^{dim}$ colon carcinoma and B16F10 melanoma (FIGS. 33A and 40B). Further examination showed higher GR expression in tumor-antigen specific (Ova) $CD8^+$ TILs (FIG. 33B), indicating increased GR signaling upon TCR engagement. Consistent with the expression pattern on murine $CD8^+$ TILs, the GR was also most highly expressed in Tim-3$^+$PD-1$^+CD8^+$ TILs from human colon carcinoma tumors (FIG. 33C). Together these data indicated a gradient of increasing GR signaling from naive to terminally dysfunctional $CD8^+$ TILs subsets.

Figure 33D:
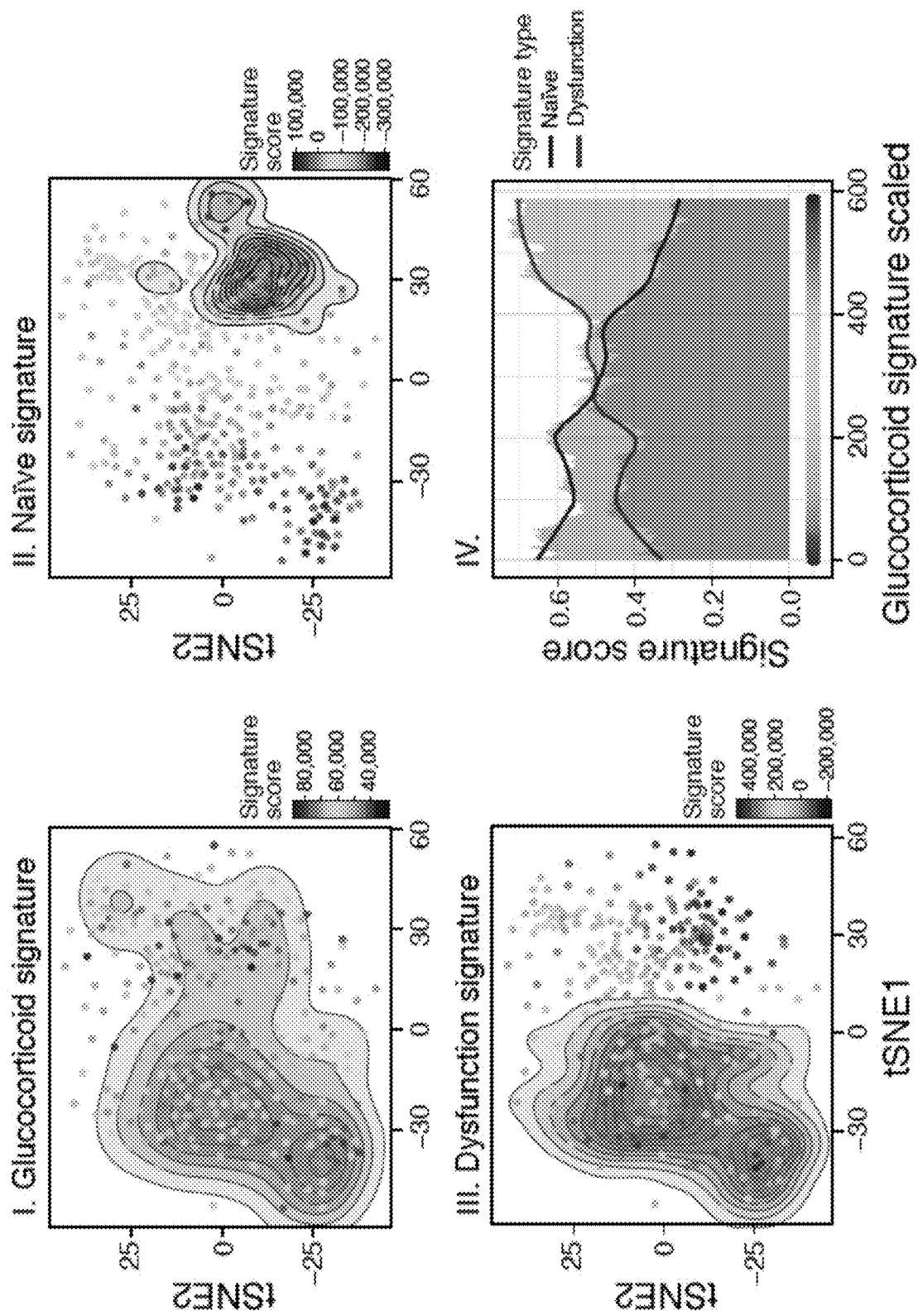
Figure 40F:
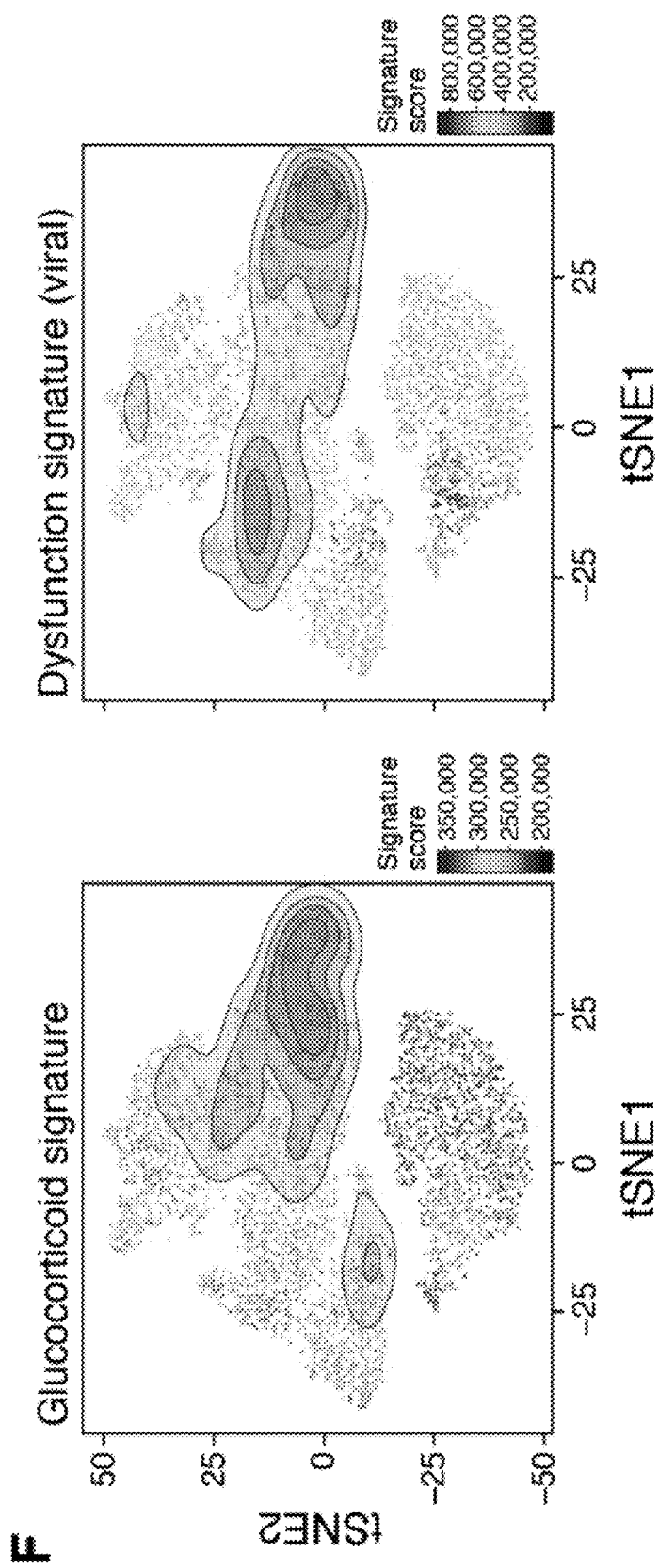

To confirm this, Applicants scored the expression of a previously established GC signature (Phuc Le et al., 2005) in the single-cell RNA-Seq (scRNA-Seq) profiles of $CD8^+$ TILs (Star Methods) (Singer et al., 2016) from B16F10 melanoma and observed a gradient of low- to high-expressing cells (FIGS. 33D, panel I and 40C). Low GC signature-expressing cells expressed high levels of genes associated with naïve T cells (Ccr7, Tcf7), while intermediate and high GC signature-expressing cells expressed high levels of effector (Tbx21, Gzmb) and dysfunction genes (Entpd1, Tox), respectively (FIG. 40D). Of note, cells with high expression of the GC signature also expressed Mt1 and Nfil3, known GR target genes (Karin and Herschman, 1979) (Carey et al., 2013) that Applicants have previously implicated in T cell dysfunction (Singer et al., 2016; Zhu et al., 2015) (FIG. 41E). These data indicated that naïve and dysfunctional CD8+ TILs mark the spectrum of low to high GC signature-expressing cells, respectively. Indeed, scoring of all of the cells for expression of the GC, naïve, and dysfunction signatures showed that as CD8+ TILs acquire high expression of the GC signature they transition from the naïve to the dysfunctional T cell state (FIG. 33D, panels II-IV). Applicants further scored the GC signature on the scRNA-Seq profiles of CD8+ T cells from chronic LCMV infection (Chen et al., 2019). Consistent with the observations in CD8+ TILs, Applicants found that many of the cells that scored highly for expression of the GC signature also scored highly for the dysfunction signature (FIG. 40F). Collectively, these data indicated that increasing GC signaling was associated with loss of effector function and acquisition of dysfunctional phenotype in CD8+ T cells.

Figure 34A:
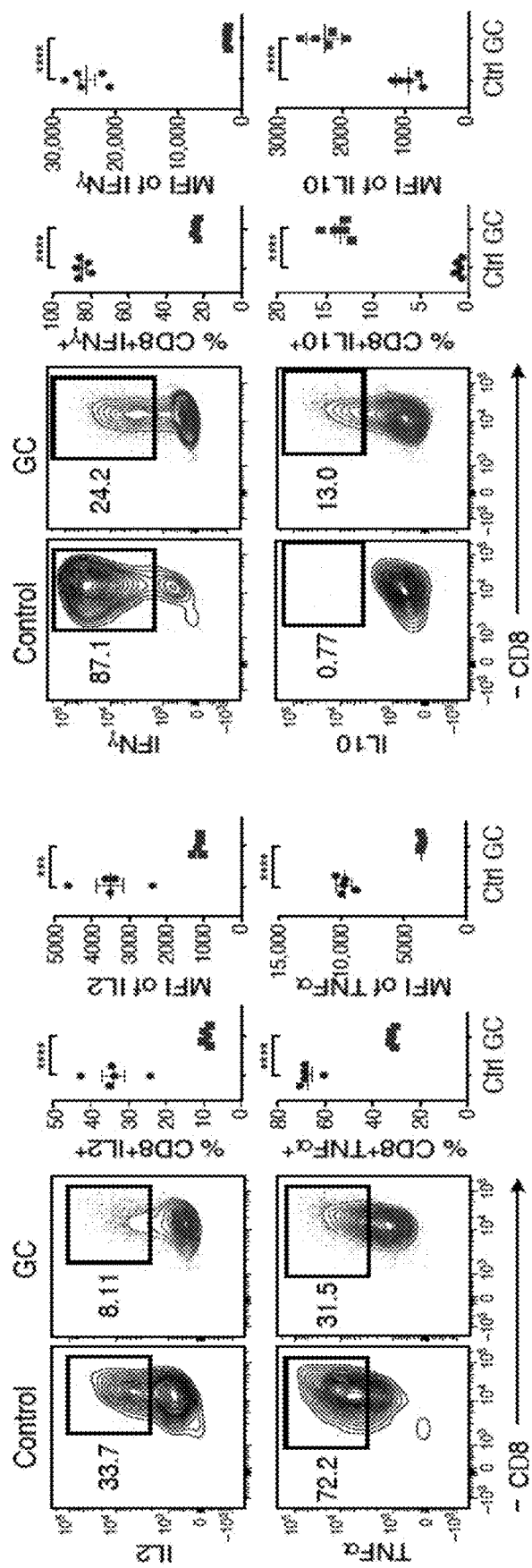
FIGS. 34A-34C—Glucocorticoid signaling promotes checkpoint receptor expression and dampens CD8+ T cell effector functions. Murine (FIGS. 34A-B) or human (FIG. 34C) naïve CD8+ T cells were repeatedly activated (anti-CD3/28) in the presence or absence of GC (Dex). Data shown are representative of 3 independent experiments.
Figure 34B:
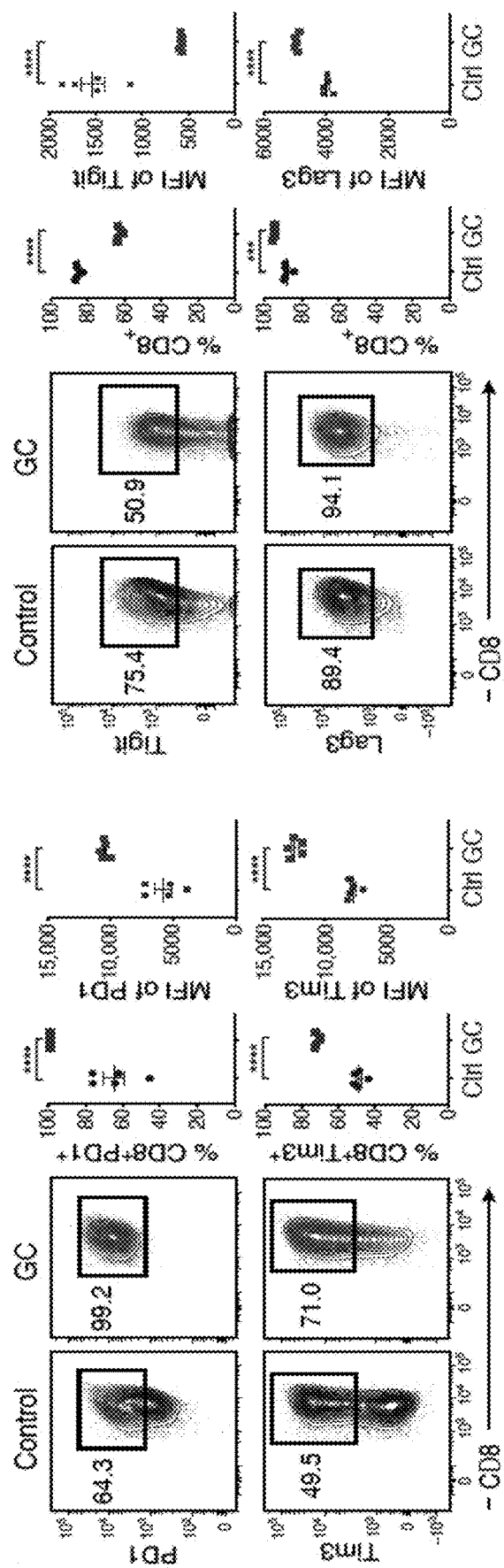
Figure 34C:
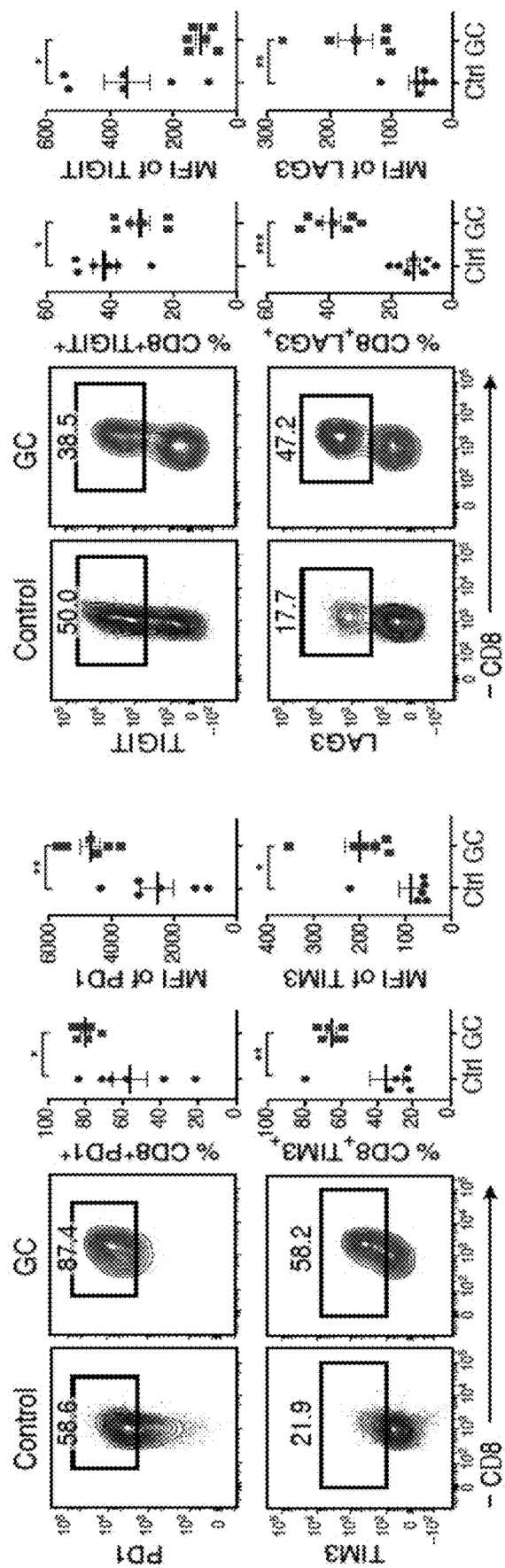

Example 11—Glucocorticoid Signaling Dampens Effector Phenotype and Promotes Features of Dysfunction in CD8+ T Cells Accordingly, Applicants hypothesized that GC signaling might promote T cell dysfunction. Applicants tested the effect of repeated activation of CD8+ T cells in the presence of synthetic GC (dexamethasone; Dex) in vitro. In line with observations in acutely activated cells (Barrat et al., 2002; Bianchi et al., 2000; Brattsand and Linden, 1996; Rhen and Cidlowski, 2005), Applicants found that repeated activation in the presence of GC profoundly suppressed the production of the pro-inflammatory cytokines IL-2, TNF-α, and IFN-γ, and induced the immune-suppressive cytokine IL-10 (FIG. 34A), a phenotype consistent with dampened effector function. Additionally, Applicants found that GC treatment dramatically induced checkpoint receptors, including PD-1, Tim-3, and Lag-3, but not Tigit (FIG. 34B). Notably, the GC-mediated induction of checkpoint receptor expression was conserved in human CD8+ T cells (FIG. 34C). Additionally, Applicants observed that GC increased the frequency of Tim-3+PD-1+ CD8+ T cells in both murine and human samples (FIG. 41A,B). The observed effects of GC were not due to reduced T cell survival or altered proliferation (FIG. 41C,D). Applicants further tested the effect of the natural GC, corticosterone, on the expression of checkpoint receptors and found that it recapitulated the effects of Dex (FIG. 41E).

The observed effects of GC on CD8+ T cells depended on Nr3c1. Applicants found that Nr3c2, which encodes the mineralocorticoid receptor (MR) that shares high structural homology with GR and can bind GCs with high affinity (Arriza et al., 1987) is not expressed by wild type (WT) CD4+ and CD8+ T cells or in CD8+ T cells from mice that lack Nr3c1 expression specifically in mature CD8+ T cells (E8i-Cre+ Nr3c1$^{fl/fl}$) (FIG. 41F). Further, comparison of the RNA profiles of WT (E8i-Cre− Nr3c1$^{fl/fl}$) and E8i-Cre+ Nr3c1$^{fl/fl}$ CD8+ T cells stimulated with or without GC showed distinct GC-induced changes in WT but not E8i-Cre+ Nr3c1$^{fl/fl}$ CD8+ T cells, indicating that GC-induced transcription in CD8+ T cells was Nr3c1 dependent (FIG. 41G). Thus, repeated stimulation in the presence of active GC signaling dramatically influenced the effector differentiation of CD8+ T cells, resulting in cells that exhibited features shared with dysfunctional T cells, including expression of multiple checkpoint receptors, dampened pro-inflammatory cytokine production, and increased IL-10 production.

Figure 42A:
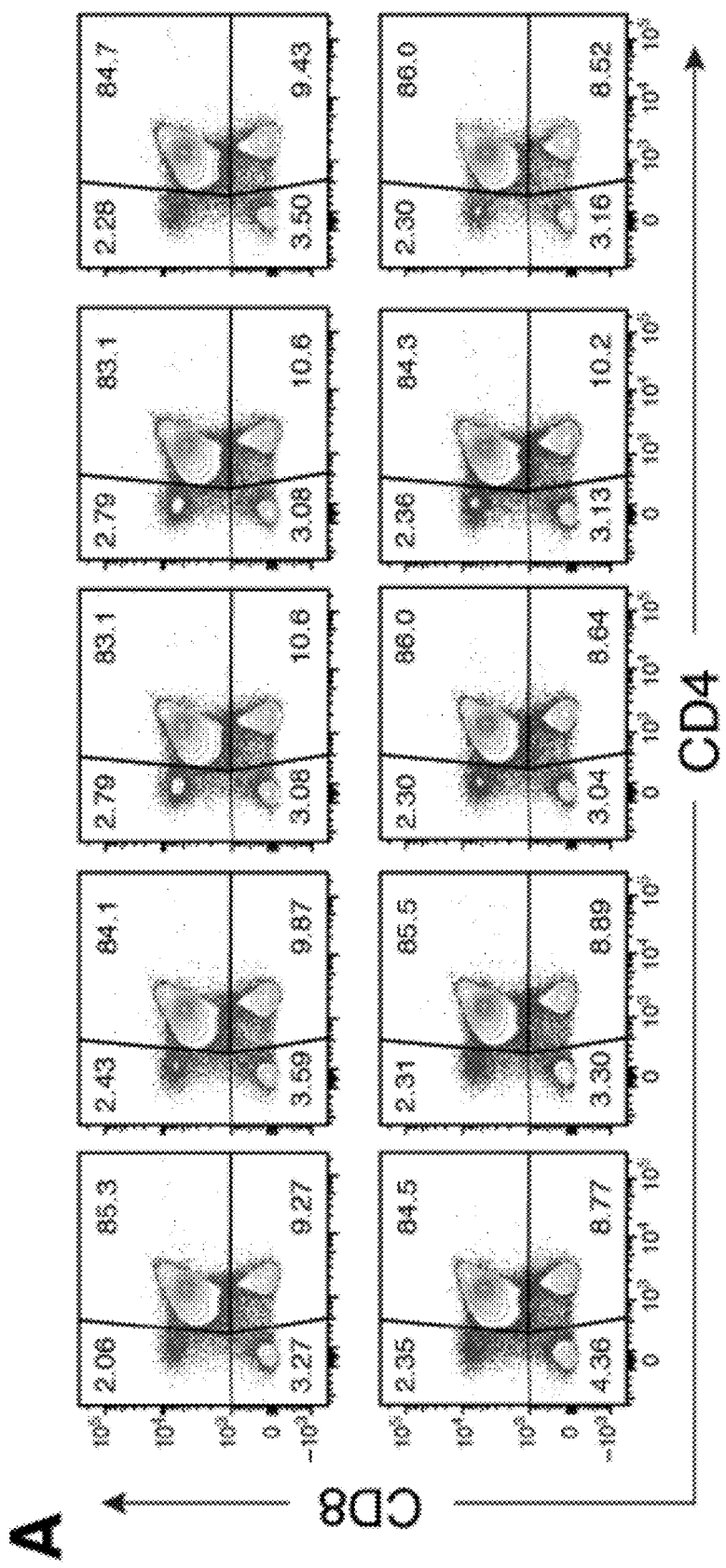
FIGS. 42A-42D—(related to FIG. 35). Normal T cell development in Nr3c1$^{fl/fl}$ E8iCre$^+$ mice.

Applicants next tested whether GC signaling impacted the functional state of CD8+ TILs in vivo using E8i-Cre+ Nr3c1$^{fl/fl}$ mice. Examination of T cell development and the steady state peripheral immune compartment of these mice showed no gross differences compared to WT littermate controls (FIGS. 42A-D). Applicants further confirmed that the deletion of N3rc1 was specific to CD8+ T cells (FIG. 42E). Applicants implanted either MC38-Ova$^{dim}$ or B16F10 melanoma cells into WT and E8i-Cre+ Nr3c1$^{fl/fl}$ mice and found that E8i-Cre+ Nr3c1$^{fl/fl}$ mice exhibited improved tumor growth control in both models (FIGS. 35A and 42A), indicating that the effect of GC signaling in CD8+ T cells was conserved across tumor types.

Figure 42B:
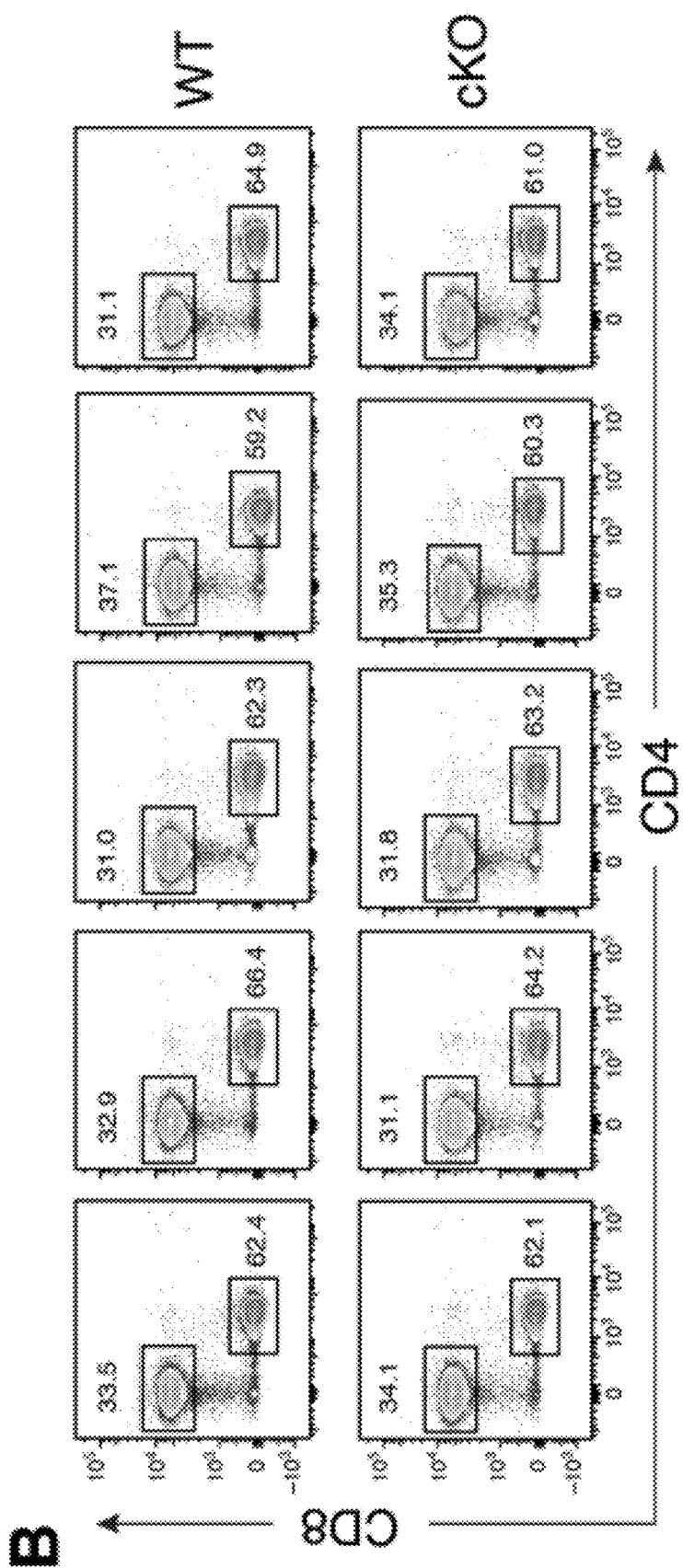
Figure 42C:
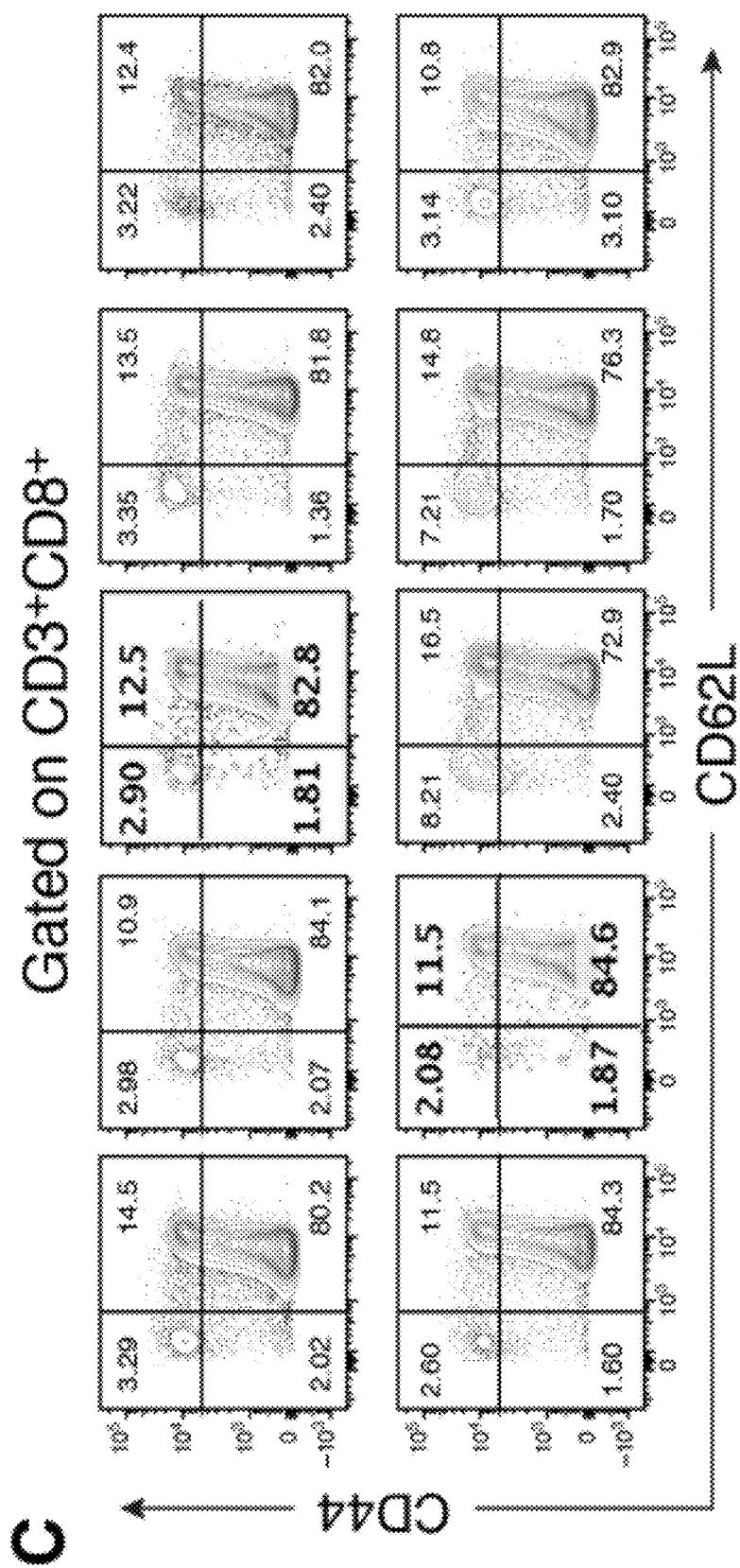
Figure 42D:
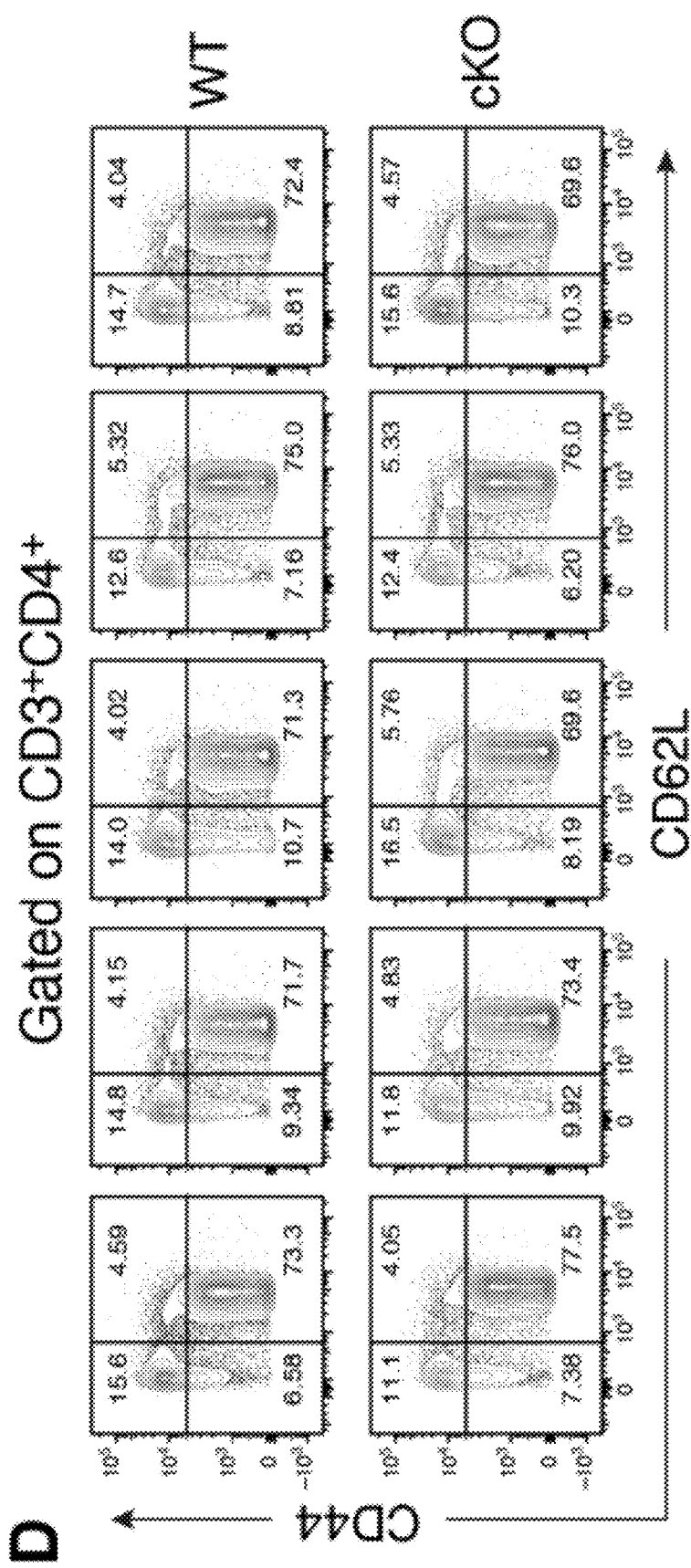

Applicants next examined how loss of GC signaling impacted the differentiation and function of CD8+ TILs by examining CD8+ TILs at the early (when tumor sizes were not significantly different across the two groups) and intermediate stages of tumor progression. At both stages, there were no significant differences in the frequency of H-2K$^b$-OVA$_{257-264}$ dextramer+ CD8+ TILs between the WT and the E8i-Cre+ Nr3c1$^{fl/fl}$ mice (FIG. 35B). However, the CD8+ TILs from E8i-Cre+ Nr3c1$^{fl/fl}$ mice exhibited enhanced responses to tumor-antigen (OVA$_{257-264}$), as well as polyclonal stimulation, producing more IL-2, TNF-α, and IFN-γ (FIGS. 35C and 42B). Indeed, the CD8+ TILs from E8i-Cre+ Nr3c1$^{fl/fl}$ mice were more polyfunctional in terms of pro-inflammatory cytokine production (FIG. 42C). CD8+ TILs from E8i-Cre+ Nr3c1$^{fl/fl}$ mice further exhibited higher cytotoxic capacity, as shown by the increased frequency of Granzyme B+CD107a+ cells upon OVA$_{257-264}$ stimulation at both stages (FIG. 35D). Applicants examined IL-10 production and found that although at the early stage there were no significant differences, at the intermediate stage the CD8+ TILs from E8i-Cre+ Nr3c1$^{fl/fl}$ mice produced lower amounts of IL-10 (FIGS. 35E and 42D). As the data indicated that CD8+ TILs from E8i-Cre+ Nr3c1$^{fl/fl}$ mice exhibited increased effector function, Applicants examined expression of the transcription factor TCF-1, which is known to play a critical role in regulating effector T cell differentiation (Danilo et al., 2018; Tiemessen et al., 2014) and whose expression has been reported to be modulated by Nr3c1 (Yu et al., 2017). At both stages, Applicants found that the lack of GR resulted in reduced expression of TCF-1 in tumor-antigen specific CD8+ TILs (FIG. 35F). Lastly, Applicants examined the expression of checkpoint receptors. At the early stage, Applicants observed low Tim-3 and PD-1 expression, which did not differ between genotypes; however, at the intermediate stage, Applicants observed that not only was there a dramatic reduction in the frequency of CD8+ TILs co-expressing PD-1, Tim-3, Lag-3, and Tigit in CD8+ TILs from E8i-Cre+ Nr3c1$^{fl/fl}$ mice (FIG. 35G), but also the expression level of each of these checkpoint receptors was significantly reduced (FIG. 42E). Of note, Tigit expression was suppressed in CD8+ TILs from E8i-Cre+ Nr3c1$^{fl/fl}$ mice (FIGS. 35G and 42E), in contrast to the in vitro observations where Tigit expression was not induced by GR stimulation (FIG. 34B). Furthermore, the few Tim-3+PD-1+CD8+ TILs in E8i-Cre+ Nr3c$^{fl/fl}$ mice exhibited increased pro-inflammatory cytokine production in response to OVA$_{257-264}$ stimulation (FIG. 43F), in contrast to their typical terminally dysfunctional phenotype observed in WT mice. These observations were not due to increased recruitment or proliferation of CD8$^+$ T cells in E8i-Cre$^+$ Nr3c1$^{fl/fl}$ mice as Applicants observed no significant differences in either the expression of Ki-67 or the absolute number of the CD8$^+$ TILs in WT and E8i-Cre×Nr3c1$^{fl/fl}$ mice (FIGS. 43G and H).

Importantly, the effects of the loss of Nr3c1 in CD8$^+$ TILs were cell intrinsic. Checkpoint receptor expression on CD4$^+$ TILs in E8i-Cre$^+$ Nr3c1$^{fl/fl}$ mice was not significantly different from that of WT CD4$^+$ TILs (FIGS. 43I and J). Further, when congenically marked CD8$^+$ T cells from WT and E8i-Cre$^+$ Nr3c1$^{fl/fl}$ mice were co-transferred into Rag$^{-/-}$ recipient mice followed by implantation of MC38-Ova$^{dim}$ tumors, only the CD8$^+$ TILs from E8i-Cre$^+$ Nr3c1$^{fl/fl}$ mice exhibited increased expression of pro-inflammatory cytokines and cytotoxic capacity concomitant with reduced expression of PD-1 and Tim-3 (FIG. 35H) Collectively, these data indicated that GC signaling acted cell intrinsically to shape effector differentiation and development of dysfunction in CD8$^+$ TILs.

Figure 44G:
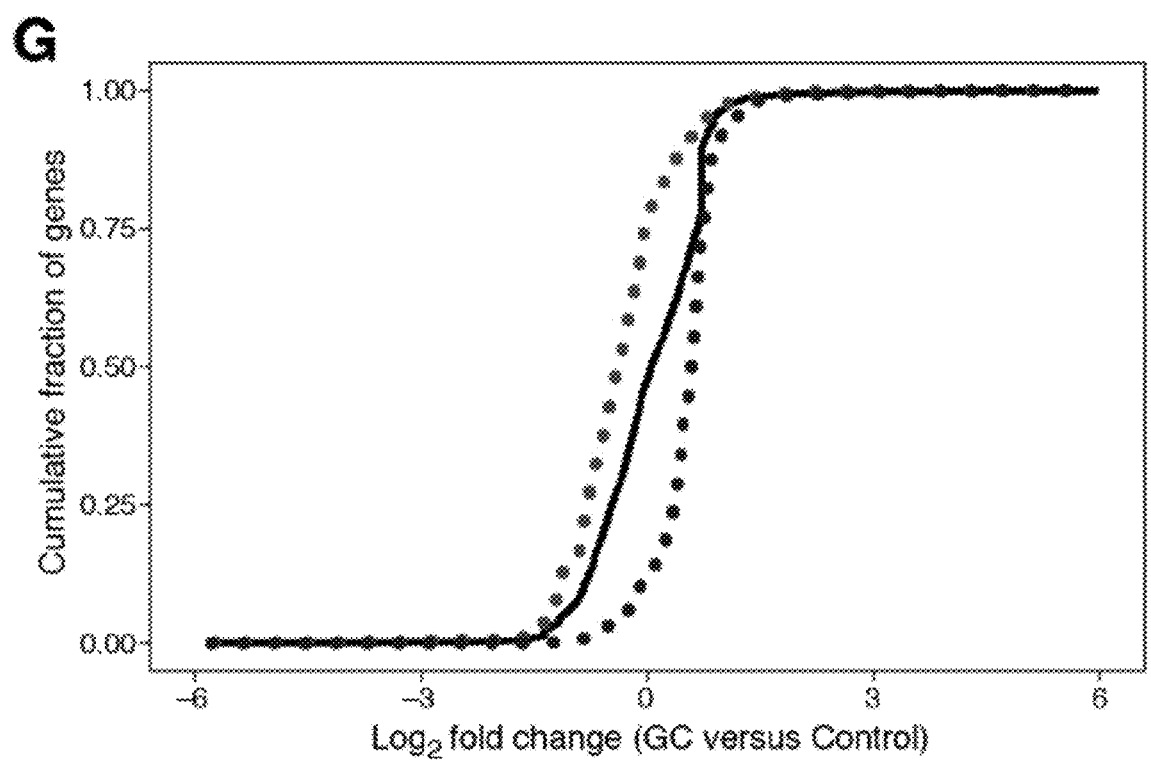

Example 12—Glucocorticoid Signaling Transactivates Checkpoint Receptor Expression and IL-10 and Induces T Cell Dysfunction Genes The in vivo data indicated a relationship between Nr3c1 and expression of checkpoint receptors and IL-10 in murine colon cancer. In line with this, a previous study implicated GC in promoting PD-1 expression on T cells (Xing et al., 2015), although the underlying mechanism was not examined. Applicants further found a strong positive correlation of NR3C1 mRNA levels with HAVCR2 (Tim-3), PDCD1 (PD-1), LAG3, TIGIT and IL10 mRNA levels in human colon adenocarcinoma from TCGA (cancergenome.nih.gov/) (FIG. 44A). Applicants therefore tested if the GR directly regulated the expression of checkpoint receptor and IL-10. First, Applicants analyzed GR-binding peaks in the loci of Havcr2 (Tim-3), Pdcd1 (PD-1), Lag3, Tigit, and IL10 in publicly available ChIP-seq data (Oh et al., 2017) from bone marrow-derived macrophages (BMDMs). Applicants found GR-binding peaks in the loci of Havcr2, Lag3, and IL10 but not Pdcd1 or Tigit, likely reflecting the lack of PD-1 and Tigit expression in BMDMs (FIG. 44B-F). Of note, some of the GR binding peaks in the Havcr2, Lag3, and IL10 loci overlapped with regions of accessible chromatin in dysfunctional CD8$^+$ TILs (Philip et al., 2017), which are known to express these checkpoint receptors as well as IL-10 (FIG. 44B-F). Applicants therefore tested the effect of GR binding to the cis-regulatory elements in the loci of Havcr2, Pdcd1, Lag3, and Tigit using luciferase reporter assays. For IL10, Applicants utilized luciferase reporters of a previously established enhancer element of Il10–HSS$^+$ 2.98 as well as the proximal promoter (−1.5 kb)(Karwacz et al., 2017). Applicants transfected the different luciferase reporter constructs along with a Nr3c1 expressing vector or empty control vector into 293T cells and treated the cells with GC to assay the transactivation capability of the GR. In line with the observations in GC-treated CD8$^+$ T cells (FIG. 34), the GR potently transactivated Tim-3, PD-1, Lag-3, and IL-10 expression (FIGS. 36A-C and E). Tigit was also induced but to a much lower degree (FIG. 36D). Given that the GR could transactivate checkpoint receptors and IL10, Applicants hypothesized that the GR could also potentially drive the expression of genes associated with CD8$^+$ T cell dysfunction. To test this, Applicants analyzed the RNA profiles from CD8$^+$ T cells undergoing repeated stimulation in the presence of GC or vehicle control. Applicants found that 463 GC-induced genes overlapped with the T cell dysfunction signature (Table 8). The genes induced by GC treatment significantly (p=9.4×0$^{-52}$, Mean-rank Gene Set Test) overlapped with the genes expressed by terminally dysfunctional Tim3$^+$PD1$^+$ CD8$^+$ TILs while the genes suppressed by GC significantly (p=1.4×10$^{-26}$, Mean-rank Gene Set Test) overlapped with the genes expressed by the Tim3$^-$PD1$^-$ CD8$^+$ T cells that exhibit effector capacity (FIGS. 36F and 44G).

Example 13—Myeloid Cells are the Primary Source of Glucocorticoid in the TME

Although steroids are mainly synthesized in the adrenal cortex, it has been suggested that tumor cells are capable of extra-adrenal steroidogenesis (Sidler et al., 2011). Accordingly, Applicants asked whether local sources in the TME provided endogenous GC. Steroids are produced by the enzymatic breakdown of cholesterol, where cytochrome P450 cholesterol side-chain cleavage enzyme (Cyp11a1) catalyzes the first and the rate-limiting step that breakdowns cholesterol to pregnenolone, the precursor of all steroid hormones (Payne and Hales, 2004). Applicants quantified pregnenolone levels in the tumor tissue and spleen of MC38-Ova$^{dim}$ tumor-bearing and tumor-free mice and found a high level of pregnenolone in the tumor tissue while levels in the spleen of tumor- and non-tumor-bearing mice did not differ (FIG. 37A). These data indicated that steroids may be produced locally in the TME. Applicants next examined which cell types might be responsible for steroid production in the TME by examining expression of Cyp11a1. Applicants found that neither in vitro cultured nor ex vivo isolated MC38-Ova$^{dim}$ cells expressed Cyp11a1 (FIG. 37B). Examination of other cells in the TME showed that cancer-associated fibroblasts (CAFs) (CD45$^-$GFP$^-$PDGFRα$^+$), tumor-associated dendritic cells (TADCs), and T cells (mostly CD4$^+$ T cells) expressed Cyp11a1 but at much lower levels compared to tumor-associated monocyte-macrophage lineage cells (FIG. 37B). To study the relevance of steroid production from monocyte-macrophage lineage cells on tumor growth, Applicants implanted MC38-Ova$^{dim}$ tumor cells in WT (LysMCre$^-$ Cyp11a1$^{fl/fl}$) and LysMCre$^+$ Cyp11a1$^{fl/fl}$ mice and observed significant tumor growth control in LysMCre$^+$ Cyp11a1$^{fl/fl}$ mice (FIG. 37C). Applicants next examined the differentiation and function of CD8$^+$ TILs from WT and LysMCre$^+$ Cyp11a1$^{fl/fl}$ mice at an early stage of tumor progression when tumor sizes were not significantly different across groups. Applicants found no significant difference in the frequency of H-2K$^b$-OVA$_{257-264}$ dextramer$^+$ CD8$^+$ TILs; however, the CD8$^+$ TILs from LysMCre$^+$ Cyp11a1$^{fl/fl}$ mice produced more pro-inflammatory cytokines and had increased cytotoxic capacity (FIG. 37D). Further, the CD8$^+$ TILs from LysMCre$^+$ Cyp11a1$^{fl/fl}$ mice had a reduced frequency of TCF-1$^+$ tumor-antigen specific cells and checkpoint receptor-expressing cells (FIG. 37D). Thus, the observed phenotype of CD8$^+$ TILs from LysMCre$^+$ Cyp11a1$^{fl/fl}$ resembled that observed in E8i-Cre$^+$ Nr3c1$^{fl/fl}$ mice (FIGS. 35 and 43).

Applicants next examined whether GC was indeed produced in tumor tissue. In line with the observations of pregnenolone production (FIG. 37A), Applicants found that corticosterone was produced at high levels in the tumor tissue whereas the levels present in the spleen of tumor- and non-tumor-bearing mice did not differ (FIG. 37E). Further, tumor explants cultured in the presence of Metyrapone, an inhibitor of GC synthesis, produced less corticosterone (FIG. 45A). Together these data indicated local GC production in the TME. Given the data indicating a key role for steroid production by tumor-associated monocyte-macrophage lineage cells, Applicants examined corticosterone production in the tumor and spleen of WT and LysMCre$^+$ Cyp11a1$^{fl/fl}$ mice and found significantly reduced corticosterone production in the tumor but not in the spleen (FIG. 45B). Intra-tumoral administration of corticosterone to LysMCre$^+$ Cyp11a1$^{fl/fl}$ mice abrogated the previously observed control of tumor progression (FIG. 45C), further pointing to monocyte-macrophage lineage-derived GC as a key determinant of anti-tumor immunity.

To confirm that tumor-associated monocyte-macrophage lineage cells were indeed capable of GC production, Applicants examined their expression of the enzymes involved in canonical GC biosynthesis (StAR, Cyp21a1, Cyp17a1, Cyp11b1, Hsd3b1). Applicants found that they expressed all enzymes to varying degrees with the exception of Hsd3b1 (FIG. 45D). Applicants therefore tested the expression of other Hsd3b isoforms (Hsd3b3, Hsd3b6) that are capable of steroid biosynthesis and have been reported in mice (Abbaszade et al., 1995; Clarke et al., 1993). Applicants found expression of Hsd3b3 but not Hsd3b6 (FIG. 45D), consistent with previous reports indicating that Hsd3b1 is expressed mainly in the adrenal glands and gonads whereas other steroidogenic tissues express Hsd3b3 (Bain et al., 1991). Applicants further confirmed that tumor-associated monocyte-macrophage lineage cells could produce GC as their production of corticosterone ex vivo was significantly inhibited by Metyrapone (FIG. 37F). Lastly, Applicants administered Metyrapone intra-tumorally to MC38-Ova$^{dim}$ tumor-bearing mice and observed dramatic tumor growth inhibition (FIG. 37G). Applicants analyzed the CD8$^+$ TILs from Metyrapone-treated mice at an early stage of tumor progression, when tumor sizes were not significantly different across groups, and found that their functional properties resembled that of CD8$^+$ TILs from E8i-Cre$^+$ Nr3c1$^{fl/fl}$ mice and LysM-Cre$^+$ Cyp11a1$^{fl/fl}$ mice (FIG. 37H). Collectively, these data indicated that tumor-associated monocyte-macrophage lineage cells were the chief source of GC that shaped anti-tumor effector CD8$^+$ T cell responses in the TME.

Figure 38D:
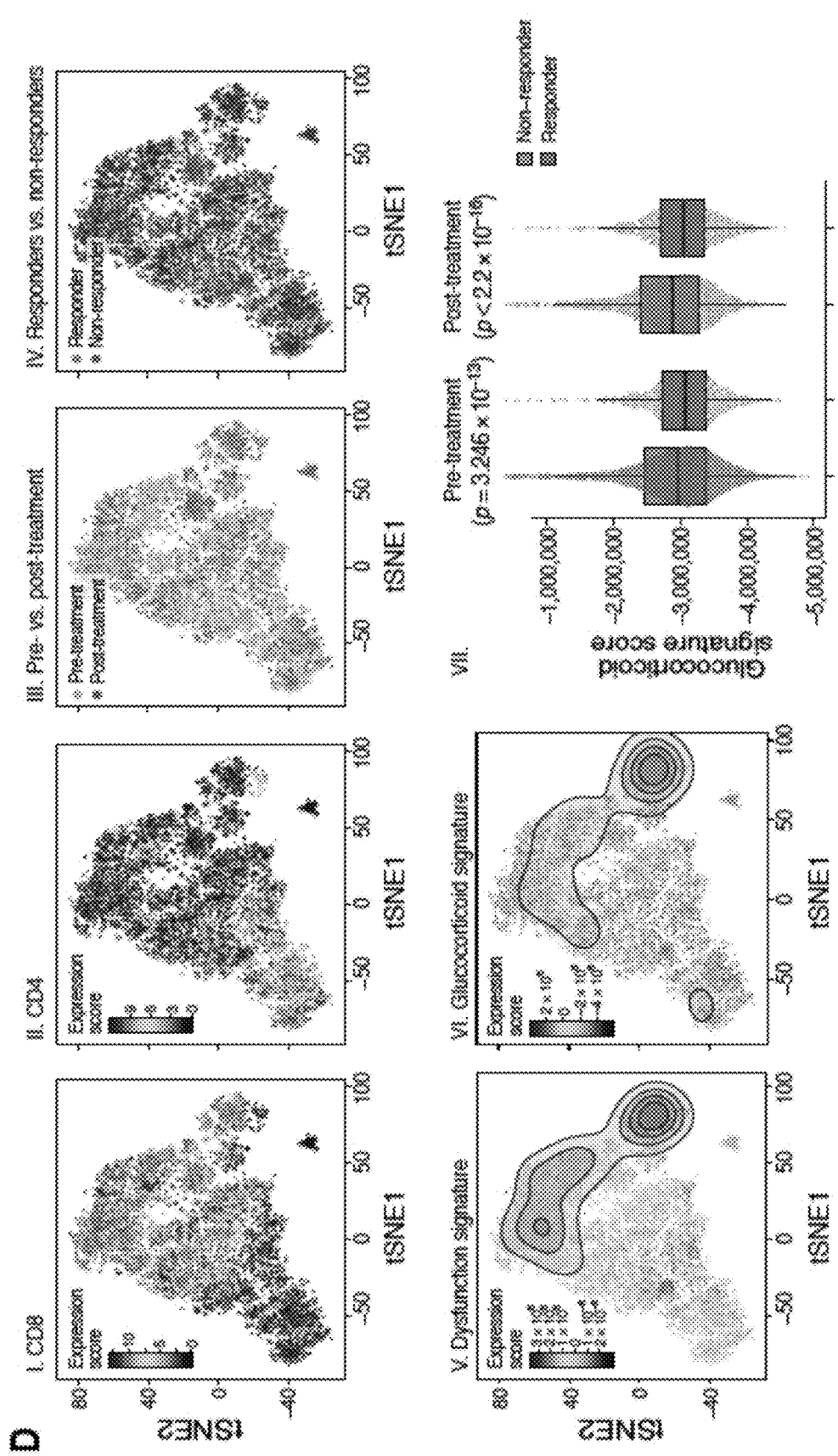

Example 14—Glucocorticoid Signaling in CD8$^+$ T Cells Affects Responses to Immunotherapy The data indicated that steroid signaling in the TME was a key determinant of anti-tumor immunity in murine colon carcinoma. Applicants therefore examined whether steroid abundance impacted on disease outcome in human gastrointestinal cancers. Applicants found that low Cyp11a1 mRNA levels were associated with a substantial survival benefit in patients with colon adenocarcinoma and stomach adenocarcinoma (FIG. 38A). Next, Applicants tested whether steroid signaling affected the response to ICB. Applicants treated WT and E8i-Cre$^+$ Nr3c1$^{fl/fl}$ mice bearing MC38-Ova$^{dim}$ tumors with anti-PD1 and found that the loss of GC signaling in CD8$^+$ T cells dramatically improved the response to anti-PD-1 (FIG. 38B). Conversely, Applicants found that administration of high-dose GC abrogated the response to anti-CTLA-4+anti-PD-1 in MC38 tumor-bearing mice (FIG. 38C). Lastly, Applicants examined the relevance of GC signaling in human cancer. Applicants scored the single-cell data of TILs from melanoma patients pre- and post-ICB (Sade-Feldman et al., 2018) for expression of the GC signature. In line with the observations in B16F10 melanoma (FIG. 33D), Applicants found that the GC signature scored highly in CD8$^+$ TILs that also scored highly for the T cell dysfunction signature (FIG. 38D, panels V and VI). Most importantly, Applicants found that expression of the GC signature in CD8$^+$ TILs positively correlated with non-responsiveness to ICB in both pre- ($p<2.2\times10^{-16}$) and post- ($p=3.246\times10^{-13}$) treatment samples (FIG. 38D, panel VII). Altogether, these data indicated that GC signaling dampened anti-tumor immunity and ICB efficacy.

Figure 39C:
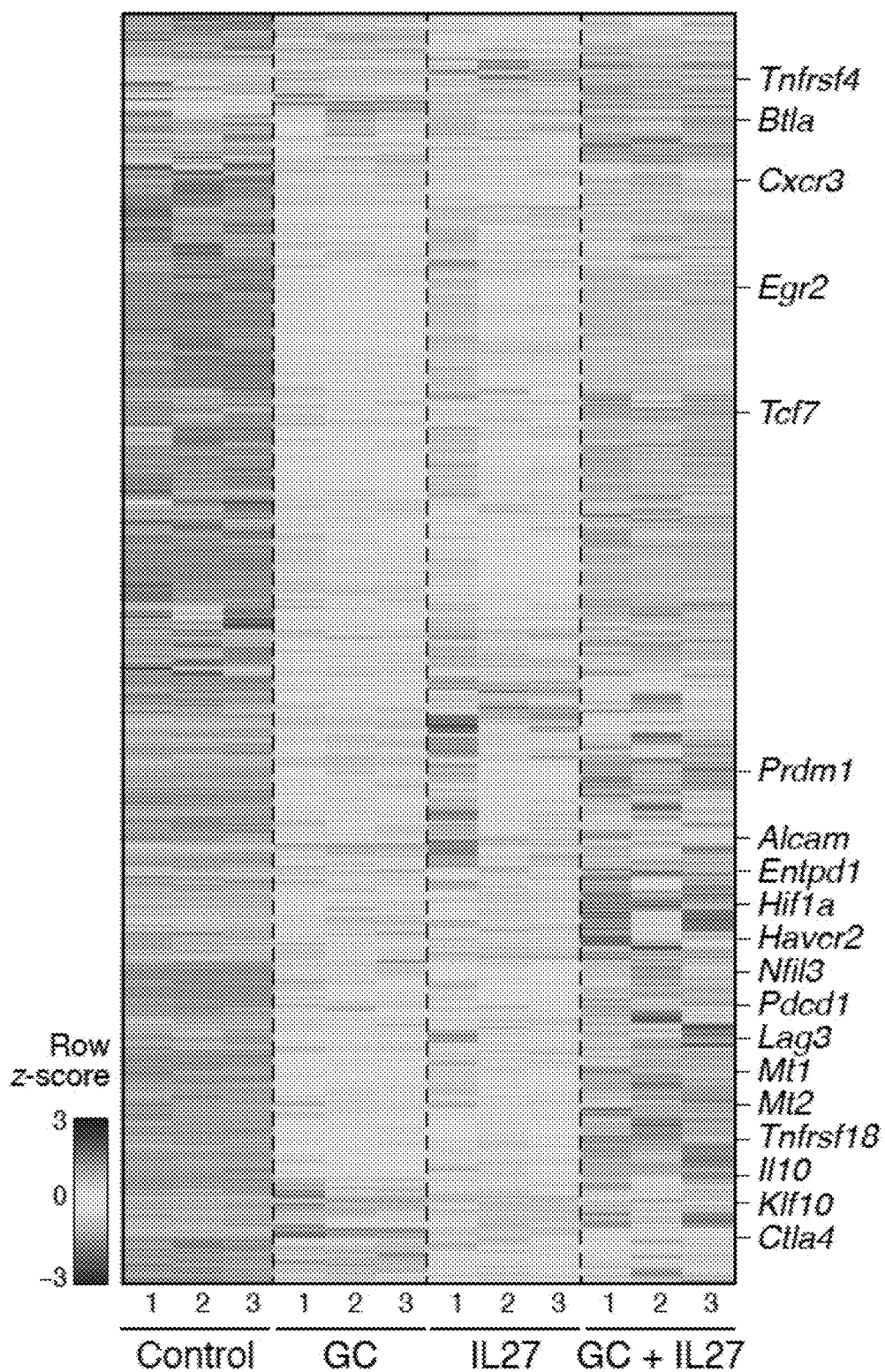

Example 15—Glucocorticoid Signaling can Co-Operate with Other Signaling Pathways to Amplify Immunosuppression in the TME The transactivation of multiple checkpoint receptors and IL-10 by the GR (FIG. 36) were reminiscent of observations from Applicants and others that IL-27 regulates a gene module that includes checkpoint receptors (Tim-3, Lag3, Tigit) and IL-10 and suppresses the responses of CD8$^+$ TILs (Chihara et al., 2018; DeLong et al., 2019; Zhu et al., 2015). GCs have been shown to work in concert with TFs such as the STAT family (Petta et al., 2016) and STAT1 and STAT3 are downstream of IL-27. Applicants therefore examined the relationship of the GC and IL-27 signaling pathways. Unsupervised principle component analysis (PCA) of the RNA profiles from cells treated with GC, IL-27, or both showed that GC and IL-27 each induced a distinct RNA profile with GC+IL-27 treatment inducing the largest transcriptional change relative to control (FIGS. 39A, B and 46A). Examination of differentially expressed (DE) genes across all three conditions relative to control showed some common as well as some distinct genes (FIGS. 39C and 46B). 3,417 out of 6,812 DE genes between GC+IL-27 compared to control genes showed non-additive regulation (FIG. 39C and Table 1) and 1,022 out of 6,812 DE genes overlapped with the dysfunction signature (Table 3 and FIG. 46C). To determine the functional consequences of the GC+IL-27 signaling pathways on T cell effector function in vivo, Applicants crossed E8i-Cre$^+$Nr3c1$^{fl/fl}$ mice with WSX1$^{-/-}$ (IL27ra$^{-/-}$) mice to generate double knock-out (DKO) mice. Applicants isolated CD8$^+$ T cells from WT, E8i-Cre$^+$Nr3c1$^{fl/fl}$, WSX-1$^{-/-}$, or DKO mice and transferred them along with WT CD4$^+$ T cells into Rag-1$^{-/-}$ mice followed by implantation of MC38-Ova$^{dim}$ colon carcinoma. In line with the previous findings, absence of either GC (FIGS. 35A and 43A) or IL-27 signaling (Zhu et al., 2015) alone individually conferred tumor growth control; however, the absence of both pathways led to significantly greater tumor growth inhibition (FIG. 39D). Applicants further identified that TADCs were the main source of IL-27 (p28 and EBi3) in the TME (FIG. 39E). Thus, GC can partner with signaling pathways like IL-27 in CD8$^+$ TILs to further dampen their anti-tumor immune responses.

Example 16—Discussion

Here, Applicants uncovered an immunoregulatory circuit wherein GC production by tumor-associated monocyte-macrophage lineage cells regulates effector differentiation and development of dysfunction in CD8$^+$ TILs. The GR transactivated multiple checkpoint receptors together with IL-10 and repeated T cell activation in the presence of GC induced many dysfunction-associated genes, thus uncovering a mechanism by which GC signaling suppresses immune responses. Importantly, the presence of active GC signaling associated with failure to respond to checkpoint blockade in both pre-clinical models and in melanoma patients (Sade-Feldman et al., 2018), underscoring the clinical relevance of the findings.

The data showing that GC signaling affects both effector transition and the development of dysfunction in CD8+ TILs, raises the issue of how the GR mediates these different effects. It is known that GR-driven regulatory networks are highly cell type context dependent. Further, the GR has also been shown to remodel chromatin (Jubb et al., 2017). Thus, GR-driven transcriptional regulation in a given cellular context may be mediated by at least two non-mutually exclusive mechanisms, chromatin remodeling and partnering with the specific repertoire of TFs present (Weikum et al., 2017). The level of GR expression in a given cell may further influence the extent to which these mechanisms operate. Indeed, Applicants observed a gradient of increasing GR expression and signaling from naïve to dysfunctional CD8+ TILs. It is therefore possible that increasing GR signaling may underlie the orchestration of the distinct transcriptional and epigenetic programs present in naïve, effector, and dysfunctional CD8+ TILs (Pauken et al., 2016; Philip et al., 2017; Sen et al., 2016). Of note, dysfunctional T cells have been shown to have increased chromatin accessibility at regions containing GR motifs (Satpathy et al., 2019).

The findings indicate that low levels of GR signaling during initial T cell activation restrain effector transition by maintaining TCF-1, which is known to regulate effector T cell differentiation (Danilo et al., 2018; Tiemessen et al., 2014). The observed reduction in TCF-1 expression in E8i-Cre+ Nr3c1$^{fl/fl}$ CD8+ TILs is in line with the demonstration by Yu et al. that RNAi of Nr3c1 reduces TCF-1 expression in CD8+ T cells in the context of bacterial infection (Yu et al., 2017). Yu et al. additionally demonstrate a role for the GR in the generation of memory precursor cells, likely via regulation of TCF-1. Applicants do not examine a role for the GR in generating memory, rather, Applicants show that the GR has a role in promoting T cell dysfunction. In this regard, a recent study showed that TCF-1 plays a critical role in maintaining the precursors of dysfunctional T cells in the context of chronic viral infection (Chen et al., 2019). In tumors, TCF-1 is important for maintaining stem-like CD8+ T cells that seed the CD8+ T cell effector pool upon checkpoint blockade (Kurtulus et al., 2019; Siddiqui et al., 2019). This study shows that the loss of GR potentiates the response to checkpoint blockade, indicating that the ability of the stem-like CD8+ T cell pool to seed the effector compartment is not compromised in E8i-Cre+ Nr3c1$^{fl/fl}$ mice. The data are consistent with a model where the loss of GR and GC signaling fine tunes the expression level of TCF-1, thereby accelerating the differentiation of precursors into effector CD8+ T cells that do not develop dysfunction and rather enhance response to checkpoint blockade.

This study focuses on the effects of endogenous GC in the TME; however, exogenous GC is often administered to cancer patients. In glioblastoma patients, Dex is given to prevent cerebral edema. How this impacts the ability of these patients to respond to ICB is not known (Kelly and Gilbert, 2020). GCs are also used as first-line agents for managing immune-related adverse events (IRAEs) (Kumar et al., 2017) associated with ICB. Although initial studies indicated that administration of GCs does not negatively impact therapeutic outcome (Beck et al., 2006; Downey et al., 2007; Johnson et al., 2015; Weber et al., 2008), a recent study comparing patients receiving either low- or high-dose GC for the treatment of IRAEs showed that patients who received high-dose GC had both reduced survival and time to treatment failure (Faje et al., 2018). Similarly, another study has shown reduced overall survival (OS) in melanoma patients who received corticosteroids along with ICB (Tokunaga et al., 2019). Lastly, baseline steroid has also been associated with poor response to PD1-/PD-L1 ICB (Arbour et al., 2018). These observations highlight the need to understand the effects of low- versus high-dose administration of exogenous GCs and how these relate to the effects of endogenous GCs. Notwithstanding these considerations, Applicants observed that patients who fail to respond to ICB (Sade-Feldman et al., 2018) have higher expression of the GC signature. The findings have implications not only for the application of GCs to treat IRAEs in patients receiving checkpoint blockade but also suggest the application of either GC synthesis or signaling inhibitors to improve anti-tumor immune responses either alone or in combination with other modalities.

Example 17—Methods and Material

Data and Code Availability

The RNA-Sequencing datasets generated during this study are available at Gene Expression Omnibus (GEO) Repository with accession code GSE153556.

Experimental Model and Subject Details

Mice. 6-8 week old male or female C57BL/6, Nr3c1$^{fl/fl}$, Rag1$^{-/-}$, E8iCre, WSX1$^{-/-}$ and LysM-Cre transgenic mice were purchased from the Jackson Laboratory. Nr3c1$^{fl/fl}$ was crossed to E8iCre and/or E8iCre×WSX1$^{-/-}$. Cryopreserved sperm from males bearing a targeted Cyp11a1 allele were obtained from EUCOMM and used to fertilize C57BL/6 oocytes. Heterozygote progeny were confirmed by PCR and bred to mice that express the FlpO recombinase (MMRC, UC Davis) to remove the neomycin resistance cassette followed by breeding with LysM-Cre. All mice were housed under SPF conditions. All experiments involving laboratory animals were performed under protocols approved by the Harvard Medical Area Standing Committee on Animals (Boston, Mass.).

Collection of colorectal carcinoma patient specimens. Primary colorectal carcinoma specimens were obtained under informed consent from untreated patients undergoing surgical resection at the Brigham and Women's/Dana Farber Cancer Center and Massachusetts General Hospital (IRB protocol 03-189 and 02-240). Freshly resected CRC tumors and adjacent normal colon were recovered in Medium 199 (Thermo Fisher) supplemented with 2% heat-inactivated FCS (Sigma Aldrich) and stored briefly on ice.

Tumor cell lines used. MC38-Ova$^{dim}$ was generously provided by Mark Smyth. B16F10 was purchased from ATCC. MC38 was generously provided by Carla Rothlin. MC38-Ova$^{dim}$-GFP was generated in Applicants lab as follows, HEK293T cells were transfected with pLenti PGK GFP Puro plasmid. The resulting Lentivirus was then used to infect Mc38Ova$^{dim}$ cell line to generate a GFP expressing cell line. MC38-Ova$^{dim}$ (0.5×10$^6$) or B16F10 (0.25×10$^6$) and MC38-Ova$^{dim}$-GFP (0.5×10$^6$) cells were implanted subcutaneously into the right flank of mice.

Method Details

Cell culture and treatment with glucocorticoid. CD8+ T cells from splenocytes and lymph nodes were isolated using CD8 microbeads (Miltenyi). Cells were further stained with antibodies against CD8, CD62L and CD44, and CD8+ CD62L$^{hi}$CD44$^-$ naive cells were sorted by BD FacsAria (BD Biosciences). Sorted cells were cultured for 9 days as described below in DMEM supplemented with 10% (vol/ vol) FCS, 50 mM mercaptoethanol, 1 mM sodium pyruvate, nonessential amino acids, L-glutamine, and 100 U/ml penicillin and 100 g/ml streptomycin. Specifically, naive $CD8^+$ cells were stimulated with plate bound anti-CD3 (145-2C11, 1 µg/ml) and anti-CD28 (PV-1, 1 g/ml) in the presence of either 10 nM dexamethasone (Sigma), 100 nM Corticosterone (Fisher Scientific), 25 ng/ml IL-27 (R&D), or both dexamethasone and IL27 for 3 days. Cells were then rested in the presence of 5 ng/ml IL2 (Miltenyi) for 3 days followed by re-stimulation with plate bound anti-CD3 (145-2C11, 1 µg/ml) and anti-CD28 (PV-1, 1 g/ml) in the presence of either 10 nM dexamethasone (Sigma), 100 nM Corticosterone (Fisher Scientific), 25 ng/ml IL-27 (R&D), or both dexamethasone and IL27 for an additional 3 days.

Human $CD8^+$ T cell culture. Peripheral blood was procured from healthy volunteers. Mononuclear cells were enriched by density gradient centrifugation on Ficoll-Paque PLUS (GE Healthcare) in SepMate-50 tubes (Stem Cell Technologies). $CD8^+$ T cells were isolated from PBMCs using CD8 microbeads (Miltenyi) according to manufacturer protocol. Cells were further stained with antibodies against CD8, CD62L, CCR7 and CD45RA. Naïve cells $CD8^+CD62L^{hi}CCR7^+CD45RA^+$ cells were sorted by BD FacsAria (BD Biosciences). Sorted $CD8^+$ T cells were cultured for 9 days in RPMI supplemented with 10% (vol/vol) autologous heat-inactivated serum, 1 mM sodium pyruvate, 1× nonessential amino acids, 2 mM L-glutamine, 100 U/ml penicillin, and 100 g/ml streptomycin. Naïve $CD8^+$ cells were stimulated with plate-bound anti-CD3 (Biolegend, clone UCHT1, 1 µg/ml) and anti-CD28 (Biolegend, clone CD28.2, 1 µg/ml) in the presence of 10 nM dexamethasone (Sigma) or vehicle control for 3 days. Cells were then rested in the presence of 100 U/ml IL2 (R&D Systems) for 3 days. Next, the cells were re-stimulated with plate-bound anti-CD3 (1 µg/ml) and anti-CD28 (1 g/ml) in the presence of either 10 nM dexamethasone (Sigma) or vehicle control for 3 days.

Tumor experiments. Tumor size was measured in two dimensions by caliper and is expressed as the product of two perpendicular diameters. In some experiments, mice were treated with anti-PD-1 (RMP1-14) (100 mg per mouse) antibodies or control immunoglobulin (Rat IgG2a) i.p. on days 5, 8 and 11 post-tumor implantation. Mice were then monitored for tumor growth. In some experiments, mice were treated with dexamethasone (Sigma) (10 mg/kg) or anti-PD1 (RMP1-14)+anti-CTLA-4 (9H10) (8 mg/kg) or both on Day 7 post-tumor implantation. Antibodies were administered bi-weekly for a total of 5 treatments (n=9-10). Dexamethasone was administered for 10 consecutive days.

Isolation of TILs. TILs were isolated by dissociating tumor tissue in the presence of collagenase D (2.5 mg/ml) for 20 minutes prior to centrifugation on a discontinuous Percoll gradient (GE Healthcare). Isolated cells were then used in various assays.

Flow cytometry. Single cell suspensions were stained with antibodies against surface molecules. For murine samples, antibodies against CD4 (RM4-5), CD8 (53-6.7), CD107a (1D4B), PD-1 (RMP1-30) CD45 (30-F11), CD3 (145-2C11), CD19 (6D5), NK1.1 (V=PK136), Ly-6C (HK1.4), Ly-6G (1A8), CD11b (M1/70), CD11c (N418), CD24 (M1/69), I-A/I-E (M5/114.15.2), F4/80 (BM8) CD103 (2E7), CD45.1 (A20), CD45.2 (104) were purchased from BioLegend. Antibodies against LAG-3 (C9B7W), Gzmb (NGZB) and Tigit (GIGD7) were purchased from eBioscience. Anti-Tim-3 (5D12) antibody was generated in house. Antibody against GR (G5) was purchased from Santa Cruz. Antibody against Siglec-F (E50-2440) was purchased from BD Biosciences. For human samples, antibodies against CD3 (UCHT1), CD8a (RPA-T8), Tim-3 (F38-2E2), PD-1 (EH12.2H7) Lag-3 (11C3C65), CCR7 (G043H7), CD62L(DREG-56) and CD45RA(HI100) were purchased from Biolegend and antibody against TIGIT (MBSA43) was purchased from Thermo Fisher. Fixable viability dye eF506 (eBioscience) or Zombie UV dye (Biolegend) were used to exclude dead cells. For GR staining, eBioscience Foxp3/transcription factor staining buffer set was used as per manufacturer's protocol. For intra-cellular cytokine (ICC) staining of $CD8^+$ T cells in culture in vitro, cells were stimulated with phorbol-12-myristate 13-acetate (PMA) (50 ng/ml, Sigma-Aldrich) and ionomycin (1 µg/ml, Sigma-Aldrich) in the presence of Golgi Plug (BD Biosciences) and Golgi Stop (BD Biosciences) for four hours prior to cell surface and ICC staining. For intra-cytoplasmic cytokine staining of TILs, cells were stimulated in vitro with 5 µg/ml OVA257-264 peptide (Sigma-Aldrich) for 4 hrs in the presence of Golgi stop (BD Biosciences) and Golgi Plug (BD Biosciences) prior to cell surface and ICC staining. Importantly, antibody detecting CD107a (1D4B) was added to the cells during stimulation. Following fixation and permeabilization, staining with antibodies against the following was performed for murine samples: IL-2 (JES6-5H4), TNF-α (MP6-XT22), IFN-g (XMG-1.2) and Granzyme B (GB11) were purchased from Biolegend. Antigen specific T cells were determined by H-2 Kb/OVA257-264 dextramer staining following the manufacturer's protocol (Immudex). Cell proliferation was studied using CellTrace violet (Thermo Fisher Scientific) following manufacturer's protocol. All data were collected on a BD LsrII (BD Biosciences) or Fortessa (BD Biosciences) and analyzed with FlowJo 10.4.2 software (TreeStar).

Adoptive transfers. For adoptive transfer experiments, $CD4^+$ ($FOXP3^+$ and $FOXP3^-$) and $CD8^+$ T cells from either WT, WT (CD45.1), $Nr3c1^{fl/fl}$ E8iCre, $WSX1^{-/-}$ or $Nr3c1^{fl/fl}$ $E8iCre^+WSX1^{-/-}$ (dKO) mice were isolated by cell sorting using a BD FACSAria. A total of $1.5\times10^6$ cells at a ratio of 1:0.5 (CD4/CD8) was mixed in PBS and injected i.v. into $Rag^{-/-}$ mice. Two days later, mice were implanted with MC38-$Ova^{dim}$ colon carcinoma cells and followed for tumor growth.

In vivo and in vitro modulation of glucocorticoid synthesis. MC38-$Ova^{dim}$ was implanted in wild type C57BL/6 mice and either Metyrapone (50 mg/kg; Fisher Scientific), Corticosterone (2.5 mg/kg) or vehicle control PBS (Gibco) was administered intra-tumorally on Day 5, 6, 7 and 9 post-tumor implantation. In some experiments, MC38-$Ova^{dim}$ tumor explants or sorted $lin^-CD45^+CD24^-$ cells were cultured in the presence or absence of Metyrapone (25 or 50 ng/ml) for 24 hrs. Supernatants were harvested and corticosterone measured by ELISA (Arbor Assays).

Measurement of corticosterone in tissue extracts. Organic phase extraction using acetonitrile and hexane (1:2) was employed to extract steroids from tissues followed by examination of corticosterone (Arbor Assays) and/or pregnenolone (Abnova) by ELISA.

Luciferase assays. HEK293T cells were transfected with firefly luciferase reporter constructs for IL-10, PD1, Tim3, Lag3 or Tigit, together with Renilla luciferase reporter as internal control and plasmids expressing Nr3c1 or empty control vector. Dex or vehicle control was added to the culture 24 hrs after transfection. Cells were analyzed at 24 hrs after the addition of Dex with the dual luciferase assay kit (Promega). Fragments containing the proximal IL10 promoter (−1.5 kb including the HSS-0.12 site), and the $HSS^+2.98$ region followed by of the IL10 minimal promoter were cloned into pGL4.10 Luciferase reporter plasmid (Promega). Fragments containing the cis-regulatory elements for the Havcr2 (chr11: 46474049-46474628, mm10) Pdcd1 (TSS+15 kb, chr1: 94034621-94036002, mm10), Tigit (proximal promoter, −2.5 kb) and Lag3 (chr6: 124901592-124902407, mm10) loci were cloned into pGL4.23 Luciferase reporter plasmid (Promega).

Quantitative PCR. Total RNA was extracted using RNeasy columns (Qiagen) or PicoPure™ RNA Isolation Kit (Thermo Fischer). Reverse transcription of mRNA was performed in a thermal cycler (Bio-Rad) using iScript cDNA Synthesis Kit (Bio-Rad) or SuperScript™ VILO™ cDNA Synthesis Kit (Thermo Fischer). qPCR was performed in the Vii7 Real-Time PCR system (Applied Biosystems) using the primers for Taqman gene expression (Applied Biosystems). Data were normalized to the expression of Actb.

RNA-Seq. 1,000 cells were sorted into 5 µL of Buffer TCL (Qiagen) supplemented with 1% 2 mercaptoethanol. Plates were thawed on ice for one minute and spun down at 2,000 rpm for one minute. Immediately following, RNA lysate was purified using a 2.2×RNAClean SPRI bead ratio (Beckman Coulter Genomics). The RNA captured beads were processed using a modified SMART-Seq2 protocol (Picelli et al., 2013) entailing RNA secondary structure denaturation (72° C. for three minutes), reverse transcription with Maxima Reverse Transcriptase (Life Technologies), and whole-transcription amplification (WTA) with KAPA HiFi HotStart ReadyMix 2X (Kapa Biosystems) for 11 cycles. WTA products were purified with Ampure XP beads (Beckman Coulter), quantified with a Qubit dsDNA HS Assay Kit (ThermoFisher), and quality accessed with a high-sensitivity DNA chip (Agilent). 0.2 ng of purified WTA product was used as input for the Nextera XT DNA Library Preparation Kit (Illumina). Uniquely barcoded libraries were pooled and sequenced with a NextSeq 500 high output V2 75 cycle kit (Illumina) using 38 and 38 paired end reads (Picelli et al., 2013).

Computational Analyses

Signature scoring in single cells. $CD8^+$ TILs single-cell data were obtained and processed as previously described (Singer et al., 2016). Briefly, Briefly, paired reads were mapped to mouse annotation mm10 using Bowtie (Langmead et al., 2009) (allowing a maximum of one mismatch in seed alignment, and suppressing reads that had more than 10 valid alignments) and TPMs were computed using RSEM (Li and Dewey, 2011), and log 2(TPM+1) values were used for subsequent analyses. Next, Applicants filtered out low quality cells and cell doublets, maintaining for subsequent analysis the 588 cells that had (1) 1,000-4,000 detected genes (defined by at least one mapped read), (2) at least 200,000 reads mapped to the transcriptome, and at least 50% of the reads mapped to the transcriptome. Here, Applicants restricted the genes considered in subsequent analyses to be the 7,790 genes expressed at log 2(TPM+1) R 2 in at least ten percent of the cells. After removal of low-quality cells/ genes, the data were normalized using quantile normalization followed by PCA. PCs 1-8 were chosen for subsequent analysis due to a drop in the proportion of variance explained following PC8. Applicants used to visualize single cells in a two-dimensional non-linear embedding. To score each cell for a gene signature, expression data was initially scaled by calculating the z-score across each gene. For each gene signature, a cell-specific signature score was computed by first sorting the normalized scaled gene expression values for each cell followed by summing up the indices (ranks) of the signature genes. For signatures consisting of an induced and suppressed set of genes, two ranking scores were obtained separately, and the suppressed associated signature score was subtracted from the induced generated signature score. A contour plot was added on top of the tSNE space, which takes into account only those cells that have a signature score above the indicated threshold to further emphasize the region of highly scored cells.

RNA-Seq data pre-processing. RNA-seq reads were aligned using Tophat (Trapnell et al., 2009) (to mouse genome version mm9), and expression levels were calculated using RSEM (Li and Dewey, 2011) using annotated transcripts (mm9), followed by further processing using the Bioconductor package DESeq in R(Anders and Huber, 2010). The data was normalized using TMM normalization, and differentially expressed genes were defined using the differential expression pipeline on the raw counts with a single call to the function DESeq (FDR- adjusted p-value <0.05). Heatmap figures were generated using pheatmap package (Kolde and Vilo, 2015) and clustered using Euclidean distance.

Analysis of additive and non-additive effects. To test whether the glucocorticoid and IL-27 signaling pathways had additive or non-additive effects on gene expression, Applicants stimulated naïve $CD8^+$ T cells in the presence of Dex, IL-27, or Dex+IL-27 in vitro. Applicants tested for non-additive effects between IL-27 and glucocorticoid signaling using a negative binomial generalized linear model in order to account for both estimations of the mean and the dispersion across conditions, where dispersion describes the relationship between the mean and variance. The model was applied to the expression data using ANOVA between a model that takes into account the interaction between IL27 and Dex versus no interaction. Applicants found that 1,675 out of 3,496 differentially expressed genes (adjusted $P<0.05$, likelihood ratio test and false discovery rate (FDR) correction) between control and Dex+IL-27 stimulated CD8+ cells have non-additive effects.

Analysis of human TILs for GC+IL27 signature. Data was downloaded from (Sade-Feldman et al., 2018) in a in log 2(TPM+1) format. PCA was performed after removal of non-expressed genes. PCs 1-8 were chosen for subsequent analysis due to a drop in the proportion of variance explained following PC8. Applicants used tSNE (Maaten, 2008) to visualize single cells in a two-dimensional non-linear embedding. The glucocorticoid signature was projected onto single cell RNA profiles of TILs from 48 melanoma patients treated with checkpoint blockade (with 35 anti-PD-1, 11 anti-CTLA4+PD-1, and 2 anti-CTLA4 samples)(Sade-Feldman et al., 2018).

Statistical analysis. Significant differences between two groups were analyzed using GraphPad Prism 8 using paired or unpaired two-tailed Student's t test or in case of multiple groups one-way or two-way ANOVA with multiple testing (Tukey). Tumor growth curves were analyzed using linear mixed effects models to test the trajectory of growth between various genotypes or treatments over time controlling for mouse. Differentially expressed genes following RNA-seq were defined using the differential expression pipeline on the raw counts with a single call to the function DESeq (FDR- adjusted p-value <0.05). Values of *$p<0.05$, $p<0.01$, *$p<0.001$ and **** $p<0.0001$ were considered statistically significant.

REFERENCES

Abbaszade, I. G., Clarke, T. R., Park, C. H., and Payne, A. H. (1995). The mouse 3 beta-hydroxysteroid dehydrogenase multigene family includes two functionally distinct groups of proteins. Mol Endocrinol 9, 1214-1222.

Anders, S., and Huber, W. (2010). Differential expression analysis for sequence count data. Genome biology 11, R106.

Arbour, K. C., Mezquita, L., Long, N., Rizvi, H., Auclin, E., Ni, A., Martinez-Bernal, G., Ferrara, R., Lai, W. V., Hendriks, L. E. L., et al. (2018). Impact of Baseline Steroids on Efficacy of Programmed Cell Death-1 and Programmed Death-Ligand 1 Blockade in Patients With Non-Small-Cell Lung Cancer. J Clin Oncol 36, 2872-2878.

Arriza, J. L., Weinberger, C., Cerelli, G., Glaser, T. M., Handelin, B. L., Housman, D. E., and Evans, R. M. (1987). Cloning of human mineralocorticoid receptor complementary DNA: structural and functional kinship with the glucocorticoid receptor. Science 237, 268-275.

Auphan, N., DiDonato, J. A., Rosette, C., Helmberg, A., and Karin, M. (1995). Immunosuppression by glucocorticoids: inhibition of NF-kappa B activity through induction of I kappa B synthesis. Science 270, 286-290.

Bain, P. A., Yoo, M., Clarke, T., Hammond, S. H., and Payne, A. H. (1991). Multiple forms of mouse 3 beta-hydroxysteroid dehydrogenase/delta 5-delta 4 isomerase and differential expression in gonads, adrenal glands, liver, and kidneys of both sexes. Proc Natl Acad Sci USA 88, 8870-8874.

Barrat, F. J., Cua, D. J., Boonstra, A., Richards, D. F., Crain, C., Savelkoul, H. F., de Waal-Malefyt, R., Coffman, R. L., Hawrylowicz, C. M., and O'Garra, A. (2002). In vitro generation of interleukin 10-producing regulatory CD4(+) T cells is induced by immunosuppressive drugs and inhibited by T helper type 1 (Th1)- and Th2-inducing cytokines. J Exp Med 195, 603-616.

Beck, K. E., Blansfield, J. A., Tran, K. Q., Feldman, A. L., Hughes, M. S., Royal, R. E., Kammula, U. S., Topalian, S. L., Sherry, R. M., Kleiner, D., et al. (2006). Enterocolitis in patients with cancer after antibody blockade of cytotoxic T-lymphocyte-associated antigen 4. J Clin Oncol 24, 2283-2289.

Bianchi, M., Meng, C., and Ivashkiv, L. B. (2000). Inhibition of IL-2-induced Jak-STAT signaling by glucocorticoids. Proc Natl Acad Sci USA 97, 9573-9578.

Brattsand, R., and Linden, M. (1996). Cytokine modulation by glucocorticoids: mechanisms and actions in cellular studies. Aliment Pharmacol Ther 10 Suppl 2, 81-90; discussion 91-82.

Cain, D. W., and Cidlowski, J. A. (2017). Immune regulation by glucocorticoids. Nat Rev Immunol 17, 233-247.

Carey, K. T., Tan, K. H., Ng, J., Liddicoat, D. R., Godfrey, D. I., and Cole, T. J. (2013). Nfil3 is a glucocorticoid-regulated gene required for glucocorticoid-induced apoptosis in male murine T cells. Endocrinology 154, 1540-1552.

Cass, C. L., Johnson, J. R., Califf, L. L., Xu, T., Hernandez, H. J., Stadecker, M. J., Yates, J. R., 3rd, and Williams, D. L. (2007). Proteomic analysis of Schistosoma mansoni egg secretions. Mol Biochem Parasitol 155, 84-93.

Chen, X., Oppenheim, J. J., Winkler-Pickett, R. T., Ortaldo, J. R., and Howard, O. M. (2006). Glucocorticoid amplifies IL-2-dependent expansion of functional FoxP3(+) CD4(+)CD25(+) T regulatory cells in vivo and enhances their capacity to suppress EAE. Eur J Immunol 36, 2139-2149.

Chen, Z., Ji, Z., Ngiow, S. F., Manne, S., Cai, Z., Huang, A. C., Johnson, J., Staupe, R. P., Bengsch, B., Xu, C., et al. (2019). TCF-1-Centered Transcriptional Network Drives an Effector versus Exhausted CD8 T Cell-Fate Decision. Immunity 51, 840-855 e845.

Chihara, N., Madi, A., Kondo, T., Zhang, H., Acharya, N., Singer, M., Nyman, J., Marjanovic, N. D., Kowalczyk, M. S., Wang, C., et al. (2018). Induction and transcriptional regulation of the co-inhibitory gene module in T cells. Nature 558, 454-459.

Clarke, T. R., Bain, P. A., Greco, T. L., and Payne, A. H. (1993). A novel mouse kidney 3 beta-hydroxysteroid dehydrogenase complementary DNA encodes a 3-ketosteroid reductase instead of a 3 beta-hydroxysteroid dehydrogenase/delta 5-delta 4-isomerase. Mol Endocrinol 7, 1569-1578.

Coutinho, A. E., and Chapman, K. E. (2011). The anti-inflammatory and immunosuppressive effects of glucocorticoids, recent developments and mechanistic insights. Mol Cell Endocrinol 335, 2-13.

Danilo, M., Chennupati, V., Silva, J. G., Siegert, S., and Held, W. (2018). Suppression of Tcf1 by Inflammatory Cytokines Facilitates Effector CD8 T Cell Differentiation. Cell Rep 22, 2107-2117.

DeLong, J. H., O'Hara Hall, A., Rausch, M., Moodley, D., Perry, J., Park, J., Phan, A. T., Beiting, D. P., Kedl, R. M., Hill, J. A., and Hunter, C. A. (2019). IL-27 and TCR Stimulation Promote T Cell Expression of Multiple Inhibitory Receptors. Immunohorizons 3, 13-25.

Dodd, D., Spitzer, M. H., Van Treuren, W., Merrill, B. D., Hryckowian, A. J., Higginbottom, S. K., Le, A., Cowan, T. M., Nolan, G. P., Fischbach, M. A., and Sonnenburg, J. L. (2017). A gut bacterial pathway metabolizes aromatic amino acids into nine circulating metabolites. Nature 551, 648-652.

Downey, S. G., Klapper, J. A., Smith, F. O., Yang, J. C., Sherry, R. M., Royal, R. E., Kammula, U. S., Hughes, M. S., Allen, T. E., Levy, C. L., et al. (2007). Prognostic factors related to clinical response in patients with metastatic melanoma treated by CTL-associated antigen-4 blockade. Clin Cancer Res 13, 6681-6688.

Faje, A. T., Lawrence, D., Flaherty, K., Freedman, C., Fadden, R., Rubin, K., Cohen, J., and Sullivan, R. J. (2018). High-dose glucocorticoids for the treatment of ipilimumab-induced hypophysitis is associated with reduced survival in patients with melanoma. Cancer 124, 3706-3714.

Fourcade, J., Sun, Z., Benallaoua, M., Guillaume, P., Luescher, I. F., Sander, C., Kirkwood, J. M., Kuchroo, V., and Zarour, H. M. (2010). Upregulation of Tim-3 and PD-1 expression is associated with tumor antigen-specific CD8+ T cell dysfunction in melanoma patients. J Exp Med 207, 2175-2186.

Hu, Y., Tian, W., Zhang, L. L., Liu, H., Yin, G. P., He, B. S., and Mao, X. M. (2012). Function of regulatory T-cells improved by dexamethasone in Graves' disease. Eur J Endocrinol 166, 641-646.

Im, S. J., Hashimoto, M., Gerner, M. Y., Lee, J., Kissick, H. T., Burger, M. C., Shan, Q., Hale, J. S., Lee, J., Nasti, T. H., et al. (2016). Defining CD8+ T cells that provide the proliferative burst after PD-1 therapy. Nature 537, 417-421.

Jin, H. T., Anderson, A. C., Tan, W. G., West, E. E., Ha, S. J., Araki, K., Freeman, G. J., Kuchroo, V. K., and Ahmed, R. (2010). Cooperation of Tim-3 and PD-1 in CD8 T-cell exhaustion during chronic viral infection. Proc Natl Acad Sci USA 107, 14733-14738.

Johnson, D. B., Friedman, D. L., Berry, E., Decker, I., Ye, F., Zhao, S., Morgans, A. K., Puzanov, I., Sosman, J. A., and Lovly, C. M. (2015). Survivorship in Immune Therapy:

Assessing Chronic Immune Toxicities, Health Outcomes, and Functional Status among Long-term Ipilimumab Survivors at a Single Referral Center. Cancer Immunol Res 3, 464-469.

Jonat, C., Rahmsdorf, H. J., Park, K. K., Cato, A. C., Gebel, S., Ponta, H., and Herrlich, P. (1990). Antitumor promotion and antiinflammation: down-modulation of AP-1 (Fos/Jun) activity by glucocorticoid hormone. Cell 62, 1189-1204.

Jubb, A. W., Boyle, S., Hume, D. A., and Bickmore, W. A. (2017). Glucocorticoid Receptor Binding Induces Rapid and Prolonged Large-Scale Chromatin Decompaction at Multiple Target Loci. Cell Rep 21, 3022-3031.

Karin, M., and Herschman, H. R. (1979). Dexamethasone stimulation of metallothionein synthesis in HeLa cell cultures. Science 204, 176-177.

Karwacz, K., Miraldi, E. R., Pokrovskii, M., Madi, A., Yosef, N., Wortman, I., Chen, X., Watters, A., Carriero, N., Awasthi, A., et al. (2017). Critical role of IRF1 and BATF in forming chromatin landscape during type 1 regulatory cell differentiation. Nat Immunol 18, 412-421.

Kelly, W. J., and Gilbert, M. R. (2020). Glucocorticoids and immune checkpoint inhibitors in glioblastoma. J Neurooncol.

Kolde, R., and Vilo, J. (2015). GOsummaries: an R Package for Visual Functional Annotation of Experimental Data. F1000Research 4, 574.

Kumar, V., Chaudhary, N., Garg, M., Floudas, C. S., Soni, P., and Chandra, A. B. (2017). Current Diagnosis and Management of Immune Related Adverse Events (irAEs) Induced by Immune Checkpoint Inhibitor Therapy. Front Pharmacol 8, 49.

Kurtulus, S., Madi, A., Escobar, G., Klapholz, M., Nyman, J., Christian, E., Pawlak, M., Dionne, D., Xia, J., Rozenblatt-Rosen, O., et al. (2019). Checkpoint Blockade Immunotherapy Induces Dynamic Changes in PD-1(−) CD8(+) Tumor-Infiltrating T Cells. Immunity 50, 181-194 e186.

Langmead, B., Trapnell, C., Pop, M., and Salzberg, S. L. (2009). Ultrafast and memory-efficient alignment of short DNA sequences to the human genome. Genome Biol 10, R25.

Li, B., and Dewey, C. N. (2011). RSEM: accurate transcript quantification from RNA-Seq data with or without a reference genome. BMC Bioinformatics 12, 323.

Li, B., Severson, E., Pignon, J. C., Zhao, H., Li, T., Novak, J., Jiang, P., Shen, H., Aster, J. C., Rodig, S., et al. (2016). Comprehensive analyses of tumor immunity: implications for cancer immunotherapy. Genome Biol 17, 174.

Ling, Y., Cao, X., Yu, Z., and Ruan, C. (2007). Circulating dendritic cells subsets and CD4+Foxp3+ regulatory T cells in adult patients with chronic ITP before and after treatment with high-dose dexamethasome. Eur J Haematol 79, 310-316.

Maaten, L. v. d., and Hinton, G. (2008). Visualizing Data using t-SNE. J Machine Learning Research 9, 2579-2605.

Miller, B. C., Sen, D. R., Al Abosy, R., Bi, K., Virkud, Y. V., LaFleur, M. W., Yates, K. B., Lako, A., Felt, K., Naik, G. S., et al. (2019). Subsets of exhausted CD8(+) T cells differentially mediate tumor control and respond to checkpoint blockade. Nat Immunol 20, 326-336.

Munck, A., Guyre, P. M., and Holbrook, N. J. (1984). Physiological functions of glucocorticoids in stress and their relation to pharmacological actions. Endocr Rev 5, 25-44.

Oakley, R. H., and Cidlowski, J. A. (2013). The biology of the glucocorticoid receptor: new signaling mechanisms in health and disease. J Allergy Clin Immunol 132, 1033-1044.

Oh, K. S., Patel, H., Gottschalk, R. A., Lee, W. S., Baek, S., Fraser, I. D. C., Hager, G. L., and Sung, M. H. (2017). Anti-Inflammatory Chromatinscape Suggests Alternative Mechanisms of Glucocorticoid Receptor Action. Immunity 47, 298-309 e295.

Pauken, K. E., Sammons, M. A., Odorizzi, P. M., Manne, S., Godec, J., Khan, O., Drake, A. M., Chen, Z., Sen, D. R., Kurachi, M., et al. (2016). Epigenetic stability of exhausted T cells limits durability of reinvigoration by PD-1 blockade. Science 354, 1160-1165.

Payne, A. H., and Hales, D. B. (2004). Overview of steroidogenic enzymes in the pathway from cholesterol to active steroid hormones. Endocr Rev 25, 947-970.

Petta, I., Dejager, L., Ballegeer, M., Lievens, S., Tavernier, J., De Bosscher, K., and Libert, C. (2016). The Interactome of the Glucocorticoid Receptor and Its Influence on the Actions of Glucocorticoids in Combatting Inflammatory and Infectious Diseases. Microbiol Mol Biol Rev 80, 495-522.

Philip, M., Fairchild, L., Sun, L., Horste, E. L., Camara, S., Shakiba, M., Scott, A. C., Viale, A., Lauer, P., Merghoub, T., et al. (2017). Chromatin states define tumour-specific T cell dysfunction and reprogramming. Nature 545, 452-456.

Phuc Le, P., Friedman, J. R., Schug, J., Brestelli, J. E., Parker, J. B., Bochkis, I. M., and Kaestner, K. H. (2005). Glucocorticoid receptor-dependent gene regulatory networks. PLoS Genet 1, e16.

Picelli, S., Bjorklund, A. K., Faridani, O. R., Sagasser, S., Winberg, G., and Sandberg, R. (2013). Smart-seq2 for sensitive full-length transcriptome profiling in single cells. Nat Methods 10, 1096-1098.

Piemonti, L., Monti, P., Allavena, P., Sironi, M., Soldini, L., Leone, B. E., Socci, C., and Di Carlo, V. (1999). Glucocorticoids affect human dendritic cell differentiation and maturation. J Immunol 162, 6473-6481.

Quatrini, L., Wieduwild, E., Escaliere, B., Filtjens, J., Chasson, L., Laprie, C., Vivier, E., and Ugolini, S. (2018). Endogenous glucocorticoids control host resistance to viral infection through the tissue-specific regulation of PD-1 expression on NK cells. Nat Immunol 19, 954-962.

Rhen, T., and Cidlowski, J. A. (2005). Antiinflammatory action of glucocorticoids—new mechanisms for old drugs. N Engl J Med 353, 1711-1723.

Rutishauser, R. L., Martins, G. A., Kalachikov, S., Chandele, A., Parish, I. A., Meffre, E., Jacob, J., Calame, K., and Kaech, S. M. (2009). Transcriptional repressor Blimp-1 promotes CD8(+) T cell terminal differentiation and represses the acquisition of central memory T cell properties. Immunity 31, 296-308.

Sade-Feldman, M., Yizhak, K., Bjorgaard, S. L., Ray, J. P., de Boer, C. G., Jenkins, R. W., Lieb, D. J., Chen, J. H., Frederick, D. T., Barzily-Rokni, M., et al. (2018). Defining T Cell States Associated with Response to Checkpoint Immunotherapy in Melanoma. Cell 175, 998-1013 e1020.

Sakuishi, K., Apetoh, L., Sullivan, J. M., Blazar, B. R., Kuchroo, V. K., and Anderson, A. C. (2010). Targeting Tim-3 and PD-1 pathways to reverse T cell exhaustion and restore anti-tumor immunity. J Exp Med 207, 2187-2194.

Satpathy, A. T., Granja, J. M., Yost, K. E., Qi, Y., Meschi, F., McDermott, G. P., Olsen, B. N., Mumbach, M. R., Pierce, S. E., Corces, M. R., et al. (2019). Massively parallel single-cell chromatin landscapes of human immune cell development and intratumoral T cell exhaustion. Nat Biotechnol 37, 925-936.

Scheinman, R. I., Cogswell, P. C., Lofquist, A. K., and Baldwin, A. S., Jr. (1995). Role of transcriptional activation of I kappa B alpha in mediation of immunosuppression by glucocorticoids. Science 270, 283-286.

Sen, D. R., Kaminski, J., Barnitz, R. A., Kurachi, M., Gerdemann, U., Yates, K. B., Tsao, H. W., Godec, J., LaFleur, M. W., Brown, F. D., et al. (2016). The epigenetic landscape of T cell exhaustion. Science 354, 1165-1169.

Shin, H., Blackburn, S. D., Intlekofer, A. M., Kao, C., Angelosanto, J. M., Reiner, S. L., and Wherry, E. J. (2009). A role for the transcriptional repressor Blimp-1 in CD8(+) T cell exhaustion during chronic viral infection. Immunity 31, 309-320.

Siddiqui, I., Schaeuble, K., Chennupati, V., Fuertes Marraco, S. A., Calderon-Copete, S., Pais Ferreira, D., Carmona, S. J., Scarpellino, L., Gfeller, D., Pradervand, S., et al. (2019). Intratumoral Tcf1(+)PD-1(+)CD8(+) T Cells with Stem-like Properties Promote Tumor Control in Response to Vaccination and Checkpoint Blockade Immunotherapy. Immunity 50, 195-211 e110.

Sidler, D., Renzulli, P., Schnoz, C., Berger, B., Schneider-Jakob, S., Fluck, C., Inderbitzin, D., Corazza, N., Candinas, D., and Brunner, T. (2011). Colon cancer cells produce immunoregulatory glucocorticoids. Oncogene 30, 2411-2419.

Singer, M., Wang, C., Cong, L., Marjanovic, N. D., Kowalczyk, M. S., Zhang, H., Nyman, J., Sakuishi, K., Kurtulus, S., Gennert, D., et al. (2016). A Distinct Gene Module for Dysfunction Uncoupled from Activation in Tumor-Infiltrating T Cells. Cell 166, 1500-1511 e1509.

Smoak, K. A., and Cidlowski, J. A. (2004). Mechanisms of glucocorticoid receptor signaling during inflammation. Mech Ageing Dev 125, 697-706.

Suarez, A., Lopez, P., Gomez, J., and Gutierrez, C. (2006). Enrichment of CD4+ CD25high T cell population in patients with systemic lupus erythematosus treated with glucocorticoids. Ann Rheum Dis 65, 1512-1517.

Tiemessen, M. M., Baert, M. R., Kok, L., van Eggermond, M. C., van den Elsen, P. J., Arens, R., and Staal, F. J. (2014). T Cell factor 1 represses CD8+ effector T cell formation and function. J Immunol 193, 5480-5487.

Tingey, Z. W. B. a. F. H. (1951). One-sided confidence contours for probability distribution functions. The Annals of Mathematical Statistics 592-596.

Tokunaga, A., Sugiyama, D., Maeda, Y., Warner, A. B., Panageas, K. S., Ito, S., Togashi, Y., Sakai, C., Wolchok, J. D., and Nishikawa, H. (2019). Selective inhibition of low-affinity memory CD8(+) T cells by corticosteroids. J Exp Med.

Trapnell, C., Pachter, L., and Salzberg, S. L. (2009). TopHat: discovering splice junctions with RNA-Seq. Bioinformatics 25, 1105-1111.

Weber, J. S., O'Day, S., Urba, W., Powderly, J., Nichol, G., Yellin, M., Snively, J., and Hersh, E. (2008). Phase I/II study of ipilimumab for patients with metastatic melanoma. J Clin Oncol 26, 5950-5956.

Weikum, E. R., Knuesel, M. T., Ortlund, E. A., and Yamamoto, K. R. (2017). Glucocorticoid receptor control of transcription: precision and plasticity via allostery. Nat Rev Mol Cell Biol 18, 159-174.

Wherry, E. J., and Kurachi, M. (2015). Molecular and cellular insights into T cell exhaustion. Nat Rev Immunol 15, 486-499.

Xing, K., Gu, B., Zhang, P., and Wu, X. (2015). Dexamethasone enhances programmed cell death 1 (PD-1) expression during T cell activation: an insight into the optimum application of glucocorticoids in anti-cancer therapy. BMC Immunol 16, 39.

Yang, H., Xia, L., Chen, J., Zhang, S., Martin, V., Li, Q., Lin, S., Chen, J., Calmette, J., Lu, M., et al. (2019). Stress-glucocorticoid-TSC22D3 axis compromises therapy-induced antitumor immunity. Nat Med 25, 1428-1441.

Yang-Yen, H. F., Chambard, J. C., Sun, Y. L., Smeal, T., Schmidt, T. J., Drouin, J., and Karin, M. (1990). Transcriptional interference between c-Jun and the glucocorticoid receptor: mutual inhibition of DNA binding due to direct protein-protein interaction. Cell 62, 1205-1215.

Yu, B., Zhang, K., Milner, J. J., Toma, C., Chen, R., Scott-Browne, J. P., Pereira, R. M., Crotty, S., Chang, J. T., Pipkin, M. E., et al. (2017). Epigenetic landscapes reveal transcription factors that regulate CD8(+) T cell differentiation. Nat Immunol 18, 573-582.

Zhu, C., Sakuishi, K., Xiao, S., Sun, Z., Zaghouani, S., Gu, G., Wang, C., Tan, D. J., Wu, C., Rangachari, M., et al. (2015). An IL-27/NFIL3 signalling axis drives Tim-3 and IL-10 expression and T-cell dysfunction. Nature communications 6, 6072.

The invention is further described by the following numbered paragraphs.

1. A method of altering T cell dysfunction in a subject in need thereof comprising administering to the subject one or more agents capable of modulating glucocorticoid signaling,
    wherein a dysfunctional immune state in the subject is increased when glucocorticoid signaling is enhanced, or
    wherein a dysfunctional immune state in the subject is decreased when glucocorticoid signaling is reduced.

2. The method of paragraph 1, further comprising administering to the subject one or more agents capable of modulating IL-27 signaling,
    wherein a dysfunctional immune state in the subject is increased when both glucocorticoid signaling and IL-27 signaling are enhanced, or
    wherein a dysfunctional immune state in the subject is decreased when both glucocorticoid signaling and IL-27 signaling are reduced.

3. The method of paragraph 1 or 2, wherein the one or more agents capable of modulating glucocorticoid signaling comprise a glucocorticoid or a glucocorticoid agonist in an amount sufficient to increase dysfunction.

4. The method of paragraph 3, wherein the glucocorticoid agonist binds glucocorticoid and enhances its binding to glucocorticoid receptor.

5. The method of paragraph 3, wherein the glucocorticoid agonist increases expression of glucocorticoid receptor.

6. The method of paragraph 3, wherein the glucocorticoid agonist increases expression or activity of an enzyme of steroid biogenesis in macrophages.

7. The method of paragraph 6, wherein the enzyme is Cyp11a1.

8. The method of paragraph 1 or 2, wherein the one or more agents capable of modulating glucocorticoid signaling comprise a glucocorticoid antagonist in an amount sufficient to decrease dysfunction.

9. The method of paragraph 8, wherein the glucocorticoid antagonist binds glucocorticoid and decreases its binding to glucocorticoid receptor.

10. The method of paragraph 8, wherein the glucocorticoid antagonist decreases expression of glucocorticoid receptor.
11. The method of paragraph 8, wherein the glucocorticoid antagonist decreases expression or activity of an enzyme of steroid biogenesis in macrophages.
12. The method of paragraph 11, wherein the enzyme is Cyp11a1.
13. The method of paragraph 2, wherein the one or more agents capable of modulating IL-27 signaling comprise IL-27 or an IL-27 agonist in an amount sufficient to increase dysfunction.
14. The method of paragraph 13, wherein the IL-27 agonist binds IL-27 and enhances its binding to IL-27R.
15. The method of paragraph 13, wherein the IL-27 agonist increases expression of IL-27Ra.
16. The method of paragraph 13, wherein the IL-27 agonist increases expression of IL-27 or an IL-27 subunit in dendritic cells.
17. The method of paragraph 2, wherein the one or more agents capable of modulating IL-27 signaling comprise an IL-27 antagonist in an amount sufficient to decrease dysfunction.
18. The method of paragraph 17, wherein the IL-27 antagonist binds IL-27 and reduces its binding to IL-27R.
19. The method of paragraph 17, wherein the IL-27 antagonist decreases expression of IL-27Ra.
20. The method of paragraph 17, wherein the IL-27 antagonist decreases expression of IL-27 or an IL-27 subunit in dendritic cells.
21. A method of altering T cell dysfunction in a subject in need thereof comprising administering to the subject one or more T cells contacted with one or more agents capable of modulating glucocorticoid signaling,
    wherein the dysfunctional state of the one or more T cells is increased when glucocorticoid signaling is enhanced, or
    wherein the dysfunctional state of the one or more T cells is decreased when glucocorticoid signaling is reduced.
22. The method of paragraph 21, wherein the one or more T cells are further contacted with one or more agents capable of modulating IL-27 signaling,
    wherein the dysfunctional state of the one or more T cells is increased when both glucocorticoid signaling and IL-27 signaling are enhanced, or
    wherein the dysfunctional state of the one or more T cells is decreased when both glucocorticoid signaling and IL-27 signaling are reduced.
23. The method of paragraph 22, wherein the one or more T cells administered to the subject are in vitro differentiated in a culture media comprising IL-27 and a glucocorticoid.
24. The method of any of paragraphs 21 to 23, wherein the T cells are CD8+ T cells or naïve T cells.
25. The method of paragraph 21 or 22, wherein the one or more agents capable of modulating glucocorticoid signaling comprise a glucocorticoid or a glucocorticoid agonist in an amount sufficient to increase dysfunction.
26. The method of paragraph 25, wherein the glucocorticoid agonist binds glucocorticoid and enhances its binding to glucocorticoid receptor.
27. The method of paragraph 25, wherein the glucocorticoid agonist increases expression of glucocorticoid receptor.
28. The method of paragraph 21 or 22, wherein the one or more agents capable of modulating glucocorticoid signaling comprise a glucocorticoid antagonist in an amount sufficient to decrease dysfunction.
29. The method of paragraph 28, wherein the glucocorticoid antagonist binds glucocorticoid and decreases its binding to glucocorticoid receptor.
30. The method of paragraph 28, wherein the glucocorticoid antagonist decreases expression of glucocorticoid receptor.
31. The method of paragraph 22, wherein the one or more agents capable of modulating IL-27 signaling comprise IL-27 or an IL-27 agonist in an amount sufficient to increase dysfunction.
32. The method of paragraph 31, wherein the IL-27 agonist binds IL-27 and enhances its binding to IL-27R.
33. The method of paragraph 31, wherein the IL-27 agonist increases expression of IL-27Ra.
34. The method of paragraph 22, wherein the one or more agents capable of modulating IL-27 signaling comprise an IL-27 antagonist in an amount sufficient to decrease dysfunction.
35. The method of paragraph 34, wherein the IL-27 antagonist binds IL-27 and reduces its binding to IL-27R.
36. The method of paragraph 34, wherein the IL-27 antagonist decreases expression of IL-27Ra.
37. A method of altering T cell dysfunction in a subject in need thereof comprising administering to the subject one or more agents capable of modulating the expression, activity or function of one or more glucocorticoid+IL-27 signature genes or gene products; or administering one or more T cells contacted with the one or more agents, wherein the one or more genes are selected from the group consisting of:
    a) Lilrb4, Bcl2, Nupr1, Tgfb3, Tnfrsf4, Il24, Ramp1, Klf10, Cd27, Cd28, Tle2, Btla, Xcl1, Egr2, Entpd1, Tcf7, Nfil3, Prdm1, Mt1, Mt2, Stat3, Tigit, Havcr2, Lag3, Itga7, Acvrl1, Gprl25, Aqp11, Kit, Trip6, Il10, Enpp2, Asb2, Jag2, Tnfrsf18, Smyd3, Dbp, Ddit3, Tnfrsf14, Zfp467, Crebl2, Hif1a, Irf6, Alcam, Bach1, Pdcd1, Ctla4, Epcam, Gpld1, Cd68, Prnp, Gab2, Vldlr, Il10, Il11r2, Nt5e, Itgae, Clqtnf4, Ccr7, Cd226, Ifng, Ccl4, Spp1, Ccl3, Cd48, Cxcr3, Nanog, Tfrc, Hmgn2, Ptrf, Icam2, Cd40lg and Il1a; or
    b) Table 7A and Table 7B; or
    c) Table 5A and Table 5B; or
    d) Table 6A and Table 6B; or
    e) Table 3; or
    f) Table 2A and Table 2B; or
    g) Table 1,
        wherein modulating the expression, activity or function comprises increasing the expression, activity or function of glucocorticoid+IL-27 signature genes that are downregulated as compared to the control according to Table 1 and decreasing the expression, activity or function of glucocorticoid+IL-27 signature genes that are upregulated as compared to the control according to Table 1, whereby dysfunction is decreased, or
        wherein modulating the expression, activity or function comprises decreasing the expression, activity or function for glucocorticoid+IL-27 signature genes that are downregulated as compared to the control according to Table 1 and increasing the expression, activity or function for glucocorticoid+IL-27 signature genes that are upregulated as compared to the control according to Table 1, whereby dysfunction is increased.

38. The method of paragraph 37, wherein Epcam, Gpld1, Cd68, Prnp, Gab2, Vldlr, Il10, Il1r2, Nt5e, Itgae, Clqtnf4, Tgfb3, Itga7, Acvrl1, Gpr125, Aqp11, Ramp1, Kit, Trip6, Il10, Enpp2, Asb2, Jag2, Tnfrsf18, Prdm1, Smyd3, Tigit, Dbp, Tle2, Ddit3, Klf10, Tnfrsf14, Zfp467, Entpd1, Nfil3, Creb12, Hif1a, Irf6, Lag3, Alcam, Mt2, Stat3, Mt1, Bach1, Cd28, Havcr2, Pdcd1, Ctla4 and Cd27 are upregulated in glucocorticoid+IL-27 as compared to the control.
39. The method of paragraph 37, wherein Ifng, Ccl4, Bcl2, Spp1, Btla, Ccl3, Cd48, Cxcr3, Nanog, Tfrc, Xcl1, Lilrb4, Nupr1, Hmgn2, Il24, Ptrf, Icam2, Cd40lg, Il1a, Tcf7, Tnfrsf4, Egr2, Ccr7 and Cd226 are downregulated in glucocorticoid+IL-27 as compared to the control.
40. The method of any of paragraphs 37 to 39, wherein the T cells are in vitro differentiated in a culture media comprising the one or more agents.
41. The method of paragraph 40, wherein the T cells are CD8+ T cells or naïve T cells.
42. The method of any of paragraphs 37 to 41, wherein the agent is:
    a) capable of targeting or binding to one or more cell surface exposed gene products; or
    b) capable of targeting or binding to one or more receptors or ligands specific for a cell surface exposed gene product; or
    c) capable of targeting or binding to one or more secreted gene products; or
    d) capable of targeting or binding to one or more receptors specific for a secreted gene product.
43. The method of any one of paragraphs 1 to 42, wherein the one or more agents comprise an antibody, antibody fragment, intrabody, antibody-like protein scaffold, aptamer, polypeptide, small molecule, small molecule degrader, genetic modifying agent, or any combination thereof.
44. The method of paragraph 43, wherein the genetic modifying agent comprises a CRISPR system, RNAi system, a zinc finger nuclease system, a TALE, or a meganuclease.
45. The method of paragraph 44, wherein the CRISPR system comprises Cas9, Cas12, or Cas14.
46. The method of paragraph 44, wherein the CRISPR system comprises a dCas fused or otherwise linked to a nucleotide deaminase.
47. The method of paragraph 46, wherein the nucleotide deaminase is a cytidine deaminase or an adenosine deaminase.
48. The method of paragraph 46, wherein the dCas is a dCas9, dCas12, dCas13, or dCas14.
49. The method of any of paragraphs 44 to 48, wherein the CRISPR system is administered as a ribonucleoprotein (RNP) complex.
50. The method of any of paragraphs 1-7, 13-16, 21-23, 25-27, 31-33 or 37-49, wherein the method is for treating an autoimmune disease in a subject in need thereof.
51. The method of paragraph 50, wherein the autoimmune disease is selected from Multiple Sclerosis (MS), Irritable Bowel Disease (IBD), Crohn's disease, spondyloarthritides, Systemic Lupus Erythematosus (SLE), Vitiligo, rheumatoid arthritis, psoriasis, Sjögren's syndrome, and diabetes.
52. The method of any of paragraphs 1-7, 13-16, 21-23, 25-27, 31-33 or 37-49, wherein the method is for treating an inflammatory disorder in a subject in need thereof.
53. The method of paragraph 52, wherein the inflammatory disorder is selected from psoriasis, inflammatory bowel diseases (IBD), allergic asthma, food allergies and rheumatoid arthritis.
54. The method of any of paragraphs 1-7, 13-16, 21-23, 25-27, 31-33 or 37-49, wherein the method is for inducing immune tolerance or preventing graft versus host disease in a subject having received an organ transplant.
55. The method of any of paragraphs 1-2, 8-12, 17-22, 28-30 or 34-49, wherein the method is for treating cancer in a subject in need thereof, whereby a tumor specific immune response is enhanced.
56. The method of paragraph 55, wherein the treatment is a cancer adjuvant therapy comprising administering glucocorticoid therapy and one or more agents capable of modulating one or more genes or gene products in the glucocorticoid+IL-27 gene signature according to paragraphs 37 to 39, whereby the subject maintains T cell immunity against tumor cells.
57. The method of paragraph 56, wherein the adjuvant therapy is administered to a subject having received chemotherapy.
58. The method of paragraph 56, wherein the one or more genes or gene products are selected from the group consisting of PD-1, TIM3, TIGIT, LAG3, MT1, MT2, and IL-10.
59. The method of paragraph 58, wherein the agent is an antibody or fragment thereof selected from the group consisting of anti-PD1, anti-TIM3, anti-TIGIT, anti-LAG3 and anti-IL-10.
60. The method of paragraph 58, wherein the agent is an MT1/2 antagonist.
61. The method of any of the preceding paragraphs, wherein the glucocorticoid is dexamethasone (Dex).
62. An isolated T cell modified to comprise altered IL-27 and glucocorticoid signaling.
63. The isolated T cell of paragraph 62, wherein the T cell is in vitro differentiated in a culture media comprising IL-27 and a glucocorticoid, whereby dysfunction is increased.
64. The isolated T cell of paragraph 62, wherein the T cell is modified to comprise decreased IL-27 signaling and glucocorticoid signaling, whereby dysfunction is decreased.
65. The isolated T cell of paragraph 64, wherein the T cell comprises decreased or abolished expression or activity of the IL-27 receptor and the glucocorticoid receptor.
66. The isolated T cell of paragraph 64, wherein the isolated T cell is modified to comprise modulated expression or activity of one or more genes or gene products according to paragraph 37.
67. The isolated T cell of any of paragraphs 62 to 66, wherein the T cell comprises a genetic modifying agent.
68. The isolated T cell of paragraph 67, wherein the genetic modifying agent comprises a CRISPR system, RNAi system, a zinc finger nuclease system, a TALE, or a meganuclease.
69. The method of paragraph 68, wherein the CRISPR system comprises Cas9, Cas12, or Cas14.

70. The method of paragraph 68, wherein the CRISPR system comprises a dCas fused or otherwise linked to a nucleotide deaminase.

71. The method of paragraph 70, wherein the nucleotide deaminase is a cytidine deaminase or an adenosine deaminase.

72. The method of paragraph 70, wherein the dCas is a dCas9, dCas12, dCas13, or dCas14.

73. The isolated T cell of any of paragraphs 62 to 72, wherein the T cell is obtained from PBMCs.

74. The isolated T cell of any of paragraphs 62 to 73, wherein the T cell is a tumor infiltrating lymphocyte (TIL).

75. The isolated T cell of any of paragraphs 62 to 74, wherein the T cell expresses an endogenous T cell receptor (TCR) or chimeric antigen receptor (CAR) specific for a tumor antigen.

76. The isolated T cell of any of paragraphs 62 to 75, wherein the T cell is expanded.

77. The isolated T cell of any of paragraphs 62 to 76, wherein the T cell is modified to express a suicide gene, wherein the T cell can be eliminated upon administration of a drug.

78. The isolated T cell of any of paragraphs 62 to 77, wherein the glucocorticoid is dexamethasone (Dex).

79. A pharmaceutical composition comprising one or more isolated T cells of any of paragraphs 62 to 78.

80. A method of treating cancer in a subject in need thereof comprising administering a pharmaceutical composition comprising one or more isolated T cells of any of paragraphs 62, 64 to 78 to the subject.

81. A method of treating an autoimmune disease or inflammatory disorder, or for inducing immune tolerance in a subject in need thereof comprising administering a pharmaceutical composition comprising one or more isolated T cells of paragraph 63 to the subject.

82. A method of generating an in vitro T cell that faithfully recapitulates an in vivo dysfunctional T cell comprising culturing a T cell in a culture media comprising IL-27 and a glucocorticoid.

83. A method of detecting a checkpoint blockade (CPB) therapy non-responder gene signature in a subject in need thereof comprising detecting in T cells obtained from a pre-treatment biological sample from the subject the expression or activity of one or more glucocorticoid+IL-27 signature genes or gene products selected from the group consisting of:
a) Table 2A and Table 2B; or
b) Lilrb4, Bcl2, Nupr1, Tgfb3, Tnfrsf4, Il24, Ramp1, Klf10, Cd27, Cd28, Tle2, Btla, Xcl1, Egr2, Entpd1, Tcf7, Nfil3, Prdm1, Mt1, Mt2, Stat3, Tigit, Havcr2, Lag3, Itga7, Acvrl1, Gprl25, Aqp11, Kit, Trip6, Il10, Enpp2, Asb2, Jag2, Tnfrsf18, Smyd3, Dbp, Ddit3, Tnfrsf14, Zfp467, Crebl2, Hif1a, Irf6, Alcam, Bach1, Pdcd1, Ctla4, Epcam, Gpld1, Cd68, Prnp, Gab2, Vldlr, Il10, Il1r2, Nt5e, Itgae, Clqtnf4, Ccr7, Cd226, Ifng, Ccl4, Spp1, Ccl3, Cd48, Cxcr3, Nanog, Tfrc, Hmgn2, Ptrf, Icam2, Cd40lg and Il1a; or
c) Table 7A and Table 7B; or
d) Table 5A and Table 5B; or
e) Table 6A and Table 6B; or
f) Table 3; or
g) Table 1,
wherein Epcam, Gpld1, Cd68, Prnp, Gab2, Vldlr, Il10, Il1r2, Nt5e, Itgae, Clqtnf4, Tgfb3, Itga7, Acvrl1, Gprl25, Aqp11, Ramp1, Kit, Trip6, Il10, Enpp2, Asb2, Jag2, Tnfrsf18, Prdm1, Smyd3, Tigit, Dbp, Tle2, Ddit3, Klf10, Tnfrsf14, Zfp467, Entpd1, Nfil3, Crebl2, Hif1a, Irf6, Lag3, Alcam, Mt2, Stat3, Mt1, Bach1, Cd28, Havcr2, Pdcd1, Ctla4 and Cd27 are upregulated in glucocorticoid+IL-27 as compared to the control, and
wherein Ifng, Ccl4, Bcl2, Spp1, Btla, Ccl3, Cd48, Cxcr3, Nanog, Tfrc, Xcl1, Lilrb4, Nupr1, Hmgn2, Il24, Ptrf, Icam2, Cd40lg, Il1a, Tcf7, Tnfrsf4, Egr2, Ccr7 and Cd226 are downregulated in glucocorticoid+IL-27 as compared to the control.

84. The method of paragraph 83, further comprising treating the subject wherein if a non-responder signature is detected treating the subject according to any of paragraphs 1-2, 8-12, 17-22, 28-30, 34-49 or 80.

85. The method of paragraph 84, further comprising administering checkpoint blockade (CPB) therapy.

86. The method of paragraph 85, wherein the CPB therapy comprises anti-PD-1, anti-CTLA4+PD-1, or anti-CTLA4.

87. A method of determining a prognosis for cancer survival in a subject in need thereof comprising detecting the expression of Cyp11a1 in CD45$^+$ cells obtained from a tumor sample of the subject, wherein low Cyp11a1 levels compared to a reference level indicates increased survival.

88. The method of paragraph 87, wherein expression is detected in CD11b+F4/80+ macrophages.

89. The method of paragraph 87, further comprising treating the subject wherein if high Cyp11a1 levels are detected treating the subject according to any of paragraphs 1-2, 8-12, 17-22, 28-30, 34-38, 40-49 or 80.

90. A method of screening for one or more agents capable of modulating a glucocorticoid+IL-27 gene signature according to paragraph 83 comprising administering to a population of T cells one or more agents; and detecting expression, activity or function of one or more genes or gene products in the signature.

91. The method of paragraph 90, wherein the one or more genes detected are selected from the group consisting of PD-1, TIM3, LAG3, MT1, MT2, and IL-10.

92. The method of paragraph 90, wherein the population of cells express one or more reporter genes.

93. The method of paragraph 90, wherein the one or more agents bind to glucocorticoid receptor and/or IL-27 receptor.

94. The method of paragraph 90, wherein the one or more agents modify chromatin structure at one or more of the signature genes.

TABLE 2A

| Downregulated genes after GC + IL27 (1558 in ranked order) | |
|---|---|
| 1 | Ccl1 |
| 2 | Il2 |
| 3 | Kmo |
| 4 | Il3 |
| 5 | Gzme |
| 6 | Il22 |
| 7 | Ugt1a9 |
| 8 | Il13 |
| 9 | Ugt1a6b |
| 10 | Il17a |
| 11 | Il6 |
| 12 | Lama3 |
| 13 | Zfp458 |
| 14 | Lrp11 |
| 15 | Sema6d |
| 16 | Csf2 |
| 17 | Tnni1 |

TABLE 2A-continued

Downregulated genes after GC + IL27 (1558 in ranked order)

| | |
|---|---|
| 18 | Eomes |
| 19 | Lad1 |
| 20 | Ifng |
| 21 | Pcsk1 |
| 22 | Psg17 |
| 23 | Lmo2 |
| 24 | Ugt1a10 |
| 25 | Il1a |
| 26 | GaInt14 |
| 27 | Igfbp2 |
| 28 | Fcer1g |
| 29 | Fbln5 |
| 30 | Ptgs2 |
| 31 | Mrvi1 |
| 32 | Tm4sf19 |
| 33 | Lif |
| 34 | Gzmd |
| 35 | Nkd2 |
| 36 | Pcdhgb2 |
| 37 | Vrtn |
| 38 | Actbl2 |
| 39 | Hist1h1a |
| 40 | Olr1 |
| 41 | Slc1a2 |
| 42 | Scin |
| 43 | Ispd |
| 44 | Cx3cl1 |
| 45 | BC016579 |
| 46 | 4930525D18Rik |
| 47 | Plch1 |
| 48 | Mcoln3 |
| 49 | D130043K22Rik |
| 50 | Ramp2 |
| 51 | P2ry1 |
| 52 | Otx1 |
| 53 | Myh11 |
| 54 | Duoxa1 |
| 55 | Dapl1 |
| 56 | Tagln3 |
| 57 | Xcl1 |
| 58 | Cd36 |
| 59 | Pdzk1ip1 |
| 60 | Hemgn |
| 61 | Ugt1a5 |
| 62 | Stra6 |
| 63 | Scn9a |
| 64 | Egr3 |
| 65 | Prokr1 |
| 66 | Alpl |
| 67 | Col6a2 |
| 68 | Actr3b |
| 69 | Cd40lg |
| 70 | 4930506M07Rik |
| 71 | Il23a |
| 72 | Ntrk3 |
| 73 | Wdfy4 |
| 74 | Enam |
| 75 | Pcdh19 |
| 76 | Acsl6 |
| 77 | Chl1 |
| 78 | Pde1a |
| 79 | Ffar4 |
| 80 | Hist1h3d |
| 81 | Gm14718 |
| 82 | Tnip3 |
| 83 | Crabp2 |
| 84 | Cyr61 |
| 85 | Nov |
| 86 | Ugt1a6a |
| 87 | Tnf |
| 88 | Lta |
| 89 | Amotl1 |
| 90 | Spry4 |
| 91 | Ccl3 |
| 92 | Nlrp6 |
| 93 | Hdac9 |
| 94 | Smoc1 |
| 95 | Egr2 |
| 96 | Rnf180 |
| 97 | Tgfb2 |
| 98 | Gm4858 |
| 99 | Camkv |
| 100 | Rgs18 |
| 101 | Tfrc |
| 102 | Ttc39c |
| 103 | Il20rb |
| 104 | Il24 |
| 105 | Cnrip1 |
| 106 | Cdc6 |
| 107 | Gmpr |
| 108 | Tnfsf11 |
| 109 | Ica1 |
| 110 | Slc2a6 |
| 111 | Tnfsf8 |
| 112 | Rai14 |
| 113 | Ttc30a1 |
| 114 | Tuba8 |
| 115 | Rpph1 |
| 116 | Idi2 |
| 117 | Klhl23 |
| 118 | Hbegf |
| 119 | Hist1h2bk |
| 120 | Zfp711 |
| 121 | Cxcl10 |
| 122 | Hist1h3a |
| 123 | Exo1 |
| 124 | Rrm2 |
| 125 | Ptprn |
| 126 | Ctnnal1 |
| 127 | Gpr55 |
| 128 | Tcam1 |
| 129 | Fam46a |
| 130 | Orc1 |
| 131 | Pnp2 |
| 132 | Fgd2 |
| 133 | Gata1 |
| 134 | Lrr1 |
| 135 | Aebp1 |
| 136 | Serpine1 |
| 137 | Gyltl1b |
| 138 | Egfr |
| 139 | Tom1l1 |
| 140 | Gad2 |
| 141 | Ccbl2 |
| 142 | Tdpoz4 |
| 143 | Cd70 |
| 144 | Igfbp7 |
| 145 | Nqo1 |
| 146 | Npw |
| 147 | Myh10 |
| 148 | Serpinc1 |
| 149 | Ceacam1 |
| 150 | Ms4a4c |
| 151 | Phlda1 |
| 152 | Shmt1 |
| 153 | Cdh15 |
| 154 | Zfp334 |
| 155 | Trpa1 |
| 156 | Stxbp6 |
| 157 | Dna2 |
| 158 | Anxa3 |
| 159 | Hist1h3f |
| 160 | Depdc7 |
| 161 | E2f8 |
| 162 | Exph5 |
| 163 | 3110082I17Rik |
| 164 | 2810417H13Rik |
| 165 | Cdk14 |
| 166 | Igj |
| 167 | Nefh |
| 168 | Shroom3 |
| 169 | Penk |
| 170 | Gm6460 |
| 171 | Dnph1 |
| 172 | Fosl1 |
| 173 | Bicd1 |

TABLE 2A-continued

Downregulated genes after GC + IL27 (1558 in ranked order)

| | |
|---|---|
| 174 | Ccdc116 |
| 175 | Cyp27a1 |
| 176 | Ddx39 |
| 177 | Pdss1 |
| 178 | Hpdl |
| 179 | Osm |
| 180 | 1110002L01Rik |
| 181 | Mlf1 |
| 182 | Dscc1 |
| 183 | Hmgn2 |
| 184 | Prpf31 |
| 185 | Gm8773 |
| 186 | Lima1 |
| 187 | Dleu7 |
| 188 | Jrk |
| 189 | Lingo3 |
| 190 | Dclk1 |
| 191 | Inhba |
| 192 | Grwd1 |
| 193 | Gucy1a3 |
| 194 | Utf1 |
| 195 | Capn3 |
| 196 | Coq7 |
| 197 | Spry1 |
| 198 | Ppic |
| 199 | Per2 |
| 200 | Heatr3 |
| 201 | Hist1h2ak |
| 202 | Hist1h2ag |
| 203 | Rad54l |
| 204 | Mcm10 |
| 205 | Ddx25 |
| 206 | Apitd1 |
| 207 | Cd302 |
| 208 | Nr4a3 |
| 209 | Hnrnpab |
| 210 | Hmgn3 |
| 211 | Ercc6l |
| 212 | Pfas |
| 213 | Grtp1 |
| 214 | Ppid |
| 215 | Syn1 |
| 216 | Gzmc |
| 217 | Bcl2l14 |
| 218 | Ccne2 |
| 219 | D430020J02Rik |
| 220 | Zbtbd6 |
| 221 | Tnfrsf11b |
| 222 | Cd200 |
| 223 | Creld2 |
| 224 | Thop1 |
| 225 | Coq4 |
| 226 | Tyms |
| 227 | Psmc3ip |
| 228 | Oaf |
| 229 | Fam43a |
| 230 | Nup85 |
| 231 | Ranbp1 |
| 232 | Tomm40 |
| 233 | Hist1h2bj |
| 234 | Gm4951 |
| 235 | Slc46a1 |
| 236 | Enpp4 |
| 237 | Gen1 |
| 238 | B4galt5 |
| 239 | Nolc1 |
| 240 | 1110032F04Rik |
| 241 | Hist1h3c |
| 242 | Fen1 |
| 243 | Pus7l |
| 244 | Tmem17 |
| 245 | Ctnnd1 |
| 246 | Ccr4 |
| 247 | Baat1 |
| 248 | Srrt |
| 249 | Lyar |
| 250 | Nop56 |
| 251 | Gemin6 |
| 252 | Papss2 |
| 253 | Nudt1 |
| 254 | Gpatch4 |
| 255 | Rrp9 |
| 256 | Ptpn5 |
| 257 | Tuba4a |
| 258 | Mthfd1 |
| 259 | Hist2h3b |
| 260 | Ptger3 |
| 261 | Prodh |
| 262 | Gins1 |
| 263 | Upb1 |
| 264 | Ticam2 |
| 265 | F2rl3 |
| 266 | Tk1 |
| 267 | Ccl4 |
| 268 | Bend3 |
| 269 | Sdf2l1 |
| 270 | Mcm5 |
| 271 | Tcf7 |
| 272 | Pop1 |
| 273 | Rmdn2 |
| 274 | Chtf18 |
| 275 | P2ry14 |
| 276 | Ppp1cb |
| 277 | Recql4 |
| 278 | Piwil4 |
| 279 | Qsox2 |
| 280 | Rpl30 |
| 281 | Fsd1l |
| 282 | Ppih |
| 283 | Mybbp1a |
| 284 | Pcna |
| 285 | Hsp90aa1 |
| 286 | Cdc45 |
| 287 | Prmt1 |
| 288 | Ftsj3 |
| 289 | Ugt1a7c |
| 290 | Ebna1bp2 |
| 291 | Imp4 |
| 292 | C330027C09Rik |
| 293 | Hist2h3c2 |
| 294 | Ifrd2 |
| 295 | Hspd1 |
| 296 | 4933430I17Rik |
| 297 | Ankle1 |
| 298 | Cinp |
| 299 | Mettl16 |
| 300 | Rrp15 |
| 301 | Mrto4 |
| 302 | Pin1 |
| 303 | Clgn |
| 304 | Tuba1b |
| 305 | Srm |
| 306 | Ccdc86 |
| 307 | Gtdc2 |
| 308 | Elovl4 |
| 309 | Wisp1 |
| 310 | Mcm2 |
| 311 | Gpr150 |
| 312 | Csgalnact1 |
| 313 | Gemin4 |
| 314 | Slc7a3 |
| 315 | Srsf6 |
| 316 | Mylk |
| 317 | Rps6kl1 |
| 318 | Trip13 |
| 319 | Timeless |
| 320 | Pdpn |
| 321 | Rrm1 |
| 322 | Ssx2ip |
| 323 | Gspt2 |
| 324 | Spin4 |
| 325 | Tmem48 |
| 326 | Bysl |
| 327 | 9630033F20Rik |
| 328 | Trmt61a |
| 329 | Rad51ap1 |

TABLE 2A-continued

Downregulated genes after GC + IL27 (1558 in ranked order)

| | |
|---|---|
| 330 | Mat2a |
| 331 | Gart |
| 332 | Mtfp1 |
| 333 | Trat1 |
| 334 | Dkc1 |
| 335 | Fancb |
| 336 | St6gal1 |
| 337 | Kbtbd8 |
| 338 | Nomo1 |
| 339 | Zcchc10 |
| 340 | Dnajc11 |
| 341 | Ruvbl1 |
| 342 | Etv5 |
| 343 | Rad51 |
| 344 | Lum |
| 345 | Dhodh |
| 346 | Mtbp |
| 347 | Rcc1 |
| 348 | Pola1 |
| 349 | Ppa1 |
| 350 | Wdr4 |
| 351 | Polr1b |
| 352 | Iigp1 |
| 353 | 4930509E16Rik |
| 354 | Clhc1 |
| 355 | Rfc5 |
| 356 | Fancd2 |
| 357 | Slc7a11 |
| 358 | Chek1 |
| 359 | C230052I12Rik |
| 360 | 9930014A18Rik |
| 361 | Prrx1 |
| 362 | Pim3 |
| 363 | Emc8 |
| 364 | Wdr89 |
| 365 | Tln2 |
| 366 | Gpx7 |
| 367 | Hist1h2ae |
| 368 | Ruvbl2 |
| 369 | Etv4 |
| 370 | Alyref |
| 371 | Orc6 |
| 372 | Gcat |
| 373 | Fkbp11 |
| 374 | Wdr18 |
| 375 | Chaf1b |
| 376 | C77080 |
| 377 | Srsf3 |
| 378 | Ufsp1 |
| 379 | Asf1b |
| 380 | Lpin3 |
| 381 | Fabp5 |
| 382 | Grhl1 |
| 383 | Trmt12 |
| 384 | Traip |
| 385 | Pbk |
| 386 | 2310014L17Rik |
| 387 | Dennd5a |
| 388 | Fastkd2 |
| 389 | Hk2 |
| 390 | Cldn25 |
| 391 | Timm8a1 |
| 392 | Shcbp1 |
| 393 | S1pr3 |
| 394 | Vmn2r-ps129 |
| 395 | Icam2 |
| 396 | Gm17296 |
| 397 | Ikzf4 |
| 398 | Clspn |
| 399 | Nop16 |
| 400 | Cd44 |
| 401 | Mybl2 |
| 402 | Cpne2 |
| 403 | Cd83 |
| 404 | Hrc |
| 405 | Car12 |
| 406 | Polr3h |
| 407 | Cth |
| 408 | Ung |
| 409 | Haus5 |
| 410 | Psmd1 |
| 411 | Polq |
| 412 | Dhfr |
| 413 | Srsf7 |
| 414 | Fads2 |
| 415 | Slc25a32 |
| 416 | Lacc1 |
| 417 | Oas1a |
| 418 | Shq1 |
| 419 | Hist2h4 |
| 420 | Nudc |
| 421 | Chchd4 |
| 422 | Tra2a |
| 423 | Arxes2 |
| 424 | Tuba1c |
| 425 | Tubb4b |
| 426 | Adsl |
| 427 | Kntc1 |
| 428 | Opn3 |
| 429 | Nek6 |
| 430 | Ivd |
| 431 | Hspbp1 |
| 432 | 2310008H09Rik |
| 433 | Nup155 |
| 434 | Sept8 |
| 435 | Stmn1 |
| 436 | Alg8 |
| 437 | Coro2a |
| 438 | Timp1 |
| 439 | Pwp2 |
| 440 | Tra2b |
| 441 | Il1rl1 |
| 442 | Tm4sf5 |
| 443 | Cad |
| 444 | Idh3a |
| 445 | A930004D18Rik |
| 446 | B3galt6 |
| 447 | Hars |
| 448 | Ptcd3 |
| 449 | Ptrf |
| 450 | Abcf2 |
| 451 | Eme1 |
| 452 | Nasp |
| 453 | Tnp2 |
| 454 | Nup107 |
| 455 | Ptgir |
| 456 | Exosc6 |
| 457 | Pitrm1 |
| 458 | Hsph1 |
| 459 | Hn1l |
| 460 | Cyb5rl |
| 461 | Plscr1 |
| 462 | Ppap2a |
| 463 | Trdmt1 |
| 464 | Lipg |
| 465 | Cacybp |
| 466 | Idi1 |
| 467 | Nkain1 |
| 468 | Ppan |
| 469 | Ubiad1 |
| 470 | Btla |
| 471 | Rpf2 |
| 472 | Fignl1 |
| 473 | Nop2 |
| 474 | Ran |
| 475 | Zfp229 |
| 476 | Cd48 |
| 477 | Siah1b |
| 478 | Timm17a |
| 479 | Rnmtl1 |
| 480 | Mtap |
| 481 | Nup160 |
| 482 | Tubg1 |
| 483 | Tuba1a |
| 484 | Utp20 |
| 485 | Noc4l |

TABLE 2A-continued

Downregulated genes after GC + IL27 (1558 in ranked order)

| | |
|---|---|
| 486 | Lrpprc |
| 487 | Cct3 |
| 488 | Hirip3 |
| 489 | Hist1h2ab |
| 490 | Trmt6 |
| 491 | Smyd5 |
| 492 | Tjp2 |
| 493 | Eme2 |
| 494 | E2f7 |
| 495 | Pla1a |
| 496 | Nop58 |
| 497 | Rpl7l1 |
| 498 | 2610318N02Rik |
| 499 | Hnrnpm |
| 500 | Spp1 |
| 501 | Egr1 |
| 502 | Fam136a |
| 503 | Ms4a4b |
| 504 | Cd74 |
| 505 | Erh |
| 506 | Col5a3 |
| 507 | Ppif |
| 508 | Cenpi |
| 509 | Tipin |
| 510 | Bop1 |
| 511 | Rbm19 |
| 512 | Nfyc |
| 513 | Eef1e1 |
| 514 | N6amt2 |
| 515 | Pdcd11 |
| 516 | Dnajc22 |
| 517 | Notch2 |
| 518 | Syncrip |
| 519 | Gmppb |
| 520 | Fkbp4 |
| 521 | Mcm8 |
| 522 | Chaf1a |
| 523 | Lsm7 |
| 524 | Ctps |
| 525 | St3gal2 |
| 526 | Tbl3 |
| 527 | Xpo5 |
| 528 | Jam2 |
| 529 | Ahsa1 |
| 530 | Nutf2-ps1 |
| 531 | Dtl |
| 532 | Wdr77 |
| 533 | Armc6 |
| 534 | Ppat |
| 535 | Rad54b |
| 536 | Nhp2 |
| 537 | Psmd6 |
| 538 | Klri2 |
| 539 | Calr |
| 540 | Dis3 |
| 541 | Slc43a3 |
| 542 | Exosc2 |
| 543 | Mgat5 |
| 544 | Slc35b1 |
| 545 | Glrp1 |
| 546 | Pole2 |
| 547 | Ift27 |
| 548 | Hmgb2 |
| 549 | Cks1b |
| 550 | Ywhab |
| 551 | Tmem97 |
| 552 | Rrp12 |
| 553 | Gcsh |
| 554 | Slc43a1 |
| 555 | Slc25a25 |
| 556 | Myo19 |
| 557 | Slc19a1 |
| 558 | Set |
| 559 | Dynll1 |
| 560 | Mcm3 |
| 561 | Pter |
| 562 | Phtf2 |
| 563 | Umps |
| 564 | Nup93 |
| 565 | 4930427A07Rik |
| 566 | Gadd45g |
| 567 | Tex30 |
| 568 | Gusb |
| 569 | Plk2 |
| 570 | Mrps2 |
| 571 | Eftud2 |
| 572 | Uchl3 |
| 573 | Myo1e |
| 574 | Utp6 |
| 575 | Cycs |
| 576 | Gm9855 |
| 577 | Lilrb4 |
| 578 | Taf6l |
| 579 | Hnrnpa2b1 |
| 580 | Mrps10 |
| 581 | Wdhd1 |
| 582 | Ddx56 |
| 583 | Cct6a |
| 584 | Uhrf1 |
| 585 | Unc5cl |
| 586 | Yy2 |
| 587 | Tespa1 |
| 588 | Lgmn |
| 589 | Bola3 |
| 590 | Cpd |
| 591 | Ehd3 |
| 592 | Uqcr11 |
| 593 | Manf |
| 594 | Ttll4 |
| 595 | Gins2 |
| 596 | Hnrpll |
| 597 | Ankrd32 |
| 598 | Tomm5 |
| 599 | Slc16a13 |
| 600 | Snrpd3 |
| 601 | Psmd7 |
| 602 | Exoc3l |
| 603 | Galnt7 |
| 604 | Pbld1 |
| 605 | Gltpd1 |
| 606 | Il1rl2 |
| 607 | Ube2v2 |
| 608 | Cdca7 |
| 609 | Nup37 |
| 610 | Socs2 |
| 611 | Nme1 |
| 612 | Gyk |
| 613 | AA414768 |
| 614 | Cmah |
| 615 | Sf3b4 |
| 616 | Mcm4 |
| 617 | Pdia6 |
| 618 | Poc1a |
| 619 | Lrrc32 |
| 620 | Dhx9 |
| 621 | Gar1 |
| 622 | Fastkd3 |
| 623 | Fh1 |
| 624 | Zfp239 |
| 625 | Ndufa4 |
| 626 | Nip7 |
| 627 | Hat1 |
| 628 | Rtel1 |
| 629 | Hapln4 |
| 630 | Rbks |
| 631 | Ifitm3 |
| 632 | Nup35 |
| 633 | Ska1 |
| 634 | Lcmt2 |
| 635 | Cdk1 |
| 636 | Spc24 |
| 637 | Ipo4 |
| 638 | Esco2 |
| 639 | Lsm3 |
| 640 | Nme6 |
| 641 | Dgcr8 |

TABLE 2A-continued

Downregulated genes after GC + IL27 (1558 in ranked order)

| | |
|---|---|
| 642 | Phf19 |
| 643 | Cse1l |
| 644 | Ptger4 |
| 645 | Fam64a |
| 646 | Timm10 |
| 647 | Nabp1 |
| 648 | Pomgnt1 |
| 649 | Mcm7 |
| 650 | Fanca |
| 651 | Gm15645 |
| 652 | Zwilch |
| 653 | Pole |
| 654 | D030028A08Rik |
| 655 | Nudt5 |
| 656 | Tmtc4 |
| 657 | Ncbp2 |
| 658 | Stip1 |
| 659 | Wdr74 |
| 660 | Srsf10 |
| 661 | Ddx3x |
| 662 | Cbwd1 |
| 663 | Psmc5 |
| 664 | Cenpn |
| 665 | Nrp1 |
| 666 | Emc4 |
| 667 | Ube2m |
| 668 | Heatr1 |
| 669 | Cdh23 |
| 670 | Mrpl20 |
| 671 | Hist1h2ao |
| 672 | Pno1 |
| 673 | Ndufaf4 |
| 674 | Lsm2 |
| 675 | Lars |
| 676 | Pole3 |
| 677 | Nid1 |
| 678 | Fam111a |
| 679 | Ipo11 |
| 680 | Dnajc27 |
| 681 | Loxl2 |
| 682 | Sigmar1 |
| 683 | Abcd3 |
| 684 | 0610010F05Rik |
| 685 | Adpgk |
| 686 | Plk1 |
| 687 | Atad3a |
| 688 | Sfxn2 |
| 689 | Uros |
| 690 | Pa2g4 |
| 691 | C1qbp |
| 692 | Rbmx2 |
| 693 | Acy1 |
| 694 | Brix1 |
| 695 | Armcx4 |
| 696 | Casc4 |
| 697 | Dcun1d2 |
| 698 | Cd226 |
| 699 | Naa50 |
| 700 | Cenph |
| 701 | Hist1h1b |
| 702 | Enthd1 |
| 703 | Wdr46 |
| 704 | Mlh1 |
| 705 | Mlf1ip |
| 706 | Polr2f |
| 707 | Nhp2l1 |
| 708 | Ncapg2 |
| 709 | Magoh |
| 710 | Psmc4 |
| 711 | Omd |
| 712 | Wdr3 |
| 713 | Polr1e |
| 714 | Znhit3 |
| 715 | Amd2 |
| 716 | Car13 |
| 717 | Ncln |
| 718 | Aff3 |
| 719 | Cysltr1 |
| 720 | Srl |
| 721 | Polr2l |
| 722 | Pmpca |
| 723 | Mki67ip |
| 724 | Spint1 |
| 725 | Slc7a5 |
| 726 | Xrcc5 |
| 727 | Slc17a6 |
| 728 | Npl |
| 729 | Shmt2 |
| 730 | Mpv17l |
| 731 | Cdc34 |
| 732 | Palb2 |
| 733 | Itgb1 |
| 734 | Atp2a2 |
| 735 | Prdx1 |
| 736 | Nr4a1 |
| 737 | Fitm2 |
| 738 | Dbi |
| 739 | Ikbkap |
| 740 | Hspa5 |
| 741 | Ttc27 |
| 742 | Kctd17 |
| 743 | Nupr1 |
| 744 | Espl1 |
| 745 | Mphosph6 |
| 746 | Dus4l |
| 747 | Alg6 |
| 748 | Acsf3 |
| 749 | Mad1l1 |
| 750 | Tfdp1 |
| 751 | Phb |
| 752 | Spred1 |
| 753 | Rars |
| 754 | Tubb6 |
| 755 | Abcb6 |
| 756 | Snrpb |
| 757 | Lty1 |
| 758 | Pilra |
| 759 | Orc2 |
| 760 | Rpp40 |
| 761 | Wrb |
| 762 | Tmem144 |
| 763 | Fubp1 |
| 764 | Kif15 |
| 765 | Tmem69 |
| 766 | BC030867 |
| 767 | Jmjd4 |
| 768 | Procr |
| 769 | Aurka |
| 770 | Lyrm7 |
| 771 | Pet112 |
| 772 | Wdr90 |
| 773 | Ddx27 |
| 774 | Bag2 |
| 775 | Ccnb1 |
| 776 | Polr3d |
| 777 | Wdr75 |
| 778 | Cltb |
| 779 | Ppp2r1b |
| 780 | Psat1 |
| 781 | Psme3 |
| 782 | Psmb7 |
| 783 | 2310057M21Rik |
| 784 | Hist1h3i |
| 785 | Rrs1 |
| 786 | Otud6b |
| 787 | Mrpl3 |
| 788 | Spdl1 |
| 789 | Pmf1 |
| 790 | Igfbp4 |
| 791 | Pkib |
| 792 | Sf3b3 |
| 793 | Eif1ad |
| 794 | Crtam |
| 795 | Rbm8a |
| 796 | Mansc1 |
| 797 | Anp32e |

TABLE 2A-continued

Downregulated genes after GC + IL27 (1558 in ranked order)

| | |
|---|---|
| 798 | Bard1 |
| 799 | Nol6 |
| 800 | Bub1 |
| 801 | Klhdc4 |
| 802 | Mov10 |
| 803 | Birc5 |
| 804 | Abcb1b |
| 805 | Rpa3 |
| 806 | Lap3 |
| 807 | Pfkfb1 |
| 808 | E2f3 |
| 809 | Mboat1 |
| 810 | Ippk |
| 811 | Pphln1 |
| 812 | Gnl3 |
| 813 | Zbtb8os |
| 814 | Ntmt1 |
| 815 | 4930579G24Rik |
| 816 | Slc25a33 |
| 817 | 2700029M09Rik |
| 818 | Dynll2 |
| 819 | Tdrkh |
| 820 | Cops7a |
| 821 | Tlr1 |
| 822 | Dek |
| 823 | Rgs16 |
| 824 | Cttn |
| 825 | Dhrs4 |
| 826 | Pfdn4 |
| 827 | Dclre1a |
| 828 | Gmnn |
| 829 | Psph |
| 830 | Abcb1a |
| 831 | Ccna2 |
| 832 | Kpna2 |
| 833 | Actb |
| 834 | Clpp |
| 835 | Pdhx |
| 836 | Dhx37 |
| 837 | Melk |
| 838 | Gca |
| 839 | Dnaja1 |
| 840 | Gcnt2 |
| 841 | Anapc15 |
| 842 | Coq10b |
| 843 | Esf1 |
| 844 | Scap |
| 845 | Siglec5 |
| 846 | Slc25a10 |
| 847 | Mrps22 |
| 848 | Ttc32 |
| 849 | Zranb3 |
| 850 | Rpp38 |
| 851 | Skp2 |
| 852 | Gpt2 |
| 853 | Pask |
| 854 | Chac2 |
| 855 | Wars |
| 856 | Smc2 |
| 857 | Atf3 |
| 858 | Hmgn1 |
| 859 | Tmem132a |
| 860 | Tnfrsf21 |
| 861 | Rbm12 |
| 862 | Pusl1 |
| 863 | Cluh |
| 864 | A230046K03Rik |
| 865 | Rpp14 |
| 866 | Fam174b |
| 867 | Cxcr2 |
| 868 | Rhot2 |
| 869 | Psma4 |
| 870 | Noc3l |
| 871 | Exosc7 |
| 872 | Ccdc14 |
| 873 | Polr2k |
| 874 | Slco4a1 |
| 875 | F2rl2 |
| 876 | Gm5531 |
| 877 | Rapsn |
| 878 | Eno3 |
| 879 | Pkd1l3 |
| 880 | D630039A03Rik |
| 881 | Fbxo5 |
| 882 | Nol11 |
| 883 | Adk |
| 884 | Timm50 |
| 885 | Galnt3 |
| 886 | L2hgdh |
| 887 | Srsf9 |
| 888 | S430427O19Rik |
| 889 | Slc35a4 |
| 890 | Mrpl12 |
| 891 | Phgdh |
| 892 | Snrpc |
| 893 | Psmc1 |
| 894 | Bcat1 |
| 895 | Atp8b4 |
| 896 | Banf1 |
| 897 | Etfb |
| 898 | Polr1a |
| 899 | Spc25 |
| 900 | Pold2 |
| 901 | 2810004N23Rik |
| 902 | Cirh1a |
| 903 | Kdm8 |
| 904 | Ddx51 |
| 905 | Dse |
| 906 | Rras2 |
| 907 | Ncbp1 |
| 908 | Smyd2 |
| 909 | Ddx18 |
| 910 | Mrps18a |
| 911 | Pros1 |
| 912 | Fasl |
| 913 | Cdc20 |
| 914 | Mfsd2a |
| 915 | Dctd |
| 916 | Atp6v1a |
| 917 | Prps1l3 |
| 918 | Ak2 |
| 919 | Cox10 |
| 920 | 2210016F16Rik |
| 921 | Kti12 |
| 922 | Cct8 |
| 923 | Mrpl28 |
| 924 | Cstf2 |
| 925 | Hnrnph1 |
| 926 | Skp1a |
| 927 | Tyw3 |
| 928 | Ifngr2 |
| 929 | Psmg3 |
| 930 | Zfp446 |
| 931 | Gps1 |
| 932 | Tmem199 |
| 933 | Nanog |
| 934 | Mrpl42 |
| 935 | Doc2a |
| 936 | Mir17hg |
| 937 | Slc35g1 |
| 938 | AI836003 |
| 939 | Diablo |
| 940 | Alg3 |
| 941 | Nle1 |
| 942 | Prps1 |
| 943 | Ubtf |
| 944 | Mogs |
| 945 | Pnpt1 |
| 946 | Snrpd1 |
| 947 | Kif20a |
| 948 | Ttk |
| 949 | Sssca1 |
| 950 | Eif5a |
| 951 | Slfn5 |
| 952 | Prim1 |
| 953 | Igsf8 |

TABLE 2A-continued

Downregulated genes after GC + IL27 (1558 in ranked order)

| | |
|---|---|
| 954 | Tmem109 |
| 955 | Yars2 |
| 956 | Med27 |
| 957 | Nudt15 |
| 958 | Ier5 |
| 959 | Rbmxl1 |
| 960 | Odc1 |
| 961 | Mrpl55 |
| 962 | Fasn |
| 963 | Rbpms2 |
| 964 | Pbdc1 |
| 965 | Ydjc |
| 966 | Mecr |
| 967 | Yrdc |
| 968 | Fanci |
| 969 | Zfp783 |
| 970 | Atpbd4 |
| 971 | Sapcd2 |
| 972 | Fkbp2 |
| 973 | Myef2 |
| 974 | Nafl |
| 975 | Ppil1 |
| 976 | Dclre1b |
| 977 | Eif6 |
| 978 | Hdac1 |
| 979 | Slmo2 |
| 980 | Ptgfrn |
| 981 | Hsd17b7 |
| 982 | Mycbp |
| 983 | Actl6a |
| 984 | U2af2 |
| 985 | Exosc3 |
| 986 | Larp4 |
| 987 | Exosc1 |
| 988 | Ino80e |
| 989 | Pelp1 |
| 990 | Sfxn1 |
| 991 | Arhgdig |
| 992 | Cyp4f16 |
| 993 | Dsn1 |
| 994 | Rfc4 |
| 995 | Psma5 |
| 996 | Mettl13 |
| 997 | Cenpk |
| 998 | Hsp90b1 |
| 999 | Dpp3 |
| 1000 | Uchl5 |
| 1001 | Irf4 |
| 1002 | Lig1 |
| 1003 | 0610007P14Rik |
| 1004 | Eif2s1 |
| 1005 | Tacc3 |
| 1006 | Dus11 |
| 1007 | Prmt5 |
| 1008 | Pdss2 |
| 1009 | U2af1 |
| 1010 | Calm1 |
| 1011 | Gpn2 |
| 1012 | Wdr61 |
| 1013 | Rpn1 |
| 1014 | Hspa14 |
| 1015 | Rbm14 |
| 1016 | Ercc8 |
| 1017 | Yae1d1 |
| 1018 | Ccdc50 |
| 1019 | Ndufs6 |
| 1020 | Aco2 |
| 1021 | Hmgb1 |
| 1022 | Txnrd1 |
| 1023 | Trim16 |
| 1024 | Gfpt2 |
| 1025 | Dimt1 |
| 1026 | Fpgs |
| 1027 | Tbrg4 |
| 1028 | Rnd1 |
| 1029 | Fam203a |
| 1030 | G6pdx |
| 1031 | Slc29a1 |
| 1032 | Psmb5 |
| 1033 | Dars2 |
| 1034 | Hnrnpu |
| 1035 | Farsa |
| 1036 | Txn1 |
| 1037 | Mettl25 |
| 1038 | Slc2a1 |
| 1039 | Lepr |
| 1040 | 2210408I21Rik |
| 1041 | Snrnp40 |
| 1042 | Spin2 |
| 1043 | Eif4g2 |
| 1044 | Pfn1 |
| 1045 | Sgol1 |
| 1046 | Nuf2 |
| 1047 | Gtf2h1 |
| 1048 | Gp49a |
| 1049 | Ccnd3 |
| 1050 | Fam118b |
| 1051 | Ube2s |
| 1052 | Elp5 |
| 1053 | Slc25a26 |
| 1054 | Dusp4 |
| 1055 | Arhgap19 |
| 1056 | Ppp5c |
| 1057 | Timm9 |
| 1058 | Usp10 |
| 1059 | Lrrc8d |
| 1060 | Aven |
| 1061 | Fus |
| 1062 | Hus1 |
| 1063 | Bms1 |
| 1064 | Leo1 |
| 1065 | Thoc3 |
| 1066 | Gzmb |
| 1067 | Mdn1 |
| 1068 | Apoo |
| 1069 | Rps27l |
| 1070 | Ssr2 |
| 1071 | Trmt2a |
| 1072 | Inpp5b |
| 1073 | Cpsf3 |
| 1074 | Zswim7 |
| 1075 | Nup205 |
| 1076 | Zfp324 |
| 1077 | Mrpl17 |
| 1078 | Vac14 |
| 1079 | Ap1s1 |
| 1080 | Cish |
| 1081 | Mbd3 |
| 1082 | Ndufa5 |
| 1083 | Slc25a13 |
| 1084 | Rrn3 |
| 1085 | Mettl1 |
| 1086 | Dlat |
| 1087 | Psmg1 |
| 1088 | Mrpl11 |
| 1089 | Elac2 |
| 1090 | Sgk3 |
| 1091 | Bzw2 |
| 1092 | Eif4a3 |
| 1093 | Rbbp7 |
| 1094 | D19Bwg1357e |
| 1095 | Eif1a |
| 1096 | Smn1 |
| 1097 | Tomm6 |
| 1098 | Hist1h4i |
| 1099 | Prmt7 |
| 1100 | Ddx39b |
| 1101 | Htra2 |
| 1102 | Slc16a1 |
| 1103 | Fastkd5 |
| 1104 | Sf3a3 |
| 1105 | Psmd12 |
| 1106 | Ndufa12 |
| 1107 | Lyrm1 |
| 1108 | Vrk1 |
| 1109 | Bdh1 |

TABLE 2A-continued

Downregulated genes after GC + IL27 (1558 in ranked order)

| | |
|---|---|
| 1110 | Enoph1 |
| 1111 | Pcyox1l |
| 1112 | Ddx1 |
| 1113 | Mrpl36 |
| 1114 | Vma21 |
| 1115 | Zmynd8 |
| 1116 | Sfn |
| 1117 | Wbscr22 |
| 1118 | Neil3 |
| 1119 | Bccip |
| 1120 | Bckdk |
| 1121 | Nup43 |
| 1122 | Bckdhb |
| 1123 | Eif5a2 |
| 1124 | Senp3 |
| 1125 | Ccnb2 |
| 1126 | Pgd |
| 1127 | Atp5g3 |
| 1128 | Farsb |
| 1129 | Comt |
| 1130 | Wdr43 |
| 1131 | Atp5g1 |
| 1132 | Pfdn2 |
| 1133 | Dbt |
| 1134 | Magohb |
| 1135 | Syce2 |
| 1136 | Ptcra |
| 1137 | Metap2 |
| 1138 | Ccnd2 |
| 1139 | Ggct |
| 1140 | Aifm1 |
| 1141 | Drg2 |
| 1142 | Rars2 |
| 1143 | Gm12504 |
| 1144 | C330018D20Rik |
| 1145 | Ccne1 |
| 1146 | Timm23 |
| 1147 | Pcyt1a |
| 1148 | 3110001I22Rik |
| 1149 | Ssrp1 |
| 1150 | Usp46 |
| 1151 | Bzw1 |
| 1152 | Myc |
| 1153 | Gfm1 |
| 1154 | Ppia |
| 1155 | Ctu2 |
| 1156 | Prmt6 |
| 1157 | Sec23b |
| 1158 | Nif3l1 |
| 1159 | Eif3b |
| 1160 | Jagn1 |
| 1161 | Suv39h2 |
| 1162 | Slc7a14 |
| 1163 | Samm50 |
| 1164 | Sgsm3 |
| 1165 | Cd3eap |
| 1166 | Dnmt1 |
| 1167 | Nupl2 |
| 1168 | Ecd |
| 1169 | Urb1 |
| 1170 | Cyb5b |
| 1171 | Mrpl37 |
| 1172 | Haus7 |
| 1173 | Xrcc2 |
| 1174 | Enkd1 |
| 1175 | Chml |
| 1176 | Mrps18b |
| 1177 | Psmb3 |
| 1178 | Mthfsd |
| 1179 | Ccnf |
| 1180 | Papd7 |
| 1181 | Cep78 |
| 1182 | Moap1 |
| 1183 | Gm6793 |
| 1184 | Lmnb2 |
| 1185 | Taf9 |
| 1186 | Mrps5 |
| 1187 | Uba2 |
| 1188 | Egfl7 |
| 1189 | Denr |
| 1190 | Sppl2b |
| 1191 | Mtr |
| 1192 | Haus6 |
| 1193 | Fancm |
| 1194 | Pus7 |
| 1195 | Snhg3 |
| 1196 | Ulbp1 |
| 1197 | Thoc6 |
| 1198 | Ptma |
| 1199 | Bclaf1 |
| 1200 | Gtpbp4 |
| 1201 | Toe1 |
| 1202 | Zdhhc6 |
| 1203 | Scoc |
| 1204 | BC003965 |
| 1205 | Mrpl49 |
| 1206 | Galntl |
| 1207 | Nek2 |
| 1208 | Wdr55 |
| 1209 | Larp7 |
| 1210 | Hyou1 |
| 1211 | Apex1 |
| 1212 | Mtg1 |
| 1213 | Ywhaq |
| 1214 | Mmd |
| 1215 | Dtymk |
| 1216 | Cops3 |
| 1217 | Rcl1 |
| 1218 | St6galnac4 |
| 1219 | Bcap29 |
| 1220 | Ect2 |
| 1221 | Utp15 |
| 1222 | Tox |
| 1223 | Echdc2 |
| 1224 | Lrdd |
| 1225 | Zfp286 |
| 1226 | Anapc5 |
| 1227 | Slc39a6 |
| 1228 | Aimp2 |
| 1229 | Camkk2 |
| 1230 | Nubp2 |
| 1231 | Dhps |
| 1232 | Atp5b |
| 1233 | Fbxo17 |
| 1234 | Atic |
| 1235 | Dph5 |
| 1236 | Sh2b3 |
| 1237 | Ptpla |
| 1238 | Pkmyt1 |
| 1239 | Dut |
| 1240 | Rtn4ip1 |
| 1241 | Lancl2 |
| 1242 | Larp1 |
| 1243 | Skiv2l2 |
| 1244 | Mrpl16 |
| 1245 | Impa1 |
| 1246 | Sfpq |
| 1247 | Zscan22 |
| 1248 | Strap |
| 1249 | 2410016O06Rik |
| 1250 | Rexo2 |
| 1251 | Cpsf6 |
| 1252 | Tnfsf14 |
| 1253 | Cdt1 |
| 1254 | Psmd14 |
| 1255 | 1810009A15Rik |
| 1256 | Glrx5 |
| 1257 | Fem1a |
| 1258 | Psmc2 |
| 1259 | Psmd13 |
| 1260 | Lsg1 |
| 1261 | Ptges3 |
| 1262 | Nt5c2 |
| 1263 | Psmc3 |
| 1264 | Gpn1 |
| 1265 | Prkrip1 |

TABLE 2A-continued

Downregulated genes after GC + IL27 (1558 in ranked order)

| | |
|---|---|
| 1266 | Pola2 |
| 1267 | Cep128 |
| 1268 | Dgkh |
| 1269 | Dpy30 |
| 1270 | Ndufb6 |
| 1271 | Ddc |
| 1272 | Pinx1 |
| 1273 | 1810055G02Rik |
| 1274 | Prpf3 |
| 1275 | Tmem185b |
| 1276 | Cyc1 |
| 1277 | Ppa2 |
| 1278 | Polr2c |
| 1279 | Clptm1l |
| 1280 | Wdr12 |
| 1281 | Ilkap |
| 1282 | Cmss1 |
| 1283 | Gtf3c6 |
| 1284 | Bud31 |
| 1285 | Selrc1 |
| 1286 | Itga5 |
| 1287 | Mtx1 |
| 1288 | Mrps28 |
| 1289 | Yif1a |
| 1290 | Lyrm4 |
| 1291 | Asns |
| 1292 | Snhg11 |
| 1293 | H2afz |
| 1294 | Ppp1r8 |
| 1295 | 1190007I07Rik |
| 1296 | Stk3 |
| 1297 | Edem2 |
| 1298 | Nsun5 |
| 1299 | Timd2 |
| 1300 | Ddx21 |
| 1301 | Hmbs |
| 1302 | Susd1 |
| 1303 | Paox |
| 1304 | Rfc2 |
| 1305 | Cenpb |
| 1306 | Zbtb45 |
| 1307 | Cd9 |
| 1308 | Mrps12 |
| 1309 | Siva1 |
| 1310 | Efcab7 |
| 1311 | Dynlt1a |
| 1312 | Asna1 |
| 1313 | Acsl4 |
| 1314 | Mrpl46 |
| 1315 | Hypk |
| 1316 | Tpx2 |
| 1317 | Cdca5 |
| 1318 | Zfp828 |
| 1319 | Sf3a2 |
| 1320 | Trnt1 |
| 1321 | Dctpp1 |
| 1322 | Tsr2 |
| 1323 | Dennd5b |
| 1324 | Dohh |
| 1325 | Ndufc1 |
| 1326 | Pcca |
| 1327 | BC055324 |
| 1328 | Eif2b1 |
| 1329 | Top1mt |
| 1330 | Isyna1 |
| 1331 | Top1 |
| 1332 | Gpr155 |
| 1333 | Slbp |
| 1334 | Adap1 |
| 1335 | Mrps7 |
| 1336 | Wdr36 |
| 1337 | Serpine2 |
| 1338 | Entpd7 |
| 1339 | Cetn3 |
| 1340 | Galm |
| 1341 | Cdk4 |
| 1342 | Srsf1 |
| 1343 | Aacs |
| 1344 | Slc10a3 |
| 1345 | Timm13 |
| 1346 | Osbpl3 |
| 1347 | Dph3 |
| 1348 | Qtrtd1 |
| 1349 | Chd1l |
| 1350 | Ada |
| 1351 | Ncoa7 |
| 1352 | Pnp |
| 1353 | Casc5 |
| 1354 | Ttc7b |
| 1355 | Furin |
| 1356 | Ftsj2 |
| 1357 | Atf6b |
| 1358 | Kcnk5 |
| 1359 | Psmb4 |
| 1360 | Tnfsf4 |
| 1361 | Cct7 |
| 1362 | Pycr2 |
| 1363 | Riok2 |
| 1364 | Dlgap5 |
| 1365 | Brca2 |
| 1366 | Elp4 |
| 1367 | Abcf1 |
| 1368 | Sco2 |
| 1369 | Znhit6 |
| 1370 | Eif4e |
| 1371 | Ddost |
| 1372 | Dbr1 |
| 1373 | Elmo1 |
| 1374 | Clns1a |
| 1375 | Tob2 |
| 1376 | Cyb561d2 |
| 1377 | Hspa9 |
| 1378 | Lrrc59 |
| 1379 | Osgin2 |
| 1380 | Ampd2 |
| 1381 | Ftsjd1 |
| 1382 | Pafah1b2 |
| 1383 | Pitpnb |
| 1384 | Fam98a |
| 1385 | Cdkn3 |
| 1386 | Atp5j |
| 1387 | Hras1 |
| 1388 | Atpif1 |
| 1389 | Apex2 |
| 1390 | Ctsz |
| 1391 | Gramd1b |
| 1392 | Msto1 |
| 1393 | Oip5 |
| 1394 | Slc29a2 |
| 1395 | Nucks1 |
| 1396 | Ccp110 |
| 1397 | Ier3 |
| 1398 | BC035044 |
| 1399 | G3bp1 |
| 1400 | Psmd9 |
| 1401 | Arpp19 |
| 1402 | Gfpt1 |
| 1403 | Depdc1a |
| 1404 | Wdr73 |
| 1405 | Fam73b |
| 1406 | D2Wsu81e |
| 1407 | Hax1 |
| 1408 | Psma3 |
| 1409 | Rwdd4a |
| 1410 | Kif22 |
| 1411 | Cd63 |
| 1412 | Pabpc4 |
| 1413 | Las1l |
| 1414 | Smarca4 |
| 1415 | Diap3 |
| 1416 | 9130401M01Rik |
| 1417 | Rpa2 |
| 1418 | Lrp8 |
| 1419 | Eaf1 |
| 1420 | Prpf38a |
| 1421 | Rrp8 |

TABLE 2A-continued

Downregulated genes after GC + IL27 (1558 in ranked order)

| | |
|---|---|
| 1422 | Trappc13 |
| 1423 | Megf8 |
| 1424 | Msrb2 |
| 1425 | Pcnxl4 |
| 1426 | Supt16 |
| 1427 | Med29 |
| 1428 | Pwp1 |
| 1429 | Kif2c |
| 1430 | Bid |
| 1431 | Blm |
| 1432 | Ints2 |
| 1433 | Spink2 |
| 1434 | Gle1 |
| 1435 | Rpgr |
| 1436 | Rnf19b |
| 1437 | Pacsin2 |
| 1438 | 2310033P09Rik |
| 1439 | Drosha |
| 1440 | Pdzd11 |
| 1441 | Lipt2 |
| 1442 | Nnt |
| 1443 | Stoml2 |
| 1444 | Rpp30 |
| 1445 | Rnaseh2b |
| 1446 | Senp5 |
| 1447 | Mul1 |
| 1448 | Nars |
| 1449 | Inpp4b |
| 1450 | Arl6ip6 |
| 1451 | Srd5a3 |
| 1452 | Tsr1 |
| 1453 | Coq6 |
| 1454 | Dusp6 |
| 1455 | Pomt2 |
| 1456 | Wdr35 |
| 1457 | L3mbtl2 |
| 1458 | Tcf19 |
| 1459 | Slc35a1 |
| 1460 | Dclre1c |
| 1461 | 6720489N17Rik |
| 1462 | Rab23 |
| 1463 | Dhx33 |
| 1464 | Atad5 |
| 1465 | Tmem70 |
| 1466 | Ttll12 |
| 1467 | Urb2 |
| 1468 | Slc39a10 |
| 1469 | Zranb2 |
| 1470 | Twistnb |
| 1471 | Polr2j |
| 1472 | Sec13 |
| 1473 | Nup88 |
| 1474 | Psma6 |
| 1475 | Camsap2 |
| 1476 | Eif4g1 |
| 1477 | Pes1 |
| 1478 | Fbxo30 |
| 1479 | Pccb |
| 1480 | Ube2n |
| 1481 | Cdca3 |
| 1482 | Recql |
| 1483 | Usp14 |
| 1484 | Prdm16 |
| 1485 | Xrcc6 |
| 1486 | Rbm34 |
| 1487 | Synj2 |
| 1488 | Ggh |
| 1489 | Thoc1 |
| 1490 | Dcaf13 |
| 1491 | Slc37a2 |
| 1492 | Sephs1 |
| 1493 | Atpaf2 |
| 1494 | Cenpm |
| 1495 | Tsfm |
| 1496 | Uqcrq |
| 1497 | Nutf2 |
| 1498 | Dpp9 |
| 1499 | Far1 |
| 1500 | Ptprk |
| 1501 | Lcp2 |
| 1502 | Psmb6 |
| 1503 | Prkar2a |
| 1504 | Tcof1 |
| 1505 | Apip |
| 1506 | Gnpnat1 |
| 1507 | Abcc4 |
| 1508 | Gtf2h4 |
| 1509 | Apoe |
| 1510 | Hsd17b12 |
| 1511 | Rwdd2b |
| 1512 | Trmu |
| 1513 | Mrpl1 |
| 1514 | Tube1 |
| 1515 | Slc7a1 |
| 1516 | Ddx20 |
| 1517 | C2cd5 |
| 1518 | Eif4a1 |
| 1519 | Rttn |
| 1520 | Ecsit |
| 1521 | Ndufab1 |
| 1522 | Crim1 |
| 1523 | Nadk |
| 1524 | Gemin5 |
| 1525 | Ndufs1 |
| 1526 | Hemk1 |
| 1527 | Neu3 |
| 1528 | Xpo1 |
| 1529 | Zcchc17 |
| 1530 | Kif4 |
| 1531 | Mthfd2 |
| 1532 | Mrps27 |
| 1533 | Pdap1 |
| 1534 | Nkiras1 |
| 1535 | Kctd14 |
| 1536 | Chrna1 |
| 1537 | Nol10 |
| 1538 | Mrpl51 |
| 1539 | Bub1b |
| 1540 | Smarcb1 |
| 1541 | Zmynd19 |
| 1542 | Ilf2 |
| 1543 | Phldb1 |
| 1544 | Prr5l |
| 1545 | Gsg2 |
| 1546 | Slc16a6 |
| 1547 | Mrps11 |
| 1548 | Wls |
| 1549 | Pms1 |
| 1550 | Nsfl1c |
| 1551 | Sco1 |
| 1552 | Gas8 |
| 1553 | Sgcb |
| 1554 | Nup133 |
| 1555 | Fkbp3 |
| 1556 | Mmachc |
| 1557 | Nfkbib |
| 1558 | Pop7 |

TABLE 2B

Upregulated genes after GC + IL27 (1592 in ranked order)

| | |
|---|---|
| 1 | Baz2a |
| 2 | Rpl22l1 |
| 3 | B4galt7 |
| 4 | Asap1 |
| 5 | Srr |
| 6 | Paip2 |
| 7 | Hsdl1 |
| 8 | Reep1 |
| 9 | Pex13 |
| 10 | Mapk14 |
| 11 | Hmg20a |

TABLE 2B-continued

Upregulated genes after GC + IL27 (1592 in ranked order)

| | |
|---|---|
| 12 | Zcchc11 |
| 13 | Zfp592 |
| 14 | Zkscan17 |
| 15 | Adam8 |
| 16 | Tmem108 |
| 17 | Lyst |
| 18 | Ppp1r12b |
| 19 | Tmem43 |
| 20 | Slc7a4 |
| 21 | Rnf38 |
| 22 | Slc25a36 |
| 23 | Arl14ep |
| 24 | Gm14308 |
| 25 | Zbtb38 |
| 26 | Klf13 |
| 27 | B3gntl1 |
| 28 | Acp6 |
| 29 | Csnk1d |
| 30 | Nxpe3 |
| 31 | Rbl2 |
| 32 | Plekha5 |
| 33 | Itgb3 |
| 34 | Tgfbr3 |
| 35 | Smim14 |
| 36 | Sec24a |
| 37 | Nit2 |
| 38 | Arhgap9 |
| 39 | Gtf2ird2 |
| 40 | A630007B06Rik |
| 41 | Zfp839 |
| 42 | Acot11 |
| 43 | Gid4 |
| 44 | Tmub2 |
| 45 | Itgav |
| 46 | S1pr4 |
| 47 | Pcnx |
| 48 | Whsc1l1 |
| 49 | Tpd52 |
| 50 | Arhgef12 |
| 51 | Cmip |
| 52 | Prkab2 |
| 53 | H2-DMb1 |
| 54 | Cers4 |
| 55 | Sh2b1 |
| 56 | Bace1 |
| 57 | Acsbg1 |
| 58 | Fmnl1 |
| 59 | Cyhr1 |
| 60 | Rere |
| 61 | Afap1 |
| 62 | Cfl2 |
| 63 | Ipcef1 |
| 64 | Zyx |
| 65 | Cdk19 |
| 66 | Pex26 |
| 67 | Gm6313 |
| 68 | Plin3 |
| 69 | Crtc3 |
| 70 | Phf8 |
| 71 | Zfp956 |
| 72 | Coq10a |
| 73 | Rps2 |
| 74 | Afg3l2 |
| 75 | Gpsm1 |
| 76 | Evi5l |
| 77 | Galc |
| 78 | Rftn1 |
| 79 | Entpd4 |
| 80 | BC022687 |
| 81 | Tnfrsf14 |
| 82 | AB124611 |
| 83 | Mms19 |
| 84 | Snx14 |
| 85 | Tmem219 |
| 86 | Rpl37a |
| 87 | Zdhhc17 |
| 88 | Rps6ka3 |
| 89 | Slc2a4rg-ps |
| 90 | Gbp10 |
| 91 | Usp11 |
| 92 | Gabarap |
| 93 | Prkd2 |
| 94 | Ppox |
| 95 | Pgap1 |
| 96 | Smg6 |
| 97 | Mnda1 |
| 98 | C2cd2 |
| 99 | Ctss |
| 100 | Hopx |
| 101 | Acsl3 |
| 102 | Limk1 |
| 103 | Kif13b |
| 104 | Cnn2 |
| 105 | Atat1 |
| 106 | Klhdc1 |
| 107 | Slc17a5 |
| 108 | Il6st |
| 109 | Bcas3 |
| 110 | Rcor3 |
| 111 | Tmx4 |
| 112 | Itga4 |
| 113 | Zmym5 |
| 114 | Plcb3 |
| 115 | Acox3 |
| 116 | Atp7a |
| 117 | Irf6 |
| 118 | Wash |
| 119 | Mif4gd |
| 120 | Marf1 |
| 121 | Xist |
| 122 | 4930486L24Rik |
| 123 | Smyd3 |
| 124 | Dopey2 |
| 125 | Cyp4v3 |
| 126 | Sfi1 |
| 127 | Tmem141 |
| 128 | Pou2f1 |
| 129 | Efemp2 |
| 130 | Gns |
| 131 | Map1lc3b |
| 132 | Gpbp1l1 |
| 133 | Heatr2 |
| 134 | H2afv |
| 135 | Nanos1 |
| 136 | Tnrc6b |
| 137 | Sirt3 |
| 138 | Helb |
| 139 | Gbp3 |
| 140 | Rsph3b |
| 141 | 1700011J10Rik |
| 142 | Lst1 |
| 143 | Sp100 |
| 144 | Arntl |
| 145 | 4632428N05Rik |
| 146 | Ccng2 |
| 147 | Zmynd11 |
| 148 | Zeb1 |
| 149 | P2rx4 |
| 150 | BC017643 |
| 151 | Rrad |
| 152 | Flcn |
| 153 | Lsm11 |
| 154 | Lrrfip2 |
| 155 | Utrn |
| 156 | Abcg3 |
| 157 | Sqstm1 |
| 158 | Trpm4 |
| 159 | Bc021614 |
| 160 | Ltb4r1 |
| 161 | Fam65a |
| 162 | Zfp688 |
| 163 | 0610030E20Rik |
| 164 | Car9 |
| 165 | Gm12942 |
| 166 | Trafd1 |
| 167 | Pfkfb3 |

TABLE 2B-continued

Upregulated genes after GC + IL27 (1592 in ranked order)

| | |
|---|---|
| 168 | Mir703 |
| 169 | Lrig2 |
| 170 | Rnf215 |
| 171 | Rps15a-ps4 |
| 172 | Pcsk4 |
| 173 | Rreb1 |
| 174 | Slc24a6 |
| 175 | Rnf31 |
| 176 | Enah |
| 177 | Tcta |
| 178 | Tnrc6c |
| 179 | Gm4827 |
| 180 | Tk2 |
| 181 | Eno2 |
| 182 | 1700113A16Rik |
| 183 | Gm2382 |
| 184 | Zbtb25 |
| 185 | Prss16 |
| 186 | Mllt4 |
| 187 | Pisd-ps2 |
| 188 | St3gal6 |
| 189 | Sipa1l1 |
| 190 | Zfp317 |
| 191 | Mcl1 |
| 192 | Rab9 |
| 193 | Trim41 |
| 194 | Chp1 |
| 195 | Taz |
| 196 | Grap |
| 197 | Fam168a |
| 198 | Ahnak |
| 199 | Trappc6a |
| 200 | Polg2 |
| 201 | Suv420h2 |
| 202 | Trp53i11 |
| 203 | Pddc1 |
| 204 | Zrsr1 |
| 205 | Slc25a30 |
| 206 | Myadm |
| 207 | Kansl11 |
| 208 | 4833420G17Rik |
| 209 | H2-DMa |
| 210 | Fam214a |
| 211 | Tmem194b |
| 212 | Osbpl1a |
| 213 | St3gal1 |
| 214 | Pcf11 |
| 215 | Idua |
| 216 | Zfp867 |
| 217 | Lmbr1l |
| 218 | 5730507C01Rik |
| 219 | Ndufa6 |
| 220 | Tspan14 |
| 221 | Ssh1 |
| 222 | Ormdl3 |
| 223 | Gbp8 |
| 224 | Gpsm3 |
| 225 | Kctd11 |
| 226 | Phxr4 |
| 227 | Slfn1 |
| 228 | Sox5 |
| 229 | Wdr91 |
| 230 | Plk1s1 |
| 231 | Bbx |
| 232 | Zfp874a |
| 233 | Gpr114 |
| 234 | Hif3a |
| 235 | Oas1b |
| 236 | Apaf1 |
| 237 | Tubg2 |
| 238 | Vamp5 |
| 239 | Lamc1 |
| 240 | Itpk1 |
| 241 | Mll5 |
| 242 | Btbd16 |
| 243 | Rps15a |
| 244 | Tmem218 |
| 245 | Rab12 |
| 246 | Hist2h2be |
| 247 | Lpin1 |
| 248 | Plekhg5 |
| 249 | Tmem123 |
| 250 | 2310067B10Rik |
| 251 | Il18 |
| 252 | Ankrd13d |
| 253 | Lamp1 |
| 254 | Kif9 |
| 255 | Ptk2b |
| 256 | 2810468N07Rik |
| 257 | Zfp580 |
| 258 | Sdf2 |
| 259 | Atf7 |
| 260 | Nol3 |
| 261 | Lancl1 |
| 262 | Chd2 |
| 263 | Zbtb7a |
| 264 | Thap4 |
| 265 | Pqlc1 |
| 266 | 1810026B05Rik |
| 267 | Zbed6 |
| 268 | Inpp4a |
| 269 | Wdr13 |
| 270 | 2900008C10Rik |
| 271 | Scand1 |
| 272 | Gramd1a |
| 273 | Prkcq |
| 274 | Acadl |
| 275 | Snrk |
| 276 | Letm2 |
| 277 | Prex1 |
| 278 | Znrf1 |
| 279 | 1700010I14Rik |
| 280 | Mafl |
| 281 | Ptms |
| 282 | Epcam |
| 283 | Angptl6 |
| 284 | Gimap4 |
| 285 | Kdm3b |
| 286 | Ogt |
| 287 | Cdc14b |
| 288 | C920025E04Rik |
| 289 | Neurl3 |
| 290 | Tmc4 |
| 291 | Mgst3 |
| 292 | Prkacb |
| 293 | Fcho2 |
| 294 | Dennd3 |
| 295 | Gcm2 |
| 296 | Prkcz |
| 297 | Tgoln1 |
| 298 | Slc25a37 |
| 299 | Taf1d |
| 300 | Ctns |
| 301 | Dennd4c |
| 302 | Trip6 |
| 303 | Fam13b |
| 304 | Pias3 |
| 305 | H2-T10 |
| 306 | Tbc1d17 |
| 307 | Rnf149 |
| 308 | D730005E14Rik |
| 309 | Slc35f5 |
| 310 | Gm16907 |
| 311 | Sec22c |
| 312 | Flt3l |
| 313 | Tpk1 |
| 314 | Ebf1 |
| 315 | Zfp954 |
| 316 | Surf1 |
| 317 | Rfx3 |
| 318 | Cox7a2l |
| 319 | Hectd3 |
| 320 | Ccdc17 |
| 321 | Bcl3 |
| 322 | Itpr2 |
| 323 | Dock6 |

TABLE 2B-continued

Upregulated genes after GC + IL27 (1592 in ranked order)

| | |
|---|---|
| 324 | Limk2 |
| 325 | Vstm5 |
| 326 | Eef2k |
| 327 | Rb1cc1 |
| 328 | Trpc4ap |
| 329 | Rps27 |
| 330 | Fndc3a |
| 331 | Zcchc6 |
| 332 | Crebzf |
| 333 | Ankrd50 |
| 334 | Pik3c2a |
| 335 | Wdr81 |
| 336 | Mef2a |
| 337 | Sfrs18 |
| 338 | Ifngr1 |
| 339 | Thap11 |
| 340 | Atraid |
| 341 | Rara |
| 342 | Dguok |
| 343 | Irf7 |
| 344 | Vamp4 |
| 345 | Dhx40 |
| 346 | Sipa1 |
| 347 | Prickle3 |
| 348 | Map3k1 |
| 349 | Cnppd1 |
| 350 | Lnpep |
| 351 | Casp1 |
| 352 | Golgb1 |
| 353 | Clybl |
| 354 | Chd7 |
| 355 | Optn |
| 356 | Arap2 |
| 357 | Abi3 |
| 358 | Lrrc61 |
| 359 | Fam105a |
| 360 | Casp9 |
| 361 | Ap3m2 |
| 362 | Gm4759 |
| 363 | Ankrd12 |
| 364 | Ikzf3 |
| 365 | Brwd1 |
| 366 | Ap1m2 |
| 367 | Tmem159 |
| 368 | Dtx3l |
| 369 | Spata13 |
| 370 | 5830432E09Rik |
| 371 | Rps15a-ps6 |
| 372 | Rassf1 |
| 373 | Fam102b |
| 374 | E4f1 |
| 375 | Plekhb2 |
| 376 | Zfp512 |
| 377 | H2-T9 |
| 378 | BC147527 |
| 379 | Tgfbr2 |
| 380 | Snhg7 |
| 381 | Plcg1 |
| 382 | Sepw1 |
| 383 | Gm13212 |
| 384 | B3galt4 |
| 385 | Fth1 |
| 386 | Sgsm2 |
| 387 | Ctsa |
| 388 | Use1 |
| 389 | Dyrk3 |
| 390 | Eif4a2 |
| 391 | Gm11127 |
| 392 | Stx5a |
| 393 | Mplkip |
| 394 | Zfp362 |
| 395 | Snx18 |
| 396 | Msl1 |
| 397 | Nt5e |
| 398 | Plcg2 |
| 399 | Ggnbp2 |
| 400 | Rlf |
| 401 | Akap9 |
| 402 | Nr2c2 |
| 403 | Atg9a |
| 404 | 2810008D09Rik |
| 405 | Naga |
| 406 | Abhd15 |
| 407 | Rdm1 |
| 408 | Dgka |
| 409 | Usp48 |
| 410 | Usf2 |
| 411 | Pde3b |
| 412 | Vps54 |
| 413 | Capn5 |
| 414 | Fam53b |
| 415 | Oxr1 |
| 416 | Fcho1 |
| 417 | Insr |
| 418 | Parp4 |
| 419 | Igbp1 |
| 420 | Eml5 |
| 421 | 2010003O02Rik |
| 422 | Hcst |
| 423 | Maml1 |
| 424 | Atg2a |
| 425 | Ubn2 |
| 426 | Arhgef1 |
| 427 | Cux1 |
| 428 | Gpi1 |
| 429 | 1810034E14Rik |
| 430 | Wdr19 |
| 431 | Hist3h2a |
| 432 | Gm5918 |
| 433 | Itm2c |
| 434 | P2ry10 |
| 435 | Ddb2 |
| 436 | Mnt |
| 437 | Sp140 |
| 438 | Mll3 |
| 439 | Sigirr |
| 440 | Tnks1bp1 |
| 441 | Efcab4b |
| 442 | Camk2d |
| 443 | Hexdc |
| 444 | Fchsd2 |
| 445 | Ltbp4 |
| 446 | Smtn |
| 447 | Itpr3 |
| 448 | Usp53 |
| 449 | Fxyd5 |
| 450 | Dzip1 |
| 451 | Sh3yl1 |
| 452 | Kat2b |
| 453 | Rala |
| 454 | Fam98c |
| 455 | Ptpn13 |
| 456 | Srgap3 |
| 457 | F8a |
| 458 | Ccpg1 |
| 459 | Rab11fip4 |
| 460 | Pfdn5 |
| 461 | Atxn7l1 |
| 462 | Tmem66 |
| 463 | Ercc5 |
| 464 | Il33 |
| 465 | Slc12a6 |
| 466 | Fhod1 |
| 467 | Gtf2i |
| 468 | Zfp768 |
| 469 | Dusp7 |
| 470 | Cst7 |
| 471 | Ubald1 |
| 472 | Lbh |
| 473 | Zfp354c |
| 474 | Pan2 |
| 475 | Glcci1 |
| 476 | Ttc38 |
| 477 | Kif7 |
| 478 | Rasgrp2 |
| 479 | Mctp2 |

TABLE 2B-continued

Upregulated genes after GC + IL27 (1592 in ranked order)

| | |
|---|---|
| 480 | Tanc1 |
| 481 | 2310001H17Rik |
| 482 | Yes1 |
| 483 | Kxd1 |
| 484 | Fam210b |
| 485 | Irgq |
| 486 | Zfp358 |
| 487 | Airn |
| 488 | 4932415G12Rik |
| 489 | Stab1 |
| 490 | C030039L03Rik |
| 491 | Arl5c |
| 492 | Peli1 |
| 493 | Fbxo32 |
| 494 | Cd97 |
| 495 | Rbm33 |
| 496 | Zbtb2 |
| 497 | Lgr4 |
| 498 | Rab11fip1 |
| 499 | Gdpd5 |
| 500 | Ing2 |
| 501 | Psrc1 |
| 502 | Inpp1 |
| 503 | A930015D03Rik |
| 504 | Fchsd1 |
| 505 | Nudt18 |
| 506 | Sytl1 |
| 507 | Zfp97 |
| 508 | Gpt |
| 509 | Irs2 |
| 510 | Rapgef4 |
| 511 | Pycard |
| 512 | Pkn1 |
| 513 | Mettl20 |
| 514 | Trim14 |
| 515 | Amz2 |
| 516 | Satb1 |
| 517 | Tbcel |
| 518 | Ar |
| 519 | Patz1 |
| 520 | Thap3 |
| 521 | Laptm5 |
| 522 | Myo6 |
| 523 | Cd1d1 |
| 524 | Jak3 |
| 525 | Glul |
| 526 | Rec8 |
| 527 | Rgp1 |
| 528 | Zfp429 |
| 529 | Gltscr2 |
| 530 | Cblb |
| 531 | Susd3 |
| 532 | Abca7 |
| 533 | Tnip2 |
| 534 | Inpp5k |
| 535 | Smarca2 |
| 536 | Aldoa |
| 537 | Zyg11b |
| 538 | Gm2a |
| 539 | Egln3 |
| 540 | Tpra1 |
| 541 | Pld2 |
| 542 | 2810013P06Rik |
| 543 | Sesn3 |
| 544 | Pde4d |
| 545 | Gna13 |
| 546 | Ddx50 |
| 547 | Atp5sl |
| 548 | Ypel5 |
| 549 | Mlxip |
| 550 | Slc22a15 |
| 551 | BC068157 |
| 552 | Kbtbd3 |
| 553 | Dip2a |
| 554 | Ccdc92 |
| 555 | Gja1 |
| 556 | Oxld1 |
| 557 | Tmem167b |
| 558 | Ccdc88c |
| 559 | Whamm |
| 560 | Fau |
| 561 | Sdf4 |
| 562 | Panx1 |
| 563 | Smpd1 |
| 564 | Rasa3 |
| 565 | Acp5 |
| 566 | Hip1r |
| 567 | Zfp260 |
| 568 | Fam102a |
| 569 | Gltscr1l |
| 570 | Scpep1 |
| 571 | Tnfaip3 |
| 572 | Zmym6 |
| 573 | Mnda |
| 574 | I730030J21Rik |
| 575 | Wdtc1 |
| 576 | Gpr146 |
| 577 | Rictor |
| 578 | Rnf138 |
| 579 | Zfp622 |
| 580 | 1600014C10Rik |
| 581 | D4Wsu53e |
| 582 | Kcnk7 |
| 583 | Mt1 |
| 584 | Arrdc2 |
| 585 | Atf7ip |
| 586 | Mfge8 |
| 587 | Pde1b |
| 588 | Megf9 |
| 589 | Phf21a |
| 590 | Pstpip1 |
| 591 | Fam149b |
| 592 | E330033B04Rik |
| 593 | Uhrf2 |
| 594 | Tctex1d1 |
| 595 | Cd200r4 |
| 596 | 9030624G23Rik |
| 597 | Ropn1l |
| 598 | Cyp4f13 |
| 599 | Uvrag |
| 600 | Carf |
| 601 | Sgpl1 |
| 602 | Fkbp7 |
| 603 | Dym |
| 604 | Smad1 |
| 605 | Sord |
| 606 | Irf1 |
| 607 | Sdc3 |
| 608 | Leng8 |
| 609 | Serinc5 |
| 610 | Cela1 |
| 611 | Mgarp |
| 612 | Crbn |
| 613 | Aaed1 |
| 614 | Ccdc28a |
| 615 | Apbb1 |
| 616 | Pak1 |
| 617 | Gm16845 |
| 618 | Dyx1c1 |
| 619 | E130317F20Rik |
| 620 | Nfatc3 |
| 621 | Spsb2 |
| 622 | Mob2 |
| 623 | 4931428F04Rik |
| 624 | Rhog |
| 625 | Ccser2 |
| 626 | Zkscan14 |
| 627 | Ctsl |
| 628 | 9130221F21Rik |
| 629 | Sepp1 |
| 630 | Lrrk2 |
| 631 | Arhgap27 |
| 632 | Zfp821 |
| 633 | Srpk2 |
| 634 | Nat2 |
| 635 | Vopp1 |

TABLE 2B-continued

Upregulated genes after GC + IL27 (1592 in ranked order)

| | |
|---|---|
| 636 | Btg2 |
| 637 | 4921511C10Rik |
| 638 | Nbeal1 |
| 639 | 4932438A13Rik |
| 640 | Acpl2 |
| 641 | Birc2 |
| 642 | Wdr45 |
| 643 | Adora2a |
| 644 | Il17ra |
| 645 | Emb |
| 646 | Pxk |
| 647 | Lsp1 |
| 648 | Mapk8ip3 |
| 649 | Eif3f |
| 650 | Lat2 |
| 651 | Bcar1 |
| 652 | Arhgef25 |
| 653 | Cd151 |
| 654 | Gm10845 |
| 655 | Tm6sf1 |
| 656 | Nipbl |
| 657 | Slc48a1 |
| 658 | A930013F10Rik |
| 659 | Pacsl |
| 660 | Kdelr1 |
| 661 | B630005N14Rik |
| 662 | Tbc1d23 |
| 663 | Sp4 |
| 664 | E130112N10Rik |
| 665 | 4933409K07Rik |
| 666 | Xlr3a |
| 667 | Trim46 |
| 668 | Ttyh2 |
| 669 | Smad7 |
| 670 | Lcorl |
| 671 | Cd37 |
| 672 | Prkra |
| 673 | Arhgef9 |
| 674 | 4931406C07Rik |
| 675 | Rftn2 |
| 676 | Vamp1 |
| 677 | Trim7 |
| 678 | Cercam |
| 679 | BC029214 |
| 680 | Snhg10 |
| 681 | Fam78a |
| 682 | Pear1 |
| 683 | 1110038B12Rik |
| 684 | Ccl27a |
| 685 | Arhgap25 |
| 686 | B130006D01Rik |
| 687 | Qsox1 |
| 688 | Gimap1 |
| 689 | Slc39a13 |
| 690 | Ankzf1 |
| 691 | 1600016N20Rik |
| 692 | Zfp395 |
| 693 | Bmpr1a |
| 694 | Tfdp2 |
| 695 | Pik3ap1 |
| 696 | Pld3 |
| 697 | Rnf19a |
| 698 | Tmem59 |
| 699 | Tmem221 |
| 700 | Sgms1 |
| 701 | Atp1a3 |
| 702 | Camkk1 |
| 703 | Gm9846 |
| 704 | 2410004N09Rik |
| 705 | Slc9a9 |
| 706 | Snx29 |
| 707 | H2-Ke6 |
| 708 | Hdac5 |
| 709 | Insrr |
| 710 | Cbx7 |
| 711 | Gyg |
| 712 | Akap8l |
| 713 | Bckdha |
| 714 | Sertad3 |
| 715 | Glrx |
| 716 | Ttc17 |
| 717 | Smpdl3a |
| 718 | Wbp1 |
| 719 | Tlr6 |
| 720 | Cnnm2 |
| 721 | Mrgpre |
| 722 | Dusp22 |
| 723 | Hscb |
| 724 | Rcn3 |
| 725 | Ptpn22 |
| 726 | Fyco1 |
| 727 | 2210039B01Rik |
| 728 | Dcaf15 |
| 729 | Hpse |
| 730 | Frat1 |
| 731 | Runx3 |
| 732 | H2-Q4 |
| 733 | Rell1 |
| 734 | Polr3gl |
| 735 | Synpo |
| 736 | Atp2b4 |
| 737 | Armcx6 |
| 738 | Slc37a4 |
| 739 | Fgd3 |
| 740 | Pgap3 |
| 741 | Guca1a |
| 742 | Narf |
| 743 | H2-Ob |
| 744 | Fbxo36 |
| 745 | Mettl7a1 |
| 746 | Kctd2 |
| 747 | Brdt |
| 748 | Wasl |
| 749 | Zfp963 |
| 750 | Ubac2 |
| 751 | 9930111J21Rik1 |
| 752 | H2-Q5 |
| 753 | Zfp120 |
| 754 | Agbl5 |
| 755 | 4930581F22Rik |
| 756 | Accs |
| 757 | Dcaf6 |
| 758 | Gm16515 |
| 759 | Rabac1 |
| 760 | Dock9 |
| 761 | Ccdc111 |
| 762 | Gm19757 |
| 763 | Dgat1 |
| 764 | Igflr1 |
| 765 | Ppp6r2 |
| 766 | Doc2g |
| 767 | Atg12 |
| 768 | Irf2 |
| 769 | Med12l |
| 770 | Syt5 |
| 771 | 1600020E01Rik |
| 772 | Crispld2 |
| 773 | Galnt6 |
| 774 | Clcf1 |
| 775 | Rac3 |
| 776 | Cul9 |
| 777 | Slc2a8 |
| 778 | Ssh2 |
| 779 | Adamts10 |
| 780 | 2810403D21Rik |
| 781 | Lrp5 |
| 782 | Cass4 |
| 783 | Adam9 |
| 784 | Rusc1 |
| 785 | Tpst2 |
| 786 | Obsl1 |
| 787 | Zfp292 |
| 788 | Lgals8 |
| 789 | Per1 |
| 790 | Cpne8 |
| 791 | Bach1 |

TABLE 2B-continued

Upregulated genes after GC + IL27 (1592 in ranked order)

| | |
|---|---|
| 792 | Zc3h6 |
| 793 | 2900076A07Rik |
| 794 | Snhg5 |
| 795 | Sh3glb1 |
| 796 | Lyn |
| 797 | Gab3 |
| 798 | Zfp831 |
| 799 | Zfp516 |
| 800 | Stard10 |
| 801 | Gltscr1 |
| 802 | Pde4c |
| 803 | Fam195b |
| 804 | Cacnb3 |
| 805 | Prdm1 |
| 806 | Syngr3 |
| 807 | Ndrg4 |
| 808 | Gm3414 |
| 809 | Gnaq |
| 810 | Dand5 |
| 811 | Arhgap15 |
| 812 | Rasa4 |
| 813 | Nfkbil1 |
| 814 | Tax1bp3 |
| 815 | Kdm5b |
| 816 | Pfn2 |
| 817 | Usp3 |
| 818 | Mthfs |
| 819 | Camk2n1 |
| 820 | Abr |
| 821 | Tanc2 |
| 822 | Tbc1d14 |
| 823 | Fas |
| 824 | Slc38a9 |
| 825 | Foxn3 |
| 826 | Tmem163 |
| 827 | Unc119b |
| 828 | Cdc42ep4 |
| 829 | Mllt3 |
| 830 | Gatsl2 |
| 831 | Fscn1 |
| 832 | Gimap3 |
| 833 | Snrnp48 |
| 834 | Zfp949 |
| 835 | Lemd2 |
| 836 | Zfp341 |
| 837 | Zfp874b |
| 838 | Slc31a2 |
| 839 | 2900026A02Rik |
| 840 | Nicn1 |
| 841 | Dhrs3 |
| 842 | Sgk1 |
| 843 | Npc2 |
| 844 | Gm15800 |
| 845 | Slc25a45 |
| 846 | 1810032O08Rik |
| 847 | Arhgef4 |
| 848 | Tmem171 |
| 849 | 4931406H21Rik |
| 850 | Sun2 |
| 851 | Zfp652 |
| 852 | Gpr18 |
| 853 | Hdac7 |
| 854 | Ssh3 |
| 855 | Il11ra1 |
| 856 | Rab37 |
| 857 | 2210417K05Rik |
| 858 | Xpa |
| 859 | Pnpla7 |
| 860 | Ly6c1 |
| 861 | 9430091E24Rik |
| 862 | Dixdc1 |
| 863 | Rdh12 |
| 864 | Zfp85-rs1 |
| 865 | Osbpl5 |
| 866 | Tmem63a |
| 867 | Ccnl2 |
| 868 | Podnl1 |
| 869 | Sft2d3 |
| 870 | A430078623Rik |
| 871 | Slc2a9 |
| 872 | Zfp36 |
| 873 | Rnf114 |
| 874 | H2-Eb1 |
| 875 | Rnase4 |
| 876 | Zfp784 |
| 877 | Cd28 |
| 878 | Kbtbd11 |
| 879 | Hist2h2aa1 |
| 880 | Styk1 |
| 881 | Tle6 |
| 882 | Arl4c |
| 883 | Arsg |
| 884 | Shisa2 |
| 885 | Cml1 |
| 886 | Mast1 |
| 887 | Amica1 |
| 888 | Zbtb4 |
| 889 | Akap5 |
| 890 | Impa2 |
| 891 | Zfyve1 |
| 892 | Hpcal1 |
| 893 | Aqp11 |
| 894 | Arfgap3 |
| 895 | Kcnq2 |
| 896 | Vmac |
| 897 | Tulp4 |
| 898 | Tcf4 |
| 899 | Tfr2 |
| 900 | A530072M11Rik |
| 901 | Zfp383 |
| 902 | Filip1 |
| 903 | Hdac4 |
| 904 | Gm17762 |
| 905 | Lsr |
| 906 | Kif21b |
| 907 | Dkkl1 |
| 908 | N4bp1 |
| 909 | Smurf2 |
| 910 | A930024E05Rik |
| 911 | Slc25a23 |
| 912 | Ralgapa2 |
| 913 | Ndst1 |
| 914 | Eva1b |
| 915 | Fam193b |
| 916 | Clk1 |
| 917 | Tigit |
| 918 | Folr4 |
| 919 | Cd109 |
| 920 | Jag2 |
| 921 | Jakmip1 |
| 922 | Atg16l2 |
| 923 | 2310047M10Rik |
| 924 | Qprt |
| 925 | Rad52 |
| 926 | Zfp787 |
| 927 | Gramd4 |
| 928 | Neb |
| 929 | Gbp2 |
| 930 | Trim62 |
| 931 | Dexi |
| 932 | Sqrdl |
| 933 | Themis2 |
| 934 | Appl2 |
| 935 | Eif2ak3 |
| 936 | Vdr |
| 937 | Slc26a11 |
| 938 | Cir1 |
| 939 | Blvrb |
| 940 | Hmha1 |
| 941 | Ttyh3 |
| 942 | Dap |
| 943 | Ltbp3 |
| 944 | Pacsin3 |
| 945 | Ube2h |
| 946 | Isoc2b |
| 947 | Malat1 |

TABLE 2B-continued

Upregulated genes after GC + IL27 (1592 in ranked order)

| | |
|---|---|
| 948 | Kcnip2 |
| 949 | Prnp |
| 950 | Gm10658 |
| 951 | Rasgrp4 |
| 952 | Slc27a1 |
| 953 | Gm12216 |
| 954 | Pcmtd2 |
| 955 | Apol7b |
| 956 | Apol7e |
| 957 | Nipal3 |
| 958 | Tmem220 |
| 959 | Itgae |
| 960 | Foxo3 |
| 961 | Gpc1 |
| 962 | Gpr160 |
| 963 | Cox7a1 |
| 964 | 5430416N02Rik |
| 965 | B3gnt9 |
| 966 | Serpinb6b |
| 967 | Plekhg2 |
| 968 | Itgb7 |
| 969 | Mt2 |
| 970 | Tmsb15l |
| 971 | Cage1 |
| 972 | Sfrp2 |
| 973 | Acap1 |
| 974 | Fyb |
| 975 | Fkbp5 |
| 976 | H2-Q1 |
| 977 | Sorl1 |
| 978 | 1700001O22Rik |
| 979 | Ss18l1 |
| 980 | Pbxip1 |
| 981 | Eaf2 |
| 982 | 2610204G22Rik |
| 983 | 2010016I18Rik |
| 984 | Klc4 |
| 985 | 3110056K07Rik |
| 986 | Izumo4 |
| 987 | Fam132a |
| 988 | Icos |
| 989 | Ston2 |
| 990 | Gabbr1 |
| 991 | Tead2 |
| 992 | Rhod |
| 993 | Tmem140 |
| 994 | Vill |
| 995 | Tsix |
| 996 | Gm19557 |
| 997 | Rgs11 |
| 998 | Ddit3 |
| 999 | Zfp524 |
| 1000 | Ccni |
| 1001 | Gm20098 |
| 1002 | Kremen2 |
| 1003 | Syt12 |
| 1004 | a |
| 1005 | 9330151L19Rik |
| 1006 | Thra |
| 1007 | Gm4285 |
| 1008 | Zfp945 |
| 1009 | Apc2 |
| 1010 | Pacs2 |
| 1011 | Jmy |
| 1012 | Tcn2 |
| 1013 | Ulk1 |
| 1014 | Col11a2 |
| 1015 | Cdnf |
| 1016 | Il7r |
| 1017 | Pram1 |
| 1018 | Rarg |
| 1019 | 6330403M23Rik |
| 1020 | Rwdd2a |
| 1021 | Gpr137b-ps |
| 1022 | Rnf128 |
| 1023 | Zfp30 |
| 1024 | Fam171b |
| 1025 | Usp35 |
| 1026 | Cysltr2 |
| 1027 | Ston1 |
| 1028 | Gm14305 |
| 1029 | Itfg3 |
| 1030 | Entpd1 |
| 1031 | 4933439C10Rik |
| 1032 | Rab6b |
| 1033 | Vgll4 |
| 1034 | Zfp69 |
| 1035 | Irak3 |
| 1036 | Pion |
| 1037 | Arhgef10 |
| 1038 | Hhat |
| 1039 | Ccr2 |
| 1040 | Dtx3 |
| 1041 | Lypd6b |
| 1042 | Adrb2 |
| 1043 | Pdcd4 |
| 1044 | Jhdm1d |
| 1045 | Nnat |
| 1046 | Tiparp |
| 1047 | Lynx1 |
| 1048 | Heca |
| 1049 | Pnrc1 |
| 1050 | Aldh6a1 |
| 1051 | Usp28 |
| 1052 | Bnip3l |
| 1053 | Atg14 |
| 1054 | Gm16973 |
| 1055 | Oit3 |
| 1056 | Sipa1l2 |
| 1057 | Dlg4 |
| 1058 | Sfxn3 |
| 1059 | Gzf1 |
| 1060 | Prss41 |
| 1061 | Stom |
| 1062 | Abcg1 |
| 1063 | Rras |
| 1064 | Aldh1l1 |
| 1065 | Mpp2 |
| 1066 | Col7a1 |
| 1067 | Dach2 |
| 1068 | Pgm2l1 |
| 1069 | Gimap6 |
| 1070 | 9330179D12Rik |
| 1071 | Ifit1 |
| 1072 | Maml3 |
| 1073 | Dab2 |
| 1074 | Osgin1 |
| 1075 | Tmem176a |
| 1076 | Haao |
| 1077 | Pitpnc1 |
| 1078 | Sult2b1 |
| 1079 | Snhg1 |
| 1080 | Tecpr1 |
| 1081 | Tjp3 |
| 1082 | Ttc12 |
| 1083 | Mapre3 |
| 1084 | Il1r2 |
| 1085 | Nrbp2 |
| 1086 | Ddx60 |
| 1087 | Card6 |
| 1088 | Mapk8ip1 |
| 1089 | Amigo1 |
| 1090 | Napb |
| 1091 | Fam65b |
| 1092 | Lgals6 |
| 1093 | R74862 |
| 1094 | Ddit4 |
| 1095 | Tmem176b |
| 1096 | Fbxl12 |
| 1097 | Kdm4b |
| 1098 | Rnf130 |
| 1099 | Ntng2 |
| 1100 | Abhd14b |
| 1101 | Tet2 |
| 1102 | Kazald1 |
| 1103 | Ezh1 |

TABLE 2B-continued

Upregulated genes after GC + IL27 (1592 in ranked order)

| | |
|---|---|
| 1104 | Metrnl |
| 1105 | Bend6 |
| 1106 | H2-Q2 |
| 1107 | Tet1 |
| 1108 | Gm9199 |
| 1109 | Gigyf1 |
| 1110 | 5830418P13Rik |
| 1111 | Plag1 |
| 1112 | Asb2 |
| 1113 | Rnf167 |
| 1114 | Ctdsp2 |
| 1115 | Kiss1r |
| 1116 | B3gnt8 |
| 1117 | Lag3 |
| 1118 | Ppp1r131 |
| 1119 | Paqr7 |
| 1120 | Zfp467 |
| 1121 | Rab31 |
| 1122 | H2-K2 |
| 1123 | Gngt2 |
| 1124 | Irak2 |
| 1125 | Khnyn |
| 1126 | Rnf166 |
| 1127 | Tmem91 |
| 1128 | Ing4 |
| 1129 | Trerf1 |
| 1130 | Mss51 |
| 1131 | Fbxl20 |
| 1132 | Noxo1 |
| 1133 | A930016O22Rik |
| 1134 | Arid5b |
| 1135 | Fam161a |
| 1136 | Klhl6 |
| 1137 | Arhgap26 |
| 1138 | A630072M18Rik |
| 1139 | Gimap7 |
| 1140 | Prss30 |
| 1141 | Nfil3 |
| 1142 | Acer2 |
| 1143 | Bmf |
| 1144 | Snx21 |
| 1145 | 2810408A11Rik |
| 1146 | Wnt4 |
| 1147 | Map1lc3a |
| 1148 | H2-Q9 |
| 1149 | Ccdc117 |
| 1150 | Disp1 |
| 1151 | Zpbp2 |
| 1152 | P4ha2 |
| 1153 | 2210408F21Rik |
| 1154 | Msantd1 |
| 1155 | Ppp4r1l-ps |
| 1156 | Parp6 |
| 1157 | Macrod1 |
| 1158 | Adck3 |
| 1159 | Zfp629 |
| 1160 | Fam117b |
| 1161 | Dirc2 |
| 1162 | Cdkn1b |
| 1163 | Sap25 |
| 1164 | Zer1 |
| 1165 | Cxcr6 |
| 1166 | Fbxl8 |
| 1167 | Emp1 |
| 1168 | Tenc1 |
| 1169 | Prtn3 |
| 1170 | 1110007C09Rik |
| 1171 | Gpr125 |
| 1172 | Trp53inp1 |
| 1173 | Ntf5 |
| 1174 | Plcxd1 |
| 1175 | 4930402H24Rik |
| 1176 | Map3k15 |
| 1177 | Aldoc |
| 1178 | 4930579K19Rik |
| 1179 | Gm11110 |
| 1180 | Kdelr3 |
| 1181 | Klf9 |
| 1182 | Gbe1 |
| 1183 | Pold4 |
| 1184 | Sorcs2 |
| 1185 | Mpzl2 |
| 1186 | Samhd1 |
| 1187 | 2810029C07Rik |
| 1188 | C1qtnf4 |
| 1189 | Serpinb1b |
| 1190 | Lgi4 |
| 1191 | Camk2b |
| 1192 | Plekha4 |
| 1193 | Ctla2b |
| 1194 | Pbx4 |
| 1195 | Apln |
| 1196 | 1500012F01Rik |
| 1197 | Ctla2a |
| 1198 | Igf1r |
| 1199 | Ovgp1 |
| 1200 | Ccno |
| 1201 | Gprc5a |
| 1202 | Apbb2 |
| 1203 | Tmie |
| 1204 | Arrb1 |
| 1205 | Plekha7 |
| 1206 | Cd93 |
| 1207 | Nod2 |
| 1208 | Hyi |
| 1209 | Tmem71 |
| 1210 | Mmp11 |
| 1211 | Cpeb2 |
| 1212 | Wdr96 |
| 1213 | Klrc3 |
| 1214 | Ctsw |
| 1215 | Insl3 |
| 1216 | Kcnab3 |
| 1217 | Btg1 |
| 1218 | Copz2 |
| 1219 | Spata2l |
| 1220 | Rsad2 |
| 1221 | Vldlr |
| 1222 | Zfp36l2 |
| 1223 | Gab2 |
| 1224 | BC028528 |
| 1225 | Phf1 |
| 1226 | Klf10 |
| 1227 | Dnm3 |
| 1228 | Pygl |
| 1229 | Sdc4 |
| 1230 | Atp10d |
| 1231 | Aplp1 |
| 1232 | Ddr1 |
| 1233 | Asap3 |
| 1234 | Bzrap1 |
| 1235 | Arhgef18 |
| 1236 | Zbtb20 |
| 1237 | Cxcr4 |
| 1238 | Rbm47 |
| 1239 | Scel |
| 1240 | Crebl2 |
| 1241 | Gstm1 |
| 1242 | 5830454E08Rik |
| 1243 | Mylip |
| 1244 | Thada |
| 1245 | Acpp |
| 1246 | Sytl2 |
| 1247 | Rhov |
| 1248 | Tmem8b |
| 1249 | E130102H24Rik |
| 1250 | Dok4 |
| 1251 | Lonrf3 |
| 1252 | Gramd3 |
| 1253 | Ceacam15 |
| 1254 | Tha1 |
| 1255 | 4921525B02Rik |
| 1256 | Grina |
| 1257 | Chit1 |
| 1258 | Gm4013 |
| 1259 | Lmtk3 |

TABLE 2B-continued

Upregulated genes after GC + IL27 (1592 in ranked order)

| | |
|---|---|
| 1260 | Shpk |
| 1261 | Frmd4b |
| 1262 | Kit |
| 1263 | Tbkbp1 |
| 1264 | Dbp |
| 1265 | Cnbd2 |
| 1266 | Pink1 |
| 1267 | Kifc2 |
| 1268 | Scml4 |
| 1269 | Plekhf1 |
| 1270 | Cxcr1 |
| 1271 | Dapk1 |
| 1272 | Tmem191c |
| 1273 | Adamtsl5 |
| 1274 | Runx1 |
| 1275 | Dyrk1b |
| 1276 | Dusp2 |
| 1277 | Abtb1 |
| 1278 | Parp16 |
| 1279 | Man1c1 |
| 1280 | B3galt5 |
| 1281 | Myo1h |
| 1282 | Carns1 |
| 1283 | Plaur |
| 1284 | Fbxo10 |
| 1285 | Pde4b |
| 1286 | Zbtb42 |
| 1287 | Abcd2 |
| 1288 | 2410066E13Rik |
| 1289 | Naprt1 |
| 1290 | Sgip1 |
| 1291 | Tesc |
| 1292 | Kank2 |
| 1293 | Ip6k1 |
| 1294 | Gpld1 |
| 1295 | Hbp1 |
| 1296 | Klra18 |
| 1297 | Spred3 |
| 1298 | Rnf122 |
| 1299 | Sept4 |
| 1300 | Snhg12 |
| 1301 | Tmem51 |
| 1302 | Esm1 |
| 1303 | Dpf1 |
| 1304 | Tmem45a |
| 1305 | H2-Ab1 |
| 1306 | Cd68 |
| 1307 | Slc38a8 |
| 1308 | Lcn4 |
| 1309 | Bend5 |
| 1310 | 5730508B09Rik |
| 1311 | Zcchc24 |
| 1312 | Cacnb4 |
| 1313 | 4831440E17Rik |
| 1314 | Sema4f |
| 1315 | Malt1 |
| 1316 | Lgals4 |
| 1317 | Pla2g4e |
| 1318 | Calcoco1 |
| 1319 | Gm2011 |
| 1320 | Myh7b |
| 1321 | 5830416P10Rik |
| 1322 | Bcl2l15 |
| 1323 | Lrrc25 |
| 1324 | Mex3b |
| 1325 | Kctd12 |
| 1326 | Got1l1 |
| 1327 | Fam46c |
| 1328 | 2410006H16Rik |
| 1329 | Aqp3 |
| 1330 | Aif1l |
| 1331 | Rasgef1a |
| 1332 | Hdac11 |
| 1333 | Fmo5 |
| 1334 | Gpx8 |
| 1335 | Bhlhe41 |
| 1336 | Btn1a1 |
| 1337 | Tceal1 |
| 1338 | 2210404O07Rik |
| 1339 | Nfia |
| 1340 | Akap7 |
| 1341 | 1700084E18Rik |
| 1342 | Slc41a3 |
| 1343 | 6430531B16Rik |
| 1344 | Ccdc114 |
| 1345 | Inha |
| 1346 | 4930565N06Rik |
| 1347 | Acrbp |
| 1348 | 4930429F24Rik |
| 1349 | Slc15a2 |
| 1350 | Tubb4a |
| 1351 | Ctsf |
| 1352 | Serpinb1a |
| 1353 | Bbc3 |
| 1354 | 5033411D12Rik |
| 1355 | Fam184b |
| 1356 | Tceal3 |
| 1357 | Eml1 |
| 1358 | Pdk2 |
| 1359 | D630029K05Rik |
| 1360 | Sy2c |
| 1361 | Gfra1 |
| 1362 | Chst15 |
| 1363 | Cd163l1 |
| 1364 | Id1 |
| 1365 | 2310015A10Rik |
| 1366 | Fam114a1 |
| 1367 | Fry |
| 1368 | Ablim2 |
| 1369 | 2610035D17Rik |
| 1370 | 1700012B09Rik |
| 1371 | Deptor |
| 1372 | Col18a1 |
| 1373 | Ddah2 |
| 1374 | A330023F24Rik |
| 1375 | Tle2 |
| 1376 | Ypel3 |
| 1377 | LOC100503496 |
| 1378 | 9430083A17Rik |
| 1379 | 4933406I18Rik |
| 1380 | B430306N03Rik |
| 1381 | Bahcc1 |
| 1382 | Fam71f2 |
| 1383 | Rdh9 |
| 1384 | Zcchc18 |
| 1385 | Adssl1 |
| 1386 | Selm |
| 1387 | 1810011H11Rik |
| 1388 | Ypel4 |
| 1389 | Mboat2 |
| 1390 | Wipi1 |
| 1391 | Mxd1 |
| 1392 | Tspan9 |
| 1393 | Cyp2s1 |
| 1394 | Gck |
| 1395 | Ramp3 |
| 1396 | Gnaz |
| 1397 | Acss1 |
| 1398 | Spsb1 |
| 1399 | Ica1l |
| 1400 | Ramp1 |
| 1401 | Pls1 |
| 1402 | Klrb1f |
| 1403 | Gpc2 |
| 1404 | N4bp2l1 |
| 1405 | Fam217b |
| 1406 | Txnip |
| 1407 | Ndrg1 |
| 1408 | Matk |
| 1409 | Zscan2 |
| 1410 | Capn11 |
| 1411 | Lhx6 |
| 1412 | B930003M22Rik |
| 1413 | Crebrf |
| 1414 | Casz1 |
| 1415 | Rgs9 |

TABLE 2B-continued

Upregulated genes after GC + IL27 (1592 in ranked order)

| | |
|---|---|
| 1416 | Mxd4 |
| 1417 | Tmcc3 |
| 1418 | Dok7 |
| 1419 | Cntnap1 |
| 1420 | Dntt |
| 1421 | Abca1 |
| 1422 | Alpk2 |
| 1423 | Slc41a2 |
| 1424 | Optc |
| 1425 | Stbd1 |
| 1426 | Col20a1 |
| 1427 | Cd33 |
| 1428 | Axin2 |
| 1429 | Tcp1l2 |
| 1430 | Ffar2 |
| 1431 | Cdc42ep2 |
| 1432 | Selenbp2 |
| 1433 | Ccl5 |
| 1434 | Klhl24 |
| 1435 | Mas1 |
| 1436 | Selebp1 |
| 1437 | Dsg2 |
| 1438 | A730043L09Rik |
| 1439 | Klf4 |
| 1440 | Krt18 |
| 1441 | Atp7b |
| 1442 | Cstad |
| 1443 | Pglyrp1 |
| 1444 | Wdr95 |
| 1445 | Leprel4 |
| 1446 | Cacna1s |
| 1447 | Sema3f |
| 1448 | Dlgap1 |
| 1449 | Pkp2 |
| 1450 | Pyroxd2 |
| 1451 | Arrdc4 |
| 1452 | Smtnl2 |
| 1453 | Itga1 |
| 1454 | Thsd7b |
| 1455 | Gpr56 |
| 1456 | Glis1 |
| 1457 | Jup |
| 1458 | Dnahc10 |
| 1459 | Gzmk |
| 1460 | Ptges |
| 1461 | Atp2a1 |
| 1462 | Dtx1 |
| 1463 | Cd24a |
| 1464 | Dgkg |
| 1465 | Serpinf1 |
| 1466 | Efhc1 |
| 1467 | Lamc2 |
| 1468 | Tbx6 |
| 1469 | Bcl2l11 |
| 1470 | Sema3a |
| 1471 | Otud1 |
| 1472 | Gm20139 |
| 1473 | Tnfsf13b |
| 1474 | Ust |
| 1475 | Fgfr1 |
| 1476 | Afap1l1 |
| 1477 | Acyr1l |
| 1478 | Snx20 |
| 1479 | Cyp46a1 |
| 1480 | Shd |
| 1481 | Dapk2 |
| 1482 | Kcna4 |
| 1483 | Chn2 |
| 1484 | Card10 |
| 1485 | Gm19705 |
| 1486 | Adamtsl4 |
| 1487 | Map3k9 |
| 1488 | Gzma |
| 1489 | Dnm1 |
| 1490 | Rassf6 |
| 1491 | Agap1 |
| 1492 | Zfp13 |
| 1493 | Gm5122 |
| 1494 | Ier5l |
| 1495 | Af529169 |
| 1496 | Rapgef3 |
| 1497 | Nxpe4 |
| 1498 | Ssc5d |
| 1499 | Zfr2 |
| 1500 | Ecm1 |
| 1501 | Ypel2 |
| 1502 | Trib2 |
| 1503 | Npcd |
| 1504 | C3 |
| 1505 | Enpp2 |
| 1506 | Irgc1 |
| 1507 | Pde2a |
| 1508 | Fam183b |
| 1509 | Pou6f1 |
| 1510 | Igsf5 |
| 1511 | Hlx |
| 1512 | Cyp2d22 |
| 1513 | Frat2 |
| 1514 | Endou |
| 1515 | Lin7b |
| 1516 | Pik3ip1 |
| 1517 | Itga11 |
| 1518 | Ovol2 |
| 1519 | Hs3st6 |
| 1520 | Nrep |
| 1521 | Bcl6 |
| 1522 | Plcd1 |
| 1523 | Spns2 |
| 1524 | Efna1 |
| 1525 | Baiap3 |
| 1526 | Rbm20 |
| 1527 | 5930412G12Rik |
| 1528 | E230016M11Rik |
| 1529 | Mmp15 |
| 1530 | Rassf4 |
| 1531 | Ace |
| 1532 | Gjc2 |
| 1533 | Matn1 |
| 1534 | Mfi2 |
| 1535 | Gipr |
| 1536 | Gpnmb |
| 1537 | Col24a1 |
| 1538 | 5031434O11Rik |
| 1539 | Tsc22d3 |
| 1540 | Sbsn |
| 1541 | BC021767 |
| 1542 | Mcin |
| 1543 | Prss55 |
| 1544 | Sertad4 |
| 1545 | Sms |
| 1546 | Muc2 |
| 1547 | Hey1 |
| 1548 | P2ry4 |
| 1549 | Sult5a1 |
| 1550 | Flt4 |
| 1551 | Adamtsl3 |
| 1552 | Bmp2 |
| 1553 | Kif1a |
| 1554 | Itgam |
| 1555 | Tnnt3 |
| 1556 | Ghr |
| 1557 | Slc30a3 |
| 1558 | Itga7 |
| 1559 | Porcn |
| 1560 | Epha7 |
| 1561 | Grin1 |
| 1562 | Ret |
| 1563 | Gm4926 |
| 1564 | D630041G03Rik |
| 1565 | 1700023L04Rik |
| 1566 | Fam5c |
| 1567 | Miat |
| 1568 | Mpped2 |
| 1569 | 4933433H22Rik |
| 1570 | Gm11435 |
| 1571 | Atp8a2 |

TABLE 2B-continued

Upregulated genes after GC + IL27 (1592 in ranked order)

| | |
|---|---|
| 1572 | Il10 |
| 1573 | Mef2b |
| 1574 | Stac2 |
| 1575 | Fn3k |
| 1576 | Htra3 |
| 1577 | Ndst3 |
| 1578 | Dysf |
| 1579 | Kctd8 |
| 1580 | Fxyd7 |
| 1581 | Klra7 |
| 1582 | Serpinb5 |
| 1583 | Tgfb3 |
| 1584 | Cd7 |
| 1585 | Acaa1b |
| 1586 | Zan |
| 1587 | 5031414D18Rik |
| 1588 | Lrrc3b |
| 1589 | Rasgrf1 |
| 1590 | Maf |
| 1591 | Arhgef28 |
| 1592 | Klra6 |

TABLE 3

(Related to FIG. 39) Shared genes between the Glucocorticoid + IL-27-induced and T cell dysfunction signature in CD8+ T cells.

| Exhaustion_up | | Exhaustion_down | |
|---|---|---|---|
| Chst12 | Pros1 | Dnajc7 | Tm4sf5 |
| Timp1 | Alcam | Fas | Vrk1 |
| Cysltr2 | Fars2 | Samhd1 | Pus3 |
| Alg8 | Elmo2 | Map4k2 | Frat2 |
| Gsg2 | Mt2 | Urb1 | Acp5 |
| Aplp1 | Fcer1g | Pus7l | Ldhb |
| Kif22 | Spin4 | Man1c1 | Commd8 |
| Ccdc109b | Rpgr | Amz2 | Pou6f1 |
| Nup107 | Usp40 | Lrp12 | Fam53b |
| Crat | Styk1 | Rftn1 | Gpr132 |
| Ifng | Ccdc6 | Il4ra | Dhx58 |
| Trib3 | Bend6 | Klf9 | Card11 |
| Rabgef1 | AF529169 | Idua | Kctd12 |
| 5330426P16Rik | Ppme1 | Clasp1 | Acpp |
| Ccl4 | Mrgpre | Snhg7 | Cxcr4 |
| Gpr160 | Mtbp | Psap | Dus2l |
| Serpine2 | Exph5 | Bcl3 | Dntt |
| Rpa2 | Slc17a6 | Zscan12 | Hpcal1 |
| Arsb | Ankle1 | Pcca | 2810013P06Rik |
| Enpp2 | Cd38 | Gpd1l | Tpst2 |
| Nsmaf | Vamp8 | Tmem50b | Aff3 |
| Cdca3 | Nipa2 | Tcp11l2 | Dapl1 |
| Cenpn | Gpt2 | Dhcr24 | Aqp9 |
| Cdc27 | Fhl2 | Rarg | Wdr59 |
| Slc35b1 | Gatm | Zer1 | Mll3 |
| Il1r2 | Id2 | Idh2 | Ado |
| Shcbp1 | Nr3c1 | Atp2a1 | Slc9a9 |
| Dclk1 | Cenpi | Nfia | Pja1 |
| Kpna2 | Gzme | Vdr | Hmgn1 |
| Esco2 | Itga5 | Mtap | Eif2ak3 |
| Ppp1r3b | Csf2 | Gramd1a | Etnk1 |
| Eno3 | Slc22a15 | Cmah | Abtb2 |
| Ero1l | Sema6d | Npc1 | 2900076A07Rik |
| Dennd4a | Slc2a8 | Gpr18 | Srpk1 |
| Sepn1 | Mettl7a1 | Nefh | D1Ertd622e |
| Mtmr1 | Cd200 | Rbm38 | Glcci1 |
| Abcb1b | Tjp2 | Macrod1 | Ceacam1 |
| Birc5 | Tox | Zc3h12d | Heatr1 |
| Magohb | Suv39h2 | Gimap6 | Itpr3 |
| Samsn1 | Mlkl | Cd24a | Gucy1a3 |
| Zfp692 | 2900026A02Rik | Slfn5 | Usp53 |
| Gcsh | Il1rl1 | Slco3a1 | Zfp1 |
| Ccl9 | Higd1a | Bdh1 | Phf17 |
| Zwilch | Car13 | Noc4l | Brap |
| Spp1 | Ica1 | Ddr1 | BC026590 |
| Zc3h12a | Kazald1 | Ctsl | Pqlc1 |
| Tmbim4 | Kif20b | Btla | Pprc1 |
| Tmem171 | Nfatc1 | Epcam | Arntl |
| Casp4 | Cd200r4 | Gramd4 | Tlr6 |
| Tnfrsf18 | Rab31 | Cryl1 | Kcnn4 |
| Ube2i | Rad54b | Mboat1 | Net1 |
| Mthfs | Dusp6 | Igfbp4 | Foxp1 |
| Plekhb2 | Arl6 | Bphl | Tha1 |
| Sdf4 | Bcl2l1 | Atp10d | Kif21b |
| Ccl3 | Mt1 | Rere | Vrk3 |
| Serpinb6a | Camk2n1 | Afap1 | Irgm2 |
| Anapc4 | Fam5c | Hs3st3b1 | Herc1 |

TABLE 3-continued (Related to FIG. 39) Shared genes between the Glucocorticoid + IL-27-induced and T cell dysfunction signature in CD8+ T cells.

| Exhaustion_up | | Exhaustion_down | |
|---|---|---|---|
| Ifitm3 | Sat1 | St6gal1 | Unc5cl |
| Ndfip2 | Rbpj | Ppa1 | Cd302 |
| Sec23a | Lamc1 | Ung | Usp28 |
| Stard4 | Agtrap | Mbp | Pgap3 |
| Fasl | Itga1 | Rpp40 | Gpr114 |
| Ccnb1 | Cxcr6 | Arhgef3 | Dedd2 |
| Nek8 | Galc | Satb1 | Sgms1 |
| Myadm | 1190002F15Rik | Cxcr3 | Mrpl30 |
| Tmem48 | Bst1 | Exosc1 | Btbd6 |
| Cenpt | L2hgdh | Sf3a2 | Fam65b |
| Gm11110 | Lyrm1 | Acss2 | Rasa3 |
| Ttk | Carhsp1 | Iigp1 | Bzw2 |
| Arhgap18 | Tpi1 | 2610035D17Rik | Dirc2 |
| Slc7a3 | Mthfd2 | Als2cl | Nudt15 |
| Chac1 | Pik3cg | Rnf157 | Dnajc27 |
| Armc1 | Fcho2 | Jhdm1d | Parp3 |
| Cars | Chn2 | Tpd52 | Mylip |
| Mlf1 | Ncapg2 | Kti12 | Gbp2 |
| Gab2 | Apobec3 | Ralgps2 | Alpl |
| Cenpa | Jam2 | Prnp | Ssh2 |
| Tmem218 | Dtl | Itgae | Phc2 |
| Nrp1 | Aldoa | Atp1b3 | Furin |
| Sephs1 | Tnf | Ecm1 | Eef2k |
| Prdm1 | Ulbp1 | Sema4f | Notch1 |
| Sh3bgrl | D630039A03Rik | Ddx54 | Wdr45 |
| Filip1 | Mapk6 | Pde4b | Tcf4 |
| Agl | 1500009L16Rik | Aldh6a1 | Ccr7 |
| Qsox1 | Igfbp7 | Socs1 | Ssbp2 |
| Plek | Kctd17 | Tlr1 | Axin2 |
| Adam9 | Pex11b | Camkk1 | 2310044G17Rik |
| Igf2r | Bnip3 | Tspan13 | Npc2 |
| Pkp2 | Xpot | Vmac | Laptm4b |
| Npnt | Unc119b | Med4 | Gimap9 |
| Kif20a | Rnf128 | Sorl1 | P2ry14 |
| Cep170 | Ehd4 | Taf5l | Fam43a |
| Idh3a | Rhbdf2 | Tecpr1 | Mcoln3 |
| Pmaip1 | Ptplb | Fads2 | Dclre1a |
| Wbp5 | Rab12 | Kbtbd11 | Fgfr1op |
| Prf1 | Tg | Hagh | Tnik |
| Lgals3 | Casp1 | AB124611 | Adrb2 |
| Gdpd5 | Tpk1 | Sesn3 | Evl |
| Ccdc50 | Plscr1 | Serinc5 | Pkd1 |
| Lpgat1 | Ftsjd1 | Fosl2 | 4921511C10Rik |
| Tyw1 | Slc43a3 | Vav2 | Gramd3 |
| Zbtb32 | Gpr56 | Tax1bp3 | Prickle1 |
| BC068157 | 4930422G04Rik | Map4k4 | Gpc1 |
| Arhgef9 | Trip10 | Gatsl3 | Ccbl1 |
| Nrn1 | Irf4 | Rras2 | Iqgap2 |
| 2310001H17Rik | Upp1 | 3110043O21Rik | Klrb1f |
| Tacc3 | Ctsd | Lcmt2 | Cdyl2 |
| Spry2 | Padi2 | Rgs10 | B430306N03Rik |
| Slco4a1 | Stx11 | Me2 | Rasgrp2 |
| Htatip2 | Ide | Ifnar2 | Tk2 |
| Nr4a2 | Tmem120b | Itga7 | Card6 |
| Trappc4 | Prrx1 | Clpb | Gpr146 |
| Abhd14a | Tpx2 | Mppe1 | Dph5 |
| Nupr1 | Ect2 | Rbm19 | Crim1 |
| AA467197 | Bcl2l15 | Ccpg1 | Fgfr1 |
| Polk | Fam57a | Dzip1 | Fbxo17 |
| Anxa3 | Acot7 | Pdlim5 | Ctps2 |
| Cnnm2 | Mylk | Ctdsp2 | Nbn |
| Ndrg1 | Pdpn | Prcp | Dse |
| Lrp1 | Rfc3 | Cdt1 | Xpc |
| Slc16a13 | Bard1 | Zcchc11 | Add3 |
| Sh2d2a | 1810011H11Rik | Ptcra | Pex26 |
| Dnajc24 | Cisd3 | Ifngr2 | Bach1 |
| Gins1 | Cenpf | Med8 | Sfrp2 |
| Cox17 | Ccnb2 | Insr | Irf1 |
| Zfp52 | Gm14288 | Slc16a6 | Enpp4 |
| Gata3 | Ubash3b | 1810043H04Rik | Thra |
| Dynlt3 | Glis1 | Stk38 | Gab3 |
| Gtf2ird1 | Cstad | Ascc1 | Bend5 |
| Vldlr | Fkbp7 | Zdhhc13 | Tmem55b |
| Dctn4 | Stk39 | Arid5a | Dtx3l |
| Syngr3 | Ap1s2 | Ddx18 | Arhgap15 |

TABLE 3-continued (Related to FIG. 39) Shared genes between the Glucocorticoid + IL-27-induced and T cell dysfunction signature in CD8+ T cells.

| Exhaustion_up | | Exhaustion_down | |
|---|---|---|---|
| Asns | Krt18 | 2610002M06Rik | Itfg3 |
| Uhrf2 | Camk4 | Tfam | Gm8369 |
| Ino80c | Spata2l | Phc1 | Acsl1 |
| Ppap2c | Trps1 | Parp9 | Faah |
| Pggt1b | Flywch1 | Sqrdl | Armcx6 |
| Cd93 | Gbe1 | Gtf2i | Smad3 |
| Ttc39c | Fam64a | Lmo4 | Zfp652 |
| Tubb6 | 1700012B09Rik | Gpx1 | Lrrc8a |
| Dab2 | Etv5 | Tmem141 | Slc11a2 |
| Zdhhc5 | Dennd3 | Trim62 | Dus4l |
| Usp46 | Nt5dc2 | Icam2 | Il6st |
| Mrps6 | Sar1a | Irf7 | Hey1 |
| Kctd11 | Sult2b1 | Utrn | Atp8a2 |
| Gnb5 | Sytl3 | Cd40lg | Smpdl3a |
| B4galt5 | Cdc14a | Smc6 | 3230401D17Rik |
| Gzmc | Tmem170b | Zfp260 | Mycbp2 |
| Tk1 | E2f3 | Dhx37 | Zfp354c |
| Rhoq | Srgap3 | Trib2 | Fbrs |
| Gja1 | Zfp511 | Ift80 | Klhdc5 |
| 3110082I17Rik | Ostf1 | Klhdc1 | Ptpla |
| Osbp13 | Fam72a | Nop2 | Kbtbd8 |
| Tm9sf3 | Endod1 | Umps | St3gal6 |
| Smc2 | Raph1 | Pim2 | Dtx1 |
| Cenpp | Nsl1 | Igf1r | Cd2 |
| Copz2 | Apoe | Osbpl9 | Dym |
| Klf10 | Hivep1 | Cdc14b | Shisa2 |
| Degs1 | Wisp1 | Ccr4 | Camkk2 |
| Nbeal1 | Tspan6 | Tom1 | Pde2a |
| Cdca5 | Csda | Fgr | Slc41a1 |
| 4932415G12Rik | Pglyrp1 | Slamf6 | Sepp1 |
| Adam15 | Serpinb6b | Sgip1 | Atp2a3 |
| Mpi | Ppp3cb | Sigmar1 | Mgst2 |
| Dapk2 | B3galt5 | Uvrag | Sipa1l1 |
| Plk1 | Ier3 | Sdccag3 | Chd8 |
| Hip1r | Ddx17 | Traf4 | Lef1 |
| Amigo1 | Osgin1 | Lpin1 | Tapt1 |
| Optn | Foxm1 | Ipcef1 | Il7r |
| 1700017S05Rik | Calu | Rab37 | Ramp1 |
| Ctsc | Rad51 | Top1mt | Elk4 |
| Ltbp3 | Anxa2 | Chst15 | Zfp53 |
| Mrps36 | Ndc80 | Ehd3 | Csrnp1 |
| Atf4 | Kif4 | Zkscan3 | Tgfbr3 |
| Rab5b | Med12l | Rcn3 | Lypd6b |
| Acadl | Efcab7 | Tnfsf8 | Kremen1 |
| Pld2 | Havcr2 | Abcc4 | Bcl9 |
| Ptrf | Lclat1 | Ephx1 | Emb |
| Nqo2 | Atp10a | Peo1 | Arl6ip6 |
| Scyl2 | Slc2a3 | A230046K03Rik | Rnf19b |
| Myo1e | Rapsn | P2rx4 | Foxo1 |
| Tmem39a | Gpd2 | Socs3 | Fbxo32 |
| Nuf2 | Depdc1a | Zeb1 | Scml4 |
| Rnaseh2c | Calm3 | Frmd4b | Ms4a4c |
| Spag9 | Sdcbp2 | Skp1a | Jakmip1 |
| Atad5 | Fkbp1a | Egln3 | Jak2 |
| Ncaph | Rab27a | Mapk1ip1 | P4ha1 |
| 2610318N02Rik | Plekhf1 | Tcf7 | Klhl6 |
| Traip | Nid1 | Adk | Frat1 |
| Gem | Plod2 | Cyp2s1 | Hmgxb3 |
| Elk3 | E2f8 | Pepd | Sos1 |
| Egr1 | Kif24 | Rcl1 | S1pr4 |
| Adssl1 | Iqgap3 | Pde7a | Crtc3 |
| 1110007C09Rik | St14 | Tmem41a | Nisch |
| Icos | Tnfsf11 | St8sia1 | Ifit1 |
| Tbc1d7 | Elovl4 | Hspb11 | Tnfaip8l2 |
| Itgav | Ifitm2 | Irf6 | Fitm2 |
| C330027C09Rik | S100a11 | Pik3ip1 | Atp1a3 |
| Anxa4 | Adam8 | Polr3a | Slfn1 |
| Entpd1 | Tnfsf9 | Lrrc33 | Jmjd1c |
| Omd | 0610010F05Rik | Nxf1 | Cpne3 |
| Pter | Dusp4 | Zbtb24 | Gcnt2 |
| Ccdc14 | Ermp1 | Itgb7 | Slc12a7 |
| Apbb1 | Hbegf | Fam117b | Abca1 |
| Gpld1 | Npl | Zfp362 | Bcl6 |
| Gabbr1 | Cyr61 | Nufip2 | Fam189b |
| Oit3 | Armc7 | Sgk3 | Il1rl2 |

TABLE 3-continued (Related to FIG. 39) Shared genes between the Glucocorticoid + IL-27-induced and T cell dysfunction signature in CD8+ T cells.

| Exhaustion_up | | Exhaustion_down | |
|---|---|---|---|
| Hmmr | Emilin2 | Arl6ip5 | Bach2 |
| Tmem159 | Ndufb4 | Yes1 | Mdn1 |
| Cenph | Hhat | Capn3 | Lif |
| Ndufaf2 | E2f7 | Cpne2 | Prkcb |
| Kdm2b | Slc30a9 | Dip2c | Kmo |
| Ptplad1 | Klra7 | Serp1 | Pcnxl3 |
| Aldoc | Neil3 | Jmy | Zrsr1 |
| Mmd | Abcb9 | Zfp281 | Myc |
| Atg16l2 | Rab19 | Zmym2 | Scpep1 |
| Ephb6 | Al836003 | 2410066E13Rik | As3mt |
| Aqp11 | Tnfsf4 | Znrf1 | Zfp592 |
| Nedd9 | Selm | Gypc | Dopey1 |
| Dkkl1 | Siglec5 | Tanc1 | Egr3 |
| Abhd4 | Actr10 | Ikbke | Zfp87 |
| Pddc1 | Il2 | Cyth1 | Smad1 |
| Exo1 | Cldn12 | Ulk1 | Dgka |
| Slc37a2 | Il33 | Ttc32 | Arhgef18 |
| Impa2 | Tmem175 | Etv3 | Rapgef4 |
| Farp1 | Tmcc3 | Rnf122 | Zfp365 |
| Gpr174 | Piwil2 | Plaur | Pitpnc1 |
| Rps6kc1 | Pear1 | Gpr155 | Gcc2 |
| Cyp20a1 | Nmt2 | Rsad2 | Lysmd1 |
| Tmem126a | Lat2 | Tctex1d1 | Ubac2 |
| Fam188a | Phf23 | Rnf149 | Ldlrap1 |
| Hif1a | Abi2 | Tdrkh | Hemgn |
| Mtmr7 | Gldc | Egr2 | Tubb2a |
| Casp3 | Lpxn | Cxcl10 | Ddx60 |
| Dut | Cdkn3 | Mmachc | Aqp3 |
| Stab1 | Fancd2 | Rab35 | Id3 |
| Ctla2a | Atxn1 | Cd7 | Spsb1 |
| E130112N10Rik | Cnrip1 | Rapgef6 | Itpr2 |
| 2810417H13Rik | Galnt3 | Trat1 | Grn |
| Pilra | Spag5 | Prkcq | 5730508B09Rik |
| Eno2 | Brca2 | Ncf1 | |
| Tnfrsf4 | Kif18a | | |
| Ptgr1 | Sytl2 | | |
| Ptprk | Plekho2 | | |
| Kit | Tbc1d2b | | |
| Crabp2 | Mid1ip1 | | |
| Tecr | A430093F15Rik | | |
| Bcat1 | Gzmd | | |
| Tmem180 | Penk | | |
| Zfp760 | Pdcd1 | | |
| Il2ra | Litaf | | |
| Ptpn11 | Bub1 | | |
| Kcna4 | Ccng1 | | |
| Ovol2 | Ccl1 | | |
| Creb3l2 | 4930429F24Rik | | |
| Pla1a | Dusp3 | | |
| Rgs16 | Ctla4 | | |
| Lag3 | Alg6 | | |
| Rai14 | Slc35f5 | | |
| Pask | Ube2c | | |
| Sestd1 | Mpzl2 | | |
| Tulp4 | Diap3 | | |
| Utf1 | Paqr4 | | |
| Cst7 | Cep55 | | |
| Hnrpll | Cdca8 | | |
| Tnfsf13b | Oaz2 | | |
| Cercam | Bub1b | | |
| Ptgs2 | Lxn | | |
| Ankra2 | Pcyt1a | | |
| Slc25a13 | Ern1 | | |
| Cyp4v3 | | | |

TABLE 4

Dysfunction Signature

Cancer_Down

| | | | | |
|---|---|---|---|---|
| KRT10 | TGFBR1 | UBE1L | MAN1C1 | PRR5 |
| SMC6 | NARG2 | CCDC45 | RNF19B | CMBL |
| BZW2 | HMGXB3 | ACP5 | PRX | NR1D2 |
| PDLIM1 | ZNRF3 | MFSD6 | KCNN4 | 6230400D17RIK |
| ITGB7 | BRAP | RPL30 | LCMT2 | FBRS |
| PHC1 | SNHG7 | CD7 | 1700021C14RIK | 3110043O21RIK |
| UNC5CL | SRPK1 | RFTN1 | 1700025G04RIK | PTGES2 |
| ARHGAP15 | BC018507 | GRAMD1A | FRAT2 | SLFN5 |
| AB124611 | GPR114 | PUS7L | ELOVL6 | FCNA |
| NPC2 | 4930432O21RIK | PRDM15 | GM568 | NCF1 |
| 1110008L16RIK | DZIP1 | DAXX | 1700028N14RIK | EHHADH |
| TNFSF8 | CTSE | CYP2S1 | SMAD5 | DTX4 |
| A630057N01RIK | SLAMF6 | 2810043O03RIK | TGFBR3 | GM3626 |
| SMAD3 | TLE4 | 3230401D17RIK | ALDH6A1 | ZCCHC11 |
| CAMKK1 | AI504432 | NSG2 | AB041803 | 6720475J19RIK |
| DOPEY1 | ZFP365 | NMNAT2 | BCL6 | PRCP |
| INSR | VRK3 | DSE | FAM134B | PRNP |
| 1200003I10RIK | CEP152 | C78516 | NRARP | MPEG1 |
| 1200015M12RIK | SLC39A11 | ITGAE | DNAJC27 | TXNDC5 |
| 1200016E24RIK | TCF7 | GBP1 | ZBTB10 | SERPINI1 |
| A130040M12RIK | 2310044G17RIK | NUDT15 | D13ERTD608E | SLC40A1 |
| E430024C06RIK | 2810453I06RIK | 1110034G24RIK | AQP3 | MAP4K3 |
| FYN | GM1060 | GM8350 | IFNAR2 | CDH5 |
| RXRA | SEMA4B | NCK2 | FAS | SH3BGR |
| DHCR24 | CXCL10 | ITFG3 | ATP2A3 | NFE2L2 |
| ADO | ATP1B3 | MYC | 1810049H13RIK | KLK1B27 |
| IGTP | CAMKK2 | KLHDC2 | H2.OA | 1190005F20RIK |
| RTP4 | HRH1 | RP23.394O9.3 | RNF122 | 2210020M01RIK |
| 9130004J05RIK | TNFRSF10B | GM14446 | ARNTL | MAGED1 |
| FOSL2 | CCPG1 | ZDHHC23 | SLC16A6 | SF3A2 |
| PPRC1 | FAM109B | COMMD9 | GTF2I | CAMK1D |
| CYTH1 | HSPB11 | C730025P13RIK | 2610201A13RIK | TAF4B |
| TAGAP.TAGAP1 | ATP1B1 | CRTC3 | GGT1 | TYROBP |
| NSMCE1 | TOP1MT | AU022434 | IL4RA | OTTMUSG00000010657 |
| HEMGN | CSRNP1 | ELK4 | IFIT2 | DUS2L |
| HPCAL1 | SEMA4F | GM8369 | GLCCI1 | LOC497255 |
| RTN4RL1 | ZFP1 | JMY | MTAP1S | PITPNC1 |
| HMGN1 | 4921511C10RIK | SIPA1L1 | LMO4 | AI465300 |
| AFF3 | PIM2 | AU015680 | TRIO | ZFP407 |
| BCL3 | RARG | GPR15 | UNG | GM5785 |
| RPL31 | IFT172 | BB163080 | 1190002H23RIK | USP18 |
| ATP10D | D19ERTD386E | CRYL1 | 9030607L20RIK | SNN |
| IL7R | TRPM1 | LPHN1 | D730040F13RIK | ELOVL7 |
| PMEPA1 | MX2 | HSPA8 | THRA | IKBKE |
| KLK1.KLK1B5 | CCM2 | GM10392 | IDH2 | GZMM |
| HAGH | YES1 | 2610002M06RIK | ASB13 | MTHFR |
| PKD1 | CCDC64 | 9130401L11RIK | DDX60 | 6720462K09RIK |
| 5730508609RIK | ENTPD5 | KLF7 | AMZ2 | CTSH |
| CHD8 | 5830468F06RIK | PARD6B | RPP40 | D130037M23RIK |
| ETNK1 | LMBR1 | KRBA1 | 9530029O12RIK | 2310009A05RIK |
| ID3 | AU021025 | SMAD1 | 9630025H16RIK | LOC625360 |
| EPCAM | TMEM108 | GRAMD4 | NKRF | WDR41 |
| IL1RL2 | SH3BP5 | CDC14B | FAM158A | ACPP |
| TMEM86A | TAPT1 | 2610035D17RIK | ALPL | TCF4 |
| RNF213 | UBAC2 | FOXO1 | RNF149 | H2.T24 |
| MPPE1 | SGMS1 | MAP4K2 | MGAT4A | 4930535I16RIK |
| MAPK1IP1 | COMMD8 | TPD52 | CHD9 | VCAM1 |
| PHF17 | SBK1 | ITGA6 | 4930523C07RIK | RCN3 |
| FAM49A | SORL1 | MKL1 | TRIM32 | LPAR6 |
| LONRF1 | ANTXR2 | ARHGAP5 | MOBKL2B | GSN |
| NBN | AXIN2 | JAG1 | MYB | 1700023D09RIK |
| FAM26F | ACYP1 | BAMBI.PS1 | RRAS2 | CSF2RB2 |
| DNMBP | ERF | TMEM55B | SYNE2 | SYDE2 |
| RASA3 | CRIM1 | GCNT2 | D7ERTD413E | 4933407O12RIK |
| ASCC1 | DTX3L | P2RX4 | DNTT | EPHX1 |
| GALNT10 | ARL6IP5 | TAF3 | TCRG.V1 | ZFP3 |
| FOXP1 | SEPP1 | THA1 | AFAP1 | BCO26590 |
| NXF1 | SERP1 | OSBPL9 | GM9958 | TRIM62 |
| KLHL6 | INO80 | POU6F1 | RAB37 | WARS2 |
| SOCS1 | RPAP3 | 2310010J17RIK | JMJD1C | ALS2CL |
| ADK | RCC2 | LY6C1 | LIN52 | WNT5B |
| KIF21B | ZBP1 | LY6C2 | D630030B22RIK | GNG12 |
| FGF13 | RGS10 | ADRB2 | HIST2H3C1 | ZBTB24 |
| HMGN1 | SELL | ZFP53 | FAM109A | CCDC125 |
| SOCS3 | EIF2AK3 | GRAP2 | KLK1B22.KLK1B9 | CXCR5 |
| 4833423F13RIK | 2810454H06RIK | ABTB2 | FBXO32 | NINJ1 |

TABLE 4-continued

Dysfunction Signature

| | | | | |
|---|---|---|---|---|
| 2010107H07RIK | E230032D23RIK | SLC12A7 | PPARD | CNN3 |
| ENC1 | ZMYM2 | 4930431H11RIK | D1ERTD646E | GPR137B |
| GATSL3 | ITGA7 | INADL | PLCXD2 | LRP12 |
| HEG1 | HEATR5A | AI131651 | BACH2 | BC017158 |
| TCF12 | TRIT1 | RCSD1 | PSAP | FGFR1OP |
| PGS1 | PLAUR | TM7SF2 | LHFPL3 | ZFP608 |
| ZSCAN12 | NFIA | DLG5 | BLNK | SPSB1 |
| GRLF1 | PEPD | CDYL2 | ST8SIA1 | RGMB |
| 2810001G20RIK | SMCHD1 | GPC1 | ZER1 | 5830443J22RIK |
| ST3GAL6 | MRPL30 | TNIK | P2RX7 | A130091K22RIK |
| DDX54 | PARP14 | PCCA | KLRB1F | BTBD11 |
| 4930445K14RIK | TSPAN13 | D18ERTD653E | GARNL4 | 2010001M09RIK |
| IFI47 | C230085N15RIK | ACAD10 | KCTD12 | EPHA2 |
| SSBP2 | BC067068 | MCOLN3 | 9130019O22RIK | TCTEX1D1 |
| FAM65B | SHB | KLK1B4 | OGFOD1 | SLC30A1 |
| YEATS2 | CD79B | FOS | RPS20 | PEX11C |
| ARHGEF3 | ZFP362 | FAM122A | LDLRAP1 | KBTBD7 |
| CTAGE5 | CAPN3 | SGTB | 4932433N03RIK | ENDOG |
| STIM2 | ALDH1B1 | GPX1 | GDAP10 | ATP2A1 |
| TUBB2B | AI429363 | PLEKHA1 | LYSMD1 | GRN |
| CARD6 | KREMEN1 | ABCA1 | GPR132 | A130001G05RIK |
| UTRN | 2210010C17RIK | H2.D1.H2.T18.H2.T3 | EMID1 | MCAM |
| DYNC1H1 | 2310050P20RIK | 1200016E24RIK | EWSR1 | SIGLECH |
| 6230458A19RIK | ARMCX6 | A630023P12RIK | GM11346 | SHISA2 |
| LOC100044376 | SLC25A15 | BTF3 | CAR2 | PARP11 |
| CEP164 | ACTN2 | IGFBP4 | ECM1 | CCR4 |
| A230046K03RIK | SETDB2 | ALDH4A1 | D16H22S680E | DIP2C |
| C77651 | NOD1 | GM5817 | 5330403D14RIK | STX1A |
| 4930513N10RIK | KLF9 | ZXDB | RASGRP2 | IGF1 |
| HS3ST3B1 | RBM4B | JAKMIP1 | KTI12 | CCNJ |
| IFIT3 | C330006K01RIK | RIC8B | DPH5 | 4921524M04RIK |
| GPR18 | PDE7A | RAMP1 | A130064L14RIK | WFS1 |
| IRF1 | STAT5A | SNTB2 | SERINC5 | 4732423E21RIK |
| UBE1L | SLCO3A1 | KCNH2 | XPC | GPR137B.PS |
| SKP1A | GRAMD3 | KTELC1 | 1500015A07RIK | 2010309G21RIK.IGL.C2.IGL.C3 |
| MBOAT1 | PTK2 | GOLM1 | ACSS2 | 2900076A13RIK |
| USP6NL | 1500011B03RIK | B130065D12RIK | SOX4 | PSD |
| RNF113A2 | GM16489 | IGF1R | 4930534I15RIK | SPIB |
| IFIT1 | JAK2 | PDE2A | NCK2 | DGAT2 |
| SPON1 | LRRC8A | PPA1 | OAS3 | DAAM1 |
| PARP9 | PRKCQ | RCL1 | LDHB | EEF1G |
| HS6ST1 | KDM1 | ZRSR1 | HDGFRP3 | NUFIP2 |
| VIPR1 | GSTK1 | 9530028C05 | B230214O09RIK | GM4814 |
| A430028G04RIK | IRGM2 | BB236558 | CLCN6 | LPHN2 |
| NME4 | NOC4L | C030034I22RIK | BACH1 | GPR137B |
| CDC2L6 | 2310003H01RIK | RBM19 | UBTD2 | PARP3 |
| DYM | CCR7 | 6230427J02RIK | ZFP809 | KLK4 |
| DDX18 | MN1 | ZFP652 | TNFRSF19 | TM4SF5 |
| PIK3R5 | CAMSAP1L1 | BCL9 | TCP11L2 | PTPRF |
| ZDHHC8 | C77626 | 9530086P17RIK | DNAHC8 | F630110N24RIK |
| EMB | CD72 | MGST2 | CD40LG | PARD6G |
| DMRTA1 | SMPDL3A | RALGPS2 | BPHL | SLC16A5 |
| USP53 | SATB1 | BC059842 | HP1BP3 | 1190002A17RIK |
| PPP1R13B | D8ERTD82E | SSFA2 | 2410066E13RIK | LAIR1 |
| 3110070M22RIK | MYCBP2 | F2RL1 | SIAH1A | FADS3 |
| P4HA1 | TUBB2A | 2810001A02RIK | HEY1 | PLD4 |
| IRF6 | LYSMD2 | GGT5 | TIMP2 | CPT2 |
| PDLIM5 | TMEM57 | NEFH | ZFP623 | 6530415H11RIK |
| TOM1 | SCML4 | ARHGAP29 | RSAD2 | 2810021J22RIK |
| IQGAP2 | PPARGC1B | OASL1 | GIGYF2 | SNURF |
| CD2 | MLL3 | A930005H10RIK | 5430434G16RIK | SNRPN |
| 4932441K18RIK | 9330175E14RIK | DYRK2 | RNF157 | IL12A |
| ZNRF1 | USP12 | FBXO34 | IL6ST | LRIG1 |
| CXCR4 | PVR | HOXB4 | SLAMF9 | 3110037C07RIK |
| SLC39A8 | FURIN | FAAH | TAF4A | GSTZ1 |
| CELSR1 | TPST1 | DCUN1D4 | C430010O01 | CPNE3 |
| EVL | RORA | FAM82B | XKRX | RNASE6 |
| FAM69A | TLR6 | BC057079 | DNAJC7 | PLXDC1 |
| LOC100047863 | SLFN1 | SIDT1 | SH3BGRL2 | SPNS3 |
| 1810043H04RIK | NEDD4L | SQRDL | CD24A | ATP1A3 |
| TPST2 | GPR183 | C230021P08RIK | LIFR | COX6A2 |
| GBP2 | 2610019N06RIK | 5430427G11RIK | RBM38 | GM5547 |
| MS4A4C | D1ERTD622E | GYPC | TRNP1 | BTLA |
| SAMHD1 | ICAM2 | SESN3 | SLC9A9 | AI449212 |
| LPIN1 | RAB35 | MYLIP | ZFAND2A | DHX58 |
| ITPR2 | LTA4H | RAI2 | MAPK8 | SYK |
| XAB2 | SAMD9L | MDN1 | BEND5 | ZKSCAN3 |
| TGTP | WDR59 | KCNJ8 | ZFP566 | HPVC.PS |

TABLE 4-continued

| Dysfunction Signature | | | | |
|---|---|---|---|---|
| TGTP2 | ZFP354C | APOL7C | AKAP2 | LAPTM4B |
| ST6GAL1 | TRAT1 | ZFYVE27 | TAX1BP3 | 1700056E22RIK |
| LY9 | UVRAG | TTC28 | L3MBTL3 | TDRKH |
| CCDC52 | GGA2 | FBXO17 | BEX1 | CYBASC3 |
| GM11696 | CTDSP2 | ZFP260 | TEAM | CYBB |
| GIMAP6 | PDLIM4 | PJA1 | FGFR1 | PELI2 |
| PHC2 | E430014B02RIK | CORO7 | DHX37 | CD302 |
| CLPB | PDE8A | CLEC2I | SESN1 | RAPGEF4 |
| MPND | NOTCH1 | CUGBP1 | EHD3 | P2RY14 |
| LPP | ASF1A | FAM53B | S1PR1 | STC2 |
| MAP4K4 | 2900064B18RIK | B430306N03RIK | 6720418B01RIK | FRAT1 |
| BC002199 | TMEM50B | ZC3H12D | ZFP87 | FADS2 |
| RCBTB2 | RAPGEF6 | CACNA2D4 | C130039O16RIK | DDR1 |
| KLHDC1 | PIK3IP1 | FAM117A | SCPEP1 | PLAT |
| INPP5F | GAB3 | PIK3CD | MMACHC | BCL11A |
| TNFAIP8L2 | BC006779 | PGLYRP2 | IRF7 | 6330509M05RIK |
| S1PR4 | GIMAP9 | CCR9 | A130006I12RIK | FCRLA |
| ARMCX2 | GPR155 | MXRA8 | RRAGD | GRIT |
| EGLN3 | FOXP3 | CHST15 | SAMD10 | CD180 |
| PRKCB | EXT1 | GALNT12 | D930015E06RIK | LEFTY1 |
| TLR1 | ETV3 | MICAL3 | CYTH3 | KLHDC5 |
| DCLRE1A | FRMD4B | E230012J19RIK | USP45 | ENTPD6 |
| C330006A16RIK | BC005561 | AS33MT | ACSL1 | MEF2C |
| CDK5RAP3 | KBTBD8 | EVL | WIZ | SDCCAG3 |
| GM10726 | CXCR3 | ZFP238 | PKN1.PTGER1 | 9630025I21RIK |
| FAM108B | 2610019F03RIK | UTP14B | IFT80 | DUS4L |
| ARHGEF18 | STXBP3A | MAP4K5 | 2010004M13RIK | C80120 |
| CDK5R1 | FAM189B | TLE1 | TMEM141 | GNAI1 |
| MED8 | SSH2 | USP28 | ZSWIM6 | CADM1 |
| LOC100046855 | ATP8A2 | JHDM1D | DUSP10 | BST2 |
| RAI1 | D530037H12RIK | ADD3 | ST8SIA4 | CMAH |
| IKBKB | ABCC4 | PANK4 | PEX26 | P2RY13 |
| UTP14A | 5830411N06RIK | NANP | EEPD1 | CD163 |
| TSHZ3 | GALNT9 | PLTP | BC050254 | TUBB2A |
| BDH1 | 1810007M14RIK | NUDT15 | AMD1 | TUBB2B |
| RERE | EGR2 | 2810488G03RIK | NPC1 | LIF |
| PDE4B | 5830405N20RIK | PACSIN1 | DEP1 | GCC2 |
| ARL6IP6 | GPD1L | 6330416G13RIK | SOCS6 | NUCB2 |
| DAPL1 | ART4 | 2310022B05RIK | MUTED | RGS20 |
| PREI4 | AQP9 | FHIT | LYPD6B | HS3ST1 |
| SOS1 | TSPAN3 | PRICKLE1 | NET1 | SH2B3 |
| NLK | 2310035P21RIK | ZFP335 | AI451458 | GUCY1A3 |
| TGFBRAP1 | HEATR1 | ARID5A | SIN3A | D17WSU92E |
| WHRN | TMEM42 | DTX1 | PCNXL3 | FGR |
| CDT1 | SPNB2 | ACOT6 | ARHGEF11 | AMIGO2 |
| NIN | BTBD6 | 6030400A10RIK | 2900093K20RIK | D930001B02 |
| RP23 | STK38 | CTPS2 | PNCK | PUS3 |
| KBTBD11 | CCBL1 | BOLL | SGIP1 | ZFYVE28 |
| TNFRSF25 | OAS2 | GPR146 | CNKSR3 | CPNE2 |
| MTAP | TNFRSF13B | POLR3A | ULK1 | TBC1D8 |
| MMP17 | CMPK2 | 3830612M24 | USP33 | HSPA12B |
| LATS2 | REV3L | ZEB1 | VDR | HAVCR1 |
| EGR3 | MBP | PTCRA | BRWD2 | D7BWG0826E |
| ZFP592 | TECPR1 | ZDHHC13 | VAV2 | GPR25 |
| RECK | WDR45 | IRGM1 | IFNGR2 | CSF2RB.CSF2RB2 |
| ZFP422 | TK2 | CDC42SE2 | 1700100M05RIK | KCTD21 |
| RHOBTB2 | IPCEF1 | TLR7 | TRIB2 | PPIFOS |
| HIST2H2BB | UMPS | EEF2K | FITM2 | AU019157 |
| C430003N24RIK | SEC11A | 8430419L09RIK | AUTS2 | CCNB1IP1 |
| IL6RA | 4930438A08RIK | ZFP281 | PQLC1 | SIGMAR1 |
| VRK1 | KIF1B | SLC41A1 | PCGF5 | KMO |
| N4BP2 | SFRP2 | SCG5 | ANKZF1.GLB1L | LY6K |
| LEF1 | PRKAG2 | LOC552906 | CREG1 | GNAT1 |
| CHD3 | KLF2 | NUAK2 | IDUA | PLEKHO1 |
| LRRC33 | TESC | MAGEF1 | ZDHHC14 | PCBP3 |
| NOB1 | ENPP4 | AFF1 | MAST4 | PRKCC |
| HERC1 | GM5617 | TANC1 | CD59A | SPIC |
| ME2 | URB1 | FAM134C | SETD6 | H2.OB |
| CLASP1 | DIRC2 | PPM1M | ADAR | PARD3 |
| MFHAS1 | CDKN1C | SPSB4 | TMEM41A | TTC32 |
| PHF2 | METAPL1 | DEDD2 | IIGP1 | LOC100040377 |
| EFCAB2 | 6330415G19RIK | D130062J21RIK | SLPI | MGL1 |
| VMAC | MBTD1 | ZBTB9 | RAMP3 | CEACAM1 |
| DLEU2 | UBE2CBP | KLK1 | 2810013P06RIK | TUBB3 |
| RASSF3 | 9130208E07RIK | SLC15A4 | GABRR2 | TIFA |
| A630038E17RIK | 2310014D11RIK | 2410002O22RIK | ZBTB40 | PIR |
| ACVR1B | MACROD1 | ACTN1 | INPP5A | EMR4 |
| SLC11A2 | Sept8 | 2900076A07RIK | FAM43A | PPFIA4 |

TABLE 4-continued

| Dysfunction Signature | | | | |
|---|---|---|---|---|
| NISCH | FAM117B | TXNRD3 | NIPAL1 | GRIA3 |
| DGKA | MED4 | FGFRL1 | TATDN2 | TCF7L2 |
| A130038J17RIK | TRAF4 | PTPLA | 1700124K17RIK | PGAP3 |
| ITPR3 | PEO1 | CTSL | NACC1 | AI447881 |
| MEX3A | RALY | FAM101B | TMEM64 | FES |
| NOP2 | AGAP3 | EXOSC1 | TREML2 | 5031439G07RIK |
| DUSP28 | PML | TAF5L | PDZD4 | KYNU |
| MMAA | CLEC2D | CARD11 | TSC22D1 | SGK3 |
| GM2643 | | | | |

| Cancer_Up | | | | |
|---|---|---|---|---|
| GM11428 | HMMR | PEAR1 | CD200 | SEMA4C |
| FAM149A | NID1 | CASP1 | CALM3 | ZFP750 |
| AIF1 | MELA | 2600002B07RIK | FKBP1A | CST7 |
| MUC20 | RGS16 | FAH | 5730493B19RIK | MASTL |
| MS4A6C | ABHD14A | NCAM1 | USP40 | FUT7 |
| TGFBI | NUP107 | SUMF2 | CCNB2 | 2610039C10RIK |
| GATM | MORN4 | 2310046K01RIK | SEC23A | KDELC2 |
| IRAK1BP1 | ARL3 | AI747699 | CCDC6 | 2410127L17RIK |
| C1QB | MS4A6D | RHOQ | SEMA6D | PLSCR4 |
| MAFB | MTBP | DUT | TEX15 | MRPS6 |
| COL4A4 | SLC15A3 | FCHO2 | OTOA | ENO3 |
| CLEC4A3 | EFCAB7 | DIAP3 | S100A4 | CHCHD8 |
| PTGER2 | PDPN | PLEKHB2 | NUDT11 | MSRB3 |
| ENO2 | AW555355 | KLHL30 | POLK | CDC25C |
| APOE | D10WSU159E | HISPPD1 | TMEM175 | HSPA13 |
| 2300004M11RIK | A930038C07RIK | FZD5 | CHAC1 | SLC16A11 |
| FCGR2B | IL18RAP | HNRPLL | B230380D07RIK | NSL1 |
| FOXG1 | DIO2 | 4932415G12RIK | B930095G15RIK | MDFIC |
| QSOX1 | CSTAD | FILIP1 | UBASH3B | NINJ2 |
| HBEGF | COCH | ERN1 | B230354K17RIK | E2F8 |
| PDDC1 | BEND6 | 9430087J23RIK | FAM188A | 2310016C08RIK |
| C1QC | SLC7A8 | SLC35F5 | 1300014I06RIK | KCTD17 |
| GM11110 | NAIP5 | TPMT | DUSP6 | GSTT3 |
| ANPEP | EBAG9 | NDUFAF2 | ANKRD39 | SERPINB9 |
| LIPE | 2600001M11RIK | LTBP3 | INO80C | CALCB |
| MYADM | SAG | 2810039B14RIK | ABCB1B | PDCD1 |
| CXCL16 | 6330412A17RIK | CKAP2 | F630043A04RIK | EHD4 |
| CALD1 | ZDHHC9 | EIF2AK2 | MGAT3 | BCL2L1 |
| VPS18 | GTPBP3 | SDCCAG10 | SPRY2 | GPR174 |
| PCOLCE | SHCBP1 | MTMR7 | NAP1L3 | PRKACA |
| CPE | SRCRB4D | PRR11 | D430041D05RIK | ATP2B2 |
| EHBP1 | LRRK1 | 9630013D21RIK | ICOS | STX11 |
| IRG1 | CCL8 | 4833442J19RIK | IFNG | FAM176B |
| RHBDF2 | SH2D5 | TMEM163 | 1110067D22RIK | COMMD5 |
| FST | CBR4 | MYLK | IPP | 2500002B13RIK |
| RSLI | 5330433J24RIK | PON3 | GM10786 | RAPSN |
| ZFP429 | AK3L1 | ERC1 | ANUBL1 | D830012I24RIK |
| ZFP455 | WWTR1 | KLRC2 | TACC3 | NMT2 |
| ZFP456 | CLDND2 | B4GALT5 | CDCA8 | ALDOA |
| S100A9 | METTL7A1 | CDC2A | VASH1 | SPATS2 |
| SNXI6 | DOCK7 | JDP2 | 9230116N13RIK | CCDC99 |
| PTRF | TMEM38B | KIF18A | PTER | CDC27 |
| LPAR1 | CSF2 | TMEM180 | AP1S2 | IRF4 |
| COL1A2 | 1200009F10RIK | ARHGAP21 | SAT1 | ARHGEF5 |
| C1QA | GNG3 | CCL1 | D3ERTD751E | TMPRSS6 |
| LTBP1 | DCLK1 | CD80 | GM9529 | DENND3 |
| TIMP1 | 1700017B05RIK | TIRAP | CHN2 | C030046G05 |
| SDPR | PEX11A | TRPT1 | ZCCHC14 | TMEM135 |
| AQP11 | 1700009P17RIK | FAM92A | CCNG1 | RAP2A |
| CD34 | JAZF1 | ACOT7 | ELOVL4 | FAM72A |
| 1700012B09RIK | PLK1 | SMC2 | PGM2 | CSF1 |
| THBS2 | NUDT10 | TJP2 | MXI1 | ASPM |
| GJAI | UBE2I | MRGPRE | ALCAM | CCNBI |
| KRT20 | FZD4 | IFITM2 | CAPG | CAMK4 |
| CAV1 | ALS2CR4 | GM9861.LITAF | STK40 | KCND3 |
| IFI204 | HIGD1C | LCLAT1 | MTHFS | SYTL2 |
| VLDLR | METTL7A1 | ADRB1 | GPR160 | XLR4A |
| ZFHX3 | METTL7A2 | CLSTN1 | DUSP3 | XLR4B |
| PRKG2 | 2900001G08RIK | MOBKL1A | CERCAM | XLR4C |
| EREG | 4833420D23RIK | CYSLTR2 | GIPC2 | UHRF2 |
| ANXA3 | 3830408D07RIK | IFITM3 | FAM110A | MTMRI |
| HMGA2 | B830008J18RIK | 4930503L19RIK | 5730469M1ORIK | NCAPH |
| EIF2AK1 | FBXO45 | KIF4 | LCMT1 | PBX3 |
| SGMS2 | GPT2 | 8430429K09RIK | ANXA5 | TECR |
| GAB2 | ATF5 | 5LC25A24 | TPX2 | PLSCRI |
| FATI | CYTSB | 0610037D15RIK | KLF10 | ACTR10 |
| CXCL3 | ATFM2 | TRPS1 | 2810408I11RIK | KIT |

TABLE 4-continued

| Dysfunction Signature | | | | |
|---|---|---|---|---|
| TM4SF1 | D1ERTD83E | SRGAP3 | DYNLT3 | AI120166 |
| MXRA7 | KAZALD1 | GDPD5 | FBXO11 | 4933437N03RIK |
| GABBR1 | BST1 | TSGA10 | CNRIP1 | TMEM126A |
| APOM | CCL9 | SYNC | PTGS1 | ANXA2 |
| DCN | IL2 | B3GALT5 | GCSH | NEDD9 |
| CD40 | CD14 | USH1C | 5330426P16RIK | OCIAD2 |
| KCNA4 | CDH17 | PHKA2 | NEIL3 | TMEM120B |
| GREM1 | RHOU | 1110035E04RIK | PDGFB | 4930595D18RIK |
| SPARC | GM14057.PPP1R14C | CENPP | PRC1 | D2ERTD750E |
| S100A8 | PLS3 | SULT2B1 | SLFN10 | ARF2 |
| LOC73899 | MMP12 | MYO16 | RFC3 | EX01 |
| SOX9 | 4930551O13RIK | A130009E19RIK | PTPLAD1 | C130068B02RIK |
| MGP | FANCF | GSG2 | BUB1B | OAZ2 |
| CNNM3 | HHAT | DDX28 | STX17 | AF529169 |
| CPA3 | DNAJC25 | NCAPG2 | BUB1 | IGF2R |
| AGTRAP | D430033H22RIK | 1700106N22RIK | NFIL3 | D10627 |
| 1110032A03RIK | RALGDS | IL2RA | PIWIL2 | GRK5 |
| CD22 | PTPN3 | ZDHHC2 | CRYBG3 | TTBK2 |
| CLEC5A | GGTA1 | BB557941 | STARD3NL | PKP2 |
| RHOX5 | HBA.A1.HBA.A2 | TARSL2 | AI845619 | C76533 |
| LAMB1.1 | TNFSF9 | KIF2C | MAPK6 | ATXN1 |
| TPSAB1 | LPAR3 | ESCO2 | CHST12 | TMEM49 |
| SIGLEC5 | FOXM1 | KIF22 | CLDN2 | TUBB6 |
| DPYSL3 | SDC1 | FGFBP3 | GCNT1 | TFF1 |
| ENSMUSG00000043151 | SPIRE1 | ATP10A | TRIM45 | PTPLB |
| MCPT4 | March8 | RNF128 | GM10397 | RPA2 |
| CYR61 | KCNK10 | PLA1A | MTAP2 | GAPDH |
| ANKRA2 | B3GNT5 | BSPRY | SLC37A2 | 6030487A22RIK |
| MMP14 | BCL6B | ADAM15 | 2310079F09RIK | EGR1 |
| Sept4 | C76872 | NBEAL1 | A930012O16RIK | GPR56 |
| PILRA | 5730453C05RIK | DNAJC12 | ALG6 | PGGT1B |
| C78115 | PPFIBP1 | WDR67 | 2210403K04RIK | RPGR |
| GM5188 | ECE1 | ST14 | KLRA3.KLRA9 | STYK1 |
| CMA1 | ECT2 | REEP2 | A930012M21RIK | MSC |
| ARSK | CCDC58 | IL33 | ATF4 | RNASEH2C |
| NUPR1 | ORC1L | NSBP1 | ID2 | 1810011H11RIK |
| CAR6 | 2810433K01RIK | STAP1 | SLC2A8 | 4930520O04RIK |
| ITGA5 | FPR2 | HIST1H2BC | CCDC112 | RBPJ |
| TWIST1 | CRABP2 | PPP1R16B | ZDHHC5 | CTSC |
| SFMBT1 | DKKL1 | FAM57A | RASL12 | SEPHS1 |
| HTR7 | SEPN1 | WIPF1 | GPR65 | ABI2 |
| 3110052M02RIK | DCXR | BIRC5 | TMED8 | ICA1 |
| CLEC7A | E130008O17RIK | FAM54A | ANKLE1 | FASL |
| CNNM2 | TMPRSS2 | CMTM7 | IMPA2 | LAMC1 |
| STAB1 | EHD2 | CALCA | SLC17A6 | DUSP14 |
| CLIP2 | IL1RN | BARD1 | FOXRED2 | ELK3 |
| PLAU | CCR5 | CENPT | SH2D2A | SERPINB6B |
| RENBP | CHST10 | NRGN | GTF2IRD1 | MYO10 |
| HSPB9 | TMEM48 | TNFSF4 | HIP1R | PENK |
| BAIAP2L1 | ARL6 | LASS6 | 6330503K22RIK | PRDM1 |
| PTGS2 | KDM2B | D5WSU178E | CCL17 | MRPS36 |
| LOC100046401 | PAQR4 | 3110073H01RIK | EPDR1 | SLC39A14 |
| SPATA2L | PLEKHO2 | SCD2 | CD200R4 | PABPC1L |
| ZFP862 | TMEM149 | S100A1 | PERP | NDRG1 |
| THBS1 | FAM69B | GCNT7 | MMD | IDE |
| PDLIM7 | CYP4V3 | CCDC109B | FGL2 | TMEM158 |
| INTS9 | MED12L | NLRX1 | DLG2 | MID1IP1 |
| 5830456J23RIK | CCDC14 | SPAG9 | OPTN | CD244 |
| 0610009O20RIK | ARMC7 | ZFP52 | ATP6V0E2 | HIVEP1 |
| SIRPB1 | C5AR1 | PRSS1 | APOBEC3 | CCNB1 |
| CCL6 | TCRG.V4 | 5830485P09RIK | PGLYRP1 | GALC |
| LRRC20 | 5430405H02R1 K | CYP20A1 | WDFY1 | SERPINA3G |
| LOH12CR1 | CENPH | DNAJC24 | EEA1 | CDK6 |
| BBS12 | AMIGO1 | COBLL1 | TRPC1 | CHSY1 |
| PEX11B | TRIM72 | 5033418A18RIK | CDCA5 | NKG7 |
| LXN | PROS1 | TK1 | LOC677224 | IL1R2 |
| F13A1 | FUCA2 | PHACTR4 | C920021A13 | 2610029I01RIK |
| CAV2 | LGALS7 | GABARAPL1 | CCDC50 | ITGAV |
| ARL4D | RAI14 | HCFC2 | PIGN | RAB12 |
| CXCL11 | LPGAT1 | GM14288 | GBE1 | ALOX5 |
| TPSB2 | KLRB1A | NFAT5 | C1QL3 | ABCB9 |
| FN1 | TSPAN6 | B4GALNT2 | 0610010F05RIK | HTRA1 |
| ELAC1 | ADAMTS6 | WBP5 | GM2663 | CASP4 |
| PLXDC2 | 1700110K17RIK | ZWILCH | 1810009J06RIK | ARMC1 |
| AI450241 | OVOL2 | PAQR3 | CETN4 | STK38L |
| 4930429F24RIK | C77545 | TBC1D8B | A930026I22RIK | E330009J07RIK |
| SLFN3 | D3ERTD246E | KLRA7 | AGL | EMILIN2 |
| TREM2 | SPO11 | 4921509J17RIK | CD38 | TM9SF3 |

TABLE 4-continued

Dysfunction Signature

| | | | | |
|---|---|---|---|---|
| ARG2 | CCL12 | TPK1 | FHL2 | TRIM36 |
| GM5113 | C330027C09RIK | DAPK2 | SLC25A40 | CTSD |
| 3110021A11RIK | MND1 | GPR97 | DEGS1 | D3ERTD740E |
| ODZ4 | SPDYA | GINS1 | NSUN3 | SAR1A |
| KIF20A | MYO1E | LRRC39 | AI314976 | DUSP16 |
| RNF216 | 1190002F15RIK | RAB39B | GAS2L1 | CALU |
| L2HGDH | WISP1 | APBB1 | PHACTR2 | OSGIN1 |
| KDM4D | C130057M05RIK | GUF1 | GATA3 | CTLA4 |
| NBEAL2 | BATF2 | ENDOD1 | MORN3 | BHLHE40 |
| RAD51 | SLC5A3 | ANXA4 | CTLA2A | ASNS |
| TLR4 | SPAG5 | BCAT1 | CTLA2B | GLDC |
| 1110007C09RIK | ABHD4 | MARVELD2 | FAM5C | SUOX |
| RPS6KC1 | IER3 | CEP170 | UNC119B | KCNF1 |
| 1700019D03RIK | ZC3H12A | RABGEF1 | SSBP3 | NRN1 |
| NDUFB4 | 2010107G23RIK | PLOD2 | HSPA2 | TNFRSF18 |
| BC046404 | AIM2 | FTSJD1 | WDR54 | LITAF |
| COMT1 | BAI2.LOC100048816 | TRIB3 | CENPA | CISD3 |
| OMD | IKZF2 | ATHL1 | CD244 | GOLGA7 |
| PPME1 | SESTD1 | ALAD | RAD54B | TBC1D7 |
| SPATA5L1 | UNC119 | PLAGL1 | 9230110C19RIK | STK39 |
| LRP1 | CARS | JMJD5 | PHLPP1 | PIK3CG |
| A230083N12RIK | GAN | TYW1 | FAM110C | OIT3 |
| 3110048L19RIK | MEST | TNFSF10 | TWSG1 | IPO8 |
| 6330416L07RIK | D330040H18RIK | UGP2 | CTLA2A | GLT8D3 |
| CCL7 | CEP55 | MAGOHB | EN01 | ITIH5 |
| ACAD11 | PXMP2 | TULP4 | PKD2 | HIGD1A |
| NPHP3 | NEBL | E030047P09RIK | PLEKHF1 | ITGA1 |
| NRP1 | TLR2 | AREG | H2.Q5 | AKTIP |
| LRRC4 | MUC1 | 4930518I15RIK | SH3BGRL | 2310001H17RIK |
| CD160 | PMAIP1 | PPAP2C | GAS2 | CCRL2 |
| PRRX1 | PAWR | ZCCHC3 | 0610010B08RIK | 2700007P21RIK |
| B3GALTL | PTPN11 | PDCD1LG2 | MTHFD2 | LYRM1 |
| CCDC34 | PLD2 | TMEM39A | NIPA2 | D630039A03RIK |
| RAB31 | FCGR1 | MYST4 | GLIS1 | IGSF5.PCP4 |
| BIRC1F | 2610318N02RIK | KIF24 | PLEK | ADAM8 |
| IL1RL1 | SLCO4A1 | FARS2 | ELMO2 | CSDA |
| RAB5B | 4930579G18RIK | NT5DC2 | VAMP8 | 3000002C10RIK |
| CD200R1 | CD93 | PTPRK | PADI2 | CCDC21 |
| NPL | GFRA2 | SUDS3 | ENPP2 | NDFIP1 |
| CLEC4E | DTL | TPI1 | ANAPC4 | SDCBP2 |
| THBS1 | TTC39C | TMEM170B | BC068157 | ARHGEF9 |
| AA408396 | LOC100046560.MAGED2 | KIFC1 | ERMP1 | SAMSN1 |
| GNB5 | TMEM218 | KCTD11 | GPD2 | GZMC |
| DDEF2 | 6430537I21RIK | BCL2L15 | HIF1A | CILP2 |
| 2610024B07RIK | ARG1 | RANBP9 | GNG11 | 4831426I19RIK |
| GPR84 | WNT10B | TROVE2 | GALNT3 | TMEM184C |
| 2610027H17RIK | 9530053H05RIK | STIL | EPS8L3 | SPA17 |
| MCPT8 | D030028M11RIK | GMEB2 | TCFAP2A | AA467197 |
| GRB10 | OLFM1 | 9630010G10RIK | OBFC2A | EPAS1 |
| TMEM106A | HIGD1C.METTL7A2 | 2010111I01RIK | DDX17 | SLC22A15 |
| ZFP692 | 3100002L24RIK | PPP2R2C | XPOT | TBX21 |
| CD79A | GM14434 | ENTPD1 | RNF170 | NPHS2 |
| 4930515G01RIK | OTTMU5G00000016609 | RGS8 | DCTN4 | WDR60 |
| DAB2 | CCHCR1 | CENPI | RAPH1 | NCOR2 |
| 3110082I17RIK | JAM2 | CAMK2N1 | POMT1 | ACADSB |
| FAM129B | CDC14A.LOC100047731 | MTAP6 | CAR13 | PRF1 |
| LRFN1 | 1700029I15RIK | CCR8 | REM2 | SYNGR3 |
| RIN3 | PHF23 | BCMO1 | FARP1 | 4933431E20RIK |
| DXERTD242E | TEAD1 | TACR1 | RYK | GALNTL4 |
| CCL2 | TMEM119 | 5830474E16RIK | TMBIM4 | IL15RA |
| CLEC4A2 | GPM6B | 5430439M09RIK | PPP3CB | C1QTNF6 |
| FRZB | PCYT1A | 2700008G24RIK | GABRR1 | SMPDL3B |
| DIP2A | HIST1H2AD | SLC7A3 | CRAT | GZMG |
| 2700097O09RIK | RABL5 | DAB2IP | KCTD9 | DUSP4 |
| RBP1 | ACADL | AKR1B8 | GM6194 | OSBPL3 |
| MPZL2 | ARHGAP18 | C230098O21RIK | TMEM189 | COX17 |
| 1700025K23RIK | BC010981 | NR3C1 | KLRD1 | CDKN3 |
| KIF20B | PPP1R14A | WWC1 | CCL3 | ARPC1B |
| CLEC4D | SELM | D17ERTD165E | TBC1D2B | DSC2 |
| CCL27A.GM13306 | SLC25A13 | USP46 | FKBP7 | OSTF1 |
| PTGR1 | SH3RF1 | APLP1 | A2LD1 | ARSB |
| HMBOX1 | COL27A1 | SCCPDH | DEPDC1A | ITLN1 |
| GDA | TCTEX1D2 | RHOC | PCK2 | MRC2 |
| AI847670 | CCL4 | 5830415L20RIK | ZFP219 | ETV5 |
| PASK | 4933424G06RIK | RAB19 | BCL2A1A | SRXN1 |
| CPA2 | PHACTR3 | SLC43A3 | BCL2A1B | TMBIM1 |
| CXCL2 | ZBTB12 | AHCYL1 | BCL2A1D | GPLD1 |
| AQP11 | IGFBP7 | SGOL2 | NDC80 | 4933413G19RIK |

TABLE 4-continued

| \multicolumn{5}{c}{Dysfunction Signature} |
|---|---|---|---|---|
| APOC2 | AI836003 | COPZ2 | ZBTB32 | FOXM1 |
| PF4 | FOXD2 | ZFP760 | ERO1L | PEBP1 |
| DMXL2 | PRICKLE2 | UBE2C | RIPPLY3 | GDAP2 |
| TNFSF11 | BACE2 | DLL1 | ST6GALNAC6 | SLC25A19 |
| 8030498B09RIK | ALG8 | NSMAF | HIP1 | GEM |
| A430093F15RIK | AMOTL2 | TJP1 | NFATC1 | LPXN |
| ZFP526 | SLC30A9 | KRT18 | FRMD4A | NR4A2 |
| LYZ2 | 2310039F13RIK | CTNND2 | IGF2BP2 | PPM1D |
| MSR1 | 2310031A07RIK | NPNT | MLKL | FLYWCH1 |
| CXCL1 | FAM178B | L00641050 | MT2 | TOX |
| GRP | CBARA1 | UPP1 | CREB3L2 | NDFIP2 |
| 1500009L16RIK | WDSUB1 | FCER1G | KIFC3 | CASP3 |
| TPBG | TNF | PI4K2B | FAM19A3 | STARD4 |
| NEK8 | ARFGAP3 | FANCD2 | CIAPIN1 | EFHD2 |
| EPHB6 | ZEB2 | LGALS3 | MLF1 | TMEM171 |
| C4B | GH | ATG16L2 | IQGAP3 | SDF4 |
| HBB.B1.HBB.B2 | SCYL2 | 9430037O13RIK | SERPINB6A | ARNT2 |
| D9ERTD26E | TRAIP | UTF1 | CENPN | TMEM159 |
| NCSTN | AA407881 | FAM64A | SLFN3.SLFN4 | POLH |
| FCGR4 | C430042M11RIK | CARHSP1 | TMCC3 | SERPINB9B |
| C3AR1 | BTBD10 | SLC35B1 | CXCR6 | SPP1 |
| MS4A7 | DPY19L4 | NUF2 | TRIP10 | EPB4.1L5 |
| ANXA1 | 2810417H13RIK | TSGA14 | LOC100048079 | ZFP511 |
| RAB27A | GM10196 | 2010002N04RIK | FZD6 | CDKN2B |
| 4930434E21RIK | GM5623 | SMPD4 | TNFSF13B | 4930448K20RIK |
| CRYZ | RPS15A | ADAM9 | LAG3 | 2900026A02RIK |
| KNDC1 | CCR1 | LANCL3 | GSTM5 | PTTG1 |
| SLC6A9 | PLXND1 | TRAPPC1 | S100A11 | GZMD.GZME |
| ATP6V1G2 | TYMS | DCI | CDC14A | SLC16A4 |
| FHL3 | ULBP1 | NAIP2 | GPR177 | MT1 |
| ATAD5 | ZFP282 | TRAPPC4 | GSTO1 | SLC2A3 |
| 1700019E19RIK | KCNQ5 | ALDOC | IDH3A | LHFPL2 |
| FAM162A | C79607 | DENND4A | ADSSL1 | GZME |
| POPDC2 | NQO2 | CDCA3 | UBASH3B | SPIN4 |
| E130112N10RIK | KPNA2 | MMD | SUV39H2 | RASD2 |
| GARNL1 | TCRG | LAT2 | SNAP47 | BNIP3 |
| CENPF | C530028O21RIK | UGT1A1 | CDCA2 | SERPINE2 |
| LPCAT4 | DSCAM | UGT1A10 | CCDC122 | GZMF |
| AA407331 | KDM2B | UGT1A2 | TNFRSF4 | GZMD |
| E2E3 | PRR15 | UGT1A5 | BCO23744 | HAVCR2 |
| RAB11FIP5 | BRCA2 | UGT1A6A | PPP1R3B | HTATIP2 |
| FOXF1A | C80258 | UGT1A6B | 6230409E13RIK | LTF |
| FAM20C | E2E7 | UGT1A7C | EXPH5 | SYTL3 |
| LYZ1 | TMEM29 | UGT1A9 | TTK | CNTLN |
| CX3CR1 | MPI | CD81 | TG | APOLD1 |
| SLC16A13 | BMPR2 | 4930422G04RIK | KLRE1 | TNFRSF9 |
| FCGR3 | | | | |

TABLE 8

(Related to FIG. 36) Shared genes between the glucocorticoid-induced and the T cell dysfunction signature in CD8+ T cells.

| Exhaustion Up | | | Exhaustion Down | |
|---|---|---|---|---|
| Chst12 | Pik3cg | Tnfsf14 | Dnajc7 | Rab33b |
| Batf3 | Ndfip2 | Med12l | Rbm25 | Fam49a |
| Cdk6 | Arhgap33 | Acot9 | Sgk3 | Cyp27a1 |
| Kit | Golga7 | Asnsd1 | Slc25a25 | Pltp |
| Eva1b | Tbc1d9b | Pstpip1 | Bst2 | Coq10b |
| Cd97 | Aldoa | C920025E04Rik | Serp1 | Neu1 |
| Cysltr2 | Hilpda | Gm2382 | Irgm1 | Enpp4 |
| Pld3 | Gm11110 | Dnajc1 | Dnaja2 | Edem2 |
| Kcna4 | Ltb4r1 | Socs2 | Ppif | Tsr1 |
| Chmp2a | Fzr1 | Gdi2 | Trub1 | Acsl1 |
| Cd200r1 | Arhgap18 | Rbl2 | Tagap | Aldh4a1 |
| Nfyb | Nlrc3 | Dapk2 | Ddx5 | Sell |
| 8430427H17Rik | F730043M19Rik | Hip1r | St8sia4 | Spns1 |
| Lag3 | Fxyd5 | Ccdc34 | Gsn | Aagab |
| Aplp1 | Ctc1 | Trmt2b | Fcer1g | Upb1 |
| Serpinb9 | Nrp1 | Tmem107 | Irf8 | Srl |
| Serhl | Casp1 | Gng2 | Trat1 | Abhd11 |
| Trpv2 | Prelid2 | Acadl | Gpd1l | BC035044 |
| Ccdc109b | Rab8b | Mical1 | Acot2 | Snx4 |
| Clip2 | Atl3 | Scyl2 | Vrk1 | Ubc |

TABLE 8-continued (Related to FIG. 36) Shared genes between the glucocorticoid-
induced and the T cell dysfunction signature in CD8+ T cells.

| Exhaustion Up | | | Exhaustion Down | |
|---|---|---|---|---|
| Cst7 | Smim3 | Mdfic | Xrn2 | Ntrk3 |
| Hjurp | Pfkp | Dpysl2 | Tob2 | Ifi47 |
| Rnh1 | Gpr56 | Trim35 | Lmo2 | Ptcra |
| Syne3 | A730008H23Rik | Mtmr6 | Ctsz | Wdfy4 |
| Uevld | Tdpoz4 | 6430706D22Rik | Cmah | Slc2a6 |
| Cercam | Ggta1 | Serpinb1b | Syngr2 | Mcmbp |
| Narf | Cd3g | Cx3cr1 | Dnajb1 | Stk38 |
| Mapk3 | Kif23 | Cd52 | Tgtp2 | Ints3 |
| Pfkfb3 | Padi2 | Klrk1 | Rbm38 | Phf11c |
| Vim | Chchd10 | Pygb | Mgat5 | S1pr1 |
| Flot2 | S100a10 | Rhof | Slfn5 | Zdhhc13 |
| Kif18b | Pmaip1 | Cd226 | Dapl1 | Mafk |
| Sh3bgrl3 | Apaf1 | Pkp3 | Slco3a1 | Wwp1 |
| Prr13 | Plcd1 | Plp2 | Hexim1 | Cdk11b |
| Serpina3f | Slamf7 | Adprh | Tns1 | Cd320 |
| Mboat2 | Crlf2 | 1110007C09Rik | Ada | Gpx1 |
| 5330426P16Rik | Phlpp1 | Ccr8 | Pvrl4 | Mtmr4 |
| Rinl | Gdpd5 | Il12rb2 | Hmgn1 | Icam2 |
| Mis18a | Fcho1 | Mapkapk3 | Abtb2 | Nek6 |
| Arhgef39 | Ckap2 | Icos | Ap3d1 | Ppp4r2 |
| Stat3 | BC068157 | Itgav | Ceacam1 | Il20rb |
| 4931406H21Rik | Gp49a | Entpd1 | Scap | Csf2rb |
| Cep85 | Arhgef9 | Bzrap1 | Wdr46 | Ddx3x |
| Jak3 | Nrn1 | Cd83 | Dgkd | Thoc2 |
| Prss16 | Twsg1 | Apbb1 | Crlf3 | Usp12 |
| Sv2c | Il10ra | Chp1 | Nup153 | Slc35e2 |
| C3 | H2-Q7 | Oit3 | Polr3b | Mgat1 |
| Il1r2 | Camk4 | Fut7 | Hivep3 | Zmynd8 |
| Rps6ka4 | Cd3e | Klrc1 | Slc29a3 | Cldn25 |
| Id2 | Plekha2 | Mif4gd | Arglu1 | Uso1 |
| Soat1 | Il12rb1 | Tmem159 | Net1 | Trim30d |
| Lrrc8c | Nrm | Gldc | Hs3st3b1 | Gcnt2 |
| Pcx | Lilrb4 | Sra1 | Tapbpl | Fgr |
| Zmiz1 | Gcnt1 | Lpxn | Adpgk | Usp36 |
| Mfsd10 | Tigit | Neb | Myb | Slamf6 |
| Ech1 | Crot | Agpat9 | Unc5cl | Rgs18 |
| Ptpn13 | Mnda | Unc13a | Ivns1abp | 2410002F23Rik |
| Asb2 | Gpr65 | Cdc25b | Atf6b | Arhgef10l |
| Ppp1r3b | Gpi1 | Aldoc | Bzw2 | Sfn |
| Afg3l2 | Zfp414 | AW112010 | Mapk11 | Mdn1 |
| Slc2a8 | Cd80 | Slc35b2 | Celf1 | Gm14085 |
| Arpc2 | AA467197 | Ephb6 | Mir17hg | Nptn |
| Adora2b | Polk | Gm16907 | Tmem229b | Kmo |
| Rora | Traf1 | Dkkl1 | Tsr2 | Pecam1 |
| Samsn1 | Sytl3 | Abhd4 | Sde2 | Egfr |
| Smpd1 | Ndrg1 | Susd3 | ligp1 | Nr2c2ap |
| Lsp1 | Dclk2 | Nfil3 | Fgd2 | Myc |
| Fundc2 | Gm16039 | Leprot | Tspan2 | Akap8 |
| Acsbg1 | Wdr67 | Ism1 | Art2b | Pik3r5 |
| Hspa4l | Zbtb7b | Impa2 | Hsd11b1 | As3mt |
| Krtcap2 | Nfat5 | Farp1 | Cd300a | Top1mt |
| Pgk1 | Ostf1 | Rdm1 | Usp7 | Cnot8 |
| Casp4 | Cd28 | Pdcd1 | Psme1 | Ehd3 |
| Wnk1 | Setd8 | 0610009O20Rik | Prodh | Abcc4 |
| Klhl25 | Zfp52 | Rac1 | Itga4 | Zfand2a |
| Tnfrsf18 | Tax1bp3 | Fam132a | P2ry14 | Slc35c2 |
| Cish | Dynlt3 | Hif1a | 2810407C02Rik | Eefsec |
| Mpp2 | Pglyrp1 | Efcab11 | Evl | Junb |
| Aif1 | Serpinb6b | Mtmr7 | Cd74 | Sp110 |
| Plekhb2 | Ebi3 | Ctla4 | Itk | Pitpna |
| Zap70 | Syngr3 | Tnfrsf9 | Slc25a12 | Adk |
| Sdf4 | Uhrf2 | Gpr107 | Usp18 | Nt5c2 |
| Prph | Zyx | Stab1 | Igtp | Pepd |
| Nusap1 | Cd86 | Cnot3 | Igj | Pde7a |
| Sat1 | Lrrk1 | Lst1 | Hsf1 | Gm16702 |
| Lamc1 | Fbxl8 | Man2b2 | Uspl1 | Tubb2a |
| 1190002F15Rik | D16Ertd472e | Cep72 | Rexo2 | Fam210a |
| H2afv | Arl14ep | Hemk1 | Fads2 | Lrrc33 |
| Fam178b | Vmp1 | Ankrd46 | Dph5 | Nxf1 |
| Cmip | Sord | Tnfrsf4 | Fbxo17 | |
| Srgap2 | Dusp22 | Ahnak | | |
| Itgam | Ehbp1l1 | Crip1 | | |

TABLE 8-continued (Related to FIG. 36) Shared genes between the glucocorticoid-
induced and the T cell dysfunction signature in CD8+ T cells.

| Exhaustion Up | | Exhaustion Down |
|---|---|---|
| Ptprv | Prrc1 | 2010111I01Rik |
| BC021614 | Pygl | Ctsw |
| Creb3l1 | Anxa2 | |

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of altering T cell dysfunction in a subject suffering from cancer comprising administering to the subject metyrapone, wherein the metyrapone is conjugated to a bispecific antibody or antibody drug conjugate targeting the metyrapone to monocytes and/or macrophages, wherein anti-tumor immunity is enhanced in the subject, wherein the metyrapone is administered directly to the tumor microenvironment of the cancer.

2. The method of claim 1, wherein the metyrapone is administered by intra-tumoral injection.

* * * * *

UNITED STATES PATENT AND TRADEMARK OFFICE
CERTIFICATE OF CORRECTION

PATENT NO. : 11,793,787 B2
APPLICATION NO. : 17/065328
DATED : October 24, 2023
INVENTOR(S) : Ana Carrizosa Anderson et al.

It is certified that error appears in the above-identified patent and that said Letters Patent is hereby corrected as shown below:

On the Title Page

On the Page 2, in Column 2, item (56) (U.S. Patent Documents), Line 14, delete "3,021,867" and insert -- 8,021,867 --.

On the Page 3, in Column 2, under item (56) "Other Publications", Line 18, delete "l/ll" and insert -- I/II --.

In the Specification

In Column 2, Line 64, delete "of." and insert -- of: --.

In Column 2, Line 67, delete "Gprl25, Aqpl1," and insert -- Gpr125, Aqp11, --.

In Column 3, Line 4, delete "Clqtnf4," and insert -- C1qtnf4, --.

In Column 3, Line 31-32, delete "Gprl25, Aqpl1," and insert -- Gpr125, Aqp11, --.

In Column 3, Line 35, delete "Clqtnf4," and insert -- C1qtnf4, --.

In Column 6, Line 5, delete "Aqpl1," and insert -- Aqp11, --.

In Column 6, Line 8, delete "Clqtnf4," and insert -- C1qtnf4, --.

In Column 6, Line 29, delete "Clqtnf4," and insert -- C1qtnf4, --.

In Column 6, Line 30, delete "Gprl25, Aqpl1," and insert -- Gpr125, Aqp11, --.

In Column 8, Line 27, delete "of." and insert -- of: --.

Signed and Sealed this
Twenty-fourth Day of December, 2024

Derrick Brent
*Acting Director of the United States Patent and Trademark Office*

CERTIFICATE OF CORRECTION (continued)
U.S. Pat. No. 11,793,787 B2

In Column 8, Line 30, delete "Gprl25, Aqpl1," and insert -- Gpr125, Aqp11, --.

In Column 8, Line 34, delete "Clqtnf4," and insert -- C1qtnf4, --.

In Column 8, Line 39, delete "Clqtnf4," and insert -- C1qtnf4, --.

In Column 8, Line 39, delete "Gprl25," and insert -- Gpr125, --.

In Column 10, Line 39, delete "5 g/ml" and insert -- 5 µg/ml --.

In Column 11, Line 1, delete "S.E.M." and insert -- ±S.E.M. --.

In Column 11, Line 25, delete "E8i-Cre$^+$Nr3c$^{fl/fl}$," and insert -- E8i-Cre$^+$Nr3c1$^{fl/fl}$, --.

In Column 11, Line 59, delete "S.E.M." and insert -- ±S.E.M. --.

In Column 12, Line 33, delete "Nr3c11$^{fl/fl}$" and insert -- Nr3c1$^{fl/fl}$ --.

In Column 13, Line 18, delete "ChTP" and insert -- ChIP --.

In Column 13, Line 39, delete "CD8$^+$TILs" and insert -- CD8+ TILs --.

In Column 13, Line 49, delete "Lin-CD45$^+$CD24$^-$" and insert -- Lin$^-$CD45$^+$CD24$^-$ --.

In Column 15, Line 29-30, delete "Mean SEM" and insert -- Mean±SEM --.

In Column 16, Line 33, delete "Lin-CD45$^+$CD24$^-$" and insert -- Lin$^-$CD45$^+$CD24$^-$ --.

In Column 17, Line 33, delete "E8i-Cre$^+$Nr3c$^{fl/fl}$" and insert -- E8i-Cre$^+$Nr3c1$^{fl/fl}$ --.

In Column 18, Line 24, delete "(Nr3c1$^{fl/fl}$ E8iCre)" and insert -- (Nr3c1$^{fl/fl}$E8iCre$^-$) --.

In Column 18, Line 31, delete "Nr3c1$^{fl/fl}$ E8iCre$^+$" and insert -- Nr3c1$^{fl/fl}$E8iCre$^+$ --.

In Column 18, Line 32, delete "Nr3c1$^{fl/fl}$ E8iCre" and insert -- Nr3c1$^{fl/fl}$ E8iCre$^-$ --.

In Column 18, Line 34, delete "Nr3c1$^f$E8iCre-(WT) and Nr3c11$^{fl/fl}$ E8iCre$^+$" and insert -- Nr3c1$^{fl/fl}$ E8iCre$^-$(WT) and Nr3c1$^{fl/fl}$ E8iCre$^+$ --.

In Column 18, Line 37, delete "Nr3c11$^{fl/fl}$ E8iCre" and insert -- Nr3c1$^{fl/fl}$ E8iCre$^-$ --.

In Column 18, Line 39, delete "Nr3c1$^{fl/fl}$ E8iCre and Nr3c1$^{fl/fl}$ E8iCre$^+$" and insert -- Nr3c1$^{fl/fl}$E8iCre$^-$ and Nr3c1$^{fl/fl}$E8iCre$^+$ --.

In Column 18, Line 37-41, delete "FIG. 42D) in the spleen of Nr3c11$^{fl/fl}$ E8iCre (WT) and Nr3c1$^{fl/fl}$ E8iCre$^+$ mice. E) MFI of GR expression on T cells from Nr3c1$^{fl/fl}$ E8iCre and Nr3c1$^{fl/fl}$ E8iCre⁺ mice. NS, not significant. **p<0.01, One-way ANOVA (Tukey's multiple comparisons test). Mean±SEM are shown." and insert the same on Column 18, Line 36, as a continuation of the same paragraph.

In Column 18, Line 44, delete "(Nr3c1'E8iCre)" and insert -- (Nr3c1$^{fl/fl}$E8iCre⁻) --.

In Column 18, Line 45, delete "Nr3c1$^{fl/fl}$ E8iCre⁺" and insert -- Nr3c1$^{fl/fl}$E8iCre⁺ --.

In Column 18, Line 48-49, delete "(Nr3c1$^{fl/fl}$E8iCre) and Nr3c1$^{fl/fl}$ E8iCre⁺" and insert -- (Nr3c1$^{fl/fl}$E8iCre⁻) and Nr3c1$^{fl/fl}$E8iCre⁺ --.

In Column 19, Line 5-12, delete "FIG. 43H) Summary plots showing the absolute number of CD8⁺ TILs at the intermediate stage of tumor progression (n=6). FIG. 43I) Summary plots representing the frequency of CD4⁺ T cells expressing checkpoint receptors at the intermediate stage of tumor progression (n=6-7). FIG. 43J) Summary plots of the MFI of checkpoint receptors on CD4⁺ T cells at the intermediate stage of tumor progression, (n=6-7). NS, not significant, *p<0.05, p<0.01, *p<0.001, unpaired Student's t-test. Data are mean±SEM." and insert the same on Column 19, Line 4, as a continuation of the same paragraph.

In Column 19, Line 24, delete "PD-1" and insert -- PD-1⁻ --.

In Column 19, Line 31, delete "Cyp11a1$^{fl/fl}$LysMCreor" and insert -- Cyp11a1$^{fl/fl}$LysMCre⁻ or --.

In Column 19, Line 33, delete "i SEM" and insert -- ±SEM --.

In Column 19, Line 35, delete "Cyp11a1$^{fl/fl}$LysMCre" and insert -- Cyp11a1$^{fl/fl}$LysMCre⁻ --.

In Column 19, Line 39, delete "Lin-" and insert -- Lin⁻ --.

In Column 25, Line 46, delete "NMC" and insert -- MHC --.

In Column 27, Line 25, delete "NR33C1," and insert -- NR3C1, --.

In Column 27, Line 28, delete "NM" and insert -- NM_ --.

In Column 27, Line 29, delete "NM" and insert -- NM_ --.

In Column 27, Line 30, delete "NM" and insert -- NM_ --.

In Column 27, Line 30, delete "NM" and insert -- NM_ --.

In Column 27, Line 30, delete "NM" and insert -- NM_ --.

In Column 27, Line 31, delete "NM" and insert -- NM_ --.

In Column 43, Line 67, delete "254rai28;" and insert -- 254ra128 --.

CERTIFICATE OF CORRECTION (continued)
U.S. Pat. No. 11,793,787 B2

In Column 50, Line 9, delete "(CLECl2A);" and insert -- (CLEC12A); --.

In Column 50, Line 21, delete "CAPI" and insert -- CAP1 --.

In Column 57, Line 58, delete "CD4$^+$" and insert -- CD4+ --.

In Column 59, Line 28, delete "$10^1$" and insert -- $10^5$ --.

In Column 61, Line 54, delete "a and J," and insert -- α and β, --.

In Column 63, Line 55, delete "PD-LI," and insert -- PD-L1, --.

In Column 64, Line 46, delete "J-2" and insert -- β-2 --.

In Column 73, Line 49-52, delete "C1-10 alkyl, C1-10 substituted alkyl, C2-10 alkenyl, C2-10 substituted alkenyl, aryl, C1-6 alkyl aryl, C(O)—(CH2)1-6-COOH, C(O)—C1-6 alkyl, C(O)-aryl, C(O)—O-C1-6 alkyl, or C(O)—O-aryl." and insert -- —C1-10 alkyl, —C1-10 substituted alkyl, —C2-10 alkenyl, —C2-10 substituted alkenyl, aryl, —C1-6 alkyl aryl, —C(O)—(CH2)1-6-COOH, —C(O)—C1-6 alkyl, —C(O)-aryl, —C(O)—O-C1-6 alkyl, or —C(O)—O-aryl. --.

In Column 76, Line 32, delete "p" and insert -- β --.

In Column 98, Line 36-37, delete "($X_{11}$—($X_{12}X_{13}$)—$X_{14}$ 33 or 34 or 35)$_z$," and insert -- ($X_{1\text{-}11}$—($X_{12}X_{13}$)—$X_{14\text{-}33}$ or 34 or 35)$_z$, --.

In Column 110, Line 52, delete "(g)" and insert -- (μg) --.

In Column 111, Line 4, delete "g/kg" and insert -- μg/kg --.

In Column 111, Line 27, delete "Adults At" and insert -- Adults—At --.

In Column 112, Line 45-46, delete "2-hydroxypropyl-p-cyclodextrin;" and insert -- 2-hydroxypropyl-β-cyclodextrin; --.

In Column 115, Line 62, delete "1×SE" and insert -- ±1×SE --.

In Column 117, Line 4, delete "CD4$^+$" and insert -- CD4+ --.

In Column 129, Line 65, delete "TL-27" and insert -- IL-27 --.

In Column 131, Line 49-50, delete "E8i-Cre×Nr3 c1$^{fl/fl}$" and insert -- E8i-Cre×Nr3c1$^{fl/fl}$ --.

In Column 131, Line 53, delete "E8i-Cre×Nr3c11$^{fl/fl}$" and insert -- E8i-Cre×Nr3c1$^{fl/fl}$ --.

In Column 139, Line 64-65, delete "(E8i-Cre$^-$ Nr3c1$^{fl/fl}$) and E8i-Cre$^+$ Nr3c1$^{fl/fl}$" and insert -- (E8i-Cre$^-$Nr3c1$^{fl/fl}$) and E8i-Cre$^+$Nr3c1$^{fl/fl}$ --.

CERTIFICATE OF CORRECTION (continued)
U.S. Pat. No. 11,793,787 B2

In Column 140, Line 66, delete "E8i-Cre$^+$ Nr3c$^{fl/fl}$" and insert -- E8i-Cre$^+$ Nr3c1$^{fl/fl}$ --.

In Column 142, Line 5, delete "(p=9.4×0$^{-52}$," and insert -- (p=9.4×10$^{-52}$, --.

In Column 147, Line 5, delete "1 g/ml)" and insert -- 1 μg/ml) --.

In Column 147, Line 11, delete "1 g/ml)" and insert -- 1 μg/ml) --.

In Column 147, Line 27, delete "1×" and insert -- 1X --.

In Column 147, Line 35, delete "(1 g/ml)" and insert -- (1 μg/ml) --.

In Column 158, Line 40, delete "Gprl25, Aqpl1," and insert -- Gpr125, Aqp11, --.

In Column 158, Line 44, delete "Clqtnf4," and insert -- C1qtnf4, --.

In Column 159, Line 6, delete "Clqtnf4," and insert -- C1qtnf4, --.

In Column 161, Line 52, delete "Gprl25, Aqpl1," and insert -- Gpr125, Aqp11, --.

In Column 161, Line 56, delete "Clqtnf4," and insert -- C1qtnf4, --.

In Column 161, Line 65, delete "Clqtnf4," and insert -- C1qtnf4, --.

In Column 161, Line 66, delete "Gprl25," and insert -- Gpr125, --.

In Column 172, Line 34, delete "Lty1" and insert -- Ltv1 --.